(12) United States Patent
Helmerhorst et al.

(10) Patent No.: US 11,124,785 B2
(45) Date of Patent: Sep. 21, 2021

(54) ROTHIA SUBTILISINS, S8A FAMILY PROTEASES, AS THERAPEUTIC ENZYMES FOR APPLICATION IN GLUTEN INTOLERANCE DISORDERS

(71) Applicant: TRUSTEES OF BOSTON UNIVERSITY, Boston, MA (US)

(72) Inventors: Eva J. Helmerhorst, Boston, MA (US); Guoxian Wei, Malden, MA (US); Na Tian, Wellesley, MA (US); Detlef Schuppan, Mainz (DE)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 342 days.

(21) Appl. No.: 16/076,852

(22) PCT Filed: Feb. 10, 2017

(86) PCT No.: PCT/US2017/017491
§ 371 (c)(1),
(2) Date: Aug. 9, 2018

(87) PCT Pub. No.: WO2017/139659
PCT Pub. Date: Aug. 17, 2017

(65) Prior Publication Data
US 2019/0040375 A1 Feb. 7, 2019

Related U.S. Application Data

(60) Provisional application No. 62/293,960, filed on Feb. 11, 2016.

(51) Int. Cl.
| | | |
|---|---|---|
| C12N 9/52 | (2006.01) | |
| A61K 38/48 | (2006.01) | |
| A61K 45/06 | (2006.01) | |
| A23L 33/135 | (2016.01) | |

(52) U.S. Cl.
CPC .............. *C12N 9/52* (2013.01); *A23L 33/135* (2016.08); *A61K 38/482* (2013.01); *A61K 45/06* (2013.01); *C12Y 304/21026* (2013.01); *C12Y 304/21062* (2013.01); *A23V 2002/00* (2013.01)

(58) Field of Classification Search
None
See application file for complete search history.

(56) References Cited

U.S. PATENT DOCUMENTS

| 7,468,267 | B2 | 12/2008 | Monod et al. |
| 7,628,985 | B2 | 12/2009 | Shan et al. |
| 8,362,222 | B2 | 1/2013 | Valtakari et al. |
| 8,685,392 | B2 | 4/2014 | Helmerhorst et al. |
| 2013/0171109 | A1 | 7/2013 | Helmerhorst et al. |

FOREIGN PATENT DOCUMENTS

| WO | 2008/115411 A1 | 9/2008 |
| WO | 2011/097266 A1 | 8/2011 |
| WO | 2013/083338 A1 | 6/2013 |

OTHER PUBLICATIONS

Wei, Guoxian; et al; "Identification of food-grade subtilisins as gluten-degrading enzymes to treat celiac disease" The American Journal of Physiology: Gastrointestinal and Liver Physiology, 311, G571-G580, 2016 (Year: 2016).*
Polgar, L; "The catalytic triad of serine peptidases" Cellular and Molecular Life Sciences, 62, 2161-2172, 2005 (Year: 2005).*
Fernandez-Feo et al., "The cultivable human oral gluten-degrading microbiome and its potential implications in coeliac disease and gluten sensitivity." Clinical Microbiology and Infection 19(9):E386-E394 (2013).
Helmerhorst et al., "Discovery of a novel and rich source of gluten-degrading microbial enzymes in the oral cavity." PloS One 5(10):e13264 (2010).
Helmerhorst et al., "Experimental strategy to discover microbes with gluten-degrading enzyme activities." Sensing Technologies for Global Health, Military Medicine, and Environmental Monitoring IV 9112D (2014) International Society for Optics and Photonics, 2014.
Helmerhorst et al., "Identification of Lys-Pro-Gln as a novel cleavage site specificity of saliva-associated proteases." Journal of Biological Chemistry 283(29):19957-19966 (2008).
http://www.inflammation-systemicenzymes.com_celiac-disease-.
Lahdeaho et al., "Glutenase ALV003 attenuates gluten-induced mucosal injury in patients with celiac disease." Gastroenterology 146(7):1649-1658 (2014).
Leszcynska et al., "Immunoreactivity reduction of wheat flour proteins modified by the treatment with subtilisin." Polish Journal of Food and Nutrition Sciences 58(3):335-340 (2008).
Siegel et al., "Safety, tolerability, and activity of ALV003: results from two phase 1 single, escalating-dose clinical trials." Digestive Diseases and Sciences 57(2):440-450 (2012).
Tack et al., "Consumption of gluten with gluten-degrading enzyme by celiac patients: a pilot-study." World journal of gastroenterology: WJG 19(35):5837-5847 (2013).

(Continued)

*Primary Examiner* — David W Berke-Schlessel
(74) *Attorney, Agent, or Firm* — Nixon Peabody LLP

(57) ABSTRACT

There are gluten-degrading enzymes found in *Rothia* species bacteria that are subtilisins that belonging to the S8A family of serine protease family. The *Rothia* sp. derived subtilisin-like enzymes have the conserved catalytic triad composed of a Ser, His, and Asp residues that is characteristic of the serine protease family. The *Rothia* subtilisin enzymes are potent at cleaving proline-containing proteins, cleaving the second peptide bond after proline in the XPX1 motif, where X is any amino acid, P is proline and X1 is a hydrophobic amino acid, e.g. the XPQ motif, where Q is glutamine. Embodiments herein provide isolated enzyme compositions and formulations comprising subtilisins gluten-degrading enzyme from a *Rothia* species bacteria. Also provided herein are methods of treatment of celiac disease or a related disorder, treatment of gluten-containing foodstuff, degrading and/or detoxifying gluten comprising the subtilisins gluten-degrading enzyme and/or compositions.

22 Claims, 42 Drawing Sheets
Specification includes a Sequence Listing.

(56) References Cited

OTHER PUBLICATIONS

Tian et al., "Effect of Rothia mucilaginosa enzymes on gliadin (gluten) structure, deamidation, and immunogenic epitopes relevant to celiac disease." American Journal of Physiology—Gastrointestinal and Liver Physiology 307(8):G769-G776 (2014).
UniProtKB/TrEMBL Direct Submission C6R5V9_9MICC (Jan. 10, 2014) [Retrieved [rom the Internet Apr. 22, 2017: <http://www.uniprot.org/uniprot!C6R5V9.txt?version=24:>]; in entirety.
Zamakhchari et al., "Identification of Rothia bacteria as gluten-degrading natural colonizers of the upper gastro-intestinal tract." PloS one 6(9):e24455 (2011).

\* cited by examiner

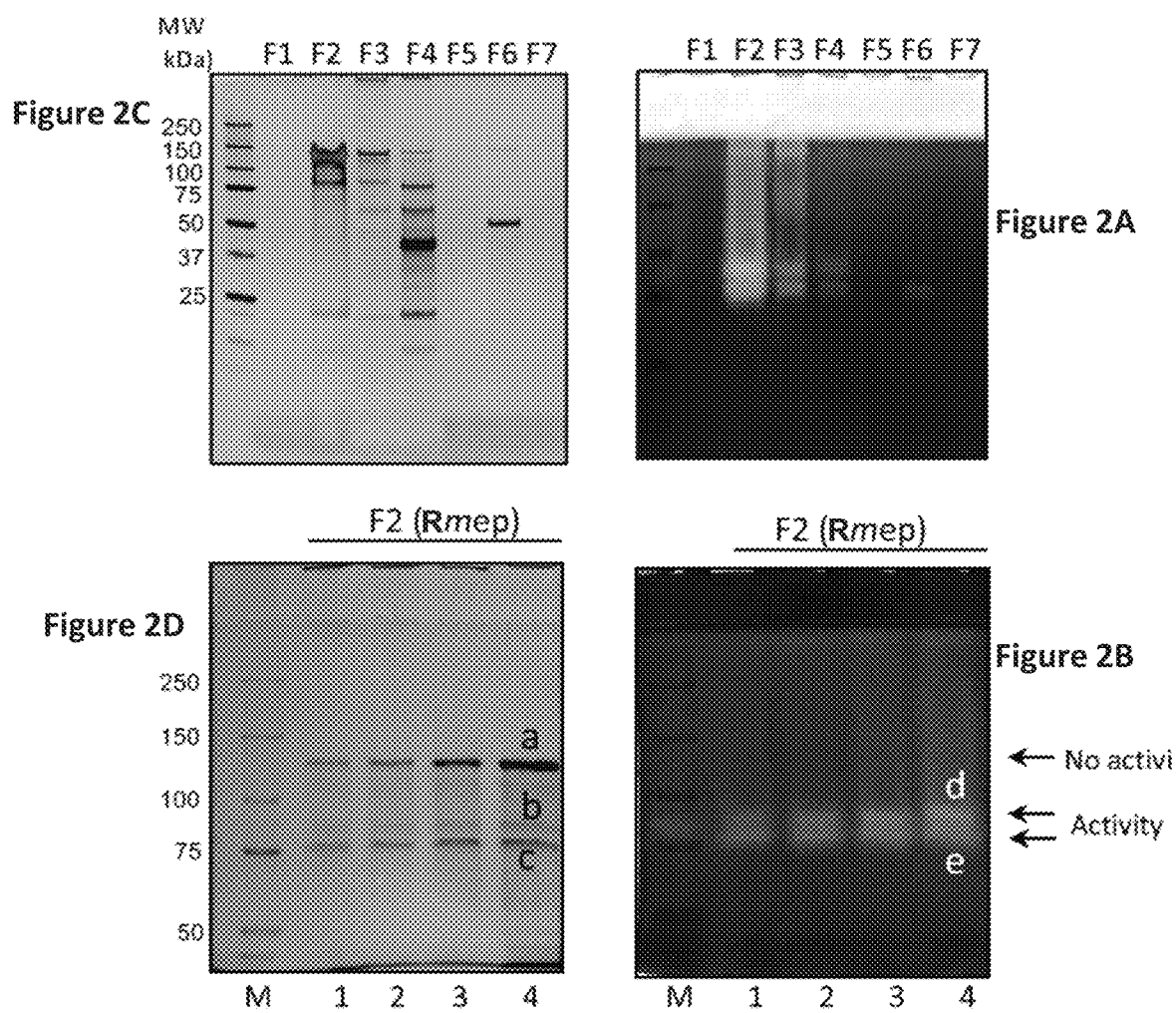

Figure 3C
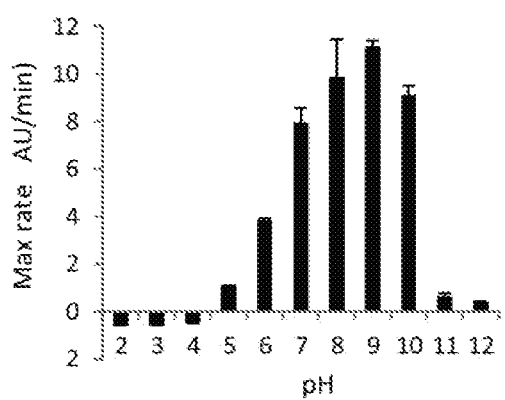
Figure 3A
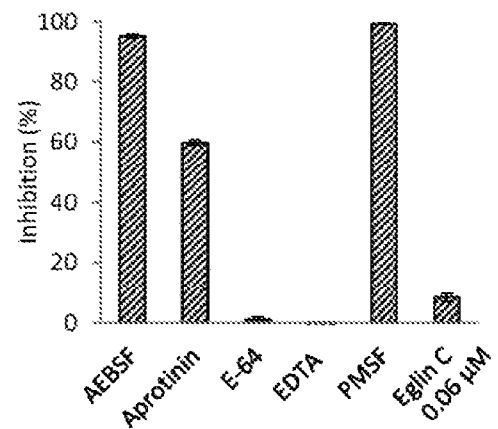
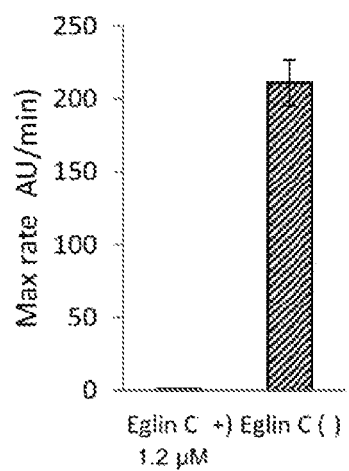
Figure 3D
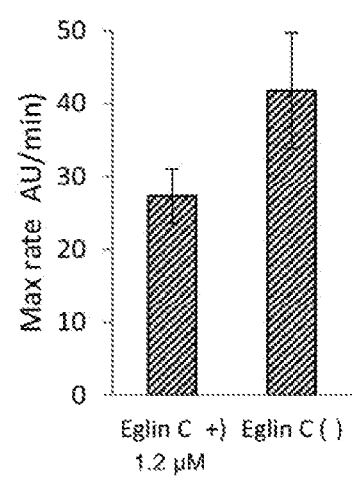
Figure 3B

Figure 5A
Figure 5B
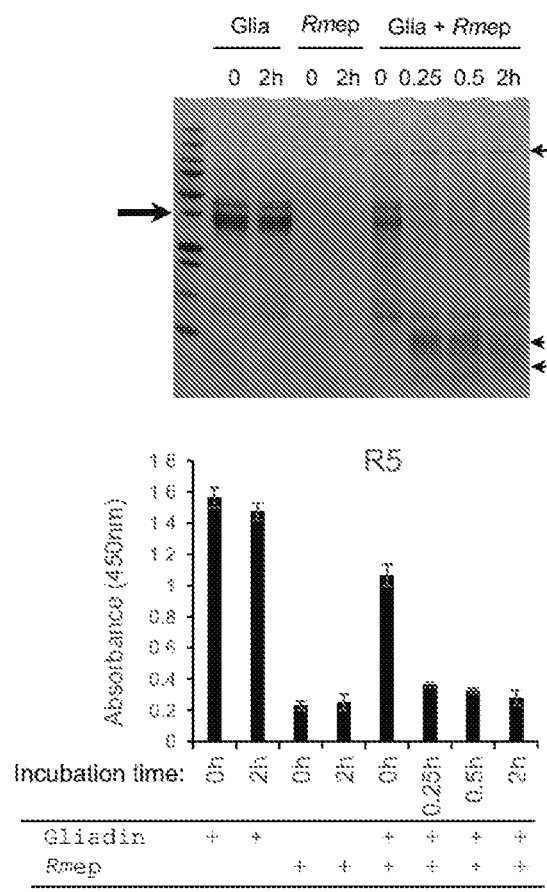
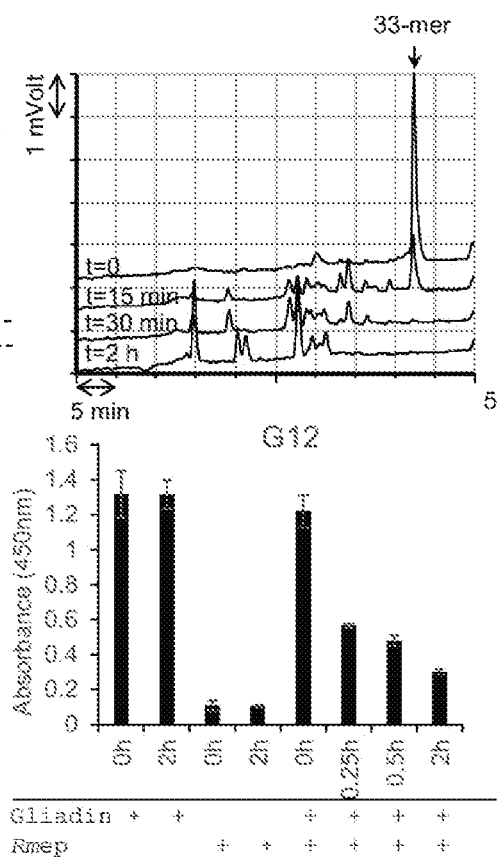
Figure 5C
Figure 5D

Figure 6A
Figure 6B
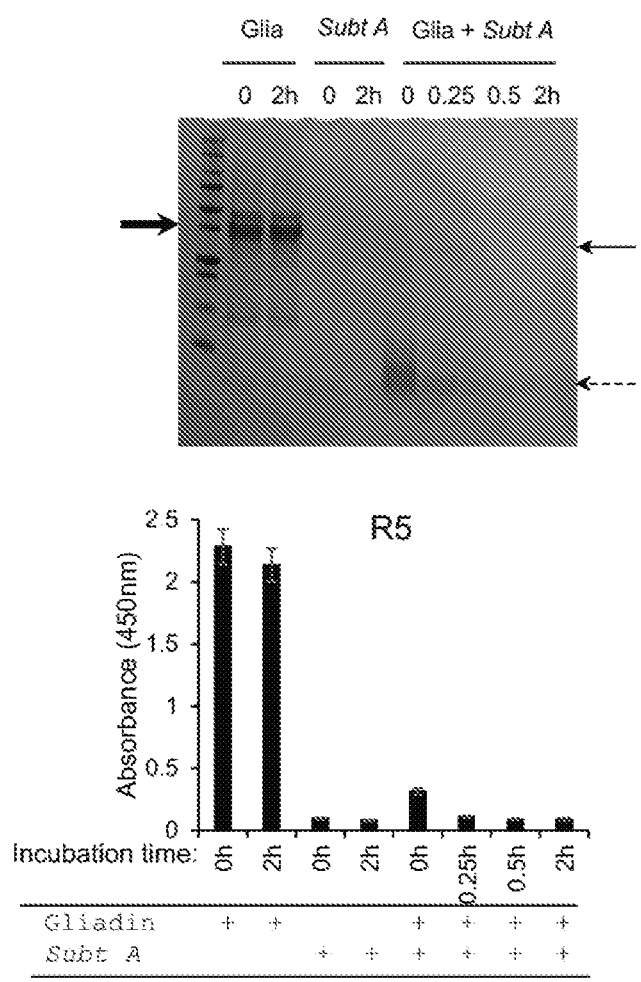
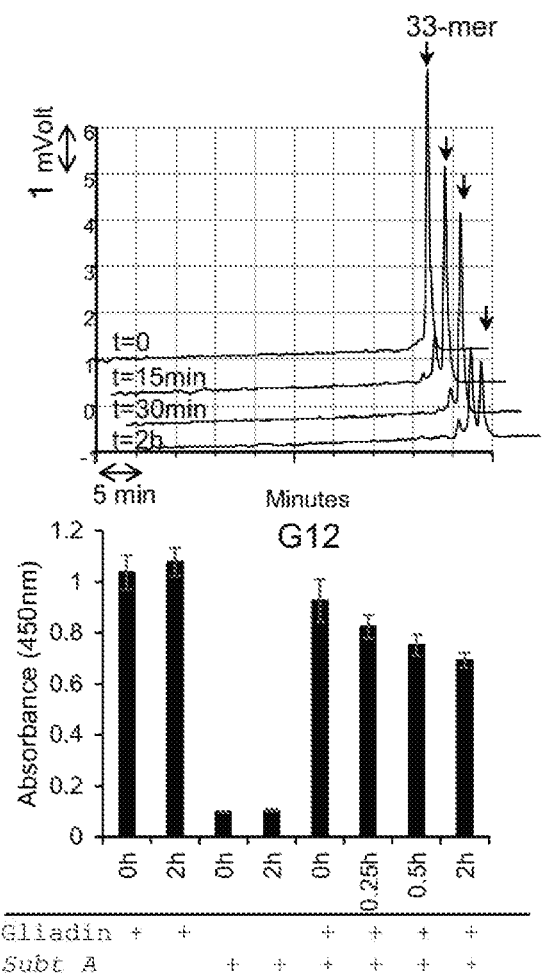
Figure 6C
Figure 6D
Figure 7
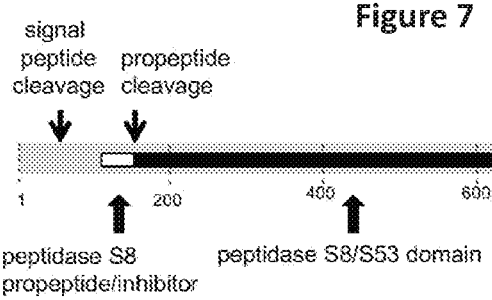
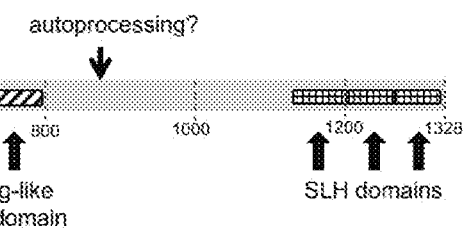

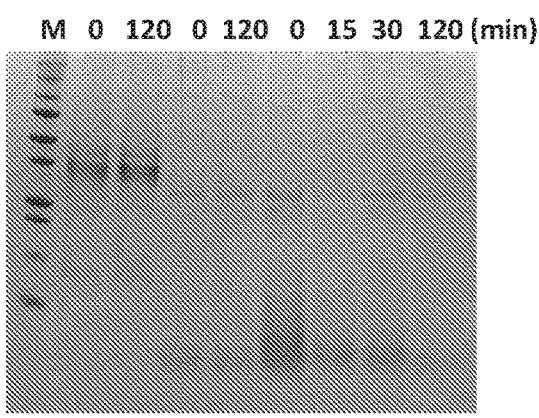
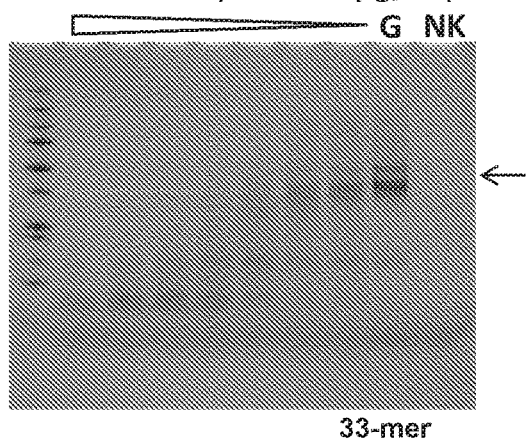
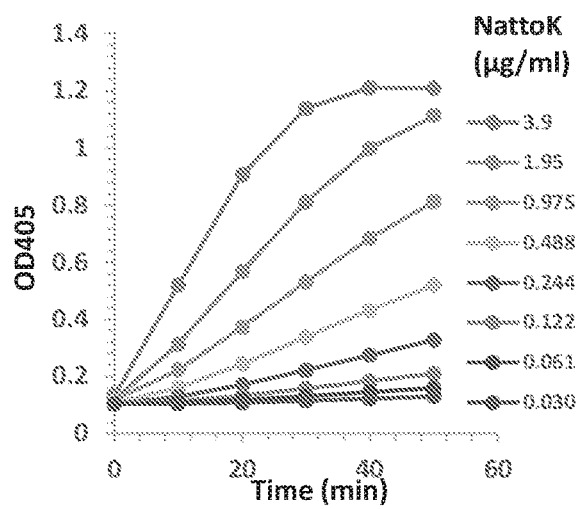
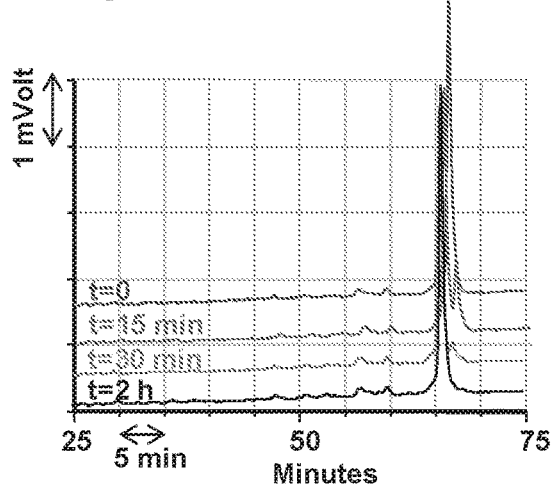
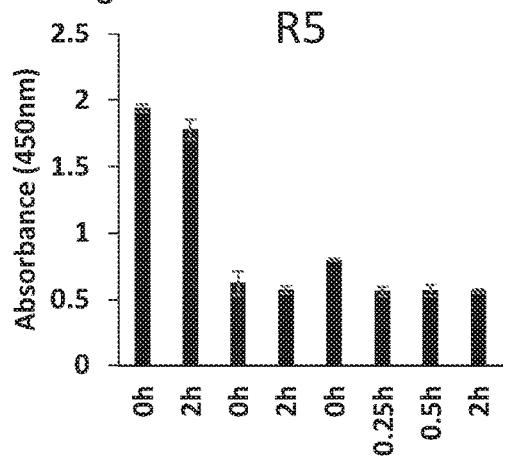
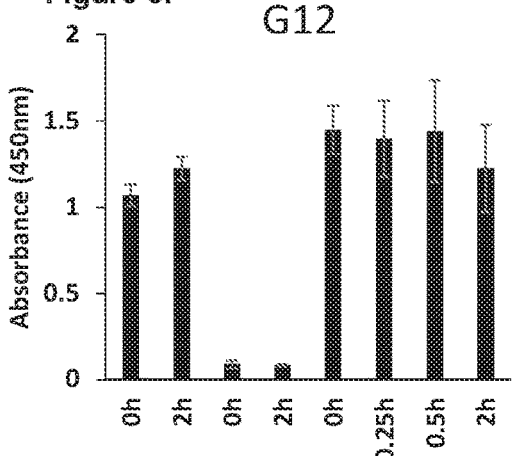

```
gi|739374901|ref|WP_037235857.1|      TILDAGTARDQG-----------GRYRQYLSSVSGNVTLTDS------SSTVVVPLHAAP
gi|694242829|gb|KGJ33663.1|           TILDAGTARDQG-----------GRYRQYLSSVSGNVTLTDS------SSTVVVPLHAAP
gi|694197664|gb|KGJ01304.1|           TILDAGTARDQG-----------GRYRQYLSSVSGNVTLTDS------SSTVVVPLHAAP
gi|383447824|gb|EID50801.1|           TILDAGTARDQG-----------GRYRQYLSSVSGNVTLTDS------SSTVVVPLHAAP
gi|551694889|gb|ERT66212.1|           TILDAGTARDQG-----------GRYRQYLSSVSGNVTLTDS------SSTVVVPLHAAP
gi|493944541|ref|WP_006888539.1|      TILDAGTARDQG-----------GRYRQYLSSVSGNVTLTDS------SSTVVVPLHAAP
gi|739425592|ref|WP_037285685.1|      TILDAGTARDQG-----------GRYRQYLSSVSGNVTLTDS------SSTVVVPLHAAP
gi|383448241|gb|EID51213.1|           TAEATANTTQRST----GEDGQVVAFGARQYVASASGQVVLTE-----GDTTLRVPVHAAP
gi|551692673|gb|ERT64166.1|           TAEATANTTQRST----GEDGQVVAFGARQYVASASGQVVLTE-----GDTTLRVPVHAAP
gi|493944011|ref|WP_006888028.1|      TAEATANTTQRST----GEDGQVVAFGARQYVASASGQVVLTE-----GDTTLRVPVHAAP
gi|739426842|ref|WP_037286935.1|      TAEATANTTQRST----GEDGQVVAFGARQYVASASGQVVLTE-----GDTTLRVPVHAAP
gi|694196457|gb|KGJ00124.1|           TAEATANTTQRST----GEDGQVVAFGARQYVASASGQVVLTE-----GDTTLRVPVHAAP
gi|694242455|gb|KGJ35061.1|           TAEATANTTQRST----GEDGQVVAFGARQYVASASGQVVLTE-----GDTTLRVPVHAAP
gi|739372487|ref|WP_037233480.1|      TRDLSMYPTQDSVN--YSTGTV-TISGARQYIASASGRLILTDADSSAAVKTLRMPLHVAP
gi|763289900|ref|WP_044150853.1|      TRDLSMYPTQDSVN--YSTGTV-TISGARQYIASASGRLILTDADSSAAVKTLRMPLHVAP
gi|283134951|dbj|BAI65716.1|          TRDLSMYPTQDSVN--YSTGTV-TISGARQYIASASGRLILTDADSSAAVKTLRMPLHVAP
tr|C6R5V8|C6R5V8_9MICC                TRDPSMYPNQDSVN--YSTGTV-TISGARQYIASASGRLILTDADSSAAVKTLRMPLHVAP
gi|491652445|ref|WP_005509166.1|      TRDPSMYPNQDSVN--YSTGTV-TISGARQYIASASGRLILTDADSSAAVKTLRMPLHVAP
gi|491650570|ref|WP_005507292.1|      TRDPSMYPQDSVN---YSTGTV-TISGARQYIASASGRLILTDADSSAAVKTLRMPLHVAP
gi|353343043|gb|EHB87363.1|           TRDPSMYPQDSVN---YSTGTV-TISGARQYIASASGRLILTDADSSAAVKTLRMPLHVAP
gi|491650568|ref|WP_005507290.1|      TRDAAMDTTQNATE--YYTGTETVPAQYRQYIASASGRLVLTEDG-----TKALRLPVHVAP
gi|491650041|gb|EHB87361.1|           TRDAAMDTTQNATE--YYTGTETVPAQYRQYIASASGRLVLTEDG-----TKALRLPVHVAP
tr|C6R5W1|C6R5W1_9MICC                TRDAAMDTTQNATD--YYTGNETVPEQYRQYIASASGRLVLTEDG-----TKALRLPVHVAP
gi|763282487|ref|WP_044143865.1|      TRDAAMDTTQNATD--YYTGNETVPEQYRQYIASASGRLVLTEDG-----TKALRLPVHVAP
gi|763289895|ref|WP_044150848.1|      TRDAAMDTTQNATD--YYTGNETVPEQYRQYIASASGRLVLTEDG-----TKALRLPVHVAP
gi|283134949|dbj|BAI65714.1|          TRDAAMDTTQNATD--YYTGNETVPEQYRQYIASASGRLVLTEDG-----TKALRLPVHVAP
gi|694196455|gb|KGJ00122.1|           TMDPAMEKTHNSVD--PYGDGTELVPEQYRQFIASESGRILLTE-G----AATLRAPIHAAP
gi|694244253|gb|KGJ35059.1|           TMDPAMEKTHNSVD--PYGDGTELVPEQYRQFIASESGRILLTE-G----AATLRAPIHAAP
gi|739372444|ref|WP_037233438.1|      TMDPAMEKTQSSIDV-NTGKTVPEQARQFIASESGRIKLAE-G-------DQTLRVPLHAAP
gi|490104625|ref|WP_004006463.1|      TMDPAMEKTQSSIDV-NTGKTVPEQARQFIASESGRIKLAE-G-------DQTLRVPLHAAP
gi|503163685|ref|WP_013398346.1|      TMDPAMEKTQSSVDV-NTGKTVPEQARQFIASESGRIKLTE-G-------DQTLRVPLHAAP
gi|310944281|gb|ADP40575.1|           TMDPAMEKTQSSVDV-NTGKTVPEQARQFIASESGRIKLTE-G-------DQTLRVPLHAAP
gi|490104624|ref|WP_004006462.1|      TIDPALEKEQTAMAYVNGQYQPIISGKRQYIASVSGRILLKDANQDNGEELIRLPVHAAP
gi|300379916|gb|EFJ76480.1|           TIDPALEKEQTAMAYVNGQYQPIISGKRQYIASVSGRILLKDANQDNGEELIRLPVHAAP
gi|503163684|ref|WP_013398345.1|      TIDPALEKEQTAMAYVNGQYQPIISGKRQYIASVSGRIIFEDANQDDGEELIRLPVHAAP
gi|310944280|gb|ADP40574.1|           TIDPALEKEQTAMAYVNGQYQPIISGKRQYIASVSGRIIFEDANQDDGEELIRLPVHAAP
gi|694196456|gb|KGJ00123.1|           TRDPALEKRQSSRNVVGDKVETTAEGDRQYVASASGRLIFS------EDGAEAMRVPVHVAP
gi|694244254|gb|KGJ35060.1|           TRDPALEKRQSSRNVVGDKVETTAEGDRQYVASASGRLIFS------EDGAEAMRVPVHVAP
gi|739372446|ref|WP_037233440.1|      TMDPAMSADQVAQDWTT---GKTLAAGKRQYIASASGRLIFS------ENGREAIRQSIHVAP
gi|763289896|ref|WP_044150849.1|      TMDPAMSADQVAQDWTT---GKTLAAGKRQYIASASGRLIFS------ENGREAIRQSIHVAP
gi|283134950|dbj|BAI65715.1|          TMDPAMSADQVAQDWTT---GKTLAAGKRQYIASASGRLIFS------ENGREAIRQSIHVAP
tr|C6R5V9|C6R5V9_9MICC                TMDPAMSADQVAQDWTT---GKTLAAGKRQYIASASGRLIFS------ENGREAIRQSIHVAP
gi|763282486|ref|WP_044143864.1|      TMDPAMSADQVAQDWTT---GKTLAAGKRQYIASASGRLIFS------ENGREAIRQSIHVAP
gi|491650569|ref|WP_005507291.1|      TMDPAMSADQVAQDWTT---GKTLAAGKRQYIASASGRLIFS------ENGREAIRQSIHVAP
gi|353343042|gb|EHB87362.1|           TMDPAMSADQVAQDWTT---GKTLAAGKRQYIASASGRLIFS------ENGREAIRQSIHVAP
                                      * :       :       **::::* **  :         :.**
```

```
gi|739374901|ref|WP_037235857.1| 0
gi|694242829|gb|KGJ33663.1| 0
gi|694197664|gb|KGJ01304.1| 0
gi|551694889|gb|ERT66212.1| 0
gi|739425592|ref|WP_037285685.1| 0
gi|383447824|gb|EID50801.1| 0
gi|493944541|ref|WP_006888539.1| 0
gi|383448241|gb|EID51213.1| 0
gi|493944011|ref|WP_006888028.1| 0
gi|551692673|gb|ERT64166.1| 0
gi|739426842|ref|WP_037286935.1| 0
gi|694196457|gb|KGJ00124.1| 0
gi|694244255|gb|KGJ35061.1| 0
gi|739372487|ref|WP_037233480.1| 0
gi|763289900|ref|WP_044150853.1| 0
gi|283134951|dbj|BAI65716.1| 0
tr|C6R5V8|C6R5V8_9MICC 0
gi|491652445|ref|WP_005509166.1| 0
gi|491650570|ref|WP_005507292.1| 0
gi|353343043|gb|EHB87363.1| 0
gi|491650568|ref|WP_005507290.1| 0
gi|353343041|gb|EHB87361.1| 0
tr|C6R5W1|C6R5W1_9MICC 0
gi|763282487|ref|WP_044143865.1| 0
gi|763289895|ref|WP_044150848.1| 0
gi|283134949|dbj|BAI65714.1| 0
gi|694196455|gb|KGJ00122.1| 0
gi|694244253|gb|KGJ35059.1| 0
gi|739372444|ref|WP_037233438.1| 0
gi|490104625|ref|WP_004006463.1| 0
gi|300379917|gb|EFJ76481.1| 0
gi|503163685|ref|WP_013398346.1| 0
gi|310944281|gb|ADP40575.1| 0
gi|490104624|ref|WP_004006462.1| 0
gi|300379916|gb|EFJ76480.1| 0
gi|503163684|ref|WP_013398345.1| 0
gi|310944280|gb|ADP40574.1| 0
gi|694196456|gb|KGJ00123.1| 0
gi|694244254|gb|KGJ35060.1| 0
gi|739372446|ref|WP_037233440.1| 0
gi|763289896|ref|WP_044150849.1| 0
gi|283134950|dbj|BAI65715.1| 0
gi|491650569|ref|WP_005507291.1| 0
gi|353343042|gb|EHB87362.1| 0
tr|C6R5V9|C6R5V9_9MICC 0
gi|763282486|ref|WP_044143864.1| 0
```

Figure 13

```
KGJ00122.1    MPKNTPIRGLSRACLSATLGVTMAITAGLPATAAPAGDPDTPVAQDIARNSREHAVLSDS
BAV86562.1    ---------------------------------MAITAGLPATAAPAGDPDTPVAQDIARNSREHAVLSDS
                                               ********************************

KGJ00122.1    MKKAEGNIPVFVQFKGKGAYEQTQSPAVLANKQAPINKQAEVQAIKTQVQSQAQAAAQST
BAV86562.1    MKKAEGNIPVFVQFKGKGAYEQTQSPAVLANKQAPTNKQAEVQAIKTQVQSQAQAAAQST
              ***********************************  ***********************

KGJ00122.1    GAKTLYTTHNIMRGVALQGDAAQIRALANNPEVERITPIVPKKKQNAGSVVDTGAAENWA
BAV86562.1    GAKTLYTTHNIMRGVALQGDAAQIRALANNPEVERITPIVPKKKQNAGSVVDTGAAENWA
              ************************************************************

KGJ00122.1    RENSGYTGKDVKIAVVDSGIDYTHSDFGGPGTVEAFNKATKLTEMPAADSGLYDAKKYIG
BAV86562.1    RENSGYTGKDVKIAVVDSGIDYTHADFGGPGTVEAFNKATKLTEMPAADSGLYDAKKYIG
              ************************ ***********************************

KGJ00122.1    GYDLVGDSYDGTNQTTPDNNPIDCSAGGHGTHVAGTAAGYGVNQDGTTFRGDYSKLTAEQ
BAV86562.1    GYDLVGDSYDGTNQTAPDNNPIDCSAGGHGTHVAGTAAGYGVNQDGTTFRGDYSKLTAEQ
              ***************.********************************************

KGJ00122.1    LNQMKIGPGAAPEAQLYSFRVFGCTGTTAVVVQALDRTLDPNGDGDFSDRANIVNLSIGG
BAV86562.1    LNQMKIGPGAAPEAQLYSFRVFGCTGTTGVVVQALDRTLDPNGDGDFSDRANIVNLSIGG
              ****************************.*******************************

KGJ00122.1    EFSPPDDADAYAVESLNRQGVLAVVSAGNATDYYGRGDTYSDSGQPANAVSALTVANSIG
BAV86562.1    EFSPPDDADAYAVESLNRQGVLAVVSAGNATDYYGRGDTYSDSGQPANAVSALTVANSIG
              ************************************************************

KGJ00122.1    SSYAVDSMEIQAPANVAGKVPGDYTVSYTYTGAKPEALTGTVVTPSESNKFGCEAFSAED
BAV86562.1    SSYAVDSMEIQAPANVAGKVPGDYTVSYTYTGAKPEALTGTVVTPSESNKFGCEAFSAED
              ************************************************************

KGJ00122.1    AAKIKDKWVFIEWANADGSLPCGSKVRFDNVEKAGGKGVVLSSEEEKPALPIGGNESIPG
BAV86562.1    AAKIKDKWVFLEWANADGSLPCGSKVRFDNVEKAGGKGVVLSSEEEKPALPIGGNESIPG
              **********.**************************************************

KGJ00122.1    FRVAKSASAKVREAAATGELKVRLGADLKESLRVPSNKKDQLTASSARGYHGTYGYTKPD
BAV86562.1    FRVAKSASAKVREAAANGELKVRLGTDLKESLRVPSNKKDQLTASSARGYHGTYGYTKPD
              ****************.*******.***********************************

KGJ00122.1    VAAPGNNISSARVGTGTGGISYTGTSMSAPFAAGVAAQVLQANQSYGPTQLKAAIMNSAN
BAV86562.1    VAAPGNNISSARVGTGTDGISYTGTSMSAPFAAGVAAQVLQANQSYGPTQLKAAIMNSAN
              *****************.******************************************

KGJ00122.1    HDVRTADGNVYAVDRVGSGRIDAKAAAETKVLLYNADRPAQVSQTFGVLEYAVNEGKQTL
BAV86562.1    HDVRTADGNVYAVDRVGSGRIDAKAAAETKVLLYNADRPAQVSQTFGVLEYAVNEGKQTL
              ************************************************************

KGJ00122.1    TREMTVENFDSHTHTYNISYAGSTDMPGVEFSLPSNITVNPGEKKNFTVTITIDPAAMEK
BAV86562.1    TREMTVENFDSHTHTYNISYAGSTDMPGVEFSLPSNITVNPGEKKNFTVTITIDPAAMEK
              ************************************************************

KGJ00122.1    TMDPAMEKTHNSVDPYGDGTELVPEQYRQFIASESGRILLTEGAATLRAPIHAAPKPASA
BAV86562.1    TMDPAMEKTHNSVDPYGDGTELVPEQYRQFIASESGRILLTEGAATLRAPIHAAPKPASA
              ************************************************************
```

Figure 13 cont.

```
KGJ00122.1_   MKVEGSSVEIPAGEHQANLKLTGTELNQRGYKSLLGAFEHGASIERTSPVKLDVSSNAKA
BAV86562.1_   MKVEGSSVEIPAGEHQANLKLTGTELNQRGYKSLLGAFEHGASIERTSPVKLDVSSNAKA
              ************************************************************

KGJ00122.1_   NMQHVGAASTAPALKASGGNPNDGLLAFGISTWANWDVVSTENTFTVNIDTDGNNRADYM
BAV86562.1_   NMQHVGAASTAPALKASGGNPNDGLLAFGISTWANWDVVSTENTFTVNIDTDGNNRADYM
              ************************************************************

KGJ00122.1_   LVTDRAKGIDFPIVRLYGYKNGNLEQIAYYPLNNAWGDTDTNMMDSNALVMAVPLKDLGL
BAV86562.1_   LVTDRAKGIDFPIVRLYGYKNGNLEQIAYYPLNNAWGDTDTNMMDSNALVMAVPLKDLGL
              ************************************************************

KGJ00122.1_   SAEKTKDIKYSVSATTQYAWTNVSETGWINYRPFDPKLWFSGTAATVPGFFADAPSSELV
BAV86562.1_   SAEKTKDIKYSVSATTQYAWTNVSETGWINYRPFDPKLWFSGTAATVPGFFADAPSSELV
              ************************************************************

KGJ00122.1_   AHRAEGATDVKALFLHMHNTTGDLSGLNGAAGNRAQVLEVTEQQQLDPAPSRFTDVPAEN
BAV86562.1_   AHRAEGATDVKALFLHMHNTTGDLSGLNGAAGNRAQVLEVTEQQQLDPAPSRFTDVPAEN
              ************************************************************

KGJ00122.1_   QFYAEINWLAQRRITTGYPDGTFRPGENVERGAMAAYFYRLAGTPQFTAPDNPTFSDVPK
BAV86562.1_   QFYAEINWLAQRRITTGYPDGTFRPGENVERGAMAAYFYRLAGTPQFTAPDNPTFSDVPK
              ************************************************************

KGJ00122.1_   SHPFYKEIEWMAARGITTGYGDGTFRPSDSVNRDAMAAFFYRYANSPQFAAPAASPFKDV
BAV86562.1_   SHPFYKEIEWMAARGITTGYGDGTFRPSASVNRDAMAAFFYRYANSPQFAAPAASPFKDV
              ****************************  *****************************

KGJ00122.1_   PANSQFYKEIAWLAEQGITKGWDDGTYRPGEPIHRDAMAAFLYRYSDKVLK
BAV86562.1_   PANSQFYKEIAWLAEQGITKGWDDGTYRPGEPIHRDAMAAFLYRYSDKVLK
              **************************************************
```

Figure 14

```
WP_044143865.1_R._muc_    MQHTASPNPRGRSHRRRIGSGLLTLSMALSP------LAALGT-TAHAAE
BAV86562.1_R._aer         MAITAG---------------LPATAAP------AGDPDTPVAQDIA
WP_044143864.1_R._muc_    MTTPHAPRRRMKAVGATGLSAALALTLGVPATFSAAHAQSPQQVEGSTAS
P00780.1__B._lich_A       --------------------------------------------------
P35835.1__B._subt_NAT     --------------------------------------------------

WP_044143865.1_R._muc_    DPDAVKQVLSESMKNASGTVTAFVRFKGKGAFEQTQPAGVRAGVQAPVNT
BAV86562.1_R._aer         RNSREHAVLSDSMKKAEGNIPVFVQFKGKGAYEQTQSPAVLANKQAPTNK
WP_044143864.1_R._muc_    ASGDAASRISPGLQKAEGQITVYVQFKGKGAYEQTQSAAVLARKEAPANR
P00780.1__B._lich_A       ----------MMRKKSFWLGMLTAFMLVFTMAFSDSASAAQPAKNVEKDYI
P35835.1__B._subt_NAT     ------------MRSKKLWISLLFALTLIFTMAFSNMSAQAAGKSSTEKKYI
                                            .:     .  .: *:.:  . .

WP_044143865.1_R._muc_    SSQVQAIASQVQSQAQQVSSQSGAQVLYTTHNAVRGVAVRGDAESIKALA
BAV86562.1_R._aer         QAEVQAIKTQVQSQAQAAAQSTGAKTLYTTHNIMRGVALQGDAAQIRALA
WP_044143864.1_R._muc_    QAQVQAIAAQVQSQAQSVAAASGAKLMYTTHNAMRGAAITGDAAQIRALA
P00780.1__B._lich_A       VGFKSGVKTAS--VKKDIIKESGGKVDKQFR-IINAAKAKLDKEALKEVK
P35835.1__B._subt_NAT     VGFKQTMSAMSSAKKKDVISEKGGKVQKQFK-YVNAAAATLDEKAVKELK
                           .   . :     :     . .*.:   : ;...  *   :: :

WP_044143865.1_R._muc_    NRPDVEKISPILPKYRQNAGAAIDAGSLATWTGTTNPAGAGGYTGKGVKI
BAV86562.1_R._aer         NNPEVERITPIVPKKKQNAGSVVDTGAAENWAREN------SGYTGKDVKI
WP_044143864.1_R._muc_    ERPDVERISPIIAKERMNSGSEIDTKTLATWTREN------TGYTGKGVKI
P00780.1__B._lich_A       NDPDVAYVEEDHVAHALAQTVPYGIPLIKADKVQA------QGFKGANVKV
P35835.1__B._subt_NAT     KDPSVAYVEEDHIAHEYAQSVPYGISQIKAPALHS------QGYTGSNVKV
                           : *.*  :          .                     *:.* .**:

WP_044143865.1_R._muc_    AVIDSGIDYTHTDFGGSGKLEDYEKASKLTELPSADSGLINRTKVAGGYD
BAV86562.1_R._aer         AVVDSGIDYTHADFGGPGTVEAFNKATKLTEMPAADSGLYDAKKYIGGYD
WP_044143864.1_R._muc_    AVVDSGVDYTHADFGGPGTVDSYLKAKAMTELPSADSGLIDRNKFIGGID
P00780.1__B._lich_A       AVLDTGIQASHPDLN----------------------------VVGGAS
P35835.1__B._subt_NAT     AVIDSGIDSSHPDLN----------------------------VRGGAS
                          **:*:*:: :*.*:.                             **  .

WP_044143865.1_R._muc_    LVGDAYDG----SNTATPDGNPLDCT------TGGHGTHVAGTAAGYGVNA
BAV86562.1_R._aer         LVGDSYDG----TNQTAPDNNPIDCS------AGGHGTHVAGTAAGYGVNQ
WP_044143864.1_R._muc_    LVGDDYNASVAEKSTPQPDNNPLDCRPDGFGSGGHGTHVAGTAAGYGVTA
P00780.1__B._lich_A       FVAGEAYN-----------TDGN-----------GHGTHVAGTVAALDNTT
P35835.1__B._subt_NAT     FVPSETNPY----------QDGS-----------SHGTHVAGTIAALNNSI
                          :*   .                *..         .*******  *.   .

WP_044143865.1_R._muc_    DGSTFTGDYSKLTAEQLKTMKIGPGVAPDAEIYAFRVFGCSGSTNVVIEA
BAV86562.1_R._aer         DGTTFRGDYSKLTAEQLNQMKIGPGAAPEAQLYSFRVFGCTGTTGVVVQA
WP_044143864.1_R._muc_    NGTTYRGDYKNLTEEQLKGMSIGPGTAPDAQILAIRVFGCYGNSSVVMKA
P00780.1__B._lich_A       G--------------------VLGVAPSVSLYAVKVLNSSGS------G
P35835.1__B._subt_NAT     G--------------------VLGVAPSASLYAVKVLDSTGS------G
                                                *.**...: :.:*:..  *.         .

WP_044143865.1_R._muc_    LDRALDPNGDGDFSDRVNVVNMSLGGEFSPQDDPEAYAVDALTRAGVLSV
BAV86562.1_R._aer         LDRTLDPNGDGDFSDRANIVNLSIGGEFSPPDDADAYAVESLNRQGVLAV
WP_044143864.1_R._muc_    LDTVMDPNGDGDFSDRADIVNLSLGGEFAPADDPESYMINTMARQGVFTV
P00780.1__B._lich_A       TYSGIVSGIEWATTNGMDVINMSLGGPSGS--TAMKQAVDNAYARGVVVV
P35835.1__B._subt_NAT     QYSWIINGIEWAISNNMDVINMSLGGPTGS--TALKTVVDKAVSSGIVVA
                           :    .  :    ::  :::*:*:**  ..   .  :    *:.  .
```

Figure 14 cont.

```
WP_044143865.1_R._muc_    ISAGNANDYSLRGDTYSNSGHPATAASAITVANAYGSTRAVDAAELTDPA
BAV86562.1_R._aer         VSAGNATDYYGRGDTYSDSGQPANAVSALTVANSIGSSYAVDSMEIQAPA
WP_044143864.1_R._muc_    AAAGNANNYNGVGDTYSDSGSPANAAAALSVANAYGSTQPIDRARVTTKT
P00780.1_B._lich_A        AAAGNS-----GSSGNTNTIGYPAKYDSVIAVG-----------------
P35835.1_B._subt_NAT      AAAGNE-----GSSGSTSTVGYPAKYPSTIAVG-----------------
                          ;***       ..   .   *  **.   .;.;*.

WP_044143865.1_R._muc_    TGTTRKVRGDYSVSYPWAQAGTKEFTGELTAISENNRYACNALSADEAAA
BAV86562.1_R._aer         N-VAGKVPGDYTVSYTYTGAKPEALTGTVVTPSESNKFGCEAFSAEDAAK
WP_044143864.1_R._muc_    G--LEWLQGDYSVNFDYSKASADQLRGEVVAAPKRNRYACEAFTAEEAKA
P00780.1_B._lich_A        --------------------------------------------------
P35835.1_B._subt_NAT      --------------------------------------------------

WP_044143865.1_R._muc_    VKGKWVLIDWAKDDGELACGSKVRFDNLEAAGAKGVLLAGNDEEPGLGIA
BAV86562.1_R._aer         IKDKWVFLEWANADGSLPCGSKVRFDNVEKAGGKGVVLSSEEEKPALPIG
WP_044143864.1_R._muc_    LKGKWVYFDWDQDDLTFPCGSKVRFDNVQAAGGVGVVMAGKAERYTIGIG
P00780.1_B._lich_A        --------------------------------------------------
P35835.1_B._subt_NAT      --------------------------------------------------

WP_044143865.1_R._muc_    GNDTLPGFRLAASAAKDLRAQITAAEAAGKPLTVRLGNELKSSLRVDTDK
BAV86562.1_R._aer         GNESIPGFRVAKSASAKVR-----EAAANGELKVRLGTDLKESLRVPSNK
WP_044143864.1_R._muc_    GNATIPGLRLTASSTKDLE-----KALAAGPVTVEMNLDYKASGRGPHSH
P00780.1_B._lich_A        --------------------------------------------------
P35835.1_B._subt_NAT      --------------------------------------------------

WP_044143865.1_R._muc_    LDQLNPMSARGFHGSYGYTKPDIAAPGSYITSAAVATGNNSVTFSGTSMA
BAV86562.1_R._aer         KDQLTASSARGYHGTYGYTKPDVAAPGNNISSARVGTGTDGISYTGTSMS
WP_044143864.1_R._muc_    AFDLNSSSARGQHGSDGFIKPDLAAPGTEIVSAAVGTGNKGVSFTGTSMA
P00780.1_B._lich_A        --AVDSNSNRASFSSVG-AELEVMAPGAGVYSTYPTS--TYATLNGTSMA
P35835.1_B._subt_NAT      --AVNSSNQRASFSSVG-SELDVMAPGVSIQSTLPGG--TYGAYNGTSMA
                          ; . .*...; * ; :: *** ; *:         ; .****;

WP_044143865.1_R._muc_    APYVTGSAALVMQSHPTYTPAQVKSALMNTATHDVRTESGATYAVDRVGA
BAV86562.1_R._aer         APFAAGVAAQVLQANQSYGPTQLKAAIMNSANHDVRTADGNVYAVDRVGS
WP_044143864.1_R._muc_    TPHVAGVAALVMQAHQDYNPQMIKAALMNGASTPIKNEQGAQYAVDRVGT
P00780.1_B._lich_A        SPHVAGAAALILSKHPNLSASQVRNRLSSTATYLGSS--------FYYGK
P35835.1_B._subt_NAT      TPHVAGAAALILSKHPTWTNAQVRDRLESTATYLGNS--------FYYGK
                          ;*..;* ** ;;. ;          ;;    ; . *.  .         *

WP_044143865.1_R._muc_    GRVDTLAAVQSKSLVYNADKSGTVSLSFGVLEYAPDAGVQTLTREVTVEN
BAV86562.1_R._aer         GRIDAKAAAETKVLLYNADRPAQVSQTFGVLEYAVNEGKQTLTREMTVEN
WP_044143864.1_R._muc_    GMVNARAAVDAKVIAYDAKTPERVSTAFGVLEYTPDSGIQTVQREIVLDN
P00780.1_B._lich_A        GLINVEAAAQ----------------------------------------
P35835.1_B._subt_NAT      GLINVQAAAQ----------------------------------------
                          *  ::.  **..:

WP_044143865.1_R._muc_    TDSVAHTYALSYAESTNIPGVEYSFPSAVTLAPGETKKFEVTVRIDPSKL
BAV86562.1_R._aer         FDSHTHTYNISYAGSTDMPGVEFSLPSNITVNPGEKKNFTVTITIDPAAM
WP_044143864.1_R._muc_    TDSQAHTYLSYEASTTIPGVEYSYPQQVSVGAGERKNVTVTVRIDPSKL
P00780.1_B._lich_A        --------------------------------------------------
P35835.1_B._subt_NAT      --------------------------------------------------
```

Figure 14 cont.

```
WP_044143865.1_R._muc_   EKTRDAAMDTTQNATDYY--TGNETVPEQYRQYIASASGRLVLTEDGTKAL
BAV86562.1_R._aer        EKTMDPAMEKTHNSVDPYGDGTELVPEQYRQFIASESGRILLTEG-AATL
WP_044143864.1_R._muc_   EKTMDPAMSADQVAQDWT--TGKTLAAGKRQYIASASGRLIFSENGREAI
P00780.1__B._lich_A      --------------------------------------------------
P35835.1__B._subt_NAT    --------------------------------------------------

WP_044143865.1_R._muc_   RLPVHVAPKPVSTMHAAEDTVTFTQKPSSDEAQKADTGWTKSQISLRGTE
BAV86562.1_R._aer        RAPIHAAPKPASAMKVEGSSVEIP------------AGEHQANLKLTGTE
WP_044143864.1_R._muc_   RQSIHVAPKPVSKMRVDASRIDYKG-----------ISDKESTVTLRGTT
P00780.1__B._lich_A      --------------------------------------------------
P35835.1__B._subt_NAT    --------------------------------------------------

WP_044143865.1_R._muc_   VNQGGYRSLLGAFEYGASVDRVAPTSLSLNSNVKANLQYVGAFSDAPALK
BAV86562.1_R._aer        LNQRGYKSLLGAFEHGASIERTSPVKLDVSSNAKANMQHVGAASTAPALK
WP_044143864.1_R._muc_   LNQGGYRSLLGAFELGAVSDRIPSGQLKLPSNQSVDLQYVGAASDAPALK
P00780.1__B._lich_A      --------------------------------------------------
P35835.1__B._subt_NAT    --------------------------------------------------

WP_044143865.1_R._muc_   AAGGNADDGTLRFGISTWANWDVVSYENTFTVEIDTDGNNRADYKLVTDR
BAV86562.1_R._aer        ASGGNPNDGLLAFGISTWANWDVVSTENTFTVNIDTDGNNRADYMLVTDR
WP_044143864.1_R._muc_   AAGKNPNDGSLFFGISTWGTWDSMHWGRQVQVQIDTNNDSTADYVLEVTR
P00780.1__B._lich_A      --------------------------------------------------
P35835.1__B._subt_NAT    --------------------------------------------------

WP_044143865.1_R._muc_   AKGLDYPLVRLYGYKNGNLVELGYYPLNGAWGDVDTNMMDTNTLIMSAPL
BAV86562.1_R._aer        AKGIDFPIVRLYGYKNGNLEQIAYYPLNNAWGDTDTMMMDSNALVMAVPL
WP_044143864.1_R._muc_   EKGLDYPLVKVWSISGNASTVVARYPLNSAWGDTDTNIMDTNTMILGVPL
P00780.1__B._lich_A      --------------------------------------------------
P35835.1__B._subt_NAT    --------------------------------------------------

WP_044143865.1_R._muc_   KDLGLTSANNPDIQYRVSATTQYEWGN--VSETGWIKYRPFSPKLWFSGD
BAV86562.1_R._aer        KDLGLSAEKTKDIKYSVSATTQYAWTN--VSETGWINYRPFDPKLWFSGT
WP_044143864.1_R._muc_   KDLGLTAEKAQSIKYTVQTDTWHNEGNSYVDTTSTIEYSPFNPGVWFTGE
P00780.1__B._lich_A      --------------------------------------------------
P35835.1__B._subt_NAT    --------------------------------------------------

WP_044143865.1_R._muc_   SSAVAGLHPDASTTTLTAHRSADAIPALGESGTPAKALLLHLHNGTGDLS
BAV86562.1_R._aer        AATVPGFFADAPSSELVAHR---------AEGATDVKALFLHMHNTTGDLS
WP_044143864.1_R._muc_   ESGVPGLFVDRDGGQLTVHR---------KNNNKERQALFLHMHNATGDLS
P00780.1__B._lich_A      --------------------------------------------------
P35835.1__B._subt_NAT    --------------------------------------------------

WP_044143865.1_R._muc_   GTNGAKGNRAEVLNIKEQQTEYITPSRFTDVKNTDQFYTEISWLAQRGIT
BAV86562.1_R._aer        GLNGAAGNRAQVLEVTEQQQLDPAPSRFTDVPAENQFYAEINWLAQRRIT
WP_044143864.1_R._muc_   GRKTANGVAAGDRAQVVKVARTIHDARFTDVPADNQFYREITWIAARQID
P00780.1__B._lich_A      --------------------------------------------------
P35835.1__B._subt_NAT    --------------------------------------------------
```

Figure 14 cont.

```
WP_044143865.1_R._muc_    TGYPDGTYRPLESVERGAMAAFFYRMQGSPQFTAPSTPSFKDVPTTHPFY
BAV86562.1_R._aer         TGYPDGTFRPGENVERGAMAAYFYRLAGTPQFTAPDNPTFSDVPKSHPFY
WP_044143864.1_R._muc_    RGYQDGTFRPLNNMDRATMAAYFYRMSGSPQYTAPSTPSFSDVPLNHPYY
P00780.1_B._lich_A        --------------------------------------------------
P35835.1_B._subt_NAT      --------------------------------------------------

WP_044143865.1_R._muc_    KEIEWMKAQGITTGYSDGTFRPSAPVNRDAMAAFFYRAAGSPHVDLPATS
BAV86562.1_R._aer         KEIEWMAARGITTGYGDGTFRPSASVNRDAMAAFFYRYANSPQFAAPAAS
WP_044143864.1_R._muc_    KEIEWMKAQGITTGWPDGTYRPEGSVNRDAMAAFFYRYAGSPEYTAPAQA
P00780.1_B._lich_A        --------------------------------------------------
P35835.1_B._subt_NAT      --------------------------------------------------

WP_044143865.1_R._muc_    HFSDVSTDNQFYREITWLASKGISTGWPDGTYRPVTPIARDAMAAFIYRY
BAV86562.1_R._aer         PFKDVPANSQFYKEIAWLAEQGITKGWDDGTYRPGEPIHRDAMAAFLYRY
WP_044143864.1_R._muc_    RFTDVPTDKQFYREISWLAEQGVTTGWPDGSFRPVEPVHRDAMAAFVYRY
P00780.1_B._lich_A        --------------------------------------------------
P35835.1_B._subt_NAT      --------------------------------------------------

WP_044143865.1_R._muc_    TEKVANQAGR-
BAV86562.1_R._aer         SDKVLK-----
WP_044143864.1_R._muc_    STGVLKESPEI
P00780.1_B._lich_A        -----------
P35835.1_B._subt_NAT      -----------
```

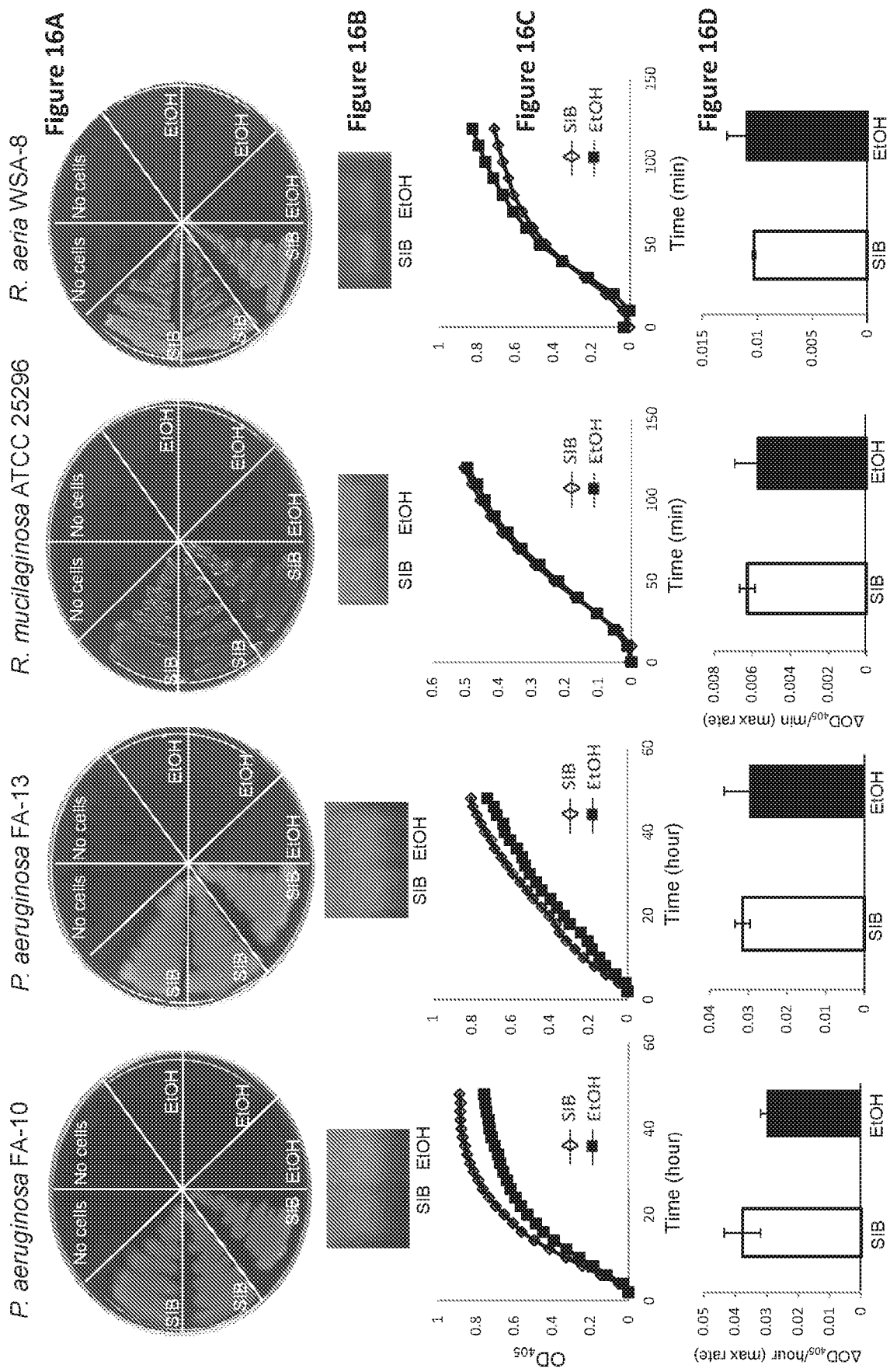

SEQUENCE LISTING

<160> NUMBER OF SEQ ID NOS: 84

<210> SEQ ID NO 1
<211> LENGTH: 1328
<212> TYPE: PRT
<213> ORGANISM: Rothia mucilaginosa

```
<400> SEQUENCE: 1

Met Thr Thr Pro His Ala Pro Arg Arg Met Lys Ala Val Gly Ala
1               5                   10                  15

Thr Gly Leu Ser Ala Ala Leu Ala Leu Thr Leu Gly Val Pro Ala Thr
            20                  25                  30

Phe Ser Ala Ala His Ala Gln Ser Pro Gln Gln Val Glu Gly Ser Thr
        35                  40                  45

Ala Ser Ala Ser Gly Asp Ala Ala Ser Arg Ile Ser Pro Gly Leu Gln
    50                  55                  60

Lys Ala Glu Gly Gln Ile Thr Val Tyr Val Gln Phe Lys Gly Lys Gly
65                  70                  75                  80

Ala Tyr Glu Gln Thr Gln Ser Ala Ala Val Leu Ala Arg Lys Glu Ala
                85                  90                  95

Pro Ala Asn Arg Gln Ala Gln Val Gln Ala Ile Ala Ala Gln Val Gln
            100                 105                 110

Ser Gln Ala Gln Ser Val Ala Ala Ser Gly Ala Lys Leu Met Tyr
        115                 120                 125

Thr Thr His Asn Ala Met Arg Gly Ala Ala Ile Thr Gly Asp Ala Ala
130                 135                 140

Gln Ile Arg Ala Leu Ala Glu Arg Pro Asp Val Glu Arg Ile Ser Pro
145                 150                 155                 160

Ile Ile Ala Lys Glu Arg Met Asn Ser Gly Ser Glu Ile Asp Thr Lys
                165                 170                 175

Thr Leu Ala Thr Trp Thr Arg Glu Asn Thr Gly Tyr Thr Gly Lys Gly
            180                 185                 190

Val Lys Ile Ala Val Val Asp Ser Gly Val Asp Tyr Thr His Ala Asp
        195                 200                 205

Phe Gly Gly Pro Gly Thr Val Asp Ser Tyr Leu Lys Ala Lys Ala Met
    210                 215                 220

Thr Glu Leu Pro Ser Ala Asp Ser Gly Leu Ile Asp Arg Asn Lys Phe
225                 230                 235                 240

Ile Gly Gly Ile Asp Leu Val Gly Asp Asp Tyr Asn Ala Ser Val Ala
                245                 250                 255

Glu Lys Ser Thr Pro Gln Pro Asp Asn Asn Pro Leu Asp Cys Arg Pro
            260                 265                 270

Asp Gly Phe Gly Ser Gly Gly His Gly Thr His Val Ala Gly Thr Ala
        275                 280                 285

Ala Gly Tyr Gly Val Thr Ala Asn Gly Thr Thr Tyr Arg Gly Asp Tyr
    290                 295                 300

Lys Asn Leu Thr Glu Glu Gln Leu Lys Gly Met Ser Ile Gly Pro Gly
305                 310                 315                 320

Thr Ala Pro Asp Ala Gln Ile Leu Ala Ile Arg Val Phe Gly Cys Tyr
                325                 330                 335

Gly Asn Ser Ser Val Val Met Lys Ala Leu Asp Thr Val Met Asp Pro
            340                 345                 350

Asn Gly Asp Gly Asp Phe Ser Asp Arg Ala Asp Ile Val Asn Leu Ser
        355                 360                 365

Leu Gly Gly Glu Phe Ala Pro Ala Asp Asp Pro Glu Ser Tyr Met Ile
    370                 375                 380

Asn Thr Met Ala Arg Gln Gly Val Phe Thr Val Ala Ala Ala Gly Asn
385                 390                 395                 400

Ala Asn Asn Tyr Asn Gly Val Gly Asp Thr Tyr Ser Asp Ser Gly Ser
                405                 410                 415
```

```
Pro Ala Asn Ala Ala Ala Ala Leu Ser Val Ala Asn Ala Tyr Gly Ser
            420                 425                 430

Thr Gln Pro Ile Asp Arg Ala Arg Val Thr Thr Lys Thr Gly Leu Glu
        435                 440                 445

Trp Leu Gln Gly Asp Tyr Ser Val Asn Phe Asp Tyr Ser Lys Ala Ser
    450                 455                 460

Ala Asp Gln Leu Arg Gly Glu Val Val Ala Pro Lys Arg Asn Arg
465                 470                 475                 480

Tyr Ala Cys Glu Ala Phe Thr Ala Glu Glu Ala Lys Ala Leu Lys Gly
                485                 490                 495

Lys Trp Val Tyr Phe Asp Trp Asp Gln Asp Leu Thr Phe Pro Cys
                500                 505                 510

Gly Ser Lys Val Arg Phe Asp Asn Val Gln Ala Gly Gly Val Gly
            515                 520                 525

Val Val Met Ala Gly Lys Ala Glu Arg Tyr Thr Ile Gly Ile Gly Gly
            530                 535                 540

Asn Ala Thr Ile Pro Gly Leu Arg Leu Thr Ala Ser Ser Thr Lys Asp
545                 550                 555                 560

Leu Glu Lys Ala Leu Ala Ala Gly Pro Val Thr Val Glu Met Asn Leu
                565                 570                 575

Asp Tyr Lys Ala Ser Gly Arg Gly Pro His Ser His Ala Phe Asp Leu
            580                 585                 590

Asn Ser Ser Ser Ala Arg Gly Gln His Gly Ser Asp Gly Phe Ile Lys
            595                 600                 605

Pro Asp Leu Ala Ala Pro Gly Thr Glu Ile Val Ser Ala Ala Val Gly
610                 615                 620

Thr Gly Asn Lys Gly Val Ser Phe Thr Gly Thr Ser Met Ala Thr Pro
625                 630                 635                 640

His Val Ala Gly Val Ala Ala Leu Val Met Gln Ala His Gln Asp Tyr
                645                 650                 655

Asn Pro Gln Met Ile Lys Ala Ala Leu Met Asn Gly Ala Ser Thr Pro
            660                 665                 670

Ile Lys Asn Glu Gln Gly Ala Gln Tyr Ala Val Asp Arg Val Gly Thr
            675                 680                 685

Gly Met Val Asn Ala Arg Ala Ala Val Asp Ala Lys Val Ile Ala Tyr
    690                 695                 700

Asp Ala Lys Thr Pro Glu Arg Val Ser Thr Ala Phe Gly Val Leu Glu
705                 710                 715                 720

Tyr Thr Pro Asp Ser Gly Ile Gln Thr Val Gln Arg Glu Ile Val Leu
                725                 730                 735

Asp Asn Thr Asp Ser Gln Ala His Thr Tyr Thr Leu Ser Tyr Glu Ala
            740                 745                 750

Ser Thr Thr Ile Pro Gly Val Glu Tyr Ser Tyr Pro Gln Gln Val Ser
            755                 760                 765

Val Gly Ala Gly Glu Arg Lys Asn Val Thr Val Thr Val Arg Ile Asp
            770                 775                 780

Pro Ser Lys Leu Glu Lys Thr Met Asp Pro Ala Met Ser Ala Asp Gln
785                 790                 795                 800

Val Ala Gln Asp Trp Thr Thr Gly Lys Thr Leu Ala Ala Gly Lys Arg
                805                 810                 815

Gln Tyr Ile Ala Ser Ala Ser Gly Arg Leu Ile Phe Ser Glu Asn Gly
            820                 825                 830
```

-continued

```
Arg Glu Ala Ile Arg Gln Ser Ile His Val Ala Pro Lys Pro Val Ser
        835                 840                 845

Lys Met Arg Val Asp Ala Ser Arg Ile Asp Tyr Lys Gly Ile Ser Asp
    850                 855                 860

Lys Glu Ser Thr Val Thr Leu Arg Gly Thr Thr Leu Asn Gln Gly Gly
865                 870                 875                 880

Tyr Arg Ser Leu Leu Gly Ala Phe Glu Leu Gly Ala Val Ser Asp Arg
            885                 890                 895

Ile Pro Ser Gly Gln Leu Lys Leu Pro Ser Asn Gln Ser Val Asp Leu
                900                 905                 910

Gln Tyr Val Gly Ala Ala Ser Asp Ala Pro Ala Leu Lys Ala Ala Gly
            915                 920                 925

Lys Asn Pro Asn Asp Gly Ser Leu Phe Phe Gly Ile Ser Thr Trp Gly
        930                 935                 940

Thr Trp Asp Ser Met His Trp Gly Arg Gln Val Gln Val Gln Ile Asp
945                 950                 955                 960

Thr Asn Asn Asp Ser Thr Ala Asp Tyr Val Leu Glu Val Thr Arg Glu
                965                 970                 975

Lys Gly Leu Asp Tyr Pro Leu Val Lys Val Trp Ser Ile Ser Gly Asn
            980                 985                 990

Ala Ser Thr Val Val Ala Arg Tyr  Pro Leu Asn Ser Ala  Trp Gly Asp
        995                 1000                1005

Thr Asp  Thr Asn Ile Met Asp  Thr Asn Met Ile  Leu Gly Val
    1010                1015                1020

Pro Leu  Lys Asp Leu Gly Leu  Thr Ala Glu Lys Ala  Gln Ser Ile
    1025                1030                1035

Lys Tyr  Thr Val Gln Thr Asp  Thr Trp His Asn Glu  Gly Asn Ser
    1040                1045                1050

Tyr Val  Asp Thr Thr Ser Thr  Ile Glu Tyr Ser Pro  Phe Asn Pro
    1055                1060                1065

Gly Val  Trp Phe Thr Gly Glu  Ser Gly Val Pro  Gly Leu Phe
    1070                1075                1080

Val Asp  Arg Asp Gly Gly Gln  Leu Thr Val His Arg  Lys Asn Asn
    1085                1090                1095

Asn Lys  Glu Arg Gln Ala Leu  Phe Leu His Met His  Asn Ala Thr
    1100                1105                1110

Gly Asp  Leu Ser Gly Arg Lys  Thr Ala Asn Gly Val  Ala Ala Gly
    1115                1120                1125

Asp Arg  Ala Gln Val Val Lys  Val Ala Arg Thr Ile  His Asp Ala
    1130                1135                1140

Arg Phe  Thr Asp Val Pro Ala  Asp Asn Gln Phe Tyr  Arg Glu Ile
    1145                1150                1155

Thr Trp  Ile Ala Ala Arg Gln  Ile Asp Arg Gly Tyr  Gln Asp Gly
    1160                1165                1170

Thr Phe  Arg Pro Leu Asn Asn  Met Asp Arg Ala Thr  Met Ala Ala
    1175                1180                1185

Tyr Phe  Tyr Arg Met Ser Gly  Ser Pro Gln Tyr Thr  Ala Pro Ser
    1190                1195                1200

Thr Pro  Ser Phe Ser Asp Val  Pro Leu Asn His Pro  Tyr Tyr Lys
    1205                1210                1215

Glu Ile  Glu Trp Met Lys Ala  Gln Gly Ile Thr Thr  Gly Trp Pro
    1220                1225                1230

Asp Gly  Thr Tyr Arg Pro Glu  Gly Ser Val Asn Arg  Asp Ala Met
```

```
                    1235                1240                1245

Ala  Ala  Phe  Phe  Tyr  Arg  Tyr  Ala  Gly  Ser  Pro  Glu  Tyr  Thr  Ala
     1250                1255                1260

Pro  Ala  Gln  Ala  Arg  Phe  Thr  Asp  Val  Pro  Thr  Asp  Lys  Gln  Phe
     1265                1270                1275

Tyr  Arg  Glu  Ile  Ser  Trp  Leu  Ala  Glu  Gln  Gly  Val  Thr  Thr  Gly
     1280                1285                1290

Trp  Pro  Asp  Gly  Ser  Phe  Arg  Pro  Val  Glu  Pro  Val  His  Arg  Asp
     1295                1300                1305

Ala  Met  Ala  Ala  Phe  Val  Tyr  Arg  Tyr  Ser  Thr  Gly  Val  Leu  Lys
     1310                1315                1320

Glu  Ser  Pro  Glu  Ile
     1325

<210> SEQ ID NO 2
<211> LENGTH: 1341
<212> TYPE: PRT
<213> ORGANISM: Rothia mucilaginosa

<400> SEQUENCE: 2

Met  Gln  His  Thr  Ala  Ser  Pro  Asn  Pro  Arg  Gly  Arg  Ser  His  Arg  Arg
1                   5                   10                  15

Arg  Ile  Gly  Ser  Gly  Leu  Leu  Thr  Leu  Ser  Met  Ala  Leu  Ser  Pro  Leu
                    20                  25                  30

Ala  Ala  Leu  Gly  Thr  Thr  Ala  His  Ala  Ala  Glu  Asp  Pro  Asp  Ala  Val
               35                   40                  45

Lys  Gln  Val  Leu  Ser  Glu  Ser  Met  Lys  Asn  Ala  Ser  Gly  Thr  Val  Thr
     50                  55                  60

Ala  Phe  Val  Arg  Phe  Lys  Gly  Lys  Gly  Ala  Phe  Glu  Gln  Thr  Gln  Pro
65                  70                  75                  80

Ala  Gly  Val  Arg  Ala  Gly  Val  Gln  Ala  Pro  Val  Asn  Thr  Ser  Ser  Gln
                    85                  90                  95

Val  Gln  Ala  Ile  Ala  Ser  Gln  Val  Gln  Ser  Gln  Ala  Gln  Gln  Val  Ser
               100                  105                 110

Ser  Gln  Ser  Gly  Ala  Gln  Val  Leu  Tyr  Thr  Thr  His  Asn  Ala  Val  Arg
     115                 120                 125

Gly  Val  Ala  Val  Arg  Gly  Asp  Ala  Glu  Ser  Ile  Lys  Ala  Leu  Ala  Asn
130                 135                 140

Arg  Pro  Asp  Val  Glu  Lys  Ile  Ser  Pro  Ile  Leu  Pro  Lys  Tyr  Arg  Gln
145                 150                 155                 160

Asn  Ala  Gly  Ala  Ala  Ile  Asp  Ala  Gly  Ser  Leu  Ala  Thr  Trp  Thr  Gly
                    165                 170                 175

Thr  Thr  Asn  Pro  Ala  Gly  Ala  Gly  Gly  Tyr  Thr  Gly  Lys  Gly  Val  Lys
               180                  185                 190

Ile  Ala  Val  Ile  Asp  Ser  Gly  Ile  Asp  Tyr  Thr  His  Thr  Asp  Phe  Gly
     195                 200                 205

Gly  Ser  Gly  Lys  Leu  Glu  Asp  Tyr  Glu  Lys  Ala  Ser  Lys  Leu  Thr  Glu
210                 215                 220

Leu  Pro  Ser  Ala  Asp  Ser  Gly  Leu  Ile  Asn  Arg  Thr  Lys  Val  Ala  Gly
225                 230                 235                 240

Gly  Tyr  Asp  Leu  Val  Gly  Asp  Ala  Tyr  Asp  Gly  Ser  Asn  Thr  Ala  Thr
                    245                 250                 255

Pro  Asp  Gly  Asn  Pro  Leu  Asp  Cys  Thr  Thr  Gly  His  Gly  Thr  His
               260                  265                 270
```

```
Val Ala Gly Thr Ala Ala Gly Tyr Gly Val Asn Ala Asp Gly Ser Thr
            275                 280                 285

Phe Thr Gly Asp Tyr Ser Lys Leu Thr Ala Glu Gln Leu Lys Thr Met
        290                 295                 300

Lys Ile Gly Pro Gly Val Ala Pro Asp Ala Glu Ile Tyr Ala Phe Arg
305                 310                 315                 320

Val Phe Gly Cys Ser Gly Ser Thr Asn Val Val Ile Glu Ala Leu Asp
                325                 330                 335

Arg Ala Leu Asp Pro Asn Gly Asp Gly Asp Phe Ser Asp Arg Val Asn
            340                 345                 350

Val Val Asn Met Ser Leu Gly Gly Glu Phe Ser Pro Gln Asp Asp Pro
        355                 360                 365

Glu Ala Tyr Ala Val Asp Ala Leu Thr Arg Ala Gly Val Leu Ser Val
    370                 375                 380

Ile Ser Ala Gly Asn Ala Asn Asp Tyr Ser Leu Arg Gly Asp Thr Tyr
385                 390                 395                 400

Ser Asn Ser Gly His Pro Ala Thr Ala Ser Ala Ile Thr Val Ala
                405                 410                 415

Asn Ala Tyr Gly Ser Thr Arg Ala Val Asp Ala Ala Glu Leu Thr Asp
            420                 425                 430

Pro Ala Thr Gly Thr Thr Arg Lys Val Arg Gly Asp Tyr Ser Val Ser
        435                 440                 445

Tyr Pro Trp Ala Gln Ala Gly Thr Lys Glu Phe Thr Gly Glu Leu Thr
    450                 455                 460

Ala Ile Ser Glu Asn Asn Arg Tyr Ala Cys Asn Ala Leu Ser Ala Asp
465                 470                 475                 480

Glu Ala Ala Ala Val Lys Gly Lys Trp Val Leu Ile Asp Trp Ala Lys
                485                 490                 495

Asp Asp Gly Glu Leu Ala Cys Gly Ser Lys Val Arg Phe Asp Asn Leu
            500                 505                 510

Glu Ala Ala Gly Ala Lys Gly Val Leu Leu Ala Gly Asn Asp Glu Glu
        515                 520                 525

Pro Gly Leu Gly Ile Ala Gly Asn Asp Thr Leu Pro Gly Phe Arg Leu
    530                 535                 540

Ala Ala Ser Ala Ala Lys Asp Leu Arg Ala Gln Ile Thr Ala Ala Glu
545                 550                 555                 560

Ala Ala Gly Lys Pro Leu Thr Val Arg Leu Gly Asn Glu Leu Lys Ser
                565                 570                 575

Ser Leu Arg Val Asp Thr Asp Lys Leu Asp Gln Leu Asn Pro Met Ser
            580                 585                 590

Ala Arg Gly Phe His Gly Ser Tyr Gly Tyr Thr Lys Pro Asp Ile Ala
        595                 600                 605

Ala Pro Gly Ser Tyr Ile Thr Ser Ala Ala Val Ala Thr Gly Asn Asn
    610                 615                 620

Ser Val Thr Phe Ser Gly Thr Ser Met Ala Ala Pro Tyr Val Thr Gly
625                 630                 635                 640

Ser Ala Ala Leu Val Met Gln Ser His Pro Thr Tyr Thr Pro Ala Gln
                645                 650                 655

Val Lys Ser Ala Leu Met Asn Thr Ala Thr His Asp Val Arg Thr Glu
            660                 665                 670

Ser Gly Ala Thr Tyr Ala Val Asp Arg Val Gly Ala Gly Arg Val Asp
        675                 680                 685

Thr Leu Ala Ala Val Gln Ser Lys Ser Leu Val Tyr Asn Ala Asp Lys
```

```
                690             695             700
Ser Gly Thr Val Ser Leu Ser Phe Gly Val Leu Glu Tyr Ala Pro Asp
705             710             715             720
Ala Gly Val Gln Thr Leu Thr Arg Glu Val Thr Val Glu Asn Thr Asp
                725             730             735
Ser Val Ala His Thr Tyr Ala Leu Ser Tyr Ala Glu Ser Thr Asn Ile
            740             745             750
Pro Gly Val Glu Tyr Ser Phe Pro Ser Ala Val Thr Leu Ala Pro Gly
        755             760             765
Glu Thr Lys Lys Phe Glu Val Thr Val Arg Ile Asp Pro Ser Lys Leu
    770             775             780
Glu Lys Thr Arg Asp Ala Ala Met Asp Thr Thr Gln Asn Ala Thr Asp
785             790             795             800
Tyr Tyr Thr Gly Asn Glu Thr Val Pro Glu Gln Tyr Arg Gln Tyr Ile
                805             810             815
Ala Ser Ala Ser Gly Arg Leu Val Leu Thr Glu Asp Gly Thr Lys Ala
            820             825             830
Leu Arg Leu Pro Val His Val Ala Pro Lys Pro Val Ser Thr Met His
        835             840             845
Ala Ala Glu Asp Thr Val Thr Phe Thr Gln Lys Pro Ser Ser Asp Glu
    850             855             860
Ala Gln Lys Ala Asp Thr Gly Trp Thr Lys Ser Gln Ile Ser Leu Arg
865             870             875             880
Gly Thr Glu Val Asn Gln Gly Gly Tyr Arg Ser Leu Leu Gly Ala Phe
                885             890             895
Glu Tyr Gly Ala Ser Val Asp Arg Val Ala Pro Thr Ser Leu Ser Leu
            900             905             910
Asn Ser Asn Val Lys Ala Asn Leu Gln Tyr Val Gly Ala Phe Ser Asp
        915             920             925
Ala Pro Ala Leu Lys Ala Ala Gly Gly Asn Ala Asp Asp Gly Thr Leu
    930             935             940
Arg Phe Gly Ile Ser Thr Trp Ala Asn Trp Asp Val Val Ser Tyr Glu
945             950             955             960
Asn Thr Phe Thr Val Glu Ile Asp Thr Asp Gly Asn Asn Arg Ala Asp
                965             970             975
Tyr Lys Leu Val Thr Asp Arg Ala Lys Gly Leu Asp Tyr Pro Leu Val
            980             985             990
Arg Leu Tyr Gly Tyr Lys Asn Gly Asn Leu Val Glu Leu Gly Tyr Tyr
        995             1000            1005
Pro Leu Asn Gly Ala Trp Gly Asp Val Asp Thr Asn Met Met Asp
    1010            1015            1020
Thr Asn Thr Leu Ile Met Ser Ala Pro Leu Lys Asp Leu Gly Leu
    1025            1030            1035
Thr Ser Ala Asn Asn Pro Asp Ile Gln Tyr Arg Val Ser Ala Thr
    1040            1045            1050
Thr Gln Tyr Glu Trp Gly Asn Val Ser Glu Thr Gly Trp Ile Lys
    1055            1060            1065
Tyr Arg Pro Phe Ser Pro Lys Leu Trp Phe Ser Gly Asp Ser Ser
    1070            1075            1080
Ala Val Ala Gly Leu His Pro Asp Ala Ser Thr Thr Thr Leu Thr
    1085            1090            1095
Ala His Arg Ser Ala Asp Ala Ile Pro Ala Leu Gly Glu Ser Gly
    1100            1105            1110
```

-continued

Thr Pro Ala Lys Ala Leu Leu His Leu His Asn Gly Thr Gly
1115                1120                1125

Asp Leu Ser Gly Thr Asn Gly Ala Lys Gly Asn Arg Ala Glu Val
    1130                1135                1140

Leu Asn Ile Lys Glu Gln Gln Thr Glu Tyr Ile Thr Pro Ser Arg
    1145                1150                1155

Phe Thr Asp Val Lys Asn Thr Asp Gln Phe Tyr Thr Glu Ile Ser
    1160                1165                1170

Trp Leu Ala Gln Arg Gly Ile Thr Thr Gly Tyr Pro Asp Gly Thr
    1175                1180                1185

Tyr Arg Pro Leu Glu Ser Val Glu Arg Gly Ala Met Ala Ala Phe
    1190                1195                1200

Phe Tyr Arg Met Gln Gly Ser Pro Gln Phe Thr Ala Pro Ser Thr
    1205                1210                1215

Pro Ser Phe Lys Asp Val Pro Thr Thr His Pro Phe Tyr Lys Glu
    1220                1225                1230

Ile Glu Trp Met Lys Ala Gln Gly Ile Thr Thr Gly Tyr Ser Asp
    1235                1240                1245

Gly Thr Phe Arg Pro Ser Ala Pro Val Asn Arg Asp Ala Met Ala
    1250                1255                1260

Ala Phe Phe Tyr Arg Ala Ala Gly Ser Pro His Val Asp Leu Pro
    1265                1270                1275

Ala Thr Ser His Phe Ser Asp Val Ser Thr Asp Asn Gln Phe Tyr
    1280                1285                1290

Arg Glu Ile Thr Trp Leu Ala Ser Lys Gly Ile Ser Thr Gly Trp
    1295                1300                1305

Pro Asp Gly Thr Tyr Arg Pro Val Thr Pro Ile Ala Arg Asp Ala
    1310                1315                1320

Met Ala Ala Phe Ile Tyr Arg Tyr Thr Glu Lys Val Ala Asn Gln
    1325                1330                1335

Ala Gly Arg
    1340

<210> SEQ ID NO 3
<211> LENGTH: 1346
<212> TYPE: PRT
<213> ORGANISM: Rothia mucilaginosa

<400> SEQUENCE: 3

Met Ala Thr Phe Pro Glu Ala Thr Pro Ala Arg Ala Ala Arg His Thr
1               5                   10                  15

Gln Pro Gly Arg Leu Lys Gln Leu Ala Arg Ser Cys Gly Ala Leu Thr
            20                  25                  30

Leu Gly Leu Thr Leu Gly Leu Thr Ala Leu Pro Phe Gly Thr Ala Ala
        35                  40                  45

Tyr Ala Ala Pro Gly Val Val Arg Gly Ala Asp Arg Asp Ala Pro His
    50                  55                  60

Gln Asn Thr Gly Thr Gly Glu Asn Asn Glu Val Leu Ser Pro Ser
65              70                  75                  80

Leu Asp Gly Ala Thr Gly Glu Arg Ala Val Phe Val Arg Phe Lys Gly
                85                  90                  95

Gln Gly Ala Tyr Ala Gln Thr Gln Pro Asp Ala Val Arg Ser Arg Ala
            100                 105                 110

Gln Ala Pro Val Asn Ala Gln Ala Gln Val Gln Ala Ile Arg Ala Ser

-continued

```
            115                 120                 125
Val Gln Gln Gln Gly Ala Ser Ala Ala Lys Glu Ser Gly Ala Gln Val
130                 135                 140

Leu Tyr Thr Thr His Asn Thr Met Arg Gly Val Ala Leu Tyr Gly Asn
145                 150                 155                 160

Val Glu Gln Ile Arg Ala Leu Ala Asn Arg Asp Asp Val Glu Arg Ile
                    165                 170                 175

Ser Ile Ile Glu Asp Met Ala Pro Gln Asn Ser Gly Thr Leu Ile Asp
                180                 185                 190

Thr Asp Thr Leu Ser Val Trp Ala Lys Ser Pro Ala Asn Pro Ala Ser
                    195                 200                 205

Thr Gly Tyr Thr Gly Lys Gly Val Lys Ile Val Leu Asp Thr Gly
210                 215                 220

Ile Asp Tyr Thr His Ala Asp Leu Gly Pro Gly Thr Gln Glu Ala
225                 230                 235                 240

Phe Asp Lys Ala Lys Ala Ser Asp Thr Ile Pro Glu Gly Thr Tyr Asp
                    245                 250                 255

Pro Lys Lys Phe Leu Gly Gly Tyr Asp Leu Val Gly Asp Tyr Asn
                260                 265                 270

Ser Gly Lys Lys Glu Thr Ser Thr Pro His Pro Asp Asn Pro Leu
                275                 280                 285

Asp Cys Gly Gly His Gly Ser His Val Ala Gly Thr Ala Ala Gly Tyr
290                 295                 300

Gly Val Asn Ala Asp Gly Ser Thr Phe His Gly Asp Tyr Ser Lys Leu
305                 310                 315                 320

Thr Glu Glu Gln Leu Lys Asp Met Lys Ile Gly Pro Gly Ser Ala Pro
                    325                 330                 335

Asp Ala Gln Leu Ile Gly Leu Arg Ile Phe Gly Cys Lys Gly Thr Thr
                    340                 345                 350

Ala Phe Val Pro Lys Gly Leu Asp Arg Val Leu Asp Pro Asn Asp Asp
                355                 360                 365

Gly Asp Phe Ser Asp Arg Ala Asp Ile Ala Asn Leu Ser Leu Gly Asn
370                 375                 380

Glu Phe Gly Val Phe Asp Glu Thr Val Asn Tyr Ala Val Gly Ser Leu
385                 390                 395                 400

Tyr Arg Glu Gly Ile Leu Ser Val Ala Ala Gly Asn Ala Asn Asn
                    405                 410                 415

Tyr Asn Ala Val Gly Asp Thr Tyr Ser Asn Ser Gly Pro Gly Thr
                420                 425                 430

Ser Ala Tyr Gly Leu Thr Val Ala Asn Ser Ile Gly Ser Thr Gln Leu
                435                 440                 445

Val Asp Arg Val Lys Ile Leu Ala Pro Ala Asn Glu Ala Asp Thr Tyr
                450                 455                 460

Gly Asp Tyr Ser Val Ser Phe Asp Tyr Ser Lys Ala Thr Glu Asp Gln
465                 470                 475                 480

Leu Arg Gly Thr Val Val Arg Ala Ala Ser Arg Asn Arg Tyr Ala Cys
                    485                 490                 495

Glu Ala Phe Thr Glu Glu Glu Ala Ala Ala Leu Lys Gly Lys Trp Ala
                500                 505                 510

Leu Ile Asp Trp Ala Asp Ala Asp Gly Thr Ala Pro Cys Gly Ser Lys
                515                 520                 525

Val Arg Phe Asp Asn Leu Gln Ala Ala Gly Ala Thr Gly Val Val Leu
530                 535                 540
```

-continued

```
Thr Ser Asn Thr Glu Val Gly Asp Thr Ala Ile Gly Asn Ser Ser
545                 550                 555                 560

Ile Pro Gly Val Arg Leu Ala Lys Ser Gln Val Glu Arg Leu Ser Val
            565                 570                 575

Gln Ile Asp Ser Gly Glu Leu Thr Leu Gln Leu Gly Glu Asn Leu Arg
            580                 585                 590

Asp Ser Ile Arg Val Pro Asn Gly Lys Leu Asp Gln Ala Asn Thr Ser
            595                 600                 605

Thr Ala Arg Gly Leu His Gly Ser His Gly Ile Thr Lys Pro Asp Val
610                 615                 620

Ala Ala Pro Gly Thr Asn Ile Ser Ser Ile Glu Val Gly Ser Gly Thr
625                 630                 635                 640

Gly Ser Ser Val Lys Thr Gly Thr Ser Met Ser Thr Pro Phe Val Ala
            645                 650                 655

Gly Val Ala Ala Leu Ile Met Gln Ala His Pro Glu Tyr Gly Pro Arg
            660                 665                 670

Met Leu Lys Thr Val Ile Met Asn Thr Ala Asp His His Met Gln Asp
            675                 680                 685

Ala Trp Gly Asn Pro Tyr Ala Val Asp Arg Val Gly Thr Gly Arg Ile
            690                 695                 700

Asn Thr Arg Ala Ala Val Ala Asp Arg Val Met Leu Phe Asn Ala Ala
705                 710                 715                 720

Arg Pro Glu Gln Val Ser Asp Thr Phe Gly Val Leu Glu Tyr Thr Pro
            725                 730                 735

Asn Ala Gly Val Gln Thr Leu Gln His Arg Val Ser Val Glu Asn Thr
            740                 745                 750

Asp Ser Val Ala His Thr Tyr Ala Leu Asn Tyr Glu Gly Ser Thr Ser
            755                 760                 765

Ile Pro Gly Val Glu Phe Ser Tyr Pro Gln Ser Val Ser Val Gly Ala
            770                 775                 780

Gly Gln Lys Ala Thr Phe Thr Val Thr Val Arg Ile Asp Pro Ser Lys
785                 790                 795                 800

Leu Glu Lys Thr Arg Asp Pro Ser Met Tyr Pro Asn Gln Asp Ser Val
            805                 810                 815

Asn Tyr Ser Thr Gly Thr Val Thr Ile Ser Gly Ala Arg Gln Tyr Ile
            820                 825                 830

Ala Ser Ala Ser Gly Arg Leu Ile Leu Thr Asp Ala Asp Ser Ser Ala
            835                 840                 845

Ala Val Lys Thr Leu Arg Met Pro Leu His Val Ala Pro Lys Pro Val
850                 855                 860

Ser Ala Met Arg Val Ala Gly Ser Asp Ile Ala Phe Asp Ala Glu Gly
865                 870                 875                 880

Ser Gly Ala Thr Glu Gln Thr Leu Thr Leu Gln Gly Thr Ala Val Asp
            885                 890                 895

Gln Gly Gly Tyr Arg Ser Leu Leu Gly Ala Phe Glu Leu Gly Ala Ser
            900                 905                 910

Ser Pro Arg Ile Pro Thr Ala Lys Leu Gly Val Gly Ser Asp Ser Arg
            915                 920                 925

Met Asp Leu Gln Tyr Val Gly Ala Ala Ser Asn Val Ala Ala Leu Lys
            930                 935                 940

Ala Ala Gly Ala Asp Thr Ser Glu Ala Arg Leu Ser Phe Gly Ile Ser
945                 950                 955                 960
```

```
Thr Trp Gly Asn Trp Gln Glu Val Thr Pro Arg Gly Thr Tyr Tyr Val
            965                 970                 975
Phe Val Asp Thr Asn Lys Asp Gly Thr Ser Asp Tyr Arg Leu Gln Thr
            980                 985                 990
Val Arg Glu Lys Gly Leu Asp Tyr Pro Leu Val Lys Val Ser Lys Arg
            995                 1000                1005
Ser Asn Gly Lys Trp Gln Ala Ile Glu Asn Ala Leu Tyr Pro Leu
            1010                1015                1020
Asn Gly Thr Trp Gly Asp Thr Asp Thr Asn Ile Met Asp Ser Asn
            1025                1030                1035
Thr Leu Val Met Thr Val Pro Leu Asn Val Leu Gly Leu Asp Pro
            1040                1045                1050
Asp Ala Glu Ser Thr Glu Ile Ser Tyr Ser Val Thr Thr Ser Ser
            1055                1060                1065
Ala Phe Ser Ala Thr Thr Val Val Asp Thr Thr Asp Ser Val Val
            1070                1075                1080
Phe Asn Tyr Ala Ala Pro Lys Leu Trp Phe Ser Gly Asp Ser Ala
            1085                1090                1095
Gly Val Pro Asn Leu Phe Val Asp Ala Pro Glu Thr Gln Leu Val
            1100                1105                1110
Ala His Arg Asn Gly Asp Ala Lys Asn Val Ser Ala Leu Phe Leu
            1115                1120                1125
His Met His Asn Ala Thr Gly Asp Leu Ser Gly Val Asn Gly Ala
            1130                1135                1140
Ala Gly Glu Arg Ala Gln Val Leu Arg Val Ser Ser Asn Ser Glu
            1145                1150                1155
Ala Thr Ala Ala Ser Ala His Phe Thr Asp Val Pro Ala Asp Tyr
            1160                1165                1170
Pro Phe Val Asn Asp Ile Asn Trp Leu Ala Gln Arg Arg Ile Thr
            1175                1180                1185
Thr Gly Tyr Pro Asp Gly Thr Phe Arg Pro Asn Gly Ser Val Glu
            1190                1195                1200
Arg Gly Ala Met Ala Ala Phe Tyr Arg Met Ala Gly Ser Pro
            1205                1210                1215
Gln Phe Thr Ala Pro Ser Thr Pro Ser Phe Lys Asp Val Pro Arg
            1220                1225                1230
Asp His Pro Phe Tyr Lys Glu Ile Glu Trp Met Arg Ala Arg Gly
            1235                1240                1245
Ile Thr Thr Gly Trp Ser Asp Gly Thr Phe Arg Pro Asn Ala Ala
            1250                1255                1260
Val Asn Arg Asp Ala Met Ala Ala Phe Phe Tyr Arg Phe Ala Gly
            1265                1270                1275
Ser Pro Ala Tyr Ser Ala Pro Ala Ala Ser Pro Phe Ser Asp Val
            1280                1285                1290
Ala Ala Gly Ser Gln Phe Tyr Arg Glu Ile Ser Trp Leu Ala Glu
            1295                1300                1305
Gln Arg Ile Thr Thr Gly Trp Ala Asp Gly Ser Phe Arg Pro Val
            1310                1315                1320
Gln Pro Ile Glu Arg Gly Ala Met Ala Ala Phe Leu His Arg Tyr
            1325                1330                1335
Asn Val Arg Val Leu Asn Asn Arg
            1340                1345
```

```
<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ala Pro Phe
1

<210> SEQ ID NO 5
<211> LENGTH: 33
<212> TYPE: PRT
<213> ORGANISM: Triticum aestivum

<400> SEQUENCE: 5

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 6
<211> LENGTH: 26
<212> TYPE: PRT
<213> ORGANISM: Triticum aestivum

<400> SEQUENCE: 6

Phe Leu Gln Pro Gln Gln Pro Phe Pro Gln Gln Pro Gln Gln Pro Tyr
1               5                   10                  15

Pro Gln Gln Pro Gln Gln Pro Phe Pro Gln
            20                  25

<210> SEQ ID NO 7
<211> LENGTH: 6
<212> TYPE: PRT
<213> ORGANISM: Unknown
<220> FEATURE:
<223> OTHER INFORMATION: Description of Unknown:
      toxic gluten oligopeptide

<400> SEQUENCE: 7

Pro Gln Pro Gln Leu Pro
1               5

<210> SEQ ID NO 8
<211> LENGTH: 12
<212> TYPE: PRT
<213> ORGANISM: Unknown
<220> FEATURE:
<223> OTHER INFORMATION: Description of Unknown:
      toxic gluten oligopeptide

<400> SEQUENCE: 8

Gln Leu Gln Pro Phe Pro Gln Pro Gln Leu Pro Tyr
1               5                   10

<210> SEQ ID NO 9
<211> LENGTH: 9
<212> TYPE: PRT
<213> ORGANISM: Unknown
<220> FEATURE:
<223> OTHER INFORMATION: Description of Unknown:
      toxic gluten oligopeptide
```

```
<400> SEQUENCE: 9

Pro Phe Pro Gln Pro Gln Leu Pro Tyr
1               5

<210> SEQ ID NO 10
<211> LENGTH: 14
<212> TYPE: PRT
<213> ORGANISM: Unknown
<220> FEATURE:
<223> OTHER INFORMATION: Description of Unknown:
      toxic gluten oligopeptide

<400> SEQUENCE: 10

Pro Gln Pro Gln Leu Pro Tyr Pro Gln Pro Gln Leu Pro Tyr
1               5                   10

<210> SEQ ID NO 11
<211> LENGTH: 9
<212> TYPE: PRT
<213> ORGANISM: Unknown
<220> FEATURE:
<223> OTHER INFORMATION: Description of Unknown:
      toxic gluten oligopeptide

<400> SEQUENCE: 11

Pro Gln Pro Gln Leu Pro Tyr Pro Gln
1               5

<210> SEQ ID NO 12
<211> LENGTH: 10
<212> TYPE: PRT
<213> ORGANISM: Unknown
<220> FEATURE:
<223> OTHER INFORMATION: Description of Unknown:
      toxic gluten oligopeptide

<400> SEQUENCE: 12

Gln Pro Gln Gln Ser Phe Pro Gln Gln Gln
1               5                   10

<210> SEQ ID NO 13
<211> LENGTH: 9
<212> TYPE: PRT
<213> ORGANISM: Unknown
<220> FEATURE:
<223> OTHER INFORMATION: Description of Unknown:
      toxic gluten oligopeptide

<400> SEQUENCE: 13

Pro Gln Gln Ser Phe Pro Gln Gln Gln
1               5

<210> SEQ ID NO 14
<211> LENGTH: 12
<212> TYPE: PRT
<213> ORGANISM: Unknown
<220> FEATURE:
<223> OTHER INFORMATION: Description of Unknown:
      toxic gluten oligopeptide

<400> SEQUENCE: 14

Gln Leu Gln Pro Phe Pro Gln Pro Glu Leu Pro Tyr
1               5                   10

<210> SEQ ID NO 15
<211> LENGTH: 14
```

```
<212> TYPE: PRT
<213> ORGANISM: Unknown
<220> FEATURE:
<223> OTHER INFORMATION: Description of Unknown:
      toxic gluten oligopeptide

<400> SEQUENCE: 15

Pro Gln Pro Glu Leu Pro Tyr Pro Gln Pro Glu Leu Pro Tyr
1               5                   10

<210> SEQ ID NO 16
<211> LENGTH: 10
<212> TYPE: PRT
<213> ORGANISM: Unknown
<220> FEATURE:
<223> OTHER INFORMATION: Description of Unknown:
      toxic gluten oligopeptide

<400> SEQUENCE: 16

Gln Pro Gln Gln Ser Phe Pro Glu Gln Gln
1               5                   10

<210> SEQ ID NO 17
<211> LENGTH: 9
<212> TYPE: PRT
<213> ORGANISM: Unknown
<220> FEATURE:
<223> OTHER INFORMATION: Description of Unknown:
      toxic gluten oligopeptide

<400> SEQUENCE: 17

Ile Gln Pro Gln Gln Pro Ala Gln Leu
1               5

<210> SEQ ID NO 18
<211> LENGTH: 9
<212> TYPE: PRT
<213> ORGANISM: Unknown
<220> FEATURE:
<223> OTHER INFORMATION: Description of Unknown:
      toxic gluten oligopeptide

<400> SEQUENCE: 18

Gln Gln Pro Gln Gln Pro Tyr Pro Gln
1               5

<210> SEQ ID NO 19
<211> LENGTH: 9
<212> TYPE: PRT
<213> ORGANISM: Unknown
<220> FEATURE:
<223> OTHER INFORMATION: Description of Unknown:
      toxic gluten oligopeptide

<400> SEQUENCE: 19

Ser Gln Pro Gln Gln Gln Phe Pro Gln
1               5

<210> SEQ ID NO 20
<211> LENGTH: 9
<212> TYPE: PRT
<213> ORGANISM: Unknown
<220> FEATURE:
<223> OTHER INFORMATION: Description of Unknown:
      toxic gluten oligopeptide

<400> SEQUENCE: 20

Gln Gln Pro Phe Pro Gln Gln Pro Gln
```

```
1               5

<210> SEQ ID NO 21
<211> LENGTH: 9
<212> TYPE: PRT
<213> ORGANISM: Unknown
<220> FEATURE:
<223> OTHER INFORMATION: Description of Unknown:
      toxic gluten oligopeptide

<400> SEQUENCE: 21

Pro Phe Ser Gln Gln Gln Gln Pro Val
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Pro Gln Leu Pro Tyr
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Gln Pro Gln Pro Gln
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gly Ser Phe Gln Pro
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Gln Pro Gln Leu Pro Tyr
1               5

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                    peptide
<220> FEATURE:
<221> NAME/KEY: MOD_RES
<222> LOCATION: (3)..(3)
<223> OTHER INFORMATION: Ile or Val
<220> FEATURE:
<221> NAME/KEY: MOD_RES
<222> LOCATION: (6)..(6)
<223> OTHER INFORMATION: Ile, Val or Leu
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (10)..(10)
<223> OTHER INFORMATION: Ile or Val
<220> FEATURE:
<221> NAME/KEY: MOD_RES
<222> LOCATION: (11)..(11)
<223> OTHER INFORMATION: Asp or Gln

<400> SEQUENCE: 26

Val Lys Xaa Ala Val Xaa Asp Xaa Gly Xaa Xaa
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ser

<400> SEQUENCE: 27

Xaa His Gly Thr His Val Ala Gly Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala or Ser

<400> SEQUENCE: 28

Gly Thr Ser Met Xaa
1               5

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly or Asp
<220> FEATURE:
<221> NAME/KEY: MOD_RES
<222> LOCATION: (5)..(5)
<223> OTHER INFORMATION: Ile or Val
```

```
<220> FEATURE:
<221> NAME/KEY: MOD_RES
<222> LOCATION: (8)..(8)
<223> OTHER INFORMATION: Ile, Val or Leu
<220> FEATURE:
<221> NAME/KEY: MOD_RES
<222> LOCATION: (10)..(10)
<223> OTHER INFORMATION: Ser or Thr
<220> FEATURE:
<221> NAME/KEY: MOD_RES
<222> LOCATION: (12)..(12)
<223> OTHER INFORMATION: Ile or Val
<220> FEATURE:
<221> NAME/KEY: MOD_RES
<222> LOCATION: (13)..(13)
<223> OTHER INFORMATION: Asp or Gln

<400> SEQUENCE: 29

Lys Xaa Val Lys Xaa Ala Val Xaa Asp Xaa Gly Xaa Xaa
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ile or Val
<220> FEATURE:
<221> NAME/KEY: MOD_RES
<222> LOCATION: (6)..(6)
<223> OTHER INFORMATION: Ile, Val or Leu
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (10)..(10)
<223> OTHER INFORMATION: Ile or Val
<220> FEATURE:
<221> NAME/KEY: MOD_RES
<222> LOCATION: (11)..(11)
<223> OTHER INFORMATION: Asp or Gln

<400> SEQUENCE: 30

Val Lys Xaa Ala Val Xaa Asp Xaa Gly Xaa Xaa Tyr Thr His
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ser

<400> SEQUENCE: 31

Xaa His Gly Thr His Val Ala Gly Thr Ala Ala Gly Tyr Gly Val
1               5                   10                  15

<210> SEQ ID NO 32
<211> LENGTH: 6
<212> TYPE: PRT
<213> ORGANISM: Artificial Sequence
```

<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (6)..(6)
<223> OTHER INFORMATION: Ala or Ser

<400> SEQUENCE: 32

```
Xaa Gly Thr Ser Met Xaa
1               5
```

<210> SEQ ID NO 33
<211> LENGTH: 1311
<212> TYPE: PRT
<213> ORGANISM: Rothia dentocariosa

<400> SEQUENCE: 33

```
Met Pro Lys Asn Thr Pro Ile Arg Gly Leu Ser Arg Ala Cys Leu Ser
1               5                   10                  15

Ala Thr Leu Gly Val Thr Met Ala Ile Thr Ala Gly Leu Pro Ala Thr
            20                  25                  30

Ala Ala Pro Ala Gly Asp Pro Asp Thr Pro Val Ala Gln Asp Ile Ala
        35                  40                  45

Arg Asn Ser Arg Glu His Ala Val Leu Ser Asp Ser Met Lys Lys Ala
    50                  55                  60

Glu Gly Asn Ile Pro Val Phe Val Gln Phe Lys Gly Lys Gly Ala Tyr
65                  70                  75                  80

Glu Gln Thr Gln Ser Pro Ala Val Leu Ala Asn Lys Gln Ala Pro Ile
                85                  90                  95

Asn Lys Gln Ala Glu Val Gln Ala Ile Lys Thr Gln Val Gln Ser Gln
            100                 105                 110

Ala Gln Ala Ala Ala Gln Ser Thr Gly Ala Lys Thr Leu Tyr Thr Thr
        115                 120                 125

His Asn Ile Met Arg Gly Val Ala Leu Gln Gly Asp Ala Ala Gln Ile
    130                 135                 140

Arg Ala Leu Ala Asn Asn Pro Glu Val Glu Arg Ile Thr Pro Ile Val
145                 150                 155                 160

Pro Lys Lys Lys Gln Asn Ala Gly Ser Val Val Asp Thr Gly Ala Ala
                165                 170                 175

Glu Asn Trp Ala Arg Glu Asn Ser Gly Tyr Thr Gly Lys Asp Val Lys
            180                 185                 190

Ile Ala Val Val Asp Ser Gly Ile Asp Tyr Thr His Ser Asp Phe Gly
        195                 200                 205

Gly Pro Gly Thr Val Glu Ala Phe Asn Lys Ala Thr Lys Leu Thr Glu
    210                 215                 220

Met Pro Ala Ala Asp Ser Gly Leu Tyr Asp Ala Lys Lys Tyr Ile Gly
225                 230                 235                 240

Gly Tyr Asp Leu Val Gly Asp Ser Tyr Asp Gly Thr Asn Gln Thr Thr
                245                 250                 255

Pro Asp Asn Asn Pro Ile Asp Cys Ser Ala Gly Gly His Gly Thr His
            260                 265                 270

Val Ala Gly Thr Ala Ala Gly Tyr Gly Val Asn Gln Asp Gly Thr Thr
        275                 280                 285
```

```
Phe Arg Gly Asp Tyr Ser Lys Leu Thr Ala Glu Gln Leu Asn Gln Met
    290                 295                 300

Lys Ile Gly Pro Gly Ala Ala Pro Glu Ala Gln Leu Tyr Ser Phe Arg
305                 310                 315                 320

Val Phe Gly Cys Thr Gly Thr Thr Ala Val Val Gln Ala Leu Asp
                325                 330                 335

Arg Thr Leu Asp Pro Asn Gly Asp Gly Asp Phe Ser Asp Arg Ala Asn
            340                 345                 350

Ile Val Asn Leu Ser Ile Gly Gly Glu Phe Ser Pro Pro Asp Asp Ala
                355                 360                 365

Asp Ala Tyr Ala Val Glu Ser Leu Asn Arg Gln Gly Val Leu Ala Val
    370                 375                 380

Val Ser Ala Gly Asn Ala Thr Asp Tyr Gly Arg Gly Asp Thr Tyr
385                 390                 395                 400

Ser Asp Ser Gly Gln Pro Ala Asn Ala Val Ser Ala Leu Thr Val Ala
                405                 410                 415

Asn Ser Ile Gly Ser Ser Tyr Ala Val Asp Ser Met Glu Ile Gln Ala
                420                 425                 430

Pro Ala Asn Val Ala Gly Lys Val Pro Gly Asp Tyr Thr Val Ser Tyr
    435                 440                 445

Thr Tyr Thr Gly Ala Lys Pro Glu Ala Leu Thr Gly Thr Val Val Thr
    450                 455                 460

Pro Ser Glu Ser Asn Lys Phe Gly Cys Glu Ala Phe Ser Ala Glu Asp
465                 470                 475                 480

Ala Ala Lys Ile Lys Asp Lys Trp Val Phe Ile Glu Trp Ala Asn Ala
                485                 490                 495

Asp Gly Ser Leu Pro Cys Gly Ser Lys Val Arg Phe Asp Asn Val Glu
            500                 505                 510

Lys Ala Gly Gly Lys Gly Val Val Leu Ser Ser Glu Glu Lys Pro
    515                 520                 525

Ala Leu Pro Ile Gly Gly Asn Glu Ser Ile Pro Gly Phe Arg Val Ala
    530                 535                 540

Lys Ser Ala Ser Ala Lys Val Arg Glu Ala Ala Thr Gly Glu Leu
545                 550                 555                 560

Lys Val Arg Leu Gly Ala Asp Leu Lys Glu Ser Leu Arg Val Pro Ser
            565                 570                 575

Asn Lys Lys Asp Gln Leu Thr Ala Ser Ser Ala Arg Gly Tyr His Gly
        580                 585                 590

Thr Tyr Gly Tyr Thr Lys Pro Asp Val Ala Ala Pro Gly Asn Asn Ile
    595                 600                 605

Ser Ser Ala Arg Val Gly Thr Gly Thr Gly Ile Ser Tyr Thr Gly
    610                 615                 620

Thr Ser Met Ser Ala Pro Phe Ala Ala Gly Val Ala Ala Gln Val Leu
625                 630                 635                 640

Gln Ala Asn Gln Ser Tyr Gly Pro Thr Gln Leu Lys Ala Ala Ile Met
                645                 650                 655

Asn Ser Ala Asn His Asp Val Arg Thr Ala Asp Gly Asn Val Tyr Ala
                660                 665                 670

Val Asp Arg Val Gly Ser Gly Arg Ile Asp Ala Lys Ala Ala Glu
            675                 680                 685

Thr Lys Val Leu Leu Tyr Asn Ala Asp Arg Pro Ala Gln Val Ser Gln
    690                 695                 700

Thr Phe Gly Val Leu Glu Tyr Ala Val Asn Glu Gly Lys Gln Thr Leu
```

```
            705                 710                 715                 720
        Thr Arg Glu Met Thr Val Glu Asn Phe Asp Ser His Thr His Thr Tyr
                        725                 730                 735
        Asn Ile Ser Tyr Ala Gly Ser Thr Asp Met Pro Gly Val Glu Phe Ser
                        740                 745                 750
        Leu Pro Ser Asn Ile Thr Val Asn Pro Gly Glu Lys Asn Phe Thr
                        755                 760                 765
        Val Thr Ile Thr Ile Asp Pro Ala Ala Met Glu Lys Thr Met Asp Pro
                770                 775                 780
        Ala Met Glu Lys Thr His Asn Ser Val Asp Pro Tyr Gly Asp Gly Thr
        785                 790                 795                 800
        Glu Leu Val Pro Glu Gln Tyr Arg Gln Phe Ile Ala Ser Glu Ser Gly
                        805                 810                 815
        Arg Ile Leu Leu Thr Glu Gly Ala Ala Thr Leu Arg Ala Pro Ile His
                        820                 825                 830
        Ala Ala Pro Lys Pro Ala Ser Ala Met Lys Val Glu Gly Ser Ser Val
                        835                 840                 845
        Glu Ile Pro Ala Gly Glu His Gln Ala Asn Leu Lys Leu Thr Gly Thr
                850                 855                 860
        Glu Leu Asn Gln Arg Gly Tyr Lys Ser Leu Leu Gly Ala Phe Glu His
        865                 870                 875                 880
        Gly Ala Ser Ile Glu Arg Thr Ser Pro Val Lys Leu Asp Val Ser Ser
                        885                 890                 895
        Asn Ala Lys Ala Asn Met Gln His Val Gly Ala Ala Ser Thr Ala Pro
                        900                 905                 910
        Ala Leu Lys Ala Ser Gly Gly Asn Pro Asn Asp Gly Leu Leu Ala Phe
                        915                 920                 925
        Gly Ile Ser Thr Trp Ala Asn Trp Asp Val Val Ser Thr Glu Asn Thr
                        930                 935                 940
        Phe Thr Val Asn Ile Asp Thr Asp Gly Asn Asn Arg Ala Asp Tyr Met
        945                 950                 955                 960
        Leu Val Thr Asp Arg Ala Lys Gly Ile Asp Phe Pro Ile Val Arg Leu
                        965                 970                 975
        Tyr Gly Tyr Lys Asn Gly Asn Leu Glu Gln Ile Ala Tyr Tyr Pro Leu
                        980                 985                 990
        Asn Asn Ala Trp Gly Asp Thr Asp  Thr Asn Met Met Asp  Ser Asn Ala
                        995                 1000                1005
        Leu Val  Met Ala Val Pro Leu  Lys Asp Leu Gly Leu  Ser Ala Glu
                        1010                1015                1020
        Lys Thr  Lys Asp Ile Lys Tyr  Ser Val Ser Ala Thr  Thr Gln Tyr
                        1025                1030                1035
        Ala Trp  Thr Asn Val Ser Glu  Thr Gly Trp Ile Asn  Tyr Arg Pro
                        1040                1045                1050
        Phe Asp  Pro Lys Leu Trp Phe  Ser Gly Thr Ala Ala  Thr Val Pro
                        1055                1060                1065
        Gly Phe  Phe Ala Asp Ala Pro  Ser Ser Glu Leu Val  Ala His Arg
                        1070                1075                1080
        Ala Glu  Gly Ala Thr Asp Val  Lys Ala Leu Phe Leu  His Met His
                        1085                1090                1095
        Asn Thr  Thr Gly Asp Leu Ser  Gly Leu Asn Gly Ala  Ala Gly Asn
                        1100                1105                1110
        Arg Ala  Gln Val Leu Glu Val  Thr Glu Gln Gln Gln  Leu Asp Pro
                        1115                1120                1125
```

Ala Pro Ser Arg Phe Thr Asp Val Pro Ala Glu Asn Gln Phe Tyr
    1130                1135                1140

Ala Glu Ile Asn Trp Leu Ala Gln Arg Arg Ile Thr Thr Gly Tyr
    1145                1150                1155

Pro Asp Gly Thr Phe Arg Pro Gly Glu Asn Val Glu Arg Gly Ala
    1160                1165                1170

Met Ala Ala Tyr Phe Tyr Arg Leu Ala Gly Thr Pro Gln Phe Thr
    1175                1180                1185

Ala Pro Asp Asn Pro Thr Phe Ser Asp Val Pro Lys Ser His Pro
    1190                1195                1200

Phe Tyr Lys Glu Ile Glu Trp Met Ala Ala Arg Gly Ile Thr Thr
    1205                1210                1215

Gly Tyr Gly Asp Gly Thr Phe Arg Pro Ser Asp Ser Val Asn Arg
    1220                1225                1230

Asp Ala Met Ala Ala Phe Tyr Arg Tyr Ala Asn Ser Pro Gln
    1235                1240                1245

Phe Ala Ala Pro Ala Ala Ser Pro Phe Lys Asp Val Pro Ala Asn
    1250                1255                1260

Ser Gln Phe Tyr Lys Glu Ile Ala Trp Leu Ala Glu Gln Gly Ile
    1265                1270                1275

Thr Lys Gly Trp Asp Asp Gly Thr Tyr Arg Pro Gly Glu Pro Ile
    1280                1285                1290

His Arg Asp Ala Met Ala Ala Phe Leu Tyr Arg Tyr Ser Asp Lys
    1295                1300                1305

Val Leu Lys
    1310

<210> SEQ ID NO 34
<211> LENGTH: 1289
<212> TYPE: PRT
<213> ORGANISM: Rothia aeria

<400> SEQUENCE: 34

Met Ala Ile Thr Ala Gly Leu Pro Ala Thr Ala Pro Ala Gly Asp
1               5                   10                  15

Pro Asp Thr Pro Val Ala Gln Asp Ile Ala Arg Asn Ser Arg Glu His
            20                  25                  30

Ala Val Leu Ser Asp Ser Met Lys Ala Glu Gly Asn Ile Pro Val
            35                  40                  45

Phe Val Gln Phe Lys Gly Lys Gly Ala Tyr Gln Thr Gln Ser Pro
    50                  55                  60

Ala Val Leu Ala Asn Lys Gln Ala Pro Thr Asn Lys Gln Ala Glu Val
65                  70                  75                  80

Gln Ala Ile Lys Thr Gln Val Gln Ser Gln Ala Gln Ala Ala Gln
                85                  90                  95

Ser Thr Gly Ala Lys Thr Leu Tyr Thr Thr His Asn Ile Met Arg Gly
                100                 105                 110

Val Ala Leu Gln Gly Asp Ala Ala Gln Ile Arg Ala Leu Ala Asn Asn
            115                 120                 125

Pro Glu Val Glu Arg Ile Thr Pro Ile Val Pro Lys Lys Gln Asn
    130                 135                 140

Ala Gly Ser Val Val Asp Thr Gly Ala Ala Glu Asn Trp Ala Arg Glu
145                 150                 155                 160

Asn Ser Gly Tyr Thr Gly Lys Asp Val Lys Ile Ala Val Val Asp Ser

```
                165                 170                 175
Gly Ile Asp Tyr Thr His Ala Asp Phe Gly Gly Pro Gly Thr Val Glu
                180                 185                 190
Ala Phe Asn Lys Ala Thr Lys Leu Thr Glu Met Pro Ala Ala Asp Ser
                195                 200                 205
Gly Leu Tyr Asp Ala Lys Lys Tyr Ile Gly Gly Tyr Asp Leu Val Gly
                210                 215                 220
Asp Ser Tyr Asp Gly Thr Asn Gln Thr Ala Pro Asp Asn Asn Pro Ile
225                 230                 235                 240
Asp Cys Ser Ala Gly His Gly Thr His Val Ala Gly Thr Ala Ala
                    245                 250                 255
Gly Tyr Gly Val Asn Gln Asp Gly Thr Thr Phe Arg Gly Asp Tyr Ser
                260                 265                 270
Lys Leu Thr Ala Glu Gln Leu Asn Gln Met Lys Ile Gly Pro Gly Ala
                275                 280                 285
Ala Pro Glu Ala Gln Leu Tyr Ser Phe Arg Val Phe Gly Cys Thr Gly
                290                 295                 300
Thr Thr Gly Val Val Gln Ala Leu Asp Arg Thr Leu Asp Pro Asn
305                 310                 315                 320
Gly Asp Gly Asp Phe Ser Asp Arg Ala Asn Ile Val Asn Leu Ser Ile
                    325                 330                 335
Gly Gly Glu Phe Ser Pro Pro Asp Asp Ala Asp Ala Tyr Ala Val Glu
                340                 345                 350
Ser Leu Asn Arg Gln Gly Val Leu Ala Val Val Ser Ala Gly Asn Ala
                355                 360                 365
Thr Asp Tyr Tyr Gly Arg Gly Asp Thr Tyr Ser Asp Ser Gly Gln Pro
                370                 375                 380
Ala Asn Ala Val Ser Ala Leu Thr Val Ala Asn Ser Ile Gly Ser Ser
385                 390                 395                 400
Tyr Ala Val Asp Ser Met Glu Ile Gln Ala Pro Ala Asn Val Ala Gly
                    405                 410                 415
Lys Val Pro Gly Asp Tyr Thr Val Ser Tyr Thr Tyr Thr Gly Ala Lys
                420                 425                 430
Pro Glu Ala Leu Thr Gly Thr Val Val Thr Pro Ser Glu Ser Asn Lys
                435                 440                 445
Phe Gly Cys Glu Ala Phe Ser Ala Glu Asp Ala Ala Lys Ile Lys Asp
                450                 455                 460
Lys Trp Val Phe Leu Glu Trp Ala Asn Ala Asp Gly Ser Leu Pro Cys
465                 470                 475                 480
Gly Ser Lys Val Arg Phe Asp Asn Val Glu Lys Ala Gly Lys Gly
                    485                 490                 495
Val Val Leu Ser Ser Glu Glu Lys Pro Ala Leu Pro Ile Gly Gly
                500                 505                 510
Asn Glu Ser Ile Pro Gly Phe Arg Val Ala Lys Ser Ala Ser Ala Lys
                515                 520                 525
Val Arg Glu Ala Ala Ala Asn Gly Glu Leu Lys Val Arg Leu Gly Thr
                530                 535                 540
Asp Leu Lys Glu Ser Leu Arg Val Pro Ser Asn Lys Lys Asp Gln Leu
545                 550                 555                 560
Thr Ala Ser Ser Ala Arg Gly Tyr His Gly Thr Tyr Gly Tyr Thr Lys
                    565                 570                 575
Pro Asp Val Ala Ala Pro Gly Asn Asn Ile Ser Ser Ala Arg Val Gly
                580                 585                 590
```

```
Thr Gly Thr Asp Gly Ile Ser Tyr Thr Gly Thr Ser Met Ser Ala Pro
        595                 600                 605

Phe Ala Ala Gly Val Ala Ala Gln Val Leu Gln Ala Asn Gln Ser Tyr
    610                 615                 620

Gly Pro Thr Gln Leu Lys Ala Ala Ile Met Asn Ser Ala Asn His Asp
625                 630                 635                 640

Val Arg Thr Ala Asp Gly Asn Val Tyr Ala Val Asp Arg Val Gly Ser
                645                 650                 655

Gly Arg Ile Asp Ala Lys Ala Ala Ala Glu Thr Lys Val Leu Leu Tyr
                660                 665                 670

Asn Ala Asp Arg Pro Ala Gln Val Ser Gln Thr Phe Gly Val Leu Glu
                675                 680                 685

Tyr Ala Val Asn Glu Gly Lys Gln Thr Leu Thr Arg Glu Met Thr Val
        690                 695                 700

Glu Asn Phe Asp Ser His Thr His Thr Tyr Asn Ile Ser Tyr Ala Gly
705                 710                 715                 720

Ser Thr Asp Met Pro Gly Val Glu Phe Ser Leu Pro Ser Asn Ile Thr
                725                 730                 735

Val Asn Pro Gly Glu Lys Lys Asn Phe Thr Val Thr Ile Thr Ile Asp
                740                 745                 750

Pro Ala Ala Met Glu Lys Thr Met Asp Pro Ala Met Glu Lys Thr His
                755                 760                 765

Asn Ser Val Asp Pro Tyr Gly Asp Gly Thr Glu Leu Val Pro Glu Gln
        770                 775                 780

Tyr Arg Gln Phe Ile Ala Ser Glu Ser Gly Arg Ile Leu Leu Thr Glu
785                 790                 795                 800

Gly Ala Ala Thr Leu Arg Ala Pro Ile His Ala Ala Pro Lys Pro Ala
                805                 810                 815

Ser Ala Met Lys Val Glu Gly Ser Ser Val Glu Ile Pro Ala Gly Glu
                820                 825                 830

His Gln Ala Asn Leu Lys Leu Thr Gly Thr Glu Leu Asn Gln Arg Gly
        835                 840                 845

Tyr Lys Ser Leu Leu Gly Ala Phe Glu His Gly Ala Ser Ile Glu Arg
    850                 855                 860

Thr Ser Pro Val Lys Leu Asp Val Ser Ser Asn Ala Lys Ala Asn Met
865                 870                 875                 880

Gln His Val Gly Ala Ser Thr Ala Pro Ala Leu Lys Ala Ser Gly
                885                 890                 895

Gly Asn Pro Asn Asp Gly Leu Leu Ala Phe Gly Ile Ser Thr Trp Ala
                900                 905                 910

Asn Trp Asp Val Val Ser Thr Glu Asn Thr Phe Thr Val Asn Ile Asp
                915                 920                 925

Thr Asp Gly Asn Asn Arg Ala Asp Tyr Met Leu Val Thr Asp Arg Ala
        930                 935                 940

Lys Gly Ile Asp Phe Pro Ile Val Arg Leu Tyr Gly Tyr Lys Asn Gly
945                 950                 955                 960

Asn Leu Glu Gln Ile Ala Tyr Tyr Pro Leu Asn Asn Ala Trp Gly Asp
                965                 970                 975

Thr Asp Thr Asn Met Met Asp Ser Asn Ala Leu Val Met Ala Val Pro
                980                 985                 990

Leu Lys Asp Leu Gly Leu Ser Ala Glu Lys Thr Lys Asp Ile Lys Tyr
        995                 1000                1005
```

```
Ser Val Ser Ala Thr Thr Gln Tyr Ala Trp Thr Asn Val Ser Glu
   1010                1015                1020

Thr Gly Trp Ile Asn Tyr Arg Pro Phe Asp Pro Lys Leu Trp Phe
   1025                1030                1035

Ser Gly Thr Ala Ala Thr Val Pro Gly Phe Phe Ala Asp Ala Pro
   1040                1045                1050

Ser Ser Glu Leu Val Ala His Arg Ala Glu Gly Ala Thr Asp Val
   1055                1060                1065

Lys Ala Leu Phe Leu His Met His Asn Thr Thr Gly Asp Leu Ser
   1070                1075                1080

Gly Leu Asn Gly Ala Ala Gly Asn Arg Ala Gln Val Leu Glu Val
   1085                1090                1095

Thr Glu Gln Gln Gln Leu Asp Pro Ala Pro Ser Arg Phe Thr Asp
   1100                1105                1110

Val Pro Ala Glu Asn Gln Phe Tyr Ala Glu Ile Asn Trp Leu Ala
   1115                1120                1125

Gln Arg Arg Ile Thr Thr Gly Tyr Pro Asp Gly Thr Phe Arg Pro
   1130                1135                1140

Gly Glu Asn Val Glu Arg Gly Ala Met Ala Ala Tyr Phe Tyr Arg
   1145                1150                1155

Leu Ala Gly Thr Pro Gln Phe Thr Ala Pro Asp Asn Pro Thr Phe
   1160                1165                1170

Ser Asp Val Pro Lys Ser His Pro Phe Tyr Lys Glu Ile Glu Trp
   1175                1180                1185

Met Ala Ala Arg Gly Ile Thr Thr Gly Tyr Gly Asp Gly Thr Phe
   1190                1195                1200

Arg Pro Ser Ala Ser Val Asn Arg Asp Ala Met Ala Ala Phe Phe
   1205                1210                1215

Tyr Arg Tyr Ala Asn Ser Pro Gln Phe Ala Ala Pro Ala Ala Ser
   1220                1225                1230

Pro Phe Lys Asp Val Pro Ala Asn Ser Gln Phe Tyr Lys Glu Ile
   1235                1240                1245

Ala Trp Leu Ala Glu Gln Gly Ile Thr Lys Gly Trp Asp Asp Gly
   1250                1255                1260

Thr Tyr Arg Pro Gly Glu Pro Ile His Arg Asp Ala Met Ala Ala
   1265                1270                1275

Phe Leu Tyr Arg Tyr Ser Asp Lys Val Leu Lys
   1280                1285

<210> SEQ ID NO 35
<211> LENGTH: 379
<212> TYPE: PRT
<213> ORGANISM: Bacillus licheniformis

<400> SEQUENCE: 35

Met Met Arg Lys Lys Ser Phe Trp Leu Gly Met Leu Thr Ala Phe Met
 1               5                  10                  15

Leu Val Phe Thr Met Ala Phe Ser Asp Ser Ala Ser Ala Ala Gln Pro
                20                  25                  30

Ala Lys Asn Val Glu Lys Asp Tyr Ile Val Gly Phe Lys Ser Gly Val
            35                  40                  45

Lys Thr Ala Ser Val Lys Lys Asp Ile Ile Lys Glu Ser Gly Gly Lys
        50                  55                  60

Val Asp Lys Gln Phe Arg Ile Ile Asn Ala Ala Lys Ala Lys Leu Asp
65                  70                  75                  80
```

```
Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Thr Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Pro Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Ser Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Gln
    370                 375

<210> SEQ ID NO 36
<211> LENGTH: 381
<212> TYPE: PRT
<213> ORGANISM: Bacillus subtilis

<400> SEQUENCE: 36

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Ser Ser Thr Glu Lys Lys Tyr Ile Val Gly Phe Lys Gln Thr Met Ser
        35                  40                  45

Ala Met Ser Ser Ala Lys Lys Lys Asp Val Ile Ser Glu Lys Gly Gly
    50                  55                  60

Lys Val Gln Lys Gln Phe Lys Tyr Val Asn Ala Ala Ala Ala Thr Leu
```

```
            65                  70                  75                  80
Asp Glu Lys Ala Val Lys Glu Leu Lys Lys Asp Pro Ser Val Ala Tyr
                    85                  90                  95

Val Glu Glu Asp His Ile Ala His Glu Tyr Ala Gln Ser Val Pro Tyr
                    100                 105                 110

Gly Ile Ser Gln Ile Lys Ala Pro Ala Leu His Ser Gln Gly Tyr Thr
                    115                 120                 125

Gly Ser Asn Val Lys Val Ala Val Ile Asp Ser Gly Ile Asp Ser Ser
                    130                 135                 140

His Pro Asp Leu Asn Val Arg Gly Gly Ala Ser Phe Val Pro Ser Glu
145                 150                 155                 160

Thr Asn Pro Tyr Gln Asp Gly Ser Ser His Gly Thr His Val Ala Gly
                    165                 170                 175

Thr Ile Ala Ala Leu Asn Asn Ser Ile Gly Val Leu Gly Val Ala Pro
                    180                 185                 190

Ser Ala Ser Leu Tyr Ala Val Lys Val Leu Asp Ser Thr Gly Ser Gly
                    195                 200                 205

Gln Tyr Ser Trp Ile Ile Asn Gly Ile Glu Trp Ala Ile Ser Asn Asn
                    210                 215                 220

Met Asp Val Ile Asn Met Ser Leu Gly Gly Pro Thr Gly Ser Thr Ala
225                 230                 235                 240

Leu Lys Thr Val Val Asp Lys Ala Val Ser Ser Gly Ile Val Val Ala
                    245                 250                 255

Ala Ala Ala Gly Asn Glu Gly Ser Ser Gly Ser Thr Ser Thr Val Gly
                    260                 265                 270

Tyr Pro Ala Lys Tyr Pro Ser Thr Ile Ala Val Gly Ala Val Asn Ser
                    275                 280                 285

Ser Asn Gln Arg Ala Ser Phe Ser Ser Val Gly Ser Glu Leu Asp Val
                    290                 295                 300

Met Ala Pro Gly Val Ser Ile Gln Ser Thr Leu Pro Gly Gly Thr Tyr
305                 310                 315                 320

Gly Ala Tyr Asn Gly Thr Ser Met Ala Thr Pro His Val Ala Gly Ala
                    325                 330                 335

Ala Ala Leu Ile Leu Ser Lys His Pro Thr Trp Thr Asn Ala Gln Val
                    340                 345                 350

Arg Asp Arg Leu Glu Ser Thr Ala Thr Tyr Leu Gly Asn Ser Phe Tyr
                    355                 360                 365

Tyr Gly Lys Gly Leu Ile Asn Val Gln Ala Ala Gln
                    370                 375                 380

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Pro Gln Gln Pro Tyr Asp
1               5

<210> SEQ ID NO 38
<211> LENGTH: 13
<212> TYPE: PRT
<213> ORGANISM: Unknown
<220> FEATURE:
```

```
<223> OTHER INFORMATION: Description of Unknown:
      gluten oligopeptide

<400> SEQUENCE: 38

Pro Gln Pro Glu Leu Pro Tyr Pro Gln Pro Gln Leu Pro
1               5                   10

<210> SEQ ID NO 39
<211> LENGTH: 14
<212> TYPE: PRT
<213> ORGANISM: Unknown
<220> FEATURE:
<223> OTHER INFORMATION: Description of Unknown:
      gluten oligopeptide

<400> SEQUENCE: 39

Pro Gln Pro Glu Leu Pro Tyr Pro Gln Pro Gln Pro Leu Pro
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Pro Phe Pro
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 41

Leu Pro Xaa Thr Gly
1               5

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

His Gly Thr His Val Ala Gly Thr Ala Ala Gly Tyr Gly Val
1               5                   10

<210> SEQ ID NO 43
<211> LENGTH: 1298
<212> TYPE: PRT
<213> ORGANISM: Rothia dentocariosa

<400> SEQUENCE: 43

Met Phe Lys Pro His Gly Ala His Arg Ala Arg Met Leu Gly Val Ala
1               5                   10                  15
```

-continued

```
Ala Leu Ser Val Cys Thr Ala Leu Leu Gly Thr Pro Ala Thr Leu Ala
            20                  25                  30
Ala Pro Ala Gln Pro Ala Pro Ala Ser Ala Gly Pro Ala Thr Gln Gly
        35                  40                  45
Thr Val Glu Gly Ala Arg Gln Gly Glu Val Val Thr Ala Ser Met Lys
 50                  55                  60
Glu Ala Thr Gly Thr Val Thr Ala Tyr Val Glu Leu Ala Gly Gln Gly
65                  70                  75                  80
Ala Tyr Gly Leu Ala Leu Asp Gly Gly Arg Arg Val Ser Pro Met
                85                  90                  95
Ser Gln Val Ser Pro Thr Ala Gln Ser Val Ala Ala His His Val
            100                 105                 110
Gln Ser Gln Val Val Thr Asn Ala Gln Ser Leu Ala Ala Ser Ser Asn
        115                 120                 125
Ser Gln Val Leu Tyr Thr Thr His Asn Leu Gln Arg Gly Val Ala Leu
    130                 135                 140
Thr Gly Asp Ala Gln Ala Ile Arg Gly Leu Ala Gly His Pro Asp Val
145                 150                 155                 160
Val Arg Ile Ser Arg Ile Val Pro Lys Glu Arg Met Asn Ala Ile Ser
                165                 170                 175
Val Val Gly Thr Gly Ala Leu Glu Ala Trp Arg Ser Thr Gly Ala Thr
            180                 185                 190
Gly Arg Gly Val Thr Ile Ala Val Ile Asp Thr Gly Leu Asp Tyr Thr
        195                 200                 205
His Ala Asp Phe Gly Gly Pro Gly Thr Lys Ala Ala Tyr Asp Lys Ala
    210                 215                 220
Lys Ser Ser Pro Thr Met Pro Ala Gly Ser Tyr Asp Pro Gln Lys Val
225                 230                 235                 240
Val Gly Gly Tyr Asp Leu Val Gly Asp Ala Tyr Asn Gly Tyr Asn Ala
                245                 250                 255
Pro Ala Pro Asp Ser Asn Pro Met Asp Cys Ser Glu Ser Gly His Gly
            260                 265                 270
Thr His Val Ala Gly Thr Ala Ala Gly Tyr Gly Val Gly Ala Asp Gly
        275                 280                 285
Lys Thr Phe Arg Gly Glu Tyr Ser Lys Leu Ser Ser Ala Asp Val Gln
    290                 295                 300
Arg Leu His Ile Gly Pro Gly Ser Ala Pro Glu Ala Arg Leu Met Pro
305                 310                 315                 320
Leu Arg Ile Phe Gly Cys Ser Gly Ser Ser Met Thr Gly Gln Ala
                325                 330                 335
Leu Asp Arg Ala Leu Asp Pro Asn Asn Asp Gly Asp Phe Ser Asp Gly
            340                 345                 350
Ala Asn Val Val Asn Leu Ser Leu Gly Ser Asp Tyr Ser Thr Val Asp
        355                 360                 365
Asp Pro Glu Asn Ala Met Leu Gln Arg Leu Ile Asp Lys Gly Val Leu
    370                 375                 380
Ala Val Val Ala Ala Gly Asn Ala Gln Ala Asn Leu Ser Gln Gly Asp
385                 390                 395                 400
Val Tyr Ser Ile Met Gly Ala Pro Ala Asn Asn Pro Ser Ala Leu Thr
                405                 410                 415
Val Ala Asn Ser Asp Ser Ser Leu Thr Arg Ser Asp Arg Phe Glu Val
            420                 425                 430
Lys Gly Pro Ser Ala Val Ala Gly Ala Tyr Ala Gly Ser Tyr Ser Thr
```

```
              435                 440                 445
Leu Tyr Thr Phe Ala Ser Asn Asn Ala Arg Val Ser Gly Thr Val Thr
450                 455                 460
Ala Ala Pro Glu Ser Asn Lys Thr Gly Cys Ala Pro Phe Thr Gly Thr
465                 470                 475                 480
Asn Phe Gly Gly Arg Trp Val Met Leu His Trp Glu Ala Ser Gly Ser
                485                 490                 495
Asp Ala Ser Cys Asp Ser Ala Arg Arg Phe Ala Asn Val Ala Ala Ala
                500                 505                 510
Asn Gly Lys Gly Val Leu Met Val Ala Pro Glu Asn Asp Asp Arg Pro
            515                 520                 525
Ile Ala Gly Ser Thr Thr Ile Pro Gly Val Leu Ile Ser Arg Ala Thr
530                 535                 540
Ala Gln Thr Leu Tyr Pro Ala Val Lys Ala Gly Thr Leu Glu Val Glu
545                 550                 555                 560
Leu Gly Ala Ala Trp Arg Asn Thr Ala Leu Thr Val Lys Gly Pro Asp
                565                 570                 575
Thr Leu Ala Ala Ser Ser Ala Arg Gly Val His Gly Ser Asp Gly Phe
            580                 585                 590
Val Lys Pro Asp Val Ala Ala Pro Gly Thr Asn Ile Tyr Ser Ala Gly
            595                 600                 605
Ala Gly Ser Gly Asn Gln Pro Phe Arg Leu Ser Gly Thr Ser Met Ala
610                 615                 620
Thr Pro His Val Ala Gly Ile Ala Ala Gln Ile Leu Ser Lys Glu Pro
625                 630                 635                 640
Phe Leu Ser Gln Gln Gln Val Lys Ala Arg Ile Met Asn Thr Ala Ser
                645                 650                 655
Gln Glu Val Arg Thr Ile Ser Gly Glu Arg Leu Gly Val Asp Arg Val
                660                 665                 670
Gly Ala Gly Arg Val Asp Ala Gln Ala Ala Val Asn Glu Arg Thr Thr
            675                 680                 685
Ala Tyr Asn Thr Gln Asn Pro Gln Gln Val Ser Leu Ser Phe Gly Val
            690                 695                 700
Ile Glu Val Thr Pro Gly Thr Gly Ala Lys Thr Val Thr Lys Glu Val
705                 710                 715                 720
Thr Val Glu Asn Ala Gly Gly Gln Gln Arg Thr Phe Arg Val Gly Phe
                725                 730                 735
Asp Ala Arg Thr Thr Thr Ala Gly Val Gln Val Lys Thr Pro Glu Ser
                740                 745                 750
Val Ser Val Ala Ala Gly Ala Lys Ala Thr Phe Arg Val Ser Val Thr
            755                 760                 765
Val Asp Pro Glu Lys Leu Ala Lys Thr Leu Asp Ala Gly Thr Ala Arg
            770                 775                 780
Asp Gln Gly Gly Arg Tyr Arg Gln Tyr Leu Ser Ser Val Ser Gly Asn
785                 790                 795                 800
Val Thr Leu Thr Asp Ser Ser Ser Thr Val Val Pro Leu His Ala
                805                 810                 815
Ala Pro Lys Pro Val Ser Glu Leu Met Val Pro Ser Ala Ser Leu Thr
            820                 825                 830
Phe Gly Thr Ser Gln Thr Ala Arg Ile Lys Pro Glu Gly Thr Pro Val
            835                 840                 845
Arg Arg Asn Gly Tyr Val Ser Gln Leu Gly Ala Phe Glu Leu Gly Tyr
850                 855                 860
```

-continued

```
Glu Glu Ser Gly Pro Ala Pro Gly Ser Ser Ala Arg Ala Met Ala
865                 870                 875                 880

Val Gln Tyr Val Gly Ala Ser Ser Asn Leu Pro Ala Leu Gly Ala Ser
            885                 890                 895

Gly Ser Ser Gln Gly Arg Gly Val Ile Ser Phe Gly Val Ala Thr Arg
                900                 905                 910

Gly Asn Trp Asp Ala Leu Thr Pro Ala Tyr Gly Ile Glu Val Glu Ile
            915                 920                 925

Asp Thr Asp Arg Asp Gly Tyr Ala Asp Tyr Ser Val Gln Val Lys Arg
        930                 935                 940

Gln Ile Gly Leu Asp Tyr Pro Val Ala Val Leu Ser Ser Arg Arg Ala
945                 950                 955                 960

Gly Ala Ser Arg Glu Val Asp Ala Leu Pro Val Asn Gly Val Trp Gly
            965                 970                 975

Asp Ile Asp Thr Asn Thr Phe Asp Thr Asn Val Ala Val Ile Pro Val
                980                 985                 990

Ala Ala Ser Ser Leu Gly Leu Ala Arg Gln Gly Ser Glu Pro Leu Gln
            995                 1000                1005

Tyr Arg Val Leu Thr Ser Leu Pro Leu Leu Gly Gln Thr Val Ser
    1010                1015                1020

Ala Thr Asp Trp Val Ser Phe Asn Pro Tyr Thr Pro Asn Leu Trp
    1025                1030                1035

Phe Asp Gly Gly Gln Gly Thr Gly Pro Ser Leu Phe Val Asp Ser
    1040                1045                1050

Pro Asp Ala Pro Val Thr Ala His Leu Arg Ser Gly Ala Ser Ala
    1055                1060                1065

Lys Met Leu Leu Leu His Leu His Asn Pro Ser Ala Ser Ala Ala
    1070                1075                1080

Gln Asn Thr Ser Gln Val Ala Ser Ala Arg Val Gln Arg Ala Gln
    1085                1090                1095

Val Leu Glu Ala Arg Ser Asp Ser Ala Gly Pro Ser Asn Pro Ala
    1100                1105                1110

Pro Ala Pro Pro Ala Ser His Arg Phe Arg Asp Val Ser Pro Thr
    1115                1120                1125

His Pro Phe Tyr Thr Glu Ile Glu Trp Leu Ala Gly Glu Arg Ile
    1130                1135                1140

Thr Arg Gly Trp Pro Asp Gly Thr Tyr Arg Pro Gly Glu Asn Ile
    1145                1150                1155

Glu Arg Gly Ala Ile Ala Ala Tyr Phe Tyr Arg Met Ala Gly Ala
    1160                1165                1170

Pro Asp Phe Thr Pro Pro Val Val Ser Pro Phe Lys Asp Val Asp
    1175                1180                1185

Pro Ser His Pro Phe Tyr Arg Glu Ile Thr Trp Leu Ala Ser Lys
    1190                1195                1200

Gly Ile Thr Arg Gly Trp Gly Asp Gly Thr Phe Arg Pro His Glu
    1205                1210                1215

Pro Val Ser Arg Glu Ala Met Ala Ala Phe Phe Tyr Arg Tyr Ala
    1220                1225                1230

Asn Ser Pro Gln Phe Asn Ala Pro Gln Gln Ser Pro Phe Arg Asp
    1235                1240                1245

Val Arg Pro Ser Asp Pro Phe Tyr Arg Glu Ile Thr Trp Leu Ala
    1250                1255                1260
```

```
Ser Lys Gly Ile Thr Arg Gly Trp Gly Asp Gly Thr Phe Arg Pro
    1265                1270                1275

Val Glu Pro Ile His Arg Asp Ala Met Ala Ala Phe Val Tyr Arg
    1280                1285                1290

Phe Arg Gly Met Lys
    1295

<210> SEQ ID NO 44
<211> LENGTH: 1298
<212> TYPE: PRT
<213> ORGANISM: Rothia dentocariosa

<400> SEQUENCE: 44

Met Phe Lys Pro His Gly Ala His Arg Ala Arg Met Leu Gly Val Ala
1               5                   10                  15

Ala Leu Ser Val Cys Thr Ala Leu Leu Gly Thr Pro Ala Thr Leu Ala
            20                  25                  30

Ala Pro Ala Gln Pro Ala Pro Ala Ser Ala Gly Pro Ala Thr Gln Gly
        35                  40                  45

Thr Val Glu Gly Ala Arg Gln Gly Glu Val Val Thr Ala Ser Met Lys
    50                  55                  60

Glu Ala Thr Gly Thr Val Thr Ala Tyr Val Glu Leu Ala Gly Gln Gly
65                  70                  75                  80

Ala Tyr Gly Leu Ala Leu Asp Gly Gly Arg Arg Val Ser Pro Met
                85                  90                  95

Ser Gln Val Ser Pro Thr Ala Gln Ser Val Ala Ala His His Val
            100                 105                 110

Gln Ser Gln Val Val Thr Asn Ala Gln Ser Leu Ala Ala Ser Ser Asn
        115                 120                 125

Ser Gln Val Leu Tyr Thr Thr His Asn Leu Gln Arg Gly Val Ala Leu
    130                 135                 140

Thr Gly Asp Ala Gln Ala Ile Arg Gly Leu Ala Gly His Pro Asp Val
145                 150                 155                 160

Val Arg Ile Ser Arg Ile Val Pro Lys Glu Arg Met Asn Ala Ile Ser
                165                 170                 175

Val Val Gly Thr Gly Ala Leu Glu Ala Trp Arg Ser Thr Gly Ala Thr
            180                 185                 190

Gly Arg Gly Val Thr Ile Ala Val Ile Asp Thr Gly Leu Asp Tyr Thr
        195                 200                 205

His Ala Asp Phe Gly Gly Pro Gly Thr Lys Ala Ala Tyr Asp Lys Ala
    210                 215                 220

Lys Ser Ser Pro Thr Met Pro Ala Gly Ser Tyr Asp Pro Gln Lys Val
225                 230                 235                 240

Val Gly Gly Tyr Asp Leu Val Gly Asp Ala Tyr Asn Gly Tyr Asn Ala
                245                 250                 255

Pro Ala Pro Asp Ser Asn Pro Met Asp Cys Ser Glu Ser Gly His Gly
            260                 265                 270

Thr His Val Ala Gly Thr Ala Ala Gly Tyr Gly Val Gly Ala Asp Gly
        275                 280                 285

Lys Thr Phe Arg Gly Glu Tyr Ser Lys Leu Ser Ser Ala Asp Val Gln
    290                 295                 300

Arg Leu His Ile Gly Pro Gly Ser Ala Pro Glu Ala Arg Leu Met Pro
305                 310                 315                 320

Leu Arg Ile Phe Gly Cys Ser Gly Ser Ser Ser Met Thr Gly Gln Ala
                325                 330                 335
```

```
Leu Asp Arg Ala Leu Asp Pro Asn Asn Asp Gly Asp Phe Ser Asp Gly
            340                 345                 350

Ala Asn Val Val Asn Leu Ser Leu Gly Ser Asp Tyr Ser Thr Val Asp
        355                 360                 365

Asp Pro Glu Asn Ala Met Leu Gln Arg Leu Ile Asp Lys Gly Val Leu
    370                 375                 380

Ala Val Val Ala Ala Gly Asn Ala Gln Ala Asn Leu Ser Gln Gly Asp
385                 390                 395                 400

Val Tyr Ser Ile Met Gly Ala Pro Ala Asn Asn Pro Ser Ala Leu Thr
                405                 410                 415

Val Ala Asn Ser Asp Ser Ser Leu Thr Arg Ser Asp Arg Phe Glu Val
            420                 425                 430

Lys Gly Pro Ser Ala Val Ala Gly Ala Tyr Ala Gly Ser Tyr Ser Thr
        435                 440                 445

Leu Tyr Thr Phe Ala Ser Asn Asn Ala Arg Val Ser Gly Thr Val Thr
    450                 455                 460

Ala Ala Pro Glu Ser Asn Lys Thr Gly Cys Ala Pro Phe Thr Gly Thr
465                 470                 475                 480

Asn Phe Gly Gly Arg Trp Val Met Leu His Trp Glu Ala Ser Gly Ser
                485                 490                 495

Asp Ala Ser Cys Asp Ser Ala Arg Arg Phe Ala Asn Val Ala Ala Ala
            500                 505                 510

Asn Gly Lys Gly Val Leu Met Val Ala Pro Glu Asn Asp Asp Arg Pro
        515                 520                 525

Ile Ala Gly Ser Thr Thr Ile Pro Gly Val Leu Ile Ser Arg Ala Thr
    530                 535                 540

Ala Gln Thr Leu Tyr Pro Ala Val Lys Ala Gly Thr Leu Glu Val Glu
545                 550                 555                 560

Leu Gly Ala Ala Trp Arg Asn Thr Ala Leu Thr Val Lys Gly Pro Asp
                565                 570                 575

Thr Leu Ala Ala Ser Ser Ala Arg Gly Val His Gly Ser Asp Gly Phe
            580                 585                 590

Val Lys Pro Asp Val Ala Ala Pro Gly Thr Asn Ile Tyr Ser Ala Gly
        595                 600                 605

Ala Gly Ser Gly Asn Gln Pro Phe Arg Leu Ser Gly Thr Ser Met Ala
    610                 615                 620

Thr Pro His Val Ala Gly Ile Ala Ala Gln Ile Leu Ser Lys Glu Pro
625                 630                 635                 640

Phe Leu Ser Gln Gln Gln Val Lys Ala Arg Ile Met Asn Thr Ala Ser
                645                 650                 655

Gln Glu Val Arg Thr Ile Ser Gly Glu Arg Leu Gly Val Asp Arg Val
            660                 665                 670

Gly Ala Gly Arg Val Asp Ala Gln Ala Ala Val Asn Glu Arg Thr Thr
        675                 680                 685

Ala Tyr Asn Thr Gln Asn Pro Gln Gln Val Ser Leu Ser Phe Gly Val
    690                 695                 700

Ile Glu Val Thr Pro Gly Thr Gly Ala Lys Thr Val Thr Lys Glu Val
705                 710                 715                 720

Thr Val Glu Asn Ala Gly Gly Gln Gln Arg Thr Phe Arg Val Gly Phe
                725                 730                 735

Asp Ala Arg Thr Thr Thr Ala Gly Val Gln Val Lys Thr Pro Glu Ser
            740                 745                 750
```

-continued

```
Val Ser Val Ala Ala Gly Ala Lys Ala Thr Phe Arg Val Ser Val Thr
            755                 760                 765
Val Asp Pro Glu Lys Leu Ala Lys Thr Leu Asp Ala Gly Thr Ala Arg
            770                 775                 780
Asp Gln Gly Gly Arg Tyr Arg Gln Tyr Leu Ser Ser Val Ser Gly Asn
785                 790                 795                 800
Val Thr Leu Thr Asp Ser Ser Ser Thr Val Val Pro Leu His Ala
            805                 810                 815
Ala Pro Lys Pro Val Ser Glu Leu Met Val Pro Ser Ala Ser Leu Thr
            820                 825                 830
Phe Gly Thr Ser Gln Thr Ala Arg Ile Lys Pro Glu Gly Thr Pro Val
            835                 840                 845
Arg Arg Asn Gly Tyr Val Ser Gln Leu Gly Ala Phe Glu Leu Gly Tyr
            850                 855                 860
Glu Glu Ser Gly Pro Ala Pro Gly Ser Ser Ser Ala Arg Ala Met Ala
865                 870                 875                 880
Val Gln Tyr Val Gly Ala Ser Ser Asn Leu Pro Ala Leu Gly Ala Ser
                    885                 890                 895
Gly Ser Ser Gln Gly Arg Gly Val Ile Ser Phe Gly Val Ala Thr Arg
                    900                 905                 910
Gly Asn Trp Asp Ala Leu Thr Pro Ala Tyr Gly Ile Glu Val Glu Ile
            915                 920                 925
Asp Thr Asp Arg Asp Gly Tyr Ala Asp Tyr Ser Val Gln Val Lys Arg
            930                 935                 940
Gln Ile Gly Leu Asp Tyr Pro Val Ala Val Leu Ser Ser Arg Arg Ala
945                 950                 955                 960
Gly Ala Ser Arg Glu Val Asp Ala Leu Pro Val Asn Gly Val Trp Gly
                    965                 970                 975
Asp Ile Asp Thr Asn Thr Phe Asp Thr Asn Val Ala Val Ile Pro Val
                    980                 985                 990
Ala Ala Ser Ser Leu Gly Leu Ala Arg Gln Gly Ser Glu Pro Leu Gln
            995                 1000                1005
Tyr Arg Val Leu Thr Ser Leu Pro Leu Leu Gly Gln Thr Val Ser
    1010                1015                1020
Ala Thr Asp Trp Val Ser Phe Asn Pro Tyr Thr Pro Asn Leu Trp
    1025                1030                1035
Phe Asp Gly Gly Gln Gly Thr Gly Pro Ser Leu Phe Val Asp Ser
    1040                1045                1050
Pro Asp Ala Pro Val Thr Ala His Leu Arg Ser Gly Ala Ser Ala
    1055                1060                1065
Lys Met Leu Leu Leu His Leu His Asn Pro Ser Ala Ser Ala Ala
    1070                1075                1080
Gln Asn Thr Ser Gln Val Ala Ser Ala Arg Val Gln Arg Ala Gln
    1085                1090                1095
Val Leu Glu Ala Arg Ser Asp Ser Ala Gly Pro Ser Asn Pro Ala
    1100                1105                1110
Pro Ala Pro Pro Ala Ser His Arg Phe Arg Asp Val Ser Pro Thr
    1115                1120                1125
His Pro Phe Tyr Thr Glu Ile Glu Trp Leu Ala Gly Glu Arg Ile
    1130                1135                1140
Thr Arg Gly Trp Pro Asp Gly Thr Tyr Arg Pro Gly Glu Asn Ile
    1145                1150                1155
Glu Arg Gly Ala Ile Ala Ala Tyr Phe Tyr Arg Met Ala Gly Ala
```

```
                    1160                1165                1170

Pro Asp Phe Thr Pro Pro Val Val Ser Pro Phe Lys Asp Val Asp
    1175                1180                1185

Pro Ser His Pro Phe Tyr Arg Glu Ile Thr Trp Leu Ala Ser Lys
    1190                1195                1200

Gly Ile Thr Arg Gly Trp Gly Asp Gly Thr Phe Arg Pro His Glu
    1205                1210                1215

Pro Val Ser Arg Glu Ala Met Ala Ala Phe Phe Tyr Arg Tyr Ala
    1220                1225                1230

Asn Ser Pro Gln Phe Asn Ala Pro Gln Gln Ser Pro Phe Arg Asp
    1235                1240                1245

Val Arg Pro Ser Asp Pro Phe Tyr Arg Glu Ile Thr Trp Leu Ala
    1250                1255                1260

Ser Lys Gly Ile Thr Arg Gly Trp Gly Asp Gly Thr Phe Arg Pro
    1265                1270                1275

Val Glu Pro Ile His Arg Asp Ala Met Ala Ala Phe Val Tyr Arg
    1280                1285                1290

Phe Arg Gly Met Lys
    1295

<210> SEQ ID NO 45
<211> LENGTH: 1298
<212> TYPE: PRT
<213> ORGANISM: Rothia dentocariosa

<400> SEQUENCE: 45

Met Phe Lys Pro His Gly Ala His Arg Ala Arg Met Leu Gly Val Ala
1               5                   10                  15

Ala Leu Ser Val Cys Thr Ala Leu Leu Gly Thr Pro Ala Thr Leu Ala
            20                  25                  30

Ala Pro Ala Gln Pro Ala Pro Ala Ser Ala Gly Pro Ala Thr Gln Gly
        35                  40                  45

Thr Val Glu Gly Ala Arg Gln Gly Glu Val Val Thr Ala Ser Met Lys
    50                  55                  60

Glu Ala Thr Gly Thr Val Thr Ala Tyr Val Glu Leu Ala Gly Gln Gly
65                  70                  75                  80

Ala Tyr Gly Leu Ala Leu Asp Gly Gly Gly Arg Arg Val Ser Pro Met
                85                  90                  95

Ser Gln Val Ser Pro Thr Ala Gln Ser Val Ala Ala His His Val
            100                 105                 110

Gln Ser Gln Val Val Thr Asn Ala Gln Ser Leu Ala Ala Ser Ser Asn
        115                 120                 125

Ser Gln Val Leu Tyr Thr Thr His Asn Leu Gln Arg Gly Val Ala Leu
    130                 135                 140

Thr Gly Asp Ala Gln Ala Ile Arg Gly Leu Ala Gly His Pro Asp Val
145                 150                 155                 160

Val Arg Ile Ser Arg Ile Val Pro Lys Glu Arg Met Asn Ala Ile Ser
                165                 170                 175

Val Val Gly Thr Gly Ala Leu Glu Ala Trp Arg Ser Thr Gly Ala Thr
            180                 185                 190

Gly Arg Gly Val Thr Ile Ala Val Ile Asp Thr Gly Leu Asp Tyr Thr
        195                 200                 205

His Ala Asp Phe Gly Gly Pro Gly Thr Lys Ala Ala Tyr Asp Lys Ala
    210                 215                 220
```

```
Lys Ser Ser Pro Thr Met Pro Ala Gly Ser Tyr Asp Pro Gln Lys Val
225                 230                 235                 240

Val Gly Gly Tyr Asp Leu Val Gly Asp Ala Tyr Asn Gly Tyr Asn Ala
            245                 250                 255

Pro Ala Pro Asp Ser Asn Pro Met Asp Cys Ser Glu Ser Gly His Gly
            260                 265                 270

Thr His Val Ala Gly Thr Ala Ala Gly Tyr Gly Val Gly Ala Asp Gly
        275                 280                 285

Lys Thr Phe Arg Gly Glu Tyr Ser Lys Leu Ser Ser Ala Asp Val Gln
        290                 295                 300

Arg Leu His Ile Gly Pro Gly Ser Ala Pro Glu Ala Arg Leu Met Pro
305                 310                 315                 320

Leu Arg Ile Phe Gly Cys Ser Gly Ser Ser Met Thr Gly Gln Ala
            325                 330                 335

Leu Asp Arg Ala Leu Asp Pro Asn Asn Asp Gly Asp Phe Ser Asp Gly
            340                 345                 350

Ala Asn Val Val Asn Leu Ser Leu Gly Ser Asp Tyr Ser Thr Val Asp
        355                 360                 365

Asp Pro Glu Asn Ala Met Leu Gln Arg Leu Ile Asp Lys Gly Val Leu
370                 375                 380

Ala Val Val Ala Ala Gly Asn Ala Gln Ala Asn Leu Ser Gln Gly Asp
385                 390                 395                 400

Val Tyr Ser Ile Met Gly Ala Pro Ala Asn Asn Pro Ser Ala Leu Thr
                405                 410                 415

Val Ala Asn Ser Asp Ser Ser Leu Thr Arg Ser Asp Arg Phe Glu Val
            420                 425                 430

Lys Gly Pro Ser Ala Val Ala Gly Ala Tyr Ala Gly Ser Tyr Ser Thr
            435                 440                 445

Leu Tyr Thr Phe Ala Ser Asn Asn Ala Arg Val Ser Gly Thr Val Thr
        450                 455                 460

Ala Ala Pro Glu Ser Asn Lys Thr Gly Cys Ala Pro Phe Thr Gly Thr
465                 470                 475                 480

Asn Phe Gly Gly Arg Trp Val Met Leu His Trp Glu Ala Ser Gly Ser
                485                 490                 495

Asp Ala Ser Cys Asp Ser Ala Arg Arg Phe Ala Asn Val Ala Ala Ala
            500                 505                 510

Asn Gly Lys Gly Val Leu Met Val Ala Pro Glu Asn Asp Asp Arg Pro
        515                 520                 525

Ile Ala Gly Ser Thr Thr Ile Pro Gly Val Leu Ile Ser Arg Ala Thr
530                 535                 540

Ala Gln Thr Leu Tyr Pro Ala Val Lys Ala Gly Thr Leu Glu Val Glu
545                 550                 555                 560

Leu Gly Ala Ala Trp Arg Asn Thr Ala Leu Thr Val Lys Gly Pro Asp
                565                 570                 575

Thr Leu Ala Ala Ser Ser Ala Arg Gly Val His Gly Ser Asp Gly Phe
            580                 585                 590

Val Lys Pro Asp Val Ala Ala Pro Gly Thr Asn Ile Tyr Ser Ala Gly
        595                 600                 605

Ala Gly Ser Gly Asn Gln Pro Phe Arg Leu Ser Gly Thr Ser Met Ala
        610                 615                 620

Thr Pro His Val Ala Gly Ile Ala Ala Gln Ile Leu Ser Lys Glu Pro
625                 630                 635                 640

Phe Leu Ser Gln Gln Gln Val Lys Ala Arg Ile Met Asn Thr Ala Ser
```

645                 650                 655
Gln Glu Val Arg Thr Ile Ser Gly Glu Arg Leu Gly Val Asp Arg Val
                660                 665                 670
Gly Ala Gly Arg Val Asp Ala Gln Ala Ala Val Asn Glu Arg Thr Thr
            675                 680                 685
Ala Tyr Asn Thr Gln Asn Pro Gln Gln Val Ser Leu Ser Phe Gly Val
        690                 695                 700
Ile Glu Val Thr Pro Gly Thr Gly Ala Lys Thr Val Thr Lys Glu Val
705                 710                 715                 720
Thr Val Glu Asn Ala Gly Gly Gln Gln Arg Thr Phe Arg Val Gly Phe
                725                 730                 735
Asp Ala Arg Thr Thr Thr Ala Gly Val Gln Val Lys Thr Pro Glu Ser
                740                 745                 750
Val Ser Val Ala Ala Gly Ala Lys Ala Thr Phe Arg Val Ser Val Thr
            755                 760                 765
Val Asp Pro Glu Lys Leu Ala Lys Thr Leu Asp Ala Gly Thr Ala Arg
        770                 775                 780
Asp Gln Gly Gly Arg Tyr Arg Gln Tyr Leu Ser Ser Val Ser Gly Asn
785                 790                 795                 800
Val Thr Leu Thr Asp Ser Ser Thr Val Val Pro Leu His Ala
                805                 810                 815
Ala Pro Lys Pro Val Ser Glu Leu Met Val Pro Ser Ala Ser Leu Thr
                820                 825                 830
Phe Gly Thr Ser Gln Thr Ala Arg Ile Lys Pro Glu Gly Thr Pro Val
            835                 840                 845
Arg Arg Asn Gly Tyr Val Ser Gln Leu Gly Ala Phe Glu Leu Gly Tyr
        850                 855                 860
Glu Glu Ser Gly Pro Ala Pro Gly Ser Ser Ala Arg Ala Met Ala
865                 870                 875                 880
Val Gln Tyr Val Gly Ala Ser Ser Asn Leu Pro Ala Leu Gly Ala Ser
                885                 890                 895
Gly Ser Ser Gln Gly Arg Gly Val Ile Ser Phe Gly Val Ala Thr Arg
            900                 905                 910
Gly Asn Trp Asp Ala Leu Thr Pro Ala Tyr Gly Ile Glu Val Glu Ile
        915                 920                 925
Asp Thr Asp Arg Asp Gly Tyr Ala Asp Tyr Ser Val Gln Val Lys Arg
930                 935                 940
Gln Ile Gly Leu Asp Tyr Pro Val Ala Val Leu Ser Ser Arg Arg Ala
945                 950                 955                 960
Gly Ala Ser Arg Glu Val Asp Ala Leu Pro Val Asn Gly Val Trp Gly
                965                 970                 975
Asp Ile Asp Thr Asn Thr Phe Asp Thr Asn Val Ala Val Ile Pro Val
            980                 985                 990
Ala Ala Ser Ser Leu Gly Leu Ala Arg Gln Gly Ser Glu Pro Leu Gln
        995                 1000                1005
Tyr Arg Val Leu Thr Ser Leu Pro Leu Leu Gly Gln Thr Val Ser
    1010                1015                1020
Ala Thr Asp Trp Val Ser Phe Asn Pro Tyr Thr Pro Asn Leu Trp
    1025                1030                1035
Phe Asp Gly Gly Gln Gly Thr Gly Pro Ser Leu Phe Val Asp Ser
    1040                1045                1050
Pro Asp Ala Pro Val Thr Ala His Leu Arg Ser Gly Ala Ser Ala
    1055                1060                1065

-continued

Lys Met Leu Leu Leu His Leu His Asn Pro Ser Ala Ser Ala Ala
1070                1075                1080

Gln Asn Thr Ser Gln Val Ala Ser Ala Arg Val Gln Arg Ala Gln
    1085                1090                1095

Val Leu Glu Ala Arg Ser Asp Ser Ala Gly Pro Ser Asn Pro Ala
1100                1105                1110

Pro Ala Pro Pro Ala Ser His Arg Phe Arg Asp Val Ser Pro Thr
    1115                1120                1125

His Pro Phe Tyr Thr Glu Ile Glu Trp Leu Ala Gly Glu Arg Ile
1130                1135                1140

Thr Arg Gly Trp Pro Asp Gly Thr Tyr Arg Pro Gly Glu Asn Ile
    1145                1150                1155

Glu Arg Gly Ala Ile Ala Ala Tyr Phe Tyr Arg Met Ala Gly Ala
1160                1165                1170

Pro Asp Phe Thr Pro Pro Val Val Ser Pro Phe Lys Asp Val Asp
    1175                1180                1185

Pro Ser His Pro Phe Tyr Arg Glu Ile Thr Trp Leu Ala Ser Lys
1190                1195                1200

Gly Ile Thr Arg Gly Trp Gly Asp Gly Thr Phe Arg Pro His Glu
    1205                1210                1215

Pro Val Ser Arg Glu Ala Met Ala Ala Phe Phe Tyr Arg Tyr Ala
1220                1225                1230

Asn Ser Pro Gln Phe Asn Ala Pro Gln Gln Ser Pro Phe Arg Asp
    1235                1240                1245

Val Arg Pro Ser Asp Pro Phe Tyr Arg Glu Ile Thr Trp Leu Ala
1250                1255                1260

Ser Lys Gly Ile Thr Arg Gly Trp Gly Asp Gly Thr Phe Arg Pro
    1265                1270                1275

Val Glu Pro Ile His Arg Asp Ala Met Ala Ala Phe Val Tyr Arg
1280                1285                1290

Phe Arg Gly Met Lys
    1295

<210> SEQ ID NO 46
<211> LENGTH: 1296
<212> TYPE: PRT
<213> ORGANISM: Rothia aeria

<400> SEQUENCE: 46

Met Phe Lys Pro His Gly Ala His Arg Ala Arg Met Leu Gly Val Ala
1               5                   10                  15

Ala Leu Ser Val Cys Thr Ala Leu Leu Gly Thr Pro Ala Thr Leu Ala
                20                  25                  30

Ala Pro Ala Gln Pro Ala Pro Ala Ser Thr Gly Pro Ala Thr Gln Gly
            35                  40                  45

Thr Val Glu Gly Ala Arg Gln Gly Glu Val Val Thr Ala Ser Met Lys
        50                  55                  60

Glu Ala Thr Gly Thr Val Thr Ala Tyr Val Glu Leu Ala Gly Gln Gly
65                  70                  75                  80

Ala Tyr Gly Leu Ala Leu Asp Gly Gly Arg Arg Val Ser Pro Met
                85                  90                  95

Asn Gln Val Pro Pro Thr Ala Gln Ser Val Ala Ala His His Val
            100                 105                 110

Gln Ser Gln Val Val Thr Asn Ala Gln Ser Leu Ala Ala Ser Ser Asn

```
            115                 120                 125
Ser Gln Val Leu Tyr Thr Thr His Asn Leu Gln Arg Gly Val Ala Leu
            130                 135                 140
Thr Gly Asp Ala Gln Ala Ile Arg Gly Leu Ala Gly His Pro Glu Val
145                 150                 155                 160
Val Arg Ile Ser Arg Ile Val Pro Lys Glu Arg Met Asn Ala Ile Ser
                165                 170                 175
Val Val Gly Thr Gly Ala Leu Glu Ala Trp Arg Ser Thr Gly Ala Thr
                180                 185                 190
Gly Arg Asp Val Thr Ile Ala Val Ile Asp Thr Gly Leu Asp Tyr Thr
                195                 200                 205
His Ala Asp Phe Gly Gly Pro Gly Thr Lys Ala Ala Tyr Asp Lys Ala
            210                 215                 220
Asn Ser Ser Pro Thr Ile Pro Ala Gly Ser Tyr Asp Pro Gln Lys Val
225                 230                 235                 240
Val Gly Gly Tyr Asp Leu Val Gly Asp Ala Tyr Asn Gly Tyr Asn Ala
                245                 250                 255
Pro Ala Pro Asp Ser Asn Pro Met Asp Cys Ser Glu Ser Gly His Gly
            260                 265                 270
Thr His Val Ala Gly Thr Ala Ala Gly Tyr Gly Val Gly Ala Asp Gly
            275                 280                 285
Lys Thr Phe Arg Gly Glu Tyr Ser Lys Leu Ser Ser Ala Asp Val Gln
            290                 295                 300
Arg Leu His Ile Gly Pro Gly Ser Ala Pro Glu Ala Arg Leu Met Pro
305                 310                 315                 320
Leu Arg Ile Phe Gly Cys Ser Gly Ser Ser Ser Met Thr Gly Gln Ala
                325                 330                 335
Leu Asp Arg Ala Leu Asp Pro Asn Asn Asp Gly Asp Phe Ser Asp Gly
            340                 345                 350
Ala Asn Ile Val Asn Leu Ser Leu Gly Ser Asp Tyr Ser Thr Val Asp
            355                 360                 365
Asp Pro Glu Asn Thr Met Leu Gln Arg Leu Ile Asp Lys Gly Val Leu
            370                 375                 380
Ala Val Val Ala Ala Gly Asn Ala Gln Ala Asn Leu Ser Gln Gly Asp
385                 390                 395                 400
Val Tyr Ser Ile Met Gly Ala Pro Ala Asn Asn Pro Ser Ala Leu Thr
                405                 410                 415
Val Ala Asn Ser Glu Ser Ala Leu Thr Arg Ser Asp Arg Phe Glu Val
                420                 425                 430
Lys Gly Pro Ser Ala Val Ala Gly Ala Tyr Ala Gly Ser Tyr Ser Thr
            435                 440                 445
Leu Tyr Thr Phe Ala Ser Asn Asn Ala Arg Val Ser Gly Thr Val Thr
            450                 455                 460
Ala Ala Pro Glu Ser Asn Lys Thr Gly Cys Ala Pro Phe Thr Gly Thr
465                 470                 475                 480
Asn Phe Gly Gly Arg Trp Val Met Leu His Trp Glu Ala Ser Gly Ser
                485                 490                 495
Asp Ser Ser Cys Asp Ser Ala Arg Arg Phe Ala Asn Val Ala Ala Ala
            500                 505                 510
Asn Gly Lys Gly Val Leu Met Val Ala Pro Glu Asn Asp Asp Arg Pro
            515                 520                 525
Ile Ala Gly Ser Thr Thr Ile Pro Gly Val Leu Ile Ser Arg Ala Thr
            530                 535                 540
```

```
Ala Gln Thr Leu Tyr Pro Ala Val Lys Ala Gly Thr Leu Glu Val Glu
545                 550                 555                 560

Leu Glu Ala Ala Trp Arg Asn Thr Ala Leu Thr Ala Lys Gly Pro Asp
                565                 570                 575

Thr Leu Ala Ala Ser Ser Ala Arg Gly Val His Gly Ser Asp Gly Phe
                580                 585                 590

Val Lys Pro Asp Val Ala Ala Pro Gly Thr Asn Ile Tyr Ser Ala Gly
                595                 600                 605

Ala Gly Ser Gly Asn Gln Pro Phe Arg Leu Ser Gly Thr Ser Met Ala
            610                 615                 620

Thr Pro His Val Ala Gly Ile Ala Ala Gln Ile Leu Ser Lys Glu Pro
625                 630                 635                 640

Phe Leu Ser Gln Gln Gln Val Lys Ala Arg Ile Met Asn Thr Ala Ser
                645                 650                 655

Gln Glu Val Arg Thr Ile Ser Gly Glu Arg Leu Gly Val Asp Arg Val
                660                 665                 670

Gly Ala Gly Arg Val Asp Ala Gln Ala Val Asn Glu Arg Thr Thr
            675                 680                 685

Ala Tyr Asn Thr Gln Asn Pro Gln Gln Val Ser Leu Ser Phe Gly Val
            690                 695                 700

Ile Glu Val Thr Pro Gly Thr Gly Ala Lys Thr Val Thr Lys Glu Val
705                 710                 715                 720

Thr Met Glu Asn Ala Gly Gly Gln Gln Arg Thr Phe Arg Val Gly Phe
                725                 730                 735

Asp Ala Arg Thr Thr Thr Ala Gly Val Gln Val Lys Thr Pro Glu Ser
                740                 745                 750

Val Ser Val Ala Ala Gly Thr Lys Ala Thr Phe Arg Val Ser Val Thr
            755                 760                 765

Val Asp Pro Glu Lys Leu Ala Lys Thr Leu Asp Ala Gly Thr Ala Arg
770                 775                 780

Asp Gln Gly Gly Arg Tyr Arg Gln Tyr Leu Ser Ser Val Ser Gly Asn
785                 790                 795                 800

Val Thr Leu Thr Asp Ser Ser Ser Thr Val Val Pro Leu His Ala
                805                 810                 815

Ala Pro Lys Pro Val Ser Glu Leu Met Val Pro Ser Ala Ser Leu Thr
                820                 825                 830

Phe Gly Thr Ser Gln Thr Ala Arg Val Lys Pro Glu Gly Thr Pro Val
            835                 840                 845

Arg Arg Asn Gly Tyr Val Ser Gln Leu Gly Ala Phe Glu Leu Gly Tyr
            850                 855                 860

Glu Glu Ser Gly Pro Ala Pro Ser Ser Ser Ala Arg Ala Met Ala
865                 870                 875                 880

Val Gln Tyr Val Gly Ala Ser Ser Asn Leu Pro Ala Leu Gly Ala Ser
            885                 890                 895

Gly Ser Ser Gln Gly Arg Gly Val Ile Ser Phe Gly Val Ala Thr Arg
            900                 905                 910

Gly Asn Trp Asp Ala Leu Thr Pro Ala Tyr Gly Ile Glu Val Glu Ile
            915                 920                 925

Asp Thr Asp Ser Asp Gly Tyr Ala Asp Tyr Ser Val Gln Val Lys Arg
            930                 935                 940

Gln Ile Gly Leu Asp Tyr Pro Val Ala Val Leu Ser Ser His Arg Ala
945                 950                 955                 960
```

```
Gly Ala Ser Arg Glu Val Asp Ala Leu Pro Val Asn Gly Val Trp Gly
                965                 970                 975

Asp Ile Asp Thr Asn Thr Phe Asp Thr Asn Val Ala Val Ile Pro Val
            980                 985                 990

Ala Ala Ser Ser Leu Gly Leu Thr Arg Gln Gly Ser Glu Pro Leu Gln
        995                 1000                1005

Tyr Arg Val Leu Thr Arg Leu Pro Leu Leu Gly Gln Thr Val Ser
    1010                1015                1020

Ala Thr Asp Trp Val Ser Phe Asn Pro Tyr Thr Pro Asn Leu Trp
    1025                1030                1035

Phe Asp Gly Gly Gln Gly Thr Ser Pro Ser Leu Phe Val Asp Ser
    1040                1045                1050

Pro Asp Ala Pro Val Thr Ala His Leu Arg Ser Gly Ala Ser Ala
    1055                1060                1065

Lys Met Leu Leu Leu His Leu His Asn Pro Ser Ala Ser Ala Ala
    1070                1075                1080

Gln Asn Thr Ser Gln Val Ala Ser Ala Arg Val Gln Arg Ala Gln
    1085                1090                1095

Val Leu Glu Ala Arg Ser Gly Ser Ala Gly Pro Ser Asn Pro Ala
    1100                1105                1110

Pro Pro Ala Ser His Arg Phe Arg Asp Val Gly Pro Ala His Pro
    1115                1120                1125

Phe Tyr Thr Glu Ile Glu Trp Leu Ala Gly Glu Arg Ile Thr Arg
    1130                1135                1140

Gly Trp Pro Asp Gly Thr Tyr Arg Pro Gly Glu Asn Ile Glu Arg
    1145                1150                1155

Gly Ala Ile Ala Ala Tyr Phe Tyr Arg Met Ala Gly Ala Pro Asp
    1160                1165                1170

Phe Thr Pro Pro Val Val Ser Pro Phe Lys Asp Val Asp Pro Ser
    1175                1180                1185

His Pro Phe Tyr Arg Glu Ile Thr Trp Leu Ala Ser Lys Gly Ile
    1190                1195                1200

Thr Arg Gly Trp Gly Asp Gly Thr Phe Arg Pro His Glu Pro Val
    1205                1210                1215

Ser Arg Glu Ala Met Ala Ala Phe Phe Tyr Arg Tyr Ala Asn Ser
    1220                1225                1230

Pro Arg Phe Asn Ala Pro Gln Gln Ser Pro Phe Arg Asp Val Arg
    1235                1240                1245

Ser Ser Asp Pro Phe Tyr Arg Glu Ile Thr Trp Leu Ala Ser Lys
    1250                1255                1260

Gly Ile Thr Arg Gly Trp Gly Asp Gly Thr Phe Arg Pro Val Glu
    1265                1270                1275

Pro Ile His Arg Asp Ala Met Ala Ala Phe Val Tyr Arg Phe Arg
    1280                1285                1290

Gly Val Lys
    1295
```

<210> SEQ ID NO 47
<211> LENGTH: 1298
<212> TYPE: PRT
<213> ORGANISM: Rothia aeria

<400> SEQUENCE: 47

```
Met Phe Lys Pro His Gly Ala His Arg Ala Arg Met Leu Gly Val Ala
1               5                   10                  15
```

```
Ala Leu Ser Val Cys Thr Ala Leu Leu Gly Thr Pro Ala Ala Leu Ala
            20                  25                  30

Ala Pro Ala Gln Pro Ala Pro Ala Ser Ala Gly Pro Ala Thr Gln Gly
            35                  40                  45

Thr Val Glu Gly Ala Arg Gln Gly Val Val Thr Ala Ser Met Lys
 50                  55                  60

Glu Ala Thr Gly Thr Val Thr Ala Tyr Val Glu Leu Ala Gly Gln Gly
 65                  70                  75                  80

Ala Tyr Gly Leu Ala Leu Asp Gly Gly Arg Arg Met Ser Pro Met
                85                  90                  95

Ser Gln Ala Ser Pro Thr Ala Gln Ser Val Ala Ala His His Val
            100                 105                 110

Gln Ser Gln Val Val Thr Asn Ala Gln Ser Leu Ala Ala Ser Ser Asn
            115                 120                 125

Ser Gln Val Leu Tyr Thr Thr His Asn Leu Gln Arg Gly Val Ala Leu
            130                 135                 140

Thr Gly Asp Ala Gln Ala Ile Arg Gly Leu Ala Gly His Pro Glu Val
145                 150                 155                 160

Val Arg Ile Ser Arg Ile Val Pro Lys Glu Arg Met Asn Ala Ile Ser
                165                 170                 175

Val Val Gly Thr Gly Ala Leu Glu Ala Trp Arg Ser Thr Gly Ala Thr
            180                 185                 190

Gly Arg Gly Val Thr Ile Ala Val Ile Asp Thr Gly Leu Asp Tyr Thr
            195                 200                 205

His Ala Asp Phe Gly Gly Pro Gly Thr Lys Ala Ala Tyr Asp Lys Ala
            210                 215                 220

Lys Ser Ser Pro Thr Met Pro Ala Gly Ser Tyr Asp Pro Gln Lys Val
225                 230                 235                 240

Val Gly Gly Tyr Asp Leu Val Gly Asp Ala Tyr Asn Gly Tyr Asn Ala
                245                 250                 255

Pro Ala Pro Asp Ser Asn Pro Met Asp Cys Ser Glu Ser Gly His Gly
            260                 265                 270

Thr His Val Ala Gly Thr Ala Ala Gly Tyr Gly Val Gly Ala Asp Gly
            275                 280                 285

Lys Thr Phe Arg Gly Glu Tyr Ser Lys Leu Ser Ala Asp Val Gln
290                 295                 300

Arg Leu His Ile Gly Pro Gly Ser Ala Pro Glu Ala Arg Leu Met Pro
305                 310                 315                 320

Leu Arg Ile Phe Gly Cys Ser Gly Ser Ser Met Thr Gly Gln Ala
                325                 330                 335

Leu Asp Arg Ala Leu Asp Pro Asn Asn Asp Gly Asp Phe Ser Asp Gly
            340                 345                 350

Ala Asn Ile Val Asn Leu Ser Leu Gly Ser Asp Tyr Ser Thr Ala Asp
            355                 360                 365

Asp Pro Glu Asn Thr Met Leu Gln Arg Leu Ile Asp Lys Gly Val Leu
            370                 375                 380

Ala Val Val Ala Ala Gly Asn Ala Gln Ala Asn Leu Ser Gln Gly Asp
385                 390                 395                 400

Val Tyr Ser Ile Met Gly Ala Pro Ala Asn Asn Pro Ser Ala Leu Thr
                405                 410                 415

Val Ala Asn Ser Glu Ser Ala Leu Thr Arg Ser Asp Arg Phe Glu Val
            420                 425                 430
```

```
Lys Gly Pro Ser Ala Val Ala Gly Ala Tyr Ala Gly Ser Tyr Ser Thr
            435                 440                 445

Leu Tyr Thr Phe Ala Ser Asn Asn Ala Arg Val Ser Gly Thr Val Thr
450                 455                 460

Ala Ala Pro Glu Ser Asn Lys Thr Gly Cys Ala Pro Phe Thr Gly Thr
465                 470                 475                 480

Asn Phe Gly Gly Arg Trp Val Met Leu His Trp Glu Ala Ser Gly Ser
                485                 490                 495

Asp Pro Ser Cys Asp Ser Ala Arg Arg Phe Ala Asn Val Ala Ala Ala
            500                 505                 510

Asn Gly Lys Gly Val Leu Met Val Ala Pro Glu Asn Asp Asp Arg Pro
            515                 520                 525

Ile Ala Gly Ser Thr Thr Ile Pro Gly Val Leu Ile Ser Arg Ala Thr
            530                 535                 540

Ala Gln Thr Leu Tyr Pro Ala Val Lys Ala Gly Thr Leu Glu Val Glu
545                 550                 555                 560

Leu Gly Ala Ala Trp Arg Asn Thr Ala Leu Thr Ala Lys Gly Pro Asp
                565                 570                 575

Thr Leu Ala Ala Ser Ser Ala Arg Gly Val His Gly Ser Asp Gly Phe
            580                 585                 590

Val Lys Pro Asp Val Ala Ala Pro Gly Thr Asn Ile Tyr Ser Ala Gly
            595                 600                 605

Ala Gly Ser Gly Asn Gln Pro Phe Arg Leu Ser Gly Thr Ser Met Ala
            610                 615                 620

Thr Pro His Val Ala Gly Ile Ala Ala Gln Ile Leu Gly Lys Glu Pro
625                 630                 635                 640

Phe Leu Ser Gln Gln Gln Val Lys Ala Arg Ile Met Asn Thr Ala Ser
                645                 650                 655

Gln Glu Val Arg Thr Ile Ser Gly Glu Arg Leu Gly Val Asp Arg Val
            660                 665                 670

Gly Ala Gly Arg Val Asp Ala Gln Ala Val Asn Glu Arg Thr Thr
            675                 680                 685

Ala Tyr Asn Thr Gln Asn Pro Gln Gln Val Ser Leu Ser Phe Gly Val
690                 695                 700

Leu Glu Val Thr Pro Gly Thr Gly Ala Lys Thr Val Thr Lys Glu Val
705                 710                 715                 720

Thr Val Glu Asn Ala Gly Gly Gln Gln Arg Thr Phe Arg Val Gly Phe
                725                 730                 735

Asp Ala Arg Thr Thr Ala Gly Val Gln Val Lys Thr Pro Glu Ser
            740                 745                 750

Val Ser Val Ala Ala Gly Ala Lys Ala Thr Phe Arg Val Ser Val Thr
            755                 760                 765

Val Asp Pro Glu Lys Leu Ala Lys Thr Leu Asp Ala Gly Thr Ala Arg
770                 775                 780

Asp Gln Gly Gly Arg Tyr Arg Gln Tyr Leu Ser Ser Val Ser Gly Asn
785                 790                 795                 800

Val Thr Leu Thr Asp Ser Ser Ser Thr Val Val Pro Leu His Ala
                805                 810                 815

Ala Pro Lys Pro Val Ser Glu Leu Met Val Pro Ser Ala Ser Leu Thr
            820                 825                 830

Phe Gly Thr Ser Gln Thr Ala Arg Ile Lys Pro Glu Gly Thr Pro Val
            835                 840                 845

Arg Arg Asn Gly Tyr Val Ser Gln Leu Gly Ala Phe Glu Leu Gly Tyr
```

```
            850                 855                 860
Glu Glu Ser Gly Pro Ala Pro Gly Ser Ser Ala Arg Ala Met Ala
865                 870                 875                 880

Val Gln Tyr Val Gly Ala Ser Ser Asn Leu Pro Ala Leu Gly Ala Ser
                885                 890                 895

Gly Ser Ser Gln Gly Arg Gly Val Ile Ser Phe Gly Val Ala Thr Arg
                900                 905                 910

Gly Asn Trp Asp Ala Leu Thr Pro Ala Tyr Ser Ile Glu Ile Glu Ile
            915                 920                 925

Asp Thr Asp Ser Asp Gly Tyr Ala Asp Tyr Ser Val Gln Val Lys Arg
            930                 935                 940

Gln Ile Gly Leu Asp Tyr Pro Val Ala Val Leu Ser Ser Arg Arg Ala
945                 950                 955                 960

Gly Ala Ser Arg Glu Val Asp Ala Leu Pro Val Asn Gly Val Trp Gly
                965                 970                 975

Asp Ile Asp Thr Asn Thr Phe Asp Thr Asn Val Ala Val Ile Pro Val
            980                 985                 990

Ala Ala Ser Ser Leu Gly Leu Thr Arg Gln Gly Ser Glu Pro Leu Gln
            995                 1000                1005

Tyr Arg Val Leu Thr Ser Leu Pro Leu Leu Gly Gln Thr Val Ser
    1010                1015                1020

Ala Thr Asp Trp Val Ser Phe Asn Pro Tyr Thr Pro Asn Leu Trp
    1025                1030                1035

Phe Asp Gly Gly Gln Gly Thr Gly Pro Ser Leu Phe Val Asp Ser
    1040                1045                1050

Pro Asp Ala Pro Val Thr Ala His Leu Arg Ser Gly Ala Ser Ala
    1055                1060                1065

Lys Met Leu Leu Leu His Leu His Asn Pro Ser Ala Ser Ala Thr
    1070                1075                1080

Gln Asn Thr Ser Gln Ala Ala Ser Ala Arg Val Gln Arg Ala Gln
    1085                1090                1095

Val Leu Glu Ala Arg Ser Gly Ser Ala Gly Pro Ser Asn Pro Ala
    1100                1105                1110

Pro Ala Pro Pro Ala Ser His Arg Phe Arg Asp Val Ser Pro Thr
    1115                1120                1125

His Pro Phe Tyr Thr Glu Ile Glu Trp Leu Ala Gly Glu Arg Ile
    1130                1135                1140

Thr Arg Gly Trp Pro Asp Gly Thr Tyr Arg Pro Gly Glu Asn Ile
    1145                1150                1155

Glu Arg Gly Ala Ile Ala Ala Tyr Phe Tyr Arg Met Ala Gly Ala
    1160                1165                1170

Pro Asp Phe Thr Pro Pro Val Val Ser Pro Phe Lys Asp Val Asp
    1175                1180                1185

Pro Ser His Pro Phe Tyr Arg Glu Ile Thr Trp Leu Ala Ser Lys
    1190                1195                1200

Gly Ile Thr Arg Gly Trp Gly Asp Gly Thr Phe Arg Pro His Glu
    1205                1210                1215

Pro Val Ser Arg Glu Ala Met Ala Ala Phe Phe Tyr Arg Tyr Ala
    1220                1225                1230

Asn Ser Pro Arg Phe Asn Ala Pro Gln Gln Ser Pro Phe Arg Asp
    1235                1240                1245

Val Arg Pro Ser Asp Pro Phe Tyr Arg Glu Ile Thr Trp Leu Ala
    1250                1255                1260
```

```
Ser Lys Gly Ile Thr Arg Gly Trp Gly Asp Gly Thr Phe Arg Pro
1265                1270                1275

Val Glu Pro Ile His Arg Asp Ala Met Ala Ala Phe Val Tyr Arg
1280                1285                1290

Phe Arg Gly Met Lys
        1295

<210> SEQ ID NO 48
<211> LENGTH: 1296
<212> TYPE: PRT
<213> ORGANISM: Rothia aeria

<400> SEQUENCE: 48

Met Phe Lys Pro His Gly Ala His Arg Ala Arg Met Leu Gly Val Ala
1               5                   10                  15

Ala Leu Ser Val Cys Thr Ala Leu Leu Gly Thr Pro Ala Thr Leu Ala
            20                  25                  30

Ala Pro Ala Gln Pro Ala Pro Ala Ser Thr Gly Pro Ala Thr Gln Gly
        35                  40                  45

Thr Val Glu Gly Ala Arg Gln Gly Glu Val Val Thr Ala Ser Met Lys
50                  55                  60

Glu Ala Thr Gly Thr Val Thr Ala Tyr Val Glu Leu Ala Gly Gln Gly
65                  70                  75                  80

Ala Tyr Gly Leu Ala Leu Asp Gly Gly Arg Arg Val Ser Pro Met
                85                  90                  95

Asn Gln Val Pro Pro Thr Ala Gln Ser Val Ala Ala His His Val
            100                 105                 110

Gln Ser Gln Val Val Thr Asn Ala Gln Ser Leu Ala Ala Ser Ser Asn
            115                 120                 125

Ser Gln Val Leu Tyr Thr Thr His Asn Leu Gln Arg Gly Val Ala Leu
130                 135                 140

Thr Gly Asp Ala Gln Ala Ile Arg Gly Leu Ala Gly His Pro Glu Val
145                 150                 155                 160

Val Arg Ile Ser Arg Ile Val Pro Lys Glu Arg Met Asn Ala Ile Ser
            165                 170                 175

Val Val Gly Thr Gly Ala Leu Glu Ala Trp Arg Ser Thr Gly Ala Thr
            180                 185                 190

Gly Arg Asp Val Thr Ile Ala Val Ile Asp Thr Gly Leu Asp Tyr Thr
            195                 200                 205

His Ala Asp Phe Gly Gly Pro Gly Thr Lys Ala Ala Tyr Asp Lys Ala
210                 215                 220

Asn Ser Ser Pro Thr Ile Pro Ala Gly Ser Tyr Asp Pro Gln Lys Val
225                 230                 235                 240

Val Gly Gly Tyr Asp Leu Val Gly Asp Ala Tyr Asn Gly Tyr Asn Ala
            245                 250                 255

Pro Ala Pro Asp Ser Asn Pro Met Asp Cys Ser Glu Ser Gly His Gly
            260                 265                 270

Thr His Val Ala Gly Thr Ala Ala Gly Tyr Gly Val Gly Ala Asp Gly
            275                 280                 285

Lys Thr Phe Arg Gly Glu Tyr Ser Lys Leu Ser Ser Ala Asp Val Gln
            290                 295                 300

Arg Leu His Ile Gly Pro Gly Ser Ala Pro Glu Ala Arg Leu Met Pro
305                 310                 315                 320

Leu Arg Ile Phe Gly Cys Ser Gly Ser Ser Ser Met Thr Gly Gln Ala
```

-continued

```
                325                 330                 335
Leu Asp Arg Ala Leu Asp Pro Asn Asn Asp Gly Asp Phe Ser Asp Gly
                340                 345                 350
Ala Asn Ile Val Asn Leu Ser Leu Gly Ser Asp Tyr Ser Thr Val Asp
                355                 360                 365
Asp Pro Glu Asn Thr Met Leu Gln Arg Leu Ile Asp Lys Gly Val Leu
                370                 375                 380
Ala Val Val Ala Ala Gly Asn Ala Gln Ala Asn Leu Ser Gln Gly Asp
385                 390                 395                 400
Val Tyr Ser Ile Met Gly Ala Pro Ala Asn Asn Pro Ser Ala Leu Thr
                405                 410                 415
Val Ala Asn Ser Glu Ser Ala Leu Thr Arg Ser Asp Arg Phe Glu Val
                420                 425                 430
Lys Gly Pro Ser Ala Val Ala Gly Ala Tyr Ala Gly Ser Tyr Ser Thr
                435                 440                 445
Leu Tyr Thr Phe Ala Ser Asn Asn Ala Arg Val Ser Gly Thr Val Thr
                450                 455                 460
Ala Ala Pro Glu Ser Asn Lys Thr Gly Cys Ala Pro Phe Thr Gly Thr
465                 470                 475                 480
Asn Phe Gly Gly Arg Trp Val Met Leu His Trp Glu Ala Ser Gly Ser
                485                 490                 495
Asp Ser Ser Cys Asp Ser Ala Arg Arg Phe Ala Asn Val Ala Ala Ala
                500                 505                 510
Asn Gly Lys Gly Val Leu Met Val Ala Pro Glu Asn Asp Asp Arg Pro
                515                 520                 525
Ile Ala Gly Ser Thr Thr Ile Pro Gly Val Leu Ile Ser Arg Ala Thr
                530                 535                 540
Ala Gln Thr Leu Tyr Pro Ala Val Lys Ala Gly Thr Leu Glu Val Glu
545                 550                 555                 560
Leu Glu Ala Ala Trp Arg Asn Thr Ala Leu Thr Ala Lys Gly Pro Asp
                565                 570                 575
Thr Leu Ala Ala Ser Ser Ala Arg Gly Val His Gly Ser Asp Gly Phe
                580                 585                 590
Val Lys Pro Asp Val Ala Ala Pro Gly Thr Asn Ile Tyr Ser Ala Gly
                595                 600                 605
Ala Gly Ser Gly Asn Gln Pro Phe Arg Leu Ser Gly Thr Ser Met Ala
                610                 615                 620
Thr Pro His Val Ala Gly Ile Ala Ala Gln Ile Leu Ser Lys Glu Pro
625                 630                 635                 640
Phe Leu Ser Gln Gln Gln Val Lys Ala Arg Ile Met Asn Thr Ala Ser
                645                 650                 655
Gln Glu Val Arg Thr Ile Ser Gly Glu Arg Leu Gly Val Asp Arg Val
                660                 665                 670
Gly Ala Gly Arg Val Asp Ala Gln Ala Ala Val Asn Glu Arg Thr Thr
                675                 680                 685
Ala Tyr Asn Thr Gln Asn Pro Gln Gln Val Ser Leu Ser Phe Gly Val
                690                 695                 700
Ile Glu Val Thr Pro Gly Thr Gly Ala Lys Thr Val Thr Lys Glu Val
705                 710                 715                 720
Thr Met Glu Asn Ala Gly Gly Gln Gln Arg Thr Phe Arg Val Gly Phe
                725                 730                 735
Asp Ala Arg Thr Thr Thr Ala Gly Val Gln Val Lys Thr Pro Glu Ser
                740                 745                 750
```

```
Val Ser Val Ala Ala Gly Thr Lys Ala Thr Phe Arg Val Ser Val Thr
        755                 760                 765

Val Asp Pro Glu Lys Leu Ala Lys Thr Leu Asp Ala Gly Thr Ala Arg
        770                 775                 780

Asp Gln Gly Gly Arg Tyr Arg Gln Tyr Leu Ser Ser Val Ser Gly Asn
785                 790                 795                 800

Val Thr Leu Thr Asp Ser Ser Thr Val Val Pro Leu His Ala
                805                 810                 815

Ala Pro Lys Pro Val Ser Glu Leu Met Val Pro Ser Ala Ser Leu Thr
                820                 825                 830

Phe Gly Thr Ser Gln Thr Ala Arg Val Lys Pro Glu Gly Thr Pro Val
            835                 840                 845

Arg Arg Asn Gly Tyr Val Ser Gln Leu Gly Ala Phe Glu Leu Gly Tyr
850                 855                 860

Glu Glu Ser Gly Pro Ala Pro Ser Ser Ser Ala Arg Ala Met Ala
865                 870                 875                 880

Val Gln Tyr Val Gly Ala Ser Ser Asn Leu Pro Ala Leu Gly Ala Ser
                885                 890                 895

Gly Ser Ser Gln Gly Arg Gly Val Ile Ser Phe Gly Val Ala Thr Arg
                900                 905                 910

Gly Asn Trp Asp Ala Leu Thr Pro Ala Tyr Gly Ile Glu Val Glu Ile
            915                 920                 925

Asp Thr Asp Ser Asp Gly Tyr Ala Asp Tyr Ser Val Gln Val Lys Arg
        930                 935                 940

Gln Ile Gly Leu Asp Tyr Pro Val Ala Val Leu Ser Ser His Arg Ala
945                 950                 955                 960

Gly Ala Ser Arg Glu Val Asp Ala Leu Pro Val Asn Gly Val Trp Gly
                965                 970                 975

Asp Ile Asp Thr Asn Thr Phe Asp Thr Asn Val Ala Val Ile Pro Val
            980                 985                 990

Ala Ala Ser Ser Leu Gly Leu Thr Arg Gln Gly Ser Glu Pro Leu Gln
        995                 1000                1005

Tyr Arg Val Leu Thr Arg Leu Pro Leu Leu Gly Gln Thr Val Ser
    1010                1015                1020

Ala Thr Asp Trp Val Ser Phe Asn Pro Tyr Thr Pro Asn Leu Trp
    1025                1030                1035

Phe Asp Gly Gly Gln Gly Thr Ser Pro Ser Leu Phe Val Asp Ser
    1040                1045                1050

Pro Asp Ala Pro Val Thr Ala His Leu Arg Ser Gly Ala Ser Ala
    1055                1060                1065

Lys Met Leu Leu Leu His Leu His Asn Pro Ser Ala Ser Ala Ala
    1070                1075                1080

Gln Asn Thr Ser Gln Val Ala Ser Ala Arg Val Gln Arg Ala Gln
    1085                1090                1095

Val Leu Glu Ala Arg Ser Gly Ser Ala Gly Pro Ser Asn Pro Ala
    1100                1105                1110

Pro Pro Ala Ser His Arg Phe Arg Asp Val Gly Pro Ala His Pro
    1115                1120                1125

Phe Tyr Thr Glu Ile Glu Trp Leu Ala Gly Glu Arg Ile Thr Arg
    1130                1135                1140

Gly Trp Pro Asp Gly Thr Tyr Arg Pro Gly Glu Asn Ile Glu Arg
    1145                1150                1155
```

-continued

```
Gly Ala Ile Ala Ala Tyr Phe Tyr Arg Met Ala Gly Ala Pro Asp
    1160                1165                1170

Phe Thr Pro Pro Val Val Ser Pro Phe Lys Asp Val Asp Pro Ser
    1175                1180                1185

His Pro Phe Tyr Arg Glu Ile Thr Trp Leu Ala Ser Lys Gly Ile
    1190                1195                1200

Thr Arg Gly Trp Gly Asp Gly Thr Phe Arg Pro His Glu Pro Val
    1205                1210                1215

Ser Arg Glu Ala Met Ala Ala Phe Phe Tyr Arg Tyr Ala Asn Ser
    1220                1225                1230

Pro Arg Phe Asn Ala Pro Gln Gln Ser Pro Phe Arg Asp Val Arg
    1235                1240                1245

Ser Ser Asp Pro Phe Tyr Arg Glu Ile Thr Trp Leu Ala Ser Lys
    1250                1255                1260

Gly Ile Thr Arg Gly Trp Gly Asp Gly Thr Phe Arg Pro Val Glu
    1265                1270                1275

Pro Ile His Arg Asp Ala Met Ala Ala Phe Val Tyr Arg Phe Arg
    1280                1285                1290

Gly Val Lys
    1295

<210> SEQ ID NO 49
<211> LENGTH: 1298
<212> TYPE: PRT
<213> ORGANISM: Rothia aeria

<400> SEQUENCE: 49

Met Phe Lys Pro His Gly Ala His Arg Ala Arg Met Leu Gly Val Ala
1               5                   10                  15

Ala Leu Ser Val Cys Thr Ala Leu Leu Gly Thr Pro Ala Ala Leu Ala
            20                  25                  30

Ala Pro Ala Gln Pro Ala Pro Ala Ser Ala Gly Pro Ala Thr Gln Gly
        35                  40                  45

Thr Val Glu Gly Ala Arg Gln Gly Glu Val Val Thr Ala Ser Met Lys
    50                  55                  60

Glu Ala Thr Gly Thr Val Thr Ala Tyr Val Glu Leu Ala Gly Gln Gly
65                  70                  75                  80

Ala Tyr Gly Leu Ala Leu Asp Gly Gly Gly Arg Arg Met Ser Pro Met
                85                  90                  95

Ser Gln Ala Ser Pro Thr Ala Gln Ser Val Ala Ala His His Val
            100                 105                 110

Gln Ser Gln Val Val Thr Asn Ala Gln Ser Leu Ala Ala Ser Ser Asn
        115                 120                 125

Ser Gln Val Leu Tyr Thr Thr His Asn Leu Gln Arg Gly Val Ala Leu
    130                 135                 140

Thr Gly Asp Ala Gln Ala Ile Arg Gly Leu Ala Gly His Pro Glu Val
145                 150                 155                 160

Val Arg Ile Ser Arg Ile Val Pro Lys Glu Arg Met Asn Ala Ile Ser
                165                 170                 175

Val Val Gly Thr Gly Ala Leu Glu Ala Trp Arg Ser Thr Gly Ala Thr
            180                 185                 190

Gly Arg Gly Val Thr Ile Ala Val Ile Asp Thr Gly Leu Asp Tyr Thr
        195                 200                 205

His Ala Asp Phe Gly Gly Pro Gly Thr Lys Ala Ala Tyr Asp Lys Ala
    210                 215                 220
```

-continued

```
Lys Ser Ser Pro Thr Met Pro Ala Gly Ser Tyr Asp Pro Gln Lys Val
225                 230                 235                 240

Val Gly Gly Tyr Asp Leu Val Gly Asp Ala Tyr Asn Gly Tyr Asn Ala
            245                 250                 255

Pro Ala Pro Asp Ser Asn Pro Met Asp Cys Ser Glu Ser Gly His Gly
        260                 265                 270

Thr His Val Ala Gly Thr Ala Ala Gly Tyr Gly Val Gly Ala Asp Gly
    275                 280                 285

Lys Thr Phe Arg Gly Glu Tyr Ser Lys Leu Ser Ser Ala Asp Val Gln
290                 295                 300

Arg Leu His Ile Gly Pro Gly Ser Ala Pro Glu Ala Arg Leu Met Pro
305                 310                 315                 320

Leu Arg Ile Phe Gly Cys Ser Gly Ser Ser Met Thr Gly Gln Ala
            325                 330                 335

Leu Asp Arg Ala Leu Asp Pro Asn Asn Asp Gly Asp Phe Ser Asp Gly
            340                 345                 350

Ala Asn Ile Val Asn Leu Ser Leu Gly Ser Asp Tyr Ser Thr Ala Asp
        355                 360                 365

Asp Pro Glu Asn Thr Met Leu Gln Arg Leu Ile Asp Lys Gly Val Leu
370                 375                 380

Ala Val Val Ala Ala Gly Asn Ala Gln Ala Asn Leu Ser Gln Gly Asp
385                 390                 395                 400

Val Tyr Ser Ile Met Gly Ala Pro Ala Asn Asn Pro Ser Ala Leu Thr
            405                 410                 415

Val Ala Asn Ser Glu Ser Ala Leu Thr Arg Ser Asp Arg Phe Glu Val
            420                 425                 430

Lys Gly Pro Ser Ala Val Ala Gly Ala Tyr Ala Gly Ser Tyr Ser Thr
            435                 440                 445

Leu Tyr Thr Phe Ala Ser Asn Asn Ala Arg Val Ser Gly Thr Val Thr
    450                 455                 460

Ala Ala Pro Glu Ser Asn Lys Thr Gly Cys Ala Pro Phe Thr Gly Thr
465                 470                 475                 480

Asn Phe Gly Gly Arg Trp Val Met Leu His Trp Glu Ala Ser Gly Ser
            485                 490                 495

Asp Pro Ser Cys Asp Ser Ala Arg Arg Phe Ala Asn Val Ala Ala Ala
        500                 505                 510

Asn Gly Lys Gly Val Leu Met Val Ala Pro Glu Asn Asp Asp Arg Pro
    515                 520                 525

Ile Ala Gly Ser Thr Thr Ile Pro Gly Val Leu Ile Ser Arg Ala Thr
    530                 535                 540

Ala Gln Thr Leu Tyr Pro Ala Val Lys Ala Gly Thr Leu Glu Val Glu
545                 550                 555                 560

Leu Gly Ala Ala Trp Arg Asn Thr Ala Leu Thr Ala Lys Gly Pro Asp
            565                 570                 575

Thr Leu Ala Ala Ser Ser Ala Arg Gly Val His Gly Ser Asp Gly Phe
            580                 585                 590

Val Lys Pro Asp Val Ala Ala Pro Gly Thr Asn Ile Tyr Ser Ala Gly
        595                 600                 605

Ala Gly Ser Gly Asn Gln Pro Phe Arg Leu Ser Gly Thr Ser Met Ala
    610                 615                 620

Thr Pro His Val Ala Gly Ile Ala Ala Gln Ile Leu Gly Lys Glu Pro
625                 630                 635                 640
```

Phe Leu Ser Gln Gln Gln Val Lys Ala Arg Ile Met Asn Thr Ala Ser
                645                 650                 655

Gln Glu Val Arg Thr Ile Ser Gly Glu Arg Leu Gly Val Asp Arg Val
            660                 665                 670

Gly Ala Gly Arg Val Asp Ala Gln Ala Val Asn Glu Arg Thr Thr
        675                 680                 685

Ala Tyr Asn Thr Gln Asn Pro Gln Gln Val Ser Leu Ser Phe Gly Val
    690                 695                 700

Leu Glu Val Thr Pro Gly Thr Gly Ala Lys Thr Val Thr Lys Glu Val
705                 710                 715                 720

Thr Val Glu Asn Ala Gly Gly Gln Gln Arg Thr Phe Arg Val Gly Phe
                725                 730                 735

Asp Ala Arg Thr Thr Thr Ala Gly Val Gln Val Lys Thr Pro Glu Ser
            740                 745                 750

Val Ser Val Ala Ala Gly Ala Lys Ala Thr Phe Arg Val Ser Val Thr
        755                 760                 765

Val Asp Pro Glu Lys Leu Ala Lys Thr Leu Asp Ala Gly Thr Ala Arg
    770                 775                 780

Asp Gln Gly Gly Arg Tyr Arg Gln Tyr Leu Ser Ser Val Ser Gly Asn
785                 790                 795                 800

Val Thr Leu Thr Asp Ser Ser Ser Thr Val Val Pro Leu His Ala
                805                 810                 815

Ala Pro Lys Pro Val Ser Glu Leu Met Val Pro Ser Ala Ser Leu Thr
            820                 825                 830

Phe Gly Thr Ser Gln Thr Ala Arg Ile Lys Pro Glu Gly Thr Pro Val
        835                 840                 845

Arg Arg Asn Gly Tyr Val Ser Gln Leu Gly Ala Phe Glu Leu Gly Tyr
    850                 855                 860

Glu Glu Ser Gly Pro Ala Pro Gly Ser Ser Ser Ala Arg Ala Met Ala
865                 870                 875                 880

Val Gln Tyr Val Gly Ala Ser Ser Asn Leu Pro Ala Leu Gly Ala Ser
                885                 890                 895

Gly Ser Ser Gln Gly Arg Gly Val Ile Ser Phe Gly Val Ala Thr Arg
            900                 905                 910

Gly Asn Trp Asp Ala Leu Thr Pro Ala Tyr Ser Ile Glu Ile Glu Ile
        915                 920                 925

Asp Thr Asp Ser Asp Gly Tyr Ala Asp Tyr Ser Val Gln Val Lys Arg
    930                 935                 940

Gln Ile Gly Leu Asp Tyr Pro Val Ala Val Leu Ser Ser Arg Arg Ala
945                 950                 955                 960

Gly Ala Ser Arg Glu Val Asp Ala Leu Pro Val Asn Gly Val Trp Gly
                965                 970                 975

Asp Ile Asp Thr Asn Thr Phe Asp Thr Asn Val Ala Val Ile Pro Val
            980                 985                 990

Ala Ala Ser Ser Leu Gly Leu Thr Arg Gln Gly Ser Glu Pro Leu Gln
        995                 1000                1005

Tyr Arg Val Leu Thr Ser Leu Pro Leu Leu Gly Gln Thr Val Ser
    1010                1015                1020

Ala Thr Asp Trp Val Ser Phe Asn Pro Tyr Thr Pro Asn Leu Trp
    1025                1030                1035

Phe Asp Gly Gly Gln Gly Thr Gly Pro Ser Leu Phe Val Asp Ser
    1040                1045                1050

Pro Asp Ala Pro Val Thr Ala His Leu Arg Ser Gly Ala Ser Ala

```
              1055                1060                1065

Lys  Met  Leu  Leu  Leu  His  Leu  His  Asn  Pro  Ser  Ala  Ser  Ala  Thr
          1070                1075                1080

Gln  Asn  Thr  Ser  Gln  Ala  Ala  Ser  Ala  Arg  Val  Gln  Arg  Ala  Gln
     1085                1090                1095

Val  Leu  Glu  Ala  Arg  Ser  Gly  Ser  Ala  Gly  Pro  Ser  Asn  Pro  Ala
1100                1105                1110

Pro  Ala  Pro  Pro  Ala  Ser  His  Arg  Phe  Arg  Asp  Val  Ser  Pro  Thr
1115                1120                1125

His  Pro  Phe  Tyr  Thr  Glu  Ile  Glu  Trp  Leu  Ala  Gly  Glu  Arg  Ile
1130                1135                1140

Thr  Arg  Gly  Trp  Pro  Asp  Gly  Thr  Tyr  Arg  Pro  Gly  Glu  Asn  Ile
     1145                1150                1155

Glu  Arg  Gly  Ala  Ile  Ala  Ala  Tyr  Phe  Tyr  Arg  Met  Ala  Gly  Ala
     1160                1165                1170

Pro  Asp  Phe  Thr  Pro  Pro  Val  Val  Ser  Pro  Phe  Lys  Asp  Val  Asp
1175                1180                1185

Pro  Ser  His  Pro  Phe  Tyr  Arg  Glu  Ile  Thr  Trp  Leu  Ala  Ser  Lys
1190                1195                1200

Gly  Ile  Thr  Arg  Gly  Trp  Gly  Asp  Gly  Thr  Phe  Arg  Pro  His  Glu
1205                1210                1215

Pro  Val  Ser  Arg  Glu  Ala  Met  Ala  Ala  Phe  Phe  Tyr  Arg  Tyr  Ala
1220                1225                1230

Asn  Ser  Pro  Arg  Phe  Asn  Ala  Pro  Gln  Gln  Ser  Pro  Phe  Arg  Asp
     1235                1240                1245

Val  Arg  Pro  Ser  Asp  Pro  Phe  Tyr  Arg  Glu  Ile  Thr  Trp  Leu  Ala
     1250                1255                1260

Ser  Lys  Gly  Ile  Thr  Arg  Gly  Trp  Gly  Asp  Gly  Thr  Phe  Arg  Pro
     1265                1270                1275

Val  Glu  Pro  Ile  His  Arg  Asp  Ala  Met  Ala  Ala  Phe  Val  Tyr  Arg
1280                1285                1290

Phe  Arg  Gly  Met  Lys
     1295

<210> SEQ ID NO 50
<211> LENGTH: 1301
<212> TYPE: PRT
<213> ORGANISM: Rothia aeria

<400> SEQUENCE: 50

Met  Gly  Gln  Ala  Arg  Cys  Thr  Leu  Ala  Thr  Ala  Leu  Ser  Leu  Ser  Leu
1                 5                   10                  15

Val  Thr  Thr  Thr  Ala  Phe  Pro  Val  Phe  Ala  Ala  Asp  Thr  Pro  Asp  Ser
              20                  25                  30

Ser  Val  Gln  Gln  Gly  Ala  Glu  Thr  Ser  Arg  Asp  Gln  Asn  Ile  Ile  Ser
         35                  40                  45

Pro  Ser  Ala  Ala  Ser  Ala  Ser  Gly  Glu  Thr  Ala  Val  Phe  Val  Gln  Phe
     50                  55                  60

Lys  Gly  Thr  Gly  Ala  Tyr  Glu  Leu  Thr  Arg  Pro  Ala  Ala  Gly  His  Ala
65                  70                  75                  80

Thr  Arg  Glu  Gln  Asn  Ala  Ala  Lys  Arg  Asp  Glu  Val  Arg  Ser  Ile  His
                 85                  90                  95

Ala  Trp  Val  Asn  Glu  Arg  Ala  Arg  Thr  Ala  Ala  Glu  Ala  Thr  Ser  Ser
             100                 105                 110
```

```
Lys Ile Leu Tyr Thr Thr Val Asn Thr Val Arg Gly Val Gly Leu Tyr
            115                 120                 125
Gly Asp Ile Glu Gln Ile Arg Lys Leu Ala Ala Arg Gln Asp Val Ala
        130                 135                 140
Arg Ile Ser Val Ile Thr Asn Val Arg Pro Gln Asn Ala Gly Thr Ala
145                 150                 155                 160
Val His Thr Asp Thr Leu Thr Thr Trp Ala Gln Lys Asn Asn Thr Gly
                165                 170                 175
Gly Tyr Gly Tyr Thr Gly Arg Asn Val Thr Val Ala Val Ile Asp Thr
            180                 185                 190
Gly Ile Asp Tyr Thr His Ala Asp Leu Gly Gly Pro Gly Thr Asp Glu
        195                 200                 205
Ala Tyr Arg Arg Ala Lys Asp Ser Ala Thr Leu Pro Asp Gly Leu Tyr
    210                 215                 220
Asp Pro Gln Lys Leu Val Gly Gly Tyr Asp Met Ala Gly Asp Gly Tyr
225                 230                 235                 240
Asn Ala Ser Thr Lys Glu His Ala Leu Pro Ile Pro Asp Ala Asn Pro
                245                 250                 255
Leu Asp Cys Ser Gly His Gly Thr His Val Ala Gly Thr Ile Ala Gly
            260                 265                 270
Tyr Gly Val Ala Ala Asp Asn Thr Ala Phe His Gly Asp Tyr Ser Ala
        275                 280                 285
Leu Ser Ala Asp Glu Leu His Arg Met Arg Ile Ala Pro Gly Ala Ala
    290                 295                 300
Pro Glu Ala Arg Leu Val Ala Phe Arg Ile Phe Gly Cys Ala Gly Thr
305                 310                 315                 320
Ser Ala Leu Thr Leu Lys Ala Leu Asp Arg Val Leu Asp Pro Asn Asp
                325                 330                 335
Asp Gly Asp Phe Ser Asp Arg Ala Asp Ile Val Asn Leu Ser Ala Gly
            340                 345                 350
Thr Asp Tyr Gly Val Phe Asp Glu Ser Thr Asn Tyr Ala Ile Gly Glu
        355                 360                 365
Leu Tyr Arg Gln Gly Val Leu Thr Val Thr Ala Ala Gly Asn Ala Ala
    370                 375                 380
Ser Gln Asn Gly Ala Gly Asp Thr Tyr Ser Ile Ser Gly Gly Pro Ala
385                 390                 395                 400
Thr Ser Ala Tyr Ala Leu Thr Val Ala Asn Ser Met Gly Ala Thr Gln
                405                 410                 415
Ser Ala Asp Arg Val Lys Val Leu Ser Pro Ala Gly Thr Ser Glu Ile
            420                 425                 430
Tyr Gly Arg Tyr Thr Thr Lys Tyr Asp Tyr Ala Arg Tyr Arg Glu Gly
        435                 440                 445
Glu Leu Thr Gly Gln Val Val Lys Ala Pro Ala Ser Asn Leu Tyr Gly
    450                 455                 460
Cys Ala Pro Phe Thr Ala Glu Glu Ala Arg Leu Lys Gly Lys Trp
465                 470                 475                 480
Val Tyr Leu Asp Trp Asp Asn Thr Ser Gly Ala Val Pro Cys Gly Ser
                485                 490                 495
Ala Val Arg Phe Ala Asn Val Glu Arg Ala Gly Ala Gly Val Val
            500                 505                 510
Leu Gly Thr Arg Gln Pro Leu Thr Asp Ile Ala Gly Thr Ala Ala Leu
        515                 520                 525
Pro Gly Val Leu Leu Pro Ser Glu Gln Ala Glu Lys Ile Arg Pro Ala
```

-continued

```
            530                 535                 540
Leu Ala Ser Gly Thr Leu Thr Leu Arg Leu Asp Asp Ala Leu Arg Thr
545                 550                 555                 560

Gly Ala Arg Ile Glu Thr Gly Ala Ala Asp Gln Pro Asn Pro Ala Ser
                565                 570                 575

Ala Arg Gly Ala His Gly Ser Trp Gly Ser Ile Lys Pro Asp Val Ser
                580                 585                 590

Ala Pro Gly Thr Gly Ile Ala Ser Ala Arg Ala Gly Ser Gly Ala Gly
                595                 600                 605

Ala Ser Thr Leu Thr Gly Thr Ser Met Ser Ala Ala Tyr Val Cys Gly
                610                 615                 620

Val Ala Ala Gln Leu Val Glu Glu His Arg Ser Tyr Ser Pro Gln Gln
625                 630                 635                 640

Leu Lys Ala Thr Leu Met Asn Thr Ala Ala His Pro Val His Asp Ala
                645                 650                 655

His Asn Arg Pro Tyr Pro Pro Asp Arg Val Gly Ser Gly Arg Ile Asp
                660                 665                 670

Ser Ala Lys Ala Val Asn Asn Arg Val Leu Val Tyr Asn Ala Ala Arg
                675                 680                 685

Pro Glu Gln Val Ser Asp Thr Phe Gly Val Leu Glu Tyr Ala Pro Asp
                690                 695                 700

Ala Pro Val Ser Val Leu Arg Arg Glu Met Val Val Glu Asn Thr Asp
705                 710                 715                 720

Thr Ile Ala His Thr Tyr Leu Leu Ser Tyr Thr Ala Ser Thr Glu Ile
                725                 730                 735

Ser Gly Val Ala Tyr Ser Leu Pro Glu Ser Val Thr Val Pro Pro Gly
                740                 745                 750

Gly Arg Thr Thr Phe Thr Val Thr Leu Thr Val Asp Pro Ala Ala Leu
                755                 760                 765

Ala Lys Thr Ala Glu Ala Thr Ala Asn Thr Thr Gln Arg Ser Thr Gly
                770                 775                 780

Glu Asp Gly Gln Val Val Ala Phe Gly Ala Arg Gln Tyr Val Ala Ser
785                 790                 795                 800

Ala Ser Gly Gln Val Val Leu Thr Glu Gly Asp Thr Thr Leu Arg Val
                805                 810                 815

Pro Val His Ala Ala Pro Lys Leu Val Ser Lys Met Arg Val Ala Ala
                820                 825                 830

Ala Glu Val Gln Phe Glu Arg Gly Gln Gln Ala Gln Leu Pro Leu
                835                 840                 845

Ser Gly Thr Gly Val Asp Gln Gly Gly Tyr Arg Ser Leu Leu Gly Ala
850                 855                 860

Phe Glu Leu Gly Val Thr Ser Gly His Ile Pro Thr Glu Asp Leu Ser
865                 870                 875                 880

Val Ser Ser Asp Gln Arg Ala Asp Ile Gln Tyr Ala Gly Ala Ala Ser
                885                 890                 895

Asp Ala Ala Leu Ala Ala Ala Gly Lys Asn Pro Asn Asp Gly Ser
                900                 905                 910

Leu Tyr Phe Gly Ile Ser Thr Trp Gly Asn Trp Ser Glu Val Thr Pro
                915                 920                 925

Arg Ser Thr Tyr Tyr Val Phe Ile Asp Thr Asp Gly Asp Gly Thr Asn
                930                 935                 940

Asp Tyr Arg Leu His Thr Met Arg Ala Ala Gly Val Asp Tyr Pro Leu
945                 950                 955                 960
```

Val Gln Leu Ser Arg Ala Asp Asn Gly Arg Trp Val Pro Val Asp Gly
            965                 970                 975

Ala Leu Tyr Pro Leu Asn Asn Thr Trp Gly Ser Thr Asp Thr Asn Thr
            980                 985                 990

Met Asp Ser Asn Thr Leu Ile Met Gly Val Pro Leu Arg Arg Leu Gly
            995                 1000                1005

Leu Ser Thr Gln Asn Pro Gly Ser Leu Ser Tyr Thr Val Ala Thr
        1010                1015                1020

Thr Ser Ser Tyr Ala Thr Thr Pro Ile Val Asp Ala Thr Glu Ala
        1025                1030                1035

Val Lys Phe Asn Pro Phe Thr Pro Thr Phe Trp Phe Thr Gly Thr
        1040                1045                1050

Ala Ser Gly Val Pro Gly Leu Phe Val Asp Ala Pro Asn Ala Ser
        1055                1060                1065

Leu Thr Val His Arg Thr Glu Gly Ala Glu Gly Lys Leu Leu Leu
        1070                1075                1080

Leu His Leu His Asn Ser Thr Gly Asn Leu Asn Gly Ala Gln Gly
        1085                1090                1095

Ala Thr Gly Asp Arg Ala Gln Val Leu Asn Val Ser Gly Glu Asn
        1100                1105                1110

Thr His Asn Thr Leu Arg Ala Arg Phe Thr Asp Val Asn Asp Ala
        1115                1120                1125

Asn Thr Ala Thr Pro Asp Ile Asp Trp Leu Ala Glu Arg Arg Ile
        1130                1135                1140

Thr Arg Gly Tyr Pro Gly Gly Thr Phe His Pro Gly Glu Asp Thr
        1145                1150                1155

Glu Arg Gly Ala Ala Ala Phe Phe Tyr Arg Leu Ala Gly Ser
        1160                1165                1170

Pro Ala Tyr Thr Pro Pro Gln Ser Pro Phe Thr Asp Val Pro
        1175                1180                1185

Thr Asn His Pro Phe Tyr Lys Glu Ile Ala Trp Met His Gln Ala
        1190                1195                1200

Gly Ile Thr Thr Gly Trp Ala Asp Gly Thr Phe Arg Pro His Glu
        1205                1210                1215

Ala Ala Thr Arg Glu Ala Met Ala Ala Phe Phe Tyr Arg Ala Ala
        1220                1225                1230

Gly Ser Pro Ala Tyr Met Pro Pro Glu Lys Ser Pro Phe Glu Asp
        1235                1240                1245

Val Pro Thr Gly Ala Arg Phe Tyr Arg Glu Ile Thr Trp Ala Tyr
        1250                1255                1260

Glu Lys Lys Ile Phe Thr Glu Glu Thr Ser Leu Leu Lys Pro Ala
        1265                1270                1275

Ala Thr Val Arg Arg Glu Ala Ala Ala Thr Met Ile His Arg Tyr
        1280                1285                1290

Ala Arg Gln Val Leu His Arg Gly
        1295                1300

<210> SEQ ID NO 51
<211> LENGTH: 1299
<212> TYPE: PRT
<213> ORGANISM: Rothia aeria

<400> SEQUENCE: 51

Met Gly Gln Ala Arg Cys Thr Leu Ala Thr Ala Leu Ser Leu Ser Leu

-continued

```
1               5               10              15
Val Thr Thr Ala Ala Phe Pro Val Phe Ala Ala Asp Thr Pro Asp Ser
                20              25              30
Ser Val Gln Gln Gly Ala Glu Thr Ser Arg Asp Gln Asn Ile Ile Ser
        35              40                      45
Pro Ser Ala Ala Ser Ala Ser Gly Glu Thr Ala Val Phe Val Gln Phe
        50              55              60
Lys Gly Thr Gly Ala Tyr Glu Leu Thr Arg Pro Ala Thr Gly Arg Ala
 65                     70              75                      80
Thr Arg Glu Gln Asn Ala Ala Lys Arg Asp Glu Val Arg Ser Ile His
                85              90                      95
Ala Trp Val Asn Glu Arg Ala Arg Thr Ala Ala Glu Ala Thr Ser Ser
                100             105             110
Lys Ile Leu Tyr Thr Thr Val Asn Thr Val Arg Gly Val Gly Leu Tyr
                115             120             125
Gly Asp Ile Glu Gln Ile Arg Lys Leu Ala Ala Arg Gln Asp Val Ala
        130             135             140
Arg Ile Ser Val Ile Thr Asn Val Arg Pro Gln Asn Ala Gly Thr Ala
145             150             155             160
Thr Asp Thr Leu Thr Thr Trp Ala Gln Lys Asn Asn Thr Gly Tyr
                165                     170             175
Gly Tyr Thr Gly Arg Asn Val Thr Val Ala Val Ile Asp Thr Gly Ile
                180             185             190
Asp Tyr Thr His Ala Asp Leu Gly Gly Pro Gly Thr Asp Glu Ala Tyr
                195             200             205
Arg Arg Ala Lys Asp Ser Ala Thr Leu Pro Asp Gly Leu Tyr Asp Pro
        210             215             220
Gln Lys Leu Val Gly Gly Tyr Asp Met Ala Gly Asp Gly Tyr Asn Ala
225             230             235             240
Ser Thr Lys Glu Arg Ala Leu Pro Ile Pro Asp Ala Asn Pro Leu Asp
                245             250             255
Cys Ser Gly His Gly Thr His Val Ala Gly Thr Ile Ala Gly Tyr Gly
                260             265             270
Val Gly Ala Asp Asn Thr Ala Phe His Gly Asp Tyr Ser Ala Leu Ser
                275             280             285
Ala Asp Ala Leu His Arg Met Arg Val Ala Pro Gly Ala Ala Pro Glu
        290             295             300
Ala Arg Leu Val Ala Phe Arg Ile Phe Gly Cys Ala Gly Thr Ser Ala
305             310             315             320
Leu Thr Leu Lys Ala Leu Asp Arg Val Leu Asp Pro Asn Asp Asp Gly
                325             330             335
Asp Phe Ser Asp Arg Ala Asp Ile Val Asn Leu Ser Val Gly Thr Asp
                340             345             350
Tyr Gly Val Phe Asp Glu Ser Thr Asn Tyr Ala Ile Gly Glu Leu Tyr
                355             360             365
Arg Gln Gly Val Leu Thr Val Thr Ala Ala Gly Asn Ala Ala Ser Gln
        370             375             380
Asn Gly Ala Gly Asp Thr Tyr Ser Ile Ser Gly Pro Ala Thr Ser
385             390             395             400
Ala Tyr Ala Leu Thr Val Ala Asn Ser Met Gly Ala Thr Gln Ser Ala
                405             410             415
Asp Arg Val Lys Val Leu Ser Pro Ala Gly Thr Ser Glu Ile Tyr Gly
                420             425             430
```

```
Arg Tyr Thr Thr Lys Tyr Asp Tyr Ala Arg His Arg Glu Gly Glu Leu
            435                 440                 445

Thr Gly Gln Val Val Lys Ala Pro Ala Ser Asn Pro Tyr Gly Cys Ala
    450                 455                 460

Pro Phe Thr Ala Glu Glu Ala Ala Arg Leu Lys Gly Lys Trp Val Tyr
465                 470                 475                 480

Leu Asp Trp Asp Asn Thr Ser Gly Ala Val Pro Cys Gly Ser Ala Val
                485                 490                 495

Arg Phe Ala Asn Val Glu Arg Ala Gly Gly Ala Gly Val Val Leu Gly
                500                 505                 510

Thr Arg Gln Pro Leu Thr Asp Ile Ala Gly Thr Ala Ala Leu Pro Gly
    515                 520                 525

Val Leu Leu Pro Ser Glu Gln Ala Glu Lys Ile Arg Pro Ala Leu Ala
530                 535                 540

Ser Gly Thr Leu Thr Leu Arg Leu Asp Gly Ala Leu Arg Thr Gly Ala
545                 550                 555                 560

Arg Ile Glu Thr Arg Ala Ala Asp Gln Pro Asn Pro Ala Ser Ala Arg
                565                 570                 575

Gly Ala His Gly Ser Trp Gly Ser Ile Lys Pro Asp Val Ser Ala Pro
                580                 585                 590

Gly Thr Gly Ile Ala Ser Ala Arg Ala Gly Ser Gly Ala Gly Ala Ser
            595                 600                 605

Thr Leu Thr Gly Thr Ser Met Ser Ala Ala Tyr Val Cys Gly Val Ala
    610                 615                 620

Ala Gln Leu Val Glu Glu His Arg Ser Tyr Ser Pro Gln Gln Leu Lys
625                 630                 635                 640

Ala Thr Leu Met Asn Thr Ala Ala His Pro Val His Asp Ala His Asn
                645                 650                 655

Arg Pro Tyr Pro Pro Asp Arg Val Gly Ser Gly Arg Ile Asp Ser Thr
                660                 665                 670

Lys Ala Val Asn Asn Arg Val Leu Val Tyr Asn Ala Ala Arg Pro Glu
    675                 680                 685

Gln Val Ser Asp Thr Phe Gly Val Leu Glu Tyr Ala Pro Asp Ala Pro
    690                 695                 700

Val Ser Val Leu Arg Arg Glu Met Val Val Glu Asn Thr Asp Thr Ile
705                 710                 715                 720

Ala His Thr Tyr Leu Leu Ser Tyr Thr Ala Ser Thr Glu Val Pro Gly
                725                 730                 735

Val Ala Tyr Ser Leu Pro Glu Ser Val Thr Val Pro Pro Gly Gly Arg
                740                 745                 750

Thr Thr Phe Thr Val Thr Leu Thr Val Asp Pro Ala Ala Leu Ala Lys
            755                 760                 765

Thr Ala Glu Ala Thr Ala Asn Thr Ala Gln Arg Ser Thr Gly Glu Asp
    770                 775                 780

Gly Gln Val Val Ala Phe Gly Ala Arg Gln Tyr Val Ser Ala Ser
785                 790                 795                 800

Gly Gln Val Val Leu Thr Glu Gly Asp Thr Thr Leu Arg Val Pro Val
                805                 810                 815

His Ala Ala Pro Lys Leu Val Ser Lys Met Arg Val Ala Ala Ala Glu
                820                 825                 830

Val Gln Phe Glu Arg Gly Glu Gln Gln Ala Gln Leu Pro Leu Ser Gly
                835                 840                 845
```

Thr Gly Val Asp Gln Gly Gly Tyr Arg Ser Leu Leu Gly Ala Phe Glu
850                 855                 860

Leu Gly Val Thr Ser Gly His Ile Pro Thr Glu Asp Leu Ser Val Ser
865                 870                 875                 880

Ser Asp Gln Arg Ala Asp Ile Gln Tyr Ala Gly Ala Ala Ser Asp Ala
            885                 890                 895

Ala Ala Leu Ala Ala Ala Gly Lys Asn Pro Asn Asp Gly Ser Leu Tyr
        900                 905                 910

Phe Gly Ile Ser Thr Trp Gly Asn Trp Ser Glu Val Thr Pro Arg Ser
        915                 920                 925

Thr Tyr Tyr Val Phe Ile Asp Thr Asp Gly Asp Gly Thr Asn Asp Tyr
    930                 935                 940

Arg Leu His Thr Met Arg Ala Ala Gly Val Asp Tyr Pro Leu Val Gln
945                 950                 955                 960

Leu Ser Arg Ala Asp Asn Asp Arg Trp Val Pro Val Asp Gly Ala Leu
            965                 970                 975

Tyr Pro Leu Asn Asn Thr Trp Gly Ser Thr Asp Thr Asn Thr Met Asp
        980                 985                 990

Ser Asn Thr Leu Ile Met Gly Val Pro Leu Arg Arg Leu Gly Leu Ser
        995                 1000                1005

Thr Gln Asn Pro Gly Ser Leu Ser Tyr Thr Val Ala Thr Thr Ser
    1010                1015                1020

Ser Tyr Ala Thr Thr Pro Ile Val Asp Ala Thr Glu Ala Val Lys
    1025                1030                1035

Phe Asn Pro Phe Thr Pro Thr Phe Trp Phe Thr Gly Thr Ala Ser
    1040                1045                1050

Gly Val Pro Gly Leu Phe Val Asp Ala Pro Asn Ala Ser Leu Thr
    1055                1060                1065

Val His Arg Thr Glu Gly Ala Glu Gly Lys Leu Leu Leu Leu His
    1070                1075                1080

Leu His Asn Ser Thr Gly Asn Leu Asn Gly Ala Gln Gly Ala Thr
    1085                1090                1095

Gly Asp Arg Ala Gln Val Leu Asn Val Ser Gly Glu Asn Thr His
    1100                1105                1110

Asn Thr Leu Arg Ala Arg Phe Thr Asp Val Asn Asp Ala Asn Thr
    1115                1120                1125

Ala Thr Pro Asp Ile Asp Trp Leu Ala Glu Arg Arg Ile Thr Arg
    1130                1135                1140

Gly Tyr Pro Gly Gly Thr Phe His Pro Gly Glu Asp Thr Glu Arg
    1145                1150                1155

Gly Ala Ala Ala Ala Phe Phe Tyr Arg Leu Ala Gly Ser Pro Ala
    1160                1165                1170

Tyr Thr Pro Pro Gln Gln Ser Pro Phe Thr Asp Val Pro Thr Asn
    1175                1180                1185

His Pro Phe Tyr Lys Glu Ile Ala Trp Met His Gln Ala Gly Ile
    1190                1195                1200

Thr Thr Gly Trp Ala Asp Gly Thr Phe Arg Pro His Glu Ala Ala
    1205                1210                1215

Thr Arg Glu Ala Met Ala Ala Phe Phe Tyr Arg Ala Ala Gly Ser
    1220                1225                1230

Pro Ala Tyr Met Pro Pro Glu Lys Ser Pro Phe Glu Asp Val Pro
    1235                1240                1245

Thr Gly Ala Arg Phe Tyr Arg Glu Ile Thr Trp Ala Tyr Glu Lys

```
                1250                1255                1260
Lys Ile Phe Thr Glu Glu Thr  Ser Leu Leu Lys Pro  Ala Ala Thr
                1265                1270                1275

Val Arg Arg Glu Ala Ala Ala  Thr Met Ile His Arg  Tyr Ala Arg
                1280                1285                1290

Gln Val Leu His Arg Gly
                1295

<210> SEQ ID NO 52
<211> LENGTH: 1301
<212> TYPE: PRT
<213> ORGANISM: Rothia aeria

<400> SEQUENCE: 52

Met Gly Gln Ala Arg Cys Thr Leu Ala Thr Ala Leu Ser Leu Ser Leu
1               5                   10                  15

Val Thr Thr Thr Ala Phe Pro Val Phe Ala Ala Asp Thr Pro Asp Ser
                20                  25                  30

Ser Val Gln Gln Gly Ala Glu Thr Ser Arg Asp Gln Asn Ile Ile Ser
            35                  40                  45

Pro Ser Ala Ala Ser Ala Ser Gly Glu Thr Ala Val Phe Val Gln Phe
        50                  55                  60

Lys Gly Thr Gly Ala Tyr Glu Leu Thr Arg Pro Ala Ala Gly His Ala
65                  70                  75                  80

Thr Arg Glu Gln Asn Ala Ala Lys Arg Asp Glu Val Arg Ser Ile His
                85                  90                  95

Ala Trp Val Asn Glu Arg Ala Arg Thr Ala Ala Glu Ala Thr Ser Ser
            100                 105                 110

Lys Ile Leu Tyr Thr Thr Val Asn Thr Val Arg Gly Val Gly Leu Tyr
        115                 120                 125

Gly Asp Ile Glu Gln Ile Arg Lys Leu Ala Ala Arg Gln Asp Val Ala
    130                 135                 140

Arg Ile Ser Val Ile Thr Asn Val Arg Pro Gln Asn Ala Gly Thr Ala
145                 150                 155                 160

Val His Thr Asp Thr Leu Thr Thr Trp Ala Gln Lys Asn Asn Thr Gly
                165                 170                 175

Gly Tyr Gly Tyr Thr Gly Arg Asn Val Thr Val Ala Val Ile Asp Thr
            180                 185                 190

Gly Ile Asp Tyr Thr His Ala Asp Leu Gly Gly Pro Gly Thr Asp Glu
        195                 200                 205

Ala Tyr Arg Arg Ala Lys Asp Ser Ala Thr Leu Pro Asp Gly Leu Tyr
    210                 215                 220

Asp Pro Gln Lys Leu Val Gly Gly Tyr Asp Met Ala Gly Asp Gly Tyr
225                 230                 235                 240

Asn Ala Ser Thr Lys Glu His Ala Leu Pro Ile Pro Asp Ala Asn Pro
                245                 250                 255

Leu Asp Cys Ser Gly His Gly Thr His Val Ala Gly Thr Ile Ala Gly
            260                 265                 270

Tyr Gly Val Ala Ala Asp Asn Thr Ala Phe His Gly Asp Tyr Ser Ala
        275                 280                 285

Leu Ser Ala Asp Glu Leu His Arg Met Arg Ile Ala Pro Gly Ala Ala
    290                 295                 300

Pro Glu Ala Arg Leu Val Ala Phe Arg Ile Phe Gly Cys Ala Gly Thr
305                 310                 315                 320
```

```
Ser Ala Leu Thr Leu Lys Ala Leu Asp Arg Val Leu Asp Pro Asn Asp
            325                 330                 335

Asp Gly Asp Phe Ser Asp Arg Ala Asp Ile Val Asn Leu Ser Ala Gly
        340                 345                 350

Thr Asp Tyr Gly Val Phe Asp Glu Ser Thr Asn Tyr Ala Ile Gly Glu
    355                 360                 365

Leu Tyr Arg Gln Gly Val Leu Thr Val Thr Ala Ala Gly Asn Ala Ala
370                 375                 380

Ser Gln Asn Gly Ala Gly Asp Thr Tyr Ser Ile Ser Gly Gly Pro Ala
385                 390                 395                 400

Thr Ser Ala Tyr Ala Leu Thr Val Ala Asn Ser Met Gly Ala Thr Gln
                405                 410                 415

Ser Ala Asp Arg Val Lys Val Leu Ser Pro Ala Gly Thr Ser Glu Ile
            420                 425                 430

Tyr Gly Arg Tyr Thr Thr Lys Tyr Asp Tyr Ala Arg Tyr Arg Glu Gly
        435                 440                 445

Glu Leu Thr Gly Gln Val Val Lys Ala Pro Ala Ser Asn Leu Tyr Gly
    450                 455                 460

Cys Ala Pro Phe Thr Ala Glu Glu Ala Ala Arg Leu Lys Gly Lys Trp
465                 470                 475                 480

Val Tyr Leu Asp Trp Asp Asn Thr Ser Gly Ala Val Pro Cys Gly Ser
                485                 490                 495

Ala Val Arg Phe Ala Asn Val Glu Arg Ala Gly Gly Ala Gly Val Val
            500                 505                 510

Leu Gly Thr Arg Gln Pro Leu Thr Asp Ile Ala Gly Thr Ala Ala Leu
        515                 520                 525

Pro Gly Val Leu Leu Pro Ser Glu Gln Ala Glu Lys Ile Arg Pro Ala
530                 535                 540

Leu Ala Ser Gly Thr Leu Thr Leu Arg Leu Asp Asp Ala Leu Arg Thr
545                 550                 555                 560

Gly Ala Arg Ile Glu Thr Gly Ala Ala Asp Gln Pro Asn Pro Ala Ser
                565                 570                 575

Ala Arg Gly Ala His Gly Ser Trp Gly Ser Ile Lys Pro Asp Val Ser
            580                 585                 590

Ala Pro Gly Thr Gly Ile Ala Ser Ala Arg Ala Gly Ser Gly Ala Gly
        595                 600                 605

Ala Ser Thr Leu Thr Gly Thr Ser Met Ser Ala Ala Tyr Val Cys Gly
610                 615                 620

Val Ala Ala Gln Leu Val Glu Glu His Arg Ser Tyr Ser Pro Gln Gln
625                 630                 635                 640

Leu Lys Ala Thr Leu Met Asn Thr Ala Ala His Pro Val His Asp Ala
                645                 650                 655

His Asn Arg Pro Tyr Pro Pro Asp Arg Val Gly Ser Gly Arg Ile Asp
            660                 665                 670

Ser Ala Lys Ala Val Asn Asn Arg Val Leu Val Tyr Asn Ala Ala Arg
        675                 680                 685

Pro Glu Gln Val Ser Asp Thr Phe Gly Val Leu Glu Tyr Ala Pro Asp
690                 695                 700

Ala Pro Val Ser Val Leu Arg Arg Glu Met Val Glu Asn Thr Asp
705                 710                 715                 720

Thr Ile Ala His Thr Tyr Leu Leu Ser Tyr Thr Ala Ser Thr Glu Ile
                725                 730                 735

Ser Gly Val Ala Tyr Ser Leu Pro Glu Ser Val Thr Val Pro Pro Gly
```

```
                740             745             750
Gly Arg Thr Thr Phe Thr Val Thr Leu Thr Val Asp Pro Ala Ala Leu
            755             760             765
Ala Lys Thr Ala Glu Ala Thr Ala Asn Thr Thr Gln Arg Ser Thr Gly
        770             775             780
Glu Asp Gly Gln Val Val Ala Phe Gly Ala Arg Gln Tyr Val Ala Ser
785             790             795             800
Ala Ser Gly Gln Val Val Leu Thr Glu Gly Asp Thr Thr Leu Arg Val
                805             810             815
Pro Val His Ala Ala Pro Lys Leu Val Ser Lys Met Arg Val Ala Ala
            820             825             830
Ala Glu Val Gln Phe Glu Arg Gly Gln Gln Ala Gln Leu Pro Leu
        835             840             845
Ser Gly Thr Gly Val Asp Gln Gly Gly Tyr Arg Ser Leu Leu Gly Ala
        850             855             860
Phe Glu Leu Gly Val Thr Ser Gly His Ile Pro Thr Glu Asp Leu Ser
865             870             875             880
Val Ser Ser Asp Gln Arg Ala Asp Ile Gln Tyr Ala Gly Ala Ala Ser
                885             890             895
Asp Ala Ala Leu Ala Ala Gly Lys Asn Pro Asn Asp Gly Ser
            900             905             910
Leu Tyr Phe Gly Ile Ser Thr Trp Gly Asn Trp Ser Glu Val Thr Pro
            915             920             925
Arg Ser Thr Tyr Tyr Val Phe Ile Asp Thr Asp Gly Asp Thr Asn
        930             935             940
Asp Tyr Arg Leu His Thr Met Arg Ala Ala Gly Val Asp Tyr Pro Leu
945             950             955             960
Val Gln Leu Ser Arg Ala Asp Asn Gly Arg Trp Val Pro Val Asp Gly
                965             970             975
Ala Leu Tyr Pro Leu Asn Asn Thr Trp Gly Ser Thr Asp Asn Thr
            980             985             990
Met Asp Ser Asn Thr Leu Ile Met Gly Val Pro Leu Arg Arg Leu Gly
            995             1000            1005
Leu Ser Thr Gln Asn Pro Gly Ser Leu Ser Tyr Thr Val Ala Thr
    1010            1015            1020
Thr Ser Ser Tyr Ala Thr Thr Pro Ile Val Asp Ala Thr Glu Ala
    1025            1030            1035
Val Lys Phe Asn Pro Phe Thr Pro Thr Phe Trp Phe Thr Gly Thr
    1040            1045            1050
Ala Ser Gly Val Pro Gly Leu Phe Val Asp Ala Pro Asn Ala Ser
    1055            1060            1065
Leu Thr Val His Arg Thr Glu Gly Ala Glu Gly Lys Leu Leu Leu
    1070            1075            1080
Leu His Leu His Asn Ser Thr Gly Asn Leu Asn Gly Ala Gln Gly
    1085            1090            1095
Ala Thr Gly Asp Arg Ala Gln Val Leu Asn Val Ser Gly Glu Asn
    1100            1105            1110
Thr His Asn Thr Leu Arg Ala Arg Phe Thr Asp Val Asn Asp Ala
    1115            1120            1125
Asn Thr Ala Thr Pro Asp Ile Asp Trp Leu Ala Glu Arg Arg Ile
    1130            1135            1140
Thr Arg Gly Tyr Pro Gly Gly Thr Phe His Pro Gly Glu Asp Thr
    1145            1150            1155
```

```
Glu Arg Gly Ala Ala Ala Ala Phe Phe Tyr Arg Leu Ala Gly Ser
    1160                1165                1170

Pro Ala Tyr Thr Pro Pro Gln Gln Ser Pro Phe Thr Asp Val Pro
    1175                1180                1185

Thr Asn His Pro Phe Tyr Lys Glu Ile Ala Trp Met His Gln Ala
    1190                1195                1200

Gly Ile Thr Thr Gly Trp Ala Asp Gly Thr Phe Arg Pro His Glu
    1205                1210                1215

Ala Ala Thr Arg Glu Ala Met Ala Ala Phe Phe Tyr Arg Ala Ala
    1220                1225                1230

Gly Ser Pro Ala Tyr Met Pro Pro Glu Lys Ser Pro Phe Glu Asp
    1235                1240                1245

Val Pro Thr Gly Ala Arg Phe Tyr Arg Glu Ile Thr Trp Ala Tyr
    1250                1255                1260

Glu Lys Lys Ile Phe Thr Glu Glu Thr Ser Leu Leu Lys Pro Ala
    1265                1270                1275

Ala Thr Val Arg Arg Glu Ala Ala Ala Thr Met Ile His Arg Tyr
    1280                1285                1290

Ala Arg Gln Val Leu His Arg Gly
    1295                1300

<210> SEQ ID NO 53
<211> LENGTH: 1299
<212> TYPE: PRT
<213> ORGANISM: Rothia aeria

<400> SEQUENCE: 53

Met Gly Gln Ala Arg Cys Thr Leu Ala Thr Ala Leu Ser Leu Ser Leu
1               5                   10                  15

Val Thr Thr Ala Ala Phe Pro Val Phe Ala Ala Asp Thr Pro Asp Ser
                20                  25                  30

Ser Val Gln Gln Gly Ala Glu Thr Ser Arg Asp Gln Asn Ile Ile Ser
            35                  40                  45

Pro Ser Ala Ala Ser Ala Ser Gly Glu Thr Ala Val Phe Val Gln Phe
        50                  55                  60

Lys Gly Thr Gly Ala Tyr Glu Leu Thr Arg Pro Ala Thr Gly Arg Ala
65                  70                  75                  80

Thr Arg Glu Gln Asn Ala Ala Lys Arg Asp Glu Val Arg Ser Ile His
                85                  90                  95

Ala Trp Val Asn Glu Arg Ala Arg Thr Ala Ala Glu Ala Thr Ser Ser
                100                 105                 110

Lys Ile Leu Tyr Thr Thr Val Asn Thr Val Arg Gly Val Gly Leu Tyr
            115                 120                 125

Gly Asp Ile Glu Gln Ile Arg Lys Leu Ala Ala Arg Gln Asp Val Ala
        130                 135                 140

Arg Ile Ser Val Ile Thr Asn Val Arg Pro Gln Asn Ala Gly Thr Ala
145                 150                 155                 160

Thr Asp Thr Leu Thr Thr Trp Ala Gln Lys Asn Asn Thr Gly Gly Tyr
                165                 170                 175

Gly Tyr Thr Gly Arg Asn Val Thr Val Ala Val Ile Asp Thr Gly Ile
            180                 185                 190

Asp Tyr Thr His Ala Asp Leu Gly Gly Pro Gly Thr Asp Glu Ala Tyr
        195                 200                 205

Arg Arg Ala Lys Asp Ser Ala Thr Leu Pro Asp Gly Leu Tyr Asp Pro
```

```
              210                 215                 220
    Gln Lys Leu Val Gly Gly Tyr Asp Met Ala Gly Asp Gly Tyr Asn Ala
    225                 230                 235                 240

Ser Thr Lys Glu Arg Ala Leu Pro Ile Pro Asp Ala Asn Pro Leu Asp
                        245                 250                 255

Cys Ser Gly His Gly Thr His Val Ala Gly Thr Ile Ala Gly Tyr Gly
                        260                 265                 270

Val Gly Ala Asp Asn Thr Ala Phe His Gly Asp Tyr Ser Ala Leu Ser
                275                 280                 285

Ala Asp Ala Leu His Arg Met Arg Val Ala Pro Gly Ala Ala Pro Glu
                290                 295                 300

Ala Arg Leu Val Ala Phe Arg Ile Phe Gly Cys Ala Gly Thr Ser Ala
    305                 310                 315                 320

Leu Thr Leu Lys Ala Leu Asp Arg Val Leu Asp Pro Asn Asp Asp Gly
                        325                 330                 335

Asp Phe Ser Asp Arg Ala Asp Ile Val Asn Leu Ser Val Gly Thr Asp
                        340                 345                 350

Tyr Gly Val Phe Asp Glu Ser Thr Asn Tyr Ala Ile Gly Glu Leu Tyr
                355                 360                 365

Arg Gln Gly Val Leu Thr Val Thr Ala Ala Gly Asn Ala Ala Ser Gln
    370                 375                 380

Asn Gly Ala Gly Asp Thr Tyr Ser Ile Ser Gly Pro Ala Thr Ser
    385                 390                 395                 400

Ala Tyr Ala Leu Thr Val Ala Asn Ser Met Gly Ala Thr Gln Ser Ala
                        405                 410                 415

Asp Arg Val Lys Val Leu Ser Pro Ala Gly Thr Ser Glu Ile Tyr Gly
                        420                 425                 430

Arg Tyr Thr Thr Lys Tyr Asp Tyr Ala Arg His Arg Glu Gly Glu Leu
                435                 440                 445

Thr Gly Gln Val Val Lys Ala Pro Ala Ser Asn Pro Tyr Gly Cys Ala
                        450                 455                 460

Pro Phe Thr Ala Glu Glu Ala Ala Arg Leu Lys Gly Lys Trp Val Tyr
    465                 470                 475                 480

Leu Asp Trp Asp Asn Thr Ser Gly Ala Val Pro Cys Gly Ser Ala Val
                        485                 490                 495

Arg Phe Ala Asn Val Glu Arg Ala Gly Gly Ala Gly Val Val Leu Gly
                        500                 505                 510

Thr Arg Gln Pro Leu Thr Asp Ile Ala Gly Thr Ala Ala Leu Pro Gly
                        515                 520                 525

Val Leu Leu Pro Ser Glu Gln Ala Glu Lys Ile Arg Pro Ala Leu Ala
    530                 535                 540

Ser Gly Thr Leu Thr Leu Arg Leu Asp Gly Ala Leu Arg Thr Gly Ala
    545                 550                 555                 560

Arg Ile Glu Thr Arg Ala Ala Asp Gln Pro Asn Pro Ala Ser Ala Arg
                        565                 570                 575

Gly Ala His Gly Ser Trp Gly Ser Ile Lys Pro Asp Val Ser Ala Pro
                        580                 585                 590

Gly Thr Gly Ile Ala Ser Ala Arg Ala Gly Ser Gly Ala Gly Ala Ser
                        595                 600                 605

Thr Leu Thr Gly Thr Ser Met Ser Ala Ala Tyr Val Cys Gly Val Ala
                        610                 615                 620

Ala Gln Leu Val Glu Glu His Arg Ser Tyr Ser Pro Gln Gln Leu Lys
    625                 630                 635                 640
```

```
Ala Thr Leu Met Asn Thr Ala Ala His Pro Val His Asp Ala His Asn
                645                 650                 655

Arg Pro Tyr Pro Pro Asp Arg Val Gly Ser Gly Arg Ile Asp Ser Thr
                660                 665                 670

Lys Ala Val Asn Asn Arg Val Leu Val Tyr Asn Ala Ala Arg Pro Glu
                675                 680                 685

Gln Val Ser Asp Thr Phe Gly Val Leu Glu Tyr Ala Pro Asp Ala Pro
            690                 695                 700

Val Ser Val Leu Arg Arg Glu Met Val Val Glu Asn Thr Asp Thr Ile
705                 710                 715                 720

Ala His Thr Tyr Leu Leu Ser Tyr Thr Ala Ser Thr Glu Val Pro Gly
                725                 730                 735

Val Ala Tyr Ser Leu Pro Glu Ser Val Thr Val Pro Pro Gly Gly Arg
                740                 745                 750

Thr Thr Phe Thr Val Thr Leu Thr Val Asp Pro Ala Ala Leu Ala Lys
                755                 760                 765

Thr Ala Glu Ala Thr Ala Asn Thr Ala Gln Arg Ser Thr Gly Glu Asp
            770                 775                 780

Gly Gln Val Val Ala Phe Gly Ala Arg Gln Tyr Val Ala Ser Ala Ser
785                 790                 795                 800

Gly Gln Val Val Leu Thr Glu Gly Asp Thr Thr Leu Arg Val Pro Val
                805                 810                 815

His Ala Ala Pro Lys Leu Val Ser Lys Met Arg Val Ala Ala Ala Glu
                820                 825                 830

Val Gln Phe Glu Arg Gly Glu Gln Ala Gln Leu Pro Leu Ser Gly
            835                 840                 845

Thr Gly Val Asp Gln Gly Gly Tyr Arg Ser Leu Leu Gly Ala Phe Glu
            850                 855                 860

Leu Gly Val Thr Ser Gly His Ile Pro Thr Glu Asp Leu Ser Val Ser
865                 870                 875                 880

Ser Asp Gln Arg Ala Asp Ile Gln Tyr Ala Gly Ala Ala Ser Asp Ala
                885                 890                 895

Ala Ala Leu Ala Ala Ala Gly Lys Asn Pro Asn Asp Gly Ser Leu Tyr
                900                 905                 910

Phe Gly Ile Ser Thr Trp Gly Asn Trp Ser Glu Val Thr Pro Arg Ser
            915                 920                 925

Thr Tyr Tyr Val Phe Ile Asp Thr Asp Gly Asp Gly Thr Asn Asp Tyr
            930                 935                 940

Arg Leu His Thr Met Arg Ala Ala Gly Val Asp Tyr Pro Leu Val Gln
945                 950                 955                 960

Leu Ser Arg Ala Asp Asn Asp Arg Trp Val Pro Val Asp Gly Ala Leu
                965                 970                 975

Tyr Pro Leu Asn Asn Thr Trp Gly Ser Thr Asp Thr Asn Thr Met Asp
            980                 985                 990

Ser Asn Thr Leu Ile Met Gly Val Pro Leu Arg Arg Leu Gly Leu Ser
                995                 1000                1005

Thr Gln Asn Pro Gly Ser Leu Ser Tyr Thr Val Ala Thr Thr Ser
            1010                1015                1020

Ser Tyr Ala Thr Thr Pro Ile Val Asp Ala Thr Glu Ala Val Lys
            1025                1030                1035

Phe Asn Pro Phe Thr Pro Thr Phe Trp Phe Thr Gly Thr Ala Ser
            1040                1045                1050
```

Gly Val Pro Gly Leu Phe Val Asp Ala Pro Asn Ala Ser Leu Thr
    1055                1060                1065

Val His Arg Thr Glu Gly Ala Glu Gly Lys Leu Leu Leu Leu His
    1070                1075                1080

Leu His Asn Ser Thr Gly Asn Leu Asn Gly Ala Gln Gly Ala Thr
    1085                1090                1095

Gly Asp Arg Ala Gln Val Leu Asn Val Ser Gly Glu Asn Thr His
    1100                1105                1110

Asn Thr Leu Arg Ala Arg Phe Thr Asp Val Asn Asp Ala Asn Thr
    1115                1120                1125

Ala Thr Pro Asp Ile Asp Trp Leu Ala Glu Arg Arg Ile Thr Arg
    1130                1135                1140

Gly Tyr Pro Gly Gly Thr Phe His Pro Gly Glu Asp Thr Glu Arg
    1145                1150                1155

Gly Ala Ala Ala Ala Phe Phe Tyr Arg Leu Ala Gly Ser Pro Ala
    1160                1165                1170

Tyr Thr Pro Pro Gln Gln Ser Pro Phe Thr Asp Val Pro Thr Asn
    1175                1180                1185

His Pro Phe Tyr Lys Glu Ile Ala Trp Met His Gln Ala Gly Ile
    1190                1195                1200

Thr Thr Gly Trp Ala Asp Gly Thr Phe Arg Pro His Glu Ala Ala
    1205                1210                1215

Thr Arg Glu Ala Met Ala Ala Phe Phe Tyr Arg Ala Ala Gly Ser
    1220                1225                1230

Pro Ala Tyr Met Pro Pro Glu Lys Ser Pro Phe Glu Asp Val Pro
    1235                1240                1245

Thr Gly Ala Arg Phe Tyr Arg Glu Ile Thr Trp Ala Tyr Glu Lys
    1250                1255                1260

Lys Ile Phe Thr Glu Glu Thr Ser Leu Leu Lys Pro Ala Ala Thr
    1265                1270                1275

Val Arg Arg Glu Ala Ala Ala Thr Met Ile His Arg Tyr Ala Arg
    1280                1285                1290

Gln Val Leu His Arg Gly
    1295

<210> SEQ ID NO 54
<211> LENGTH: 1301
<212> TYPE: PRT
<213> ORGANISM: Rothia dentocariosa

<400> SEQUENCE: 54

Met Gly Gln Ala Arg Cys Thr Leu Ala Thr Ala Leu Ser Leu Ser Leu
1               5                   10                  15

Val Thr Thr Ala Ala Phe Pro Val Phe Ala Ala Asp Thr Pro Asp Ser
            20                  25                  30

Ser Val Gln Gln Gly Ala Glu Thr Ser Arg Asp Gln Asn Ile Ile Ser
        35                  40                  45

Pro Ser Ala Ala Ser Ala Ser Gly Glu Thr Ala Val Phe Val Gln Phe
    50                  55                  60

Lys Gly Thr Gly Ala Tyr Glu Leu Thr Arg Pro Ala Thr Gly Arg Ala
65                  70                  75                  80

Thr Arg Glu Gln Asn Ala Ala Lys Arg Asp Glu Val Arg Ser Ile His
                85                  90                  95

Ala Trp Val Asn Glu Arg Ala Arg Thr Val Ala Glu Ala Thr Ser Ser
            100                 105                 110

```
Lys Ile Leu Tyr Thr Thr Val Asn Thr Val Arg Gly Val Gly Leu Tyr
            115                 120                 125

Gly Asp Ile Glu Gln Ile Arg Lys Leu Ala Ala Arg Gln Asp Val Ala
        130                 135                 140

Arg Ile Ser Val Ile Thr Asn Val Arg Pro Gln Asn Ala Gly Thr Ala
145                 150                 155                 160

Val His Thr Asp Thr Leu Thr Thr Trp Ala Gln Lys Asn Asn Thr Gly
                165                 170                 175

Gly Tyr Gly Tyr Thr Gly Arg Asn Val Thr Val Ala Val Ile Asp Thr
            180                 185                 190

Gly Ile Asp Tyr Thr His Ala Asp Leu Gly Gly Pro Gly Thr Asp Glu
        195                 200                 205

Ala Tyr Arg Arg Ala Lys Asp Ser Ala Thr Leu Pro Asp Gly Leu Tyr
        210                 215                 220

Asp Pro Gln Lys Leu Val Gly Gly Tyr Asp Met Ala Gly Asp Gly Tyr
225                 230                 235                 240

Asn Ala Ser Val Lys Glu His Ala Leu Pro Ile Pro Asp Ala Asn Pro
                245                 250                 255

Leu Asp Cys Ser Gly His Gly Thr His Val Ala Gly Thr Ile Ala Gly
            260                 265                 270

Tyr Gly Val Ala Ala Asp Asn Thr Ala Phe His Gly Asp Tyr Ser Ala
        275                 280                 285

Leu Ser Ala Asp Glu Leu His Arg Met Arg Ile Ala Pro Gly Ala Ala
        290                 295                 300

Pro Glu Ala Arg Leu Val Ala Phe Arg Ile Phe Gly Cys Ala Gly Thr
305                 310                 315                 320

Ser Ala Leu Thr Leu Lys Ala Leu Asp Arg Val Leu Asp Pro Asn Asp
                325                 330                 335

Asp Gly Asp Phe Ser Asp Arg Ala Asp Ile Val Asn Leu Ser Val Gly
            340                 345                 350

Thr Asp Tyr Gly Val Phe Asp Glu Ser Thr Asn Tyr Ala Ile Gly Glu
        355                 360                 365

Leu Tyr Arg Gln Gly Val Leu Thr Val Thr Ala Ala Gly Asn Ala Ala
        370                 375                 380

Ser Gln Asn Gly Ala Gly Asp Thr Tyr Ser Val Ser Gly Gly Pro Ala
385                 390                 395                 400

Thr Ser Ala Tyr Ala Leu Thr Val Ala Asn Ser Met Gly Ala Thr Gln
                405                 410                 415

Ser Ala Asp Arg Val Lys Val Leu Ser Pro Ala Gly Thr Ser Glu Ile
            420                 425                 430

Tyr Gly Arg Tyr Thr Thr Lys Tyr Asp Tyr Ala Arg His Arg Glu Gly
        435                 440                 445

Glu Leu Thr Gly Gln Val Val Lys Ala Pro Ala Ser Asn Leu Tyr Gly
        450                 455                 460

Cys Ala Pro Phe Thr Ala Glu Glu Ala Ala Arg Leu Lys Gly Lys Trp
465                 470                 475                 480

Val Tyr Leu Asp Trp Asp Asn Thr Ser Gly Ala Val Pro Cys Gly Ser
                485                 490                 495

Ala Val Arg Phe Ala Asn Val Glu Arg Ala Gly Gly Ala Gly Val Val
            500                 505                 510

Leu Gly Thr Gly Gln Pro Leu Thr Asp Ile Ala Gly Thr Ala Ala Leu
        515                 520                 525
```

```
Pro Gly Val Leu Leu Pro Ser Glu Gln Ala Glu Lys Ile Arg Leu Ala
            530                 535                 540

Leu Ala Ser Gly Thr Leu Thr Leu Arg Leu Asp Asp Ala Leu Arg Thr
545                 550                 555                 560

Gly Ala Arg Ile Glu Thr Gly Ala Thr Asp Gln Pro Asn Pro Ala Ser
                565                 570                 575

Ala Arg Gly Ala His Gly Ser Trp Gly Ser Ile Lys Pro Asp Val Ser
            580                 585                 590

Ala Pro Gly Thr Gly Ile Ala Ser Ala Arg Ala Gly Ser Gly Ala Gly
            595                 600                 605

Ala Ser Thr Leu Thr Gly Thr Ser Met Ser Ala Ala Tyr Val Cys Gly
            610                 615                 620

Val Ala Ala Gln Leu Val Glu Glu His His Ser Tyr Thr Pro Gln Gln
625                 630                 635                 640

Leu Lys Ala Thr Leu Met Asn Thr Ala Ala His Pro Val His Asp Ala
                645                 650                 655

His Asn Arg Pro Tyr Pro Pro Asp Arg Val Gly Ser Gly Arg Ile Asp
                660                 665                 670

Ser Ala Lys Ala Val Asn Asn Arg Val Leu Val Tyr Asn Ala Ala Arg
                675                 680                 685

Pro Glu Gln Val Ser Asp Thr Ser Gly Val Leu Glu Tyr Ala Pro Asp
            690                 695                 700

Ala Pro Val Ser Thr Leu Arg Arg Glu Met Val Val Glu Asn Thr Asp
705                 710                 715                 720

Thr Ile Ala His Thr Tyr Leu Leu Ser Tyr Thr Ala Ser Ala Glu Ile
                725                 730                 735

Pro Gly Val Ala Tyr Ser Leu Pro Glu Ser Val Thr Val Pro Pro Gly
            740                 745                 750

Gly Arg Thr Thr Phe Thr Val Thr Leu Thr Val Asp Pro Ala Ala Leu
            755                 760                 765

Ala Lys Thr Ala Glu Ala Thr Ala Asn Thr Thr Gln Arg Ser Thr Gly
770                 775                 780

Glu Asp Gly Gln Val Val Ala Phe Gly Ala Arg Gln Tyr Val Ala Ser
785                 790                 795                 800

Ala Ser Gly Gln Val Val Leu Thr Glu Gly Asp Thr Thr Leu Arg Val
            805                 810                 815

Pro Val His Ala Ala Pro Lys Leu Val Ser Gln Met Arg Val Ala Ala
            820                 825                 830

Ala Glu Val Gln Phe Glu Arg Gly Gln Gln Ala Gln Leu Pro Leu
            835                 840                 845

Ser Gly Thr Gly Val Asp Gln Gly Gly Tyr Arg Ser Leu Leu Gly Ala
850                 855                 860

Phe Glu Leu Gly Val Thr Ser Gly His Ile Pro Thr Glu Asp Leu Ser
865                 870                 875                 880

Val Ser Ser Asp Gln Arg Ala Asp Ile Gln Tyr Ala Gly Ala Ala Ser
                885                 890                 895

Asp Ala Ala Ala Leu Ala Ala Ala Gly Lys Asn Pro Asn Asp Gly Ser
            900                 905                 910

Leu Tyr Phe Gly Ile Ser Thr Trp Gly Asn Trp Ser Glu Val Thr Pro
            915                 920                 925

Arg Ser Thr Tyr Val Phe Ile Asp Thr Asp Gly Asp Gly Thr Asn
            930                 935                 940

Asp Tyr Arg Leu His Thr Met Arg Ala Ala Gly Val Asp Tyr Pro Leu
```

|   |   |   | 945 |   |   |   | 950 |   |   |   | 955 |   |   |   | 960 |
|---|---|---|---|---|---|---|---|---|---|---|---|---|---|---|---|
| Val | Gln | Leu | Ser | Arg | Ala | Asp | Asn | Gly | Arg | Trp | Val | Pro | Val | Asp | Gly |
|   |   |   |   | 965 |   |   |   | 970 |   |   |   | 975 |   |   |   |
| Ala | Leu | Tyr | Pro | Leu | Asn | Asn | Thr | Trp | Gly | Ser | Thr | Asp | Thr | Asn | Thr |
|   |   |   | 980 |   |   |   | 985 |   |   |   | 990 |   |   |   |   |
| Met | Asp | Ser | Asn | Thr | Leu | Ile | Met | Gly | Val | Pro | Leu | Arg | Gln | Leu | Gly |
|   |   |   |   | 995 |   |   |   | 1000 |   |   |   | 1005 |   |   |   |
| Leu | Ser | Thr | Gln | Asn | Pro | Gly | Ser | Leu | Ser | Tyr | Thr | Val | Ala | Thr |   |
|   |   |   | 1010 |   |   |   | 1015 |   |   |   | 1020 |   |   |   |   |
| Thr | Ser | Ser | Tyr | Ala | Thr | Thr | Pro | Ile | Val | Asp | Ala | Thr | Glu | Ala |   |
|   |   |   | 1025 |   |   |   | 1030 |   |   |   | 1035 |   |   |   |   |
| Val | Lys | Phe | Asn | Pro | Phe | Thr | Pro | Ala | Phe | Trp | Phe | Thr | Gly | Thr |   |
|   |   |   | 1040 |   |   |   | 1045 |   |   |   | 1050 |   |   |   |   |
| Ala | Ser | Gly | Val | Pro | Gly | Leu | Phe | Val | Asp | Ala | Pro | Asn | Ala | Ser |   |
|   |   |   | 1055 |   |   |   | 1060 |   |   |   | 1065 |   |   |   |   |
| Leu | Thr | Val | His | Arg | Thr | Glu | Gly | Ala | Glu | Gly | Lys | Leu | Leu | Leu |   |
|   |   |   | 1070 |   |   |   | 1075 |   |   |   | 1080 |   |   |   |   |
| Leu | His | Leu | His | Asn | Ser | Thr | Gly | Asn | Leu | Asn | Gly | Thr | Leu | Gly |   |
|   |   |   | 1085 |   |   |   | 1090 |   |   |   | 1095 |   |   |   |   |
| Ala | Thr | Gly | Asp | Arg | Ala | Gln | Val | Leu | Asn | Val | Ser | Gly | Glu | Asn |   |
|   |   |   | 1100 |   |   |   | 1105 |   |   |   | 1110 |   |   |   |   |
| Thr | His | Asn | Thr | Val | Arg | Ala | Arg | Phe | Thr | Asp | Val | Asn | Asp | Ala |   |
|   |   |   | 1115 |   |   |   | 1120 |   |   |   | 1125 |   |   |   |   |
| Asn | Ala | Ala | Thr | Pro | Asp | Ile | Asp | Trp | Leu | Ala | Glu | Arg | Arg | Ile |   |
|   |   |   | 1130 |   |   |   | 1135 |   |   |   | 1140 |   |   |   |   |
| Thr | Arg | Gly | Tyr | Pro | Gly | Gly | Thr | Phe | His | Leu | Gly | Glu | Asp | Thr |   |
|   |   |   | 1145 |   |   |   | 1150 |   |   |   | 1155 |   |   |   |   |
| Glu | Arg | Gly | Ala | Ala | Ala | Ala | Phe | Phe | Tyr | Arg | Leu | Ala | Gly | Ser |   |
|   |   |   | 1160 |   |   |   | 1165 |   |   |   | 1170 |   |   |   |   |
| Pro | Ala | Tyr | Thr | Pro | Pro | Gln | Gln | Ser | Pro | Phe | Thr | Asp | Val | Pro |   |
|   |   |   | 1175 |   |   |   | 1180 |   |   |   | 1185 |   |   |   |   |
| Thr | Asn | His | Pro | Phe | Tyr | Lys | Glu | Ile | Ala | Trp | Met | His | Gln | Ala |   |
|   |   |   | 1190 |   |   |   | 1195 |   |   |   | 1200 |   |   |   |   |
| Gly | Ile | Thr | Thr | Gly | Trp | Ala | Asp | Gly | Thr | Phe | Arg | Pro | His | Lys |   |
|   |   |   | 1205 |   |   |   | 1210 |   |   |   | 1215 |   |   |   |   |
| Ala | Ala | Thr | Arg | Glu | Ala | Met | Ala | Ala | Phe | Phe | Tyr | Arg | Ala | Ala |   |
|   |   |   | 1220 |   |   |   | 1225 |   |   |   | 1230 |   |   |   |   |
| Gly | Ser | Pro | Ala | Tyr | Thr | Pro | Pro | Glu | Lys | Ser | Pro | Phe | Glu | Asp |   |
|   |   |   | 1235 |   |   |   | 1240 |   |   |   | 1245 |   |   |   |   |
| Val | Pro | Thr | Gly | Ala | Arg | Phe | Tyr | Arg | Glu | Ile | Thr | Trp | Ala | Tyr |   |
|   |   |   | 1250 |   |   |   | 1255 |   |   |   | 1260 |   |   |   |   |
| Glu | Lys | Lys | Ile | Phe | Thr | Glu | Glu | Thr | Ser | Leu | Leu | Lys | Pro | Ala |   |
|   |   |   | 1265 |   |   |   | 1270 |   |   |   | 1275 |   |   |   |   |
| Ala | Thr | Val | Arg | Arg | Glu | Ala | Ala | Ala | Thr | Met | Ile | His | Arg | Tyr |   |
|   |   |   | 1280 |   |   |   | 1285 |   |   |   | 1290 |   |   |   |   |
| Ala | Arg | Gln | Val | Leu | His | Arg | Gly |   |   |   |   |   |   |   |   |
|   |   |   | 1295 |   |   |   | 1300 |   |   |   |   |   |   |   |   |

<210> SEQ ID NO 55
<211> LENGTH: 1301
<212> TYPE: PRT
<213> ORGANISM: Rothia dentocariosa

<400> SEQUENCE: 55

```
Met Gly Gln Ala Arg Cys Thr Leu Ala Thr Ala Leu Ser Leu Ser Leu
1               5                   10                  15

Val Thr Thr Ala Ala Phe Pro Val Phe Ala Ala Asp Thr Pro Asp Ser
            20                  25                  30

Ser Val Gln Gln Gly Ala Glu Thr Ser Arg Asp Gln Asn Ile Ile Ser
        35                  40                  45

Pro Ser Ala Ala Ser Ala Ser Gly Glu Thr Ala Val Phe Val Gln Phe
    50                  55                  60

Lys Gly Thr Gly Ala Tyr Glu Leu Thr Arg Pro Ala Thr Gly Arg Ala
65                  70                  75                  80

Thr Arg Glu Gln Asn Ala Ala Lys Arg Asp Glu Val Arg Ser Ile His
                85                  90                  95

Ala Trp Val Asn Glu Arg Ala Arg Thr Val Ala Glu Ala Thr Ser Ser
            100                 105                 110

Lys Ile Leu Tyr Thr Thr Val Asn Thr Val Arg Gly Val Gly Leu Tyr
            115                 120                 125

Gly Asp Ile Glu Gln Ile Arg Lys Leu Ala Ala Arg Gln Asp Val Ala
            130                 135                 140

Arg Ile Ser Val Ile Thr Asn Val Arg Pro Gln Asn Ala Gly Thr Ala
145                 150                 155                 160

Val His Thr Asp Thr Leu Thr Thr Trp Ala Gln Lys Asn Asn Thr Gly
                165                 170                 175

Gly Tyr Gly Tyr Thr Gly Arg Asn Val Thr Val Ala Val Ile Asp Thr
            180                 185                 190

Gly Ile Asp Tyr Thr His Ala Asp Leu Gly Gly Pro Gly Thr Asp Glu
            195                 200                 205

Ala Tyr Arg Arg Ala Lys Asp Ser Ala Thr Leu Pro Asp Gly Leu Tyr
        210                 215                 220

Asp Pro Gln Lys Leu Val Gly Gly Tyr Asp Met Ala Gly Asp Gly Tyr
225                 230                 235                 240

Asn Ala Ser Val Lys Glu His Ala Leu Pro Ile Pro Asp Ala Asn Pro
            245                 250                 255

Leu Asp Cys Ser Gly His Gly Thr His Val Ala Gly Thr Ile Ala Gly
            260                 265                 270

Tyr Gly Val Ala Ala Asp Asn Thr Ala Phe His Gly Asp Tyr Ser Ala
        275                 280                 285

Leu Ser Ala Asp Glu Leu His Arg Met Arg Ile Ala Pro Gly Ala Ala
        290                 295                 300

Pro Glu Ala Arg Leu Val Ala Phe Arg Ile Phe Gly Cys Ala Gly Thr
305                 310                 315                 320

Ser Ala Leu Thr Leu Lys Ala Leu Asp Arg Val Leu Asp Pro Asn Asp
            325                 330                 335

Asp Gly Asp Phe Ser Asp Arg Ala Asp Ile Val Asn Leu Ser Val Gly
            340                 345                 350

Thr Asp Tyr Gly Val Phe Asp Glu Ser Thr Asn Tyr Ala Ile Gly Glu
            355                 360                 365

Leu Tyr Arg Gln Gly Val Leu Thr Val Thr Ala Ala Gly Asn Ala Ala
        370                 375                 380

Ser Gln Asn Gly Ala Gly Asp Thr Tyr Ser Val Ser Gly Gly Pro Ala
385                 390                 395                 400

Thr Ser Ala Tyr Ala Leu Thr Val Ala Asn Ser Met Gly Ala Thr Gln
            405                 410                 415

Ser Ala Asp Arg Val Lys Val Leu Ser Pro Ala Gly Thr Ser Glu Ile
```

-continued

```
                420             425             430
Tyr Gly Arg Tyr Thr Thr Lys Tyr Asp Tyr Ala Arg His Arg Glu Gly
            435                 440                 445
Glu Leu Thr Gly Gln Val Val Lys Ala Pro Ala Ser Asn Leu Tyr Gly
        450                 455                 460
Cys Ala Pro Phe Thr Glu Glu Ala Ala Arg Leu Lys Gly Lys Trp
465                 470                 475                 480
Val Tyr Leu Asp Trp Asp Asn Thr Ser Gly Ala Val Pro Cys Gly Ser
                485                 490                 495
Ala Val Arg Phe Ala Asn Val Glu Arg Ala Gly Ala Gly Val Val
            500                 505                 510
Leu Gly Thr Gly Gln Pro Leu Thr Asp Ile Ala Gly Thr Ala Ala Leu
        515                 520                 525
Pro Gly Val Leu Leu Pro Ser Glu Gln Ala Glu Lys Ile Arg Leu Ala
            530                 535                 540
Leu Ala Ser Gly Thr Leu Thr Leu Arg Leu Asp Asp Ala Leu Arg Thr
545                 550                 555                 560
Gly Ala Arg Ile Glu Thr Gly Ala Thr Asp Gln Pro Asn Pro Ala Ser
                565                 570                 575
Ala Arg Gly Ala His Gly Ser Trp Gly Ser Ile Lys Pro Asp Val Ser
            580                 585                 590
Ala Pro Gly Thr Gly Ile Ala Ser Ala Arg Ala Gly Ser Gly Ala Gly
        595                 600                 605
Ala Ser Thr Leu Thr Gly Thr Ser Met Ser Ala Ala Tyr Val Cys Gly
        610                 615                 620
Val Ala Ala Gln Leu Val Glu Glu His His Ser Tyr Thr Pro Gln Gln
625                 630                 635                 640
Leu Lys Ala Thr Leu Met Asn Thr Ala Ala His Pro Val His Asp Ala
                645                 650                 655
His Asn Arg Pro Tyr Pro Pro Asp Arg Val Gly Ser Gly Arg Ile Asp
            660                 665                 670
Ser Ala Lys Ala Val Asn Asn Arg Val Leu Val Tyr Asn Ala Ala Arg
        675                 680                 685
Pro Glu Gln Val Ser Asp Thr Ser Gly Val Leu Glu Tyr Ala Pro Asp
        690                 695                 700
Ala Pro Val Ser Thr Leu Arg Arg Glu Met Val Val Glu Asn Thr Asp
705                 710                 715                 720
Thr Ile Ala His Thr Tyr Leu Leu Ser Tyr Thr Ala Ser Ala Glu Ile
                725                 730                 735
Pro Gly Val Ala Tyr Ser Leu Pro Glu Ser Val Thr Val Pro Pro Gly
            740                 745                 750
Gly Arg Thr Thr Phe Thr Val Thr Leu Thr Val Asp Pro Ala Ala Leu
        755                 760                 765
Ala Lys Thr Ala Glu Ala Thr Ala Asn Thr Thr Gln Arg Ser Thr Gly
        770                 775                 780
Glu Asp Gly Gln Val Val Ala Phe Gly Ala Arg Gln Tyr Val Ala Ser
785                 790                 795                 800
Ala Ser Gly Gln Val Val Leu Thr Glu Gly Asp Thr Thr Leu Arg Val
                805                 810                 815
Pro Val His Ala Ala Pro Lys Leu Val Ser Gln Met Arg Val Ala Ala
            820                 825                 830
Ala Glu Val Gln Phe Glu Arg Gly Gln Gln Gln Ala Gln Leu Pro Leu
        835                 840                 845
```

-continued

Ser Gly Thr Gly Val Asp Gln Gly Gly Tyr Arg Ser Leu Leu Gly Ala
    850                 855                 860

Phe Glu Leu Gly Val Thr Ser Gly His Ile Pro Thr Glu Asp Leu Ser
865                 870                 875                 880

Val Ser Ser Asp Gln Arg Ala Asp Ile Gln Tyr Ala Gly Ala Ala Ser
                885                 890                 895

Asp Ala Ala Ala Leu Ala Ala Ala Gly Lys Asn Pro Asn Asp Gly Ser
                900                 905                 910

Leu Tyr Phe Gly Ile Ser Thr Trp Gly Asn Trp Ser Glu Val Thr Pro
                915                 920                 925

Arg Ser Thr Tyr Tyr Val Phe Ile Asp Thr Asp Gly Asp Gly Thr Asn
    930                 935                 940

Asp Tyr Arg Leu His Thr Met Arg Ala Ala Gly Val Asp Tyr Pro Leu
945                 950                 955                 960

Val Gln Leu Ser Arg Ala Asp Asn Gly Arg Trp Val Pro Val Asp Gly
                965                 970                 975

Ala Leu Tyr Pro Leu Asn Asn Thr Trp Gly Ser Thr Asp Thr Asn Thr
                980                 985                 990

Met Asp Ser Asn Thr Leu Ile Met Gly Val Pro Leu Arg Gln Leu Gly
                995                 1000                1005

Leu Ser Thr Gln Asn Pro Gly Ser Leu Ser Tyr Thr Val Ala Thr
    1010                1015                1020

Thr Ser Ser Tyr Ala Thr Thr Pro Ile Val Asp Ala Thr Glu Ala
    1025                1030                1035

Val Lys Phe Asn Pro Phe Thr Pro Ala Phe Trp Phe Thr Gly Thr
    1040                1045                1050

Ala Ser Gly Val Pro Gly Leu Phe Val Asp Ala Pro Asn Ala Ser
    1055                1060                1065

Leu Thr Val His Arg Thr Glu Gly Ala Glu Gly Lys Leu Leu Leu
    1070                1075                1080

Leu His Leu His Asn Ser Thr Gly Asn Leu Asn Gly Thr Leu Gly
    1085                1090                1095

Ala Thr Gly Asp Arg Ala Gln Val Leu Asn Val Ser Gly Glu Asn
    1100                1105                1110

Thr His Asn Thr Val Arg Ala Arg Phe Thr Asp Val Asn Asp Ala
    1115                1120                1125

Asn Ala Ala Thr Pro Asp Ile Asp Trp Leu Ala Glu Arg Arg Ile
    1130                1135                1140

Thr Arg Gly Tyr Pro Gly Gly Thr Phe His Leu Gly Glu Asp Thr
    1145                1150                1155

Glu Arg Gly Ala Ala Ala Phe Phe Tyr Arg Leu Ala Gly Ser
    1160                1165                1170

Pro Ala Tyr Thr Pro Pro Gln Gln Ser Pro Phe Thr Asp Val Pro
    1175                1180                1185

Thr Asn His Pro Phe Tyr Lys Glu Ile Ala Trp Met His Gln Ala
    1190                1195                1200

Gly Ile Thr Thr Gly Trp Ala Asp Gly Thr Phe Arg Pro His Lys
    1205                1210                1215

Ala Ala Thr Arg Glu Ala Met Ala Ala Phe Phe Tyr Arg Ala Ala
    1220                1225                1230

Gly Ser Pro Ala Tyr Thr Pro Pro Glu Lys Ser Pro Phe Glu Asp
    1235                1240                1245

```
Val Pro Thr Gly Ala Arg Phe Tyr Arg Glu Ile Thr Trp Ala Tyr
1250                1255                1260

Glu Lys Lys Ile Phe Thr Glu Thr Ser Leu Leu Lys Pro Ala
1265                1270                1275

Ala Thr Val Arg Arg Glu Ala Ala Ala Thr Met Ile His Arg Tyr
1280                1285                1290

Ala Arg Gln Val Leu His Arg Gly
1295                1300

<210> SEQ ID NO 56
<211> LENGTH: 1301
<212> TYPE: PRT
<213> ORGANISM: Rothia dentocariosa

<400> SEQUENCE: 56

Met Gly Gln Ala Arg Cys Thr Leu Ala Thr Ala Leu Ser Leu Ser Leu
1               5                   10                  15

Val Thr Thr Ala Ala Phe Pro Val Phe Ala Ala Asp Thr Pro Asp Ser
                20                  25                  30

Ser Val Gln Gln Gly Ala Glu Thr Ser Arg Asp Gln Asn Ile Ile Ser
            35                  40                  45

Pro Ser Ala Ala Ser Ala Ser Gly Glu Thr Ala Val Phe Val Gln Phe
        50                  55                  60

Lys Gly Thr Gly Ala Tyr Glu Leu Thr Arg Pro Ala Thr Gly Arg Ala
65                  70                  75                  80

Thr Arg Glu Gln Asn Ala Ala Lys Arg Asp Glu Val Arg Ser Ile His
                85                  90                  95

Ala Trp Val Asn Glu Arg Ala Arg Thr Val Ala Glu Ala Thr Ser Ser
                100                 105                 110

Lys Ile Leu Tyr Thr Thr Val Asn Thr Val Arg Gly Val Gly Leu Tyr
            115                 120                 125

Gly Asp Ile Glu Gln Ile Arg Lys Leu Ala Ala Arg Gln Asp Val Ala
        130                 135                 140

Arg Ile Ser Val Ile Thr Asn Val Arg Pro Gln Asn Ala Gly Thr Ala
145                 150                 155                 160

Val His Thr Asp Thr Leu Thr Thr Trp Ala Gln Lys Asn Asn Thr Gly
                165                 170                 175

Gly Tyr Gly Tyr Thr Gly Arg Asn Val Thr Val Ala Val Ile Asp Thr
                180                 185                 190

Gly Ile Asp Tyr Thr His Ala Asp Leu Gly Gly Pro Gly Thr Asp Glu
            195                 200                 205

Ala Tyr Arg Arg Ala Lys Asp Ser Ala Thr Leu Pro Asp Gly Leu Tyr
        210                 215                 220

Asp Pro Gln Lys Leu Val Gly Gly Tyr Asp Met Ala Gly Asp Gly Tyr
225                 230                 235                 240

Asn Ala Ser Val Lys Glu His Ala Leu Pro Ile Pro Asp Ala Asn Pro
                245                 250                 255

Leu Asp Cys Ser Gly His Gly Thr His Val Ala Gly Thr Ile Ala Gly
                260                 265                 270

Tyr Gly Val Ala Ala Asp Asn Thr Ala Phe His Gly Asp Tyr Ser Ala
            275                 280                 285

Leu Ser Ala Asp Glu Leu His Arg Met Arg Ile Ala Pro Gly Ala Ala
        290                 295                 300

Pro Glu Ala Arg Leu Val Ala Phe Arg Ile Phe Gly Cys Ala Gly Thr
305                 310                 315                 320
```

```
Ser Ala Leu Thr Leu Lys Ala Leu Asp Arg Val Leu Asp Pro Asn Asp
                325                 330                 335

Asp Gly Asp Phe Ser Asp Arg Ala Asp Ile Val Asn Leu Ser Val Gly
            340                 345                 350

Thr Asp Tyr Gly Val Phe Asp Glu Ser Thr Asn Tyr Ala Ile Gly Glu
        355                 360                 365

Leu Tyr Arg Gln Gly Val Leu Thr Val Thr Ala Ala Gly Asn Ala Ala
    370                 375                 380

Ser Gln Asn Gly Ala Gly Asp Thr Tyr Ser Val Ser Gly Gly Pro Ala
385                 390                 395                 400

Thr Ser Ala Tyr Ala Leu Thr Val Ala Asn Ser Met Gly Ala Thr Gln
            405                 410                 415

Ser Ala Asp Arg Val Lys Val Leu Ser Pro Ala Gly Thr Ser Glu Ile
        420                 425                 430

Tyr Gly Arg Tyr Thr Thr Lys Tyr Asp Tyr Ala Arg His Arg Glu Gly
    435                 440                 445

Glu Leu Thr Gly Gln Val Val Lys Ala Pro Ala Ser Asn Leu Tyr Gly
    450                 455                 460

Cys Ala Pro Phe Thr Ala Glu Glu Ala Ala Arg Leu Lys Gly Lys Trp
465                 470                 475                 480

Val Tyr Leu Asp Trp Asp Asn Thr Ser Gly Ala Val Pro Cys Gly Ser
            485                 490                 495

Ala Val Arg Phe Ala Asn Val Glu Arg Ala Gly Gly Ala Gly Val Val
        500                 505                 510

Leu Gly Thr Gly Gln Pro Leu Thr Asp Ile Ala Gly Thr Ala Ala Leu
    515                 520                 525

Pro Gly Val Leu Leu Pro Ser Glu Gln Ala Glu Lys Ile Arg Leu Ala
530                 535                 540

Leu Ala Ser Gly Thr Leu Thr Leu Arg Leu Asp Asp Ala Leu Arg Thr
545                 550                 555                 560

Gly Ala Arg Ile Glu Thr Gly Ala Thr Asp Gln Pro Asn Pro Ala Ser
            565                 570                 575

Ala Arg Gly Ala His Gly Ser Trp Gly Ser Ile Lys Pro Asp Val Ser
        580                 585                 590

Ala Pro Gly Thr Gly Ile Ala Ser Ala Arg Ala Gly Ser Gly Ala Gly
    595                 600                 605

Ala Ser Thr Leu Thr Gly Thr Ser Met Ser Ala Ala Tyr Val Cys Gly
    610                 615                 620

Val Ala Ala Gln Leu Val Glu Glu His His Ser Tyr Thr Pro Gln Gln
625                 630                 635                 640

Leu Lys Ala Thr Leu Met Asn Thr Ala Ala His Pro Val His Asp Ala
            645                 650                 655

His Asn Arg Pro Tyr Pro Pro Asp Arg Val Gly Ser Gly Arg Ile Asp
        660                 665                 670

Ser Ala Lys Ala Val Asn Asn Arg Val Leu Val Tyr Asn Ala Ala Arg
    675                 680                 685

Pro Glu Gln Val Ser Asp Thr Ser Gly Val Leu Glu Tyr Ala Pro Asp
    690                 695                 700

Ala Pro Val Ser Thr Leu Arg Arg Glu Met Val Val Glu Asn Thr Asp
705                 710                 715                 720

Thr Ile Ala His Thr Tyr Leu Leu Ser Tyr Thr Ala Ser Ala Glu Ile
            725                 730                 735
```

```
Pro Gly Val Ala Tyr Ser Leu Pro Glu Ser Val Thr Val Pro Pro Gly
            740                 745                 750

Gly Arg Thr Thr Phe Thr Val Thr Leu Thr Val Asp Pro Ala Ala Leu
        755                 760                 765

Ala Lys Thr Ala Glu Ala Thr Ala Asn Thr Thr Gln Arg Ser Thr Gly
    770                 775                 780

Glu Asp Gly Gln Val Val Ala Phe Gly Ala Arg Gln Tyr Val Ala Ser
785                 790                 795                 800

Ala Ser Gly Gln Val Val Leu Thr Glu Gly Asp Thr Thr Leu Arg Val
            805                 810                 815

Pro Val His Ala Ala Pro Lys Leu Val Ser Gln Met Arg Val Ala Ala
            820                 825                 830

Ala Glu Val Gln Phe Glu Arg Gly Gln Gln Ala Gln Leu Pro Leu
            835                 840                 845

Ser Gly Thr Gly Val Asp Gln Gly Gly Tyr Arg Ser Leu Leu Gly Ala
    850                 855                 860

Phe Glu Leu Gly Val Thr Ser Gly His Ile Pro Thr Glu Asp Leu Ser
865                 870                 875                 880

Val Ser Ser Asp Gln Arg Ala Asp Ile Gln Tyr Ala Gly Ala Ala Ser
                885                 890                 895

Asp Ala Ala Leu Ala Ala Ala Gly Lys Asn Pro Asn Asp Gly Ser
            900                 905                 910

Leu Tyr Phe Gly Ile Ser Thr Trp Gly Asn Trp Ser Glu Val Thr Pro
            915                 920                 925

Arg Ser Thr Tyr Tyr Val Phe Ile Asp Thr Asp Gly Asp Gly Thr Asn
    930                 935                 940

Asp Tyr Arg Leu His Thr Met Arg Ala Ala Gly Val Asp Tyr Pro Leu
945                 950                 955                 960

Val Gln Leu Ser Arg Ala Asp Asn Gly Arg Trp Val Pro Val Asp Gly
                965                 970                 975

Ala Leu Tyr Pro Leu Asn Asn Thr Trp Gly Ser Thr Asp Thr Asn Thr
            980                 985                 990

Met Asp Ser Asn Thr Leu Ile Met Gly Val Pro Leu Arg Gln Leu Gly
        995                 1000                1005

Leu Ser Thr Gln Asn Pro Gly Ser Leu Ser Tyr Thr Val Ala Thr
    1010                1015                1020

Thr Ser Ser Tyr Ala Thr Thr Pro Ile Val Asp Ala Thr Glu Ala
    1025                1030                1035

Val Lys Phe Asn Pro Phe Thr Pro Ala Phe Trp Phe Thr Gly Thr
    1040                1045                1050

Ala Ser Gly Val Pro Gly Leu Phe Val Asp Ala Pro Asn Ala Ser
    1055                1060                1065

Leu Thr Val His Arg Thr Glu Gly Ala Glu Gly Lys Leu Leu Leu
    1070                1075                1080

Leu His Leu His Asn Ser Thr Gly Asn Leu Asn Gly Thr Leu Gly
    1085                1090                1095

Ala Thr Gly Asp Arg Ala Gln Val Leu Asn Val Ser Gly Glu Asn
    1100                1105                1110

Thr His Asn Thr Val Arg Ala Arg Phe Thr Asp Val Asn Asp Ala
    1115                1120                1125

Asn Ala Ala Thr Pro Asp Ile Asp Trp Leu Ala Glu Arg Arg Ile
    1130                1135                1140

Thr Arg Gly Tyr Pro Gly Gly Thr Phe His Leu Gly Glu Asp Thr
```

```
                    1145                1150                1155

Glu Arg Gly Ala Ala Ala Ala Phe Phe Tyr Arg Leu Ala Gly Ser
            1160                1165                1170

Pro Ala Tyr Thr Pro Pro Gln Gln Ser Pro Phe Thr Asp Val Pro
        1175                1180                1185

Thr Asn His Pro Phe Tyr Lys Glu Ile Ala Trp Met His Gln Ala
    1190                1195                1200

Gly Ile Thr Thr Gly Trp Ala Asp Gly Thr Phe Arg Pro His Lys
1205                1210                1215

Ala Ala Thr Arg Glu Ala Met Ala Ala Phe Phe Tyr Arg Ala Ala
        1220                1225                1230

Gly Ser Pro Ala Tyr Thr Pro Pro Glu Lys Ser Pro Phe Glu Asp
    1235                1240                1245

Val Pro Thr Gly Ala Arg Phe Tyr Arg Glu Ile Thr Trp Ala Tyr
1250                1255                1260

Glu Lys Lys Ile Phe Thr Glu Glu Thr Ser Leu Leu Lys Pro Ala
        1265                1270                1275

Ala Thr Val Arg Arg Glu Ala Ala Ala Thr Met Ile His Arg Tyr
    1280                1285                1290

Ala Arg Gln Val Leu His Arg Gly
1295                1300
```

<210> SEQ ID NO 57
<211> LENGTH: 1346
<212> TYPE: PRT
<213> ORGANISM: Rothia mucilaginosa

<400> SEQUENCE: 57

```
Met Ala Thr Phe Pro Glu Ala Thr Pro Ala Arg Val Ala Arg His Thr
1               5                   10                  15

Gln Pro Gly Arg Leu Lys Gln Leu Ala Arg Ser Cys Gly Ala Leu Thr
            20                  25                  30

Leu Gly Leu Thr Leu Gly Leu Thr Ala Leu Pro Phe Gly Thr Ala Ala
        35                  40                  45

Tyr Ala Ala Pro Gly Val Val Arg Gly Ala Asp Arg Asp Ala Pro His
    50                  55                  60

His Asp Thr Gly Thr Gly Glu Asn Asn Asn Asp Val Leu Ser Pro Ser
65                  70                  75                  80

Leu Asp Gly Ala Thr Gly Glu Arg Ala Val Phe Val Arg Phe Lys Gly
                85                  90                  95

Gln Gly Ala Tyr Ala Gln Thr Gln Pro Asp Ala Val Arg Ser Arg Ala
            100                 105                 110

Gln Ala Pro Val Asn Ala Gln Ala Gln Val Gln Ala Ile Arg Ala Ser
        115                 120                 125

Val Gln Gln Gln Gly Ala Ser Ala Ala Lys Glu Ser Gly Ala Gln Val
    130                 135                 140

Leu Tyr Thr Thr His Asn Thr Met Arg Gly Val Ala Leu Tyr Gly Asn
145                 150                 155                 160

Val Glu Gln Ile Arg Ala Leu Ala Asn Arg Asp Asp Val Glu Arg Ile
                165                 170                 175

Ser Ile Ile Glu Asp Met Ala Pro Gln Asn Ser Gly Thr Leu Leu Asp
            180                 185                 190

Thr Asp Thr Leu Ser Val Trp Ala Lys Ser Pro Ala Asn Pro Ala Ser
        195                 200                 205
```

```
Thr Gly Tyr Thr Gly Lys Gly Val Lys Ile Val Leu Asp Thr Gly
    210             215                 220

Ile Asp Tyr Thr His Ala Asp Leu Gly Pro Gly Thr Gln Glu Ala
225             230                 235                 240

Phe Glu Lys Ala Lys Ala Ser Asp Thr Ile Pro Glu Gly Ser Tyr Asp
                245                 250                 255

Pro Lys Lys Phe Leu Gly Gly Tyr Asp Leu Val Gly Asp Asp Tyr Asn
                260                 265                 270

Ser Ala Lys Lys Glu Thr Ser Thr Pro His Pro Asp Asn Asn Pro Leu
                275                 280                 285

Asp Cys Gly Gly His Gly Ser His Val Ala Gly Thr Ala Ala Gly Tyr
        290                 295                 300

Gly Val Asn Ala Asp Gly Ser Thr Phe His Gly Asp Tyr Ser Lys Leu
305             310                 315                 320

Thr Glu Glu Gln Leu Lys Asp Met Lys Ile Gly Pro Gly Ser Ala Pro
                325                 330                 335

Asp Ala Gln Leu Ile Gly Leu Arg Ile Phe Gly Cys Lys Gly Thr Thr
                340                 345                 350

Ala Phe Val Pro Lys Gly Leu Asp Arg Val Leu Asp Pro Asn Asp Asp
                355                 360                 365

Gly Asp Phe Ser Asp Arg Ala Asp Ile Ala Asn Leu Ser Leu Gly Asn
370             375                 380

Glu Phe Gly Val Phe Asp Glu Thr Val Asn Tyr Ala Val Gly Ser Leu
385             390                 395                 400

Tyr Arg Glu Gly Ile Leu Ser Val Val Ala Ala Gly Asn Ala Asn Asn
                405                 410                 415

Tyr Asn Ala Val Gly Asp Thr Tyr Ser Asn Ser Gly Pro Gly Thr
                420                 425                 430

Ser Ala Tyr Gly Leu Thr Val Ala Asn Ser Ile Gly Ser Thr Gln Leu
        435                 440                 445

Val Asp Arg Val Lys Ile Leu Ala Pro Ala Asn Glu Ala Asp Thr Tyr
        450                 455                 460

Gly Asp Tyr Ser Val Asn Phe Asp Tyr Ala Lys Ala Thr Glu Glu Gln
465                 470                 475                 480

Leu Arg Gly Thr Val Val Arg Ala Ala Ser Arg Asn Arg Tyr Gly Cys
                485                 490                 495

Glu Ala Phe Thr Glu Glu Ala Ala Leu Lys Gly Lys Trp Ala
                500                 505                 510

Leu Ile Asp Trp Ala Asp Ala Asp Gly Ser Ala Pro Cys Gly Ser Lys
        515                 520                 525

Val Arg Phe Asp Asn Leu Gln Ala Ala Gly Ala Thr Gly Val Val Leu
        530                 535                 540

Thr Ser Asn Thr Glu Val Gly Asp Thr Ala Ile Gly Gly Asn Ser Ser
545                 550                 555                 560

Ile Pro Gly Val Arg Leu Ser Lys Ser Gln Val Glu Arg Leu Ser Ala
                565                 570                 575

Gln Ile Asp Ser Gly Glu Leu Thr Leu Gln Leu Gly Glu Asn Leu Arg
        580                 585                 590

Asp Ser Ile Arg Val Pro Asn Gly Lys Leu Asp Gln Ala Asn Thr Ser
        595                 600                 605

Thr Ala Arg Gly Leu His Gly Ser His Gly Ile Thr Lys Pro Asp Val
        610                 615                 620

Ala Ala Pro Gly Thr Asn Ile Ser Ser Ile Glu Val Gly Ser Gly Thr
```

```
            625                 630                 635                 640
        Gly Ser Ser Val Lys Thr Gly Thr Ser Met Ser Thr Pro Phe Val Ala
                        645                 650                 655
        Gly Val Ala Ala Leu Ile Met Gln Ala His Pro Glu Tyr Gly Pro Arg
                        660                 665                 670
        Met Ile Lys Thr Ala Ile Met Asn Thr Ala Asp His His Met Gln Asp
                        675                 680                 685
        Ala Trp Gly Asn Pro Tyr Ala Val Asp Arg Val Gly Thr Gly Arg Ile
                        690                 695                 700
        Asn Thr Arg Ala Ala Val Ala Asp Arg Val Met Leu Phe Asn Ala Ala
        705                 710                 715                 720
        Arg Pro Glu Gln Val Ser Asp Thr Phe Gly Val Leu Glu Tyr Thr Pro
                        725                 730                 735
        Asn Ala Gly Val Gln Thr Leu Gln His Arg Val Ser Val Glu Asn Thr
                        740                 745                 750
        Asp Ser Val Ala His Thr Tyr Thr Leu Asn Tyr Glu Gly Ser Thr Ser
                        755                 760                 765
        Ile Pro Gly Val Glu Phe Ser Tyr Pro Gln Ser Val Ser Ala Gly Ala
                        770                 775                 780
        Gly Gln Lys Ala Thr Phe Thr Val Thr Val Arg Ile Asp Pro Ser Lys
        785                 790                 795                 800
        Leu Glu Lys Thr Arg Asp Leu Ser Met Tyr Pro Thr Gln Asp Ser Val
                        805                 810                 815
        Asn Tyr Ser Thr Gly Thr Val Thr Ile Ser Gly Ala Arg Gln Tyr Ile
                        820                 825                 830
        Ala Ser Ala Ser Gly Arg Leu Ile Leu Thr Asp Ala Asp Ser Ser Ala
                        835                 840                 845
        Ala Val Lys Thr Leu Arg Met Pro Leu His Val Ala Pro Lys Pro Val
                        850                 855                 860
        Ser Ala Met Arg Val Ala Gly Ala Asp Ile His Phe Asp Thr Asn Gly
        865                 870                 875                 880
        Val Gly Ala Leu Glu Gln Pro Leu Thr Leu Gln Gly Thr Ala Val Asp
                        885                 890                 895
        Gln Gly Gly Tyr Arg Ser Leu Leu Gly Ala Phe Glu Leu Gly Ala Ser
                        900                 905                 910
        Ser Pro Arg Ile Pro Thr Ala Lys Leu Gly Val Gly Ser Asp Ser Arg
                        915                 920                 925
        Met Asp Leu Gln Tyr Val Gly Ala Ala Ser Asn Val Ala Ala Leu Lys
        930                 935                 940
        Ala Ala Gly Ala Asp Thr Ser Asp Ala Arg Leu Ser Phe Gly Ile Ser
        945                 950                 955                 960
        Thr Trp Gly Asn Trp Gln Glu Val Thr Pro Arg Gly Ser Tyr Tyr Val
                        965                 970                 975
        Phe Val Asp Thr Asn Lys Asp Gly Thr Ser Asp Tyr Arg Leu Gln Thr
                        980                 985                 990
        Val Arg Glu Lys Gly Leu Asp Tyr Pro Leu Val Lys Val Ser Lys Arg
                        995                 1000                1005
        Ser Asn Gly Lys Trp Val Ala Ile Glu Asn Gly Leu Tyr Pro Leu
                        1010                1015                1020
        Asn Gly Thr Trp Gly Asp Thr Asp Thr Asn Ile Met Asp Ser Asn
                        1025                1030                1035
        Thr Leu Val Met Thr Val Pro Leu Ser Val Leu Gly Leu Asp Pro
                        1040                1045                1050
```

Asn Ala Glu Ser Thr Glu Ile Ser Tyr Ser Val Thr Thr Ser Ser
1055                1060                1065

Ala Phe Ser Ala Thr Thr Val Val Asp Thr Thr Asp Ser Val Ala
1070                1075                1080

Phe Asn Tyr Ala Thr Pro Lys Leu Trp Phe Ser Gly Asp Ser Ala
1085                1090                1095

Gly Val Pro Asn Leu Phe Val Asp Ala Pro Glu Thr Gln Leu Val
1100                1105                1110

Ala His Arg Asn Gly Asp Ala Lys Asn Val Ser Ala Leu Phe Leu
1115                1120                1125

His Met His Asn Ala Thr Gly Asp Leu Ser Gly Thr Asn Gly Ala
1130                1135                1140

Ala Gly Glu Arg Ala Gln Val Leu Arg Val Ser Ser Ser Ser Glu
1145                1150                1155

Ala Pro Ala Glu Ser Ala His Phe Lys Asp Val Pro Ala Asp Tyr
1160                1165                1170

Pro Phe Val Asn Asp Ile Asn Trp Leu Ala Gln Arg Arg Ile Thr
1175                1180                1185

Thr Gly Tyr Pro Asp Gly Thr Phe Arg Pro Asn Gly Ser Val Glu
1190                1195                1200

Arg Gly Ala Met Ala Ala Phe Phe Tyr Arg Met Ala Gly Ser Pro
1205                1210                1215

Gln Phe Thr Ala Pro Ser Thr Pro Ser Phe Lys Asp Val Pro Arg
1220                1225                1230

Asp His Pro Phe Tyr Lys Glu Ile Glu Trp Met Arg Ala Arg Gly
1235                1240                1245

Ile Thr Thr Gly Trp Ser Asp Gly Thr Phe Arg Pro Asn Asp Ala
1250                1255                1260

Val Asn Arg Asp Ala Met Ala Ala Phe Phe Tyr Arg Tyr Ala Gly
1265                1270                1275

Ser Pro Ala Tyr Ser Ala Pro Ala Val Ser Pro Phe Ser Asp Val
1280                1285                1290

Ser Thr Gly Ser Gln Phe Tyr Arg Glu Ile Ala Trp Leu Ala Asp
1295                1300                1305

Gln Arg Ile Thr Thr Gly Trp Pro Asp Gly Ser Phe Arg Pro Val
1310                1315                1320

Gln Pro Ile Glu Arg Gly Ala Met Ala Ala Phe Leu His Arg Tyr
1325                1330                1335

Asn Val Arg Val Leu Asn Asn Arg
1340                1345

<210> SEQ ID NO 58
<211> LENGTH: 1346
<212> TYPE: PRT
<213> ORGANISM: Rothia mucilaginosa

<400> SEQUENCE: 58

Met Ala Thr Phe Pro Glu Ala Thr Pro Ala Arg Val Ala Arg His Thr
1               5                   10                  15

Gln Pro Gly Arg Leu Lys Gln Leu Ala Arg Ser Cys Gly Ala Leu Thr
                20                  25                  30

Leu Gly Leu Thr Leu Gly Leu Thr Ala Leu Pro Phe Gly Thr Ala Ala
            35                  40                  45

Tyr Ala Ala Pro Gly Val Val Arg Gly Ala Asp Arg Asp Ala Pro His

-continued

```
                50                  55                  60
    His Asp Thr Gly Thr Gly Glu Asn Asn Asn Asp Val Leu Ser Pro Ser
    65                      70                  75                  80

Leu Asp Gly Ala Thr Gly Glu Arg Ala Val Phe Val Arg Phe Lys Gly
                        85                  90                  95

Gln Gly Ala Tyr Ala Gln Thr Gln Pro Asp Ala Val Arg Ser Arg Ala
                    100                 105                 110

Gln Ala Pro Val Asn Ala Gln Ala Gln Val Gln Ala Ile Arg Ala Ser
                    115                 120                 125

Val Gln Gln Gln Gly Ala Ser Ala Ala Lys Glu Ser Gly Ala Gln Val
    130                 135                 140

Leu Tyr Thr Thr His Asn Thr Met Arg Gly Val Ala Leu Tyr Gly Asn
    145                 150                 155                 160

Val Glu Gln Ile Arg Ala Leu Ala Asn Arg Asp Asp Val Glu Arg Ile
                    165                 170                 175

Ser Ile Ile Glu Asp Met Ala Pro Gln Asn Ser Gly Thr Leu Leu Asp
                180                 185                 190

Thr Asp Thr Leu Ser Val Trp Ala Lys Ser Pro Ala Asn Pro Ala Ser
                195                 200                 205

Thr Gly Tyr Thr Gly Lys Gly Val Lys Ile Val Val Leu Asp Thr Gly
    210                 215                 220

Ile Asp Tyr Thr His Ala Asp Leu Gly Pro Gly Thr Gln Glu Ala
    225                 230                 235                 240

Phe Glu Lys Ala Lys Ala Ser Asp Thr Ile Pro Glu Gly Ser Tyr Asp
                    245                 250                 255

Pro Lys Lys Phe Leu Gly Gly Tyr Asp Leu Val Gly Asp Asp Tyr Asn
                    260                 265                 270

Ser Ala Lys Lys Glu Thr Ser Thr Pro His Pro Asp Asn Asn Pro Leu
                275                 280                 285

Asp Cys Gly His Gly Ser His Val Ala Gly Thr Ala Ala Gly Tyr
                290                 295                 300

Gly Val Asn Ala Asp Gly Ser Thr Phe His Gly Asp Tyr Ser Lys Leu
    305                 310                 315                 320

Thr Glu Glu Gln Leu Lys Asp Met Lys Ile Gly Pro Gly Ser Ala Pro
                    325                 330                 335

Asp Ala Gln Leu Ile Gly Leu Arg Ile Phe Gly Cys Lys Gly Thr Thr
                    340                 345                 350

Ala Phe Val Pro Lys Gly Leu Asp Arg Val Leu Asp Pro Asn Asp Asp
                    355                 360                 365

Gly Asp Phe Ser Asp Arg Ala Asp Ile Ala Asn Leu Ser Leu Gly Asn
                370                 375                 380

Glu Phe Gly Val Phe Asp Glu Thr Val Asn Tyr Ala Val Gly Ser Leu
    385                 390                 395                 400

Tyr Arg Glu Gly Ile Leu Ser Val Val Ala Ala Gly Asn Ala Asn Asn
                    405                 410                 415

Tyr Asn Ala Val Gly Asp Thr Tyr Ser Asn Ser Gly Pro Gly Thr
                    420                 425                 430

Ser Ala Tyr Gly Leu Thr Val Ala Asn Ser Ile Gly Ser Thr Gln Leu
                435                 440                 445

Val Asp Arg Val Lys Ile Leu Ala Pro Ala Asn Glu Ala Asp Thr Tyr
    450                 455                 460

Gly Asp Tyr Ser Val Asn Phe Asp Tyr Ala Lys Ala Thr Glu Glu Gln
    465                 470                 475                 480
```

-continued

```
Leu Arg Gly Thr Val Val Arg Ala Ala Ser Arg Asn Arg Tyr Gly Cys
            485                 490                 495
Glu Ala Phe Thr Glu Glu Ala Ala Leu Lys Gly Lys Trp Ala
        500                 505                 510
Leu Ile Asp Trp Ala Asp Ala Asp Gly Ser Ala Pro Cys Gly Ser Lys
            515                 520                 525
Val Arg Phe Asp Asn Leu Gln Ala Ala Gly Ala Thr Gly Val Val Leu
        530                 535                 540
Thr Ser Asn Thr Glu Val Gly Asp Thr Ala Ile Gly Gly Asn Ser Ser
545                 550                 555                 560
Ile Pro Gly Val Arg Leu Ser Lys Ser Gln Val Glu Arg Leu Ser Ala
                565                 570                 575
Gln Ile Asp Ser Gly Glu Leu Thr Leu Gln Leu Gly Glu Asn Leu Arg
            580                 585                 590
Asp Ser Ile Arg Val Pro Asn Gly Lys Leu Asp Gln Ala Asn Thr Ser
        595                 600                 605
Thr Ala Arg Gly Leu His Gly Ser His Gly Ile Thr Lys Pro Asp Val
    610                 615                 620
Ala Ala Pro Gly Thr Asn Ile Ser Ser Ile Glu Val Gly Ser Gly Thr
625                 630                 635                 640
Gly Ser Ser Val Lys Thr Gly Thr Ser Met Ser Thr Pro Phe Val Ala
                645                 650                 655
Gly Val Ala Ala Leu Ile Met Gln Ala His Pro Glu Tyr Gly Pro Arg
            660                 665                 670
Met Ile Lys Thr Ala Ile Met Asn Thr Ala Asp His His Met Gln Asp
        675                 680                 685
Ala Trp Gly Asn Pro Tyr Ala Val Asp Arg Val Gly Thr Gly Arg Ile
    690                 695                 700
Asn Thr Arg Ala Ala Val Ala Asp Arg Val Met Leu Phe Asn Ala Ala
705                 710                 715                 720
Arg Pro Glu Gln Val Ser Asp Thr Phe Gly Val Leu Glu Tyr Thr Pro
                725                 730                 735
Asn Ala Gly Val Gln Thr Leu Gln His Arg Val Ser Val Glu Asn Thr
            740                 745                 750
Asp Ser Val Ala His Thr Tyr Thr Leu Asn Tyr Glu Gly Ser Thr Ser
        755                 760                 765
Ile Pro Gly Val Glu Phe Ser Tyr Pro Gln Ser Val Ser Ala Gly Ala
    770                 775                 780
Gly Gln Lys Ala Thr Phe Thr Val Thr Val Arg Ile Asp Pro Ser Lys
785                 790                 795                 800
Leu Glu Lys Thr Arg Asp Leu Ser Met Tyr Pro Thr Gln Asp Ser Val
                805                 810                 815
Asn Tyr Ser Thr Gly Thr Val Thr Ile Ser Gly Ala Arg Gln Tyr Ile
            820                 825                 830
Ala Ser Ala Ser Gly Arg Leu Ile Leu Thr Asp Ala Asp Ser Ser Ala
        835                 840                 845
Ala Val Lys Thr Leu Arg Met Pro Leu His Val Ala Pro Lys Pro Val
    850                 855                 860
Ser Ala Met Arg Val Ala Gly Ala Asp Ile His Phe Asp Thr Asn Gly
865                 870                 875                 880
Val Gly Ala Leu Glu Gln Pro Leu Thr Leu Gln Gly Thr Ala Val Asp
                885                 890                 895
```

Gln Gly Gly Tyr Arg Ser Leu Leu Gly Ala Phe Glu Leu Gly Ala Ser
            900                 905                 910

Ser Pro Arg Ile Pro Thr Ala Lys Leu Gly Val Gly Ser Asp Ser Arg
        915                 920                 925

Met Asp Leu Gln Tyr Val Gly Ala Ala Ser Asn Val Ala Ala Leu Lys
    930                 935                 940

Ala Ala Gly Ala Asp Thr Ser Asp Ala Arg Leu Ser Phe Gly Ile Ser
945                 950                 955                 960

Thr Trp Gly Asn Trp Gln Glu Val Thr Pro Arg Gly Ser Tyr Tyr Val
                965                 970                 975

Phe Val Asp Thr Asn Lys Asp Gly Thr Ser Asp Tyr Arg Leu Gln Thr
            980                 985                 990

Val Arg Glu Lys Gly Leu Asp Tyr Pro Leu Val Lys Val Ser Lys Arg
        995                 1000                1005

Ser Asn Gly Lys Trp Val Ala Ile Glu Asn Gly Leu Tyr Pro Leu
    1010                1015                1020

Asn Gly Thr Trp Gly Asp Thr Asp Thr Asn Ile Met Asp Ser Asn
    1025                1030                1035

Thr Leu Val Met Thr Val Pro Leu Ser Val Leu Gly Leu Asp Pro
    1040                1045                1050

Asn Ala Glu Ser Thr Glu Ile Ser Tyr Ser Val Thr Thr Ser Ser
    1055                1060                1065

Ala Phe Ser Ala Thr Thr Val Val Asp Thr Thr Asp Ser Val Ala
    1070                1075                1080

Phe Asn Tyr Ala Thr Pro Lys Leu Trp Phe Ser Gly Asp Ser Ala
    1085                1090                1095

Gly Val Pro Asn Leu Phe Val Asp Ala Pro Glu Thr Gln Leu Val
    1100                1105                1110

Ala His Arg Asn Gly Asp Ala Lys Asn Val Ser Ala Leu Phe Leu
    1115                1120                1125

His Met His Asn Ala Thr Gly Asp Leu Ser Gly Thr Asn Gly Ala
    1130                1135                1140

Ala Gly Glu Arg Ala Gln Val Leu Arg Val Ser Ser Ser Ser Glu
    1145                1150                1155

Ala Pro Ala Glu Ser Ala His Phe Lys Asp Val Pro Ala Asp Tyr
    1160                1165                1170

Pro Phe Val Asn Asp Ile Asn Trp Leu Ala Gln Arg Arg Ile Thr
    1175                1180                1185

Thr Gly Tyr Pro Asp Gly Thr Phe Arg Pro Asn Gly Ser Val Glu
    1190                1195                1200

Arg Gly Ala Met Ala Ala Phe Phe Tyr Arg Met Ala Gly Ser Pro
    1205                1210                1215

Gln Phe Thr Ala Pro Ser Thr Pro Ser Phe Lys Asp Val Pro Arg
    1220                1225                1230

Asp His Pro Phe Tyr Lys Glu Ile Glu Trp Met Arg Ala Arg Gly
    1235                1240                1245

Ile Thr Thr Gly Trp Ser Asp Gly Thr Phe Arg Pro Asn Asp Ala
    1250                1255                1260

Val Asn Arg Asp Ala Met Ala Ala Phe Phe Tyr Arg Tyr Ala Gly
    1265                1270                1275

Ser Pro Ala Tyr Ser Ala Pro Ala Val Ser Pro Phe Ser Asp Val
    1280                1285                1290

Ser Thr Gly Ser Gln Phe Tyr Arg Glu Ile Ala Trp Leu Ala Asp

```
              1295                1300                1305
     Gln Arg Ile Thr Thr Gly Trp Pro Asp Gly Ser Phe Arg Pro Val
         1310                1315                1320

Gln Pro Ile Glu Arg Gly Ala Met Ala Ala Phe Leu His Arg Tyr
         1325                1330                1335

Asn Val Arg Val Leu Asn Asn Arg
         1340                1345

<210> SEQ ID NO 59
<211> LENGTH: 1346
<212> TYPE: PRT
<213> ORGANISM: Rothia mucilaginosa

<400> SEQUENCE: 59

Met Ala Thr Phe Pro Glu Ala Thr Pro Ala Arg Ala Ala Arg His Thr
1               5                   10                  15

Gln Pro Gly Arg Leu Lys Gln Leu Ala Arg Ser Cys Gly Ala Leu Thr
            20                  25                  30

Leu Gly Leu Thr Leu Gly Leu Thr Ala Leu Pro Phe Gly Thr Ala Ala
        35                  40                  45

Tyr Ala Ala Pro Gly Val Val Arg Gly Ala Asp Arg Asp Ala Pro His
    50                  55                  60

Gln Asn Thr Gly Thr Gly Glu Asn Asn Asn Glu Val Leu Ser Pro Ser
65                  70                  75                  80

Leu Asp Gly Ala Thr Gly Glu Arg Ala Val Phe Val Arg Phe Lys Gly
                85                  90                  95

Gln Gly Ala Tyr Ala Gln Thr Gln Pro Asp Ala Val Arg Ser Arg Ala
            100                 105                 110

Gln Ala Pro Val Asn Ala Gln Ala Gln Val Gln Ala Ile Arg Ala Ser
        115                 120                 125

Val Gln Gln Gln Gly Ala Ser Ala Ala Lys Glu Ser Gly Ala Gln Val
    130                 135                 140

Leu Tyr Thr Thr His Asn Thr Met Arg Gly Val Ala Leu Tyr Gly Asn
145                 150                 155                 160

Val Glu Gln Ile Arg Ala Leu Ala Asn Arg Asp Asp Val Glu Arg Ile
                165                 170                 175

Ser Ile Ile Glu Asp Met Ala Pro Gln Asn Ser Gly Thr Leu Ile Asp
            180                 185                 190

Thr Asp Thr Leu Ser Val Trp Ala Lys Ser Pro Ala Asn Pro Ala Ser
        195                 200                 205

Thr Gly Tyr Thr Gly Lys Gly Val Lys Ile Val Leu Asp Thr Gly
    210                 215                 220

Ile Asp Tyr Thr His Ala Asp Leu Gly Gly Pro Gly Thr Gln Glu Ala
225                 230                 235                 240

Phe Asp Lys Ala Lys Ala Ser Asp Thr Ile Pro Glu Gly Thr Tyr Asp
                245                 250                 255

Pro Lys Lys Phe Leu Gly Gly Tyr Leu Val Gly Asp Tyr Asn
            260                 265                 270

Ser Gly Lys Lys Glu Thr Ser Thr Pro His Pro Asp Asn Asn Pro Leu
        275                 280                 285

Asp Cys Gly Gly His Gly Ser His Val Ala Gly Thr Ala Ala Gly Tyr
    290                 295                 300

Gly Val Asn Ala Asp Gly Ser Thr Phe His Gly Asp Tyr Ser Lys Leu
305                 310                 315                 320
```

```
Thr Glu Glu Gln Leu Lys Asp Met Lys Ile Gly Pro Gly Ser Ala Pro
                325                 330                 335

Asp Ala Gln Leu Ile Gly Leu Arg Ile Phe Gly Cys Lys Gly Thr Thr
            340                 345                 350

Ala Phe Val Pro Lys Gly Leu Asp Arg Val Leu Asp Pro Asn Asp Asp
        355                 360                 365

Gly Asp Phe Ser Asp Arg Ala Asp Ile Ala Asn Leu Ser Leu Gly Asn
    370                 375                 380

Glu Phe Gly Val Phe Asp Glu Thr Val Asn Tyr Ala Val Gly Ser Leu
385                 390                 395                 400

Tyr Arg Glu Gly Ile Leu Ser Val Val Ala Ala Gly Asn Ala Asn Asn
                405                 410                 415

Tyr Asn Ala Val Gly Asp Thr Tyr Ser Asn Ser Gly Pro Gly Thr
            420                 425                 430

Ser Ala Tyr Gly Leu Thr Val Ala Asn Ser Ile Gly Ser Thr Gln Leu
        435                 440                 445

Val Asp Arg Val Lys Ile Leu Ala Pro Ala Asn Glu Ala Asp Thr Tyr
    450                 455                 460

Gly Asp Tyr Ser Val Ser Phe Asp Tyr Ser Lys Ala Thr Glu Asp Gln
465                 470                 475                 480

Leu Arg Gly Thr Val Val Arg Ala Ala Ser Arg Asn Arg Tyr Ala Cys
                485                 490                 495

Glu Ala Phe Thr Glu Glu Ala Ala Ala Leu Lys Gly Lys Trp Ala
            500                 505                 510

Leu Ile Asp Trp Ala Asp Ala Asp Gly Thr Ala Pro Cys Gly Ser Lys
        515                 520                 525

Val Arg Phe Asp Asn Leu Gln Ala Ala Gly Ala Thr Gly Val Val Leu
    530                 535                 540

Thr Ser Asn Thr Glu Val Gly Asp Thr Ala Ile Gly Gly Asn Ser Ser
545                 550                 555                 560

Ile Pro Gly Val Arg Leu Ala Lys Ser Gln Val Glu Arg Leu Ser Val
                565                 570                 575

Gln Ile Asp Ser Gly Glu Leu Thr Leu Gln Leu Gly Glu Asn Leu Arg
            580                 585                 590

Asp Ser Ile Arg Val Pro Asn Gly Lys Leu Asp Gln Ala Asn Thr Ser
        595                 600                 605

Thr Ala Arg Gly Leu His Gly Ser His Gly Ile Thr Lys Pro Asp Val
    610                 615                 620

Ala Ala Pro Gly Thr Asn Ile Ser Ser Ile Glu Val Gly Ser Gly Thr
625                 630                 635                 640

Gly Ser Ser Val Lys Thr Gly Thr Ser Met Ser Thr Pro Phe Val Ala
                645                 650                 655

Gly Val Ala Ala Leu Ile Met Gln Ala His Pro Glu Tyr Gly Pro Arg
            660                 665                 670

Met Leu Lys Thr Val Ile Met Asn Thr Ala Asp His His Met Gln Asp
        675                 680                 685

Ala Trp Gly Asn Pro Tyr Ala Val Asp Arg Val Gly Thr Gly Arg Ile
    690                 695                 700

Asn Thr Arg Ala Ala Val Ala Asp Arg Val Met Leu Phe Asn Ala Ala
705                 710                 715                 720

Arg Pro Glu Gln Val Ser Asp Thr Phe Gly Val Leu Glu Tyr Thr Pro
                725                 730                 735

Asn Ala Gly Val Gln Thr Leu Gln His Arg Val Ser Val Glu Asn Thr
```

```
              740                 745                 750
Asp Ser Val Ala His Thr Tyr Ala Leu Asn Tyr Glu Gly Ser Thr Ser
            755                 760                 765
Ile Pro Gly Val Glu Phe Ser Tyr Pro Gln Ser Val Ser Val Gly Ala
            770                 775                 780
Gly Gln Lys Ala Thr Phe Thr Val Thr Val Arg Ile Asp Pro Ser Lys
785                 790                 795                 800
Leu Glu Lys Thr Arg Asp Pro Ser Met Tyr Pro Asn Gln Asp Ser Val
                805                 810                 815
Asn Tyr Ser Thr Gly Thr Val Thr Ile Ser Gly Ala Arg Gln Tyr Ile
            820                 825                 830
Ala Ser Ala Ser Gly Arg Leu Ile Leu Thr Asp Ala Asp Ser Ser Ala
            835                 840                 845
Ala Val Lys Thr Leu Arg Met Pro Leu His Val Ala Pro Lys Pro Val
            850                 855                 860
Ser Ala Met Arg Val Ala Gly Ser Asp Ile Ala Phe Asp Ala Glu Gly
865                 870                 875                 880
Ser Gly Ala Thr Glu Gln Thr Leu Thr Leu Gln Gly Thr Ala Val Asp
                885                 890                 895
Gln Gly Gly Tyr Arg Ser Leu Leu Gly Ala Phe Glu Leu Gly Ala Ser
                900                 905                 910
Ser Pro Arg Ile Pro Thr Ala Lys Leu Gly Val Gly Ser Asp Ser Arg
            915                 920                 925
Met Asp Leu Gln Tyr Val Gly Ala Ala Ser Asn Val Ala Ala Leu Lys
            930                 935                 940
Ala Ala Gly Ala Asp Thr Ser Glu Ala Arg Leu Ser Phe Gly Ile Ser
945                 950                 955                 960
Thr Trp Gly Asn Trp Gln Glu Val Thr Pro Arg Gly Thr Tyr Tyr Val
                965                 970                 975
Phe Val Asp Thr Asn Lys Asp Gly Thr Ser Asp Tyr Arg Leu Gln Thr
                980                 985                 990
Val Arg Glu Lys Gly Leu Asp Tyr Pro Leu Val Lys Val Ser Lys Arg
            995                 1000                1005
Ser Asn Gly Lys Trp Gln Ala Ile Glu Asn Ala Leu Tyr Pro Leu
    1010                1015                1020
Asn Gly Thr Trp Gly Asp Thr Asp Thr Asn Ile Met Asp Ser Asn
    1025                1030                1035
Thr Leu Val Met Thr Val Pro Leu Asn Val Leu Gly Leu Asp Pro
    1040                1045                1050
Asp Ala Glu Ser Thr Glu Ile Ser Tyr Ser Val Thr Thr Ser Ser
    1055                1060                1065
Ala Phe Ser Ala Thr Thr Val Val Asp Thr Thr Asp Ser Val Val
    1070                1075                1080
Phe Asn Tyr Ala Ala Pro Lys Leu Trp Phe Ser Gly Asp Ser Ala
    1085                1090                1095
Gly Val Pro Asn Leu Phe Val Asp Ala Pro Glu Thr Gln Leu Val
    1100                1105                1110
Ala His Arg Asn Gly Asp Ala Lys Asn Val Ser Ala Leu Phe Leu
    1115                1120                1125
His Met His Asn Ala Thr Gly Asp Leu Ser Gly Val Asn Gly Ala
    1130                1135                1140
Ala Gly Glu Arg Ala Gln Val Leu Arg Val Ser Ser Asn Ser Glu
    1145                1150                1155
```

```
Ala Thr Ala Ala Ser Ala His Phe Thr Asp Val Pro Ala Asp Tyr
    1160                1165                1170

Pro Phe Val Asn Asp Ile Asn Trp Leu Ala Gln Arg Arg Ile Thr
    1175                1180                1185

Thr Gly Tyr Pro Asp Gly Thr Phe Arg Pro Asn Gly Ser Val Glu
    1190                1195                1200

Arg Gly Ala Met Ala Ala Phe Phe Tyr Arg Met Ala Gly Ser Pro
    1205                1210                1215

Gln Phe Thr Ala Pro Ser Thr Pro Ser Phe Lys Asp Val Pro Arg
    1220                1225                1230

Asp His Pro Phe Tyr Lys Glu Ile Glu Trp Met Arg Ala Arg Gly
    1235                1240                1245

Ile Thr Thr Gly Trp Ser Asp Gly Thr Phe Arg Pro Asn Ala Ala
    1250                1255                1260

Val Asn Arg Asp Ala Met Ala Ala Phe Phe Tyr Arg Phe Ala Gly
    1265                1270                1275

Ser Pro Ala Tyr Ser Ala Pro Ala Ala Ser Pro Phe Ser Asp Val
    1280                1285                1290

Ala Ala Gly Ser Gln Phe Tyr Arg Glu Ile Ser Trp Leu Ala Glu
    1295                1300                1305

Gln Arg Ile Thr Thr Gly Trp Ala Asp Gly Ser Phe Arg Pro Val
    1310                1315                1320

Gln Pro Ile Glu Arg Gly Ala Met Ala Ala Phe Leu His Arg Tyr
    1325                1330                1335

Asn Val Arg Val Leu Asn Asn Arg
    1340                1345

<210> SEQ ID NO 60
<211> LENGTH: 1346
<212> TYPE: PRT
<213> ORGANISM: Rothia mucilaginosa

<400> SEQUENCE: 60

Met Ala Thr Phe Pro Glu Ala Thr Pro Ala Arg Ala Ala Arg His Thr
1               5                   10                  15

Gln Pro Gly Arg Leu Lys Gln Leu Ala Arg Ser Cys Gly Ala Leu Thr
            20                  25                  30

Leu Gly Leu Thr Leu Gly Leu Thr Ala Leu Pro Phe Gly Thr Ala Ala
        35                  40                  45

Tyr Ala Ala Pro Gly Val Val Arg Ser Ala Asp Arg Asp Ala Pro His
    50                  55                  60

Gln Asn Thr Gly Thr Gly Glu Asn Asn Glu Val Leu Ser Pro Ser
65                  70                  75                  80

Leu Asp Gly Ala Thr Gly Glu Arg Ala Val Phe Val Arg Phe Lys Gly
                85                  90                  95

Gln Gly Ala Tyr Ala Gln Thr Gln Pro Asp Ala Val Arg Ser Arg Ala
            100                 105                 110

Gln Ala Pro Val Asn Ala Gln Ala Gln Val Gln Ala Ile Arg Ala Ser
        115                 120                 125

Val Gln Gln Gln Gly Ala Ser Ala Ala Lys Glu Ser Gly Ala Gln Val
    130                 135                 140

Leu Tyr Thr Thr His Asn Thr Met Arg Gly Val Ala Leu Tyr Gly Asn
145                 150                 155                 160

Val Glu Gln Ile Arg Ala Leu Ala Asn Arg Asp Asp Val Glu Arg Ile
```

```
                165                 170                 175
Ser Ile Ile Glu Asp Met Ala Pro Gln Asn Ser Gly Thr Leu Ile Asp
            180                 185                 190

Thr Asp Thr Leu Ser Val Trp Ala Lys Ser Pro Ala Asn Pro Ala Ser
        195                 200                 205

Thr Gly Tyr Thr Gly Lys Gly Val Lys Ile Val Val Leu Asp Thr Gly
    210                 215                 220

Ile Asp Tyr Thr His Ala Asp Leu Gly Pro Gly Thr Gln Glu Ala
225                 230                 235                 240

Phe Glu Lys Ala Lys Ala Ser Asp Thr Ile Pro Glu Gly Thr Tyr Asp
                245                 250                 255

Pro Lys Lys Phe Leu Gly Gly Tyr Asp Leu Val Gly Asp Asp Tyr Asn
            260                 265                 270

Ser Gly Lys Lys Glu Thr Ser Thr Pro His Pro Asp Asn Asn Pro Leu
        275                 280                 285

Asp Cys Gly Gly His Gly Ser His Val Ala Gly Thr Ala Ala Gly Tyr
    290                 295                 300

Gly Val Asn Ala Asp Gly Ser Thr Phe His Gly Asp Tyr Ser Lys Leu
305                 310                 315                 320

Thr Glu Glu Gln Leu Lys Asp Met Lys Ile Gly Pro Gly Ser Ala Pro
                325                 330                 335

Asp Ala Gln Leu Ile Gly Leu Arg Ile Phe Gly Cys Lys Gly Thr Thr
            340                 345                 350

Ala Phe Val Pro Lys Gly Leu Asp Arg Val Leu Asp Pro Asn Asp Asp
        355                 360                 365

Gly Asp Phe Ser Asp Arg Ala Asp Ile Ala Asn Leu Ser Leu Gly Asn
    370                 375                 380

Glu Phe Gly Val Phe Asp Glu Thr Val Asn Tyr Ala Val Gly Ser Leu
385                 390                 395                 400

Tyr Arg Glu Gly Ile Leu Ser Val Val Ala Gly Asn Ala Asn Asn
                405                 410                 415

Tyr Asn Ala Val Gly Asp Thr Tyr Ser Asn Ser Gly Pro Gly Thr
            420                 425                 430

Ser Ala Tyr Gly Leu Thr Val Ala Asn Ser Ile Gly Ser Thr Gln Leu
        435                 440                 445

Val Asp Arg Val Lys Val Leu Ala Pro Ala Asn Glu Ala Asp Thr Tyr
    450                 455                 460

Gly Asp Tyr Ser Val Asn Phe Asp Tyr Thr Lys Ala Thr Glu Glu Gln
465                 470                 475                 480

Leu Arg Gly Thr Val Val Arg Ala Ala Ser Arg Asn Arg Tyr Ala Cys
                485                 490                 495

Glu Ala Phe Thr Glu Glu Ala Ala Leu Lys Gly Lys Trp Ala
            500                 505                 510

Leu Ile Asp Trp Ala Asp Ala Asp Gly Ser Ala Pro Cys Gly Ser Lys
        515                 520                 525

Val Arg Phe Asp Asn Leu Gln Ala Ala Gly Ala Thr Gly Val Val Leu
    530                 535                 540

Thr Ser Asn Thr Glu Val Gly Asp Thr Ala Ile Gly Gly Asn Ser Ser
545                 550                 555                 560

Ile Pro Gly Val Arg Leu Ala Lys Ser Gln Val Glu Arg Leu Ser Ala
                565                 570                 575

Gln Ile Asp Ala Gly Glu Leu Thr Leu Gln Leu Gly Glu Asn Leu Arg
            580                 585                 590
```

```
Asp Ser Ile Arg Val Pro Asn Gly Lys Leu Asp Gln Ala Asn Thr Ser
        595                 600                 605

Thr Ala Arg Gly Leu His Gly Ser His Gly Ile Thr Lys Pro Asp Val
610                 615                 620

Ala Ala Pro Gly Thr Asn Ile Ser Ser Ile Glu Val Gly Ser Gly Thr
625                 630                 635                 640

Gly Ser Ser Val Lys Thr Gly Thr Ser Met Ser Thr Pro Phe Val Ala
                645                 650                 655

Gly Val Ala Ala Leu Ile Met Gln Ala His Pro Glu Tyr Gly Pro Arg
                660                 665                 670

Met Ile Lys Thr Ala Ile Met Asn Thr Ala Asp His His Met Gln Asp
                675                 680                 685

Ala Trp Gly Asn Pro Tyr Ala Val Asp Arg Val Gly Thr Gly Arg Ile
                690                 695                 700

Asn Thr Arg Ala Ala Val Ala Asp Arg Val Met Leu Phe Asn Ala Ala
705                 710                 715                 720

Arg Pro Glu Gln Val Ser Asp Thr Phe Gly Val Leu Glu Tyr Thr Pro
                725                 730                 735

Asn Ala Gly Val Gln Thr Leu Gln His Arg Val Ser Val Glu Asn Thr
                740                 745                 750

Asp Ser Val Ala His Thr Tyr Thr Leu Asn Tyr Glu Gly Ser Thr Ser
                755                 760                 765

Ile Pro Gly Val Glu Phe Ser Tyr Pro Gln Ser Val Ser Val Gly Ala
                770                 775                 780

Gly Gln Lys Ala Thr Phe Thr Val Thr Val Arg Ile Asp Pro Ser Lys
785                 790                 795                 800

Leu Glu Lys Thr Arg Asp Pro Ser Met Tyr Pro Asn Gln Asp Ser Val
                805                 810                 815

Asn Tyr Ser Thr Gly Thr Val Thr Ile Ser Gly Ala Arg Gln Tyr Ile
                820                 825                 830

Ala Ser Ala Ser Gly Arg Leu Ile Leu Thr Asp Ala Asp Ser Ser Ala
                835                 840                 845

Ala Val Lys Thr Leu Arg Met Pro Leu His Val Ala Pro Lys Pro Val
                850                 855                 860

Ser Ala Met Arg Val Ala Gly Ser Asp Ile Ala Phe Asp Ala Glu Gly
865                 870                 875                 880

Ser Gly Ala Thr Glu Gln Thr Leu Thr Leu Gln Gly Thr Ala Val Asp
                885                 890                 895

Gln Gly Gly Tyr Arg Ser Leu Leu Gly Ala Phe Glu Leu Gly Ala Ser
                900                 905                 910

Ser Pro Arg Ile Pro Thr Ala Lys Leu Gly Val Gly Ser Asp Ser Arg
                915                 920                 925

Met Asp Leu Gln Tyr Val Gly Ala Ala Ser Asp Val Ala Ala Leu Lys
930                 935                 940

Ala Ala Gly Ala Asp Thr Ser Glu Ala Arg Leu Ser Phe Gly Ile Ser
945                 950                 955                 960

Thr Trp Gly Asn Trp Gln Glu Val Thr Pro Arg Gly Thr Tyr Tyr Val
                965                 970                 975

Phe Val Asp Thr Asp Lys Asp Gly Thr Ser Asp Tyr Arg Leu Gln Thr
                980                 985                 990

Val Arg Glu Lys Gly Leu Asp Tyr  Pro Leu Val Lys Val  Ser Lys Arg
                995                 1000                1005
```

Ser Asn Gly Lys Trp Gln Ala Ile Glu Asn Ala Leu Tyr Pro Leu
    1010                1015                1020

Asn Gly Thr Trp Gly Asp Asp Thr Asn Ile Met Asp Ser Asn
    1025                1030                1035

Thr Leu Val Met Thr Val Pro Leu Ser Val Leu Gly Leu Asp Pro
    1040                1045                1050

Asn Ala Glu Ser Thr Glu Ile Ser Tyr Ser Val Thr Thr Ser Ser
    1055                1060                1065

Ala Phe Ser Ala Thr Thr Val Val Asp Thr Thr Asp Ser Val Val
    1070                1075                1080

Phe Asn Tyr Ala Ala Pro Lys Leu Trp Phe Ser Gly Asp Ser Ala
    1085                1090                1095

Gly Val Pro Asn Leu Phe Val Asp Ala Pro Glu Thr Gln Leu Val
    1100                1105                1110

Ala His Arg Asn Gly Asp Ala Lys Asn Val Ser Ala Leu Phe Leu
    1115                1120                1125

His Met His Asn Ala Thr Gly Asp Leu Ser Gly Thr Asn Gly Ser
    1130                1135                1140

Ala Gly Glu Arg Ala Gln Val Leu Arg Val Ser Ser Asn Ser Glu
    1145                1150                1155

Asp Thr Ala Ala Ser Ala His Phe Thr Asp Val Pro Ala Asp Tyr
    1160                1165                1170

Pro Phe Val Asn Asp Ile Asn Trp Leu Ala Gln Arg Arg Ile Thr
    1175                1180                1185

Thr Gly Tyr Pro Asp Gly Thr Phe Arg Pro Asn Gly Ser Val Glu
    1190                1195                1200

Arg Gly Ala Met Ala Ala Phe Phe Tyr Arg Met Ala Gly Ser Pro
    1205                1210                1215

Gln Phe Thr Ala Pro Ser Thr Pro Ser Phe Lys Asp Val Pro Arg
    1220                1225                1230

Asp His Pro Phe Tyr Lys Glu Ile Glu Trp Met Arg Ala Arg Gly
    1235                1240                1245

Ile Thr Thr Gly Trp Ser Asp Gly Thr Phe Arg Pro Asn Ala Ala
    1250                1255                1260

Val Asn Arg Asp Ala Met Ala Ala Phe Phe Tyr Arg Phe Ala Gly
    1265                1270                1275

Ser Pro Ala Tyr Ser Ala Pro Val Ala Ser Pro Phe Ser Asp Val
    1280                1285                1290

Ser Ala Gly Ser Gln Phe Tyr Arg Glu Ile Ser Trp Leu Ala Glu
    1295                1300                1305

Gln Arg Ile Thr Thr Gly Trp Ala Asp Gly Ser Phe Arg Pro Val
    1310                1315                1320

Gln Pro Ile Glu Arg Gly Ala Met Ala Ala Phe Leu His Arg Tyr
    1325                1330                1335

Asn Val Arg Val Leu Asn Asn Arg
    1340                1345

<210> SEQ ID NO 61
<211> LENGTH: 1346
<212> TYPE: PRT
<213> ORGANISM: Rothia mucilaginosa

<400> SEQUENCE: 61

Met Ala Thr Phe Pro Glu Ala Thr Pro Ala Arg Ala Ala Arg His Thr
1               5                   10                  15

```
Gln Pro Gly Arg Leu Lys Gln Leu Ala Arg Ser Cys Gly Ala Leu Thr
             20                  25                  30

Leu Gly Leu Thr Leu Gly Leu Thr Ala Leu Pro Phe Gly Thr Ala Ala
         35                  40                  45

Tyr Ala Ala Pro Gly Val Val Arg Ser Ala Asp Arg Asp Ala Pro His
     50                  55                  60

Gln Asn Thr Gly Thr Gly Glu Asn Asn Asn Glu Val Leu Ser Pro Ser
 65                  70                  75                  80

Leu Asp Gly Ala Thr Gly Glu Arg Ala Val Phe Val Arg Phe Lys Gly
                 85                  90                  95

Gln Gly Ala Tyr Ala Gln Thr Gln Pro Asp Ala Val Arg Ser Arg Ala
            100                 105                 110

Gln Ala Pro Val Asn Ala Gln Ala Gln Val Gln Ala Ile Arg Ala Ser
        115                 120                 125

Val Gln Gln Gln Gly Ala Ser Ala Ala Lys Glu Ser Gly Ala Gln Val
130                 135                 140

Leu Tyr Thr Thr His Asn Thr Met Arg Gly Val Ala Leu Tyr Gly Asn
145                 150                 155                 160

Val Glu Gln Ile Arg Ala Leu Ala Asn Arg Asp Asp Val Glu Arg Ile
                165                 170                 175

Ser Ile Ile Glu Asp Met Ala Pro Gln Asn Ser Gly Thr Leu Ile Asp
            180                 185                 190

Thr Asp Thr Leu Ser Val Trp Ala Lys Ser Pro Ala Asn Pro Ala Ser
        195                 200                 205

Thr Gly Tyr Thr Gly Lys Gly Val Lys Ile Val Leu Asp Thr Gly
    210                 215                 220

Ile Asp Tyr Thr His Ala Asp Leu Gly Gly Pro Gly Thr Gln Glu Ala
225                 230                 235                 240

Phe Glu Lys Ala Lys Ala Ser Asp Thr Ile Pro Glu Gly Thr Tyr Asp
                245                 250                 255

Pro Lys Lys Phe Leu Gly Gly Tyr Asp Leu Val Gly Asp Asp Tyr Asn
            260                 265                 270

Ser Gly Lys Lys Glu Thr Ser Thr Pro His Pro Asp Asn Asn Pro Leu
        275                 280                 285

Asp Cys Gly Gly His Gly Ser His Val Ala Gly Thr Ala Ala Gly Tyr
290                 295                 300

Gly Val Asn Ala Asp Gly Ser Thr Phe His Gly Asp Tyr Ser Lys Leu
305                 310                 315                 320

Thr Glu Glu Gln Leu Lys Asp Met Lys Ile Gly Pro Gly Ser Ala Pro
                325                 330                 335

Asp Ala Gln Leu Ile Gly Leu Arg Ile Phe Gly Cys Lys Gly Thr Thr
            340                 345                 350

Ala Phe Val Pro Lys Gly Leu Asp Arg Val Leu Asp Pro Asn Asp Asp
        355                 360                 365

Gly Asp Phe Ser Asp Arg Ala Asp Ile Ala Asn Leu Ser Leu Gly Asn
370                 375                 380

Glu Phe Gly Val Phe Asp Glu Thr Val Asn Tyr Ala Val Gly Ser Leu
385                 390                 395                 400

Tyr Arg Glu Gly Ile Leu Ser Val Val Ala Ala Gly Asn Ala Asn Asn
                405                 410                 415

Tyr Asn Ala Val Gly Asp Thr Tyr Ser Asn Ser Gly Gly Pro Gly Thr
            420                 425                 430
```

```
Ser Ala Tyr Gly Leu Thr Val Ala Asn Ser Ile Gly Ser Thr Gln Leu
        435                 440                 445

Val Asp Arg Val Lys Val Leu Ala Pro Ala Asn Glu Ala Asp Thr Tyr
450                 455                 460

Gly Asp Tyr Ser Val Asn Phe Asp Tyr Thr Lys Ala Thr Glu Glu Gln
465                 470                 475                 480

Leu Arg Gly Thr Val Arg Ala Ala Ser Arg Asn Arg Tyr Ala Cys
                485                 490                 495

Glu Ala Phe Thr Glu Glu Ala Ala Leu Lys Gly Lys Trp Ala
            500                 505                 510

Leu Ile Asp Trp Ala Asp Ala Asp Gly Ser Ala Pro Cys Gly Ser Lys
        515                 520                 525

Val Arg Phe Asp Asn Leu Gln Ala Ala Gly Ala Thr Gly Val Val Leu
530                 535                 540

Thr Ser Asn Thr Glu Val Gly Asp Thr Ala Ile Gly Gly Asn Ser Ser
545                 550                 555                 560

Ile Pro Gly Val Arg Leu Ala Lys Ser Gln Val Glu Arg Leu Ser Ala
                565                 570                 575

Gln Ile Asp Ala Gly Glu Leu Thr Leu Gln Leu Gly Glu Asn Leu Arg
        580                 585                 590

Asp Ser Ile Arg Val Pro Asn Gly Lys Leu Asp Gln Ala Asn Thr Ser
        595                 600                 605

Thr Ala Arg Gly Leu His Gly Ser His Gly Ile Thr Lys Pro Asp Val
        610                 615                 620

Ala Ala Pro Gly Thr Asn Ile Ser Ser Ile Glu Val Gly Ser Gly Thr
625                 630                 635                 640

Gly Ser Ser Val Lys Thr Gly Thr Ser Met Ser Thr Pro Phe Val Ala
                645                 650                 655

Gly Val Ala Ala Leu Ile Met Gln Ala His Pro Glu Tyr Gly Pro Arg
            660                 665                 670

Met Ile Lys Thr Ala Ile Met Asn Thr Ala Asp His His Met Gln Asp
        675                 680                 685

Ala Trp Gly Asn Pro Tyr Ala Val Asp Arg Val Gly Thr Gly Arg Ile
690                 695                 700

Asn Thr Arg Ala Ala Val Ala Asp Arg Val Met Leu Phe Asn Ala Ala
705                 710                 715                 720

Arg Pro Glu Gln Val Ser Asp Thr Phe Gly Val Leu Glu Tyr Thr Pro
                725                 730                 735

Asn Ala Gly Val Gln Thr Leu Gln His Arg Val Ser Val Glu Asn Thr
            740                 745                 750

Asp Ser Val Ala His Thr Tyr Thr Leu Asn Tyr Glu Gly Ser Thr Ser
        755                 760                 765

Ile Pro Gly Val Glu Phe Ser Tyr Pro Gln Ser Val Ser Val Gly Ala
770                 775                 780

Gly Gln Lys Ala Thr Phe Thr Val Thr Val Arg Ile Asp Pro Ser Lys
785                 790                 795                 800

Leu Glu Lys Thr Arg Asp Pro Ser Met Tyr Pro Asn Gln Asp Ser Val
                805                 810                 815

Asn Tyr Ser Thr Gly Thr Val Thr Ile Ser Gly Ala Arg Gln Tyr Ile
            820                 825                 830

Ala Ser Ala Ser Gly Arg Leu Ile Leu Thr Asp Ala Asp Ser Ser Ala
        835                 840                 845

Ala Val Lys Thr Leu Arg Met Pro Leu His Val Ala Pro Lys Pro Val
```

```
            850                 855                 860
Ser Ala Met Arg Val Ala Gly Ser Asp Ile Ala Phe Asp Ala Glu Gly
865                 870                 875                 880

Ser Gly Ala Thr Glu Gln Thr Leu Thr Leu Gln Gly Thr Ala Val Asp
                885                 890                 895

Gln Gly Gly Tyr Arg Ser Leu Leu Gly Ala Phe Glu Leu Gly Ala Ser
            900                 905                 910

Ser Pro Arg Ile Pro Thr Ala Lys Leu Gly Val Gly Ser Asp Ser Arg
        915                 920                 925

Met Asp Leu Gln Tyr Val Gly Ala Ala Ser Asp Val Ala Ala Leu Lys
    930                 935                 940

Ala Ala Gly Ala Asp Thr Ser Glu Ala Arg Leu Ser Phe Gly Ile Ser
945                 950                 955                 960

Thr Trp Gly Asn Trp Gln Glu Val Thr Pro Arg Gly Tyr Tyr Val
                965                 970                 975

Phe Val Asp Thr Asp Lys Asp Gly Thr Ser Tyr Arg Leu Gln Thr
                980                 985                 990

Val Arg Glu Lys Gly Leu Asp Tyr Pro Leu Val Lys Val Ser Lys Arg
        995                 1000                1005

Ser Asn Gly Lys Trp Gln Ala Ile Glu Asn Ala Leu Tyr Pro Leu
    1010                1015                1020

Asn Gly Thr Trp Gly Asp Thr Asn Ile Met Asp Ser Asn
    1025                1030                1035

Thr Leu Val Met Thr Val Pro Leu Ser Val Leu Gly Leu Asp Pro
    1040                1045                1050

Asn Ala Glu Ser Thr Glu Ile Ser Tyr Ser Val Thr Thr Ser Ser
    1055                1060                1065

Ala Phe Ser Ala Thr Thr Val Val Asp Thr Asp Ser Val Val
    1070                1075                1080

Phe Asn Tyr Ala Ala Pro Lys Leu Trp Phe Ser Gly Asp Ser Ala
    1085                1090                1095

Gly Val Pro Asn Leu Phe Val Asp Ala Pro Glu Thr Gln Leu Val
    1100                1105                1110

Ala His Arg Asn Gly Asp Ala Lys Asn Val Ser Ala Leu Phe Leu
    1115                1120                1125

His Met His Asn Ala Thr Gly Asp Leu Ser Gly Thr Asn Gly Ser
    1130                1135                1140

Ala Gly Glu Arg Ala Gln Val Leu Arg Val Ser Asn Ser Glu
    1145                1150                1155

Asp Thr Ala Ala Ser Ala His Phe Thr Asp Val Pro Ala Asp Tyr
    1160                1165                1170

Pro Phe Val Asn Asp Ile Asn Trp Leu Ala Gln Arg Arg Ile Thr
    1175                1180                1185

Thr Gly Tyr Pro Asp Gly Thr Phe Arg Pro Asn Gly Ser Val Glu
    1190                1195                1200

Arg Gly Ala Met Ala Ala Phe Phe Tyr Arg Met Ala Gly Ser Pro
    1205                1210                1215

Gln Phe Thr Ala Pro Ser Thr Pro Ser Phe Lys Asp Val Pro Arg
    1220                1225                1230

Asp His Pro Phe Tyr Lys Glu Ile Glu Trp Met Arg Ala Arg Gly
    1235                1240                1245

Ile Thr Thr Gly Trp Ser Asp Gly Thr Phe Arg Pro Asn Ala Ala
    1250                1255                1260
```

```
Val Asn Arg Asp Ala Met Ala Ala Phe Phe Tyr Arg Phe Ala Gly
    1265            1270                1275

Ser Pro Ala Tyr Ser Ala Pro Val Ala Ser Pro Phe Ser Asp Val
    1280            1285                1290

Ser Ala Gly Ser Gln Phe Tyr Arg Glu Ile Ser Trp Leu Ala Glu
    1295            1300                1305

Gln Arg Ile Thr Thr Gly Trp Ala Asp Gly Ser Phe Arg Pro Val
    1310            1315                1320

Gln Pro Ile Glu Arg Gly Ala Met Ala Ala Phe Leu His Arg Tyr
    1325            1330                1335

Asn Val Arg Val Leu Asn Asn Arg
    1340            1345

<210> SEQ ID NO 62
<211> LENGTH: 1341
<212> TYPE: PRT
<213> ORGANISM: Rothia mucilaginosa

<400> SEQUENCE: 62

Met Lys His Thr Ala Ser Pro Asn Pro Arg Gly Arg Ser His Arg Arg
1               5                   10                  15

Arg Ile Gly Ser Gly Leu Leu Thr Leu Ser Met Ala Leu Ser Pro Leu
            20                  25                  30

Ala Ala Leu Gly Thr Thr Ala His Ala Ala Glu Asp Pro Asp Ala Val
        35                  40                  45

Lys Gln Val Leu Ser Glu Ser Met Lys Asn Ala Ser Gly Thr Val Thr
50                  55                  60

Ala Phe Ile Arg Phe Lys Gly Lys Gly Ala Phe Glu Gln Thr Gln Pro
65                  70                  75                  80

Ala Gly Val Arg Ala Gly Val Gln Ala Pro Val Asn Thr Ser Ser Gln
                85                  90                  95

Val Gln Ala Ile Ala Ser Gln Val Gln Ser Gln Ala Gln Val Ser
            100                 105                 110

Ser Gln Ser Gly Ala Gln Val Leu Tyr Thr Thr His Asn Ala Val Arg
        115                 120                 125

Gly Val Ala Val Arg Gly Asp Ala Glu Ser Ile Lys Ala Leu Ala Asn
    130                 135                 140

Arg Pro Asp Val Glu Lys Ile Ser Pro Ile Leu Pro Lys Tyr Arg Gln
145                 150                 155                 160

Asn Ala Gly Ala Ala Ile Asp Ala Gly Ser Leu Ala Thr Trp Thr Gly
                165                 170                 175

Thr Thr Asn Pro Ala Gly Ala Gly Gly Tyr Thr Gly Lys Gly Val Lys
            180                 185                 190

Ile Ala Val Ile Asp Ser Gly Ile Asp Tyr Thr His Thr Asp Phe Gly
        195                 200                 205

Gly Ser Gly Lys Leu Glu Asp Tyr Glu Lys Ala Ser Lys Leu Thr Glu
    210                 215                 220

Leu Pro Ser Ala Asp Ser Gly Leu Ile Asn Arg Thr Lys Val Val Gly
225                 230                 235                 240

Gly Tyr Asp Leu Val Gly Asp Ala Tyr Asp Gly Ser Asn Thr Ala Val
                245                 250                 255

Pro Asp Gly Asn Pro Leu Asp Cys Thr Thr Gly Gly His Gly Thr His
            260                 265                 270

Val Ala Gly Thr Ala Ala Gly Tyr Gly Val Asn Ala Asp Gly Thr Thr
```

275                     280                     285
Phe Thr Gly Asp Tyr Ser Lys Leu Thr Ala Glu Gln Leu Lys Thr Met
290                     295                     300
Lys Ile Gly Pro Gly Val Ala Pro Asp Ala Glu Ile Tyr Ala Phe Arg
305                     310                     315                     320
Val Phe Gly Cys Ser Gly Ser Thr Asn Val Val Ile Glu Ala Leu Asp
                        325                     330                     335
Arg Ala Leu Asp Pro Asn Gly Asp Gly Asp Phe Ser Asp Arg Val Asn
                340                     345                     350
Val Val Asn Met Ser Leu Gly Gly Glu Phe Ser Pro Gln Asp Asp Pro
            355                     360                     365
Glu Ala Tyr Ala Val Asp Ala Leu Thr Arg Ala Gly Val Leu Ser Val
        370                     375                     380
Ile Ser Ala Gly Asn Ala Asn Asp Tyr Ser Leu Arg Gly Asp Thr Tyr
385                     390                     395                     400
Ser Asn Ser Gly His Pro Ala Thr Ala Ala Ser Ala Ile Thr Val Ala
                        405                     410                     415
Asn Ala Tyr Gly Ser Thr Arg Ala Val Asp Ala Ala Glu Leu Thr Asp
                420                     425                     430
Pro Ala Thr Gly Thr Thr Arg Lys Val Arg Gly Asp Tyr Ser Val Ser
            435                     440                     445
Tyr Pro Trp Ala Gln Ala Gly Ser Lys Glu Phe Thr Gly Glu Leu Thr
        450                     455                     460
Ala Ile Ser Glu Asn Asn Arg Tyr Ala Cys Asn Ala Leu Ser Ala Asp
465                     470                     475                     480
Glu Ala Ala Val Lys Gly Lys Trp Val Leu Ile Asp Trp Ala Lys
                        485                     490                     495
Asp Asp Gly Glu Leu Ala Cys Gly Ser Lys Val Arg Phe Asp Asn Leu
                500                     505                     510
Glu Ala Ala Gly Ala Lys Gly Val Leu Leu Ala Gly Asn Asp Glu Glu
            515                     520                     525
Pro Gly Leu Gly Ile Ala Gly Asn Asp Thr Leu Pro Gly Phe Arg Leu
        530                     535                     540
Ala Ala Ser Ala Ala Lys Asp Leu Arg Ala Gln Ile Thr Ala Ala Glu
545                     550                     555                     560
Ala Ala Gly Lys Pro Leu Thr Val Arg Leu Gly Asn Glu Leu Lys Ser
                        565                     570                     575
Ser Leu Arg Val Asp Thr Asp Lys Leu Asp Gln Leu Asn Pro Met Ser
                580                     585                     590
Ala Arg Gly Phe His Gly Ser Tyr Gly Tyr Thr Lys Pro Asp Ile Ala
            595                     600                     605
Ala Pro Gly Ser Tyr Ile Thr Ser Ala Ala Val Ala Thr Gly Ser Asn
        610                     615                     620
Ser Val Thr Phe Ser Gly Thr Ser Met Ala Ala Pro Tyr Val Thr Gly
625                     630                     635                     640
Ser Ala Ala Leu Val Met Gln Ser His Pro Thr Tyr Thr Pro Ala Gln
                        645                     650                     655
Val Lys Ser Ala Leu Met Asn Thr Ala Thr His Asp Val Arg Thr Glu
                660                     665                     670
Ser Gly Ala Ala Tyr Ala Val Asp Arg Val Gly Ala Gly Arg Val Asp
            675                     680                     685
Thr Leu Ala Ala Val Gln Ser Lys Ser Leu Val Tyr Asn Ala Asp Lys
        690                     695                     700

```
Ser Gly Thr Val Ser Leu Ser Phe Gly Val Leu Glu Tyr Ala Pro Asp
705                 710                 715                 720

Ala Gly Val Gln Ile Leu Thr Arg Glu Val Thr Val Glu Asn Thr Asp
                725                 730                 735

Ser Val Ala His Thr Tyr Ala Leu Ser Tyr Ala Glu Ser Thr Asn Ile
            740                 745                 750

Pro Gly Val Glu Tyr Ser Phe Pro Ser Ala Val Thr Leu Ala Pro Gly
        755                 760                 765

Glu Thr Lys Lys Phe Glu Val Thr Val Arg Ile Asp Pro Ser Lys Leu
770                 775                 780

Glu Lys Thr Arg Asp Ala Ala Met Asp Thr Thr Gln Asn Ala Thr Glu
785                 790                 795                 800

Tyr Tyr Thr Gly Thr Glu Thr Val Pro Ala Gln Tyr Arg Gln Tyr Ile
                805                 810                 815

Ala Ser Ala Ser Gly Arg Leu Val Leu Thr Glu Asp Gly Thr Lys Ala
            820                 825                 830

Leu Arg Leu Pro Val His Val Ala Pro Lys Pro Val Ser Thr Met His
        835                 840                 845

Ala Ala Glu Asp Thr Val Thr Phe Thr Gln Lys Pro Ser Ser Asp Glu
850                 855                 860

Ala Gln Lys Ala Asp Thr Gly Trp Thr Lys Ser Gln Ile Ser Leu Arg
865                 870                 875                 880

Gly Thr Glu Val Asn Gln Gly Gly Tyr Arg Ser Leu Leu Gly Ala Phe
                885                 890                 895

Glu Tyr Gly Ala Ser Val Asp Arg Val Ala Pro Thr Ser Leu Ser Leu
            900                 905                 910

Asn Ser Asn Val Lys Ala Asn Leu Gln Tyr Val Gly Ala Ser Ser Asp
        915                 920                 925

Ala Pro Ala Leu Lys Ala Gly Gly Asn Ala Asp Asp Gly Thr Leu
930                 935                 940

Arg Phe Gly Ile Ser Thr Trp Ala Asn Trp Asp Val Val Ser Tyr Glu
945                 950                 955                 960

Asn Thr Phe Thr Val Glu Ile Asp Thr Asp Gly Asn Asn Arg Ala Asp
                965                 970                 975

Tyr Lys Leu Val Thr Asp Arg Ala Lys Gly Leu Asp Tyr Pro Leu Val
            980                 985                 990

Arg Leu Tyr Gly Tyr Lys Asn Gly Asn Leu Val Glu Leu Gly Tyr Tyr
        995                 1000                1005

Pro Leu Asn Gly Ala Trp Gly Asp Val Asp Thr Asn Met Met Asp
    1010                1015                1020

Thr Asn Thr Leu Ile Met Ser Ala Pro Leu Lys Asp Leu Gly Leu
    1025                1030                1035

Thr Ser Ala Asn Asn Pro Asp Ile Gln Tyr Arg Val Ser Ala Thr
    1040                1045                1050

Thr Gln Tyr Glu Trp Gly Asn Val Ser Glu Thr Gly Trp Ile Lys
    1055                1060                1065

Tyr Arg Pro Phe Ser Pro Lys Leu Trp Phe Ser Gly Asp Ser Ser
    1070                1075                1080

Ala Val Ala Gly Leu His Pro Asp Ala Ser Thr Thr Leu Thr
    1085                1090                1095

Ala His Arg Ser Ala Asp Ala Ile Pro Ala Leu Gly Glu Ser Gly
    1100                1105                1110
```

Thr Pro Ala Lys Ala Leu Leu Leu His Leu His Asn Gly Thr Gly
    1115                1120                1125

Asp Leu Ser Gly Thr Asn Gly Ala Lys Gly Asn Arg Ala Glu Val
    1130                1135                1140

Leu Ser Ile Lys Glu Gln Gln Thr Glu Tyr Ile Thr Pro Ser Arg
    1145                1150                1155

Phe Thr Asp Val Lys Asn Gly Asp Gln Phe Tyr Thr Glu Ile Ser
    1160                1165                1170

Trp Leu Ala Gln Arg Gly Ile Thr Thr Gly Tyr Pro Asp Gly Thr
    1175                1180                1185

Tyr Arg Pro Leu Glu Ser Val Glu Arg Gly Ala Met Ala Ala Phe
    1190                1195                1200

Phe Tyr Arg Met Gln Gly Ser Pro Gln Phe Thr Ala Pro Ser Thr
    1205                1210                1215

Pro Ser Phe Lys Asp Val Pro Thr Thr His Pro Phe Tyr Lys Glu
    1220                1225                1230

Ile Glu Trp Met Lys Ala Gln Gly Ile Thr Thr Gly Tyr Ser Asp
    1235                1240                1245

Gly Thr Phe Arg Pro Ser Ala Pro Val Asn Arg Asp Ala Met Ala
    1250                1255                1260

Ala Phe Phe Tyr Arg Ala Ala Gly Ser Pro His Val Asp Leu Pro
    1265                1270                1275

Ala Thr Ser His Phe Ser Asp Val Ser Thr Asp Asn Gln Phe Tyr
    1280                1285                1290

Arg Glu Ile Thr Trp Leu Ala Ser Lys Gly Ile Ser Thr Gly Trp
    1295                1300                1305

Pro Asp Gly Thr Tyr Arg Pro Val Thr Pro Ile Ala Arg Asp Ala
    1310                1315                1320

Met Ala Ala Phe Ile Tyr Arg Tyr Thr Glu Lys Val Ala Asn Gln
    1325                1330                1335

Ala Gly Arg
    1340

<210> SEQ ID NO 63
<211> LENGTH: 1341
<212> TYPE: PRT
<213> ORGANISM: Rothia mucilaginosa

<400> SEQUENCE: 63

Met Lys His Thr Ala Ser Pro Asn Pro Arg Gly Arg Ser His Arg Arg
1               5                   10                  15

Arg Ile Gly Ser Gly Leu Leu Thr Leu Ser Met Ala Leu Ser Pro Leu
                20                  25                  30

Ala Ala Leu Gly Thr Thr Ala His Ala Ala Glu Asp Pro Asp Ala Val
            35                  40                  45

Lys Gln Val Leu Ser Glu Ser Met Lys Asn Ala Ser Gly Thr Val Thr
        50                  55                  60

Ala Phe Ile Arg Phe Lys Gly Lys Gly Ala Phe Glu Gln Thr Gln Pro
65                  70                  75                  80

Ala Gly Val Arg Ala Gly Val Gln Ala Pro Val Asn Thr Ser Ser Gln
                85                  90                  95

Val Gln Ala Ile Ala Ser Gln Val Ser Gln Ala Gln Gln Val Ser
            100                 105                 110

Ser Gln Ser Gly Ala Gln Val Leu Tyr Thr Thr His Asn Ala Val Arg
        115                 120                 125

-continued

```
Gly Val Ala Val Arg Gly Asp Ala Glu Ser Ile Lys Ala Leu Ala Asn
            130                 135                 140

Arg Pro Asp Val Glu Lys Ile Ser Pro Ile Leu Pro Lys Tyr Arg Gln
145                 150                 155                 160

Asn Ala Gly Ala Ala Ile Asp Ala Gly Ser Leu Ala Thr Trp Thr Gly
                165                 170                 175

Thr Thr Asn Pro Ala Gly Ala Gly Tyr Thr Gly Lys Gly Val Lys
            180                 185                 190

Ile Ala Val Ile Asp Ser Gly Ile Asp Tyr Thr His Thr Asp Phe Gly
            195                 200                 205

Gly Ser Gly Lys Leu Glu Asp Tyr Glu Lys Ala Ser Lys Leu Thr Glu
    210                 215                 220

Leu Pro Ser Ala Asp Ser Gly Leu Ile Asn Arg Thr Lys Val Val Gly
225                 230                 235                 240

Gly Tyr Asp Leu Val Gly Asp Ala Tyr Asp Gly Ser Asn Thr Ala Val
                245                 250                 255

Pro Asp Gly Asn Pro Leu Asp Cys Thr Thr Gly Gly His Gly Thr His
            260                 265                 270

Val Ala Gly Thr Ala Ala Gly Tyr Gly Val Asn Ala Asp Gly Thr Thr
        275                 280                 285

Phe Thr Gly Asp Tyr Ser Lys Leu Thr Ala Glu Gln Leu Lys Thr Met
    290                 295                 300

Lys Ile Gly Pro Gly Val Ala Pro Asp Ala Glu Ile Tyr Ala Phe Arg
305                 310                 315                 320

Val Phe Gly Cys Ser Gly Ser Thr Asn Val Ile Glu Ala Leu Asp
                325                 330                 335

Arg Ala Leu Asp Pro Asn Gly Asp Gly Asp Phe Ser Asp Arg Val Asn
            340                 345                 350

Val Val Asn Met Ser Leu Gly Gly Glu Phe Ser Pro Gln Asp Asp Pro
        355                 360                 365

Glu Ala Tyr Ala Val Asp Ala Leu Thr Arg Ala Gly Val Leu Ser Val
    370                 375                 380

Ile Ser Ala Gly Asn Ala Asn Asp Tyr Ser Leu Arg Gly Asp Thr Tyr
385                 390                 395                 400

Ser Asn Ser Gly His Pro Ala Thr Ala Ala Ser Ala Ile Thr Val Ala
                405                 410                 415

Asn Ala Tyr Gly Ser Thr Arg Ala Val Asp Ala Ala Glu Leu Thr Asp
            420                 425                 430

Pro Ala Thr Gly Thr Thr Arg Lys Val Arg Gly Asp Tyr Ser Val Ser
        435                 440                 445

Tyr Pro Trp Ala Gln Ala Gly Ser Lys Glu Phe Thr Gly Glu Leu Thr
    450                 455                 460

Ala Ile Ser Glu Asn Asn Arg Tyr Ala Cys Asn Ala Leu Ser Ala Asp
465                 470                 475                 480

Glu Ala Ala Ala Val Lys Gly Lys Trp Val Leu Ile Asp Trp Ala Lys
                485                 490                 495

Asp Asp Gly Glu Leu Ala Cys Gly Ser Lys Val Arg Phe Asp Asn Leu
            500                 505                 510

Glu Ala Ala Gly Ala Lys Gly Val Leu Leu Ala Gly Asn Asp Glu Glu
        515                 520                 525

Pro Gly Leu Gly Ile Ala Gly Asn Asp Thr Leu Pro Gly Phe Arg Leu
    530                 535                 540
```

```
Ala Ala Ser Ala Ala Lys Asp Leu Arg Ala Gln Ile Thr Ala Ala Glu
545                 550                 555                 560

Ala Ala Gly Lys Pro Leu Thr Val Arg Leu Gly Asn Glu Leu Lys Ser
            565                 570                 575

Ser Leu Arg Val Asp Thr Asp Lys Leu Asp Gln Leu Asn Pro Met Ser
        580                 585                 590

Ala Arg Gly Phe His Gly Ser Tyr Gly Tyr Thr Lys Pro Asp Ile Ala
    595                 600                 605

Ala Pro Gly Ser Tyr Ile Thr Ser Ala Ala Val Ala Thr Gly Ser Asn
610                 615                 620

Ser Val Thr Phe Ser Gly Thr Ser Met Ala Ala Pro Tyr Val Thr Gly
625                 630                 635                 640

Ser Ala Ala Leu Val Met Gln Ser His Pro Thr Tyr Thr Pro Ala Gln
            645                 650                 655

Val Lys Ser Ala Leu Met Asn Thr Ala Thr His Asp Val Arg Thr Glu
        660                 665                 670

Ser Gly Ala Ala Tyr Ala Val Asp Arg Val Gly Ala Gly Arg Val Asp
    675                 680                 685

Thr Leu Ala Ala Val Gln Ser Lys Ser Leu Val Tyr Asn Ala Asp Lys
690                 695                 700

Ser Gly Thr Val Ser Leu Ser Phe Gly Val Leu Glu Tyr Ala Pro Asp
705                 710                 715                 720

Ala Gly Val Gln Ile Leu Thr Arg Glu Val Thr Val Glu Asn Thr Asp
            725                 730                 735

Ser Val Ala His Thr Tyr Ala Leu Ser Tyr Ala Glu Ser Thr Asn Ile
        740                 745                 750

Pro Gly Val Glu Tyr Ser Phe Pro Ser Ala Val Thr Leu Ala Pro Gly
    755                 760                 765

Glu Thr Lys Lys Phe Glu Val Thr Val Arg Ile Asp Pro Ser Lys Leu
770                 775                 780

Glu Lys Thr Arg Asp Ala Ala Met Asp Thr Thr Gln Asn Ala Thr Glu
785                 790                 795                 800

Tyr Tyr Thr Gly Thr Glu Thr Val Pro Ala Gln Tyr Arg Gln Tyr Ile
            805                 810                 815

Ala Ser Ala Ser Gly Arg Leu Val Leu Thr Glu Asp Gly Thr Lys Ala
        820                 825                 830

Leu Arg Leu Pro Val His Val Ala Pro Lys Pro Val Ser Thr Met His
    835                 840                 845

Ala Ala Glu Asp Thr Val Thr Phe Thr Gln Lys Pro Ser Ser Asp Glu
850                 855                 860

Ala Gln Lys Ala Asp Thr Gly Trp Thr Lys Ser Gln Ile Ser Leu Arg
865                 870                 875                 880

Gly Thr Glu Val Asn Gln Gly Tyr Arg Ser Leu Leu Gly Ala Phe
            885                 890                 895

Glu Tyr Gly Ala Ser Val Asp Arg Val Ala Pro Thr Ser Leu Ser Leu
        900                 905                 910

Asn Ser Asn Val Lys Ala Asn Leu Gln Tyr Val Gly Ala Ser Ser Asp
    915                 920                 925

Ala Pro Ala Leu Lys Ala Gly Gly Asn Ala Asp Asp Gly Thr Leu
930                 935                 940

Arg Phe Gly Ile Ser Thr Trp Ala Asn Trp Asp Val Val Ser Tyr Glu
945                 950                 955                 960

Asn Thr Phe Thr Val Glu Ile Asp Thr Asp Gly Asn Asn Arg Ala Asp
```

965                 970                 975
Tyr Lys Leu Val Thr Asp Arg Ala Lys Gly Leu Asp Tyr Pro Leu Val
            980                 985                 990
Arg Leu Tyr Gly Tyr Lys Asn Gly Asn Leu Val Glu Leu Gly Tyr Tyr
            995                1000                1005
Pro Leu Asn Gly Ala Trp Gly Asp Val Asp Thr Asn Met Met Asp
        1010                1015                1020
Thr Asn Thr Leu Ile Met Ser Ala Pro Leu Lys Asp Leu Gly Leu
        1025                1030                1035
Thr Ser Ala Asn Asn Pro Asp Ile Gln Tyr Arg Val Ser Ala Thr
        1040                1045                1050
Thr Gln Tyr Glu Trp Gly Asn Val Ser Glu Thr Gly Trp Ile Lys
        1055                1060                1065
Tyr Arg Pro Phe Ser Pro Lys Leu Trp Phe Ser Gly Asp Ser Ser
        1070                1075                1080
Ala Val Ala Gly Leu His Pro Asp Ala Ser Thr Thr Leu Thr
        1085                1090                1095
Ala His Arg Ser Ala Asp Ala Ile Pro Ala Leu Gly Glu Ser Gly
        1100                1105                1110
Thr Pro Ala Lys Ala Leu Leu Leu His Leu His Asn Gly Thr Gly
        1115                1120                1125
Asp Leu Ser Gly Thr Asn Gly Ala Lys Gly Asn Arg Ala Glu Val
        1130                1135                1140
Leu Ser Ile Lys Glu Gln Gln Thr Glu Tyr Ile Thr Pro Ser Arg
        1145                1150                1155
Phe Thr Asp Val Lys Asn Gly Asp Gln Phe Tyr Thr Glu Ile Ser
        1160                1165                1170
Trp Leu Ala Gln Arg Gly Ile Thr Thr Gly Tyr Pro Asp Gly Thr
        1175                1180                1185
Tyr Arg Pro Leu Glu Ser Val Glu Arg Gly Ala Met Ala Ala Phe
        1190                1195                1200
Phe Tyr Arg Met Gln Gly Ser Pro Gln Phe Thr Ala Pro Ser Thr
        1205                1210                1215
Pro Ser Phe Lys Asp Val Pro Thr Thr His Pro Phe Tyr Lys Glu
        1220                1225                1230
Ile Glu Trp Met Lys Ala Gln Gly Ile Thr Thr Gly Tyr Ser Asp
        1235                1240                1245
Gly Thr Phe Arg Pro Ser Ala Pro Val Asn Arg Asp Ala Met Ala
        1250                1255                1260
Ala Phe Phe Tyr Arg Ala Ala Gly Ser Pro His Val Asp Leu Pro
        1265                1270                1275
Ala Thr Ser His Phe Ser Asp Val Ser Thr Asp Asn Gln Phe Tyr
        1280                1285                1290
Arg Glu Ile Thr Trp Leu Ala Ser Lys Gly Ile Ser Thr Gly Trp
        1295                1300                1305
Pro Asp Gly Thr Tyr Arg Pro Val Thr Pro Ile Ala Arg Asp Ala
        1310                1315                1320
Met Ala Ala Phe Ile Tyr Arg Tyr Thr Glu Lys Val Ala Asn Gln
        1325                1330                1335
Ala Gly Arg
        1340

<210> SEQ ID NO 64

```
<211> LENGTH: 1341
<212> TYPE: PRT
<213> ORGANISM: Rothia mucilaginosa

<400> SEQUENCE: 64
```

| | | | | | | | | | | | | | | | |
|---|---|---|---|---|---|---|---|---|---|---|---|---|---|---|---|
| Met | Gln | His | Thr | Ala | Ser | Pro | Asn | Pro | Arg | Gly | Arg | Ser | His | Arg | Arg |
| 1 | | | | 5 | | | | | 10 | | | | | 15 | |
| Arg | Ile | Gly | Ser | Gly | Leu | Leu | Thr | Leu | Ser | Met | Ala | Leu | Ser | Pro | Leu |
| | | | 20 | | | | | 25 | | | | | 30 | | |
| Ala | Ala | Leu | Gly | Thr | Thr | Ala | His | Ala | Ala | Glu | Asp | Pro | Asp | Ala | Val |
| | | | | 35 | | | | | 40 | | | | | 45 | |
| Lys | Gln | Val | Leu | Ser | Glu | Ser | Met | Lys | Asn | Ala | Ser | Gly | Thr | Val | Thr |
| | 50 | | | | | 55 | | | | | 60 | | | | |
| Ala | Phe | Val | Arg | Phe | Lys | Gly | Lys | Gly | Ala | Phe | Glu | Gln | Thr | Gln | Pro |
| 65 | | | | | 70 | | | | | 75 | | | | | 80 |
| Ala | Gly | Val | Arg | Ala | Gly | Val | Gln | Ala | Pro | Val | Asn | Thr | Ser | Ser | Gln |
| | | | | 85 | | | | | 90 | | | | | 95 | |
| Val | Gln | Ala | Ile | Ala | Ser | Gln | Val | Gln | Ser | Gln | Ala | Gln | Val | Ser | |
| | | | 100 | | | | | 105 | | | | | 110 | | |
| Ser | Gln | Ser | Gly | Ala | Gln | Val | Leu | Tyr | Thr | Thr | His | Asn | Ala | Val | Arg |
| | | | 115 | | | | | 120 | | | | | 125 | | |
| Gly | Val | Ala | Val | Arg | Gly | Asp | Ala | Glu | Ser | Ile | Lys | Ala | Leu | Ala | Asn |
| | 130 | | | | | 135 | | | | | 140 | | | | |
| Arg | Pro | Asp | Val | Glu | Lys | Ile | Ser | Pro | Ile | Leu | Pro | Lys | Tyr | Arg | Gln |
| 145 | | | | | 150 | | | | | 155 | | | | | 160 |
| Asn | Ala | Gly | Ala | Ala | Ile | Asp | Ala | Gly | Ser | Leu | Ala | Thr | Trp | Thr | Gly |
| | | | | 165 | | | | | 170 | | | | | 175 | |
| Thr | Thr | Asn | Pro | Ala | Gly | Ala | Gly | Gly | Tyr | Thr | Gly | Lys | Gly | Val | Lys |
| | | | 180 | | | | | 185 | | | | | 190 | | |
| Ile | Ala | Val | Ile | Asp | Ser | Gly | Ile | Asp | Tyr | Thr | His | Thr | Asp | Phe | Gly |
| | | | 195 | | | | | 200 | | | | | 205 | | |
| Gly | Ser | Gly | Lys | Leu | Glu | Asp | Tyr | Glu | Lys | Ala | Ser | Lys | Leu | Thr | Glu |
| | 210 | | | | | 215 | | | | | 220 | | | | |
| Leu | Pro | Ser | Ala | Asp | Ser | Gly | Leu | Ile | Asn | Arg | Thr | Lys | Val | Ala | Gly |
| 225 | | | | | 230 | | | | | 235 | | | | | 240 |
| Gly | Tyr | Asp | Leu | Val | Gly | Asp | Ala | Tyr | Asp | Gly | Ser | Asn | Thr | Ala | Thr |
| | | | | 245 | | | | | 250 | | | | | 255 | |
| Pro | Asp | Gly | Asn | Pro | Leu | Asp | Cys | Thr | Thr | Gly | Gly | His | Gly | Thr | His |
| | | | 260 | | | | | 265 | | | | | 270 | | |
| Val | Ala | Gly | Thr | Ala | Ala | Gly | Tyr | Gly | Val | Asn | Ala | Asp | Gly | Ser | Thr |
| | | | 275 | | | | | 280 | | | | | 285 | | |
| Phe | Thr | Gly | Asp | Tyr | Ser | Lys | Leu | Thr | Ala | Glu | Gln | Leu | Lys | Thr | Met |
| | 290 | | | | | 295 | | | | | 300 | | | | |
| Lys | Ile | Gly | Pro | Gly | Val | Ala | Pro | Asp | Ala | Glu | Ile | Tyr | Ala | Phe | Arg |
| 305 | | | | | 310 | | | | | 315 | | | | | 320 |
| Val | Phe | Gly | Cys | Ser | Gly | Ser | Thr | Asn | Val | Val | Ile | Glu | Ala | Leu | Asp |
| | | | | 325 | | | | | 330 | | | | | 335 | |
| Arg | Ala | Leu | Asp | Pro | Asn | Gly | Asp | Gly | Asp | Phe | Ser | Asp | Arg | Val | Asn |
| | | | 340 | | | | | 345 | | | | | 350 | | |
| Val | Val | Asn | Met | Ser | Leu | Gly | Gly | Glu | Phe | Ser | Pro | Gln | Asp | Asp | Pro |
| | | | 355 | | | | | 360 | | | | | 365 | | |
| Glu | Ala | Tyr | Ala | Val | Asp | Ala | Leu | Thr | Arg | Ala | Gly | Val | Leu | Ser | Val |
| | 370 | | | | | 375 | | | | | 380 | | | | |
| Ile | Ser | Ala | Gly | Asn | Ala | Asn | Asp | Tyr | Ser | Leu | Arg | Gly | Asp | Thr | Tyr |

```
            385                 390                 395                 400
        Ser Asn Ser Gly His Pro Ala Thr Ala Ala Ser Ala Ile Thr Val Ala
                        405                 410                 415

Asn Ala Tyr Gly Ser Thr Arg Ala Val Asp Ala Ala Glu Leu Thr Asp
                        420                 425                 430

Pro Ala Thr Gly Thr Thr Arg Lys Val Arg Gly Asp Tyr Ser Val Ser
                        435                 440                 445

Tyr Pro Trp Ala Gln Ala Gly Thr Lys Glu Phe Thr Gly Glu Leu Thr
                        450                 455                 460

Ala Ile Ser Glu Asn Asn Arg Tyr Ala Cys Asn Ala Leu Ser Ala Asp
        465                 470                 475                 480

Glu Ala Ala Ala Val Lys Gly Lys Trp Val Leu Ile Asp Trp Ala Lys
                        485                 490                 495

Asp Asp Gly Glu Leu Ala Cys Gly Ser Lys Val Arg Phe Asp Asn Leu
                        500                 505                 510

Glu Ala Ala Gly Ala Lys Gly Val Leu Leu Ala Gly Asn Asp Glu Glu
                        515                 520                 525

Pro Gly Leu Gly Ile Ala Gly Asn Asp Thr Leu Pro Gly Phe Arg Leu
                        530                 535                 540

Ala Ala Ser Ala Ala Lys Asp Leu Arg Ala Gln Ile Thr Ala Ala Glu
        545                 550                 555                 560

Ala Ala Gly Lys Pro Leu Thr Val Arg Leu Gly Asn Glu Leu Lys Ser
                        565                 570                 575

Ser Leu Arg Val Asp Thr Asp Lys Leu Asp Gln Leu Asn Pro Met Ser
                        580                 585                 590

Ala Arg Gly Phe His Gly Ser Tyr Gly Tyr Thr Lys Pro Asp Ile Ala
                        595                 600                 605

Ala Pro Gly Ser Tyr Ile Thr Ser Ala Val Ala Thr Gly Asn Asn
                        610                 615                 620

Ser Val Thr Phe Ser Gly Thr Ser Met Ala Ala Pro Tyr Val Thr Gly
        625                 630                 635                 640

Ser Ala Ala Leu Val Met Gln Ser His Pro Thr Tyr Thr Pro Ala Gln
                        645                 650                 655

Val Lys Ser Ala Leu Met Asn Thr Ala Thr His Asp Val Arg Thr Glu
                        660                 665                 670

Ser Gly Ala Thr Tyr Ala Val Asp Arg Val Gly Ala Gly Arg Val Asp
                        675                 680                 685

Thr Leu Ala Ala Val Gln Ser Lys Ser Leu Val Tyr Asn Ala Asp Lys
                        690                 695                 700

Ser Gly Thr Val Ser Leu Ser Phe Gly Val Leu Glu Tyr Ala Pro Asp
        705                 710                 715                 720

Ala Gly Val Gln Thr Leu Thr Arg Glu Val Thr Val Glu Asn Thr Asp
                        725                 730                 735

Ser Val Ala His Thr Tyr Ala Leu Ser Tyr Ala Glu Ser Thr Asn Ile
                        740                 745                 750

Pro Gly Val Glu Tyr Ser Phe Pro Ser Ala Val Thr Leu Ala Pro Gly
                        755                 760                 765

Glu Thr Lys Lys Phe Glu Val Thr Val Arg Ile Asp Pro Ser Lys Leu
                        770                 775                 780

Glu Lys Thr Arg Asp Ala Ala Met Asp Thr Thr Gln Asn Ala Thr Asp
        785                 790                 795                 800

Tyr Tyr Thr Gly Asn Glu Thr Val Pro Glu Gln Tyr Arg Gln Tyr Ile
                        805                 810                 815
```

-continued

Ala Ser Ala Ser Gly Arg Leu Val Leu Thr Glu Asp Gly Thr Lys Ala
                820                 825                 830

Leu Arg Leu Pro Val His Val Ala Pro Lys Pro Val Ser Thr Met His
            835                 840                 845

Ala Ala Glu Asp Thr Val Thr Phe Thr Gln Lys Pro Ser Ser Asp Glu
850                 855                 860

Ala Gln Lys Ala Asp Thr Gly Trp Thr Lys Ser Gln Ile Ser Leu Arg
865                 870                 875                 880

Gly Thr Glu Val Asn Gln Gly Gly Tyr Arg Ser Leu Leu Gly Ala Phe
                885                 890                 895

Glu Tyr Gly Ala Ser Val Asp Arg Val Ala Pro Thr Ser Leu Ser Leu
            900                 905                 910

Asn Ser Asn Val Lys Ala Asn Leu Gln Tyr Val Gly Ala Phe Ser Asp
                915                 920                 925

Ala Pro Ala Leu Lys Ala Ala Gly Gly Asn Ala Asp Asp Gly Thr Leu
        930                 935                 940

Arg Phe Gly Ile Ser Thr Trp Ala Asn Trp Asp Val Val Ser Tyr Glu
945                 950                 955                 960

Asn Thr Phe Thr Val Glu Ile Asp Thr Asp Gly Asn Asn Arg Ala Asp
                965                 970                 975

Tyr Lys Leu Val Thr Asp Arg Ala Lys Gly Leu Asp Tyr Pro Leu Val
            980                 985                 990

Arg Leu Tyr Gly Tyr Lys Asn Gly  Asn Leu Val Glu Leu  Gly Tyr Tyr
        995                 1000                1005

Pro Leu Asn Gly Ala Trp Gly  Asp Val Asp Thr Asn  Met Met Asp
    1010                1015                1020

Thr Asn Thr Leu Ile Met Ser  Ala Pro Leu Lys Asp  Leu Gly Leu
    1025                1030                1035

Thr Ser Ala Asn Asn Pro Asp  Ile Gln Tyr Arg Val  Ser Ala Thr
    1040                1045                1050

Thr Gln Tyr Glu Trp Gly Asn  Val Ser Glu Thr Gly  Trp Ile Lys
    1055                1060                1065

Tyr Arg Pro Phe Ser Pro Lys  Leu Trp Phe Ser Gly  Asp Ser Ser
    1070                1075                1080

Ala Val Ala Gly Leu His Pro  Asp Ala Ser Thr Thr  Thr Leu Thr
    1085                1090                1095

Ala His Arg Ser Ala Asp Ala  Ile Pro Ala Leu Gly  Glu Ser Gly
    1100                1105                1110

Thr Pro Ala Lys Ala Leu Leu  Leu His Leu His Asn  Gly Thr Gly
    1115                1120                1125

Asp Leu Ser Gly Thr Asn Gly  Ala Lys Gly Asn Arg  Ala Glu Val
    1130                1135                1140

Leu Asn Ile Lys Glu Gln Gln  Thr Glu Tyr Ile Thr  Pro Ser Arg
    1145                1150                1155

Phe Thr Asp Val Lys Asn Thr  Asp Gln Phe Tyr Thr  Glu Ile Ser
    1160                1165                1170

Trp Leu Ala Gln Arg Gly Ile  Thr Thr Gly Tyr Pro  Asp Gly Thr
    1175                1180                1185

Tyr Arg Pro Leu Glu Ser Val  Glu Arg Gly Ala Met  Ala Ala Phe
    1190                1195                1200

Phe Tyr Arg Met Gln Gly Ser  Pro Gln Phe Thr Ala  Pro Ser Thr
    1205                1210                1215

-continued

```
Pro Ser Phe Lys Asp Val Pro Thr Thr His Pro Phe Tyr Lys Glu
    1220                1225                1230

Ile Glu Trp Met Lys Ala Gln Gly Ile Thr Thr Gly Tyr Ser Asp
    1235                1240                1245

Gly Thr Phe Arg Pro Ser Ala Pro Val Asn Arg Asp Ala Met Ala
    1250                1255                1260

Ala Phe Phe Tyr Arg Ala Ala Gly Ser Pro His Val Asp Leu Pro
    1265                1270                1275

Ala Thr Ser His Phe Ser Asp Val Ser Thr Asp Asn Gln Phe Tyr
    1280                1285                1290

Arg Glu Ile Thr Trp Leu Ala Ser Lys Gly Ile Ser Thr Gly Trp
    1295                1300                1305

Pro Asp Gly Thr Tyr Arg Pro Val Thr Pro Ile Ala Arg Asp Ala
    1310                1315                1320

Met Ala Ala Phe Ile Tyr Arg Tyr Thr Glu Lys Val Ala Asn Gln
    1325                1330                1335

Ala Gly Arg
    1340

<210> SEQ ID NO 65
<211> LENGTH: 1341
<212> TYPE: PRT
<213> ORGANISM: Rothia mucilaginosa

<400> SEQUENCE: 65

Met Thr His Thr Ala Ser Pro Asn Pro Arg Gly Arg Ser His Arg Arg
1               5                   10                  15

Arg Ile Ser Ser Gly Leu Leu Thr Leu Ser Met Ala Leu Ser Pro Leu
                20                  25                  30

Ala Ala Leu Gly Thr Thr Ala His Ala Ala Glu Asp Pro Asp Ala Val
            35                  40                  45

Lys Gln Val Leu Ser Glu Ser Met Lys Asn Ala Ser Gly Thr Val Thr
        50                  55                  60

Ala Phe Val Arg Phe Lys Gly Lys Gly Ala Phe Glu Gln Thr Gln Pro
65                  70                  75                  80

Ala Gly Val Arg Ala Gly Val Gln Ala Pro Val Asn Thr Ser Ser Gln
                85                  90                  95

Val Gln Ala Ile Ala Ser Gln Val Gln Ser Gln Ala Gln Gln Val Ser
            100                 105                 110

Ser Gln Ser Gly Ala Gln Val Leu Tyr Thr Thr His Asn Ala Val Arg
        115                 120                 125

Gly Val Ala Val Arg Gly Asp Ala Glu Ser Ile Lys Ala Leu Ala Asn
    130                 135                 140

Arg Ser Asp Val Glu Lys Ile Ser Pro Ile Leu Pro Lys Tyr Arg Gln
145                 150                 155                 160

Asn Ala Gly Ala Ala Val Asp Ala Gly Ser Leu Ala Thr Trp Thr Gly
                165                 170                 175

Thr Thr Asn Pro Ala Gly Ala Gly Tyr Thr Gly Lys Gly Val Lys
            180                 185                 190

Ile Ala Val Ile Asp Ser Gly Ile Asp Tyr Thr His Thr Asp Phe Gly
        195                 200                 205

Gly Ser Gly Lys Leu Glu Asp Tyr Glu Lys Ala Ser Lys Leu Thr Glu
    210                 215                 220

Leu Pro Ser Ala Asp Ser Gly Leu Ile Asn Arg Thr Lys Val Ala Gly
225                 230                 235                 240
```

-continued

Gly Tyr Asp Leu Val Gly Asp Ala Tyr Asp Gly Ser Asn Thr Ala Thr
                245                 250                 255

Pro Asp Gly Asn Pro Leu Asp Cys Thr Thr Gly Gly His Gly Thr His
            260                 265                 270

Val Ala Gly Thr Ala Ala Gly Tyr Gly Val Asn Ala Asp Gly Thr Thr
        275                 280                 285

Phe Thr Gly Asp Tyr Ser Lys Leu Thr Ala Glu Gln Leu Lys Thr Met
    290                 295                 300

Lys Ile Gly Pro Gly Val Ala Pro Asp Ala Glu Ile Tyr Ala Phe Arg
305                 310                 315                 320

Val Phe Gly Cys Ser Gly Ser Thr Asn Val Val Ile Glu Ala Leu Asp
                325                 330                 335

Arg Ala Leu Asp Pro Asn Gly Asp Gly Asp Phe Ser Asp Arg Val Asn
            340                 345                 350

Val Val Asn Met Ser Leu Gly Gly Glu Phe Ser Pro Gln Asp Asp Pro
        355                 360                 365

Glu Ala Tyr Ala Val Asp Ala Leu Thr Arg Ala Gly Val Leu Ser Val
    370                 375                 380

Ile Ser Ala Gly Asn Ala Asn Asp Tyr Ser Leu Arg Gly Asp Thr Tyr
385                 390                 395                 400

Ser Asn Ser Gly His Pro Ala Thr Ala Ala Ser Ala Ile Thr Val Ala
                405                 410                 415

Asn Ala Tyr Gly Ser Thr Arg Val Val Asp Ala Ala Glu Leu Thr Asp
            420                 425                 430

Pro Ala Thr Gly Thr Thr Arg Lys Val Arg Gly Asp Tyr Ser Val Ser
        435                 440                 445

Tyr Pro Trp Ala Gln Ala Gly Thr Lys Glu Phe Thr Gly Glu Leu Thr
    450                 455                 460

Ala Ile Ser Glu Asn Asn Arg Tyr Ala Cys Asn Ala Leu Ser Ala Asp
465                 470                 475                 480

Glu Ala Ala Ala Val Lys Gly Lys Trp Val Leu Ile Asp Trp Ala Lys
                485                 490                 495

Asp Asp Gly Glu Leu Ala Cys Gly Ser Lys Val Arg Phe Asp Asn Leu
            500                 505                 510

Glu Ala Ala Gly Ala Lys Gly Val Leu Leu Val Gly Asn Asp Glu Glu
        515                 520                 525

Pro Gly Leu Gly Ile Ala Gly Asn Asp Thr Leu Pro Gly Phe Arg Leu
    530                 535                 540

Ala Ala Ser Ala Ala Lys Asp Leu Arg Ala Gln Ile Thr Ala Ala Glu
545                 550                 555                 560

Ala Ala Gly Lys Pro Leu Thr Val Arg Leu Gly Asn Glu Leu Lys Ser
                565                 570                 575

Ser Leu Arg Val Asp Thr Asp Lys Leu Asp Gln Leu Asn Pro Met Ser
            580                 585                 590

Ala Arg Gly Phe His Gly Ser Tyr Gly Tyr Thr Lys Pro Asp Ile Ala
        595                 600                 605

Ala Pro Gly Ser Tyr Ile Thr Ser Ala Val Ala Thr Gly Asn Asn
    610                 615                 620

Ser Val Thr Phe Ser Gly Thr Ser Met Ala Ala Pro Tyr Val Thr Gly
625                 630                 635                 640

Ser Ala Ala Leu Val Met Gln Ser His Pro Thr Tyr Thr Pro Ala Gln
                645                 650                 655

```
Val Lys Ser Ala Leu Met Asn Thr Ala Thr His Asp Val Arg Thr Glu
            660                 665                 670

Ser Gly Ala Ala Tyr Ala Val Asp Arg Val Gly Ala Gly Arg Val Asp
        675                 680                 685

Thr Leu Ala Ala Val Gln Ser Lys Ser Leu Val Tyr Asn Ala Asp Lys
    690                 695                 700

Ser Gly Thr Val Ser Leu Ser Phe Gly Val Leu Glu Tyr Ala Pro Asp
705                 710                 715                 720

Ala Gly Val Gln Thr Leu Thr Arg Glu Val Thr Val Glu Asn Thr Asp
                725                 730                 735

Ser Val Ala His Thr Tyr Ala Leu Ser Tyr Ala Glu Ser Thr Asn Ile
            740                 745                 750

Pro Gly Val Glu Tyr Ser Phe Pro Ser Ala Val Thr Leu Ala Pro Gly
        755                 760                 765

Glu Thr Lys Lys Phe Glu Val Ala Val Arg Ile Asp Pro Ser Lys Leu
    770                 775                 780

Glu Lys Thr Arg Asp Ala Ala Met Asp Thr Thr Gln Asn Ala Thr Asp
785                 790                 795                 800

Tyr Tyr Thr Gly Asn Glu Thr Val Pro Glu Gln Tyr Arg Gln Tyr Ile
                805                 810                 815

Ala Ser Ala Ser Gly Arg Leu Val Leu Thr Glu Asp Gly Thr Lys Ala
            820                 825                 830

Leu Arg Leu Pro Val His Val Ala Pro Lys Pro Val Ser Thr Met His
        835                 840                 845

Ala Ala Glu Asp Thr Val Thr Phe Thr Gln Lys Pro Ser Ser Asp Glu
    850                 855                 860

Ala Gln Lys Ala Asp Thr Gly Trp Thr Lys Ser Gln Ile Ser Leu Arg
865                 870                 875                 880

Gly Thr Glu Val Asn Gln Gly Gly Tyr Arg Ser Leu Leu Gly Ala Phe
                885                 890                 895

Glu Tyr Gly Ala Ser Val Asp Arg Val Ala Pro Thr Ser Leu Ser Leu
            900                 905                 910

Asn Ser Asn Val Lys Ala Asn Leu Gln Tyr Val Gly Ala Ser Ser Asp
        915                 920                 925

Ala Pro Ala Leu Lys Ala Gly Gly Asn Ala Asp Asp Gly Thr Leu
    930                 935                 940

Arg Phe Gly Ile Ser Thr Trp Ala Asn Trp Asp Val Val Ser Tyr Glu
945                 950                 955                 960

Asn Thr Phe Thr Val Glu Ile Asp Thr Asp Gly Asn Asn Arg Ala Asp
                965                 970                 975

Tyr Lys Leu Val Thr Asp Arg Ala Lys Gly Leu Asp Tyr Pro Leu Val
            980                 985                 990

Arg Leu Tyr Gly Tyr Lys Asn Gly Asn Leu Val Glu Leu Gly Tyr Tyr
        995                 1000                1005

Pro Leu Asn Gly Ala Trp Gly Asp Val Asp Thr Asn Met Met Asp
    1010                1015                1020

Thr Asn Thr Leu Ile Met Ser Ala Pro Leu Lys Asp Leu Gly Leu
    1025                1030                1035

Thr Ser Ala Asn Asn Pro Asp Ile Gln Tyr Arg Val Ser Ala Thr
    1040                1045                1050

Thr Gln Tyr Glu Trp Gly Asn Val Ser Glu Thr Gly Trp Ile Lys
    1055                1060                1065

Tyr Arg Pro Phe Ser Pro Lys Leu Trp Phe Ser Gly Asp Ser Ser
```

```
                    1070                1075                1080
Ala Val Ala Gly Leu His Pro Asp Ala Pro Thr Thr Thr Leu Thr
            1085                1090                1095

Ala His Arg Ser Ala Asp Ala Ile Pro Ala Leu Gly Glu Ser Gly
        1100                1105                1110

Thr Pro Ala Lys Ala Leu Leu Leu His Leu His Asn Gly Thr Gly
        1115                1120                1125

Asp Leu Ser Gly Thr Asn Gly Ala Lys Gly Asn Arg Ala Glu Val
        1130                1135                1140

Leu Ser Ile Lys Glu Gln Gln Thr Glu Tyr Ile Thr Pro Ser Arg
        1145                1150                1155

Phe Thr Asp Val Lys Asn Thr Asp Gln Phe Tyr Thr Glu Ile Ser
        1160                1165                1170

Trp Leu Ala Gln Arg Gly Ile Thr Thr Gly Tyr Pro Asp Gly Thr
        1175                1180                1185

Tyr Arg Pro Leu Glu Ser Val Glu Arg Gly Ala Met Ala Ala Phe
        1190                1195                1200

Phe Tyr Arg Met Gln Gly Ser Pro Gln Phe Thr Ala Pro Ser Thr
        1205                1210                1215

Pro Ser Phe Lys Asp Val Pro Thr Thr His Pro Phe Tyr Lys Glu
        1220                1225                1230

Ile Glu Trp Met Lys Ala Gln Gly Ile Thr Thr Gly Tyr Ser Asp
        1235                1240                1245

Gly Thr Phe Arg Pro Ser Ala Pro Val Asn Arg Asp Ala Met Ala
        1250                1255                1260

Ala Phe Phe Tyr Arg Ala Ala Gly Ser Pro His Val Asp Leu Pro
        1265                1270                1275

Ala Thr Ser His Phe Ser Asp Val Ser Thr Asp Asn Gln Phe Tyr
        1280                1285                1290

Arg Glu Ile Thr Trp Leu Ala Ser Lys Gly Ile Ser Thr Gly Trp
        1295                1300                1305

Pro Asp Gly Thr Tyr Arg Pro Val Thr Pro Ile Ala Arg Asp Ala
        1310                1315                1320

Met Ala Ala Phe Ile Tyr Arg Tyr Thr Glu Lys Val Ala Asn Gln
        1325                1330                1335

Ala Gly Arg
        1340

<210> SEQ ID NO 66
<211> LENGTH: 1341
<212> TYPE: PRT
<213> ORGANISM: Rothia mucilaginosa

<400> SEQUENCE: 66

Met Thr His Thr Ala Ser Pro Asn Pro Arg Gly Arg Ser His Arg Arg
1               5                   10                  15

Arg Ile Ser Ser Gly Leu Leu Thr Leu Ser Met Ala Leu Ser Pro Leu
            20                  25                  30

Ala Ala Leu Gly Thr Thr Ala His Ala Ala Glu Asp Pro Asp Ala Val
        35                  40                  45

Lys Gln Val Leu Ser Glu Ser Met Lys Asn Ala Ser Gly Thr Val Thr
    50                  55                  60

Ala Phe Val Arg Phe Lys Gly Lys Gly Ala Phe Glu Gln Thr Gln Pro
65                  70                  75                  80
```

-continued

```
Ala Gly Val Arg Ala Gly Val Gln Ala Pro Val Asn Thr Ser Ser Gln
                85                  90                  95
Val Gln Ala Ile Ala Ser Gln Val Gln Ser Gln Ala Gln Gln Val Ser
            100                 105                 110
Ser Gln Ser Gly Ala Gln Val Leu Tyr Thr Thr His Asn Ala Val Arg
        115                 120                 125
Gly Val Ala Val Arg Gly Asp Ala Glu Ser Ile Lys Ala Leu Ala Asn
    130                 135                 140
Arg Ser Asp Val Glu Lys Ile Ser Pro Ile Leu Pro Lys Tyr Arg Gln
145                 150                 155                 160
Asn Ala Gly Ala Ala Val Asp Ala Gly Ser Leu Ala Thr Trp Thr Gly
                165                 170                 175
Thr Thr Asn Pro Ala Gly Ala Gly Tyr Thr Gly Lys Gly Val Lys
            180                 185                 190
Ile Ala Val Ile Asp Ser Gly Ile Asp Tyr Thr His Thr Asp Phe Gly
        195                 200                 205
Gly Ser Gly Lys Leu Glu Asp Tyr Glu Lys Ala Ser Lys Leu Thr Glu
    210                 215                 220
Leu Pro Ser Ala Asp Ser Gly Leu Ile Asn Arg Thr Lys Val Ala Gly
225                 230                 235                 240
Gly Tyr Asp Leu Val Gly Asp Ala Tyr Asp Gly Ser Asn Thr Ala Thr
                245                 250                 255
Pro Asp Gly Asn Pro Leu Asp Cys Thr Thr Gly Gly His Gly Thr His
            260                 265                 270
Val Ala Gly Thr Ala Ala Gly Tyr Gly Val Asn Ala Asp Gly Thr Thr
        275                 280                 285
Phe Thr Gly Asp Tyr Ser Lys Leu Thr Ala Glu Gln Leu Lys Thr Met
    290                 295                 300
Lys Ile Gly Pro Gly Val Ala Pro Asp Ala Glu Ile Tyr Ala Phe Arg
305                 310                 315                 320
Val Phe Gly Cys Ser Gly Ser Thr Asn Val Val Ile Glu Ala Leu Asp
                325                 330                 335
Arg Ala Leu Asp Pro Asn Gly Asp Gly Asp Phe Ser Asp Arg Val Asn
            340                 345                 350
Val Val Asn Met Ser Leu Gly Gly Glu Phe Ser Pro Gln Asp Asp Pro
        355                 360                 365
Glu Ala Tyr Ala Val Asp Ala Leu Thr Arg Ala Gly Val Leu Ser Val
    370                 375                 380
Ile Ser Ala Gly Asn Ala Asn Asp Tyr Ser Leu Arg Gly Asp Thr Tyr
385                 390                 395                 400
Ser Asn Ser Gly His Pro Ala Thr Ala Ala Ser Ala Ile Thr Val Ala
                405                 410                 415
Asn Ala Tyr Gly Ser Thr Arg Val Val Asp Ala Ala Glu Leu Thr Asp
            420                 425                 430
Pro Ala Thr Gly Thr Thr Arg Lys Val Arg Gly Asp Tyr Ser Val Ser
        435                 440                 445
Tyr Pro Trp Ala Gln Ala Gly Thr Lys Glu Phe Thr Gly Glu Leu Thr
    450                 455                 460
Ala Ile Ser Glu Asn Asn Arg Tyr Ala Cys Asn Ala Leu Ser Ala Asp
465                 470                 475                 480
Glu Ala Ala Ala Val Lys Gly Lys Trp Val Leu Ile Asp Trp Ala Lys
                485                 490                 495
Asp Asp Gly Glu Leu Ala Cys Gly Ser Lys Val Arg Phe Asp Asn Leu
```

-continued

```
                500                 505                 510
Glu Ala Ala Gly Ala Lys Gly Val Leu Leu Val Gly Asn Asp Glu Glu
            515                 520                 525
Pro Gly Leu Gly Ile Ala Gly Asn Asp Thr Leu Pro Gly Phe Arg Leu
        530                 535                 540
Ala Ala Ser Ala Ala Lys Asp Leu Arg Ala Gln Ile Thr Ala Ala Glu
545                 550                 555                 560
Ala Ala Gly Lys Pro Leu Thr Val Arg Leu Gly Asn Glu Leu Lys Ser
                565                 570                 575
Ser Leu Arg Val Asp Thr Asp Lys Leu Asp Gln Leu Asn Pro Met Ser
            580                 585                 590
Ala Arg Gly Phe His Gly Ser Tyr Gly Tyr Thr Lys Pro Asp Ile Ala
        595                 600                 605
Ala Pro Gly Ser Tyr Ile Thr Ser Ala Ala Val Ala Thr Gly Asn Asn
        610                 615                 620
Ser Val Thr Phe Ser Gly Thr Ser Met Ala Ala Pro Tyr Val Thr Gly
625                 630                 635                 640
Ser Ala Ala Leu Val Met Gln Ser His Pro Thr Tyr Thr Pro Ala Gln
                645                 650                 655
Val Lys Ser Ala Leu Met Asn Thr Ala Thr His Asp Val Arg Thr Glu
            660                 665                 670
Ser Gly Ala Ala Tyr Ala Val Asp Arg Val Gly Ala Gly Arg Val Asp
        675                 680                 685
Thr Leu Ala Ala Val Gln Ser Lys Ser Leu Val Tyr Asn Ala Asp Lys
        690                 695                 700
Ser Gly Thr Val Ser Leu Ser Phe Gly Val Leu Glu Tyr Ala Pro Asp
705                 710                 715                 720
Ala Gly Val Gln Thr Leu Thr Arg Glu Val Thr Val Glu Asn Thr Asp
                725                 730                 735
Ser Val Ala His Thr Tyr Ala Leu Ser Tyr Ala Glu Ser Thr Asn Ile
            740                 745                 750
Pro Gly Val Glu Tyr Ser Phe Pro Ser Ala Val Thr Leu Ala Pro Gly
        755                 760                 765
Glu Thr Lys Lys Phe Glu Val Ala Val Arg Ile Asp Pro Ser Lys Leu
        770                 775                 780
Glu Lys Thr Arg Asp Ala Ala Met Asp Thr Thr Gln Asn Ala Thr Asp
785                 790                 795                 800
Tyr Tyr Thr Gly Asn Glu Thr Val Pro Glu Gln Tyr Arg Gln Tyr Ile
                805                 810                 815
Ala Ser Ala Ser Gly Arg Leu Val Leu Thr Glu Asp Gly Thr Lys Ala
            820                 825                 830
Leu Arg Leu Pro Val His Val Ala Pro Lys Pro Val Ser Thr Met His
        835                 840                 845
Ala Ala Glu Asp Thr Val Thr Phe Thr Gln Lys Pro Ser Ser Asp Glu
        850                 855                 860
Ala Gln Lys Ala Asp Thr Gly Trp Thr Lys Ser Gln Ile Ser Leu Arg
865                 870                 875                 880
Gly Thr Glu Val Asn Gln Gly Gly Tyr Arg Ser Leu Leu Gly Ala Phe
                885                 890                 895
Glu Tyr Gly Ala Ser Val Asp Arg Val Ala Pro Thr Ser Leu Ser Leu
            900                 905                 910
Asn Ser Asn Val Lys Ala Asn Leu Gln Tyr Val Gly Ala Ser Ser Asp
        915                 920                 925
```

```
Ala Pro Ala Leu Lys Ala Ala Gly Gly Asn Ala Asp Asp Gly Thr Leu
    930                 935                 940

Arg Phe Gly Ile Ser Thr Trp Ala Asn Trp Asp Val Val Ser Tyr Glu
945                 950                 955                 960

Asn Thr Phe Thr Val Glu Ile Asp Thr Asp Gly Asn Asn Arg Ala Asp
                965                 970                 975

Tyr Lys Leu Val Thr Asp Arg Ala Lys Gly Leu Asp Tyr Pro Leu Val
            980                 985                 990

Arg Leu Tyr Gly Tyr Lys Asn Gly Asn Leu Val Glu Leu Gly Tyr Tyr
        995                 1000                1005

Pro Leu Asn Gly Ala Trp Gly Asp Val Asp Thr Asn Met Met Asp
    1010                1015                1020

Thr Asn Thr Leu Ile Met Ser Ala Pro Leu Lys Asp Leu Gly Leu
    1025                1030                1035

Thr Ser Ala Asn Asn Pro Asp Ile Gln Tyr Arg Val Ser Ala Thr
    1040                1045                1050

Thr Gln Tyr Glu Trp Gly Asn Val Ser Glu Thr Gly Trp Ile Lys
    1055                1060                1065

Tyr Arg Pro Phe Ser Pro Lys Leu Trp Phe Ser Gly Asp Ser Ser
    1070                1075                1080

Ala Val Ala Gly Leu His Pro Asp Ala Pro Thr Thr Leu Thr
    1085                1090                1095

Ala His Arg Ser Ala Asp Ala Ile Pro Ala Leu Gly Glu Ser Gly
    1100                1105                1110

Thr Pro Ala Lys Ala Leu Leu Leu His Leu His Asn Gly Thr Gly
    1115                1120                1125

Asp Leu Ser Gly Thr Asn Gly Ala Lys Gly Asn Arg Ala Glu Val
    1130                1135                1140

Leu Ser Ile Lys Glu Gln Gln Thr Glu Tyr Ile Thr Pro Ser Arg
    1145                1150                1155

Phe Thr Asp Val Lys Asn Thr Asp Gln Phe Tyr Thr Glu Ile Ser
    1160                1165                1170

Trp Leu Ala Gln Arg Gly Ile Thr Thr Gly Tyr Pro Asp Gly Thr
    1175                1180                1185

Tyr Arg Pro Leu Glu Ser Val Glu Arg Gly Ala Met Ala Ala Phe
    1190                1195                1200

Phe Tyr Arg Met Gln Gly Ser Pro Gln Phe Thr Ala Pro Ser Thr
    1205                1210                1215

Pro Ser Phe Lys Asp Val Pro Thr Thr His Pro Phe Tyr Lys Glu
    1220                1225                1230

Ile Glu Trp Met Lys Ala Gln Gly Ile Thr Thr Gly Tyr Ser Asp
    1235                1240                1245

Gly Thr Phe Arg Pro Ser Ala Pro Val Asn Arg Asp Ala Met Ala
    1250                1255                1260

Ala Phe Phe Tyr Arg Ala Ala Gly Ser Pro His Val Asp Leu Pro
    1265                1270                1275

Ala Thr Ser His Phe Ser Asp Val Ser Thr Asp Asn Gln Phe Tyr
    1280                1285                1290

Arg Glu Ile Thr Trp Leu Ala Ser Lys Gly Ile Ser Thr Gly Trp
    1295                1300                1305

Pro Asp Gly Thr Tyr Arg Pro Val Thr Pro Ile Ala Arg Asp Ala
    1310                1315                1320
```

Met Ala Ala Phe Ile Tyr Arg Tyr Thr Glu Lys Val Ala Asn Gln
    1325                1330                1335

Ala Gly Arg
    1340

<210> SEQ ID NO 67
<211> LENGTH: 1311
<212> TYPE: PRT
<213> ORGANISM: Rothia dentocariosa

<400> SEQUENCE: 67

Met Pro Lys Asn Thr Pro Ile Arg Gly Leu Ser Arg Ala Cys Leu Ser
1               5                   10                  15

Ala Thr Leu Gly Val Thr Met Ala Ile Thr Ala Gly Leu Pro Ala Thr
            20                  25                  30

Ala Ala Pro Ala Gly Asp Pro Asp Thr Pro Val Ala Gln Asp Ile Ala
        35                  40                  45

Arg Asn Ser Arg Glu His Ala Val Leu Ser Asp Ser Met Lys Lys Ala
50                  55                  60

Glu Gly Asn Ile Pro Val Phe Val Gln Phe Lys Gly Lys Gly Ala Tyr
65                  70                  75                  80

Glu Gln Thr Gln Ser Pro Ala Val Leu Ala Asn Lys Gln Ala Pro Ile
                85                  90                  95

Asn Lys Gln Ala Glu Val Gln Ala Ile Lys Thr Gln Val Gln Ser Gln
            100                 105                 110

Ala Gln Ala Ala Gln Ser Thr Gly Ala Lys Thr Leu Tyr Thr Thr
        115                 120                 125

His Asn Ile Met Arg Gly Val Ala Leu Gln Gly Asp Ala Ala Gln Ile
130                 135                 140

Arg Ala Leu Ala Asn Asn Pro Glu Val Glu Arg Ile Thr Pro Ile Val
145                 150                 155                 160

Pro Lys Lys Lys Gln Asn Ala Gly Ser Val Val Asp Thr Gly Ala Ala
                165                 170                 175

Glu Asn Trp Ala Arg Glu Asn Ser Gly Tyr Thr Gly Lys Asp Val Lys
            180                 185                 190

Ile Ala Val Val Asp Ser Gly Ile Asp Tyr Thr His Ser Asp Phe Gly
        195                 200                 205

Gly Pro Gly Thr Val Glu Ala Phe Asn Lys Ala Thr Lys Leu Thr Glu
    210                 215                 220

Met Pro Ala Ala Asp Ser Gly Leu Tyr Asp Ala Lys Lys Tyr Ile Gly
225                 230                 235                 240

Gly Tyr Asp Leu Val Gly Asp Ser Tyr Asp Gly Thr Asn Gln Thr Thr
                245                 250                 255

Pro Asp Asn Asn Pro Ile Asp Cys Ser Ala Gly His Gly Thr His
            260                 265                 270

Val Ala Gly Thr Ala Ala Gly Tyr Gly Val Asn Gln Asp Gly Thr Thr
        275                 280                 285

Phe Arg Gly Asp Tyr Ser Lys Leu Thr Ala Glu Gln Leu Asn Gln Met
    290                 295                 300

Lys Ile Gly Pro Gly Ala Ala Pro Glu Ala Gln Leu Tyr Ser Phe Arg
305                 310                 315                 320

Val Phe Gly Cys Thr Gly Thr Thr Ala Val Val Gln Ala Leu Asp
                325                 330                 335

Arg Thr Leu Asp Pro Asn Gly Asp Gly Asp Phe Ser Arg Ala Asn
            340                 345                 350

```
Ile Val Asn Leu Ser Ile Gly Gly Glu Phe Ser Pro Pro Asp Asp Ala
            355                 360                 365

Asp Ala Tyr Ala Val Glu Ser Leu Asn Arg Gln Gly Val Leu Ala Val
        370                 375                 380

Val Ser Ala Gly Asn Ala Thr Asp Tyr Tyr Gly Arg Gly Asp Thr Tyr
385                 390                 395                 400

Ser Asp Ser Gly Gln Pro Ala Asn Ala Val Ser Ala Leu Thr Val Ala
                405                 410                 415

Asn Ser Ile Gly Ser Ser Tyr Ala Val Asp Ser Met Glu Ile Gln Ala
            420                 425                 430

Pro Ala Asn Val Ala Gly Lys Val Pro Gly Asp Tyr Thr Val Ser Tyr
        435                 440                 445

Thr Tyr Thr Gly Ala Lys Pro Glu Ala Leu Thr Gly Thr Val Val Thr
    450                 455                 460

Pro Ser Glu Ser Asn Lys Phe Gly Cys Glu Ala Phe Ser Ala Glu Asp
465                 470                 475                 480

Ala Ala Lys Ile Lys Asp Lys Trp Val Phe Ile Glu Trp Ala Asn Ala
                485                 490                 495

Asp Gly Ser Leu Pro Cys Gly Ser Lys Val Arg Phe Asn Val Glu
            500                 505                 510

Lys Ala Gly Gly Lys Gly Val Val Leu Ser Ser Glu Glu Lys Pro
        515                 520                 525

Ala Leu Pro Ile Gly Gly Asn Glu Ser Ile Pro Gly Phe Arg Val Ala
        530                 535                 540

Lys Ser Ala Ser Ala Lys Val Arg Glu Ala Ala Thr Gly Glu Leu
545                 550                 555                 560

Lys Val Arg Leu Gly Ala Asp Leu Lys Glu Ser Leu Arg Val Pro Ser
                565                 570                 575

Asn Lys Lys Asp Gln Leu Thr Ala Ser Ser Ala Arg Gly Tyr His Gly
            580                 585                 590

Thr Tyr Gly Tyr Thr Lys Pro Asp Val Ala Ala Pro Gly Asn Asn Ile
        595                 600                 605

Ser Ser Ala Arg Val Gly Thr Gly Thr Gly Ile Ser Tyr Thr Gly
    610                 615                 620

Thr Ser Met Ser Ala Pro Phe Ala Ala Gly Val Ala Ala Gln Val Leu
625                 630                 635                 640

Gln Ala Asn Gln Ser Tyr Gly Pro Thr Gln Leu Lys Ala Ala Ile Met
                645                 650                 655

Asn Ser Ala Asn His Asp Val Arg Thr Ala Asp Gly Asn Val Tyr Ala
            660                 665                 670

Val Asp Arg Val Gly Ser Gly Arg Ile Asp Ala Lys Ala Ala Glu
        675                 680                 685

Thr Lys Val Leu Leu Tyr Asn Ala Asp Arg Pro Ala Gln Val Ser Gln
    690                 695                 700

Thr Phe Gly Val Leu Glu Tyr Ala Val Asn Glu Gly Lys Gln Thr Leu
705                 710                 715                 720

Thr Arg Glu Met Thr Val Glu Asn Phe Asp Ser His Thr His Thr Tyr
                725                 730                 735

Asn Ile Ser Tyr Ala Gly Ser Thr Asp Met Pro Gly Val Glu Phe Ser
            740                 745                 750

Leu Pro Ser Asn Ile Thr Val Asn Pro Gly Glu Lys Lys Asn Phe Thr
        755                 760                 765
```

-continued

Val Thr Ile Thr Ile Asp Pro Ala Ala Met Glu Lys Thr Met Asp Pro
770                 775                 780

Ala Met Glu Lys Thr His Asn Ser Val Asp Pro Tyr Gly Asp Gly Thr
785                 790                 795                 800

Glu Leu Val Pro Glu Gln Tyr Arg Gln Phe Ile Ala Ser Glu Ser Gly
            805                 810                 815

Arg Ile Leu Leu Thr Glu Gly Ala Ala Thr Leu Arg Ala Pro Ile His
        820                 825                 830

Ala Ala Pro Lys Pro Ala Ser Ala Met Lys Val Glu Gly Ser Ser Val
    835                 840                 845

Glu Ile Pro Ala Gly Glu His Gln Ala Asn Leu Lys Leu Thr Gly Thr
850                 855                 860

Glu Leu Asn Gln Arg Gly Tyr Lys Ser Leu Leu Gly Ala Phe Glu His
865                 870                 875                 880

Gly Ala Ser Ile Glu Arg Thr Ser Pro Val Lys Leu Asp Val Ser Ser
            885                 890                 895

Asn Ala Lys Ala Asn Met Gln His Val Gly Ala Ala Ser Thr Ala Pro
        900                 905                 910

Ala Leu Lys Ala Ser Gly Gly Asn Pro Asn Asp Gly Leu Leu Ala Phe
    915                 920                 925

Gly Ile Ser Thr Trp Ala Asn Trp Asp Val Val Ser Thr Glu Asn Thr
930                 935                 940

Phe Thr Val Asn Ile Asp Thr Asp Gly Asn Asn Arg Ala Asp Tyr Met
945                 950                 955                 960

Leu Val Thr Asp Arg Ala Lys Gly Ile Asp Phe Pro Ile Val Arg Leu
            965                 970                 975

Tyr Gly Tyr Lys Asn Gly Asn Leu Glu Gln Ile Ala Tyr Tyr Pro Leu
        980                 985                 990

Asn Asn Ala Trp Gly Asp Thr Asp  Thr Asn Met Met Asp  Ser Asn Ala
            995                 1000                1005

Leu Val  Met Ala Val Pro Leu  Lys Asp Leu Gly Leu  Ser Ala Glu
    1010                1015                1020

Lys Thr  Lys Asp Ile Lys Tyr  Ser Val Ser Ala Thr  Thr Gln Tyr
    1025                1030                1035

Ala Trp  Thr Asn Val Ser Glu  Thr Gly Trp Ile Asn  Tyr Arg Pro
    1040                1045                1050

Phe Asp  Pro Lys Leu Trp Phe  Ser Gly Thr Ala Ala  Thr Val Pro
    1055                1060                1065

Gly Phe  Phe Ala Asp Ala Pro  Ser Ser Glu Leu Val  Ala His Arg
    1070                1075                1080

Ala Glu  Gly Ala Thr Asp Val  Lys Ala Leu Phe Leu  His Met His
    1085                1090                1095

Asn Thr  Thr Gly Asp Leu Ser  Gly Leu Asn Gly Ala  Ala Gly Asn
    1100                1105                1110

Arg Ala  Gln Val Leu Glu Val  Thr Glu Gln Gln Gln  Leu Asp Pro
    1115                1120                1125

Ala Pro  Ser Arg Phe Thr Asp  Val Pro Ala Glu Asn  Gln Phe Tyr
    1130                1135                1140

Ala Glu  Ile Asn Trp Leu Ala  Gln Arg Arg Ile Thr  Thr Gly Tyr
    1145                1150                1155

Pro Asp  Gly Thr Phe Arg Pro  Gly Glu Asn Val Glu  Arg Gly Ala
    1160                1165                1170

Met Ala  Ala Tyr Phe Tyr Arg  Leu Ala Gly Thr Pro  Gln Phe Thr

```
                1175                1180                1185

Ala Pro Asp Asn Pro Thr Phe Ser Asp Val Pro Lys Ser His Pro
            1190                1195                1200

Phe Tyr Lys Glu Ile Glu Trp Met Ala Ala Arg Gly Ile Thr Thr
        1205                1210                1215

Gly Tyr Gly Asp Gly Thr Phe Arg Pro Ser Asp Ser Val Asn Arg
    1220                1225                1230

Asp Ala Met Ala Ala Phe Tyr Arg Tyr Ala Asn Ser Pro Gln
1235                1240                1245

Phe Ala Ala Pro Ala Ala Ser Pro Phe Lys Asp Val Pro Ala Asn
    1250                1255                1260

Ser Gln Phe Tyr Lys Glu Ile Ala Trp Leu Ala Glu Gln Gly Ile
    1265                1270                1275

Thr Lys Gly Trp Asp Asp Gly Thr Tyr Arg Pro Gly Glu Pro Ile
    1280                1285                1290

His Arg Asp Ala Met Ala Ala Phe Leu Tyr Arg Tyr Ser Asp Lys
    1295                1300                1305

Val Leu Lys
    1310

<210> SEQ ID NO 68
<211> LENGTH: 1311
<212> TYPE: PRT
<213> ORGANISM: Rothia dentocariosa

<400> SEQUENCE: 68

Met Pro Lys Asn Thr Pro Ile Arg Gly Leu Ser Arg Ala Cys Leu Ser
1               5                   10                  15

Ala Thr Leu Gly Val Thr Met Ala Ile Thr Ala Gly Leu Pro Ala Thr
            20                  25                  30

Ala Ala Pro Ala Gly Asp Pro Asp Thr Pro Val Ala Gln Asp Ile Ala
        35                  40                  45

Arg Asn Ser Arg Glu His Ala Val Leu Ser Asp Ser Met Lys Lys Ala
    50                  55                  60

Glu Gly Asn Ile Pro Val Phe Val Gln Phe Lys Gly Lys Gly Ala Tyr
65                  70                  75                  80

Glu Gln Thr Gln Ser Pro Ala Val Leu Ala Asn Lys Gln Ala Pro Ile
            85                  90                  95

Asn Lys Gln Ala Glu Val Gln Ala Ile Lys Thr Gln Val Gln Ser Gln
        100                 105                 110

Ala Gln Ala Ala Ala Gln Ser Thr Gly Ala Lys Thr Leu Tyr Thr Thr
    115                 120                 125

His Asn Ile Met Arg Gly Val Ala Leu Gln Gly Asp Ala Ala Gln Ile
130                 135                 140

Arg Ala Leu Ala Asn Asn Pro Glu Val Glu Arg Ile Thr Pro Ile Val
145                 150                 155                 160

Pro Lys Lys Lys Gln Asn Ala Gly Ser Val Val Asp Thr Gly Ala Ala
            165                 170                 175

Glu Asn Trp Ala Arg Glu Asn Ser Gly Tyr Thr Gly Lys Asp Val Lys
        180                 185                 190

Ile Ala Val Val Asp Ser Gly Ile Asp Tyr Thr His Ser Asp Phe Gly
    195                 200                 205

Gly Pro Gly Thr Val Glu Ala Phe Asn Lys Ala Thr Lys Leu Thr Glu
    210                 215                 220
```

```
Met Pro Ala Ala Asp Ser Gly Leu Tyr Asp Ala Lys Lys Tyr Ile Gly
225                 230                 235                 240

Gly Tyr Asp Leu Val Gly Asp Ser Tyr Asp Gly Thr Asn Gln Thr Thr
            245                 250                 255

Pro Asp Asn Asn Pro Ile Asp Cys Ser Ala Gly Gly His Gly Thr His
        260                 265                 270

Val Ala Gly Thr Ala Ala Gly Tyr Gly Val Asn Gln Asp Gly Thr Thr
    275                 280                 285

Phe Arg Gly Asp Tyr Ser Lys Leu Thr Ala Glu Gln Leu Asn Gln Met
290                 295                 300

Lys Ile Gly Pro Gly Ala Ala Pro Glu Ala Gln Leu Tyr Ser Phe Arg
305                 310                 315                 320

Val Phe Gly Cys Thr Gly Thr Thr Ala Val Val Gln Ala Leu Asp
                325                 330                 335

Arg Thr Leu Asp Pro Asn Gly Asp Gly Asp Phe Ser Asp Arg Ala Asn
            340                 345                 350

Ile Val Asn Leu Ser Ile Gly Gly Glu Phe Ser Pro Pro Asp Asp Ala
        355                 360                 365

Asp Ala Tyr Ala Val Glu Ser Leu Asn Arg Gln Gly Val Leu Ala Val
    370                 375                 380

Val Ser Ala Gly Asn Ala Thr Asp Tyr Tyr Gly Arg Gly Asp Thr Tyr
385                 390                 395                 400

Ser Asp Ser Gly Gln Pro Ala Asn Ala Val Ser Ala Leu Thr Val Ala
                405                 410                 415

Asn Ser Ile Gly Ser Ser Tyr Ala Val Asp Ser Met Glu Ile Gln Ala
            420                 425                 430

Pro Ala Asn Val Ala Gly Lys Val Pro Gly Asp Tyr Thr Val Ser Tyr
        435                 440                 445

Thr Tyr Thr Gly Ala Lys Pro Glu Ala Leu Thr Gly Thr Val Val Thr
    450                 455                 460

Pro Ser Glu Ser Asn Lys Phe Gly Cys Glu Ala Phe Ser Ala Glu Asp
465                 470                 475                 480

Ala Ala Lys Ile Lys Asp Lys Trp Val Phe Ile Glu Trp Ala Asn Ala
                485                 490                 495

Asp Gly Ser Leu Pro Cys Gly Ser Lys Val Arg Phe Asp Asn Val Glu
            500                 505                 510

Lys Ala Gly Gly Lys Gly Val Val Leu Ser Ser Glu Glu Lys Pro
        515                 520                 525

Ala Leu Pro Ile Gly Gly Asn Glu Ser Ile Pro Gly Phe Arg Val Ala
530                 535                 540

Lys Ser Ala Ser Ala Lys Val Arg Glu Ala Ala Thr Gly Glu Leu
545                 550                 555                 560

Lys Val Arg Leu Gly Ala Asp Leu Lys Glu Ser Leu Arg Val Pro Ser
            565                 570                 575

Asn Lys Lys Asp Gln Leu Thr Ala Ser Ala Arg Gly Tyr His Gly
        580                 585                 590

Thr Tyr Gly Tyr Thr Lys Pro Asp Val Ala Ala Pro Gly Asn Asn Ile
    595                 600                 605

Ser Ser Ala Arg Val Gly Thr Gly Gly Ile Ser Tyr Thr Gly
610                 615                 620

Thr Ser Met Ser Ala Pro Phe Ala Ala Gly Val Ala Ala Gln Val Leu
625                 630                 635                 640

Gln Ala Asn Gln Ser Tyr Gly Pro Thr Gln Leu Lys Ala Ala Ile Met
```

```
                    645                 650                 655
Asn Ser Ala Asn His Asp Val Arg Thr Ala Asp Gly Asn Val Tyr Ala
            660                 665                 670

Val Asp Arg Val Gly Ser Gly Arg Ile Asp Ala Lys Ala Ala Glu
675                 680                 685

Thr Lys Val Leu Leu Tyr Asn Ala Asp Arg Pro Ala Gln Val Ser Gln
690                 695                 700

Thr Phe Gly Val Leu Glu Tyr Ala Val Asn Glu Gly Lys Gln Thr Leu
705                 710                 715                 720

Thr Arg Glu Met Thr Val Glu Asn Phe Asp Ser His Thr His Thr Tyr
            725                 730                 735

Asn Ile Ser Tyr Ala Gly Ser Thr Asp Met Pro Gly Val Glu Phe Ser
            740                 745                 750

Leu Pro Ser Asn Ile Thr Val Asn Pro Gly Lys Lys Asn Phe Thr
            755                 760                 765

Val Thr Ile Thr Ile Asp Pro Ala Ala Met Glu Lys Thr Met Asp Pro
770                 775                 780

Ala Met Glu Lys Thr His Asn Ser Val Asp Pro Tyr Gly Asp Gly Thr
785             790                 795                 800

Glu Leu Val Pro Glu Gln Tyr Arg Gln Phe Ile Ala Ser Glu Ser Gly
                805                 810                 815

Arg Ile Leu Leu Thr Glu Gly Ala Ala Thr Leu Arg Ala Pro Ile His
            820                 825                 830

Ala Ala Pro Lys Pro Ala Ser Ala Met Lys Val Glu Gly Ser Ser Val
        835                 840                 845

Glu Ile Pro Ala Gly Glu His Gln Ala Asn Leu Lys Leu Thr Gly Thr
    850                 855                 860

Glu Leu Asn Gln Arg Gly Tyr Lys Ser Leu Leu Gly Ala Phe Glu His
865                 870                 875                 880

Gly Ala Ser Ile Glu Arg Thr Ser Pro Val Lys Leu Asp Val Ser Ser
                885                 890                 895

Asn Ala Lys Ala Asn Met Gln His Val Gly Ala Ala Ser Thr Ala Pro
            900                 905                 910

Ala Leu Lys Ala Ser Gly Gly Asn Pro Asn Asp Gly Leu Leu Ala Phe
        915                 920                 925

Gly Ile Ser Thr Trp Ala Asn Trp Asp Val Val Ser Thr Glu Asn Thr
    930                 935                 940

Phe Thr Val Asn Ile Asp Thr Asp Gly Asn Asn Arg Ala Asp Tyr Met
945                 950                 955                 960

Leu Val Thr Asp Arg Ala Lys Gly Ile Asp Phe Pro Ile Val Arg Leu
                965                 970                 975

Tyr Gly Tyr Lys Asn Gly Asn Leu Glu Gln Ile Ala Tyr Pro Leu
            980                 985                 990

Asn Asn Ala Trp Gly Asp Thr Asp Thr Asn Met Met Asp Ser Asn Ala
        995                 1000                1005

Leu Val Met Ala Val Pro Leu Lys Asp Leu Gly Leu Ser Ala Glu
    1010                1015                1020

Lys Thr Lys Asp Ile Lys Tyr Ser Val Ser Ala Thr Thr Gln Tyr
    1025                1030                1035

Ala Trp Thr Asn Val Ser Glu Thr Gly Trp Ile Asn Tyr Arg Pro
    1040                1045                1050

Phe Asp Pro Lys Leu Trp Phe Ser Gly Thr Ala Ala Thr Val Pro
    1055                1060                1065
```

```
Gly Phe Phe Ala Asp Ala Pro Ser Ser Glu Leu Val Ala His Arg
    1070            1075                1080

Ala Glu Gly Ala Thr Asp Val Lys Ala Leu Phe Leu His Met His
    1085            1090                1095

Asn Thr Thr Gly Asp Leu Ser Gly Leu Asn Gly Ala Ala Gly Asn
    1100            1105                1110

Arg Ala Gln Val Leu Glu Val Thr Glu Gln Gln Gln Leu Asp Pro
    1115            1120                1125

Ala Pro Ser Arg Phe Thr Asp Val Pro Ala Glu Asn Gln Phe Tyr
    1130            1135                1140

Ala Glu Ile Asn Trp Leu Ala Gln Arg Arg Ile Thr Thr Gly Tyr
    1145            1150                1155

Pro Asp Gly Thr Phe Arg Pro Gly Glu Asn Val Glu Arg Gly Ala
    1160            1165                1170

Met Ala Ala Tyr Phe Tyr Arg Leu Ala Gly Thr Pro Gln Phe Thr
    1175            1180                1185

Ala Pro Asp Asn Pro Thr Phe Ser Asp Val Pro Lys Ser His Pro
    1190            1195                1200

Phe Tyr Lys Glu Ile Glu Trp Met Ala Ala Arg Gly Ile Thr Thr
    1205            1210                1215

Gly Tyr Gly Asp Gly Thr Phe Arg Pro Ser Asp Ser Val Asn Arg
    1220            1225                1230

Asp Ala Met Ala Ala Phe Phe Tyr Arg Tyr Ala Asn Ser Pro Gln
    1235            1240                1245

Phe Ala Ala Pro Ala Ala Ser Pro Phe Lys Asp Val Pro Ala Asn
    1250            1255                1260

Ser Gln Phe Tyr Lys Glu Ile Ala Trp Leu Ala Glu Gln Gly Ile
    1265            1270                1275

Thr Lys Gly Trp Asp Asp Gly Thr Tyr Arg Pro Gly Glu Pro Ile
    1280            1285                1290

His Arg Asp Ala Met Ala Ala Phe Leu Tyr Arg Tyr Ser Asp Lys
    1295            1300                1305

Val Leu Lys
    1310

<210> SEQ ID NO 69
<211> LENGTH: 1313
<212> TYPE: PRT
<213> ORGANISM: Rothia dentocariosa

<400> SEQUENCE: 69

Met Ala Ser Thr Asn Thr Trp Arg Ala Cys Thr Arg Ile Gly Leu Ser
1               5                   10                  15

Ala Val Leu Gly Leu Gly Leu Ile Ala Ser Thr Ala Val Pro Leu Asn
                20                  25                  30

Ala Ala Glu Thr Pro Leu Arg Gly Gln Asp Pro Asp Leu Arg Thr Ser
            35                  40                  45

Gln Gln His Thr Gln Gln Val Leu Ser Pro Ser Met Leu Lys Ala
    50                  55                  60

Gln Gly Thr Ile Pro Val Tyr Val Lys Phe Lys Gly Gln Gly Ala Tyr
65                  70                  75                  80

Glu Gln Thr Gln Pro Arg Ala Val Leu Gln Asn Arg Gln Ala Pro Val
                85                  90                  95

Asn Ala Gln Ala Gln Val Gln Ala Ile Lys Thr Arg Val Glu Ser Gln
```

-continued

```
                100                 105                 110
Ala Gln Ser Val Ala Gly Glu Ser His Ala Lys Val Leu Tyr Thr Thr
            115                 120                 125
His Asn Val Met Pro Gly Val Ala Leu Met Gly Asp Ala Gln Ala Ile
        130                 135                 140
Arg Asp Leu Ala Ser Arg Pro Asp Val Glu Arg Ile Ser Pro Ile Val
145                 150                 155                 160
Pro Lys Tyr Arg Gln Asn Ala Gly Ser Val Val Asp Thr Gly Ala Ala
                165                 170                 175
Glu Asn Trp Ala Arg Gln Asn Thr Gly Tyr Thr Gly Lys Gly Ile Lys
            180                 185                 190
Ile Ala Val Ile Asp Ser Gly Ile Asp Tyr Thr His Ala Asp Phe Gly
        195                 200                 205
Gly Pro Gly Thr Lys Glu Ala Phe Asp Glu Ala Thr Lys Leu Thr Asn
    210                 215                 220
Met Pro Glu Ala Ser Ser Gly Leu Tyr Asp Pro Ala Lys Phe Leu Gly
225                 230                 235                 240
Gly Tyr Asp Leu Ala Gly Asp Tyr Asn Gly Leu Asn Thr Ala Val
                245                 250                 255
Pro Asp Asn Asn Pro Ile Asp Cys Ile Ser Gly His Gly Thr His
            260                 265                 270
Val Ala Gly Thr Ala Ala Gly Trp Gly Val Asp Ala Gln Gly Lys Thr
        275                 280                 285
Phe Arg Gly Asp Tyr Ser Thr Leu Thr Pro Glu Lys Leu Gly Glu Met
    290                 295                 300
Lys Ile Gly Pro Gly Ser Ala Pro Asp Ala Gln Leu Tyr Ser Phe Arg
305                 310                 315                 320
Val Phe Gly Cys Ser Gly Ala Thr Asn Leu Val Gly Gln Ala Leu Asp
                325                 330                 335
Lys Val Leu Asp Pro Asn Gly Asp Gly Asp Phe Ser Arg Ala Gln
            340                 345                 350
Val Val Asn Met Ser Leu Gly Gly Glu Phe Ser Pro Glu Asp Asp Pro
        355                 360                 365
Glu Ser Tyr Ala Val Glu Thr Leu Phe Arg Gln Gly Val Leu Ala Val
    370                 375                 380
Val Ser Ala Gly Asn Ala Asn Gly Tyr Asn Gly Ala Gly Asp Thr Tyr
385                 390                 395                 400
Ser Asn Ser Gly Gln Pro Ala Asn Ala Ile Ser Ala Leu Thr Val Ala
                405                 410                 415
Asn Ser Val Gly Ser Thr Tyr Ala Met Asp Ala Ala Gln Ile Leu Ala
            420                 425                 430
Pro Ser Gln Ile Ala Gly Lys Ile Pro Gly Asp Tyr Ser Val Asp Tyr
        435                 440                 445
Asn Tyr Ser Lys Ala Ser Glu Glu Thr Leu Arg Gly Gln Val Val Ala
    450                 455                 460
Ala Pro Ala Ser Asn Lys Phe Gly Cys Glu Ala Phe Ser Ala Glu Tyr
465                 470                 475                 480
Ala Ala Lys Leu Lys Asp Arg Trp Ile Phe Ile Glu Trp Ala Asn Glu
                485                 490                 495
Asp Gly Thr Ile Ser Cys Gly Ser Lys Val Arg Phe Asp Asn Ala Glu
            500                 505                 510
Lys Ala Gly Ala Lys Gly Val Val Leu Ser Ser Gln Glu Glu Arg Ala
        515                 520                 525
```

```
Glu Leu Gly Ile Ala Gly Asn Glu Thr Ile Pro Gly Phe Arg Val Ala
    530                 535                 540

Lys Ser Ala Ser Asp Lys Val Arg Glu Ala Ala Gln Ala Gly Thr Leu
545                 550                 555                 560

Glu Ile Arg Leu Gly Glu Asp Leu Lys Gly Gly Leu Arg Val Gln Ser
                565                 570                 575

Gly Lys Phe Asp Glu Leu Thr Thr Ser Ser Ala Arg Gly Phe His Gly
                580                 585                 590

Ser Tyr Gly Tyr Thr Lys Pro Asp Leu Ala Ala Pro Gly Asn Asn Ile
            595                 600                 605

Ser Ser Ala Ala Val Gly Thr Gly Thr Gly Ser Ile Gln Tyr Thr Gly
610                 615                 620

Thr Ser Met Ser Ala Pro Phe Ala Ser Gly Val Ala Ala Gln Val Leu
625                 630                 635                 640

Gln Ala His Gln Asp Tyr Ser Pro Ile Gln Ile Lys Ala Ala Met Met
                645                 650                 655

Asn Ser Ala Asp His Asp Leu His Asp Ala Ala Gly His Thr Tyr Ala
                660                 665                 670

Val Asp Arg Val Gly Ser Gly Arg Ile Asp Ala Lys Ala Ala Val Asp
                675                 680                 685

Thr Arg Val Leu Leu Tyr Asn Ala Asp Arg Pro Glu Gln Val Ser Gln
690                 695                 700

Thr Phe Gly Val Leu Glu Tyr Ala Ala Asp Ala Gly Gln Gln Ser Leu
705                 710                 715                 720

Thr Arg Glu Met Thr Val Glu Asn Phe Asp Ser Lys Ala His Thr Tyr
                725                 730                 735

Ser Ile Ser Tyr Ala Gly Ser Thr Asp Met Pro Gly Val Glu Phe Ser
                740                 745                 750

Met Pro Ser Ser Ile Thr Val Gln Pro Ser Glu Lys Lys Asn Phe Gln
                755                 760                 765

Val Lys Val Thr Ile Asp Pro Ala Arg Leu Glu Lys Thr Met Asp Pro
770                 775                 780

Ala Met Glu Lys Thr Gln Ser Ser Ile Asp Val Asn Thr Gly Lys Thr
785                 790                 795                 800

Val Val Pro Glu Gln Ala Arg Gln Phe Ile Ala Ser Glu Ser Gly Arg
                805                 810                 815

Ile Lys Leu Ala Glu Gly Asp Gln Thr Leu Arg Val Pro Leu His Ala
                820                 825                 830

Ala Pro Lys Pro Val Ser Thr Met Lys Val Ala Gly Asn Asn Val Gln
                835                 840                 845

Val Pro Ser Gly Ser Ser Gln Thr Arg Val Thr Leu Glu Gly Thr Glu
850                 855                 860

Leu Asn Gln Gly Gly Tyr Arg Ser Leu Leu Gly Ala Phe Glu Trp Gly
865                 870                 875                 880

Ala Ser Val Asn Arg Ile Asn Pro Ser Asn Leu Trp Val Ser Ser Asp
                885                 890                 895

Met Lys Ala Asn Leu Gln His Val Gly Ala Ala Ser Asn Ala Pro Ala
                900                 905                 910

Leu Lys Asp Ala Gly Lys Asp Pro Asn Glu Gly Thr Leu Ser Phe Gly
                915                 920                 925

Ile Ser Thr Trp Arg Asn Trp Asp Val Ile Ser Glu Glu Asn Thr Phe
930                 935                 940
```

```
Thr Val Asn Ile Asp Thr Asp Gly Asn Asn Arg Ala Asp Tyr Val Leu
945                 950                 955                 960

Lys Thr Asp Arg Ser Ala Gly Leu Asp Phe Pro Ile Val Arg Leu Met
            965                 970                 975

Gly Tyr Lys Asn Gly Ser Leu Glu Gln Leu Ala Tyr Tyr Pro Leu Asn
        980                 985                 990

Gly Ala Trp Gly Asp Thr Asp Thr Asn Met Met Asp Thr Asn Thr Leu
    995                 1000                1005

Ile Met Ser Val Pro Leu Lys Asp Leu Gly Leu Thr Ala Glu Asn
1010                1015                1020

Ala Pro Gln Ile Arg Tyr Ser Val Glu Ser Ile Thr Gln Tyr Glu
1025                1030                1035

Trp Glu Asn Val Asn Gln Thr Asp Trp Ile Thr Tyr Ser Pro Phe
1040                1045                1050

Ala Pro Lys Val Trp Phe Ser Gly Thr Glu Ser Ser Ile Pro Gly
1055                1060                1065

Leu Phe Ala Asp Ala Pro Thr Thr Glu Leu Thr Leu His Arg Ala
1070                1075                1080

Ser Asp Ala Gly Ser Ala Lys Ala Leu Phe Leu His Leu His Asn
1085                1090                1095

Gly Thr Gly Asp Leu Ser Gly Ser Gln Gly Ala Ser Gly Glu Arg
1100                1105                1110

Ala Gln Val Leu Pro Val Ser Glu Gln Ser Thr Glu Thr Pro Ser
1115                1120                1125

Ala Pro Arg Phe Thr Asp Val Lys Glu Gly Asp Met Phe Tyr Thr
1130                1135                1140

Glu Ile Ala Trp Leu Ala Gln Arg Arg Ile Thr Thr Gly Tyr Pro
1145                1150                1155

Asp Gly Ser Phe Arg Pro Ala Glu Asn Thr Ser Arg Ala Ala Met
1160                1165                1170

Ala Ala Tyr Phe Tyr Arg Leu Ala Gly Ser Pro Gln Phe Thr Ala
1175                1180                1185

Pro Ser Thr Pro Thr Phe Lys Asp Val Ala Pro Gly Asp Gln Phe
1190                1195                1200

Tyr Lys Glu Ile Glu Trp Phe Ala Ala Gln Arg Leu Thr Thr Gly
1205                1210                1215

Tyr Ala Asp Gly Thr Phe Arg Pro Gln Asp Ala Val Asn Arg Asp
1220                1225                1230

Ala Met Ala Ala Phe Phe Tyr Arg Tyr Ala Gly Ser Pro Ala Phe
1235                1240                1245

Thr Ala Pro Asp Lys Pro Thr Phe Lys Asp Val Ala Pro Asn Ser
1250                1255                1260

Met Phe Tyr Arg Glu Ile Glu Trp Leu Ala Ala Gln Lys Val Thr
1265                1270                1275

Thr Gly Trp Pro Asp Gln Thr Tyr Arg Pro Leu Glu Pro Ile His
1280                1285                1290

Arg Asp Ala Met Ala Ala Phe Leu Tyr Arg Tyr Asn Gln Gly Val
1295                1300                1305

Leu Lys Ala Glu Gly
    1310

<210> SEQ ID NO 70
<211> LENGTH: 1313
<212> TYPE: PRT
```

<213> ORGANISM: Rothia dentocariosa

<400> SEQUENCE: 70

```
Met Ala Ser Thr Asn Thr Trp Arg Ala Cys Thr Arg Ile Gly Leu Ser
1               5                   10                  15

Ala Val Leu Gly Leu Gly Leu Ile Ala Ser Thr Ala Val Pro Leu Asn
            20                  25                  30

Ala Ala Glu Thr Pro Leu Arg Gly Gln Asp Pro Asp Leu Arg Thr Ser
        35                  40                  45

Gln Gln His Thr Gln Gln Val Leu Ser Pro Ser Met Leu Lys Ala
    50                  55                  60

Gln Gly Thr Ile Pro Val Tyr Val Lys Phe Lys Gly Gln Gly Ala Tyr
65                  70                  75                  80

Glu Gln Thr Gln Pro Arg Ala Val Leu Gln Asn Arg Gln Ala Pro Val
                85                  90                  95

Asn Ala Gln Ala Gln Val Gln Ala Ile Lys Thr Arg Val Glu Ser Gln
            100                 105                 110

Ala Gln Ser Val Ala Gly Glu Ser His Ala Lys Val Leu Tyr Thr Thr
        115                 120                 125

His Asn Val Met Pro Gly Val Ala Leu Met Gly Asp Ala Gln Ala Ile
    130                 135                 140

Arg Asp Leu Ala Ser Arg Pro Asp Val Glu Arg Ile Ser Pro Ile Val
145                 150                 155                 160

Pro Lys Tyr Arg Gln Asn Ala Gly Ser Val Val Asp Thr Gly Ala Ala
                165                 170                 175

Glu Asn Trp Ala Arg Gln Asn Thr Gly Tyr Thr Gly Lys Gly Ile Lys
            180                 185                 190

Ile Ala Val Ile Asp Ser Gly Ile Asp Tyr Thr His Ala Asp Phe Gly
        195                 200                 205

Gly Pro Gly Thr Lys Glu Ala Phe Asp Glu Ala Thr Lys Leu Thr Asn
    210                 215                 220

Met Pro Glu Ala Ser Ser Gly Leu Tyr Asp Pro Ala Lys Phe Leu Gly
225                 230                 235                 240

Gly Tyr Asp Leu Ala Gly Asp Tyr Asn Gly Leu Asn Thr Ala Val
                245                 250                 255

Pro Asp Asn Asn Pro Ile Asp Cys Ile Ser Gly Gly His Gly Thr His
            260                 265                 270

Val Ala Gly Thr Ala Ala Gly Trp Gly Val Asp Ala Gln Gly Lys Thr
        275                 280                 285

Phe Arg Gly Asp Tyr Ser Thr Leu Thr Pro Glu Lys Leu Gly Glu Met
    290                 295                 300

Lys Ile Gly Pro Gly Ser Ala Pro Asp Ala Gln Leu Tyr Ser Phe Arg
305                 310                 315                 320

Val Phe Gly Cys Ser Gly Ala Thr Asn Leu Val Gly Gln Ala Leu Asp
                325                 330                 335

Lys Val Leu Asp Pro Asn Gly Asp Gly Phe Ser Asp Arg Ala Gln
            340                 345                 350

Val Val Asn Met Ser Leu Gly Gly Glu Phe Ser Pro Glu Asp Pro
        355                 360                 365

Glu Ser Tyr Ala Val Glu Thr Leu Phe Arg Gln Gly Val Leu Ala Val
    370                 375                 380

Val Ser Ala Gly Asn Ala Asn Gly Tyr Asn Gly Ala Gly Asp Thr Tyr
385                 390                 395                 400
```

```
Ser Asn Ser Gly Gln Pro Ala Asn Ala Ile Ser Ala Leu Thr Val Ala
                405                 410                 415
Asn Ser Val Gly Ser Thr Tyr Ala Met Asp Ala Ala Gln Ile Leu Ala
            420                 425                 430
Pro Ser Gln Ile Ala Gly Lys Ile Pro Gly Asp Tyr Ser Val Asp Tyr
        435                 440                 445
Asn Tyr Ser Lys Ala Ser Glu Glu Thr Leu Arg Gly Gln Val Val Ala
    450                 455                 460
Ala Pro Ala Ser Asn Lys Phe Gly Cys Glu Ala Phe Ser Ala Glu Tyr
465                 470                 475                 480
Ala Ala Lys Leu Lys Asp Arg Trp Ile Phe Ile Glu Trp Ala Asn Glu
            485                 490                 495
Asp Gly Thr Ile Ser Cys Gly Ser Lys Val Arg Phe Asp Asn Ala Glu
            500                 505                 510
Lys Ala Gly Ala Lys Gly Val Val Leu Ser Ser Gln Glu Glu Arg Ala
            515                 520                 525
Glu Leu Gly Ile Ala Gly Asn Glu Thr Ile Pro Gly Phe Arg Val Ala
        530                 535                 540
Lys Ser Ala Ser Asp Lys Val Arg Glu Ala Ala Gln Ala Gly Thr Leu
545                 550                 555                 560
Glu Ile Arg Leu Gly Glu Asp Leu Lys Gly Gly Leu Arg Val Gln Ser
                565                 570                 575
Gly Lys Phe Asp Glu Leu Thr Thr Ser Ser Ala Arg Gly Phe His Gly
            580                 585                 590
Ser Tyr Gly Tyr Thr Lys Pro Asp Leu Ala Ala Pro Gly Asn Asn Ile
        595                 600                 605
Ser Ser Ala Ala Val Gly Thr Gly Thr Gly Ser Ile Gln Tyr Thr Gly
    610                 615                 620
Thr Ser Met Ser Ala Pro Phe Ala Ser Gly Val Ala Ala Gln Val Leu
625                 630                 635                 640
Gln Ala His Gln Asp Tyr Ser Pro Ile Gln Ile Lys Ala Ala Met Met
                645                 650                 655
Asn Ser Ala Asp His Asp Leu His Asp Ala Ala Gly His Thr Tyr Ala
            660                 665                 670
Val Asp Arg Val Gly Ser Gly Arg Ile Asp Ala Lys Ala Ala Val Asp
        675                 680                 685
Thr Arg Val Leu Leu Tyr Asn Ala Asp Arg Pro Glu Gln Val Ser Gln
    690                 695                 700
Thr Phe Gly Val Leu Glu Tyr Ala Ala Asp Ala Gly Gln Gln Ser Leu
705                 710                 715                 720
Thr Arg Glu Met Thr Val Glu Asn Phe Asp Ser Lys Ala His Thr Tyr
                725                 730                 735
Ser Ile Ser Tyr Ala Gly Ser Thr Asp Met Pro Gly Val Glu Phe Ser
            740                 745                 750
Met Pro Ser Ser Ile Thr Val Gln Pro Ser Glu Lys Lys Asn Phe Gln
        755                 760                 765
Val Lys Val Thr Ile Asp Pro Ala Arg Leu Glu Lys Thr Met Asp Pro
    770                 775                 780
Ala Met Glu Lys Thr Gln Ser Ser Ile Asp Val Asn Thr Gly Lys Thr
785                 790                 795                 800
Val Val Pro Glu Gln Ala Arg Gln Phe Ile Ala Ser Glu Ser Gly Arg
                805                 810                 815
Ile Lys Leu Ala Glu Gly Asp Gln Thr Leu Arg Val Pro Leu His Ala
```

-continued

Ala Pro Lys Pro Val Ser Thr Met Lys Val Ala Gly Asn Asn Val Gln
820             825                 830

Val Pro Ser Gly Ser Ser Gln Thr Arg Val Thr Leu Glu Gly Thr Glu
835             840                 845

Leu Asn Gln Gly Gly Tyr Arg Ser Leu Leu Gly Ala Phe Glu Trp Gly
850             855                 860

Ala Ser Val Asn Arg Ile Asn Pro Ser Asn Leu Trp Val Ser Ser Asp
865             870                 875                 880

Met Lys Ala Asn Leu Gln His Val Gly Ala Ala Ser Asn Ala Pro Ala
            885                 890                 895

Leu Lys Asp Ala Gly Lys Asp Pro Asn Glu Gly Thr Leu Ser Phe Gly
    900                 905                 910

Ile Ser Thr Trp Arg Asn Trp Asp Val Ile Ser Glu Glu Asn Thr Phe
915                 920                 925

Thr Val Asn Ile Asp Thr Asp Gly Asn Asn Arg Ala Asp Tyr Val Leu
930                 935                 940

Lys Thr Asp Arg Ser Ala Gly Leu Asp Phe Pro Ile Val Arg Leu Met
945                 950                 955                 960

Gly Tyr Lys Asn Gly Ser Leu Glu Gln Leu Ala Tyr Tyr Pro Leu Asn
            965                 970                 975

Gly Ala Trp Gly Asp Thr Asp Thr Asn Met Met Asp Thr Asn Thr Leu
    980                 985                 990

Ile Met Ser Val Pro Leu Lys Asp Leu Gly Leu Thr Ala Glu Asn
    995                 1000                1005

Ala Pro Gln Ile Arg Tyr Ser Val Glu Ser Ile Thr Gln Tyr Glu
1010                1015                1020

Trp Glu Asn Val Asn Gln Thr Asp Trp Ile Thr Tyr Ser Pro Phe
1025                1030                1035

Ala Pro Lys Val Trp Phe Ser Gly Thr Glu Ser Ser Ile Pro Gly
1040                1045                1050

Leu Phe Ala Asp Ala Pro Thr Thr Glu Leu Thr Leu His Arg Ala
1055                1060                1065

Ser Asp Ala Gly Ser Ala Lys Ala Leu Phe Leu His Leu His Asn
1070                1075                1080

Gly Thr Gly Asp Leu Ser Gly Ser Gln Gly Ala Ser Gly Glu Arg
1085                1090                1095

Ala Gln Val Leu Pro Val Ser Glu Gln Ser Thr Glu Thr Pro Ser
1100                1105                1110

Ala Pro Arg Phe Thr Asp Val Lys Glu Gly Asp Met Phe Tyr Thr
1115                1120                1125

Glu Ile Ala Trp Leu Ala Gln Arg Arg Ile Thr Thr Gly Tyr Pro
1130                1135                1140

Asp Gly Ser Phe Arg Pro Ala Glu Asn Thr Ser Arg Ala Ala Met
1145                1150                1155

Ala Ala Tyr Phe Tyr Arg Leu Ala Gly Ser Pro Gln Phe Thr Ala
1160                1165                1170

Pro Ser Thr Pro Thr Phe Lys Asp Val Ala Pro Gly Asp Gln Phe
1175                1180                1185

Tyr Lys Glu Ile Glu Trp Phe Ala Ala Gln Arg Leu Thr Thr Gly
1190                1195                1200

Tyr Ala Asp Gly Thr Phe Arg Pro Gln Asp Ala Val Asn Arg Asp
1205                1210                1215

```
Ala Met Ala Ala Phe Phe Tyr Arg Tyr Ala Gly Ser Pro Ala Phe
    1235                1240                1245

Thr Ala Pro Asp Lys Pro Thr Phe Lys Asp Val Ala Pro Asn Ser
1250                1255                1260

Met Phe Tyr Arg Glu Ile Glu Trp Leu Ala Ala Gln Lys Val Thr
1265                1270                1275

Thr Gly Trp Pro Asp Gln Thr Tyr Arg Pro Leu Glu Pro Ile His
    1280                1285                1290

Arg Asp Ala Met Ala Ala Phe Leu Tyr Arg Tyr Asn Gln Gly Val
    1295                1300                1305

Leu Lys Ala Glu Gly
        1310

<210> SEQ ID NO 71
<211> LENGTH: 1313
<212> TYPE: PRT
<213> ORGANISM: Rothia dentocariosa

<400> SEQUENCE: 71

Met Ala Ser Thr Asn Thr Trp Arg Ala Cys Thr Arg Ile Gly Leu Ser
1               5                   10                  15

Ala Val Leu Gly Leu Gly Leu Ile Ala Ser Thr Ala Val Pro Leu Asn
            20                  25                  30

Ala Ala Glu Thr Pro Leu Arg Gly Gln Asp Pro Asp Leu Arg Thr Ser
        35                  40                  45

Gln Gln His Thr Gln Gln Val Leu Ser Pro Ser Met Leu Lys Ala
    50                  55                  60

Gln Gly Thr Ile Pro Val Tyr Val Lys Phe Lys Gly Gln Gly Ala Tyr
65                  70                  75                  80

Glu Gln Thr Gln Pro Arg Ala Val Leu Gln Asn Arg Gln Ala Pro Val
                85                  90                  95

Asn Ala Gln Ala Gln Val Gln Ala Ile Lys Thr Arg Val Glu Ser Gln
            100                 105                 110

Ala Gln Ser Val Ala Gly Glu Ser His Ala Lys Val Leu Tyr Thr Thr
        115                 120                 125

His Asn Val Met Pro Gly Val Ala Leu Met Gly Asp Ala Gln Ala Ile
    130                 135                 140

Arg Asp Leu Ala Ser Arg Pro Asp Val Glu Arg Ile Ser Pro Ile Val
145                 150                 155                 160

Pro Lys Tyr Arg Gln Asn Ala Gly Ser Val Val Asp Thr Gly Ala Ala
                165                 170                 175

Glu Asn Trp Ala Arg Gln Asn Thr Gly Tyr Thr Gly Lys Gly Ile Lys
            180                 185                 190

Ile Ala Val Ile Asp Ser Gly Ile Asp Tyr Thr His Ala Asp Phe Gly
        195                 200                 205

Gly Pro Gly Thr Lys Glu Ala Phe Asp Glu Ala Thr Lys Leu Thr Asn
    210                 215                 220

Met Pro Glu Ala Ser Ser Gly Leu Tyr Asp Pro Ala Lys Phe Leu Gly
225                 230                 235                 240

Gly Tyr Asp Leu Ala Gly Asp Tyr Asn Gly Leu Asn Thr Ala Val
                245                 250                 255

Pro Asp Asn Asn Pro Ile Asp Cys Ile Ser Gly Gly His Gly Thr His
            260                 265                 270

Val Ala Gly Thr Ala Ala Gly Trp Gly Val Asp Ala Gln Gly Lys Thr
```

```
            275                 280                 285
Phe Arg Gly Asp Tyr Ser Thr Leu Thr Pro Glu Lys Leu Gly Glu Met
290                 295                 300

Lys Ile Gly Pro Gly Ser Ala Pro Asp Ala Gln Leu Tyr Ser Phe Arg
305                 310                 315                 320

Val Phe Gly Cys Ser Gly Ala Thr Asn Leu Val Gly Gln Ala Leu Asp
                325                 330                 335

Lys Val Leu Asp Pro Asn Gly Asp Gly Asp Phe Ser Asp Arg Ala Gln
                340                 345                 350

Val Val Asn Met Ser Leu Gly Gly Glu Phe Ser Pro Glu Asp Asp Pro
                355                 360                 365

Glu Ser Tyr Ala Val Glu Thr Leu Phe Arg Gln Gly Val Leu Ala Val
370                 375                 380

Val Ser Ala Gly Asn Ala Thr Gly Tyr Asn Gly Val Gly Asp Thr Tyr
385                 390                 395                 400

Ser Asp Ser Gly Gln Pro Ala Asn Ala Ile Ser Ala Leu Thr Val Ala
                405                 410                 415

Asn Ser Val Gly Ser Thr Tyr Ala Met Asp Ala Ala Gln Ile Leu Ala
                420                 425                 430

Pro Ser Gln Ile Ala Gly Lys Ile Pro Gly Asp Tyr Ser Val Asp Tyr
                435                 440                 445

Asn Tyr Ser Lys Ala Ser Glu Glu Thr Leu Arg Gly Gln Val Val Ala
450                 455                 460

Ala Ser Ala Ser Asn Lys Phe Gly Cys Glu Ala Phe Ser Ala Glu Asp
465                 470                 475                 480

Ala Ala Lys Ile Lys Asp Arg Trp Val Phe Ile Glu Trp Ala Asn Glu
                485                 490                 495

Asp Gly Thr Ile Ser Cys Gly Ser Lys Val Arg Phe Asp Asn Ala Glu
                500                 505                 510

Lys Ala Gly Ala Lys Gly Val Val Leu Ser Ser Gln Glu Glu Arg Ala
                515                 520                 525

Glu Leu Gly Ile Ala Gly Asn Glu Thr Leu Pro Gly Phe Arg Val Ala
530                 535                 540

Lys Ser Ala Ser Asp Lys Val Arg Glu Ala Ala Gln Ala Gly Thr Leu
545                 550                 555                 560

Glu Ile Arg Leu Gly Glu Asp Leu Lys Gly Gly Leu Arg Val Gln Ser
                565                 570                 575

Gly Lys Phe Asp Glu Leu Thr Thr Ser Ser Ala Arg Gly Phe His Gly
                580                 585                 590

Ser Tyr Gly Tyr Thr Lys Pro Asp Leu Ala Ala Pro Gly Asn Asn Ile
                595                 600                 605

Ser Ser Ala Ala Val Gly Thr Gly Thr Gly Ser Ile Gln Tyr Thr Gly
                610                 615                 620

Thr Ser Met Ser Ala Pro Phe Ala Ser Gly Val Ala Ala Gln Val Leu
625                 630                 635                 640

Gln Ala His Gln Asp Tyr Ser Pro Ile Gln Ile Lys Ala Ala Met Met
                645                 650                 655

Asn Ser Ala Asp His Asp Leu His Asp Ala Asp Gly His Thr Tyr Ala
                660                 665                 670

Val Asp Arg Val Gly Ser Gly Arg Ile Asp Ala Lys Ala Ala Val Asp
                675                 680                 685

Thr Arg Val Leu Leu Tyr Asn Ala Asp Arg Pro Glu Gln Val Ser Gln
                690                 695                 700
```

```
Thr Phe Gly Val Leu Glu Tyr Ala Ala Asp Ala Gly Gln Gln Ser Leu
705                 710                 715                 720

Ala Arg Glu Met Thr Val Glu Asn Phe Asp Ser Lys Ala His Thr Tyr
            725                 730                 735

Ser Ile Ser Tyr Ala Gly Ser Thr Asp Met Pro Gly Val Glu Phe Ser
                740                 745                 750

Met Pro Ser Ser Ile Thr Val Gln Pro Gly Glu Lys Lys Asn Phe Gln
        755                 760                 765

Val Lys Val Thr Ile Asp Pro Ala Arg Leu Glu Lys Thr Met Asp Pro
770                 775                 780

Ala Met Glu Lys Thr Gln Ser Ser Val Asp Val Asn Thr Gly Lys Thr
785                 790                 795                 800

Val Val Pro Glu Gln Ala Arg Gln Phe Ile Ala Ser Glu Ser Gly Arg
                805                 810                 815

Ile Lys Leu Thr Glu Gly Asp Gln Thr Leu Arg Val Pro Leu His Ala
                820                 825                 830

Ala Pro Lys Pro Val Ser Thr Met Lys Val Ala Gly Asn Asn Val Gln
                835                 840                 845

Val Pro Ala Gly Ser Ser Gln Thr Arg Val Thr Leu Glu Gly Thr Glu
850                 855                 860

Leu Asn Gln Gly Gly Tyr Arg Ser Leu Leu Gly Ala Phe Glu Trp Gly
865                 870                 875                 880

Ala Ser Val Asn Arg Val Asn Pro Ser Asn Leu Trp Val Ser Ser Asp
                885                 890                 895

Met Lys Ala Asn Leu Gln His Val Gly Ala Ala Ser Asn Ala Pro Ala
                900                 905                 910

Leu Lys Asp Ala Gly Lys Asp Pro Asn Glu Gly Thr Leu Ser Phe Gly
                915                 920                 925

Ile Ser Thr Trp Arg Asn Trp Asp Val Ile Ser Glu Glu Asn Thr Phe
                930                 935                 940

Thr Val Asn Ile Asp Thr Asp Gly Asn Asn Arg Ala Asp Tyr Val Leu
945                 950                 955                 960

Lys Thr Asp Arg Ser Ala Gly Leu Asp Phe Pro Ile Val Arg Leu Leu
                965                 970                 975

Gly Tyr Lys Asn Gly Ser Leu Glu Gln Leu Ala Tyr Tyr Pro Leu Asn
                980                 985                 990

Gly Ala Trp Gly Asp Thr Asp Thr Asn Met Met Asp Thr Asn Thr Leu
            995                 1000                1005

Ile Met Ser Val Pro Leu Lys Asp Leu Gly Leu Thr Ala Glu Asn
        1010                1015                1020

Ala Pro Gln Ile Arg Tyr Ser Val Glu Ser Ile Thr Gln Tyr Glu
        1025                1030                1035

Trp Glu Asn Val Ser Gln Thr Asp Trp Ile Thr Tyr Ser Pro Phe
        1040                1045                1050

Ala Pro Lys Val Trp Phe Ser Gly Thr Glu Ser Ser Ile Pro Gly
        1055                1060                1065

Leu Phe Ala Asp Ala Pro Thr Glu Leu Thr Leu His Arg Ala
        1070                1075                1080

Ser Asp Ala Gly Ser Ala Lys Ala Leu Phe Leu His Leu His Asn
        1085                1090                1095

Gly Thr Gly Asp Leu Ser Gly Ser Gln Gly Ala Ser Gly Glu Arg
        1100                1105                1110
```

```
Ala Gln Val Leu Pro Val Ser Glu Gln Ser Thr Glu Ser Pro Ser
    1115                1120                1125

Ala Pro Arg Phe Met Asp Val Lys Glu Gly Asp Met Phe Tyr Thr
    1130                1135                1140

Glu Ile Ala Trp Leu Ala Gln Arg Arg Ile Thr Thr Gly Tyr Pro
    1145                1150                1155

Asp Gly Ser Phe Arg Pro Ala Glu Asn Thr Ser Arg Ala Ala Met
    1160                1165                1170

Ala Ala Tyr Phe Tyr Arg Leu Ala Gly Ser Pro Gln Phe Thr Ala
    1175                1180                1185

Pro Ser Thr Pro Thr Phe Lys Asp Val Ala Pro Gly Asp Gln Phe
    1190                1195                1200

Tyr Lys Glu Ile Glu Trp Phe Ala Ala Gln Arg Leu Thr Thr Gly
    1205                1210                1215

Tyr Ala Asp Gly Thr Phe Arg Pro Gln Asp Ala Val Asn Arg Asp
    1220                1225                1230

Ala Met Ala Ala Phe Phe Tyr Arg Tyr Ala Gly Ser Pro Ala Phe
    1235                1240                1245

Thr Ala Pro Asp Lys Pro Thr Phe Lys Asp Val Ala Pro Asn Ser
    1250                1255                1260

Met Phe Tyr Arg Glu Ile Glu Trp Leu Ala Ala Gln Lys Val Thr
    1265                1270                1275

Thr Gly Trp Pro Asp Gln Thr Tyr Arg Pro Leu Glu Pro Ile His
    1280                1285                1290

Arg Asp Ala Met Ala Ala Phe Leu Tyr Arg Tyr Asn Gln Gly Val
    1295                1300                1305

Leu Lys Ala Glu Gly
    1310

<210> SEQ ID NO 72
<211> LENGTH: 1313
<212> TYPE: PRT
<213> ORGANISM: Rothia dentocariosa

<400> SEQUENCE: 72

Met Ala Ser Thr Asn Thr Trp Arg Ala Cys Thr Arg Ile Gly Leu Ser
1               5                   10                  15

Ala Val Leu Gly Leu Gly Leu Ile Ala Ser Thr Ala Val Pro Leu Asn
            20                  25                  30

Ala Ala Glu Thr Pro Leu Arg Gly Gln Asp Pro Asp Leu Arg Thr Ser
        35                  40                  45

Gln Gln His Thr Gln Gln Val Leu Ser Pro Ser Met Leu Lys Ala
    50                  55                  60

Gln Gly Thr Ile Pro Val Tyr Val Lys Phe Lys Gly Gln Gly Ala Tyr
65                  70                  75                  80

Glu Gln Thr Gln Pro Arg Ala Val Leu Gln Asn Arg Gln Ala Pro Val
                85                  90                  95

Asn Ala Gln Ala Gln Val Gln Ala Ile Lys Thr Arg Val Glu Ser Gln
            100                 105                 110

Ala Gln Ser Val Ala Gly Glu Ser His Ala Lys Val Leu Tyr Thr Thr
        115                 120                 125

His Asn Val Met Pro Gly Val Ala Leu Met Gly Asp Ala Gln Ala Ile
    130                 135                 140

Arg Asp Leu Ala Ser Arg Pro Asp Val Glu Arg Ile Ser Pro Ile Val
145                 150                 155                 160
```

```
Pro Lys Tyr Arg Gln Asn Ala Gly Ser Val Val Asp Thr Gly Ala Ala
                165                 170                 175

Glu Asn Trp Ala Arg Gln Asn Thr Gly Tyr Thr Gly Lys Gly Ile Lys
                180                 185                 190

Ile Ala Val Ile Asp Ser Gly Ile Asp Tyr Thr His Ala Asp Phe Gly
                195                 200                 205

Gly Pro Gly Thr Lys Glu Ala Phe Asp Glu Ala Thr Lys Leu Thr Asn
            210                 215                 220

Met Pro Glu Ala Ser Ser Gly Leu Tyr Asp Pro Ala Lys Phe Leu Gly
225                 230                 235                 240

Gly Tyr Asp Leu Ala Gly Asp Tyr Asn Gly Leu Asn Thr Ala Val
                245                 250                 255

Pro Asp Asn Asn Pro Ile Asp Cys Ile Ser Gly Gly His Gly Thr His
                260                 265                 270

Val Ala Gly Thr Ala Ala Gly Trp Gly Val Asp Ala Gln Gly Lys Thr
                275                 280                 285

Phe Arg Gly Asp Tyr Ser Thr Leu Thr Pro Glu Lys Leu Gly Glu Met
                290                 295                 300

Lys Ile Gly Pro Gly Ser Ala Pro Asp Ala Gln Leu Tyr Ser Phe Arg
305                 310                 315                 320

Val Phe Gly Cys Ser Gly Ala Thr Asn Leu Val Gly Gln Ala Leu Asp
                325                 330                 335

Lys Val Leu Asp Pro Asn Gly Asp Gly Asp Phe Ser Asp Arg Ala Gln
                340                 345                 350

Val Val Asn Met Ser Leu Gly Gly Glu Phe Ser Pro Glu Asp Asp Pro
                355                 360                 365

Glu Ser Tyr Ala Val Glu Thr Leu Phe Arg Gln Gly Val Leu Ala Val
            370                 375                 380

Val Ser Ala Gly Asn Ala Thr Gly Tyr Asn Gly Val Gly Asp Thr Tyr
385                 390                 395                 400

Ser Asp Ser Gly Gln Pro Ala Asn Ala Ile Ser Ala Leu Thr Val Ala
                405                 410                 415

Asn Ser Val Gly Ser Thr Tyr Ala Met Asp Ala Ala Gln Ile Leu Ala
                420                 425                 430

Pro Ser Gln Ile Ala Gly Lys Ile Pro Gly Asp Tyr Ser Val Asp Tyr
                435                 440                 445

Asn Tyr Ser Lys Ala Ser Glu Glu Thr Leu Arg Gly Gln Val Val Ala
            450                 455                 460

Ala Ser Ala Ser Asn Lys Phe Gly Cys Glu Ala Phe Ser Ala Glu Asp
465                 470                 475                 480

Ala Ala Lys Ile Lys Asp Arg Trp Val Phe Ile Glu Trp Ala Asn Glu
                485                 490                 495

Asp Gly Thr Ile Ser Cys Gly Ser Lys Val Arg Phe Asp Asn Ala Glu
                500                 505                 510

Lys Ala Gly Ala Lys Gly Val Val Leu Ser Ser Gln Glu Glu Arg Ala
            515                 520                 525

Glu Leu Gly Ile Ala Gly Asn Glu Thr Leu Pro Gly Phe Arg Val Ala
            530                 535                 540

Lys Ser Ala Ser Asp Lys Val Arg Glu Ala Gln Ala Gly Thr Leu
545                 550                 555                 560

Glu Ile Arg Leu Gly Glu Asp Leu Lys Gly Gly Leu Arg Val Gln Ser
                565                 570                 575
```

```
Gly Lys Phe Asp Glu Leu Thr Thr Ser Ser Ala Arg Gly Phe His Gly
                580                 585                 590

Ser Tyr Gly Tyr Thr Lys Pro Asp Leu Ala Ala Pro Gly Asn Asn Ile
            595                 600                 605

Ser Ser Ala Ala Val Gly Thr Gly Thr Gly Ser Ile Gln Tyr Thr Gly
        610                 615                 620

Thr Ser Met Ser Ala Pro Phe Ala Ser Gly Val Ala Ala Gln Val Leu
625                 630                 635                 640

Gln Ala His Gln Asp Tyr Ser Pro Ile Gln Ile Lys Ala Ala Met Met
                645                 650                 655

Asn Ser Ala Asp His Asp Leu His Asp Ala Asp Gly His Thr Tyr Ala
            660                 665                 670

Val Asp Arg Val Gly Ser Gly Arg Ile Asp Ala Lys Ala Ala Val Asp
        675                 680                 685

Thr Arg Val Leu Leu Tyr Asn Ala Asp Arg Pro Glu Gln Val Ser Gln
690                 695                 700

Thr Phe Gly Val Leu Glu Tyr Ala Ala Asp Ala Gly Gln Gln Ser Leu
705                 710                 715                 720

Ala Arg Glu Met Thr Val Glu Asn Phe Asp Ser Lys Ala His Thr Tyr
                725                 730                 735

Ser Ile Ser Tyr Ala Gly Ser Thr Asp Met Pro Gly Val Glu Phe Ser
            740                 745                 750

Met Pro Ser Ser Ile Thr Val Gln Pro Gly Glu Lys Lys Asn Phe Gln
        755                 760                 765

Val Lys Val Thr Ile Asp Pro Ala Arg Leu Glu Lys Thr Met Asp Pro
770                 775                 780

Ala Met Glu Lys Thr Gln Ser Ser Val Asp Val Asn Thr Gly Lys Thr
785                 790                 795                 800

Val Val Pro Glu Gln Ala Arg Gln Phe Ile Ala Ser Glu Ser Gly Arg
                805                 810                 815

Ile Lys Leu Thr Glu Gly Asp Gln Thr Leu Arg Val Pro Leu His Ala
            820                 825                 830

Ala Pro Lys Pro Val Ser Thr Met Lys Val Ala Gly Asn Asn Val Gln
        835                 840                 845

Val Pro Ala Gly Ser Ser Gln Thr Arg Val Thr Leu Glu Gly Thr Glu
850                 855                 860

Leu Asn Gln Gly Gly Tyr Arg Ser Leu Leu Gly Ala Phe Glu Trp Gly
865                 870                 875                 880

Ala Ser Val Asn Arg Val Asn Pro Ser Asn Leu Trp Val Ser Ser Asp
                885                 890                 895

Met Lys Ala Asn Leu Gln His Val Gly Ala Ala Ser Asn Ala Pro Ala
            900                 905                 910

Leu Lys Asp Ala Gly Lys Asp Pro Asn Glu Gly Thr Leu Ser Phe Gly
        915                 920                 925

Ile Ser Thr Trp Arg Asn Trp Asp Val Ile Ser Glu Glu Asn Thr Phe
930                 935                 940

Thr Val Asn Ile Asp Thr Asp Gly Asn Asn Arg Ala Asp Tyr Val Leu
945                 950                 955                 960

Lys Thr Asp Arg Ser Ala Gly Leu Asp Phe Pro Ile Val Arg Leu Leu
                965                 970                 975

Gly Tyr Lys Asn Gly Ser Leu Glu Gln Leu Ala Tyr Tyr Pro Leu Asn
            980                 985                 990

Gly Ala Trp Gly Asp Thr Asp Thr  Asn Met Met Asp Thr  Asn Thr Leu
```

```
            995                 1000                1005
Ile Met Ser Val Pro Leu Lys Asp Leu Gly Leu Thr Ala Glu Asn
    1010                1015                1020

Ala Pro Gln Ile Arg Tyr Ser Val Glu Ser Ile Thr Gln Tyr Glu
    1025                1030                1035

Trp Glu Asn Val Ser Gln Thr Asp Trp Ile Thr Tyr Ser Pro Phe
    1040                1045                1050

Ala Pro Lys Val Trp Phe Ser Gly Thr Glu Ser Ser Ile Pro Gly
    1055                1060                1065

Leu Phe Ala Asp Ala Pro Ala Thr Glu Leu Thr Leu His Arg Ala
    1070                1075                1080

Ser Asp Ala Gly Ser Ala Lys Ala Leu Phe Leu His Leu His Asn
    1085                1090                1095

Gly Thr Gly Asp Leu Ser Gly Ser Gln Gly Ala Ser Gly Glu Arg
    1100                1105                1110

Ala Gln Val Leu Pro Val Ser Glu Gln Ser Thr Glu Ser Pro Ser
    1115                1120                1125

Ala Pro Arg Phe Met Asp Val Lys Glu Gly Asp Met Phe Tyr Thr
    1130                1135                1140

Glu Ile Ala Trp Leu Ala Gln Arg Arg Ile Thr Thr Gly Tyr Pro
    1145                1150                1155

Asp Gly Ser Phe Arg Pro Ala Glu Asn Thr Ser Arg Ala Ala Met
    1160                1165                1170

Ala Ala Tyr Phe Tyr Arg Leu Ala Gly Ser Pro Gln Phe Thr Ala
    1175                1180                1185

Pro Ser Thr Pro Thr Phe Lys Asp Val Ala Pro Gly Asp Gln Phe
    1190                1195                1200

Tyr Lys Glu Ile Glu Trp Phe Ala Ala Gln Arg Leu Thr Thr Gly
    1205                1210                1215

Tyr Ala Asp Gly Thr Phe Arg Pro Gln Asp Ala Val Asn Arg Asp
    1220                1225                1230

Ala Met Ala Ala Phe Phe Tyr Arg Tyr Ala Gly Ser Pro Ala Phe
    1235                1240                1245

Thr Ala Pro Asp Lys Pro Thr Phe Lys Asp Val Ala Pro Asn Ser
    1250                1255                1260

Met Phe Tyr Arg Glu Ile Glu Trp Leu Ala Ala Gln Lys Val Thr
    1265                1270                1275

Thr Gly Trp Pro Asp Gln Thr Tyr Arg Pro Leu Glu Pro Ile His
    1280                1285                1290

Arg Asp Ala Met Ala Ala Phe Leu Tyr Arg Tyr Asn Gln Gly Val
    1295                1300                1305

Leu Lys Ala Glu Gly
    1310

<210> SEQ ID NO 73
<211> LENGTH: 1203
<212> TYPE: PRT
<213> ORGANISM: Rothia dentocariosa

<400> SEQUENCE: 73

Met Pro Pro Asn His Arg Arg Arg Gly Ala Leu Gly Cys Leu Ala Ala
1               5                   10                  15

Ala Thr Ser Ile Leu Leu Ala Leu Gly Thr Pro Ala Ser Ala Asp Ile
            20                  25                  30
```

```
Asn Pro Gly Gly Ile Asn Glu Asn Gly Gln Tyr Leu Ala Thr Pro Thr
             35                  40                  45

Pro Gln Ser Ser Asp Ala Leu Ser Pro Thr Met Lys Lys Ala Glu Gly
 50                  55                  60

Asp Val Leu Val Phe Val Lys Phe Lys Gly Gln Gly Ala Tyr Glu Gln
 65                  70                  75                  80

Thr Gln Pro Asp Glu Val Leu His Asn Lys Gln Glu Pro Val Lys Lys
                 85                  90                  95

Gln Gly Glu Ala Ile Ser Ile Lys Asp Gln Val Glu Asn Gln Ala Arg
                100                 105                 110

Gln Ala Ala Gln Asp Ser Gly Ala Glu Ile Arg Tyr Thr Val His Asn
                115                 120                 125

Thr Met Arg Gly Val Ala Leu His Gly Asn Ala Glu Lys Ile Arg Ser
        130                 135                 140

Leu Ala Gly Arg Asp Asp Val Glu Arg Ile Thr Pro Ile Val Ala Lys
145                 150                 155                 160

Lys Ser Met Asn Ala Tyr Ser Asp Ile Asp Ser Lys Ala Val Gln Ala
                165                 170                 175

Trp Ala Glu Ser Thr Gly Tyr Thr Gly Lys Gly Val Lys Ile Ala Val
                180                 185                 190

Val Asp Ser Gly Ile Asp Tyr Thr His Thr Asp Phe Gly Gly Pro Gly
                195                 200                 205

Thr Lys Glu Ala Tyr Glu Lys Ala Lys Thr Leu Thr Asp Leu Pro Asp
        210                 215                 220

Ala Gly Ser Gly Leu Ile Asp Arg Ser Lys Val Val Gly Gly Ile Asp
225                 230                 235                 240

Leu Val Gly Asp Asp Tyr Asn Ala Leu Asp Thr Gly Ser Ala Pro Lys
                245                 250                 255

Pro Asp Asn Asn Pro Leu Asp Cys Arg Pro Glu Gly Tyr Gly Thr Gly
                260                 265                 270

Gly His Gly Thr His Val Ala Gly Thr Ala Ala Gly Tyr Gly Val Asn
        275                 280                 285

Ala Asp Gly Ser Thr Phe Arg Gly Asp Tyr Ser Lys Leu Thr Glu Asn
        290                 295                 300

Asp Leu Lys Asn Met Lys Ile Gly Pro Gly Ser Ala Pro Glu Ala Gln
305                 310                 315                 320

Leu Leu Ser Ile Arg Val Phe Gly Cys Gln Gly Ser Ser Asn Val Val
                325                 330                 335

Met Gln Gly Leu Asp Arg Ala Leu Asp Pro Asn Glu Asp Gly Asp Phe
        340                 345                 350

Ser Asp Arg Ala Asn Ile Ile Asn Leu Ser Leu Gly Ser Glu Phe Ser
        355                 360                 365

Pro Ala Asp Asp Pro Asp Ser Ala Met Val Asp Ser Leu Ala Gln Gln
370                 375                 380

Gly Ile Leu Thr Val Thr Ala Ala Gly Asn Ala Asn Glu Phe Asn Gly
385                 390                 395                 400

Val Gly Asp Thr Tyr Ser Asp Ser Gly Ser Pro Ala Asn Ala Ala Ser
                405                 410                 415

Ser Ile Ser Val Ala Asn Ala Asn Gly Thr Met Ser Val Ser Asp Gln
                420                 425                 430

Leu Lys Ile Val Ser Pro Glu Asn Gly Ile Pro Leu Asp Phe Ile Asp
        435                 440                 445

Gly Ile Phe Arg Asp Phe Lys Phe Ile Asp Gly Asp Tyr Ser Leu Asn
```

-continued

```
            450                 455                 460
Phe Pro Leu Asp Lys Ala Pro Ala Asp Lys Arg Thr Gly Tyr Val Thr
465                 470                 475                 480

Leu Ala Pro Glu Arg Asn His Asp Gly Cys Lys Pro Phe Thr Pro Glu
                485                 490                 495

Glu Ala Glu Lys Ile Asn Gly Lys Trp Val Met Leu Asp Trp Glu Val
            500                 505                 510

Asp Tyr Thr Tyr Lys Val Asn Cys Ser Ser Ala Glu Arg Phe Asp His
            515                 520                 525

Val Ala Gln Ala Gly Thr Gly Val Leu Val Leu Lys Asp Tyr
        530                 535                 540

Pro Ala Gln Gln Gly Phe Gly Gly Asn Ala Thr Ile Pro Gly Phe Arg
545                 550                 555                 560

Ile Asn Thr Ala Phe Ala Ala Asp Ile Lys Pro Tyr Val Glu Ala Gly
                565                 570                 575

Thr Phe Lys Val Glu Ala Asn Glu Ala Tyr Lys Lys Ala Thr His Ile
            580                 585                 590

Pro Thr Arg Leu Glu Phe Gly Leu Asn Ser Met Ser Ser Arg Gly Gln
            595                 600                 605

His Gly Thr Glu Gly Phe Ile Lys Pro Asp Val Ala Ala Pro Gly Val
        610                 615                 620

Asp Ile Phe Ser Ala Ser Val Gly Gln Gly Thr Glu Gly Val Tyr Asn
625                 630                 635                 640

Thr Gly Thr Ser Met Ala Ala Pro His Val Ser Gly Ile Ala Ala Gln
                645                 650                 655

Val Met Gln Ala His Pro Asp Tyr Thr Pro Ala Met Val Lys Ala Ala
            660                 665                 670

Ile Met Asn Ser Ala Asp Thr Asn Ile Thr Asn Ser Gly Tyr Lys
            675                 680                 685

Tyr Ala Val Asp Arg Met Gly Ser Gly Phe Val Asn Ala Lys Lys Ala
        690                 695                 700

Val Asn Ala Lys Val Leu Val Tyr Asn Glu Glu Thr Pro Glu Arg Val
705                 710                 715                 720

Ser Leu Ser Phe Gly Val Leu Glu Tyr Pro Leu Asp Gly Glu Asp His
                725                 730                 735

Thr Val Thr Arg Asp Ile Val Val Arg Asn Met Asp Ser Val Ala His
            740                 745                 750

Thr Tyr Glu Leu Ser Tyr Gln Tyr Gly Pro Glu Ile Pro Gly Ser Arg
            755                 760                 765

Pro Glu Val Pro Pro Leu Val Thr Val Glu Pro Gly Glu Thr Val Lys
        770                 775                 780

Val Pro Ile Thr Phe Ser Thr Tyr Thr Pro Phe Leu Glu Lys Thr Ile
785                 790                 795                 800

Asp Pro Ala Leu Glu Lys Glu Gln Thr Ala Met Ala Tyr Val Asn Gly
                805                 810                 815

Gln Tyr Gln Pro Ile Ile Ser Gly Lys Arg Gln Tyr Ile Ala Ser Val
            820                 825                 830

Ser Gly Arg Ile Leu Leu Lys Asp Ala Asn Gln Asp Asn Gly Glu Glu
            835                 840                 845

Leu Ile Arg Leu Pro Val His Ala Ala Pro Lys Pro Ile Ser Thr Met
        850                 855                 860

Lys Val Gln Gly Ser Glu Ile Gln Phe Glu Asn Gly Lys Ala Thr Glu
865                 870                 875                 880
```

Thr Thr Val Lys Leu Ala Gly Gln Asp Val Asn Gln Gly Gly Tyr Arg
                885                 890                 895

Ser Met Met Gly Ala Phe Glu Leu Gly Ala Ala Ser Pro Arg Ile Pro
            900                 905                 910

Thr Glu Asn Leu Asp Leu Pro Ser Ser Gln Ser Met Asp Leu Gln Tyr
            915                 920                 925

Val Gly Ala Ala Ser Asp Ala Pro Ala Leu Lys Ala Ala Gly Gln Asn
        930                 935                 940

Pro Asn Asp Gly Lys Ile Tyr Phe Gly Ile Ser Thr Trp Gly Ile Trp
945                 950                 955                 960

Asp Ser Met His Pro Gly Arg Gln Leu Gln Val Thr Leu Asp Thr Asn
                965                 970                 975

Arg Asp Gly Lys Pro Asp Tyr Asn Leu Glu Val Gly Pro Glu Lys Gly
            980                 985                 990

Leu Asp Tyr Pro Leu Val Lys Val Trp Lys Ala Asn Gly Asp Thr Trp
            995                 1000                1005

Glu Ile Thr Asn Arg Tyr Pro Leu Asn Gly Ala Trp Gly Asp Thr
    1010                1015                1020

Asp Thr Asn Ile Met Asp Thr Asn Val Met Val Leu Gly Val Pro
    1025                1030                1035

Leu Lys Asp Leu Gly Leu Thr Ala Asp Thr Ala Ser Ser Ile Asp
    1040                1045                1050

Tyr Ala Val Ser Thr Asn Thr Trp Ser Asn Ala Lys Ala Gly Gly
    1055                1060                1065

Asp Tyr Val Asp Ala Thr Glu Lys Ile Ser Phe Asn Pro Phe Ala
    1070                1075                1080

Pro Lys Val Trp Phe Glu Gly Glu Ser Ala Gly Val Pro Gly Leu
    1085                1090                1095

Phe Ala Asp Arg Asn Gly Gly Glu Val Lys Val His Arg Val Glu
    1100                1105                1110

Gly Glu Lys Pro Ser Ala Leu Phe Leu His Leu His Asn Gly Thr
    1115                1120                1125

Gly Asn Leu Ser Gly Gln Asn Gly Ala Ala Gly Glu Arg Ala Gln
    1130                1135                1140

Val Val Pro Leu Ser Glu Gln Gln Gln Ser Ser Leu Pro Ser Pro
    1145                1150                1155

Ser Glu Pro Thr Asp Ser Pro Lys Asp Ser Ser Leu Pro Gly Pro
    1160                1165                1170

Ser Glu Pro Thr Asp Ser Pro Lys Asp Ser Ser Leu Pro Gly Pro
    1175                1180                1185

Ser Glu Pro Thr Asp Ser Pro Lys Thr Asp Thr Ser Leu Pro Lys
    1190                1195                1200

<210> SEQ ID NO 74
<211> LENGTH: 1203
<212> TYPE: PRT
<213> ORGANISM: Rothia dentocariosa

<400> SEQUENCE: 74

Met Pro Pro Asn His Arg Arg Arg Gly Ala Leu Gly Cys Leu Ala Ala
1               5                   10                  15

Ala Thr Ser Ile Leu Leu Ala Leu Gly Thr Pro Ala Ser Ala Asp Ile
            20                  25                  30

Asn Pro Gly Gly Ile Asn Glu Asn Gly Gln Tyr Leu Ala Thr Pro Thr

```
            35                  40                  45
Pro Gln Ser Ser Asp Ala Leu Ser Pro Thr Met Lys Lys Ala Glu Gly
            50                  55                  60
Asp Val Leu Val Phe Val Lys Phe Lys Gly Gln Gly Ala Tyr Glu Gln
 65                  70                  75                  80
Thr Gln Pro Asp Glu Val Leu His Asn Lys Gln Glu Pro Val Lys Lys
                85                  90                  95
Gln Gly Glu Ala Ile Ser Ile Lys Asp Gln Val Glu Asn Gln Ala Arg
            100                 105                 110
Gln Ala Ala Gln Asp Ser Gly Ala Glu Ile Arg Tyr Thr Val His Asn
            115                 120                 125
Thr Met Arg Gly Val Ala Leu His Gly Asn Ala Glu Lys Ile Arg Ser
            130                 135                 140
Leu Ala Gly Arg Asp Asp Val Glu Arg Ile Thr Pro Ile Val Ala Lys
145                 150                 155                 160
Lys Ser Met Asn Ala Tyr Ser Asp Ile Asp Ser Lys Ala Val Gln Ala
                165                 170                 175
Trp Ala Glu Ser Thr Gly Tyr Thr Gly Lys Gly Val Lys Ile Ala Val
            180                 185                 190
Val Asp Ser Gly Ile Asp Tyr Thr His Thr Asp Phe Gly Gly Pro Gly
            195                 200                 205
Thr Lys Glu Ala Tyr Glu Lys Ala Lys Thr Leu Thr Asp Leu Pro Asp
            210                 215                 220
Ala Gly Ser Gly Leu Ile Asp Arg Ser Lys Val Val Gly Gly Ile Asp
225                 230                 235                 240
Leu Val Gly Asp Asp Tyr Asn Ala Leu Asp Thr Gly Ser Ala Pro Lys
                245                 250                 255
Pro Asp Asn Asn Pro Leu Asp Cys Arg Pro Glu Gly Tyr Gly Thr Gly
            260                 265                 270
Gly His Gly Thr His Val Ala Gly Thr Ala Ala Gly Tyr Gly Val Asn
            275                 280                 285
Ala Asp Gly Ser Thr Phe Arg Gly Asp Tyr Ser Lys Leu Thr Glu Asn
            290                 295                 300
Asp Leu Lys Asn Met Lys Ile Gly Pro Gly Ser Ala Pro Glu Ala Gln
305                 310                 315                 320
Leu Leu Ser Ile Arg Val Phe Gly Cys Gln Gly Ser Ser Asn Val Val
                325                 330                 335
Met Gln Gly Leu Asp Arg Ala Leu Asp Pro Asn Glu Asp Gly Asp Phe
            340                 345                 350
Ser Asp Arg Ala Asn Ile Ile Asn Leu Ser Leu Gly Ser Glu Phe Ser
            355                 360                 365
Pro Ala Asp Asp Pro Asp Ser Ala Met Val Asp Ser Leu Ala Gln Gln
            370                 375                 380
Gly Ile Leu Thr Val Thr Ala Ala Gly Asn Ala Asn Glu Phe Asn Gly
385                 390                 395                 400
Val Gly Asp Thr Tyr Ser Asp Ser Gly Ser Pro Ala Asn Ala Ala Ser
                405                 410                 415
Ser Ile Ser Val Ala Asn Ala Asn Gly Thr Met Ser Val Ser Asp Gln
                420                 425                 430
Leu Lys Ile Val Ser Pro Glu Asn Gly Ile Pro Leu Asp Phe Ile Asp
            435                 440                 445
Gly Ile Phe Arg Asp Phe Lys Phe Ile Asp Gly Asp Tyr Ser Leu Asn
            450                 455                 460
```

```
Phe Pro Leu Asp Lys Ala Pro Ala Asp Lys Arg Thr Gly Tyr Val Thr
465                 470                 475                 480

Leu Ala Pro Glu Arg Asn His Asp Gly Cys Lys Pro Phe Thr Pro Glu
            485                 490                 495

Glu Ala Glu Lys Ile Asn Gly Lys Trp Val Met Leu Asp Trp Glu Val
        500                 505                 510

Asp Tyr Thr Tyr Lys Val Asn Cys Ser Ser Ala Glu Arg Phe Asp His
    515                 520                 525

Val Ala Gln Ala Gly Thr Gly Val Leu Leu Val Leu Lys Asp Tyr
530                 535                 540

Pro Ala Gln Gln Gly Phe Gly Gly Asn Ala Thr Ile Pro Gly Phe Arg
545                 550                 555                 560

Ile Asn Thr Ala Phe Ala Ala Asp Ile Lys Pro Tyr Val Glu Ala Gly
                565                 570                 575

Thr Phe Lys Val Glu Ala Asn Glu Ala Tyr Lys Lys Ala Thr His Ile
            580                 585                 590

Pro Thr Arg Leu Glu Phe Gly Leu Asn Ser Met Ser Ser Arg Gly Gln
        595                 600                 605

His Gly Thr Glu Gly Phe Ile Lys Pro Asp Val Ala Ala Pro Gly Val
610                 615                 620

Asp Ile Phe Ser Ala Ser Val Gly Gln Gly Thr Glu Gly Val Tyr Asn
625                 630                 635                 640

Thr Gly Thr Ser Met Ala Ala Pro His Val Ser Gly Ile Ala Ala Gln
                645                 650                 655

Val Met Gln Ala His Pro Asp Tyr Thr Pro Ala Met Val Lys Ala Ala
            660                 665                 670

Ile Met Asn Ser Ala Asp Thr Asn Ile Thr Asn Asn Ser Gly Tyr Lys
        675                 680                 685

Tyr Ala Val Asp Arg Met Gly Ser Gly Phe Val Asn Ala Lys Lys Ala
690                 695                 700

Val Asn Ala Lys Val Leu Val Tyr Asn Glu Glu Thr Pro Glu Arg Val
705                 710                 715                 720

Ser Leu Ser Phe Gly Val Leu Glu Tyr Pro Leu Asp Gly Glu Asp His
                725                 730                 735

Thr Val Thr Arg Asp Ile Val Val Arg Asn Met Asp Ser Val Ala His
            740                 745                 750

Thr Tyr Glu Leu Ser Tyr Gln Tyr Gly Pro Glu Ile Pro Gly Ser Arg
        755                 760                 765

Pro Glu Val Pro Pro Leu Val Thr Val Glu Pro Gly Glu Thr Val Lys
770                 775                 780

Val Pro Ile Thr Phe Ser Thr Tyr Thr Pro Phe Leu Glu Lys Thr Ile
785                 790                 795                 800

Asp Pro Ala Leu Glu Lys Glu Gln Thr Ala Met Ala Tyr Val Asn Gly
                805                 810                 815

Gln Tyr Gln Pro Ile Ile Ser Gly Lys Arg Gln Tyr Ile Ala Ser Val
            820                 825                 830

Ser Gly Arg Ile Leu Leu Lys Asp Ala Asn Gln Asp Asn Gly Glu Glu
        835                 840                 845

Leu Ile Arg Leu Pro Val His Ala Pro Lys Pro Ile Ser Thr Met
850                 855                 860

Lys Val Gln Gly Ser Glu Ile Gln Phe Glu Asn Gly Lys Ala Thr Glu
865                 870                 875                 880
```

Thr Thr Val Lys Leu Ala Gly Gln Asp Val Asn Gln Gly Gly Tyr Arg
            885                 890                 895

Ser Met Met Gly Ala Phe Glu Leu Gly Ala Ala Ser Pro Arg Ile Pro
        900                 905                 910

Thr Glu Asn Leu Asp Leu Pro Ser Ser Gln Ser Met Asp Leu Gln Tyr
            915                 920                 925

Val Gly Ala Ala Ser Asp Ala Pro Leu Lys Ala Ala Gly Gln Asn
        930                 935                 940

Pro Asn Asp Gly Lys Ile Tyr Phe Gly Ile Ser Thr Trp Gly Ile Trp
945                 950                 955                 960

Asp Ser Met His Pro Gly Arg Gln Leu Gln Val Thr Leu Asp Thr Asn
            965                 970                 975

Arg Asp Gly Lys Pro Asp Tyr Asn Leu Glu Val Gly Pro Glu Lys Gly
            980                 985                 990

Leu Asp Tyr Pro Leu Val Lys Val Trp Lys Ala Asn Gly Asp Thr Trp
        995                 1000                1005

Glu Ile Thr Asn Arg Tyr Pro Leu Asn Gly Ala Trp Gly Asp Thr
        1010                1015                1020

Asp Thr Asn Ile Met Asp Thr Asn Val Met Val Leu Gly Val Pro
        1025                1030                1035

Leu Lys Asp Leu Gly Leu Thr Ala Asp Thr Ala Ser Ser Ile Asp
        1040                1045                1050

Tyr Ala Val Ser Thr Asn Thr Trp Ser Asn Ala Lys Ala Gly Gly
        1055                1060                1065

Asp Tyr Val Asp Ala Thr Glu Lys Ile Ser Phe Asn Pro Phe Ala
        1070                1075                1080

Pro Lys Val Trp Phe Glu Gly Glu Ser Ala Gly Val Pro Gly Leu
        1085                1090                1095

Phe Ala Asp Arg Asn Gly Gly Glu Val Lys Val His Arg Val Glu
        1100                1105                1110

Gly Glu Lys Pro Ser Ala Leu Phe Leu His Leu His Asn Gly Thr
        1115                1120                1125

Gly Asn Leu Ser Gly Gln Asn Gly Ala Ala Gly Glu Arg Ala Gln
        1130                1135                1140

Val Val Pro Leu Ser Glu Gln Gln Ser Ser Leu Pro Ser Pro
        1145                1150                1155

Ser Glu Pro Thr Asp Ser Pro Lys Asp Ser Ser Leu Pro Gly Pro
        1160                1165                1170

Ser Glu Pro Thr Asp Ser Pro Lys Asp Ser Ser Leu Pro Gly Pro
        1175                1180                1185

Ser Glu Pro Thr Asp Ser Pro Lys Thr Asp Thr Ser Leu Pro Lys
        1190                1195                1200

<210> SEQ ID NO 75
<211> LENGTH: 1203
<212> TYPE: PRT
<213> ORGANISM: Rothia dentocariosa

<400> SEQUENCE: 75

Met Pro Pro Asn His Arg Arg Arg Gly Ala Leu Gly Cys Leu Ala Ala
1               5                   10                  15

Ala Thr Ser Ile Leu Leu Ala Leu Gly Thr Pro Ala Ser Ala Asp Ile
            20                  25                  30

Asn Pro Gly Gly Thr Asn Glu Asn Gly Gln Tyr Val Ala Asn Pro Ala
        35                  40                  45

```
Pro Gln Asn Ser Asp Ala Leu Ser Pro Thr Met Lys Lys Ala Glu Gly
     50                  55                  60
Asp Val Leu Val Phe Val Lys Phe Lys Gly Gln Gly Ala Tyr Glu Gln
 65                  70                  75                  80
Thr Gln Pro Asn Glu Val Leu His Asn Lys Gln Glu Pro Val Lys Lys
                 85                  90                  95
Gln Gly Glu Ala Thr Ser Ile Lys Asp Gln Val Glu Asn Gln Ala Arg
            100                 105                 110
Gln Ala Ala Gln Asp Ser Gly Ala Glu Ile Arg Tyr Thr Val His Asn
        115                 120                 125
Thr Met Arg Gly Ala Ala Leu His Gly Asp Ala Glu Lys Ile Arg Ser
    130                 135                 140
Leu Ala Gly Arg Asp Asp Val Glu Arg Ile Thr Pro Ile Val Ala Lys
145                 150                 155                 160
Lys Ser Met Asn Ala Tyr Ser Asp Ile Asp Ser Lys Ala Val Gln Ala
                165                 170                 175
Trp Ala Glu Ser Thr Gly Tyr Thr Gly Lys Gly Val Lys Ile Ala Val
            180                 185                 190
Val Asp Ser Gly Ile Asp Tyr Thr His Thr Asp Phe Gly Gly Pro Gly
        195                 200                 205
Thr Lys Glu Ala Tyr Glu Lys Ala Lys Thr Leu Thr Asp Leu Pro Asp
    210                 215                 220
Ala Gly Ser Gly Leu Ile Asp Arg Ser Lys Val Val Gly Ile Asp
225                 230                 235                 240
Leu Val Gly Asp Gly Tyr Asn Ala Leu Asp Ala Gly Ser Thr Pro Lys
                245                 250                 255
Pro Asp Ser Asn Pro Leu Asp Cys Arg Pro Glu Gly Tyr Gly Thr Gly
            260                 265                 270
Gly His Gly Thr His Val Ala Gly Thr Ala Ala Gly Tyr Gly Val Asn
        275                 280                 285
Ala Asp Gly Ser Thr Phe Arg Gly Asp Tyr Ser Lys Leu Thr Glu Asn
    290                 295                 300
Asp Leu Lys Asn Met Lys Ile Gly Pro Gly Ser Ala Pro Glu Ala Gln
305                 310                 315                 320
Leu Leu Ser Ile Arg Val Phe Gly Cys Gln Gly Ser Ser Asn Val Val
                325                 330                 335
Met Gln Gly Leu Asp Arg Ala Leu Asp Pro Asn Glu Asp Gly Asp Phe
            340                 345                 350
Ser Asp Arg Ala Asn Ile Ile Asn Leu Ser Leu Gly Ser Glu Phe Ser
    355                 360                 365
Pro Ala Asp Asp Pro Asp Ser Ala Met Val Asp Ala Leu Ala Gln Gln
370                 375                 380
Gly Ile Leu Thr Val Thr Ala Ala Gly Asn Ala Asn Glu Phe Asn Gly
385                 390                 395                 400
Val Gly Asp Thr Tyr Ser Asp Ser Gly Ser Pro Ala Asn Ala Ala Ser
                405                 410                 415
Ser Ile Ser Val Ala Asn Ala Asn Gly Ala Met Ser Val Ser Asp Gln
            420                 425                 430
Leu Lys Ile Val Ser Pro Glu Asn Gly Ile Pro Leu Asp Phe Ile Asp
    435                 440                 445
Gly Thr Phe Arg Asp Phe Lys Phe Ile Asp Gly Asp Tyr Ser Leu Asn
450                 455                 460
```

-continued

```
Phe Pro Leu Asp Lys Ala Pro Ala Asp Lys Leu Thr Gly Tyr Val Thr
465                 470                 475                 480

Leu Ala Pro Glu Arg Asn Arg Asp Gly Cys Lys Pro Phe Thr Pro Glu
            485                 490                 495

Glu Ala Glu Lys Ile Lys Gly Lys Trp Val Met Leu Asp Trp Glu Val
            500                 505                 510

Asp Tyr Ser Tyr Lys Val Glu Cys Thr Ser Ala Glu Arg Phe Asp His
            515                 520                 525

Val Ala Gln Ala Gly Gly Thr Gly Val Leu Leu Val Leu Lys Asp Tyr
            530                 535                 540

Pro Ala Gln Gln Gly Phe Gly Gly Asn Ala Thr Ile Pro Gly Phe Arg
545                 550                 555                 560

Ile Asn Thr Ala Phe Ala Ala Asp Ile Lys Pro Tyr Val Glu Ala Gly
            565                 570                 575

Thr Phe Lys Val Glu Ala Asn Glu Ala Tyr Lys Lys Ala Thr His Ile
            580                 585                 590

Pro Thr Arg Leu Asp Phe Gly Leu Asn Ser Met Ser Ser Arg Gly Gln
595                 600                 605

His Gly Thr Glu Gly Phe Ile Lys Pro Asp Val Ala Ala Pro Gly Val
610                 615                 620

Asp Ile Phe Ser Ala Ser Val Gly Gln Gly Thr Glu Gly Val Tyr Asn
625                 630                 635                 640

Thr Gly Thr Ser Met Ala Ala Pro His Val Ser Gly Ile Ala Ala Gln
            645                 650                 655

Val Met Gln Ala His Pro Asp Tyr Thr Pro Ala Met Val Lys Ala Ala
            660                 665                 670

Ile Met Asn Ser Ala Asp Thr Asn Leu Thr Asn Asn Ala Gly Ser Lys
            675                 680                 685

Tyr Ala Val Asp Arg Met Gly Ser Gly Phe Val Asn Ala Lys Lys Ala
690                 695                 700

Val Asn Ala Lys Val Leu Val Tyr Asp Glu Glu Asn Pro Glu Arg Val
705                 710                 715                 720

Ser Leu Ser Phe Gly Val Leu Glu Tyr Pro Leu Asp Gly Glu Gly His
            725                 730                 735

Thr Val Thr Arg Asn Ile Val Arg Asn Met Asp Ser Val Ala His
            740                 745                 750

Thr Tyr Glu Leu Ser Tyr Gln Tyr Gly Pro Glu Ile Pro Gly Ser Arg
            755                 760                 765

Pro Glu Val Pro Pro Leu Val Thr Val Glu Pro Gly Glu Thr Val Lys
770                 775                 780

Val Pro Ile Thr Phe Ser Thr Tyr Thr Pro Phe Leu Glu Lys Thr Ile
785                 790                 795                 800

Asp Pro Ala Leu Glu Lys Glu Gln Thr Ala Met Ala Tyr Val Asn Gly
            805                 810                 815

Gln Tyr Gln Pro Ile Ile Ser Gly Lys Arg Gln Tyr Ile Ala Ser Val
            820                 825                 830

Ser Gly Arg Ile Ile Phe Glu Asp Ala Asn Gln Asp Asp Gly Glu Glu
            835                 840                 845

Leu Ile Arg Leu Pro Val His Ala Ala Pro Lys Pro Ile Ser Thr Met
850                 855                 860

Lys Val Gln Gly Ser Glu Ile Gln Phe Glu Asn Gly Lys Ala Thr Glu
865                 870                 875                 880

Thr Thr Val Lys Leu Ala Gly Gln Asp Val Asn Gln Gly Gly Tyr Arg
```

```
                    885                 890                 895
Ser Met Met Gly Ala Phe Glu Leu Gly Ala Ala Ser Pro Arg Ile Pro
                900                 905                 910

Thr Glu Asn Leu Asp Leu Pro Ser Ser Gln Ser Met Asp Leu Gln Tyr
            915                 920                 925

Val Gly Ala Ala Ser Asp Ala Pro Ala Leu Lys Ala Ala Gly Gln Asn
        930                 935                 940

Pro Asn Asp Gly Lys Ile Tyr Phe Gly Ile Ser Thr Trp Gly Ile Trp
945                 950                 955                 960

Asp Ser Met His Pro Gly Arg Gln Leu Gln Val Thr Leu Asp Thr Asn
                965                 970                 975

Arg Asp Gly Lys Pro Asp Tyr Asn Leu Glu Val Gly Pro Glu Lys Gly
            980                 985                 990

Leu Asp Tyr Pro Leu Val Lys Val Trp Lys Ala Asn Gly Asp Thr Trp
        995                 1000                1005

Glu Ile Thr Asn Arg Tyr Pro Leu Asn Gly Ala Trp Gly Asp Thr
    1010                1015                1020

Asp Thr Asn Ile Met Asp Thr Asn Val Met Val Leu Gly Val Pro
    1025                1030                1035

Leu Lys Asp Leu Gly Leu Thr Ala Asp Thr Ala Ser Ser Ile Asp
    1040                1045                1050

Tyr Ala Val Ser Thr Asn Thr Trp Ser Asn Ala Lys Ala Gly Gly
    1055                1060                1065

Asp Tyr Val Asp Ala Thr Glu Lys Ile Ser Phe Asn Pro Phe Ala
    1070                1075                1080

Pro Lys Val Trp Phe Glu Gly Glu Ser Ala Gly Val Pro Gly Leu
    1085                1090                1095

Phe Ala Asp Arg Asn Gly Gly Glu Val Lys Val His Arg Val Glu
    1100                1105                1110

Gly Glu Lys Pro Ser Ala Leu Phe Leu His Leu His Asn Gly Thr
    1115                1120                1125

Gly Asp Leu Ser Gly Gln Asn Gly Ala Ala Gly Glu Arg Ala Gln
    1130                1135                1140

Val Val Pro Leu Ser Glu Gln Gln Gln Ser Ser Leu Pro Ser Pro
    1145                1150                1155

Ser Glu Pro Thr Glu Ser Pro Lys Asp Ser Ser Leu Pro Gly Pro
    1160                1165                1170

Ser Glu Pro Thr Glu Ser Pro Lys Asp Ser Ser Leu Pro Gly Pro
    1175                1180                1185

Ser Glu Pro Thr Glu Ser Pro Lys Thr Asp Thr Ser Leu Pro Lys
    1190                1195                1200

<210> SEQ ID NO 76
<211> LENGTH: 1203
<212> TYPE: PRT
<213> ORGANISM: Rothia dentocariosa

<400> SEQUENCE: 76

Met Pro Pro Asn His Arg Arg Arg Gly Ala Leu Gly Cys Leu Ala Ala
1               5                   10                  15

Ala Thr Ser Ile Leu Leu Ala Leu Gly Thr Pro Ala Ser Ala Asp Ile
            20                  25                  30

Asn Pro Gly Gly Thr Asn Glu Asn Gly Gln Tyr Val Ala Asn Pro Ala
        35                  40                  45
```

```
Pro Gln Asn Ser Asp Ala Leu Ser Pro Thr Met Lys Lys Ala Glu Gly
    50                  55                  60

Asp Val Leu Val Phe Val Lys Phe Lys Gly Gln Gly Ala Tyr Glu Gln
65                  70                  75                  80

Thr Gln Pro Asn Glu Val Leu His Asn Lys Gln Glu Pro Val Lys Lys
                85                  90                  95

Gln Gly Glu Ala Thr Ser Ile Lys Asp Gln Val Glu Asn Gln Ala Arg
                100                 105                 110

Gln Ala Ala Gln Asp Ser Gly Ala Glu Ile Arg Tyr Thr Val His Asn
            115                 120                 125

Thr Met Arg Gly Ala Ala Leu His Gly Asp Ala Glu Lys Ile Arg Ser
    130                 135                 140

Leu Ala Gly Arg Asp Asp Val Glu Arg Ile Thr Pro Ile Val Ala Lys
145                 150                 155                 160

Lys Ser Met Asn Ala Tyr Ser Asp Ile Asp Ser Lys Ala Val Gln Ala
                165                 170                 175

Trp Ala Glu Ser Thr Gly Tyr Thr Gly Lys Gly Val Lys Ile Ala Val
            180                 185                 190

Val Asp Ser Gly Ile Asp Tyr Thr His Thr Asp Phe Gly Gly Pro Gly
            195                 200                 205

Thr Lys Glu Ala Tyr Glu Lys Ala Lys Thr Leu Thr Asp Leu Pro Asp
    210                 215                 220

Ala Gly Ser Gly Leu Ile Asp Arg Ser Lys Val Val Gly Gly Ile Asp
225                 230                 235                 240

Leu Val Gly Asp Gly Tyr Asn Ala Leu Asp Ala Gly Ser Thr Pro Lys
                245                 250                 255

Pro Asp Ser Asn Pro Leu Asp Cys Arg Pro Glu Gly Tyr Gly Thr Gly
                260                 265                 270

Gly His Gly Thr His Val Ala Gly Thr Ala Ala Gly Tyr Gly Val Asn
            275                 280                 285

Ala Asp Gly Ser Thr Phe Arg Gly Asp Tyr Ser Lys Leu Thr Glu Asn
    290                 295                 300

Asp Leu Lys Asn Met Lys Ile Gly Pro Gly Ser Ala Pro Glu Ala Gln
305                 310                 315                 320

Leu Leu Ser Ile Arg Val Phe Gly Cys Gln Gly Ser Ser Asn Val Val
                325                 330                 335

Met Gln Gly Leu Asp Arg Ala Leu Asp Pro Asn Glu Asp Gly Asp Phe
            340                 345                 350

Ser Asp Arg Ala Asn Ile Ile Asn Leu Ser Leu Gly Ser Glu Phe Ser
    355                 360                 365

Pro Ala Asp Asp Pro Asp Ser Ala Met Val Asp Ala Leu Ala Gln Gln
370                 375                 380

Gly Ile Leu Thr Val Thr Ala Ala Gly Asn Ala Asn Glu Phe Asn Gly
385                 390                 395                 400

Val Gly Asp Thr Tyr Ser Asp Ser Gly Ser Pro Ala Asn Ala Ala Ser
                405                 410                 415

Ser Ile Ser Val Ala Asn Ala Asn Gly Ala Met Ser Val Ser Asp Gln
                420                 425                 430

Leu Lys Ile Val Ser Pro Glu Asn Gly Ile Pro Leu Asp Phe Ile Asp
            435                 440                 445

Gly Thr Phe Arg Asp Phe Lys Phe Ile Asp Gly Asp Tyr Ser Leu Asn
    450                 455                 460

Phe Pro Leu Asp Lys Ala Pro Ala Asp Lys Leu Thr Gly Tyr Val Thr
```

```
                465                 470                 475                 480
Leu Ala Pro Glu Arg Asn Arg Asp Gly Cys Lys Pro Phe Thr Pro Glu
                    485                 490                 495
Glu Ala Glu Lys Ile Lys Gly Lys Trp Val Met Leu Asp Trp Glu Val
                    500                 505                 510
Asp Tyr Ser Tyr Lys Val Glu Cys Thr Ser Ala Glu Arg Phe Asp His
                    515                 520                 525
Val Ala Gln Ala Gly Gly Thr Gly Val Leu Leu Val Leu Lys Asp Tyr
                    530                 535                 540
Pro Ala Gln Gln Gly Phe Gly Gly Asn Ala Thr Ile Pro Gly Phe Arg
545                 550                 555                 560
Ile Asn Thr Ala Phe Ala Ala Asp Ile Lys Pro Tyr Val Glu Ala Gly
                    565                 570                 575
Thr Phe Lys Val Glu Ala Asn Glu Ala Tyr Lys Lys Ala Thr His Ile
                    580                 585                 590
Pro Thr Arg Leu Asp Phe Gly Leu Asn Ser Met Ser Ser Arg Gly Gln
                    595                 600                 605
His Gly Thr Glu Gly Phe Ile Lys Pro Asp Val Ala Ala Pro Gly Val
    610                 615                 620
Asp Ile Phe Ser Ala Ser Val Gly Gln Gly Thr Glu Gly Val Tyr Asn
625                 630                 635                 640
Thr Gly Thr Ser Met Ala Ala Pro His Val Ser Gly Ile Ala Ala Gln
                    645                 650                 655
Val Met Gln Ala His Pro Asp Tyr Thr Pro Ala Met Val Lys Ala Ala
                    660                 665                 670
Ile Met Asn Ser Ala Asp Thr Asn Leu Thr Asn Asn Ala Gly Ser Lys
                    675                 680                 685
Tyr Ala Val Asp Arg Met Gly Ser Gly Phe Val Asn Ala Lys Lys Ala
                    690                 695                 700
Val Asn Ala Lys Val Leu Val Tyr Asp Glu Glu Asn Pro Glu Arg Val
705                 710                 715                 720
Ser Leu Ser Phe Gly Val Leu Glu Tyr Pro Leu Asp Gly Glu Gly His
                    725                 730                 735
Thr Val Thr Arg Asn Ile Val Val Arg Asn Met Asp Ser Val Ala His
                    740                 745                 750
Thr Tyr Glu Leu Ser Tyr Gln Tyr Gly Pro Glu Ile Pro Gly Ser Arg
                    755                 760                 765
Pro Glu Val Pro Pro Leu Val Thr Val Glu Pro Gly Glu Thr Val Lys
                    770                 775                 780
Val Pro Ile Thr Phe Ser Thr Tyr Thr Pro Phe Leu Glu Lys Thr Ile
785                 790                 795                 800
Asp Pro Ala Leu Glu Lys Glu Gln Thr Ala Met Ala Tyr Val Asn Gly
                    805                 810                 815
Gln Tyr Gln Pro Ile Ile Ser Gly Lys Arg Gln Tyr Ile Ala Ser Val
                    820                 825                 830
Ser Gly Arg Ile Ile Phe Glu Asp Ala Asn Gln Asp Asp Gly Glu Glu
                    835                 840                 845
Leu Ile Arg Leu Pro Val His Ala Ala Pro Lys Pro Ile Ser Thr Met
                    850                 855                 860
Lys Val Gln Gly Ser Glu Ile Gln Phe Glu Asn Gly Lys Ala Thr Glu
865                 870                 875                 880
Thr Thr Val Lys Leu Ala Gly Gln Asp Val Asn Gln Gly Gly Tyr Arg
                    885                 890                 895
```

```
Ser Met Met Gly Ala Phe Glu Leu Gly Ala Ala Ser Pro Arg Ile Pro
                900                 905                 910

Thr Glu Asn Leu Asp Leu Pro Ser Gln Ser Met Asp Leu Gln Tyr
            915                 920                 925

Val Gly Ala Ala Ser Asp Ala Pro Ala Leu Lys Ala Ala Gly Gln Asn
            930                 935                 940

Pro Asn Asp Gly Lys Ile Tyr Phe Gly Ile Ser Thr Trp Gly Ile Trp
945                 950                 955                 960

Asp Ser Met His Pro Gly Arg Gln Leu Gln Val Thr Leu Asp Thr Asn
                965                 970                 975

Arg Asp Gly Lys Pro Asp Tyr Asn Leu Glu Val Gly Pro Glu Lys Gly
            980                 985                 990

Leu Asp Tyr Pro Leu Val Lys Val Trp Lys Ala Asn Gly Asp Thr Trp
            995                 1000                1005

Glu Ile Thr Asn Arg Tyr Pro Leu Asn Gly Ala Trp Gly Asp Thr
    1010                1015                1020

Asp Thr Asn Ile Met Asp Thr Asn Val Met Val Leu Gly Val Pro
    1025                1030                1035

Leu Lys Asp Leu Gly Leu Thr Ala Asp Thr Ala Ser Ser Ile Asp
    1040                1045                1050

Tyr Ala Val Ser Thr Asn Thr Trp Ser Asn Ala Lys Ala Gly Gly
    1055                1060                1065

Asp Tyr Val Asp Ala Thr Glu Lys Ile Ser Phe Asn Pro Phe Ala
    1070                1075                1080

Pro Lys Val Trp Phe Glu Glu Ser Ala Gly Val Pro Gly Leu
    1085                1090                1095

Phe Ala Asp Arg Asn Gly Gly Glu Val Lys Val His Arg Val Glu
    1100                1105                1110

Gly Glu Lys Pro Ser Ala Leu Phe Leu His Leu His Asn Gly Thr
    1115                1120                1125

Gly Asp Leu Ser Gly Gln Asn Gly Ala Ala Gly Glu Arg Ala Gln
    1130                1135                1140

Val Val Pro Leu Ser Glu Gln Gln Gln Ser Ser Leu Pro Ser Pro
    1145                1150                1155

Ser Glu Pro Thr Glu Ser Pro Lys Asp Ser Ser Leu Pro Gly Pro
    1160                1165                1170

Ser Glu Pro Thr Glu Ser Pro Lys Asp Ser Ser Leu Pro Gly Pro
    1175                1180                1185

Ser Glu Pro Thr Glu Ser Pro Lys Thr Asp Thr Ser Leu Pro Lys
    1190                1195                1200

<210> SEQ ID NO 77
<211> LENGTH: 1323
<212> TYPE: PRT
<213> ORGANISM: Rothia dentocariosa

<400> SEQUENCE: 77

Met Arg Pro Leu Ser Thr Pro Arg Leu Phe Ala Lys Ser Cys Leu Ala
1               5                   10                  15

Ala Thr Met Gly Leu Ala Leu Thr Leu Ser Ala Ala Pro Ala Ser
            20                  25                  30

Ala Val Gln Pro Pro Ala Asp Glu Thr Gly Ile Val Thr Ser Gly Asp
        35                  40                  45

Thr Ala Lys Asp Val Leu Ser Pro Gly Met Lys Lys Ala Glu Gly Asn
```

```
            50                  55                  60
Ile Val Phe Val His Phe Lys Gly Lys Gly Ala Tyr Glu Gln Thr
 65                  70                  75                  80

Gln Ser Ala Ala Val Leu Ala Asn Lys Gln Ala Pro Ile Asn Lys Gln
                     85                  90                  95

Ala Glu Val Gln Ala Ile Lys Thr Gln Val Gln Ser Gln Ala Gln Ala
                    100                 105                 110

Ala Ala Arg Gln Ser Ser Ser Gln Ala Leu Tyr Thr Val His Asn Thr
                    115                 120                 125

Ala Arg Gly Val Val Leu Gln Gly Asn Ala Ala Gln Ile Arg Glu Leu
                    130                 135                 140

Ala Arg Arg Gly Asp Val Glu Arg Ile Thr Pro Ile Ile Ala Lys Glu
145                 150                 155                 160

Arg Gln Asn Ala Ser Ser Val Val Asp Thr Lys Thr Val Asn Thr Trp
                    165                 170                 175

Thr Arg Glu Asn Thr Gly Tyr Thr Gly Lys Asp Val Thr Ile Ala Val
                    180                 185                 190

Val Asp Ser Gly Val Asp Tyr Thr His Ser Asp Phe Gly Gly Pro Gly
                    195                 200                 205

Thr Ala Glu Ala Tyr Gln Lys Ala Lys Asp Met Pro Glu Leu Pro Ser
210                 215                 220

Ala Asp Ser Gly Leu Ile Asp Arg Asn Lys Ile Ala Ala Gly Val Asp
225                 230                 235                 240

Leu Val Gly Asp Ser Tyr Asn Ala Ser Ser Thr Asn Thr Glu Gln Ser
                    245                 250                 255

Thr Pro His Pro Asp Asn Asn Pro Leu Asp Cys Arg Pro Asp Gly Phe
                    260                 265                 270

Gly Ser Gly Gly His Gly Thr His Val Ala Gly Thr Ala Ala Gly Tyr
                    275                 280                 285

Gly Val Asn Gln Asp Gly Thr Thr Phe Arg Gly Asp Tyr Ser Lys Leu
                    290                 295                 300

Thr Ala Glu Gln Leu Asn Gln Met Lys Ile Gly Pro Gly Thr Ala Pro
305                 310                 315                 320

Glu Ala Lys Ile Leu Pro Val Arg Val Phe Gly Cys His Gly Thr Thr
                    325                 330                 335

His Met Val Ile Lys Ala Leu Asp Thr Val Met Asp Pro Asn Gly Asp
                    340                 345                 350

Gly Asp Phe Ser Asp Arg Ala Asn Ile Val Asn Leu Ser Leu Gly Gly
                    355                 360                 365

Glu Phe Thr Pro Val Asp Asp Pro Glu Ser Tyr Ile Val Asn Thr Met
                    370                 375                 380

Ala Arg Gln Gly Val Phe Thr Val Ala Ala Ala Gly Asn Ala Asn Asn
385                 390                 395                 400

Tyr Asn Gly Val Gly Asp Thr Tyr Ser Asn Ser Gly Ser Pro Ala Asn
                    405                 410                 415

Ala Ala Ala Gly Leu Ser Val Ala Asn Ala Tyr Gly Thr Thr Gln Pro
                    420                 425                 430

Thr Asp Gln Met Lys Val Leu Ala Pro Glu Gln Gln Ala Gly Phe Val
                    435                 440                 445

Asn Gly Met Tyr Thr Ser Ser Phe Gly Tyr Ala Ala Ala Ser Ala Asp
                    450                 455                 460

Lys Leu Thr Gly Glu Val Val Lys Ala Pro Ala Ser Asn Arg Tyr Gly
465                 470                 475                 480
```

-continued

```
Cys Glu Ala Phe Ser Glu Gln Asp Ala Ala Gln Leu Lys Gly Lys Trp
            485                 490                 495

Val Tyr Ile Asp Trp Glu Asp Pro Ala Thr Gly Lys Phe Pro Cys Gly
            500                 505                 510

Ser Ala Val Arg Phe Asn His Val Glu Ala Ala Gly Gly Gln Gly Val
            515                 520                 525

Ile Leu Gly Ser Met Gln Glu Arg His Glu Val Gly Ile Ala Gly Asn
530                 535                 540

Ala Thr Ile Pro Gly Phe Met Leu Ser Lys Ser Ala Thr Asp Lys Leu
545                 550                 555                 560

Ala Thr Ala Ile Asn Asp Gly Thr Leu Arg Val Glu Leu Asn Asn Asp
            565                 570                 575

Tyr Lys Ala Gln Gly Arg Thr Ser His Ser Lys Ala Leu Asp Leu Val
            580                 585                 590

Ser Ser Ser Ala Arg Gly Gln His Gly Ser Asp Gly Tyr Ile Lys Pro
            595                 600                 605

Asp Val Ala Ala Pro Gly Ala Glu Ile Val Ser Ala Ala Val Gly Gly
            610                 615                 620

Gly Thr Lys Gly Val Ala Phe Thr Gly Thr Ser Met Ala Ala Pro His
625                 630                 635                 640

Ala Ser Gly Val Ala Ala Leu Val Leu Gln Ala His Gln Asp Tyr Ser
            645                 650                 655

Pro Thr Met Leu Lys Ala Ala Leu Met Asn Gly Ala Asn Thr Asp Leu
            660                 665                 670

Lys Asp Ser Gln Gly His Thr Tyr Ala Val Asp Arg Val Gly Ser Gly
            675                 680                 685

Met Ile Asn Ala Lys Ala Ala Val Glu Ala Lys Val Leu Ala Tyr Asp
            690                 695                 700

Thr Lys Gln Pro Glu Arg Val Ser Thr Ala Phe Gly Val Leu Glu Tyr
705                 710                 715                 720

Thr Pro Asp Ser Gly Val Gln Thr Val Thr Arg Asp Ile Thr Leu Asp
            725                 730                 735

Asn Thr Asp Ser Arg Ala His Thr Tyr Thr Pro Glu Tyr Val Ala Ser
            740                 745                 750

Thr Asp Ile Pro Gly Val Ser Phe Ser Leu Pro Ser Thr Val Ser Val
            755                 760                 765

Gly Ala Gly Glu Lys Lys Asn Val Thr Val Thr Val Thr Ile Asp Pro
770                 775                 780

Ala Lys Leu Glu Lys Thr Arg Asp Pro Ala Leu Glu Lys Arg Gln Ser
785                 790                 795                 800

Ser Arg Asn Val Val Gly Asp Lys Val Glu Thr Thr Ala Glu Gly Asp
            805                 810                 815

Arg Gln Tyr Val Ala Ser Ala Ser Gly Arg Val Val Phe Lys Glu Asp
            820                 825                 830

Gly Ala Glu Ala Met Arg Val Pro Val His Val Ala Pro Lys Pro Val
            835                 840                 845

Ser Ala Met Arg Ala Asp Thr Ser Lys Ile Glu Phe Gly Thr Gly Ala
850                 855                 860

Glu Gln Lys Val Lys Leu Thr Gly Thr Thr Leu Asp Gln Gly Gly Tyr
865                 870                 875                 880

Arg Ser Met Leu Gly Val Phe Glu Leu Gly Ala Ala Ser Gly Arg Ile
            885                 890                 895
```

```
Pro Thr Gln Asn Leu Thr Leu Ala Ser Asp Gln Val Val Asp Val Gln
            900                 905                 910
Tyr Val Gly Ala Ala Ser Asp Ala Pro Ala Leu Ala Ala Ala Gly Lys
        915                 920                 925
Asn Pro Asp Glu Gly Asn Leu Tyr Phe Gly Ile Ser Thr Trp Ser Asn
    930                 935                 940
Trp Asp Val Leu His Ser Gly Arg Ser Val Glu Val Ser Val Asp Thr
945                 950                 955                 960
Asn Gly Asp Asp Gln Arg Asp Tyr Val Leu Glu Val Ala Arg Glu Lys
                965                 970                 975
Gly Leu Asp Phe Pro Leu Val Lys Val Trp Lys Ala Thr Gly Asp Lys
            980                 985                 990
Trp Asp Phe Ile Asn Gln Tyr Pro Leu Asn Ser Ala Trp Gly Asp Thr
        995                 1000                1005
Asp Thr Asn Met Met Asp Ser Asn Val Met Val Leu Gly Val Pro
    1010                1015                1020
Leu Lys Asp Leu Gly Leu Thr Ser Ala Asn Ala Lys Asp Met Ser
    1025                1030                1035
Tyr Thr Val Leu Thr Asn Thr Trp Ser Asn Glu Gly Ser Asp Asp
    1040                1045                1050
Val Asp Arg Thr Glu Lys Ala Thr Phe Asn Pro Phe Ala Pro Lys
    1055                1060                1065
Val Trp Phe Glu Gly Glu Ser Ala Gly Val Pro Gly Phe Phe Ala
    1070                1075                1080
Asp Arg Ala Gly Ala Glu Leu Thr Ala His Arg Gln Ala Gly Ala
    1085                1090                1095
Phe Glu Ala Lys Ala Leu Phe Leu His Met His Asn Gly Thr Gly
    1100                1105                1110
Asp Leu Ser Gly Ile Gly Ala Gly His Gly Glu Arg Ala Gln Val
    1115                1120                1125
Val Glu Val Ser Ala Ala Ser Ala Asn Ser Arg Asp Ala Arg Phe
    1130                1135                1140
Lys Asp Val Pro Ala Asp Asn Gln Phe Tyr Thr Glu Ile Asn Trp
    1145                1150                1155
Leu Ala Gln Arg Gln Ile Thr Leu Gly Tyr Pro Asp Gly Thr Phe
    1160                1165                1170
Arg Pro Gly Glu Asn Val Glu Arg Gly Ala Met Ala Ala Phe Phe
    1175                1180                1185
Tyr Arg Leu Asn Gly Ser Pro Gln Phe Thr Pro Thr Lys Pro
    1190                1195                1200
Thr Phe Ser Asp Val Pro Thr Asn His Pro Phe Tyr Lys Glu Ile
    1205                1210                1215
Glu Trp Met Ala Ala Arg Gly Ile Thr Thr Gly Tyr Gly Asp Gly
    1220                1225                1230
Thr Phe Arg Pro Ser Ala Ser Val Asn Arg Asp Ala Met Ala Ala
    1235                1240                1245
Phe Phe Tyr Arg Asn Ala Gly Ser Pro Gln Phe Ala Ala Pro Ala
    1250                1255                1260
Arg Ala Pro Phe Ala Asp Val Pro Ala Asp Ser Gln Phe Tyr Lys
    1265                1270                1275
Glu Ile Ala Trp Leu Ala Glu Gln Gly Ile Thr Lys Gly Trp Asp
    1280                1285                1290
Asp Gly Thr Tyr Arg Pro Ser Glu Pro Ile His Arg Asp Ala Met
```

```
                1295                1300                1305
Ala Ala  Phe Leu Tyr Arg Tyr  His Glu Lys Val Leu  Ser Arg Arg
        1310                1315                1320

<210> SEQ ID NO 78
<211> LENGTH: 1323
<212> TYPE: PRT
<213> ORGANISM: Rothia dentocariosa

<400> SEQUENCE: 78

Met Arg Pro Leu Ser Thr Pro Arg Leu Phe Ala Lys Ser Cys Leu Ala
1               5                   10                  15

Ala Thr Met Gly Leu Ala Leu Thr Leu Ser Ala Ala Pro Ala Ser
            20                  25                  30

Ala Val Gln Pro Pro Ala Asp Glu Thr Gly Ile Val Thr Ser Gly Asp
            35                  40                  45

Thr Ala Lys Asp Val Leu Ser Pro Gly Met Lys Lys Ala Glu Gly Asn
    50                  55                  60

Ile Val Val Phe Val His Phe Lys Gly Lys Gly Ala Tyr Glu Gln Thr
65                  70                  75                  80

Gln Ser Ala Ala Val Leu Ala Asn Lys Gln Ala Pro Ile Asn Lys Gln
                85                  90                  95

Ala Glu Val Gln Ala Ile Lys Thr Gln Val Gln Ser Gln Ala Gln Ala
            100                 105                 110

Ala Ala Arg Gln Ser Ser Ser Gln Ala Leu Tyr Thr Val His Asn Thr
        115                 120                 125

Ala Arg Gly Val Val Leu Gln Gly Asn Ala Ala Gln Ile Arg Glu Leu
    130                 135                 140

Ala Arg Arg Gly Asp Val Glu Arg Ile Thr Pro Ile Ile Ala Lys Glu
145                 150                 155                 160

Arg Gln Asn Ala Ser Ser Val Val Asp Thr Lys Thr Val Asn Thr Trp
                165                 170                 175

Thr Arg Glu Asn Thr Gly Tyr Thr Gly Lys Asp Val Thr Ile Ala Val
            180                 185                 190

Val Asp Ser Gly Val Asp Tyr Thr His Ser Asp Phe Gly Gly Pro Gly
        195                 200                 205

Thr Ala Glu Ala Tyr Gln Lys Ala Lys Asp Met Pro Glu Leu Pro Ser
    210                 215                 220

Ala Asp Ser Gly Leu Ile Asp Arg Asn Lys Ile Ala Ala Gly Val Asp
225                 230                 235                 240

Leu Val Gly Asp Ser Tyr Asn Ala Ser Ser Thr Asn Thr Glu Gln Ser
                245                 250                 255

Thr Pro His Pro Asp Asn Asn Pro Leu Asp Cys Arg Pro Asp Gly Phe
            260                 265                 270

Gly Ser Gly Gly His Gly Thr His Val Ala Gly Thr Ala Ala Gly Tyr
        275                 280                 285

Gly Val Asn Gln Asp Gly Thr Thr Phe Arg Gly Asp Tyr Ser Lys Leu
    290                 295                 300

Thr Ala Glu Gln Leu Asn Gln Met Lys Ile Gly Pro Gly Thr Ala Pro
305                 310                 315                 320

Glu Ala Lys Ile Leu Pro Val Arg Val Phe Gly Cys His Gly Thr Thr
                325                 330                 335

His Met Val Ile Lys Ala Leu Asp Thr Val Met Asp Pro Asn Gly Asp
            340                 345                 350
```

```
Gly Asp Phe Ser Asp Arg Ala Asn Ile Val Asn Leu Ser Leu Gly Gly
            355                 360                 365
Glu Phe Thr Pro Val Asp Pro Glu Ser Tyr Ile Val Asn Thr Met
    370                 375                 380
Ala Arg Gln Gly Val Phe Thr Val Ala Ala Gly Asn Ala Asn Asn
385                 390                 395                 400
Tyr Asn Gly Val Gly Asp Thr Tyr Ser Asn Ser Gly Ser Pro Ala Asn
                405                 410                 415
Ala Ala Ala Gly Leu Ser Val Ala Asn Ala Tyr Gly Thr Thr Gln Pro
                420                 425                 430
Thr Asp Gln Met Lys Val Leu Ala Pro Glu Gln Ala Gly Phe Val
    435                 440                 445
Asn Gly Met Tyr Thr Ser Ser Phe Gly Tyr Ala Ala Ala Ser Ala Asp
    450                 455                 460
Lys Leu Thr Gly Glu Val Val Lys Ala Pro Ala Ser Asn Arg Tyr Gly
465                 470                 475                 480
Cys Glu Ala Phe Ser Glu Gln Asp Ala Ala Gln Leu Lys Gly Lys Trp
                485                 490                 495
Val Tyr Ile Asp Trp Glu Asp Pro Ala Thr Gly Lys Phe Pro Cys Gly
            500                 505                 510
Ser Ala Val Arg Phe Asn His Val Glu Ala Ala Gly Gly Gln Gly Val
            515                 520                 525
Ile Leu Gly Ser Met Gln Glu Arg His Glu Val Gly Ile Ala Gly Asn
            530                 535                 540
Ala Thr Ile Pro Gly Phe Met Leu Ser Lys Ser Ala Thr Asp Lys Leu
545                 550                 555                 560
Ala Thr Ala Ile Asn Asp Gly Thr Leu Arg Val Glu Leu Asn Asn Asp
                565                 570                 575
Tyr Lys Ala Gln Gly Arg Thr Ser His Ser Lys Ala Leu Asp Leu Val
                580                 585                 590
Ser Ser Ser Ala Arg Gly Gln His Gly Ser Asp Gly Tyr Ile Lys Pro
            595                 600                 605
Asp Val Ala Ala Pro Gly Ala Glu Ile Val Ser Ala Val Gly Gly
    610                 615                 620
Gly Thr Lys Gly Val Ala Phe Thr Gly Thr Ser Met Ala Ala Pro His
625                 630                 635                 640
Ala Ser Gly Val Ala Ala Leu Val Leu Gln Ala His Gln Asp Tyr Ser
                645                 650                 655
Pro Thr Met Leu Lys Ala Ala Leu Met Asn Gly Ala Asn Thr Asp Leu
    660                 665                 670
Lys Asp Ser Gln Gly His Thr Tyr Ala Val Asp Arg Val Gly Ser Gly
            675                 680                 685
Met Ile Asn Ala Lys Ala Ala Val Glu Ala Lys Val Leu Ala Tyr Asp
    690                 695                 700
Thr Lys Gln Pro Glu Arg Val Ser Thr Ala Phe Gly Val Leu Glu Tyr
705                 710                 715                 720
Thr Pro Asp Ser Gly Val Gln Thr Val Thr Arg Asp Ile Thr Leu Asp
                725                 730                 735
Asn Thr Asp Ser Arg Ala His Thr Tyr Thr Pro Glu Tyr Val Ala Ser
            740                 745                 750
Thr Asp Ile Pro Gly Val Ser Phe Ser Leu Pro Ser Thr Val Ser Val
            755                 760                 765
Gly Ala Gly Glu Lys Lys Asn Val Thr Val Thr Val Thr Ile Asp Pro
```

```
                770             775             780
Ala Lys Leu Glu Lys Thr Arg Asp Pro Ala Leu Glu Lys Arg Gln Ser
785             790             795             800

Ser Arg Asn Val Val Gly Asp Lys Val Glu Thr Thr Ala Glu Gly Asp
                805             810             815

Arg Gln Tyr Val Ala Ser Ala Ser Gly Arg Val Val Phe Lys Glu Asp
                820             825             830

Gly Ala Glu Ala Met Arg Val Pro Val His Val Ala Pro Lys Pro Val
                835             840             845

Ser Ala Met Arg Ala Asp Thr Ser Lys Ile Glu Phe Gly Thr Gly Ala
850             855             860

Glu Gln Lys Val Lys Leu Thr Gly Thr Thr Leu Asp Gln Gly Gly Tyr
865             870             875             880

Arg Ser Met Leu Gly Val Phe Glu Leu Gly Ala Ser Gly Arg Ile
                885             890             895

Pro Thr Gln Asn Leu Thr Leu Ala Ser Asp Gln Val Val Asp Val Gln
                900             905             910

Tyr Val Gly Ala Ala Ser Asp Ala Pro Ala Leu Ala Ala Ala Gly Lys
                915             920             925

Asn Pro Asp Glu Gly Asn Leu Tyr Phe Gly Ile Ser Thr Trp Ser Asn
930             935             940

Trp Asp Val Leu His Ser Gly Arg Ser Val Glu Val Ser Val Asp Thr
945             950             955             960

Asn Gly Asp Asp Gln Arg Asp Tyr Val Leu Glu Val Ala Arg Glu Lys
                965             970             975

Gly Leu Asp Phe Pro Leu Val Lys Val Trp Lys Ala Thr Gly Asp Lys
                980             985             990

Trp Asp Phe Ile Asn Gln Tyr Pro Leu Asn Ser Ala Trp Gly Asp Thr
                995             1000            1005

Asp Thr Asn Met Met Asp Ser Asn Val Met Val Leu Gly Val Pro
            1010            1015            1020

Leu Lys Asp Leu Gly Leu Thr Ser Ala Asn Ala Lys Asp Met Ser
            1025            1030            1035

Tyr Thr Val Leu Thr Asn Thr Trp Ser Asn Glu Gly Ser Asp Asp
            1040            1045            1050

Val Asp Arg Thr Glu Lys Ala Thr Phe Asn Pro Phe Ala Pro Lys
            1055            1060            1065

Val Trp Phe Glu Gly Glu Ser Ala Gly Val Pro Gly Phe Phe Ala
            1070            1075            1080

Asp Arg Ala Gly Ala Glu Leu Thr Ala His Arg Gln Ala Gly Ala
            1085            1090            1095

Phe Glu Ala Lys Ala Leu Phe Leu His Met His Asn Gly Thr Gly
            1100            1105            1110

Asp Leu Ser Gly Ile Gly Ala Gly His Gly Glu Arg Ala Gln Val
            1115            1120            1125

Val Glu Val Ser Ala Ala Ser Ala Asn Ser Arg Asp Ala Arg Phe
            1130            1135            1140

Lys Asp Val Pro Ala Asp Asn Gln Phe Tyr Thr Glu Ile Asn Trp
            1145            1150            1155

Leu Ala Gln Arg Gln Ile Thr Leu Gly Tyr Pro Asp Gly Thr Phe
            1160            1165            1170

Arg Pro Gly Glu Asn Val Glu Arg Gly Ala Met Ala Ala Phe Phe
            1175            1180            1185
```

```
Tyr Arg Leu Asn Gly Ser Pro Gln Phe Thr Pro Thr Lys Pro
    1190            1195            1200

Thr Phe Ser Asp Val Pro Thr Asn His Pro Phe Tyr Lys Glu Ile
    1205            1210            1215

Glu Trp Met Ala Ala Arg Gly Ile Thr Thr Gly Tyr Gly Asp Gly
    1220            1225            1230

Thr Phe Arg Pro Ser Ala Ser Val Asn Arg Asp Ala Met Ala Ala
    1235            1240            1245

Phe Phe Tyr Arg Asn Ala Gly Ser Pro Gln Phe Ala Ala Pro Ala
    1250            1255            1260

Arg Ala Pro Phe Ala Asp Val Pro Ala Asp Ser Gln Phe Tyr Lys
    1265            1270            1275

Glu Ile Ala Trp Leu Ala Glu Gln Gly Ile Thr Lys Gly Trp Asp
    1280            1285            1290

Asp Gly Thr Tyr Arg Pro Ser Glu Pro Ile His Arg Asp Ala Met
    1295            1300            1305

Ala Ala Phe Leu Tyr Arg Tyr His Glu Lys Val Leu Ser Arg Arg
    1310            1315            1320

<210> SEQ ID NO 79
<211> LENGTH: 1323
<212> TYPE: PRT
<213> ORGANISM: Rothia dentocariosa

<400> SEQUENCE: 79

Met Arg Pro Leu Ser Thr Pro Arg Leu Phe Ala Lys Ser Cys Leu Ala
1               5                   10                  15

Ala Thr Met Gly Leu Ala Leu Thr Leu Ser Ala Ala Pro Ala Ser
            20                  25                  30

Ala Val Gln Pro Pro Ala Asp Glu Thr Gly Ile Val Thr Ser Gly Asp
                35                  40                  45

Thr Ala Lys Asp Val Leu Ser Pro Gly Met Lys Lys Ala Glu Gly Asn
    50                  55                  60

Ile Val Val Phe Val His Phe Lys Gly Lys Gly Ala Tyr Glu Gln Thr
65                  70                  75                  80

Gln Ser Ala Ala Val Leu Ala Asn Lys Gln Ala Pro Ile Asn Lys Gln
                85                  90                  95

Ala Glu Val Gln Ala Ile Lys Thr Gln Val Gln Ser Gln Ala Gln Ala
            100                 105                 110

Ala Ala Arg Gln Ser Ser Gln Ala Leu Tyr Thr Val His Asn Thr
        115                 120                 125

Ala Arg Gly Val Val Leu Gln Gly Asn Ala Ala Gln Ile Arg Glu Leu
    130                 135                 140

Ala Arg Arg Gly Asp Val Glu Arg Ile Thr Pro Ile Ile Ala Lys Glu
145                 150                 155                 160

Arg Gln Asn Ala Ser Ser Val Asp Thr Lys Thr Val Asn Thr Trp
                165                 170                 175

Thr Arg Glu Asn Thr Gly Tyr Thr Gly Lys Asp Val Thr Ile Ala Val
            180                 185                 190

Val Asp Ser Gly Val Asp Tyr Thr His Ser Asp Phe Gly Gly Pro Gly
                195                 200                 205

Thr Ala Glu Ala Tyr Gln Lys Ala Lys Asp Met Pro Glu Leu Pro Ser
    210                 215                 220

Ala Asp Ser Gly Leu Ile Asp Arg Asn Lys Ile Ala Ala Gly Val Asp
```

```
                225                 230                 235                 240
Leu Val Gly Asp Ser Tyr Asn Ala Ser Ser Thr Asn Thr Glu Gln Ser
                245                 250                 255

Thr Pro His Pro Asp Asn Asn Pro Leu Asp Cys Arg Pro Asp Gly Phe
                260                 265                 270

Gly Ser Gly Gly His Gly Thr His Val Ala Gly Thr Ala Ala Gly Tyr
                275                 280                 285

Gly Val Asn Gln Asp Gly Thr Thr Phe Arg Gly Asp Tyr Ser Lys Leu
                290                 295                 300

Thr Ala Glu Gln Leu Asn Gln Met Lys Ile Gly Pro Gly Thr Ala Pro
305                 310                 315                 320

Glu Ala Lys Ile Leu Pro Val Arg Val Phe Gly Cys His Gly Thr Thr
                325                 330                 335

His Met Val Ile Lys Ala Leu Asp Thr Val Met Asp Pro Asn Gly Asp
                340                 345                 350

Gly Asp Phe Ser Asp Arg Ala Asn Ile Val Asn Leu Ser Leu Gly Gly
                355                 360                 365

Glu Phe Thr Pro Val Asp Asp Pro Glu Ser Tyr Ile Val Asn Thr Met
                370                 375                 380

Ala Arg Gln Gly Val Phe Thr Val Ala Ala Ala Gly Asn Ala Asn Asn
385                 390                 395                 400

Tyr Asn Gly Val Gly Asp Thr Tyr Ser Asn Ser Gly Ser Pro Ala Asn
                405                 410                 415

Ala Ala Ala Gly Leu Ser Val Ala Asn Ala Tyr Gly Thr Thr Gln Pro
                420                 425                 430

Thr Asp Gln Met Lys Val Leu Ala Pro Glu Gln Gln Ala Gly Phe Val
                435                 440                 445

Asn Gly Met Tyr Thr Ser Ser Phe Gly Tyr Ala Ala Ala Ser Ala Asp
                450                 455                 460

Lys Leu Thr Gly Glu Val Val Lys Ala Pro Ala Ser Asn Arg Tyr Gly
465                 470                 475                 480

Cys Glu Ala Phe Ser Glu Gln Asp Ala Ala Gln Leu Lys Gly Lys Trp
                485                 490                 495

Val Tyr Ile Asp Trp Glu Asp Pro Ala Thr Gly Lys Phe Pro Cys Gly
                500                 505                 510

Ser Ala Val Arg Phe Asn His Val Glu Ala Ala Gly Gly Gln Gly Val
                515                 520                 525

Ile Leu Gly Ser Met Gln Glu Arg His Glu Val Gly Ile Ala Gly Asn
                530                 535                 540

Ala Thr Ile Pro Gly Phe Met Leu Ser Lys Ser Ala Thr Asp Lys Leu
545                 550                 555                 560

Ala Thr Ala Ile Asn Asp Gly Thr Leu Arg Val Glu Leu Asn Asn Asp
                565                 570                 575

Tyr Lys Ala Gln Gly Arg Thr Ser His Ser Lys Ala Leu Asp Leu Val
                580                 585                 590

Ser Ser Ser Ala Arg Gly Gln His Gly Ser Asp Gly Tyr Ile Lys Pro
                595                 600                 605

Asp Val Ala Ala Pro Gly Ala Glu Ile Val Ser Ala Val Gly Gly
                610                 615                 620

Gly Thr Lys Gly Val Ala Phe Thr Gly Thr Ser Met Ala Ala Pro His
625                 630                 635                 640

Ala Ser Gly Val Ala Ala Leu Val Leu Gln Ala His Gln Asp Tyr Ser
                645                 650                 655
```

```
Pro Thr Met Leu Lys Ala Ala Leu Met Asn Gly Ala Asn Thr Asp Leu
        660                 665                 670

Lys Asp Ser Gln Gly His Thr Tyr Ala Val Asp Arg Val Gly Ser Gly
        675                 680                 685

Met Ile Asn Ala Lys Ala Val Glu Ala Lys Val Leu Ala Tyr Asp
        690                 695                 700

Thr Lys Gln Pro Glu Arg Val Ser Thr Ala Phe Gly Val Leu Glu Tyr
705                 710                 715                 720

Thr Pro Asp Ser Gly Val Gln Thr Val Thr Arg Asp Ile Thr Leu Asp
                725                 730                 735

Asn Thr Asp Ser Arg Ala His Thr Tyr Thr Pro Glu Tyr Val Ala Ser
                740                 745                 750

Thr Asp Ile Pro Gly Val Ser Phe Ser Leu Pro Ser Thr Val Ser Val
                755                 760                 765

Gly Ala Gly Glu Lys Lys Asn Val Thr Val Thr Val Thr Ile Asp Pro
770                 775                 780

Ala Lys Leu Glu Lys Thr Arg Asp Pro Ala Leu Glu Lys Arg Gln Ser
785                 790                 795                 800

Ser Arg Asn Val Val Gly Asp Lys Val Glu Thr Thr Ala Glu Gly Asp
                805                 810                 815

Arg Gln Tyr Val Ala Ser Ala Ser Gly Arg Val Val Phe Lys Glu Asp
                820                 825                 830

Gly Ala Glu Ala Met Arg Val Pro Val His Val Ala Pro Lys Pro Val
                835                 840                 845

Ser Ala Met Arg Ala Asp Thr Ser Lys Ile Glu Phe Gly Thr Gly Ala
850                 855                 860

Glu Gln Lys Val Lys Leu Thr Gly Thr Thr Leu Asp Gln Gly Gly Tyr
865                 870                 875                 880

Arg Ser Met Leu Gly Val Phe Glu Leu Gly Ala Ala Ser Gly Arg Ile
                885                 890                 895

Pro Thr Gln Asn Leu Thr Leu Ala Ser Asp Gln Val Val Asp Val Gln
                900                 905                 910

Tyr Val Gly Ala Ala Ser Asp Ala Pro Ala Leu Ala Ala Ala Gly Lys
                915                 920                 925

Asn Pro Asp Glu Gly Asn Leu Tyr Phe Gly Ile Ser Thr Trp Ser Asn
930                 935                 940

Trp Asp Val Leu His Ser Gly Arg Ser Val Glu Val Ser Val Asp Thr
945                 950                 955                 960

Asn Gly Asp Asp Gln Arg Asp Tyr Val Leu Glu Val Ala Arg Glu Lys
                965                 970                 975

Gly Leu Asp Phe Pro Leu Val Lys Val Trp Lys Ala Thr Gly Asp Lys
                980                 985                 990

Trp Asp Phe Ile Asn Gln Tyr Pro Leu Asn Ser Ala Trp Gly Asp Thr
                995                 1000                1005

Asp Thr Asn Met Met Asp Ser Asn Val Met Val Leu Gly Val Pro
        1010                1015                1020

Leu Lys Asp Leu Gly Leu Thr Ser Ala Asn Ala Lys Asp Met Ser
        1025                1030                1035

Tyr Thr Val Leu Thr Asn Thr Trp Ser Asn Glu Gly Ser Asp Asp
        1040                1045                1050

Val Asp Arg Thr Glu Lys Ala Thr Phe Asn Pro Phe Ala Pro Lys
        1055                1060                1065
```

Val Trp Phe Glu Gly Glu Ser Ala Gly Val Pro Gly Phe Phe Ala
1070                1075                1080

Asp Arg Ala Gly Ala Glu Leu Thr Ala His Arg Gln Ala Gly Ala
    1085                1090                1095

Phe Glu Ala Lys Ala Leu Phe Leu His Met His Asn Gly Thr Gly
1100                1105                1110

Asp Leu Ser Gly Ile Gly Ala Gly His Gly Glu Arg Ala Gln Val
    1115                1120                1125

Val Glu Val Ser Ala Ala Ser Ala Asn Ser Arg Asp Ala Arg Phe
1130                1135                1140

Lys Asp Val Pro Ala Asp Asn Gln Phe Tyr Thr Glu Ile Asn Trp
    1145                1150                1155

Leu Ala Gln Arg Gln Ile Thr Leu Gly Tyr Pro Asp Gly Thr Phe
1160                1165                1170

Arg Pro Gly Glu Asn Val Glu Arg Gly Ala Met Ala Ala Phe Phe
    1175                1180                1185

Tyr Arg Leu Asn Gly Ser Pro Gln Phe Thr Pro Pro Thr Lys Pro
1190                1195                1200

Thr Phe Ser Asp Val Pro Thr Asn His Pro Phe Tyr Lys Glu Ile
    1205                1210                1215

Glu Trp Met Ala Ala Arg Gly Ile Thr Thr Gly Tyr Gly Asp Gly
1220                1225                1230

Thr Phe Arg Pro Ser Ala Ser Val Asn Arg Asp Ala Met Ala Ala
    1235                1240                1245

Phe Phe Tyr Arg Asn Ala Gly Ser Pro Gln Phe Ala Ala Pro Ala
1250                1255                1260

Arg Ala Pro Phe Ala Asp Val Pro Ala Asp Ser Gln Phe Tyr Lys
    1265                1270                1275

Glu Ile Ala Trp Leu Ala Glu Gln Gly Ile Thr Lys Gly Trp Asp
1280                1285                1290

Asp Gly Thr Tyr Arg Pro Ser Glu Pro Ile His Arg Asp Ala Met
    1295                1300                1305

Ala Ala Phe Leu Tyr Arg Tyr His Glu Lys Val Leu Ser Arg Arg
1310                1315                1320

<210> SEQ ID NO 80
<211> LENGTH: 1328
<212> TYPE: PRT
<213> ORGANISM: Rothia mucilaginosa

<400> SEQUENCE: 80

Met Thr Thr Pro His Ala Pro Arg Arg Met Lys Ala Val Gly Ala
1               5                   10                  15

Thr Gly Leu Ser Ala Ala Leu Ala Leu Thr Leu Gly Ile Pro Ala Thr
                20                  25                  30

Phe Ser Ala Ala His Ala Gln Ser Pro Gln Val Glu Gly Ser Thr
                35                  40                  45

Ala Ser Ala Ser Gly Asp Ala Ala Ser Arg Ile Ser Pro Gly Leu Gln
        50                  55                  60

Lys Ala Glu Gly Gln Ile Thr Val Tyr Val Gln Phe Lys Gly Lys Gly
65                  70                  75                  80

Ala Tyr Glu Gln Thr Gln Ser Ala Ala Val Leu Ala Arg Lys Glu Ala
                85                  90                  95

Pro Ala Asn Arg Gln Ala Gln Val Gln Ala Ile Ala Ala Gln Val Gln
                100                 105                 110

```
Ser Gln Ala Gln Ser Val Ala Ala Ser Gly Ala Lys Leu Met Tyr
        115                 120                 125
Thr Thr His Asn Ala Met Arg Gly Ala Ala Ile Thr Gly Asp Ala Ala
130                 135                 140
Gln Ile Arg Ala Leu Ala Glu Arg Pro Asp Val Glu Arg Ile Ser Pro
145                 150                 155                 160
Ile Ile Ala Lys Glu Arg Met Asn Ser Gly Ser Glu Ile Asp Thr Lys
                165                 170                 175
Thr Leu Ala Thr Trp Thr Arg Glu Asn Thr Gly Tyr Thr Gly Lys Gly
                180                 185                 190
Val Lys Ile Ala Val Val Asp Ser Gly Val Asp Tyr Thr His Ala Asp
        195                 200                 205
Phe Gly Gly Pro Gly Thr Val Asp Ser Tyr Leu Lys Ala Lys Ala Met
210                 215                 220
Thr Glu Leu Pro Ser Ala Asp Ser Gly Leu Ile Asp Arg Asn Lys Phe
225                 230                 235                 240
Ile Gly Gly Ile Asp Leu Val Gly Asp Asp Tyr Asn Ala Ser Val Ala
                245                 250                 255
Glu Lys Ser Thr Pro Gln Pro Asp Asn Asn Pro Leu Asp Cys Arg Pro
                260                 265                 270
Asp Gly Phe Gly Ser Gly Gly His Gly Thr His Val Ala Gly Thr Ala
        275                 280                 285
Ala Gly Tyr Gly Val Thr Ala Asn Gly Thr Thr Tyr Arg Gly Asp Tyr
290                 295                 300
Lys Asn Leu Thr Glu Glu Gln Leu Lys Gly Met Ser Ile Gly Pro Gly
305                 310                 315                 320
Thr Ala Pro Glu Ala Gln Ile Leu Ala Ile Arg Val Phe Gly Cys Tyr
                325                 330                 335
Gly Asn Ser Ser Val Val Met Lys Ala Leu Asp Thr Val Met Asp Pro
                340                 345                 350
Asn Gly Asp Gly Asp Phe Ser Asp Arg Ala Asp Ile Val Asn Leu Ser
        355                 360                 365
Leu Gly Gly Glu Phe Ala Pro Ala Asp Asp Pro Glu Ser Tyr Met Ile
370                 375                 380
Asn Thr Met Ala Arg Gln Gly Val Phe Thr Val Ala Ala Ala Gly Asn
385                 390                 395                 400
Ala Asn Asn Tyr Asn Gly Val Gly Asp Thr Tyr Ser Asp Ser Gly Ser
                405                 410                 415
Pro Ala Asn Ala Ala Ala Leu Ser Val Ala Asn Ala Tyr Gly Ser
                420                 425                 430
Thr Gln Pro Ile Asp Arg Ala Arg Val Thr Thr Lys Thr Gly Leu Glu
                435                 440                 445
Trp Leu Gln Gly Asp Tyr Ser Val Asn Phe Asp Tyr Ser Lys Ala Ser
450                 455                 460
Ala Asp Gln Leu Arg Gly Glu Val Val Ala Ala Pro Lys Arg Asn Arg
465                 470                 475                 480
Tyr Ala Cys Glu Ala Phe Thr Ala Glu Glu Lys Ala Leu Lys Gly
                485                 490                 495
Lys Trp Val Tyr Phe Glu Trp Asp Gln Asp Leu Ser Phe Pro Cys
                500                 505                 510
Gly Ser Lys Val Arg Phe Asp Asn Val Gln Ala Ala Gly Gly Val Gly
        515                 520                 525
```

-continued

Val Val Met Ala Gly Lys Ala Glu Arg Tyr Thr Ile Gly Ile Gly
        530                 535                 540

Asn Thr Thr Ile Pro Gly Leu Arg Leu Thr Ala Ser Ser Thr Lys Asp
545                 550                 555                 560

Leu Glu Lys Ala Leu Ala Ala Gly Pro Val Thr Val Glu Met Asn Met
                565                 570                 575

Asp Tyr Lys Ala Ser Gly Arg Gly Pro His Ser His Ala Phe Asp Leu
            580                 585                 590

Asn Ser Ser Ala Arg Gly Gln His Gly Ser Asp Gly Phe Ile Lys
        595                 600                 605

Pro Asp Leu Ala Ala Pro Gly Thr Glu Ile Val Ser Ala Ala Val Gly
610                 615                 620

Met Gly Asn Lys Gly Val Ser Phe Thr Gly Thr Ser Met Ala Thr Pro
625                 630                 635                 640

His Val Ala Gly Val Ala Ala Leu Val Met Gln Ala His Gln Asp Tyr
                645                 650                 655

Asn Pro Gln Met Ile Lys Ala Ala Leu Met Asn Gly Ala Ser Thr Pro
            660                 665                 670

Ile Lys Asn Glu Gln Gly Ala Gln Tyr Ala Val Asp Arg Val Gly Thr
        675                 680                 685

Gly Met Val Asn Ala Arg Ala Ala Val Asp Lys Val Ile Ala Tyr
690                 695                 700

Asp Ala Lys Thr Pro Glu Arg Val Ser Thr Ala Phe Gly Val Leu Glu
705                 710                 715                 720

Tyr Thr Pro Asp Ser Gly Ile Gln Thr Val Gln Arg Glu Ile Val Leu
                725                 730                 735

Asp Asn Thr Asp Ser Gln Ala His Thr Tyr Thr Leu Asn Tyr Glu Ala
            740                 745                 750

Ser Thr Thr Ile Pro Gly Val Glu Tyr Ser Tyr Pro Gln Gln Val Ser
        755                 760                 765

Val Gly Ala Gly Glu Arg Lys Asn Val Thr Val Thr Val Arg Ile Asp
770                 775                 780

Pro Ser Lys Leu Glu Lys Thr Met Asp Pro Ala Met Ser Ala Asp Gln
785                 790                 795                 800

Val Ala Gln Asp Trp Thr Thr Gly Lys Thr Leu Ala Ala Gly Lys Arg
                805                 810                 815

Gln Tyr Ile Ala Ser Ala Ser Gly Arg Leu Ile Phe Ser Glu Asn Gly
            820                 825                 830

Arg Glu Ala Ile Arg Gln Ser Ile His Val Ala Pro Lys Pro Val Ser
        835                 840                 845

Lys Met Arg Val Asp Ala Ser Arg Ile Asp Tyr Lys Gly Thr Ala Asp
850                 855                 860

Lys Glu Ser Thr Val Thr Leu Arg Gly Thr Thr Leu Asn Gln Gly Gly
865                 870                 875                 880

Tyr Arg Ser Leu Leu Gly Ala Phe Glu Leu Gly Ala Val Ser Asp Arg
                885                 890                 895

Ile Pro Ser Gly Gln Leu Lys Leu Pro Ser Asn Gln Ala Val Asp Leu
            900                 905                 910

Gln Tyr Val Gly Ala Ala Ser Asp Ala Pro Ala Leu Lys Ala Ala Gly
        915                 920                 925

Lys Asn Pro Asn Asp Gly Ser Leu Phe Phe Gly Ile Ser Thr Trp Gly
930                 935                 940

Thr Trp Asp Ser Met His Trp Gly Arg Gln Val Gln Val Gln Ile Asp

```
            945                 950                 955                 960
        Thr Asn Asn Asp Ser Thr Ala Asp Tyr Val Leu Glu Val Thr Arg Glu
                        965                 970                 975
        Lys Gly Leu Asp Tyr Pro Leu Val Lys Val Trp Ser Ile Ser Gly Asn
                        980                 985                 990
        Ala Ser Thr Val Val Ala Arg Tyr Pro Leu Asn Ser Ala Trp Gly Asp
                        995                 1000                1005
        Thr Asp Thr Asn Ile Met Asp Thr Asn Thr Met Ile Leu Gly Val
            1010                1015                1020
        Pro Leu Lys Asp Leu Gly Leu Thr Ala Glu Lys Ala Gln Thr Ile
            1025                1030                1035
        Lys Tyr Thr Val Gln Thr Asp Thr Trp Tyr Asn Asp Gly Asn Pro
            1040                1045                1050
        Tyr Val Asp Thr Thr Ser Ala Ile Glu Tyr Ser Pro Phe Lys Pro
            1055                1060                1065
        Gly Val Trp Phe Thr Gly Glu Glu Ser Gly Val Pro Gly Leu Phe
            1070                1075                1080
        Val Asp Arg Asp Gly Gly Gln Leu Thr Val His Arg Lys Asn Asn
            1085                1090                1095
        Asn Lys Glu Arg Gln Ala Leu Phe Leu His Met His Asn Ala Thr
            1100                1105                1110
        Gly Asp Leu Ser Gly Arg Lys Thr Ala Asn Gly Val Ala Ala Gly
            1115                1120                1125
        Asp Arg Ala Gln Val Val Lys Val Ala Arg Thr Ile His Asp Ala
            1130                1135                1140
        Arg Phe Thr Asp Val Pro Ala Asp Asn Gln Phe Tyr Arg Glu Ile
            1145                1150                1155
        Thr Trp Ile Ala Ala Arg Gln Ile Asp Arg Gly Tyr Gln Asp Gly
            1160                1165                1170
        Thr Phe Arg Pro Leu Asn Asn Met Asp Arg Ala Thr Met Ala Ala
            1175                1180                1185
        Tyr Phe Tyr Arg Met Ser Gly Ser Pro Gln Tyr Thr Ala Pro Ser
            1190                1195                1200
        Thr Pro Ser Phe Ser Asp Val Pro Leu Asn His Pro Tyr Tyr Lys
            1205                1210                1215
        Glu Ile Glu Trp Met Lys Ala Gln Gly Ile Thr Thr Gly Trp Pro
            1220                1225                1230
        Asp Gly Thr Tyr Arg Pro Glu Gly Ser Val Asn Arg Asp Ala Met
            1235                1240                1245
        Ala Ala Phe Phe Tyr Arg Tyr Ala Gly Ser Pro Glu Tyr Thr Ala
            1250                1255                1260
        Pro Ala Gln Ala Arg Phe Thr Asp Val Pro Thr Asp Lys Gln Phe
            1265                1270                1275
        Tyr Arg Glu Ile Ser Trp Leu Ala Glu Gln Gly Val Thr Thr Gly
            1280                1285                1290
        Trp Pro Asp Gly Ser Phe Arg Pro Val Glu Pro Val His Arg Asp
            1295                1300                1305
        Ala Met Ala Ala Phe Val Tyr Arg Tyr Ser Thr Gly Val Leu Lys
            1310                1315                1320
        Glu Ser Pro Glu Ile
            1325

<210> SEQ ID NO 81
```

<211> LENGTH: 1328
<212> TYPE: PRT
<213> ORGANISM: Rothia mucilaginosa

<400> SEQUENCE: 81

```
Met Thr Thr Pro His Ala Pro Arg Arg Met Lys Ala Val Gly Ala
1               5                   10                  15

Thr Gly Leu Ser Ala Ala Leu Ala Leu Thr Leu Gly Ile Pro Ala Thr
            20                  25                  30

Phe Ser Ala Ala His Ala Gln Ser Pro Gln Val Glu Gly Ser Thr
        35                  40                  45

Ala Ser Ala Ser Gly Asp Ala Ala Ser Arg Ile Ser Pro Gly Leu Gln
    50                  55                  60

Lys Ala Glu Gly Gln Ile Thr Val Tyr Val Gln Phe Lys Gly Lys Gly
65                  70                  75                  80

Ala Tyr Glu Gln Thr Gln Ser Ala Ala Val Leu Ala Arg Lys Glu Ala
                85                  90                  95

Pro Ala Asn Arg Gln Ala Gln Val Gln Ala Ile Ala Ala Gln Val Gln
            100                 105                 110

Ser Gln Ala Gln Ser Val Ala Ala Ala Ser Gly Ala Lys Leu Met Tyr
        115                 120                 125

Thr Thr His Asn Ala Met Arg Gly Ala Ala Ile Thr Gly Asp Ala Ala
130                 135                 140

Gln Ile Arg Ala Leu Ala Glu Arg Pro Asp Val Glu Arg Ile Ser Pro
145                 150                 155                 160

Ile Ile Ala Lys Glu Arg Met Asn Ser Gly Ser Glu Ile Asp Thr Lys
                165                 170                 175

Thr Leu Ala Thr Trp Thr Arg Glu Asn Thr Gly Tyr Thr Gly Lys Gly
            180                 185                 190

Val Lys Ile Ala Val Val Asp Ser Gly Val Asp Tyr Thr His Ala Asp
        195                 200                 205

Phe Gly Gly Pro Gly Thr Val Asp Ser Tyr Leu Lys Ala Lys Ala Met
    210                 215                 220

Thr Glu Leu Pro Ser Ala Asp Ser Gly Leu Ile Asp Arg Asn Lys Phe
225                 230                 235                 240

Ile Gly Gly Ile Asp Leu Val Gly Asp Asp Tyr Asn Ala Ser Val Ala
                245                 250                 255

Glu Lys Ser Thr Pro Gln Pro Asp Asn Asn Pro Leu Asp Cys Arg Pro
            260                 265                 270

Asp Gly Phe Gly Ser Gly Gly His Gly Thr His Val Ala Gly Thr Ala
        275                 280                 285

Ala Gly Tyr Gly Val Thr Ala Asn Gly Thr Thr Tyr Arg Gly Asp Tyr
    290                 295                 300

Lys Asn Leu Thr Glu Glu Gln Leu Lys Gly Met Ser Ile Gly Pro Gly
305                 310                 315                 320

Thr Ala Pro Glu Ala Gln Ile Leu Ala Ile Arg Val Phe Gly Cys Tyr
                325                 330                 335

Gly Asn Ser Ser Val Val Met Lys Ala Leu Asp Thr Val Met Asp Pro
            340                 345                 350

Asn Gly Asp Gly Asp Phe Ser Asp Arg Ala Asp Ile Val Asn Leu Ser
        355                 360                 365

Leu Gly Gly Glu Phe Ala Pro Ala Asp Asp Pro Glu Ser Tyr Met Ile
    370                 375                 380

Asn Thr Met Ala Arg Gln Gly Val Phe Thr Val Ala Ala Ala Gly Asn
```

-continued

```
            385                 390                 395                 400
        Ala Asn Asn Tyr Asn Gly Val Gly Asp Thr Tyr Ser Asp Ser Gly Ser
                        405                 410                 415

Pro Ala Asn Ala Ala Ala Ala Leu Ser Val Ala Asn Ala Tyr Gly Ser
                        420                 425                 430

Thr Gln Pro Ile Asp Arg Ala Arg Val Thr Thr Lys Thr Gly Leu Glu
                        435                 440                 445

Trp Leu Gln Gly Asp Tyr Ser Val Asn Phe Asp Tyr Ser Lys Ala Ser
                450                 455                 460

Ala Asp Gln Leu Arg Gly Glu Val Val Ala Pro Lys Arg Asn Arg
        465                 470                 475                 480

Tyr Ala Cys Glu Ala Phe Thr Ala Glu Glu Ala Lys Ala Leu Lys Gly
                        485                 490                 495

Lys Trp Val Tyr Phe Glu Trp Asp Gln Asp Leu Ser Phe Pro Cys
                        500                 505                 510

Gly Ser Lys Val Arg Phe Asp Asn Val Gln Ala Gly Gly Val Gly
                    515                 520                 525

Val Val Met Ala Gly Lys Ala Glu Arg Tyr Thr Ile Gly Ile Gly Gly
                530                 535                 540

Asn Thr Thr Ile Pro Gly Leu Arg Leu Thr Ala Ser Ser Thr Lys Asp
        545                 550                 555                 560

Leu Glu Lys Ala Leu Ala Ala Gly Pro Val Thr Val Glu Met Asn Met
                        565                 570                 575

Asp Tyr Lys Ala Ser Gly Arg Gly Pro His Ser His Ala Phe Asp Leu
                        580                 585                 590

Asn Ser Ser Ser Ala Arg Gly Gln His Gly Ser Asp Gly Phe Ile Lys
                    595                 600                 605

Pro Asp Leu Ala Ala Pro Gly Thr Glu Ile Val Ser Ala Ala Val Gly
                    610                 615                 620

Met Gly Asn Lys Gly Val Ser Phe Thr Gly Thr Ser Met Ala Thr Pro
        625                 630                 635                 640

His Val Ala Gly Val Ala Ala Leu Val Met Gln Ala His Gln Asp Tyr
                        645                 650                 655

Asn Pro Gln Met Ile Lys Ala Ala Leu Met Asn Gly Ala Ser Thr Pro
                        660                 665                 670

Ile Lys Asn Glu Gln Gly Ala Gln Tyr Ala Val Asp Arg Val Gly Thr
                    675                 680                 685

Gly Met Val Asn Ala Arg Ala Ala Val Asp Ala Lys Val Ile Ala Tyr
                690                 695                 700

Asp Ala Lys Thr Pro Glu Arg Val Ser Thr Ala Phe Gly Val Leu Glu
        705                 710                 715                 720

Tyr Thr Pro Asp Ser Gly Ile Gln Thr Val Gln Arg Glu Ile Val Leu
                        725                 730                 735

Asp Asn Thr Asp Ser Gln Ala His Thr Tyr Thr Leu Asn Tyr Glu Ala
                        740                 745                 750

Ser Thr Thr Ile Pro Gly Val Glu Tyr Ser Tyr Pro Gln Gln Val Ser
                    755                 760                 765

Val Gly Ala Gly Glu Arg Lys Asn Val Thr Val Thr Val Arg Ile Asp
                770                 775                 780

Pro Ser Lys Leu Glu Lys Thr Met Asp Pro Ala Met Ser Ala Asp Gln
        785                 790                 795                 800

Val Ala Gln Asp Trp Thr Thr Gly Lys Thr Leu Ala Ala Gly Lys Arg
                        805                 810                 815
```

-continued

Gln Tyr Ile Ala Ser Ala Ser Gly Arg Leu Ile Phe Ser Glu Asn Gly
            820                 825                 830

Arg Glu Ala Ile Arg Gln Ser Ile His Val Ala Pro Lys Pro Val Ser
        835                 840                 845

Lys Met Arg Val Asp Ala Ser Arg Ile Asp Tyr Lys Gly Thr Ala Asp
    850                 855                 860

Lys Glu Ser Thr Val Thr Leu Arg Gly Thr Thr Leu Asn Gln Gly Gly
865                 870                 875                 880

Tyr Arg Ser Leu Leu Gly Ala Phe Glu Leu Gly Ala Val Ser Asp Arg
                885                 890                 895

Ile Pro Ser Gly Gln Leu Lys Leu Pro Ser Asn Gln Ala Val Asp Leu
            900                 905                 910

Gln Tyr Val Gly Ala Ala Ser Asp Ala Pro Ala Leu Lys Ala Ala Gly
        915                 920                 925

Lys Asn Pro Asn Asp Gly Ser Leu Phe Phe Gly Ile Ser Thr Trp Gly
    930                 935                 940

Thr Trp Asp Ser Met His Trp Gly Arg Gln Val Gln Val Gln Ile Asp
945                 950                 955                 960

Thr Asn Asn Asp Ser Thr Ala Asp Tyr Val Leu Glu Val Thr Arg Glu
                965                 970                 975

Lys Gly Leu Asp Tyr Pro Leu Val Lys Val Trp Ser Ile Ser Gly Asn
            980                 985                 990

Ala Ser Thr Val Val Ala Arg Tyr Pro Leu Asn Ser Ala Trp Gly Asp
        995                1000                1005

Thr Asp Thr Asn Ile Met Asp Thr Asn Thr Met Ile Leu Gly Val
    1010                1015                1020

Pro Leu Lys Asp Leu Gly Leu Thr Ala Glu Lys Ala Gln Thr Ile
    1025                1030                1035

Lys Tyr Thr Val Gln Thr Asp Thr Trp Tyr Asn Asp Gly Asn Pro
    1040                1045                1050

Tyr Val Asp Thr Thr Ser Ala Ile Glu Tyr Ser Pro Phe Lys Pro
    1055                1060                1065

Gly Val Trp Phe Thr Gly Glu Glu Ser Gly Val Pro Gly Leu Phe
    1070                1075                1080

Val Asp Arg Asp Gly Gly Gln Leu Thr Val His Arg Lys Asn Asn
    1085                1090                1095

Asn Lys Glu Arg Gln Ala Leu Phe Leu His Met His Asn Ala Thr
    1100                1105                1110

Gly Asp Leu Ser Gly Arg Lys Thr Ala Asn Gly Val Ala Ala Gly
    1115                1120                1125

Asp Arg Ala Gln Val Val Lys Val Ala Arg Thr Ile His Asp Ala
    1130                1135                1140

Arg Phe Thr Asp Val Pro Ala Asp Asn Gln Phe Tyr Arg Glu Ile
    1145                1150                1155

Thr Trp Ile Ala Ala Arg Gln Ile Asp Arg Gly Tyr Gln Asp Gly
    1160                1165                1170

Thr Phe Arg Pro Leu Asn Asn Met Asp Arg Ala Thr Met Ala Ala
    1175                1180                1185

Tyr Phe Tyr Arg Met Ser Gly Ser Pro Gln Tyr Thr Ala Pro Ser
    1190                1195                1200

Thr Pro Ser Phe Ser Asp Val Pro Leu Asn His Pro Tyr Tyr Lys
    1205                1210                1215

```
Glu Ile Glu Trp Met Lys Ala Gln Gly Ile Thr Thr Gly Trp Pro
    1220                1225                1230

Asp Gly Thr Tyr Arg Pro Glu Gly Ser Val Asn Arg Asp Ala Met
    1235                1240                1245

Ala Ala Phe Phe Tyr Arg Tyr Ala Gly Ser Pro Glu Tyr Thr Ala
    1250                1255                1260

Pro Ala Gln Ala Arg Phe Thr Asp Val Pro Thr Asp Lys Gln Phe
    1265                1270                1275

Tyr Arg Glu Ile Ser Trp Leu Ala Glu Gln Gly Val Thr Thr Gly
    1280                1285                1290

Trp Pro Asp Gly Ser Phe Arg Pro Val Glu Pro Val His Arg Asp
    1295                1300                1305

Ala Met Ala Ala Phe Val Tyr Arg Tyr Ser Thr Gly Val Leu Lys
    1310                1315                1320

Glu Ser Pro Glu Ile
    1325

<210> SEQ ID NO 82
<211> LENGTH: 1328
<212> TYPE: PRT
<213> ORGANISM: Rothia mucilaginosa

<400> SEQUENCE: 82

Met Thr Thr Pro His Ala Pro Arg Arg Met Lys Ala Val Gly Ala
1               5                   10                  15

Thr Gly Leu Ser Ala Ala Leu Ala Leu Thr Leu Gly Val Pro Ala Thr
                20                  25                  30

Phe Ser Ala Ala His Ala Gln Ser Pro Gln Gln Val Glu Gly Ser Thr
                35                  40                  45

Ala Ser Ala Ser Gly Asp Ala Ser Arg Ile Ser Pro Gly Leu Gln
    50                  55                  60

Lys Ala Glu Gly Gln Ile Thr Val Tyr Val Gln Phe Lys Gly Lys Gly
65                  70                  75                  80

Ala Tyr Glu Gln Thr Gln Ser Ala Ala Val Leu Ala Arg Lys Glu Ala
                85                  90                  95

Pro Ala Asn Arg Gln Ala Gln Val Gln Ala Ile Ala Ala Gln Val Gln
                100                 105                 110

Ser Gln Ala Gln Ser Val Ala Ala Ser Gly Ala Lys Leu Met Tyr
    115                 120                 125

Thr Thr His Asn Ala Met Arg Gly Ala Ala Ile Thr Gly Asp Ala Ala
    130                 135                 140

Gln Ile Arg Ala Leu Ala Glu Arg Pro Asp Val Glu Arg Ile Ser Pro
145                 150                 155                 160

Ile Ile Ala Lys Glu Arg Met Asn Ser Gly Ser Glu Ile Asp Thr Lys
                165                 170                 175

Thr Leu Ala Thr Trp Thr Arg Glu Asn Thr Gly Tyr Thr Gly Lys Gly
                180                 185                 190

Val Lys Ile Ala Val Val Asp Ser Gly Val Asp Tyr Thr His Ala Asp
        195                 200                 205

Phe Gly Gly Pro Gly Thr Val Asp Ser Tyr Leu Lys Ala Lys Ala Met
    210                 215                 220

Thr Glu Leu Pro Ser Ala Asp Ser Gly Leu Ile Asp Arg Asn Lys Phe
225                 230                 235                 240

Ile Gly Gly Ile Asp Leu Val Gly Asp Asp Tyr Asn Ala Ser Val Ala
                245                 250                 255
```

```
Glu Lys Ser Thr Pro Gln Pro Asp Asn Asn Pro Leu Asp Cys Arg Pro
            260                 265                 270

Asp Gly Phe Gly Ser Gly Gly His Gly Thr His Val Ala Gly Thr Ala
            275                 280                 285

Ala Gly Tyr Gly Val Thr Ala Asn Gly Thr Thr Tyr Arg Gly Asp Tyr
            290                 295                 300

Lys Asn Leu Thr Glu Glu Gln Leu Lys Gly Met Ser Ile Gly Pro Gly
305                 310                 315                 320

Thr Ala Pro Asp Ala Gln Ile Leu Ala Ile Arg Val Phe Gly Cys Tyr
            325                 330                 335

Gly Asn Ser Ser Val Val Met Lys Ala Leu Asp Thr Val Met Asp Pro
            340                 345                 350

Asn Gly Asp Gly Asp Phe Ser Asp Arg Ala Asp Ile Val Asn Leu Ser
            355                 360                 365

Leu Gly Gly Glu Phe Ala Pro Ala Asp Asp Pro Glu Ser Tyr Met Ile
            370                 375                 380

Asn Thr Met Ala Arg Gln Gly Val Phe Thr Val Ala Ala Ala Gly Asn
385                 390                 395                 400

Ala Asn Asn Tyr Asn Gly Val Gly Asp Thr Tyr Ser Asp Ser Gly Ser
            405                 410                 415

Pro Ala Asn Ala Ala Ala Leu Ser Val Ala Asn Ala Tyr Gly Ser
            420                 425                 430

Thr Gln Pro Ile Asp Arg Ala Arg Val Thr Thr Lys Thr Gly Leu Glu
            435                 440                 445

Trp Leu Gln Gly Asp Tyr Ser Val Asn Phe Asp Tyr Ser Lys Ala Ser
            450                 455                 460

Ala Asp Gln Leu Arg Gly Glu Val Val Ala Ala Pro Lys Arg Asn Arg
465                 470                 475                 480

Tyr Ala Cys Glu Ala Phe Thr Ala Glu Glu Ala Lys Ala Leu Lys Gly
            485                 490                 495

Lys Trp Val Tyr Phe Asp Trp Asp Gln Asp Asp Leu Thr Phe Pro Cys
            500                 505                 510

Gly Ser Lys Val Arg Phe Asp Asn Val Gln Ala Ala Gly Gly Val Gly
            515                 520                 525

Val Val Met Ala Gly Lys Ala Glu Arg Tyr Thr Ile Gly Ile Gly Gly
            530                 535                 540

Asn Ala Thr Ile Pro Gly Leu Arg Leu Thr Ala Ser Ser Thr Lys Asp
545                 550                 555                 560

Leu Glu Lys Ala Leu Ala Ala Gly Pro Val Thr Val Glu Met Asn Leu
            565                 570                 575

Asp Tyr Lys Ala Ser Gly Arg Gly Pro His Ser His Ala Phe Asp Leu
            580                 585                 590

Asn Ser Ser Ser Ala Arg Gly Gln His Gly Ser Asp Gly Phe Ile Lys
            595                 600                 605

Pro Asp Leu Ala Ala Pro Gly Thr Glu Ile Val Ser Ala Ala Val Gly
            610                 615                 620

Thr Gly Asn Lys Gly Val Ser Phe Thr Gly Thr Ser Met Ala Thr Pro
625                 630                 635                 640

His Val Ala Gly Val Ala Ala Leu Val Met Gln Ala His Gln Asp Tyr
            645                 650                 655

Asn Pro Gln Met Ile Lys Ala Ala Leu Met Asn Gly Ala Ser Thr Pro
            660                 665                 670
```

```
Ile Lys Asn Glu Gln Gly Ala Gln Tyr Ala Val Asp Arg Val Gly Thr
            675                 680                 685

Gly Met Val Asn Ala Arg Ala Val Asp Ala Lys Val Ile Ala Tyr
    690                 695                 700

Asp Ala Lys Thr Pro Glu Arg Val Ser Thr Ala Phe Gly Val Leu Glu
705                 710                 715                 720

Tyr Thr Pro Asp Ser Gly Ile Gln Thr Val Gln Arg Glu Ile Val Leu
                725                 730                 735

Asp Asn Thr Asp Ser Gln Ala His Thr Tyr Thr Leu Ser Tyr Glu Ala
                740                 745                 750

Ser Thr Thr Ile Pro Gly Val Glu Tyr Ser Tyr Pro Gln Gln Val Ser
        755                 760                 765

Val Gly Ala Gly Glu Arg Lys Asn Val Thr Val Thr Val Arg Ile Asp
    770                 775                 780

Pro Ser Lys Leu Glu Lys Thr Met Asp Pro Ala Met Ser Ala Asp Gln
785                 790                 795                 800

Val Ala Gln Asp Trp Thr Thr Gly Lys Thr Leu Ala Ala Gly Lys Arg
                805                 810                 815

Gln Tyr Ile Ala Ser Ala Ser Gly Arg Leu Ile Phe Ser Glu Asn Gly
                820                 825                 830

Arg Glu Ala Ile Arg Gln Ser Ile His Val Ala Pro Lys Pro Val Ser
            835                 840                 845

Lys Met Arg Val Asp Ala Ser Arg Ile Asp Tyr Lys Gly Ile Ser Asp
    850                 855                 860

Lys Glu Ser Thr Val Thr Leu Arg Gly Thr Thr Leu Asn Gln Gly Gly
865                 870                 875                 880

Tyr Arg Ser Leu Leu Gly Ala Phe Glu Leu Gly Ala Val Ser Asp Arg
                885                 890                 895

Ile Pro Ser Gly Gln Leu Lys Leu Pro Ser Asn Gln Ser Val Asp Leu
                900                 905                 910

Gln Tyr Val Gly Ala Ala Ser Asp Ala Pro Ala Leu Lys Ala Ala Gly
            915                 920                 925

Lys Asn Pro Asn Asp Gly Ser Leu Phe Phe Gly Ile Ser Thr Trp Gly
    930                 935                 940

Thr Trp Asp Ser Met His Trp Gly Arg Gln Val Gln Val Gln Ile Asp
945                 950                 955                 960

Thr Asn Asn Asp Ser Thr Ala Asp Tyr Val Leu Glu Val Thr Arg Glu
                965                 970                 975

Lys Gly Leu Asp Tyr Pro Leu Val Lys Val Trp Ser Ile Ser Gly Asn
            980                 985                 990

Ala Ser Thr Val Val Ala Arg Tyr Pro Leu Asn Ser Ala Trp Gly Asp
    995                 1000                1005

Thr Asp Thr Asn Ile Met Asp Thr Asn Thr Met Ile Leu Gly Val
    1010                1015                1020

Pro Leu Lys Asp Leu Gly Leu Thr Ala Glu Lys Ala Gln Ser Ile
    1025                1030                1035

Lys Tyr Thr Val Gln Thr Asp Thr Trp His Asn Glu Gly Asn Ser
    1040                1045                1050

Tyr Val Asp Thr Thr Ser Thr Ile Glu Tyr Ser Pro Phe Asn Pro
    1055                1060                1065

Gly Val Trp Phe Thr Gly Glu Ser Gly Val Pro Gly Leu Phe
    1070                1075                1080

Val Asp Arg Asp Gly Gly Gln Leu Thr Val His Arg Lys Asn Asn
```

1085                1090                1095

Asn Lys Glu Arg Gln Ala Leu Phe Leu His Met His Asn Ala Thr
        1100                1105                1110

Gly Asp Leu Ser Gly Arg Lys Thr Ala Asn Gly Val Ala Ala Gly
        1115                1120                1125

Asp Arg Ala Gln Val Val Lys Val Ala Arg Thr Ile His Asp Ala
    1130                1135                1140

Arg Phe Thr Asp Val Pro Ala Asp Asn Gln Phe Tyr Arg Glu Ile
    1145                1150                1155

Thr Trp Ile Ala Ala Arg Gln Ile Asp Arg Gly Tyr Gln Asp Gly
    1160                1165                1170

Thr Phe Arg Pro Leu Asn Asn Met Asp Arg Ala Thr Met Ala Ala
    1175                1180                1185

Tyr Phe Tyr Arg Met Ser Gly Ser Pro Gln Tyr Thr Ala Pro Ser
    1190                1195                1200

Thr Pro Ser Phe Ser Asp Val Pro Leu Asn His Pro Tyr Tyr Lys
    1205                1210                1215

Glu Ile Glu Trp Met Lys Ala Gln Gly Ile Thr Thr Gly Trp Pro
    1220                1225                1230

Asp Gly Thr Tyr Arg Pro Glu Gly Ser Val Asn Arg Asp Ala Met
    1235                1240                1245

Ala Ala Phe Phe Tyr Arg Tyr Ala Gly Ser Pro Glu Tyr Thr Ala
    1250                1255                1260

Pro Ala Gln Ala Arg Phe Thr Asp Val Pro Thr Asp Lys Gln Phe
    1265                1270                1275

Tyr Arg Glu Ile Ser Trp Leu Ala Glu Gln Gly Val Thr Thr Gly
    1280                1285                1290

Trp Pro Asp Gly Ser Phe Arg Pro Val Glu Pro Val His Arg Asp
    1295                1300                1305

Ala Met Ala Ala Phe Val Tyr Arg Tyr Ser Thr Gly Val Leu Lys
    1310                1315                1320

Glu Ser Pro Glu Ile
    1325

<210> SEQ ID NO 83
<211> LENGTH: 1328
<212> TYPE: PRT
<213> ORGANISM: Rothia mucilaginosa

<400> SEQUENCE: 83

Met Thr Thr Pro His Ala Pro Arg Arg Arg Met Lys Ala Val Gly Ala
1               5                   10                  15

Thr Gly Leu Ser Ala Ala Leu Ala Leu Thr Leu Gly Val Pro Ala Thr
            20                  25                  30

Phe Ser Ala Ala His Ala Gln Ser Pro Gln Gln Val Glu Gly Ser Thr
        35                  40                  45

Ala Ser Ala Ser Gly Asp Ala Thr Ser Arg Ile Ser Pro Gly Leu Gln
    50                  55                  60

Lys Ala Glu Gly Gln Ile Thr Val Tyr Val Gln Phe Lys Gly Lys Gly
65                  70                  75                  80

Ala Tyr Glu Gln Thr Gln Ser Ala Ala Val Leu Ala Arg Lys Glu Ala
                85                  90                  95

Pro Ala Asn Arg Gln Ala Gln Val Gln Ala Ile Ala Ala Gln Val Gln
            100                 105                 110

```
Ser Gln Ala Gln Ser Val Ala Ala Ser Gly Ala Lys Leu Met Tyr
            115                 120                 125

Thr Thr His Asn Ala Met Arg Gly Ala Ala Ile Thr Gly Asp Ala Ala
130                 135                 140

Gln Ile Arg Ala Leu Ala Glu Arg Pro Asp Val Glu Arg Ile Ser Pro
145                 150                 155                 160

Ile Ile Ala Lys Glu Arg Met Asn Ser Gly Ser Glu Ile Asp Thr Lys
                165                 170                 175

Thr Leu Ala Thr Trp Thr Arg Glu Asn Thr Gly Tyr Thr Gly Lys Gly
            180                 185                 190

Val Lys Ile Ala Ile Val Asp Ser Gly Val Asp Tyr Thr His Ala Asp
                195                 200                 205

Phe Gly Gly Pro Gly Thr Val Asp Ser Tyr Leu Lys Ala Lys Ala Met
            210                 215                 220

Thr Glu Leu Pro Thr Ala Asp Ser Gly Leu Ile Asp Arg Asn Lys Phe
225                 230                 235                 240

Ile Gly Gly Ile Asp Leu Val Gly Asp Tyr Asn Ala Ser Val Ala
                245                 250                 255

Glu Lys Ser Thr Pro Gln Pro Asp Asn Asn Pro Leu Asp Cys Arg Pro
                260                 265                 270

Asp Gly Phe Gly Ser Gly Gly His Gly Thr His Val Ala Gly Thr Ala
            275                 280                 285

Ala Gly Tyr Gly Val Thr Ala Asn Gly Thr Thr Tyr Arg Gly Asp Tyr
            290                 295                 300

Lys Asn Leu Thr Glu Glu Gln Leu Lys Gly Met Ser Ile Gly Pro Gly
305                 310                 315                 320

Thr Ala Pro Asp Ala Gln Ile Leu Ala Ile Arg Val Phe Gly Cys Tyr
                325                 330                 335

Gly Asn Ser Ser Val Val Met Lys Ala Leu Asp Thr Val Met Asp Pro
            340                 345                 350

Asn Gly Asp Gly Asp Phe Ser Asp Arg Ala Asp Ile Val Asn Leu Ser
            355                 360                 365

Leu Gly Gly Glu Phe Ala Pro Ala Asp Pro Glu Ser Tyr Met Ile
370                 375                 380

Asn Thr Met Ala Arg Gln Gly Val Phe Thr Val Ala Ala Ala Gly Asn
385                 390                 395                 400

Ala Asn Asn Tyr Asn Gly Val Gly Asp Thr Tyr Ser Asp Ser Gly Ser
                405                 410                 415

Pro Ala Asn Ala Ala Ala Leu Ser Val Ala Asn Ala Tyr Gly Ser
                420                 425                 430

Thr Gln Pro Ile Asp Arg Ala Arg Val Thr Thr Lys Thr Gly Leu Glu
            435                 440                 445

Trp Leu Gln Gly Asp Tyr Ser Val Asn Phe Asp Tyr Ser Lys Ala Ser
            450                 455                 460

Ala Asp Gln Leu Arg Gly Glu Val Val Ala Pro Lys Arg Asn Arg
465                 470                 475                 480

Tyr Ala Cys Glu Ala Phe Thr Ala Glu Glu Ala Lys Ala Leu Lys Gly
                485                 490                 495

Lys Trp Val Tyr Phe Glu Trp Asp Gln Asp Leu Thr Phe Pro Cys
            500                 505                 510

Gly Ser Lys Val Arg Phe Asp Asn Val Gln Ala Gly Gly Val Gly
            515                 520                 525

Val Val Met Ala Gly Lys Ala Glu Arg Tyr Thr Ile Gly Ile Gly Gly
```

```
              530                 535                 540
Asn Ala Thr Ile Pro Gly Leu Arg Leu Thr Ala Ser Ser Thr Lys Asp
545                 550                 555                 560

Leu Glu Lys Ala Leu Ala Ala Gly Pro Val Thr Val Glu Met Asn Leu
                    565                 570                 575

Asp Tyr Lys Ala Ser Gly Arg Gly Pro His Ser His Ala Phe Asp Leu
                    580                 585                 590

Asn Ser Ser Ser Ala Arg Gly Gln His Gly Ser Asp Gly Phe Ile Lys
                595                 600                 605

Pro Asp Leu Ala Ala Pro Gly Thr Glu Ile Val Ser Ala Ala Val Gly
            610                 615                 620

Thr Gly Asn Lys Gly Val Ser Phe Thr Gly Thr Ser Met Ala Thr Pro
625                 630                 635                 640

His Val Thr Gly Ile Ala Ala Leu Val Met Gln Ala His Gln Asp Tyr
                    645                 650                 655

Asn Pro Gln Met Ile Lys Ala Ala Leu Met Asn Gly Ala Ser Thr Pro
                660                 665                 670

Ile Lys Asn Glu Gln Gly Ala Gln Tyr Ala Val Asp Arg Val Gly Thr
            675                 680                 685

Gly Met Val Asn Ala Arg Ala Ala Val Asp Ala Lys Val Ile Ala Tyr
            690                 695                 700

Asp Ala Lys Thr Pro Glu Arg Val Ser Thr Ala Phe Gly Val Leu Glu
705                 710                 715                 720

Tyr Thr Pro Asp Ser Gly Ile Gln Thr Val Gln Arg Glu Ile Val Leu
                    725                 730                 735

Asp Asn Thr Asp Ser Gln Ala His Thr Tyr Thr Leu Asn Tyr Glu Ala
                740                 745                 750

Ser Thr Thr Ile Pro Gly Val Glu Tyr Ser Tyr Pro Gln Gln Val Ser
            755                 760                 765

Val Gly Ala Gly Glu Arg Lys Asn Val Thr Val Thr Val Arg Ile Asp
        770                 775                 780

Pro Ser Lys Leu Glu Lys Thr Met Asp Pro Ala Met Ser Ala Asp Gln
785                 790                 795                 800

Val Ala Gln Asp Trp Thr Thr Gly Lys Thr Leu Ala Ala Gly Lys Arg
                    805                 810                 815

Gln Tyr Ile Ala Ser Ala Ser Gly Arg Leu Ile Phe Ser Glu Asn Gly
                820                 825                 830

Arg Glu Ala Ile Arg Gln Ser Ile His Val Ala Pro Lys Pro Val Ser
            835                 840                 845

Lys Met Arg Val Asp Ala Ser Arg Ile Asp Tyr Lys Gly Ile Ala Asp
850                 855                 860

Lys Glu Ser Thr Val Thr Leu Arg Gly Thr Thr Leu Asn Gln Gly Gly
865                 870                 875                 880

Tyr Arg Ser Leu Leu Gly Ala Phe Glu Leu Gly Ala Val Ser Asp Arg
                    885                 890                 895

Ile Pro Ser Gly Gln Leu Lys Leu Pro Ser Asn Gln Ala Val Asp Leu
                900                 905                 910

Gln Tyr Val Gly Ala Ala Ser Asp Ala Pro Ala Leu Lys Ala Ala Gly
            915                 920                 925

Lys Asn Pro Asn Asp Gly Ser Leu Phe Phe Gly Ile Ser Thr Trp Gly
            930                 935                 940

Thr Trp Asp Ser Met His Trp Gly Arg Gln Val Gln Val Gln Ile Asp
945                 950                 955                 960
```

```
Thr Asn Asn Asp Ser Thr Ala Asp Tyr Val Leu Glu Val Thr Arg Glu
            965                 970                 975

Lys Gly Leu Asp Tyr Pro Leu Val Lys Val Trp Ser Ile Ser Gly Asn
            980                 985                 990

Ala Ser Thr Val Val Ala Arg Tyr Pro Leu Asn Ser Ala Trp Gly Asp
        995                 1000                1005

Thr Asp Thr Asn Ile Met Asp Thr Asn Thr Met Ile Leu Gly Val
    1010                1015                1020

Pro Leu Lys Asp Leu Gly Leu Thr Ala Glu Lys Ala Gln Ser Ile
    1025                1030                1035

Lys Tyr Thr Val Gln Thr Asp Thr Trp Tyr Asn Asp Gly Asn Pro
    1040                1045                1050

Tyr Val Asp Thr Thr Ser Ala Ile Glu Tyr Ser Pro Phe Asn Pro
    1055                1060                1065

Gly Val Trp Phe Thr Gly Glu Glu Ser Gly Val Pro Gly Leu Phe
    1070                1075                1080

Val Asp Arg Asp Gly Gly Gln Leu Thr Val His Arg Lys Asn Asn
    1085                1090                1095

Asn Lys Glu Arg Gln Ala Leu Phe Leu His Met His Asn Ala Thr
    1100                1105                1110

Gly Asp Leu Ser Gly Arg Lys Thr Ala Asn Gly Val Ala Ala Gly
    1115                1120                1125

Asp Arg Ala Gln Val Val Lys Val Ala Arg Thr Ile His Asp Ala
    1130                1135                1140

Arg Phe Thr Asp Val Pro Ala Asp Asn Gln Phe Tyr Arg Glu Ile
    1145                1150                1155

Thr Trp Ile Ala Ala Arg Gln Ile Asp Arg Gly Tyr Gln Asp Gly
    1160                1165                1170

Thr Phe Arg Pro Leu Asn Asn Met Asp Arg Ala Thr Met Ala Ala
    1175                1180                1185

Tyr Phe Tyr Arg Met Ser Gly Ser Pro Gln Tyr Thr Ala Pro Ser
    1190                1195                1200

Thr Pro Ser Phe Ser Asp Val Pro Leu Asn His Pro Tyr Tyr Lys
    1205                1210                1215

Glu Ile Glu Trp Met Lys Ala Gln Gly Ile Thr Thr Gly Trp Pro
    1220                1225                1230

Asp Gly Thr Tyr Arg Pro Glu Gly Ser Val Asn Arg Asp Ala Met
    1235                1240                1245

Ala Ala Phe Phe Tyr Arg Tyr Ala Gly Ser Pro Glu Tyr Thr Ala
    1250                1255                1260

Pro Ala Gln Ala Arg Phe Thr Asp Val Pro Thr Asp Lys Gln Phe
    1265                1270                1275

Tyr Arg Glu Ile Ser Trp Leu Ala Glu Gln Gly Val Thr Thr Gly
    1280                1285                1290

Trp Pro Asp Gly Ser Phe Arg Pro Val Glu Pro Val His Arg Asp
    1295                1300                1305

Ala Met Ala Ala Phe Val Tyr Arg Tyr Ser Thr Gly Val Leu Lys
    1310                1315                1320

Glu Ser Pro Glu Ile
    1325

<210> SEQ ID NO 84
<211> LENGTH: 1328
```

<212> TYPE: PRT
<213> ORGANISM: Rothia mucilaginosa

<400> SEQUENCE: 84

Met Thr Thr Pro His Ala Pro Arg Arg Met Lys Ala Val Gly Ala
1               5                   10                  15

Thr Gly Leu Ser Ala Ala Leu Ala Leu Thr Leu Gly Val Pro Ala Thr
            20                  25                  30

Phe Ser Ala Ala His Ala Gln Ser Pro Gln Gln Val Glu Gly Ser Thr
            35                  40                  45

Ala Ser Ala Ser Gly Asp Ala Thr Ser Arg Ile Ser Pro Gly Leu Gln
        50                  55                  60

Lys Ala Glu Gly Gln Ile Thr Val Tyr Val Gln Phe Lys Gly Lys Gly
65                  70                  75                  80

Ala Tyr Glu Gln Thr Gln Ser Ala Ala Val Leu Ala Arg Lys Glu Ala
                85                  90                  95

Pro Ala Asn Arg Gln Ala Gln Val Gln Ala Ile Ala Ala Gln Val Gln
            100                 105                 110

Ser Gln Ala Gln Ser Val Ala Ala Ser Gly Ala Lys Leu Met Tyr
            115                 120                 125

Thr Thr His Asn Ala Met Arg Gly Ala Ala Ile Thr Gly Asp Ala Ala
130                 135                 140

Gln Ile Arg Ala Leu Ala Glu Arg Pro Asp Val Glu Arg Ile Ser Pro
145                 150                 155                 160

Ile Ile Ala Lys Glu Arg Met Asn Ser Gly Ser Glu Ile Asp Thr Lys
                165                 170                 175

Thr Leu Ala Thr Trp Thr Arg Glu Asn Thr Gly Tyr Thr Gly Lys Gly
            180                 185                 190

Val Lys Ile Ala Ile Val Asp Ser Gly Val Asp Tyr Thr His Ala Asp
        195                 200                 205

Phe Gly Gly Pro Gly Thr Val Asp Ser Tyr Leu Lys Ala Lys Ala Met
    210                 215                 220

Thr Glu Leu Pro Thr Ala Asp Ser Gly Leu Ile Asp Arg Asn Lys Phe
225                 230                 235                 240

Ile Gly Gly Ile Asp Leu Val Gly Asp Asp Tyr Asn Ala Ser Val Ala
                245                 250                 255

Glu Lys Ser Thr Pro Gln Pro Asp Asn Asn Pro Leu Asp Cys Arg Pro
            260                 265                 270

Asp Gly Phe Gly Ser Gly Gly His Gly Thr His Val Ala Gly Thr Ala
        275                 280                 285

Ala Gly Tyr Gly Val Thr Ala Asn Gly Thr Thr Tyr Arg Gly Asp Tyr
    290                 295                 300

Lys Asn Leu Thr Glu Glu Gln Leu Lys Gly Met Ser Ile Gly Pro Gly
305                 310                 315                 320

Thr Ala Pro Asp Ala Gln Ile Leu Ala Ile Arg Val Phe Gly Cys Tyr
                325                 330                 335

Gly Asn Ser Ser Val Val Met Lys Ala Leu Asp Thr Val Met Asp Pro
            340                 345                 350

Asn Gly Asp Gly Asp Phe Ser Arg Ala Asp Ile Val Asn Leu Ser
        355                 360                 365

Leu Gly Gly Glu Phe Ala Pro Ala Asp Pro Glu Ser Tyr Met Ile
    370                 375                 380

Asn Thr Met Ala Arg Gln Gly Val Phe Thr Val Ala Ala Ala Gly Asn
385                 390                 395                 400

-continued

Ala Asn Asn Tyr Asn Gly Val Gly Asp Thr Tyr Ser Asp Ser Gly Ser
            405                 410                 415

Pro Ala Asn Ala Ala Ala Leu Ser Val Ala Asn Ala Tyr Gly Ser
        420                 425                 430

Thr Gln Pro Ile Asp Arg Ala Arg Val Thr Lys Thr Gly Leu Glu
        435                 440                 445

Trp Leu Gln Gly Asp Tyr Ser Val Asn Phe Asp Tyr Ser Lys Ala Ser
    450                 455                 460

Ala Asp Gln Leu Arg Gly Glu Val Val Ala Ala Pro Lys Arg Asn Arg
465                 470                 475                 480

Tyr Ala Cys Glu Ala Phe Thr Ala Glu Glu Ala Lys Ala Leu Lys Gly
                485                 490                 495

Lys Trp Val Tyr Phe Glu Trp Asp Gln Asp Asp Leu Thr Phe Pro Cys
                500                 505                 510

Gly Ser Lys Val Arg Phe Asp Asn Val Gln Ala Ala Gly Gly Val Gly
            515                 520                 525

Val Val Met Ala Gly Lys Ala Glu Arg Tyr Thr Ile Gly Ile Gly Gly
        530                 535                 540

Asn Ala Thr Ile Pro Gly Leu Arg Leu Thr Ala Ser Ser Thr Lys Asp
545                 550                 555                 560

Leu Glu Lys Ala Leu Ala Ala Gly Pro Val Thr Val Glu Met Asn Leu
                565                 570                 575

Asp Tyr Lys Ala Ser Gly Arg Gly Pro His Ser His Ala Phe Asp Leu
            580                 585                 590

Asn Ser Ser Ser Ala Arg Gly Gln His Gly Ser Asp Gly Phe Ile Lys
        595                 600                 605

Pro Asp Leu Ala Ala Pro Gly Thr Glu Ile Val Ser Ala Ala Val Gly
610                 615                 620

Thr Gly Asn Lys Gly Val Ser Phe Thr Gly Thr Ser Met Ala Thr Pro
625                 630                 635                 640

His Val Thr Gly Ile Ala Ala Leu Val Met Gln Ala His Gln Asp Tyr
                645                 650                 655

Asn Pro Gln Met Ile Lys Ala Ala Leu Met Asn Gly Ala Ser Thr Pro
            660                 665                 670

Ile Lys Asn Glu Gln Gly Ala Gln Tyr Ala Val Asp Arg Val Gly Thr
        675                 680                 685

Gly Met Val Asn Ala Arg Ala Ala Val Asp Lys Val Ile Ala Tyr
        690                 695                 700

Asp Ala Lys Thr Pro Glu Arg Val Ser Thr Ala Phe Gly Val Leu Glu
705                 710                 715                 720

Tyr Thr Pro Asp Ser Gly Ile Gln Thr Val Gln Arg Glu Ile Val Leu
                725                 730                 735

Asp Asn Thr Asp Ser Gln Ala His Thr Tyr Thr Leu Asn Tyr Glu Ala
            740                 745                 750

Ser Thr Thr Ile Pro Gly Val Glu Tyr Ser Tyr Pro Gln Gln Val Ser
        755                 760                 765

Val Gly Ala Gly Glu Arg Lys Asn Val Thr Val Thr Val Arg Ile Asp
        770                 775                 780

Pro Ser Lys Leu Glu Lys Thr Met Asp Pro Ala Met Ser Ala Asp Gln
785                 790                 795                 800

Val Ala Gln Asp Trp Thr Thr Gly Lys Thr Leu Ala Ala Gly Lys Arg
                805                 810                 815

```
Gln Tyr Ile Ala Ser Ala Ser Gly Arg Leu Ile Phe Ser Glu Asn Gly
                820                 825                 830

Arg Glu Ala Ile Arg Gln Ser Ile His Val Ala Pro Lys Pro Val Ser
            835                 840                 845

Lys Met Arg Val Asp Ala Ser Arg Ile Asp Tyr Lys Gly Ile Ala Asp
        850                 855                 860

Lys Glu Ser Thr Val Thr Leu Arg Gly Thr Thr Leu Asn Gln Gly Gly
865                 870                 875                 880

Tyr Arg Ser Leu Leu Gly Ala Phe Glu Leu Gly Ala Val Ser Asp Arg
                885                 890                 895

Ile Pro Ser Gly Gln Leu Lys Leu Pro Ser Asn Gln Ala Val Asp Leu
            900                 905                 910

Gln Tyr Val Gly Ala Ala Ser Asp Ala Pro Ala Leu Lys Ala Ala Gly
        915                 920                 925

Lys Asn Pro Asn Asp Gly Ser Leu Phe Phe Gly Ile Ser Thr Trp Gly
    930                 935                 940

Thr Trp Asp Ser Met His Trp Gly Arg Gln Val Gln Val Gln Ile Asp
945                 950                 955                 960

Thr Asn Asn Asp Ser Thr Ala Asp Tyr Val Leu Glu Val Thr Arg Glu
                965                 970                 975

Lys Gly Leu Asp Tyr Pro Leu Val Lys Val Trp Ser Ile Ser Gly Asn
            980                 985                 990

Ala Ser Thr Val Val Ala Arg Tyr Pro Leu Asn Ser Ala Trp Gly Asp
        995                 1000                1005

Thr Asp Thr Asn Ile Met Asp Thr Asn Thr Met Ile Leu Gly Val
    1010                1015                1020

Pro Leu Lys Asp Leu Gly Leu Thr Ala Glu Lys Ala Gln Ser Ile
    1025                1030                1035

Lys Tyr Thr Val Gln Thr Asp Thr Trp Tyr Asn Asp Gly Asn Pro
    1040                1045                1050

Tyr Val Asp Thr Thr Ser Ala Ile Glu Tyr Ser Pro Phe Asn Pro
    1055                1060                1065

Gly Val Trp Phe Thr Gly Glu Glu Ser Gly Val Pro Gly Leu Phe
    1070                1075                1080

Val Asp Arg Asp Gly Gly Gln Leu Thr Val His Arg Lys Asn Asn
    1085                1090                1095

Asn Lys Glu Arg Gln Ala Leu Phe Leu His Met His Asn Ala Thr
    1100                1105                1110

Gly Asp Leu Ser Gly Arg Lys Thr Ala Asn Gly Val Ala Ala Gly
    1115                1120                1125

Asp Arg Ala Gln Val Val Lys Val Ala Arg Thr Ile His Asp Ala
    1130                1135                1140

Arg Phe Thr Asp Val Pro Ala Asp Asn Gln Phe Tyr Arg Glu Ile
    1145                1150                1155

Thr Trp Ile Ala Ala Arg Gln Ile Asp Arg Gly Tyr Gln Asp Gly
    1160                1165                1170

Thr Phe Arg Pro Leu Asn Asn Met Asp Arg Ala Thr Met Ala Ala
    1175                1180                1185

Tyr Phe Tyr Arg Met Ser Gly Ser Pro Gln Tyr Thr Ala Pro Ser
    1190                1195                1200

Thr Pro Ser Phe Ser Asp Val Pro Leu Asn His Pro Tyr Tyr Lys
    1205                1210                1215
```

-continued

```
Glu Ile Glu Trp Met Lys Ala Gln Gly Ile Thr Thr Gly Trp Pro
    1220            1225               1230

Asp Gly Thr Tyr Arg Pro Glu Gly Ser Val Asn Arg Asp Ala Met
    1235            1240               1245

Ala Ala Phe Phe Tyr Arg Tyr Ala Gly Ser Pro Glu Tyr Thr Ala
    1250            1255               1260

Pro Ala Gln Ala Arg Phe Thr Asp Val Pro Thr Asp Lys Gln Phe
    1265            1270               1275

Tyr Arg Glu Ile Ser Trp Leu Ala Glu Gln Gly Val Thr Thr Gly
    1280            1285               1290

Trp Pro Asp Gly Ser Phe Arg Pro Val Glu Pro Val His Arg Asp
    1295            1300               1305

Ala Met Ala Ala Phe Val Tyr Arg Tyr Ser Thr Gly Val Leu Lys
    1310            1315               1320

Glu Ser Pro Glu Ile
    1325
```

ROTHIA SUBTILISINS, S8A FAMILY PROTEASES, AS THERAPEUTIC ENZYMES FOR APPLICATION IN GLUTEN INTOLERANCE DISORDERS

CROSS REFERENCE TO RELATED APPLICATIONS

This application is a 371 National Phase Entry of International Patent Application No. PCT/US2017/017491 filed Feb. 10, 2017 which claims benefit under 35 U.S.C. § 119(e) of the U.S. provisional application No. 62/293,960 filed Feb. 11, 2016, the contents of which are incorporated herein by reference in their entireties.

GOVERNMENT SUPPORT

This invention was made with Government support under contract No. AI087803 and AI101067 awarded by the National Institutes of Health. The Government has certain rights in the invention.

SEQUENCE LISTING

The instant application contains a Sequence Listing which has been submitted electronically in ASCII format and is hereby incorporated by reference in its entirety. The ASCII copy, created on Aug. 3, 2018, is named 701586-086341-PCT_SL.txt and is 549,085 bytes in size. The sequence listing submitted via EFS-Web is part of the specification and is herein incorporated by reference in its entirety.

FIELD OF THE DISCLOSURE

The field of the invention relates to gluten-degrading enzymes and/or the treatment of celiac disease or a related disorder.

BACKGROUND OF THE DISCLOSURE

Celiac disease, also called celiac sprue or gluten-sensitive enteropathy, is a disease which develops in susceptible individuals in response to the intake of dietary gluten. The disease is caused by an immune reaction to gluten, most noticeably, to gliadin-derived peptides. These peptides elicit an immune response damaging the villi, which are tiny protrusions that line the small intestine. Their destruction causes malabsorption of nutrients leading to a variety of generalized gastro-intestinal disease symptoms such as diarrhea and abdominal pain. Additional and secondary symptoms include weight loss, fatigue, anemia, osteopenia and skin and tooth enamel defects.

A related disease/disorder is dermatitis herpetiformis, which is a chronic eruption of the skin characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Gluten allergy/gluten intolerance is a related ailment which results from overreaction of a subject's immune system to gluten and gliadin that are normally considered harmless. The symptoms are very similar to celiac sprue or gluten-sensitive enteropathy but without the enteropathy. Afflicted subjects have an abundance of IgG, IgA antibodies against α/β-gliadin. Typical symptoms are abdominal pain, gas, bloating and diarrhea; there is a general feeling of sickness and fatigue after grain-based products are consumed. Severe allergy can lead to Gluten-sensitive idiopathic neuropathy where the typical symptoms are ataxia and peripheral neuropathies because the primary tissue targeted are the central nervous system and peripheral nerves.

There is currently no good marketed treatment for celiac disease. In most cases, the symptoms are reversible and can be avoided if the patients refrain from the intake of gluten. However, complete elimination of gluten from the diet is not easy to achieve and maintain. Glutens are abundantly contained in dietary products made of wheat, barley and rye. Moreover, gluten is also widely used, for example in commercial soups, sauces, ice creams, hot dogs, and other foods, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg b.i.d) may induce response.

The gluten-free diet advice is to be followed for a lifetime, and intake of gluten, even in small amounts, can cause an immediate immunological response. In view of the serious and widespread nature of Celiac Sprue, the development of a non-dietary therapy would allow patients to lead a more normal life and find a broad application in the gluten-sensitive patient population.

Current approaches geared towards the development of treatment options for celiac disease and allergic gluten sensitivity focus on enzyme preparations that are able to digest the immunogenic gluten/gliadin oligopeptides into smaller fragments that do not elicit an immune response. Gluten proteins are remarkably resistant to human digestive enzymes operating in the gastro-intestinal tract due to the low content of lysine/arginine and the high proline content. Enzymes capable of gluten digestion are considered an attractive therapeutic option.

Moreover, gluten containing foods contain another class of non-gluten proteins with innate immune stimulatory and thus proinflammatory activity, namely the amylase trypsin inhibitors (ATIs). ATIs induce the condition of non-celiac wheat sensitivity (formerly "gluten sensitivity") which worsens both intestinal and extraintestinal chronic inflammatory diseases, including inflammatory bowel diseases, and autoimmune diseases like SLE, multiple sclerosis, the metabolic syndrome or allergic asthma—therefore affecting even more people that celiac disease. Notably, these diseases are not exacerbated by gluten. Here, a protease that would degrade and thus inactivate ATIs in gluten containing food stuffs would be highly desirable.

SUMMARY OF THE DISCLOSURE

The compositions, formulations, foodstuffs, and methods described herein are based, in part, on the discovery of subtilisins and subtilisin-like enzymes from *Rothia* species bacteria that are found in human plaque or saliva. These subtilisins and subtilisin-like enzymes from *Rothia* species bacteria have gluten-degrading activity. The subtilisins and subtilisin-like, gluten-degrading enzymes of *Rothia* were identified as members of the subtilisin protease family, and the gluten-degrading activities of this class of enzymes were shown to extend beyond the *Rothia* genus. In addition, these subtilisins and subtilisin-like enzymes were able to degrade amylase-trypsin inhibitors (ATIs) that are highly resistant to degradation by mammalian digestive enzymes. A dietary enzyme that could eliminate immunotoxicity of both gluten and ATIs would clearly be beneficial for the treatment of the spectrum of wheat (cereal)-associated gastrointestinal disorders comprising CD and NCWS. These subtilisins and subtilisin-like, gluten-degrading enzymes can be formulated for the treatment of celiac disease, non-celiac/non-allergy wheat sensitivity due to ATIs, and/or a related disorder, and are especially useful for oral delivery as they retain their activity.

Embodiments of the present disclosure relate to use of subtilisins and subtilisin-like enzymes having gluten-degrading activities from the *Rothia* bacteria spp. for the production of formulations and compositions comprising the subtilisins and subtilisin-like enzymes therein, the methods of treatment of gluten-containing foodstuff, and for the methods of treating individuals with gluten allergy or celiac disease. Gluten degrading enzymes have been isolated from *Rothia mucilaginosa* ATCC 25296 and *Rothia aeria* (e.g., *R. aeria* Oral Taxon 188, also called *Rothia* species of 188, *Rothia* sp. HOT-188, *R. aeria* strain F0474 (HMP ID 1324), *R. aeria* HM-818, and *R. aeria* strain WSA), and are identified, by sequence alignment, to be subtilisins that belonging to the S8A family of serine protease family. The *Rothia* sp. derived subtilisin-like enzymes have the conserved catalytic triad composed of a Ser (S), His (H), and Asp (D) residues that is characteristic of the serine protease family. The *Rothia* subtilisin enzymes are potent at cleaving proline-containing proteins, cleaving the second peptide bond after proline in the $XPX_1$ motif, where X is any amino acid, P is proline and $X_1$ is a hydrophobic amino acid; e.g. the XPQ motif, where Q is glutamine, and cleavage occurs after Q. Gluten-degrading activities are also shown for a well-known subtilisin A, derived from bacteria of the *Bacillus* sp. Therefore, subtilisins can useful for breaking down proline-glutamine rich proteins and peptides such as glutens, gliadins and peptides that are resistant to further digestion by other peptidases where these have been shown to elicit an immune response in celiac disease (CD). These enzymes can be used to pre-digest or pre-treatment of food containing such proteins or the enzyme can be taken together with the food containing such proteins.

Furthermore, the inventors have also developed a method that effectively kills bacteria, while fully preserving their enzymatic activities therein. Here, the inventors treated four gluten-degrading microbial strains with ethanol (e.g., 1%, 2%, . . . 50%) for a period of time (e.g., 30 min-1 hr). Treatment with ethanol effectively kills the bacteria, so that the bacteria cannot replicate and are not viable. However, the gluten-degrading enzymatic activities of the bacteria remain intact in the ethanol-treated bacteria. Compositions comprising of such ethanol-treated and lyophilized bacteria would be useful for the methods described herein, for example, for the production or treatment or both the production and treatment of gluten-containing foodstuff or amylase-trypsin inhibitor containing foodstuff, and for the methods of treating individuals with gluten allergy or CD, and other related disorders described herein.

Accordingly, it is the objective of this disclosure to provide uses of subtilisins for the methods of production or treatment or both production and treatment of gluten-containing foodstuff or amylase-trypsin inhibitor containing foodstuff, and for the methods of treating individuals with gluten allergy or CD, and other related disorders described herein.

It is also the objective of this disclosure to provide of subtilisins and subtilisin-like enzymes derived from *Rothia* bacteria sp. for methods of the production or treatment or both production and treatment of gluten-containing foodstuff or amylase-trypsin inhibitor containing foodstuff, and for the methods of treating individuals with gluten allergy or celiac disease, or other related disorders described herein.

Also contemplated is to provide compositions and formulations of compositions comprising ethanol-treated, and lyophilized bacteria that have gluten-degrading enzymatic activities therein for methods of the production or treatment or both production and treatment of gluten-containing foodstuff or amylase-trypsin inhibitor containing foodstuff, and for the methods of treating individuals with gluten allergy or celiac disease, or other related disorders described herein.

In some embodiments, provided herein are gluten-free foodstuff compositions comprising a gluten-containing foodstuff in an admixture with a formulation or a composition comprising an isolated subtilisin or a subtilisin-like enzyme or both a subtilisin and a subtilisin-like enzyme derived a *Rothia* bacteria sp. as described herein, e.g., SEQ ID NO: 1-3, 33 and 34. More than one isolated subtilisin or a subtilisin-like enzyme is comtemplated. In other embodiments, the gluten-free foodstuff compositions comprise a gluten-containing foodstuff in an admixture with a formulation or a composition comprising an isolated subtilisin and/or subtilisin-like enzyme derived *Rothia* bacteria sp. and at least another isolated endopeptidase selected from a gluten-degrading enzyme from *Rothia* species bacteria, an isolated glutamine endopeptidase and a prolyl endopeptidase. Combinations of two or more isolated endopeptidases are comtemplated, e.g., gluten-degrading enzyme and an isolated glutamine endopeptidase, or an isolated glutamine endopeptidase and a prolyl endopeptidase, in addition the isolated subtilisin and/or subtilisin-like enzyme derived *Rothia* bacteria sp.

Accordingly, in one embodiment, provided herein is a foodstuff comprising a formulation or a composition comprising a subtilisin enzyme derived from a *Rothia* sp. bacteria described herein.

In another embodiment, provided herein is a method for degrading gluten or attenuating gluten toxicity in a gluten-containing foodstuff, the method comprises contacting the gluten-containing foodstuff with an effective dose of a formulation or composition comprising a subtilisin enzyme derived from a *Rothia* sp. bacteria described herein.

In another embodiment, provided herein is a formulation or composition comprising (a) an isolated subtilisin and/or subtilisin-like enzyme derived from a *Rothia* sp. bacteria, and (b) a prolyl endopeptidase (PEP).

In another embodiment, provided herein is a formulation or composition comprising (a) an isolated subtilisin and/or subtilisin-like enzyme derived from a *Rothia* sp. bacteria, and (b) an additional glutamine endopeptidase that is a not a subtilisin and/or subtilisin-like enzyme.

In another embodiment, provided herein is a formulation or composition comprising (a) an isolated subtilisin and/or subtilisin-like enzyme derived from a *Rothia* sp. bacteria, and (b) an additional gluten-degrading enzyme derived from a *Rothia* sp. bacteria and the gluten-degrading enzyme is a not a subtilisin and/or subtilisin-like enzyme.

In another embodiment, provided herein is a method for treating celiac disease or a related disorder such as gluten allergy, gluten intolerance, non-celiac/non-allergy wheat sensitivity due to in amylase-trypsin inhibitors, and dermatitis herpetiformis, the method comprising administering to a subject an effective dose of a formulation or composition comprising a subtilisin enzyme derived from a *Rothia* sp. bacteria, or administering an effective dose of any one composition comprising a subtilisin enzyme derived from a *Rothia* sp. bacteria described herein.

In another embodiment, provided herein is a use of a subtilisin enzyme derived from a *Rothia* sp. bacteria to attenuate gluten toxicity in gluten-containing food stuff or for the treatment of celiac disease or a related disorder.

In another embodiment, provided herein is a use of a subtilisin enzyme derived from a *Rothia* sp. bacteria for the manufacture of medicament to treat of celiac disease or a related disorder.

In another embodiment, provided herein is a use of a formulation comprising a subtilisin enzyme derived from a *Rothia* sp. bacteria, or any one composition described herein to attenuate gluten toxicity in gluten-containing food stuff or for the treatment of celiac disease or a related disorder.

In another embodiment, provided herein is a use of a formulation or composition comprising a subtilisin enzyme derived from a *Rothia* sp. bacteria, or any one composition comprising a subtilisin enzyme derived from a *Rothia* sp. bacteria described herein for the manufacture of medicament for the treatment of celiac disease or a related disorder.

In one embodiment, provided herein is a foodstuff comprising a formulation or a composition comprising ethanol-treated, and lyophilized bacteria that have gluten-degrading enzymatic activities therein described herein, wherein the bacteria are cannot cell divide and are not alive or viable.

In one embodiment, provided herein is a method for degrading gluten or attenuating gluten toxicity in a gluten-containing foodstuff or degrading an amylase-trypsin inhibitor in a foodstuff, the method comprises contacting the gluten-containing foodstuff or the amylase-trypsin inhibitor containing foodstuff with an effective dose of a formulation or composition comprising ethanol-treated, and lyophilized bacteria that have gluten-degrading enzymatic activities therein described herein, wherein the bacteria cannot cell divide and are not alive or viable.

In another embodiment, provided herein is a formulation or composition comprising ethanol-treated, and lyophilized bacteria that have gluten-degrading enzymatic activities therein described herein, wherein the bacteria cannot cell divide and are not alive or viable.

In another embodiment, provided herein is a method for treating celiac disease or a related disorder such as gluten allergy, gluten intolerance, non-celiac/non-allergy wheat sensitivity due to in amylase-trypsin inhibitors, and dermatitis herpetiformis, the method comprising administering to a subject an effective dose of a formulation or composition comprising ethanol-treated, and lyophilized bacteria that have gluten-degrading enzymatic activities therein described herein, wherein the bacteria cannot cell divide and are not alive or viable.

In another embodiment, provided herein is a use of a formulation or composition comprising ethanol-treated, and lyophilized bacteria that have gluten-degrading enzymatic activities therein described herein to attenuate gluten toxicity in gluten-containing food stuff or to degrade an amylase-trypsin inhibitor in a foodstuff for the treatment of celiac disease or a related disorder, wherein the bacteria cannot cell divide and are not alive or viable.

In another embodiment, provided herein is a use of a formulation or composition comprising ethanol-treated, and lyophilized bacteria that have gluten-degrading enzymatic activities therein described herein for the manufacture of medicament to treat of celiac disease or a related disorder, wherein the bacteria cannot cell divide and are not alive or viable.

In one embodiment of the degrading or attenuating method described, the contacting of the gluten-containing food stuff or the amylase-trypsin inhibitor containing foodstuff is performed in vitro prior to consumption of the gluten-containing food stuff or the amylase-trypsin inhibitor containing foodstuff respectively.

In one embodiment of the degrading or attenuating method described, the contacting of the gluten-containing food stuff or the amylase-trypsin inhibitor containing foodstuff is performed in vivo concurrent with or after consumption of the gluten-containing food stuff or the amylase-trypsin inhibitor containing foodstuff respectively.

In one embodiment of the treatment method described, the administering of the formulation or composition is performed in vitro prior to consumption of the gluten-containing food stuff or the amylase-trypsin inhibitor containing foodstuff respectively.

In one embodiment of the treatment method described, the administering of the formulation or composition is performed in vivo concurrent with or after consumption of the gluten-containing food stuff or the amylase-trypsin inhibitor containing foodstuff respectively.

In one embodiment of the treatment method described, the administering of the formulation or composition is performed in vitro prior to and also concurrent with or after consumption of the gluten-containing food stuff or the amylase-trypsin inhibitor containing foodstuff respectively.

In any aspect described herein, the *Rothia* sp. bacteria is selected from the group consisting of *Rothia mucilaginosa* ot 681 (strain WSA-2B), *Rothia mucilaginosa* ATCC 25296, *Rothia* species ot 188 (strain WSA-8), *Rothia* sp. HOT-188, *Rothia aeria* strain F0474 (HMP ID 1324), *Rothia aeria* HM-818, *Rothia aeria* strain WSA-8, *Rothia aeria* BAV86562.1 and *Rothia dentocariosa* KGJ00122.1.

In any aspect described herein, the *Rothia* sp. bacteria is selected from the group consisting of *Rothia mucilaginosa*, *Rothia aeria* and *Rothia dentocariosa*.

In any aspect described herein, the subtilisin comprises, or consists of, or consists essentially of the sequence of the hypothetical ROTMU0001_0241 (C6R5V9_9MICC), ROTMU0001_0243 (C6R5W1_9MICC) or ROTMU0001_240 (C6R5V8_9MICC) proteins. (See Section on subtilisins and subtilisin-like enzymes), (SEQ ID NOS: 1-3). The hypothetical ROTMU0001_0241 (C6R5V9_9MICC) is protein WP_044143864.1, ROTMU0001_0243 (C6R5W1_9MICC) is protein WP_044143865.1, and ROTMU0001_240 (C6R5V8_9MICC) is protein WP_005509166.1.

In any aspect described herein, the subtilisin is at least 90% identical to the sequences of the hypothetical ROTMU0001_0241 (C6R5V9_9MICC), ROTMU0001_0243 (C6R5W1_9MICC) or ROTMU0001_240 (C6R5V8_9MICC) proteins.

In any aspect described herein, the subtilisin is a truncated protein of the sequences of the hypothetical ROTMU0001_0241 (C6R5V9_9MICC), ROTMU0001_0243 (C6R5W1_9MICC) or ROTMU0001_240 (C6R5V8_9MICC) protein. For example, at least 60% identical to the sequences of the hypothetical ROTMU0001_0241 (C6R5V9_9MICC), ROTMU0001_0243 (C6R5W1_9MICC) or ROTMU0001_240 (C6R5V8_9MICC) proteins as described in SEQ ID NOS: 1-3.

In any aspect described herein, the subtilisin comprises the catalytic triad with Asp (D), His (H) and Ser (S) in the D-H-S order that is characteristic of the S8A family of serine protease family.

In any aspect described herein, the subtilisin cleaves proline-containing proteins, cleaving the second peptide bond after proline in the $XPX_1$ motif, where X is any amino acid, P is proline and $X_1$ is a hydrophobic amino acid, i.e., cleaving at the peptide bond after $X_1$, e.g. the XPQ motif, where Q is glutamine and the cleavage occurs after Q.

In any aspect described herein, the subtilisin cleaves proline-containing proteins after the proline in the $XPX_1$ motif.

In any aspect described herein, the subtilisin cleaves succinyl-Ala-Ala-Pro-Phe-paranitroanilide (SEQ ID NO: 4), a substrate for subtilisin, cleaving at the second peptide bond after proline in the P2 position. The numbering of the amino acid position (e.g., P1, P2, P3) is with respect to the peptide bond that is cleaved by the enzyme described. The amino acid residue immediately upstream of the cleavage peptide bond is designated the position P1, the amino acid residue immediately upstream of the P1 amino acid residue is P2. Here, in the substrate for subtilisin, Phe=P1 position, and Pro=P2 position, Ala=P3 and P4 positions.

In any aspect described herein, the subtilisin degrades the highly immunogenic gliadin-derived 33-mer peptide. In any aspect described herein, the subtilisin degrades an amylase-trypsin inhibitor.

In any aspect described herein, the subtilisin does not cleave the second peptide bond after proline in the P2 position in a tripeptide having the -$P_1FP_2$-motif, wherein $P_1$ and $P_2$ are P=proline=Pro; F=Phenylalanine=Phe (in P1 position); and $P_1$ is in the $P_2$ position. The presence of $P_2$ in this position is well known to interfere with protease activity. In any aspect described herein, the subtilisin does not cleave the peptide bond after Phe.

In any aspect described herein, the subtilisin does not cleave the second peptide bond after proline in the P2 position in a tripeptide having the -PPF-motif, wherein F=Phenylalanine=Phe (in the P0 position); P=proline=Pro (in the P1 and P2 positions).

In any aspect described herein, the subtilisin is more effective glutenase compared with *Bacillus* sp. subtilisin A with respect to certain immunogenic epitopes.

In any aspect described herein, the subtilisin has an apparent molecular weight of about 75-80 kDa as determined by gliadin zymograms or by sodium dodecyl sulfate polyacrylamide gel electrophoresis (SDS-PAGE) or as described in FIGS. 2A-2E in the Example section; or have a predicted molecular weight of ~125 kDa as described in the Example section.

In any aspect described herein, the subtilisin undergoes activation to produce a shorter mature enzyme. For example, the subtilisin undergoes activation from a ~125 kDa protein to a ~75-80 kDa protein as determined by SDS-PAGE.

In any aspect described herein, the subtilisin enzyme has a functional pH range of 6.0-10.0. as determined by detectable Z-YPQ-pNA cleaving activity described herein. For example, a detectable Z-YPQ-pNA cleaving activity within a 72 hour digestion period or substantially complete Z-YPQ-pNA cleavage within a 1 hour digestion period.

In any aspect described herein, the subtilisin enzyme has low or negligible enzyme activity at pH values below 5.0 or pH values higher than 11.0.

In any aspect described herein, the subtilisin enzyme is a *R. mucilaginosa*-derived subtilisin enzyme.

In any aspect described herein, the subtilisin is inhibited PMSF. In another embodiment, the subtilisin is 100% inhibited by 1 mM of PMSF.

In any aspect described herein, the subtilisin is not inhibited by E64 or EDTA.

In any aspect described herein, the subtilisin is not stable in acid conditions.

In any aspect described herein, the subtilisin is lyophilized.

In any aspect described herein, the lyophilized subtilisin is formulated into granules or is encapsulated.

In any aspect described herein, the subtilisin is a protein isolated from *Rothia* sp. bacteria. For example, by protein purification methods from cell extracts of *Rothia* sp., methods that are known in the art, for example, as described in the Example section.

In any aspect described herein, the subtilisin is an isolated recombinant protein. For example, the subtilisin nucleic acid coding sequence is expressed in another organism other than *Rothia* sp. For example, expression in yeast or *Escherichia coli*, or any mammalian cells such as COS cells.

In any aspect described herein, the subtilisin has an amino acid sequence that show at least 60% similarity to SEQ ID NO: 1, 2 or 3 (See Section on subtilisins and subtilisin-like enzymes).

In any aspect described herein, the subtilisin comprises SEQ ID NO: 1, 2 or 3.

In any aspect described herein, the subtilisin consists of SEQ ID NO: 1, 2 or 3.

In any aspect described herein, the subtilisin consists essentially of SEQ ID NO: 1, 2 or 3.

In any aspect described herein, the subtilisin is SEQ ID NO: 1, 2 or 3.

In any aspect described herein, the formulation further comprising a prolyl endopeptidase (PEP).

In any aspect described herein, the formulation further comprising at least one additional gluten-degrading enzyme isolated from a *Rothia* species bacteria, wherein the at least one additional gluten-degrading enzyme retains protease activity at an acidic pH of 3.0 as measured in an in vitro gliadin degradation assay for 3 hours using a synthetic substrate Z-YPQ-pNA, and wherein the at least one enzyme comprises an isoelectric point in a pH range of 2.0-7.0, inclusive.

In any aspect described herein, the at least one additional gluten-degrading enzyme is not a subtilisin or a subtilisin-like protein isolated from a *Rothia* sp. bacteria.

In any aspect described herein, the at least one additional gluten-degrading enzyme that retains protease activity at acidic pH of 3.0 is derived from the *Rothia* species *Rothia* species of 188, also known as *Rothia* sp. HOT-188, *R._aeria* strain F0474 (HMP ID 1324), *R. aeria* HM-818, and *Rothia aeria* strain WSA-8.

In any aspect described herein, the at least one additional gluten-degrading enzyme that retains protease activity at acidic pH of 3.0 has an iso-electric point in a pH range of 2.0-4.0, inclusive.

In any aspect described herein, the at least one additional gluten-degrading enzyme that retains protease activity at acidic pH of 3.0 has an estimated molecular weight between 120-150 kDa, inclusive.

In any aspect described herein, the at least one additional gluten-degrading enzyme that retains protease activity at acidic pH of 3.0 has an estimated molecular weight of 135-145 kDa, inclusive.

In any aspect described herein, the at least one additional gluten-degrading enzyme that retains protease activity at acidic pH of 3.0 has an estimated molecular weight between 50 and 90 kDa, inclusive.

In any aspect described herein, the at least one additional gluten-degrading enzyme that retains protease activity at acidic pH of 3.0 has molecular weight between 65 and 75 kDa, inclusive.

In any aspect described herein, the at least one additional gluten-degrading enzyme that retains protease activity at acidic pH of 3.0 has molecular weight between 75 and 80 kDa, inclusive.

In any aspect described herein, the at least one additional gluten-degrading enzyme that retains protease activity at acidic pH of 3.0 has molecular weight between 65 and 80 kDa, inclusive.

In any aspect described herein, the at least one additional gluten-degrading enzyme that retains protease activity at acidic pH of 3.0 retains activity at the pH between 2.5 and 5.0, inclusive.

In any aspect described herein, the at least one additional gluten-degrading enzyme that retains protease activity at acidic pH of 3.0 degrades a gliadin protein, a fragment thereof, or a gluten-containing foodstuff or ingredient thereof.

In any aspect described herein, the degradation is partial.

In any aspect described herein, the degradation is complete.

In any aspect described herein, the fragment thereof is a 33-mer peptide of α2-gliadin or a 26-mer domain derived from γ-gliadin.

In any aspect described herein, the 33-mer peptide is LQLQPFPQPQLPYPQPQLPYPQPQLPYPQPQPF (SEQ ID NO: 5).

In any aspect described herein, the 26-mer domain is FLQPQQPFPQQPQQPYPQQPQQPFPQ (SEQ ID NO: 6).

In any aspect described herein, the degradation by the at least one additional gluten-degrading enzyme that retains protease activity at acidic pH of 3.0 occurs by cleaving the peptide bond after an amino acid sequence selected from the group consisting of -XPQ- -QQP-, -PPF-, -LPY-, -XPY- and -PFP-.

In any aspect described herein, the formulation or composition further comprising at least one isolated additional glutamine endopeptidase enzyme that cleaves a peptide bond after a QPF and a PFP motif in glutens.

In any aspect described herein, the at least one additional glutamine endopeptidase enzyme is not a subtilisin or a subtilisin-like protein isolated from a Rothia sp. bacteria.

In any aspect described herein, the degradation by the at least one additional gluten-degrading enzyme that retains protease activity at acidic pH of 3.0 occurs by cleaving the peptide bond after an amino acid sequence selected from the group consisting of -XPQ-, -QQP-, -PPF-, -LPY-, -XPY- and -PFP-. In other embodiments, degradation or digestion occurs by cleaving the peptide bonds after amino acid sequences XPQ and QQP; XPQ and PPF; XPQ and PFP; XPQ and LPY; QQP and LPY; PPF and LPY; PFP and LPY; XPQ, QQP and PPF; XPQ, QQP and PFP; XPQ, QQP and LPY; QQP, PPF, and PFP; XPQ, PPF and PFP; QQP, PPF and LPY; XPQ, PPF and LPY; PY, PPF, and PFP; QQP, PFP and LPY; XPQ, PFP and LPY; XPQ, QQP, PPF and LPY; LPY, QQP, PPF and PFP; XPQ, LPY, PPF and PFP; XPQ, QQP, PFP and LPY; XPQ, QQP, PPF and PFP; or XPQ, QQP, PPF, LPY and PFP.

In any aspect described herein, the PEP is derived from the microorganism selected from the group consisting of Aspergillus niger, Flavobacterium meningosepticum, Sphingomonas capsulata, Penicillium citrinum, Hordeum vulgare, and Myxococcus xanthus.

In any aspect described herein, the formulation or composition further comprising a glutamine specific protease which is selected from the group consisting of Hordeum vulgare endoprotease, Aspergillus oryzae X-Pro dipeptidase, and Aspergillus saitoi carboxypeptidase. For example, glutamine specific proteases as described in U.S. Pat. No. 7,628,985, the contents are incorporated by reference in their entirety.

In any aspect described herein, the formulation or composition further comprising a pharmaceutically acceptable carrier. In any aspect described herein, the composition is a pharmaceutical composition comprising the subtilisin described herein and a pharmaceutically acceptable carrier.

In any aspect described herein, the related disorder is selected from the group consisting of refractory celiac disease, gluten allergy, gluten intolerance, non-celiac/non-allergy wheat sensitivity due to in amylase-trypsin inhibitors, and dermatitis herpetiformis.

Definitions

As used herein, the term "treating" or "treatment" with respect to a medical disease or disorder means to stabilize and/or improve the clinical symptoms of a subject afflicted with celiac disease or a related disorder. In one embodiment, "treating" or "treatment" means to relieve or alleviate at least one symptom associated with such condition, or to slow or reverse the progression or anticipated progression of such condition, or bringing about ameliorations of the symptoms of the pathology. Evidence of a therapeutic effect may be any diminution in the severity of disease, particularly as measured by the severity of one or more symptoms such as fatigue, chronic diarrhea, malabsorption of nutrients, weight loss, abdominal distension, anemia, and other symptoms of Celiac Sprue. Other disease indicia include the presence of antibodies specific for glutens, the presence of antibodies specific for tissue transglutaminase, the presence of pro-inflammatory T cells and cytokines, damage to the villus structure of the small intestine as evidenced by histological or other examination, enhanced intestinal permeability, and the like. In some embodiment, effective treatment according to the methods described herein is determined by a reduction in at least one symptom of Celiac Sprue, gluten allergy, gluten intolerance and/or dermatitis herpetiformis by at least 20%, at least 30%, at least 40%, at least 50%, at least 60%, at least 70%, at least 80%, at least 90%, at least 95%, at least 99% or even 100% (e.g., remission or absence of symptoms). In one embodiment, treatment according to the methods and compositions described herein induces a state of remission in celiac disease, or a related disorder, or non-celiac/non-allergy wheat sensitivity due to in amylase-trypsin inhibitors.

As used herein, the term "treating" or "treatment" with respect to a gluten-containing foodstuff means degrading or digesting the foodstuff to reduce the production of toxic gluten oligopeptides when the foodstuff is subsequently ingested and further digestion by a subject. Preferably the subject is a human. In one embodiment, "treating" or "treatment" of a gluten-containing foodstuff results in complete elimination of toxic gluten oligopeptides when the foodstuff is subsequently ingested and further digestion by a subject. In another embodiment, the "treating" or "treatment" of a gluten-containing foodstuff results in at least 10% reduction of toxic gluten oligopeptides when the foodstuff is subsequently ingested and further digestion by a subject. In other embodiments, the "treating" or "treatment" of a gluten-containing foodstuff results in at least 20%, at least 30%, at least 40%, at least 50%, at least 60%, at least 70%, at least 80%, at least 90%, at least 95%, at least 99% or even 100% reduction of toxic gluten oligopeptides when the foodstuff is subsequently ingested and further digestion by a subject.

As used herein, the term "effective dose" with respect to a medical disease or disorder refers to an amount of a biologically active molecule or conjugate thereof, enzyme, or bacterial formulation (e.g., probiotic formulation) sufficient to exhibit a detectable therapeutic effect, e.g. reduction in the symptoms associated with Celiac sprue, gluten allergy and/or dermatitis herpetiformis, e. g. fatigue, chronic diarrhea, malabsorption of nutrients, weight loss, abdominal distension, anemia, the presence of antibodies specific for tissue transglutaminase, the presence of pro-inflammatory T cells and cytokines, and damage to the villus structure of the small intestines. The specific amount that is therapeutically effective can be readily determined by an ordinary medical practitioner, and can vary depending on factors known in the art, such as, for example, the subject's history and age, the stage of pathological processes, and the administration of other agents or therapeutics that inhibit pathological processes in Celiac sprue, gluten allergy and/or dermatitis herpetiformis.

As used herein, the term "effective dose" or "effective amount" with respect to the treatment of a gluten-containing foodstuff refers to the amount of a biologically active molecule or conjugate thereof, enzyme, or bacterial formulation (e.g., probiotic formulation) sufficient to produce at least 10% reduction of toxic gluten oligopeptides when the foodstuff is subsequently ingested and further digestion by a subject.

As used herein, the term "an extract from a *Rothia* species" refers to a clarified aqueous solution that formerly comprised a *Rothia* species for example, a suspension of *Rothia* species in phosphate buffered saline (PBS) that was agitated for 1 hour at room temperature and then centrifuged at 1000×G for 10 minutes to sediment the bacteria. The supernatant PBS fluid is "an extract from a *Rothia* species". Similarly, a clarified saliva sample is "an extract from a *Rothia* species". "An extract from a *Rothia* species" can also mean a clarified periplasmic extraction of a *Rothia* species, for example, a suspension of *Rothia* species in phosphate buffered saline (PBS) with 20% or 500 mM sucrose and is then agitated for 1 hour at 4° C. and then centrifuged at 1000×G for 10 minutes to sediment the bacteria. In the presence of high sucrose concentration, the bacteria undergo osmotic shock. Such methods of making periplasm extracts are well known to those skilled in the art, e. g. as described in U.S. Pat. No. 5,856,142. "An extract from a *Rothia* species" can also mean a clarified cell lysate of a *Rothia* species, wherein the bacteria are lysed in a suitable buffer and the lysate is centrifuged at 20,000×G for 30 minutes to sediment the cell debris. Ultracentrifugation clarified cell lysate of a *Rothia* species is also "an extract from a *Rothia* species". "An extract from a *Rothia* species" can also mean a chromatography fraction containing a ~70-80 kDa protein or a ~125-~140 kDA with gluten-degrading activity (e.g., glutamine endopeptidase activity) as assayed by gliadin zymography and other methods described herein.

As used herein, in one embodiment, the term "a glutamine endopeptidase" refers to a proteolytic peptidase that breaks peptide bonds of non-terminal amino acids (i.e. within a protein or peptide molecule) at the -XPQ- or -Xaa-Pro-Gln-triplet sequence and the breakage occurs immediately after the glutamine residue. X or Xaa=any amino acids, P or Pro=proline, and Q or Gln=glutamine (e.g., -YPQ- where Y or Tyr=tyrosine). In another embodiment, a glutamine endopeptidase cleaves peptide bonds at either one of the following the -QQP-, and -PFP triplet sequences. In one embodiment, a glutamine endopeptidase can also cleave a -XPY- or -Xaa-Pro-Tyr triplet sequence. In other embodiments, a glutamine endopeptidase is capable of cleaving several of the -XPQ-, -QQP-, -PPF- and -PFP-triplet sequences. It is also noted that the term "glutamine endopeptidase" encompasses proteases that typically degrade salivary basic proline-rich proteins in saliva, and as such, have glutamine endopeptidase activity to degrade proline-rich glutens.

As used herein, in one embodiment, the term "digest" or "degrade" with respect to a gluten-containing foodstuff, gluten, gliadin or fragment thereof refers to breaking a peptide bond in the protein or peptide molecule in the gluten-containing foodstuff, gluten, gliadin or fragment thereof.

As used herein, the term "acidic pH" refers to pH values less than 7.0 (e.g., 1.0, 1.5, 2.0, 2.5, 3.0, 3.5, 4.0, 4.5, 5.0, 5.5, 6.0, 6.5). As used herein the term "basic pH" refers to pH values greater than 8.0 (e.g., 8.5, 9.0, 9.5, 10.0, 10.5, 11.0, 11.5, 12.0, 12.5, 13.0, 13.5, 14.0). As used herein the term "neutral pH" refers to pH values from 7.0 to 8.0, inclusive (e.g., 7.0, 7.2, 7.4, 7.6, 7.8, 8.0).

As used herein, the term "attenuates gluten toxicity" refers to a decrease in the level of gluten proteins or gluten toxic intermediates (e.g., as measured in a subject having celiac disease and administered a gluten challenge) of at least 20% following treatment with the enzyme compositions described herein compared to an untreated subject; preferably the level of gluten proteins or gluten toxic intermediates are decreased by at least 30%, at least 40%, at least 50%, at least 60%, at least 70%, at least 80%, at least 90%, at least 95%, at least 99%, or even 100% (i.e. no detectable glutens or gluten toxic intermediates).

As used herein, the term "toxic intermediates" refers to gluten protein fragments produced by the digestion of gluten with human digestive enzymes such as trypsin, chymotrypsin, and pepsin, that induce symptoms of celiac disease or a related disorder (see also "toxic gluten oligopeptides" definition herein).

As used herein, the term "related disorder" refers to diseases induced by gluten and include, but are not limited to, gluten intolerance, non-celiac/non-allergy wheat sensitivity due to in amylase-trypsin inhibitors, gluten allergy, refractory celiac disease, and dermatitis herpetiformis.

As used herein, the term "admix" in the context of gluten-containing foodstuff refers to mixing or blending with gluten-containing foodstuff. The product arising from the mixing or blending is an "admixture."

As used herein, the term "glutens" refers to a mixture of proteins, including gliadins and glutelins, found in wheat grains, which are not soluble in water and which give wheat dough its elastic texture. "Glutens" also refer to the prolamins that are found in rye, barley, and oats.

As used herein, the term "glutelin" refers to prolamin-like proteins that are found in grass seeds, e. g. wheat, and are soluble in dilute acids or bases, detergents, chaotropic or reducing agents. "Glutelin" tend to be rich in prolines and glutamine.

As used herein, the term "prolamins" refers to a group of plant storage proteins having high proline content and is found in the seeds of cereal grains such as wheat (gliadin), barley (hordein), rye (secalin), corn (zein) and as a minor protein, avenin in oats. They are characterized by a high glutamine and proline content and are generally soluble only in strong alcohol solutions. Some prolamins, notably gliadin from wheat, and similar proteins found in the grass seed of the Triticeae species can induce celiac disease in genetically predisposed individuals.

As used herein, the term "gliadin" refers to the alcohol-soluble, glutamine and proline-rich prolamin glycoprotein that is found in wheat. This is one of the proteins that induce celiac disease in genetically predisposed individuals. Examples of gliadin sequences include but are not limited to wheat alpha gliadin sequences, for example as provided in GENBANK accession numbers AJ133612; AJ133611; AJ133610; AJ133609; AJ133608; AJ133607; AJ133606; AJ133605; AJ133604; AJ133603; AJ133602; D84341.1; U51307; U51306; U51304; U51303; U50984; and U08287. A sequence of wheat omega gliadin is set forth in Genbank accession number AF280605.

As used herein, the term "gluten-containing foodstuff" refers to food and/or ingredients of food that has gluten and other proteins found in wheat, barley, and rye. "Gluten-containing foodstuff" also refers to food and/or ingredients of foods that are made of wheat, barley, and rye. It is also contemplated that "gluten-containing foodstuff" can be foodstuff that is merely contaminated with gluten by way of the use of common manufacturing equipment. For example, oats do not contain gluten, however, because oats are a major agricultural product they are handled by the same mills, processing plants, and grain elevators that handle wheat, barley and rye. This results in enough contamination of the oats that they can readily trigger a gluten allergy when ingested. Also included in the term "gluten-containing foodstuff" are formulations of drugs, medications, vitamin supplements or mineral supplements that are contaminated by or prepared using gluten-containing foods such as wheat, barley, or rye.

As used herein, the term "consuming gluten-containing foodstuff" refers to ingesting food made of wheat, rye, and barley, e. g. pizza, cake, bread, etc. as well as ingesting food made with ingredients that are made with wheat, rye, and barley, e. g. soy sauce.

As used herein, the term "diagnosed of Celiac sprue, gluten allergy/gluten intolerance and/or dermatitis herpetiformis" refers to having the symptoms associated with Celiac sprue, gluten allergy and/or dermatitis herpetiformis, e. g. fatigue, chronic diarrhea, malabsorption of nutrients, weight loss, abdominal distension, anemia, the presence of antibodies specific for tissue transglutaminase (ATA), antibodies specific for α/β,γ-gliadin (AGA), the presence of pro-inflammatory T cells and cytokines, and damage to the villus structure of the small intestines.

As used herein, the term "toxic gluten oligopeptides" refers to peptides derived during normal human digestion of gliadins and related storage proteins from dietary cereals, e.g. wheat, rye, barley, and the like. Such oligopeptides act as antigens for T cells in Celiac Sprue. For binding to Class II MHC proteins, immunogenic peptides are usually from about 8 to 20 amino acids in length, more usually from about 10 to 18 amino acids. Such peptides may include PXP motifs, such as the motif PQPQLP (SEQ ID NO: 7). Determination of whether an oligopeptide is immunogenic for a particular patient is readily determined by standard T cell activation and other assays known to those of skill in the art. Other examples of immunogenic gliadin oligopeptides are described in Wieser (1995) Baillieres Clin Gastroenterol 9(2):191-207. "Toxic gluten oligopeptides" also refers to peptides that comprise known T cell epitopes in gluten, e.g. QLQPFPQPQLPY (SEQ ID NO: 8) or PFPQPQLPY (SEQ ID NO: 9), PQPQLPYPQPQLPY (SEQ ID NO: 10) or PQPQLPYPQ (SEQ ID NO: 11), QPQQSFPQQQ (SEQ ID NO: 12) or PQQSFPQQQ (SEQ ID NO: 13), QLQPFPQPELPY (SEQ ID NO: 14), PQPELPYPQPELPY (SEQ ID NO: 15), QPQQSFPEQQ (SEQ ID NO: 16); IQPQQPAQL (SEQ ID NO: 17); QQPQQPYPQ (SEQ ID NO: 18); SQPQQQFPQ (SEQ ID NO: 19); QQPFPQQPQ (SEQ ID NO: 20); or PFSQQQQPV (SEQ ID NO: 21), including 33-mer from alpha-gliadin, LQLQPF(PQPQLPY)$_3$PQPQPF (SEQ ID NO: 5), and the 26-mer from gamma-gliadin, FLQPQQPFPQQPQQPYPQQPQQPFPQ (SEQ ID NO: 6).

The term "isolated" refers to an enzyme protein which is substantially or essentially free from bacterial components which normally accompany or interact with the enzyme as found in the bacteria. As used herein, the term "isolated" can also refer to mixtures of enzyme proteins comprising a plurality of different enzymes substantially free from bacterial components (e.g., 2, 3, 4, 5, 6, 7, 8, 9, 10, 15, 20 or more different enzymes).

As used herein, the term "inhibited" or "inhibition" when used in the context with the glutamine endopeptidase activity means the reduction of the cleavage of -XPQ-, —XPY—, -QQP-, —PPF— and/or -PFP-containing peptides by at least about 50%, about 60%, about 70%, about 80%, about 90%, about 100% (i.e., level of XPQ-containing peptides is undetectable by standard methods) by any assay described herein or known in the art, wherein X is any amino acid, P is proline, Q is glutamine, Y is tyrosine, and F is phenylalanine.

As used herein, the term "gluten degrading activity" with respect to the compositions comprising an isolated enzyme, a plurality of isolated enzymes, an extract from Rothia species, a plurality of extracts from more than one Rothia species, a Rothia species bacteria itself, or a plurality of Rothia species bacteria refers to the capability of the composition to cleave -XPQ-, -XPY-, -QQP-, -PPF- and/or -PFP-containing peptides by at least about 50%, about 60%, about 70%, about 80%, about 90%, about 100% (i.e., level of XPQ-containing peptides is undetectable by standard methods) by any assay described herein or known in the art, wherein X is any amino acid, P is proline and Q is glutamine. In one embodiment, the cleavage is preferably at peptide bonds of non-terminal amino acids (i.e. within a protein or peptide molecule) and the breakage occurs immediately after the glutamine residue for -XPQ-sequence, immediately after the proline residue for -QQP- or -PFP-sequence, and immediately after the phenylalanine residue for -PPF- sequence.

As used herein, the phrase "retain activity in acidic pH environment" or "retain protease activity" refers to an isolated enzyme from Rothia species described herein that is still has gluten degrading activity when the enzyme is in an environment with pH less than 7.0.

As used herein, the term "inclusive" when used with pH or molecular weight of a molecule means that all possible gradation of the pH or molecular weight in contemplated within the specified range. For example, if pH is 3.0 to 4.0 inclusive, then pHs of 3.02, 3.1, 3.14, 3.2, 3.75, 3.99 etc are also contemplated.

As used herein, the terms "subtilisin" and "subtilisin-like enzyme" means a protease that comprises the catalytic triad with Asp (D), His (H) and Ser (S) in the D-H-S order that is characteristic of the S8A family of serine protease family. Subtilisin and subtilisin-like enzyme are used interchangeably when referring to the enzyme derived from the *Rothia* sp. bacteria.

An enzyme that is "derived from *Rothia* sp." means the enzyme is isolated directly from the bacteria or the enzyme is a recombinant expressed protein from a coding nucleic acid sequence deduced from the *Rothia* sp."

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in e.g., absorption, carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

BRIEF DESCRIPTION OF THE FIGURES

FIG. 1A shows the separation of proteins by DEAE chromatography applying an isocratic gradient containing 0.3M NaCl and 50 mM TrisHCl pH 7.0.

FIG. 1B shows a representative SDS-PAGE gel of the DEAE chromatography fractions. Protein content in 100 µl fraction aliquots investigated by 4-12% SDS PAGE.

FIG. 1C is a histogram showing the enzyme activity in 50 µl fraction aliquots investigated with Z-YPQ-pNA as the substrate. The data shown are representative of two independent experiments.

FIGS. 2A-2E demonstrate the identification of the gluten-degrading enzymes of *R. mucilaginosa*. DEAE fractions 1-65 were pooled into 7 fractions designated F1-F7 (see Example section for details).

FIG. 2A shows a representative SDS-PAGE gel of the DEAE chromatography pooled fractions. Protein content in 400 µl aliquots of F1-F7 were analyzed on a 4-12% SDS-PAGE gel.

FIG. 2B shows a representative gliadin zymogram gel of the DEAE chromatography pooled fractions. Gliadin-degrading enzyme activity in 200 µl desalted aliquots of F1-F7 were analyzed on a 6% gliadin zymogram gel.

FIG. 2C shows a representative non-reducing PAGE gel of the DEAE chromatography fraction F2. The PAGE gel under non-reducing conditions of *R. mucilaginosa* enzyme preparation (Rmep) (F2) was loaded amounts 4, 8, 16, 32 µg protein in lanes 1-4, respectively.

FIG. 2D shows a representative casein zymogram of the DEAE chromatography fraction F2. The casein zymogram of F2 was loaded amounts 2, 4, 8, and 16 µg in lanes 1-4, respectively.

FIG. 2E is a table showing the proteins identified in excised gel bands labeled a-e in FIGS. 2C and 2D. The data shown are representative of at least four independent experiments.

FIGS. 3A-3D are representative histograms showing the effects of pH and inhibitors on *R. mucilaginosa* enzyme preparation (Rmep) activity.

FIG. 3A shows the enzymatic activity of *R. mucilaginosa* enzyme preparation (Rmep) at various pH. Activity of Rmep in 0.1M Citric acid/0.2M phosphate buffer mixtures, pH 2-12, was measured with Suc-AAPF-pNA (SEQ ID NO: 4) (200 µM) as the substrate.

FIG. 3B shows the inhibitor profile of *R. mucilaginosa* enzyme preparation (Rmep). Inhibitors AEBSF, Aprotinin, E-64, EDTA, PMSF and Eglin C were tested at final concentrations of 10 mM, 0.08 mM, 0.1 mM, 1.5 mM, 1 mM, and 0.06 µM, respectively. Rmep was added at a final concentration of 5.7 µg/ml. The percent inhibition was determined from the ratio of the initial velocities of hydrolysis of Suc-AAPF-pNA (SEQ ID NO: 4) in the absence and presence of inhibitor.

FIG. 3C shows the inhibition of *Bacillus subtilis* sp. subtilisin A with a higher concentration Eglin C (1.2 µM).

FIG. 3D show the inhibition of *R. mucilaginosa* enzyme preparation (Rmep) with a higher concentration Eglin C (1.2 µM).

FIG. 4A and FIG. 4B are representative graphs of the hydrolysis of the substrates: Suc-AAPF-pNA (SEQ ID NO: 4), Z-YPQ-pNA, and Z-LPY-pNA, each at 200 µM, by Rmep and subtilisin A, respectively, each at 1 µg/ml.

FIG. 4C show a representative graph of the hydrolysis of the substrate, LPY, by Rmep and subtilisin A at 5 µg/ml and extended incubation times.

FIG. 4D and FIG. 4E are representative graphs of the hydrolysis of gliadin-derived FRET substrates. FRET substrates containing QPQLPY (SEQ ID NO: 22), PQPQPQ (SEQ ID NO: 23) and QGSFQP (SEQ ID NO: 24), each at 100 µM, were incubated with Rmep (FIG. 4E) and subtilisin A (FIG. 4E), at 1 µg/ml and 0.5 µg/ml, respectively. Controls were boiled Rmep and subtilisin A incubated with PQPQLPY (+) (SEQ ID NO: 25), PQPQPQ (◇) (SEQ ID NO: 23) and QGSFQP (*) (SEQ ID NO: 24) (no activity, baseline).

FIGS. 5A-5D demonstrate the degradation of mixed gliadins by *R. mucilaginosa* enzyme preparation (Rmep) and the abolishment of immunogenic epitopes by Rmep.

FIG. 5A is a representative SDS-PAGE gel of non-digested gliadins (control) and Rmep-treated gliadins. Gliadins (250 µg/ml) in 50 mM Tris/HCl pH 8.0 were incubated with Rmep at 57 µg/ml. After 0, 15 min, 30 min and 2 h incubation 100 µl aliquots were removed, boiled and analyzed by SDS-PAGE and stained with COOMASSIE Brilliant Blue. The bold arrow (left) points to the position of the major band in the gliadin preparation; the thin arrow (right) to the 125 kDa band in the Rmep preparation, and the dotted arrows (right) to the gliadin degradation fragments.

FIG. 5B is a representative chromatogram of the RP-HPLC of the degradation of the immunogenic 33-mer peptide from α-gliadin. Arrow (top) points to the intact 33-mer.

FIG. 5C and FIG. 5D show the assessment of the survival of epitopes in the gliadin-Rmep degradation mixture employing the R5 ELISA (FIG. 5C) or G12 ELISA (FIG. 5D) assays.

FIGS. 6A-6D demonstrate the degradation of mixed gliadins by *B. subtilisis* subtilisin A and abolishment of immunogenic epitopes by *B. subtilisis* subtilisin A.

FIG. 6A is a representative SDS-PAGE gel of non-digested gliadins (control) and subtilisin A-treated gliadins. Gliadins (250 µg/ml) in 50 mM Tris/HCl pH 8.0 were incubated with subtilisin A at 57 µg/ml. Experiments were conducted as described in the legend of FIG. 5 with subtilisin A instead of Rmep.

FIG. 6B is a representative chromatogram of the RP-HPLC of the degradation of the immunogenic 33-mer peptide from α-gliadin with subtilisin A. Arrow (top) points to the intact 33-mer.

FIG. 6C and FIG. 6D show the assessment of the survival of epitopes in the gliadin-subtilisin A degradation mixture employing the R5 ELISA (FIG. 6C) or G12 ELISA (FIG. 6D) assays.

FIG. 7. Domain composition of C6R5V9_9MICC. The protein of 1328 amino acids contains a peptidase S8 propeptide domain (also called proteinase inhibitor 19), a peptidase S8/S53 family domain, an immunoglobulin-like fold domain, and 3 surface layer homology domains. This figure is based on InterPro analysis.

FIGS. 8A-8F demonstrate the gliadin degradation and epitope abolishment by a nattokinase enzyme (NattoK) derived from *B. subtilis*.

FIG. 8A is a representative SDS-PAGE gel of non-digested gliadins (control) and NattoK-treated gliadins. Mixed gliadins (G, 250 µg/ml) were incubated with NattoK (57 µg/ml) for 0, 15, 30 and 120 min. Left four lanes: controls without enzyme or gliadins, respectively, each at t=0 and 120 min. Arrow points to the major components in the gliadin mixture represented by α and γ-gliadins containing most of the immunogenic epitopes.

FIG. 8B is a representative SDS-PAGE gel of non-digested gliadins (control) and diluted NattoK-treated gliadins. Dilution series of NattoK (3.5-0.06 µg/ml) incubated for 30 min with mixed gliadins. Right lanes, gliadin (G) and NattoK (NK) control.

FIG. 8C show a representative graph of the hydrolysis of the substrate, Suc-AAPF-pNA (SEQ ID NO: 4), with a dilution series of NattoK. Suc-AAPF-pNA (SEQ ID NO: 4) was incubated Suc-AAPF-pNA (SEQ ID NO: 4). Hydrolysis was measured at 405 nm.

FIG. 8D is a representative chromatogram of the RP-HPLC analysis of the degradation of the gliadin-derived 33-mer (250 µg/ml) incubated for 0, 15, 30 and 120 min with NattoK 57 µg/ml).

FIG. 8E and FIG. 8F show the assessment of the survival of epitopes in the gliadin-NattoK degradation mixture employing the R5 ELISA (FIG. 8E) or G12 ELISA (FIG. 8F) assays. Epitope abolishment in Mixed gliadins (250 µg/ml) were incubated with NattoK (57 µg/ml) for 0, 15, 30 and 120 min and then assayed by the R5 ELISA or G12 ELISA.

FIG. 10. Multiple sequence alignment of subtilisins derived *Rothia* using CLUSTAL O (1.2.1) (SEQ ID NOs: 43-58, 3, 59-63, 2, 64-66, 33, 67-81, 1, and 82-84, respectively, in order of appearance). Underlined enzymes, C6R5V8_9MICC, C6R5W1_9MICC, and C6R5V9 9MICC are those identified in this disclosure.

FIG. 11 shows the phylogenetic tree (Clustal Omega) of *Rothia* subtilisins revealing 8-9 distinct groups. Boxed are the enzymes identified in this disclosure.

FIG. 12A shows a representative SDS-PAGE gel part stained with Coomassie Brilliant Blue.

FIG. 12B shows a representative zymogram gel corresponding to the SDS-PAGE gel part, the zymogram was developed as a using externally added casein as the enzyme substrate to visualize bands with enzyme activity (indicated with an asterisk). Bands 1-4 were excised and subjected to mass spectrometric analysis of the amino acid sequences and identification of the protein. The protein was identified as BAV86562.1 from *Rothia aeria*.

FIG. 13 show the CLUSTAL 2.0.12 alignment of protein KGJ00122.1 (SEQ ID NO: 33) from *Rothia dentocariosa*, and protein BAV86562.1 (SEQ ID NO: 34) from *Rothia aeria*. Both enzymes belong to the peptidase S8 family of subtilisin enzymes. The * symbol underneath the sequence indicates an identical amino acid at that position in both protein sequences. The proteins are >99% homologous.

FIG. 14 shows the alignment of the amino acid sequences of subtilisins from *R. mucilaginosa* (WP_044143865.1, (SEQ ID NO: 64); WP_044143864.1, (SEQ ID NO: 82)), *R. aeria* (BAV86562.1, (SEQ ID NO: 34)), *B. licheniformis* (P00780.1, (SEQ ID NO: 35)) and *B. subtilis* NAT (P35835.1, (SEQ ID NO: 35)). Underlined conserved amino acids are the D, H and S residues that participates in the catalytic triad of subtilisins.

FIGS. 15B and 15D, Gliadins (500 µg/ml) incubated with Rmep (FIG. 15B) or nattokinase (FIG. 15D) at 25 µg/ml. FIGS. 15E and 15F, ATIs incubated with control heat inactivated enzymes, Rmep (FIG. 15E) or nattokinase (FIG. 15F).

FIGS. 16A-16D demonstrate that ethanol treated gluten-degrading enzyme contain bacteria are not viable but their intrinsic gluten-degrading enzymatic activities are intact after ethanol treatment.

DETAILED DESCRIPTION OF THE DISCLOSURE

Figure 1A:
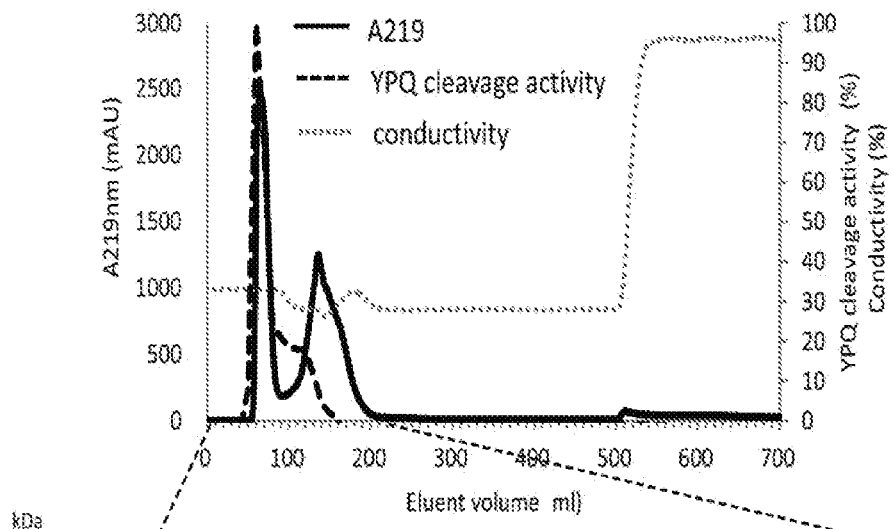
FIGS. 1A-1C show the isolation of *R. mucilaginosa* gluten-degrading enzymes by DEAE chromatography. *R. mucilaginosa* cells were lysed, sonicated, the supernatant ultracentrifuged, and the pellet dissolved in n-Octyl-β-D-glucopyranoside.

The *Rothia*-derived proteins with gluten-degrading enzymatic activity were identified as hypothetical proteins ROTMU0001_0241 (C6R5V9_9MICC, WP_044143864.1 peptidase S8), ROTMU0001_0243 (C6R5W1_9MICC, WP_044143865.1 peptidase S8) and ROTMU0001_240 (C6R5V8_9MICC, WP_005509166.1 peptidase S8) SEQ ID NO: 1-3 respectively. A blast search revealed that these are subtilisin-like serine proteases belonging to the peptidase S8 family. Alignment of the major *Rothia* subtilisins indicated that all contain the catalytic triad with Asp (D), His (H) and Ser (S) in the D-H-S order that is characteristic of the S8 protease family. They cleaved succinyl-Ala-Ala-Pro-Phe-paranitroanilide (SEQ ID NO: 4), a substrate for subtilisin with proline (Pro) in the P2 position, as in Tyr-Pro-Gln↓ and Leu-Pro-Tyr↓ cleavage specificities that were reported earlier for the *Rothia* gluten-degrading enzymes. The downward pointed arrow indicates the cleavage position or the location of the peptide bond that is cleaved. The numbering of the amino acid position (e.g., P1, P2, P3) is with respect to the peptide bond that is cleaved by the enzyme described. The amino acid residue immediately upstream of the cleavage peptide bond is designated the position P1, the amino acid residue immediately upstream of the P1 amino acid residue is P2. Here, in the substrate for subtilisin, Phe=P1 position, and Pro=P2 position, Ala=P3 and P4 positions. Moreover, FRET substrates of gliadin immunogenic epitopes comprising Xaa-Pro-Xaa motives were rapidly hydrolyzed. The *Rothia* subtilisins as well as other subtilisins from *Bacillus* sp., subtilisin A and nattokinase, could degrade the highly immunogenic gliadin-derived 33-mer peptide. Furthermore, major gluten antigenic epitopes were efficiently eliminated by both subtilisins, as demonstrated with R5 and G12 gliadin ELISA assays. Therefore, this study identified *Rothia* and food-grade *Bacillus* subtilisins as promising new candidates for enzyme therapeutics in celiac disease (CD).

Accordingly, described herein are gluten-degrading enzyme formulations and compositions comprising subtilisin derived from *Rothia* species bacteria, as well as uses thereof in the treatment of CD or a related disorder, and the treatment of gluten-containing foodstuff.

The methods, formulations, and compositions described herein are advantageous over other *Rothia* species enzyme compositions in that they retain gluten-degrading activity over a wide range of pH and thus, are active throughout the digestive tract of a subject diagnosed with celiac disease or a related disorder or non-celiac/non-allergy wheat sensitivity due to in amylase-trypsin inhibitors.

Sensitivity to gluten-containing foods is widespread, and manifests predominantly in the form of celiac disease (CD). The increased awareness for CD in the medical community and the general public has led to improved diagnosis and earlier initiation of preventive strategies. The prevalence of CD ranges between ~1:100-1:200 in most populations (1). The development of CD is dependent on exogenous and host-associated factors, whereby ingested gluten is the direct trigger of the disease, and the presence of HLA-DQ2 or HLA-DQ8 alleles, and tissue transglutaminase (TG2) activity are the major contributing host-associated factors (2). The disease is characterized by inflammation and flattening of the duodenal and jejunal villi, with a broad spectrum of symptoms, ranging from a clinically silent disease to severe malabsorption and a high risk for secondary autoimmune diseases (3).

To date, a strict gluten-free diet is the only treatment option for CD, which is difficult to maintain, and this poses a significant social and psychological burden to the patient. Traces of gluten are present in nearly all refined foods, and the felt quality of life of many patients equals that of hemodialysis patients (4). Therefore, novel therapies that would relieve patients from the need to adhere to the highly restrictive gluten-free diet are highly desired (5, 6).

The major therapies currently being pursued target the immunogenic gluten peptides and the immune system, e.g. using a vaccine-based strategy, gluten-degrading enzymes, luminal gluten binders, and inhibitors of the body's enzyme tissue transglutaminase which potentiates gluten antigenicity by deamidation (7). Enzyme therapies cleave gluten and thereby abolish immunogenic epitopes before they reach the lamina propria of the small intestine where T cell activation occurs (8, 9). Enzyme therapeutics have advantages. First, enzyme therapeutics are targeting the most upstream trigger, i.e. antigenic gluten peptides, rather than endogenous molecules or cells downstream in the cascade of intestinal inflammation; second, they are amenable to optimization of substrate specificity and pH activity (10).

Bacterial and barley-derived gluten-degrading enzymes have been isolated (11, 12) and are being explored for clinical application (9, 13, 14). Furthermore, gluten-degrading bacteria, mostly lactobacilli and bifidobacteria, which are already used in the food industry have been found potentially useful for CD treatment (15-17), with a few reports indicating actual gluten digestion_(18, 19). The inventors have found that exceptionally high gluten-degrading enzyme activities are naturally associated with bacteria that colonize the oral cavity (20). Thus *Rothia* bacteria from human saliva can hydrolyze gluten domains that are highly immunogenic and resistant to mammalian digestive enzymes (21, 22). This recent discovery has identified these natural microbes as novel sources of gluten-degrading enzymes, with the added advantage that they exhibit an expected low toxicity profile (23). Here the inventors isolated the gluten-degrading enzymes from *Rothia mucilaginosa* and *Rothia aeria*, of which the complete genome sequence is available, and identified the proteinases as subtilisin family members. The discoveries highlight this group of enzymes, with cleavage specificities after Xaa-Pro-Xaa↓, and some with proven safety in the food industry, as hitherto unrecognized candidates for dietary enzyme therapeutics for CD.

Accordingly, in one embodiment, provided herein is a foodstuff comprising a formulation or composition comprising a subtilisin enzyme derived from a *Rothia* sp. bacteria.

In another embodiment, provided herein is a method for degrading gluten or attenuating the gluten in a gluten-containing foodstuff the method comprises contacting the gluten-containing foodstuff or an amylase-trypsin inhibitor containing foodstuff with an effective dose of a formulation or composition comprising a subtilisin enzyme derived from a *Rothia* sp. bacteria.

In another embodiment, provided herein is a composition comprising (a) an isolated subtilisin and/or subtilisin-like enzyme derived from a *Rothia* sp. bacteria, and (b) a prolyl endopeptidase (PEP).

In another embodiment, provided herein is a method for treating celiac disease or a related disorder such as gluten allergy, gluten intolerance, non-celiac/non-allergy wheat sensitivity due to in amylase-trypsin inhibitors, and dermatitis herpetiformis the method comprising administering to a subject an effective dose of a formulation comprising a subtilisin enzyme derived from a *Rothia* sp. bacteria, or administering an effective dose of any one composition comprising a subtilisin enzyme derived from a *Rothia* sp. bacteria described herein.

In another embodiment, provided herein is a use of a subtilisin enzyme derived from a *Rothia* sp. bacteria to attenuate gluten toxicity in gluten-containing food stuff or for the treatment of celiac disease or a related disorder.

In another embodiment, provided herein is a use of a subtilisin enzyme derived from a *Rothia* sp. bacteria for the manufacture of medicament to treat of celiac disease or a related disorder.

In another embodiment, provided herein is a use of a formulation comprising a subtilisin enzyme derived from a *Rothia* sp. bacteria, or any one composition described herein to attenuate gluten toxicity in gluten-containing food stuff or for the treatment of celiac disease or a related disorder.

In another embodiment, provided herein is a use of a formulation comprising a subtilisin enzyme derived from a *Rothia* sp. bacteria, or any one composition described herein for the manufacture of medicament for the treatment of celiac disease or a related disorder.

In one embodiment, provided herein is a method for detoxifying gluten, the method comprising contacting gluten-containing foodstuff with an effective amount of with an effective dose of a formulation comprising a subtilisin enzyme derived from a *Rothia* sp. bacteria or a composition comprising a subtilisin enzyme derived from a *Rothia* sp. bacteria described herein.

In one embodiment, provided herein is a method for detoxifying an amylase-trypsin inhibitor, the method comprising contacting an amylase-trypsin inhibitor-containing foodstuff with an effective amount of a formulation comprising a subtilisin enzyme derived from a *Rothia* sp. bacteria or a composition comprising a subtilisin enzyme derived from a *Rothia* sp. bacteria described herein.

In another embodiment, provided herein is a method for detoxifying gluten, the method comprising contacting a gluten-containing foodstuff with an effective amount of the isolated enzyme composition comprising a subtilisin enzyme derived from a *Rothia* sp. bacteria described herein.

In one embodiment, provided herein is a method for detoxifying an amylase-trypsin inhibitor, the method comprising contacting the amylase-trypsin inhibitor-containing foodstuff with an effective amount an isolated enzyme composition comprising a subtilisin enzyme derived from a *Rothia* sp. bacteria described herein.

In one embodiment, provided herein is a gluten-free foodstuff composition comprising a gluten-containing foodstuff in an admixture with a subtilisin enzyme derived from a *Rothia* sp. bacteria described herein. In one embodiment, the subtilisin enzyme is isolated from a *Rothia* sp. bacteria. In another embodiment, the subtilisin enzyme is a recombinant protein expressed from any protein expression system known in the art and the protein expression system is not *Rothia* sp. bacteria. For example, the recombinant subtilisin enzyme is expressed in expression bacteria *Escherichia coli*.

In one embodiment, provided herein is a gluten-free foodstuff composition comprising a gluten-containing foodstuff in an admixture with the isolated enzyme formulation or composition comprising subtilisin enzyme derived from a *Rothia* sp. bacteria described herein and/or the probiotic composition comprising a *Rothia* sp. bacteria that expresses subtilisin enzyme described herein.

In one embodiment, provided herein is a method of killing gluten-degrading bacteria without affecting their enzyme activities therein, the method comprises incubation the bacteria with ethanol for a period of time sufficient for the bacteria to not be able to cell divide.

In one embodiment, provided herein is a method for detoxifying gluten, the method comprising contacting gluten-containing foodstuff with an effective amount of with an effective dose of a formulation or composition comprising ethanol-treated, and lyophilized bacteria that have gluten-degrading enzymatic activities therein described herein, wherein the bacteria are cannot cell divide and are not alive or viable.

In one embodiment, provided herein is a method for detoxifying an amylase-trypsin inhibitor, the method comprising contacting amylase-trypsin inhibitor-containing foodstuff with an effective amount of with an effective dose of a formulation or composition comprising ethanol-treated, and lyophilized bacteria that have gluten-degrading enzymatic activities therein described herein, wherein the bacteria are cannot cell divide and are not alive or viable.

In another embodiment, provided herein is a method for detoxifying gluten, the method comprising contacting gluten-containing foodstuff with an effective amount of the isolated enzyme composition comprising a subtilisin enzyme derived from a *Rothia* sp. bacteria described herein.

In one embodiment, provided herein is a method for detoxifying an amylase-trypsin inhibitor, the method comprising contacting the amylase-trypsin inhibitor-containing foodstuff with an effective amount of ethanol-treated, and lyophilized bacteria that have gluten-degrading enzymatic activities therein described herein, wherein the bacteria are cannot cell divide and are not alive or viable.

In one embodiment, provided herein is a foodstuff comprising a formulation or a composition comprising ethanol-treated, and lyophilized bacteria that have gluten-degrading enzymatic activities therein described herein, wherein the bacteria are cannot cell divide and are not alive or viable.

In one embodiment, provided herein is a gluten-free foodstuff composition comprising a gluten-containing foodstuff in an admixture with formulation or composition comprising ethanol-treated, and lyophilized bacteria that have gluten-degrading enzymatic activities therein, or with an effective amount of ethanol-treated, and lyophilized bacteria that have gluten-degrading enzymatic activities therein, wherein the bacteria are cannot cell divide and are not alive or viable.

In one embodiment, provided herein is a method for degrading gluten or attenuating gluten toxicity in a gluten-containing foodstuff or degrading an amylase-trypsin inhibitor in a foodstuff, the method comprises contacting the gluten-containing foodstuff or the amylase-trypsin inhibitor containing foodstuff with an effective dose of a formulation or composition comprising ethanol-treated, and lyophilized bacteria that have gluten-degrading enzymatic activities therein described herein, wherein the bacteria cannot cell divide and are not alive or viable.

In another embodiment, provided herein is a formulation or composition comprising ethanol-treated, and lyophilized bacteria that have gluten-degrading enzymatic activities therein described herein, wherein the bacteria cannot cell divide and are not alive or viable.

In another embodiment, provided herein is a method for treating celiac disease or a related disorder such as gluten allergy, gluten intolerance, non-celiac/non-allergy wheat sensitivity due to in amylase-trypsin inhibitors, and dermatitis herpetiformis, the method comprising administering to a subject an effective dose of a formulation or composition comprising ethanol-treated, and lyophilized bacteria that have gluten-degrading enzymatic activities therein described herein, wherein the bacteria cannot cell divide and are not alive or viable.

In another embodiment, provided herein is a use of a formulation or composition comprising ethanol-treated, and lyophilized bacteria that have gluten-degrading enzymatic activities therein described herein to attenuate gluten toxicity in gluten-containing food stuff or to degrade an amylase-trypsin inhibitor in foodstuff for the treatment of celiac disease or a related disorder, wherein the bacteria cannot cell divide and are not alive or viable.

In another embodiment, provided herein is a use of a formulation or composition comprising ethanol-treated, and lyophilized bacteria that have gluten-degrading enzymatic activities therein described herein for the manufacture of medicament to treat of celiac disease or a related disorder, wherein the bacteria cannot cell divide and are not alive or viable.

In one embodiment of the degrading method described, the contacting of the gluten-containing food stuff is performed in vitro prior to consumption of the gluten-containing food stuff or the amylase-trypsin inhibitor containing foodstuff respectively.

In one embodiment of the degrading method described, the contacting of the gluten-containing food stuff is performed in vivo concurrent with or after consumption of the gluten-containing food stuff or the amylase-trypsin inhibitor containing foodstuff respectively.

In one embodiment of the treatment method described, the administering of the formulation or composition is performed in vitro prior to consumption of the gluten-containing food stuff or the amylase-trypsin inhibitor containing foodstuff respectively.

In one embodiment of the treatment method described, the administering of the formulation or composition is performed in vivo concurrent with or after consumption of the gluten-containing food stuff or the amylase-trypsin inhibitor containing foodstuff respectively.

In one embodiment of the treatment method described, the administering of the formulation or composition is performed in vitro prior to and also concurrent with or after consumption of the gluten-containing food stuff or the amylase-trypsin inhibitor containing foodstuff respectively.

In any aspect described herein, the *Rothia* sp. bacteria is selected from the group consisting of *Rothia mucilaginosa* ot 681 (strain WSA-2B), *Rothia mucilaginosa* ATCC 25296, *Rothia* species ot 188, *Rothia* sp. HOT-188, *Rothia aeria* strain F0474 (HMP ID 1324), *Rothia aeria* HM-818, *Rothia aeria* strain WSA-8, *Rothia aeria* BAV86562.1 and *Rothia dentocariosa* KGJ00122.1.

In any aspect described herein, the *Rothia* sp. bacteria is selected from the group consisting of *R. mucilaginosa, R. aeria* and *R. dentocariosa*.

In any aspect described herein, the subtilisin has the sequence ROTMU0001_0241 (also identified as C6R5V9_9MICC and WP_044143864.1 peptidase S8), ROTMU0001_0243 (also identified as C6R5W1_9MICC and WP_044143865.1 peptidase S8) and ROTMU0001_240 (also identified as C6R5V8_9MICC and WP_005509166.1 peptidase S8), KGJ00122.1 peptidase S8, and BAV86562.1 glycerol-3-phosphate ABC transporter. These subtilisins are identified as SEQ ID NO: 1-3, 33, and 34 respectively.

In any aspect described herein, the subtilisin is at least 90% identical to the sequences of ROTMU0001_0241 (C6R5V9_9MICC; WP_044143864.1 peptidase S8), ROTMU0001_0243 (C6R5W1_9MICC; WP_044143865.1 peptidase S8) and ROTMU0001_240 (C6R5V8_9MICC; WP_005509166.1 peptidase S8), KGJ00122.1 peptidase S8, and BAV86562.1 glycerol-3-phosphate ABC transporter proteins described herein (See Section on subtilisins and subtilisin-like enzymes), (SEQ ID NOS: 1-3, 33, and 34).

In any aspect described herein, the subtilisin is derived from a *Rothia* spp. and degrades gluten G12 epitope at least 50% faster than *Bacillus* spp.-derived subtilisin. The gluten G12 epitope degradation assay is known in the art and can be performed using any assay known. For example, as described in the Example section of this disclosure. In other embodiments, the *Rothia* spp. subtilisin is at least 55%, at least 60%, at least 65%, at least 70%, at least 75%, at least 80%, or at least 85%, at least 90% faster than *Bacillus* spp. derived subtilisin.

In any aspect described herein, the subtilisin comprises the conserved catalytic triad that is characteristic of the S8A family of serine protease family, the conserved catalytic triad being Asp (D), His (H) and Ser (S) in the D-H-S order in the polypeptide.

Conserved regions of the catalytic triad in subtilisins comprises the D, H and S residues. These regions are predicted to define cleavage specificity towards the gluten R5 epitope. Regions 1-3 are conserved in both *Rothia* and *Bacillus* subtilisins and flank the D, H and S residues, respectively. Regions 4 to 7 flank the regions 1 to 3 are found in the *Rothia* subtilisins only.

```
(region 1)
                                       (SEQ ID NO: 26)
VK(I/V)AV(I/V/L)D(S/T)G(I/V)(D/Q)

(region 2)
                                       (SEQ ID NO: 27)
(G/S)HGTHVAGT (region 3)
                                       (SEQ ID NO: 28)
GTSM(A/S)
```

Variable domains flanking the conserved regions 1 to 3 described above. These are predicted to confer enzyme cleavage specificity towards the gluten G12 epitope:

```
(region 5)
                                       (SEQ ID NO: 29)
K(G/D)(region 1)

(region 6)
                                       (SEQ ID NO: 30)
(region 1)YTH (region 7)
                                       (SEQ ID NO: 31)
(region 2)AAGYGV (region 8)
                                       (SEQ ID NO: 32)
(S/T)(region 3)
```

In any aspect described herein, the subtilisin cleaves proline-containing proteins, cleaving the second peptide bond after proline in the $XPX_1$ motif, where X is any amino acid, P is proline and $X_1$ is a hydrophobic amino acid, i.e., cleaving at the peptide bond after $X_1$, e.g. the XPQ motif, where Q is glutamine, and subtilisin cleaves the peptide bond after Q.

A hydrophobic amino acid is one that has a hydrophobic side chain. The nine amino acids that have hydrophobic side chains are glycine (Gly), alanine (Ala), valine (Val), leucine (Leu), isoleucine (Ile), proline (Pro), phenylalanine (Phe), methionine (Met), and tryptophan (Trp).

In any aspect described herein, the subtilisin cleaves succinyl-Ala-Ala-Pro-Phe-↓paranitroanilide (SEQ ID NO: 4), a substrate for subtilisin, cleaving at the second peptide bond after the proline located at the P2 position in the substrate. The downward arrow indicates the site of cleavage by subtilisin. The numbering of the amino acid position is with respect to the peptide bond that is cleaved by the enzyme described. The amino acid residue immediately upstream of the cleavage peptide bond has designate the position P1, the amino acid residue immediately upstream of the P1 amino acid residue is P2. Hence, the peptide bond that is cleaved is that after Phe, and Phe is the amino acid residue at the P1 position, and Pro is the amino acid residue at the P2 position.

In any aspect described herein, the subtilisin degrades the highly immunogenic gliadin-derived 33-mer peptide.

In any aspect described herein, the subtilisin does not cleave the second peptide bond after proline in the P2 position in a tripeptide having the -$P_xFP_y$-motif, wherein F=phenylalanine=Phe; P=proline=Pro. In this tripeptide, F is the amino acid residue at the P1 position, $P_x$ is the amino acid residue at the P2 position, and Py is the amino acid in the P1' position (downstream from the sessile bond).

In any aspect described herein, the subtilisin does not cleave the second peptide bond after proline in the P2 position in a tripeptide having the -$P_xP_yF$-motif, wherein F=phenylalanine; P=proline. In this tripeptide, $P_y$ is the amino acid residue at the P1 position, and $P_x$ is the amino acid residue at the P2 position.

In any aspect described herein, the subtilisin is more effective glutenase compared with *Bacillus* sp. subtilisin A with respect to certain immunogenic epitopes.

In any aspect described herein, the subtilisin has an apparent molecular weight of about 75-80 kDa as determined by gliadin zymograms or by sodium dodecyl sulfate polyacrylamide gel electrophoresis or as described in FIGS. 2A-2E; or have a predicted molecular weight of ~125 kDa as described in the Example section.

In any aspect described herein, the subtilisin undergoes autocatalytic activation to produce a shorter mature enzyme. Autocatalytic activation refers to the self-cleavage exhibited by subtilisin on its own polypeptide to form a shorter polypeptide that has further enzymatic cleavage on other proteins. The self-cleaving brings forth the enzymatic cleavage activity using other proteins as substrate. In any aspect described herein, the shorter mature enzyme subtilisin is about 75-80 kDa as determined by gliadin zymograms or by sodium dodecyl sulfate polyacrylamide gel electrophoresis as described herein.

In any aspect described herein, the subtilisin enzyme has a functional pH range of 6.0-10.0. as determined by detectable Z-YPQ-pNA cleaving activity. For example, a detectable Z-YPQ-pNA cleaving activity within a 72 hour digestion period or substantially complete Z-YPQ-pNA cleavage within a 1 hour digestion period.

In any aspect described herein, the subtilisin enzyme from *R. mucilaginosa* has low or negligible enzyme activity at pH values below 5.0 or pH values higher than 11.0.

In any aspect described herein, the subtilisin enzyme has low or negligible enzyme activity at pH values below 5.0 or pH values higher than 11.0.

In any aspect described herein, the subtilisin is inhibited by phenylmethane sulfonyl fluoride (PMSF), a serine protease inhibitor. In another embodiment, the subtilisin is 100% inhibited by 1 mM of PMSF.

In any aspect described herein, the subtilisin is not inhibited by E64 or (ethylenediaminetetraacetic acid) EDTA.

In any aspect described herein, the subtilisin is not stable in acid conditions.

In any aspect described herein, the subtilisin is lyophilized.

In any aspect described herein, the subtilisin is a protein isolated from *Rothia* sp. bacteria. For example, by protein purification methods from cell extracts of *Rothia* sp.

In any aspect described herein, the subtilisin is an isolated recombinant protein. For example, the subtilisin nucleic acid coding sequence is expressed in another organism other than *Rothia* sp. For example, expression in yeast or *Escherichia coli*. Method of recombinantly expressing proteins in other eukaryote or prokaryotic protein expression systems are known in the art.

In any aspect described herein, the subtilisin nucleic acid coding sequence is codon optimized for efficient protein expression for the selected eukaryote protein expression systems in order to produce large quantities of recombinant *Rothia* sp. subtilisin.

In any aspect described herein, the subtilisin has an amino acid sequence that show at least 60% similarity to SEQ ID NO: 1-3, 33, and 34. (See Section on subtilisins and subtilisin-like enzymes).

In any aspect described herein, the subtilisin comprises SEQ ID NO: 1-3, 33, and 34.

In any aspect described herein, the subtilisin consists essentially of SEQ ID NO: 1-3, 33, and 34.

In any aspect described herein, the subtilisin is SEQ ID NO: 1-3, 33, and 34.

In any aspect described herein, the formulation or composition further comprising a prolyl endopeptidase (PEP). PEP are also known as prolyl oligopeptidase (POP) or post-proline cleaving enzyme. For example, PEP degrade the nonapeptide bradykinin at the Pro-Phe bond.

In any aspect described herein, the PEP is derived from a microorganism selected from the group consisting of *Aspergillus niger, Flavobacterium meningosepticum, Sphingomonas capsulata, Penicillium citrinum, Hordeum vulgare*, and *Myxococcus xanthus*.

In any aspect described herein, the formulation or composition further comprising at least one additional gluten-degrading enzyme isolated from a *Rothia* species bacteria that is not a subtilisin or subtilisin-like enzyme and does not contain the conserved catalytic triad, amino acids D, H, and S in the catalytic domain of S8 protease family.

In any aspect described herein, the formulation or composition described, the at least one additional gluten-degrading enzyme retains protease activity at an acidic pH of 3.0 as measured in an in vitro gliadin degradation assay for 3 hours using a synthetic substrate Z-YPQ-pNA.

In any aspect described herein, the formulation or composition described, the at least one additional gluten-degrading enzyme comprises an isoelectric point in a pH range of 2.0-7.0, inclusive.

In any aspect described herein, the at least one additional gluten-degrading enzyme that retains protease activity at acidic pH of 3.0 is derived from the *Rothia* species are the enzymes disclosed in the PCT Patent Application No: PCT/US11/43118, PCT Patent publication No: WO2012006384, and the US Patent Application No. 20130171109, the contents of each are incorporated by reference in their entity.

In any aspect described herein, the at least one additional gluten-degrading enzyme that retains protease activity at acidic pH of 3.0 is derived from the *Rothia* species *Rothia* species of 188, also known as *Rothia* sp. HOT-188, *Rothia aeria* strain F0474 (HMP ID 1324), *Rothia aeria* HM-818, and *Rothia aeria* strain WSA-8.

In any aspect described herein, the at least one additional gluten-degrading enzyme that retains protease activity at acidic pH of 3.0 has an iso-electric point in a pH range of 2.0-4.0, inclusive.

In any aspect described herein, the at least one additional gluten-degrading enzyme that retains protease activity at acidic pH of 3.0 has an estimated molecular weight between 120-150 kDa, inclusive.

In any aspect described herein, the at least one additional gluten-degrading enzyme that retains protease activity at acidic pH of 3.0 has an estimated molecular weight of 135-145 kDa, inclusive.

In any aspect described herein, the at least one additional gluten-degrading enzyme that retains protease activity at acidic pH of 3.0 has an estimated molecular weight of 125-145 kDa, inclusive.

In any aspect described herein, the at least one additional gluten-degrading enzyme that retains protease activity at acidic pH of 3.0 has an estimated molecular weight between 50 and 90 kDa, inclusive.

In any aspect described herein, the at least one additional gluten-degrading enzyme that retains protease activity at acidic pH of 3.0 has molecular weight between 65 and 75 kDa, inclusive.

In any aspect described herein, the at least one additional gluten-degrading enzyme that retains protease activity at acidic pH of 3.0 has molecular weight between 65 and 80 kDa, inclusive.

In any aspect described herein, the at least one additional gluten-degrading enzyme that retains protease activity at acidic pH of 3.0 has molecular weight between 75 and 80 kDa, inclusive.

In any aspect described herein, the at least one additional gluten-degrading enzyme that retains protease activity at acidic pH of 3.0 retains activity at the pH between 2.5 and 5.0, inclusive.

In any aspect described herein, the at least one additional gluten-degrading enzyme that retains protease activity at acidic pH of 3.0 degrades a gliadin protein, a fragment thereof, or a gluten-containing foodstuff or ingredient thereof.

In any aspect described herein, the fragment thereof is a 33-mer peptide of α2-gliadin or a 26-mer domain derived from γ-gliadin.

In any aspect described herein, the 33-mer peptide is LQLQPFPQPQLPYPQPQLPYPQPQLPYPQPQPF (SEQ ID NO: 5).

In any aspect described herein, the 26-mer domain is FLQPQQPFPQQPQQPYPQQPQQPFPQ (SEQ ID NO: 6).

In any aspect described herein, the degradation by the at least one additional gluten-degrading enzyme that retains protease activity at acidic pH of 3.0 occurs by cleaving the peptide bond after an amino acid sequence selected from the group consisting of -XPQ- -QQP-, -PPF-, -LPY- and -PFP-.

In any aspect described herein, the formulation or composition further comprising at least one isolated additional glutamine endopeptidase enzyme that cleaves a peptide bond after a QPF and a PFP motif in glutens.

In any aspect described herein, the additional glutamine endopeptidase enzyme are those enzymes disclosed in the U.S. Pat. No. 8,685,392, the contents are incorporated by reference in its entity.

In any aspect described herein, the degradation by the subtilisin, or by the at least one enzyme that retains protease activity at acidic pH of 3.0 or the glutamine endopeptidase described herein is partial. For example, the degradation is about 20%, about 25%, about 30%, about 35%, about 40%, about 45%, about 50%, about 55%, about 60%, about 65%, about 70%, about 75%, about 80%, about 85%, about 90%, or about 95%. Various percentages of degradation between 20% to 99% are encompassed herein.

In any aspect described herein, the degradation by the subtilisin, or by the at least one additional gluten-degrading enzyme that retains protease activity at acidic pH of 3.0 or the glutamine endopeptidase described herein is complete.

In any aspect described herein, the degradation by the at least one additional gluten-degrading enzyme that retains protease activity at acidic pH of 3.0 occurs by cleaving the peptide bond after an amino acid sequence selected from the group consisting of -XPQ-, -QQP-, -PPF-, -LPY- and -PFP-. In other embodiments, degradation or digestion occurs by cleaving the peptide bonds after amino acid sequences XPQ and QQP; XPQ and PPF; XPQ and PFP; XPQ and LPY; QQP and LPY; PPF and LPY; PFP and LPY; XPQ, QQP and PPF; XPQ, QQP and PFP; XPQ, QQP and LPY; QQP, PPF, and PFP; XPQ, PPF and PFP; QQP, PPF and LPY; XPQ, PPF and LPY; LPY, PPF, and PFP; QQP, PFP and LPY; XPQ, PFP and LPY; XPQ, QQP, PPF and LPY; LPY, QQP, PPF and PFP; XPQ, LPY, PPF and PFP; XPQ, QQP, PFP and LPY; XPQ, QQP, PPF and PFP; or XPQ, QQP, PPF, LPY and PFP.

In any aspect described herein, the formulation or composition further comprising a glutamine specific protease which is selected from the group consisting of *Hordeum vulgare* endoprotease, *Aspergillus oryzae* X-Pro dipeptidase, and *Aspergillus saitoi* carboxypeptidase. For example, glutamine specific proteases as described in U.S. Pat. No. 7,628,985, and US Patent Application Publication No. 20130171109, the contents of each are incorporated by reference in their entirety.

In any aspect described herein, the formulation or composition further comprising a pharmaceutically acceptable carrier.

In any aspect described herein, the related disorder is selected from the group consisting of refractory celiac disease, gluten allergy, gluten intolerance, non-celiac/non-allergy wheat sensitivity due to in amylase-trypsin inhibitors, and dermatitis herpetiformis.

In any aspect described herein, the composition is formulated into granules. For example, lyophilized enzyme protein granular preparation.

In any aspect described herein, the composition comprises lyophilized enzyme protein preparation.

In any aspect described herein, the composition is an oral formulation, such as in the form of a capsule, liquid, tablet, suspension, or enteric coated capsule or tablet.

In any aspect described herein, the composition is formulated for treatment of celiac disease or a related disorder in a subject In any aspect described herein, the composition is formulated for treatment of a gluten-containing foodstuff prior to ingestion by a subject having celiac disease or a related disorder, wherein the gluten-containing foodstuff is degraded in vitro.

In any aspect described herein, the subtilisin that is derived from *Rothia* sp., the at least one gluten-degrading enzyme, the isolated enzyme composition and/or the probiotic composition is administered in an admixture with a gluten-containing foodstuff for the purpose of degrading the gluten in the food. In one embodiment, the enzyme is admixed with the ingredients during the manufacture of the food. In one embodiment, the enzyme is admixed with the ingredients during the preparation and/or cooking of the food.

In any aspect described herein, the isolated subtilisin enzyme retains activity in the admixture.

In any aspect described herein, the gluten-containing foodstuff is degraded partially prior to ingestion by the subject. For example, the gluten-containing foodstuff is partially degraded to about 20%, about 25%, about 30%, about 35%, about 40%, about 45%, about 50%, about 55%, about 60%, about 65%, about 70%, about 75%, about 80%, about 85%, about 90%, or about 95% prior to ingestion by the subject. Various percentages of degradation between 20% to 99% are encompassed herein.

In any aspect described herein, the gluten-containing foodstuff is degraded completely prior to ingestion by the subject.

In any aspect described herein, the subtilisin that is derived from *Rothia* sp., the at least one additional gluten-degrading enzyme, the isolated enzyme composition or formulation described herein is administered to the subject as an oral formulation.

In any aspect described herein, the subtilisin that is derived from *Rothia* sp., the at least one additional gluten-degrading enzyme, the isolated enzyme composition or formulation described herein is administered just prior to, during or just after consumption of a gluten-containing foodstuff.

Celiac Disease and Related Disorders

The gastrointestinal (GI) tract consists of distinct but connected anatomical regions, comprising the oral cavity, the oesophagus, the stomach, the small and the large intestine (DeSesso J M, and Jacobson C F. Food Chem Toxicol 2001; 39:209-28). The oral microbiome is described in Dewhirst et al., J Bacteriol. 2010, 192:5002-17. The entire GI tract is colonized with microorganisms with colonization levels showing a gradient being lowest in the stomach and increasing in density toward the proximal and distal ends. The proximal region, the oral cavity, provides a rich environment for bacterial colonization as it contains a variety of different habitats and ecological niches. It harbors over 600 different types of bacteria belonging to 141 different taxa representing 6 different bacterial phyla, including the Firmicutes, Actinobacteria, Proteobacteria, Bacteroidetes, Fusobacteria and the TM7 phylum (Aas J A, et al. J Clin Microbiol 2005; 43:5721-32; Paster B J, et al. J Bacteriol 2001; 183:3770-83). The distal GI microbiome is likewise phylogenetically diverse with members representing at least 9 different phyla (Eckburg P B, et al. Science 2005; 308: 1635-8; Frank D N, et al. Proc Natl Acad Sci USA 2007; 104:13780-5).

The GI tract is considered a "super organ" with functions contributed by human as well as bacterial genes (Camp J G, et al. Gastroenterology 2009; 136:1989-2002; Turnbaugh P J, et al. Nature 2006; 444:1027-31). Most GI-colonizing microorganisms live in symbiosis with the host. The mutually beneficial relationship between the host and its colonizers is most evident in aspects related to digestion. Complex carbohydrates that cannot be degraded by the arsenal of human digestive enzymes can in most cases be hydrolyzed by bacterial glycosidases. For instance, bacteria belonging to the *Bacteroides* genus, turn the non-digestable polysaccharides into small chain fatty acids that are subsequently metabolized by the host (Turnbaugh P J, et al. Nature 2006; 444:1027-31). Ingested proteins are in part degraded by host proteolytic enzymes such as pepsin, elastase, carboxypeptidase, trypsin, and chymotrypsin converting them into oligopeptides and single amino acids which can then enter the enterocyte via selective transporters and be further metabolized or transported (Daniel H. Annu Rev Physiol 2004; 66:361-84). Evidently, this mechanism is contingent upon the susceptibility of the substrate proteins to digestion by host enzymes.

Examples of dietary proteins that are difficult to digest by host proteolytic enzymes are glutens. Gluten proteins, comprising gliadins and glutenins, are abundantly contained in dietary products made of wheat, barley and rye (Wieser H. Food Microbiol 2007; 24:115-9). They are unusual with respect to their high content of the amino acids proline and glutamine, which are largely resistant to cleavage by the major human GI digestive enzymes (e.g., pepsin, trypsin, chymotrypsin). Thus pepsin or trypsin are unable to cleave the peptide bonds C-terminal to these residues (Siegel M, et al. Chem Biol 2006; 13:649-58). The proteolytic resistance of some highly T cell stimulatory gluten-derived peptides that reach the duodenum, e.g. a 33-mer peptide from α2-gliadin and a 26-mer peptide from γ-gliadin, is paradigmatic for the inability of the human body to thoroughly digest gluten, resulting in the destructive immunological responses in the proximal intestine of patients with celiac disease (Koning F, et al. Best Pract Res Clin Gastroenterol 2005; 19:373-87; Jabri B, and Sollid L M. Nat Clin Pract Gastroenterol Hepatol 2006; 3:516-25; Schuppan D, et al., Gastroenterology 2009; 137:1912-33).

Celiac sprue, also known as celiac disease, gluten-sensitive enteropathy, and gluten-induced enteropathy, is a chronic disease of the digestive tract that interferes with the digestion and absorption of nutrients from food. People with celiac sprue cannot tolerate gluten. Celiac disease is an inherited, autoimmune disease in which the lining of the small intestine is damaged from eating gluten and other proteins found in wheat, barley, rye, and gluten-contaminated oats. There is a propensity of Celiac disease in individuals who possess the HLA-DQ8 class II antigen receptor gene. The exact cause of celiac disease is unknown although it is believed that intestinal damage is caused by interactions between specific gliadin oligopeptides and the HLA-DQ2, DQ2.5, DQ2.2/DQ7 or DQ8 antigen, which in turn induce proliferation of T lymphocytes in the subepithelial layers. T helper 1 cells and cytokines can play a major role in a local inflammatory process leading to villus atrophy of the small intestine. The intestines contain projections, called villi that absorb nutrients. The lining villi become damaged due to the body's immune reaction. In undiagnosed or untreated celiac disease, these villi become flattened. Because the lining of the intestine contains essential enzymes for digestion and absorption, its destruction leads to malabsorption, a difficulty in absorption of food and essential nutrients. As a result, Celiac sprue is often considered a malabsorption disorder. This affects the ability to absorb nutrients properly. The disease can develop at any point in life, from infancy to late adulthood. Those with a family member with celiac disease are at greater risk for developing the disease. The disorder is most common in Caucasians and those of European ancestry and women are affected more commonly than men.

The symptoms of celiac disease can vary significantly from person to person. This is part of the reason the diagnosis is frequently delayed. For example, one person may have constipation, a second may have diarrhea, and a third may have no irregularity in stools. A non-limiting list of gastrointestinal symptoms include abdominal pain, abdominal distention, bloating, gas, indigestion, constipation, decreased appetite that may also be increased or unchanged, diarrhea, chronic or occasional lactose intolerance which is common upon diagnosis, but usually goes away following treatment, nausea and vomiting, stools that float, are foul smelling, bloody, or "fatty", and unexplained weight loss although people can be overweight or of normal weight upon diagnosis.

A non-limiting list of non-intestinal symptoms include anemia (low red blood cell count), bone and joint pain, bone disease such as osteoporosis, kyphoscoliosis, and fracture, breathlessness due to anemia, bruising easily, dental enamel defects and discoloration, depression, fatigue, growth delay in children, hair loss, hypoglycemia, irritability and behavioral changes, malnutrition, mouth ulcers, muscle cramps, nosebleeds, seizures, short stature, unexplained skin disorders (dermatitis herpetiformis), swelling which can be general or abdominal, and vitamin or mineral deficiency which can include single or multiple nutrient (for example, iron, folate, vitamin K).

There is currently no treatment for celiac disease except the advice to follow a lifelong gluten-free diet, which allows the intestinal villi to heal. Patients are advised to eliminate foods, beverages, and medications that contain wheat, barley, rye, and in some cases oats. The health care provider may prescribe vitamin and mineral supplements to correct nutritional deficiencies. Occasionally, corticosteroids (such as prednisone) may also be prescribed for short-term use or in patients suffering from refractory sprue. Following a well-balanced, gluten-free diet is generally the only treatment needed to stay well.

The current diagnosis method includes a complete blood count (CBC) to detect signs of anemia, testing for an increase in alkaline phosphatase level which may indicate bone loss, testing for low cholesterol and albumin levels which may be signs of malabsorption and malnutrition, testing for an increase in liver enzymes and abnormal blood clotting, and detection of specific antibodies to tissue transglutaminase and gliadin. The health care provider will order these antibody tests if Celiac sprue is suspected. If the tests are positive, upper endoscopy is usually performed to sample a piece of tissue (biopsy) from the first part of the small intestine (duodenum). An endoscopy with enteroscopy, particularly of the lower sections of the intestine most commonly affected, will show a flattening of the villi. A follow-up biopsy or blood work may be ordered several months after the diagnosis and treatment to confirm the disease. Normal results mean that the patient has responded to treatment, thereby confirming the diagnosis.

In one embodiment, the subject treated according to the methods and compositions described herein has been diagnosed with Celiac Sprue, gluten allergy/gluten intolerance and/or dermatitis herpetiformis. In another embodiment, the subject is a mammal, preferably a human. Current diagnosis methods for Celiac sprue include but are not limited to one or more of serological tests, e.g. anti-gliadin antibodies, anti-transglutaminase antibodies, anti-endomysial antibodies; endoscopic evaluation, e.g. to identify celiac lesions; histological assessment of small intestinal mucosa, e.g. to detect villous atrophy, crypt hyperplasia, infiltration of intra-epithelial lymphocytes; and any GI symptoms dependent on inclusion of gluten in the diet.

Non-celiac/non-allergy wheat sensitivity (NCWS) due to amylase-trypsin inhibitors (ATIs) has an estimated prevalence of 5-10% in wheat (cereal) consuming populations. NCWS is characterized by intestinal and extra-intestinal symptoms related to the consumption of gluten-containing foods that are also enriched in ATIs. The diagnosis is made after CD and wheat allergy have been excluded and if the patients display typical symptoms and complaints within hours to days after consumption of ATI-containing cereals, mainly wheat, and remission of these symptoms within a few hours to days after stopping their consumption1. The wheat components responsible for the initiation of an innate immune responses to wheat and related cereals in NCWS have been identified as ATIs. Wheat ATIs are a family of disulfide-linked and protease resistant proteins that occur as monomers, dimers and tetramers with molecular weights ranging from 12-60 kDa. ATIs bind to and activate the TLR4-MD2-CD14 complex on mainly myeloid cells (dendritic cells, macrophages, monocytes), ultimately resulting in the release of proinflammatory innate cytokines.

*Rothia* Bacteria Spp. Subtilisins and Subtilisin-Like Enzymes

There were three sequences of *R. mucilaginosa* proteins identified in excised protein bands in the "Rmep" fraction in the Example section. These three *R. mucilaginosa* proteins have been identified and are shown here. Start codons were determined using Artemis (correcting the start codons listed for C6R5V9 and C6R5W1 at NCBI). Bold and underlined residues are the predicted signal peptide cleavage sites AHA, and conserved enzyme catalytic triad D-H-S that is characteristic of the S8 protease family. SEQ ID NOS: 1-3 in order of appearance.

C6R5V9|C6R5V9_9MICC Uncharacterized protein OS=*Rothia mucilaginosa* ATCC 25296 GN=ROTMU0001_0241 PE=3 SV=1, also known as WP_044143864.1 peptidase S8. The section indicated by the amino acid residues in bold is the cd07474 domain

```
                                            (SEQ. ID. NO: 1)
MTTPHAPRRRMKAVGATGLSAALALTLGVPATFSAAHAQSPQQVEGSTAS

ASGDAASRISPGLQKAEGQITVYVQFKGKGAYEQTQSAAVLARKEAPANR

QAQVQAIAAQVQSQAQSVAAASGAKLMYTTHNAMRGAAITGDAAQIRALA

ERPDVERISPITAKERMNSGSEIDTKTLATWTRENTGYTGKGVKIAVVDS

GVDYTHADFGGPGTVDSYLKAKAMTELPSADSGLIDRNKFIGGIDINGDD

YNASVAEKSTPQPDNNPLDCRPDGEGSGGHGTHVAGTAAGYGVTANGTTY

RGDYKNLTEEQLKGMSIGPGTAPDAQILAIRVEGCYGNSSVVNEALDTVM

DPNGDGDFSDRADIVNLSLGGEFAPADDPESYMINTMARQGVETVAAAGN

ANNYNGVGDTYSDSGSPANAAAALSVANAYGSTQPIDRARVTTKTGLEWL

QGDYSVNEDYSKASADQLRGEVVAAPKRNRYACEAFTAEEAKALKGKWVY

FDWDQDDLTFPCGSKVREDNVQAAGGVGVVMAGKAERYTIGIGGNATIPG

LRLTASSTKDLEKALAAGPVTVEMNLDYKASGRGPHSHAFDLNSSSARGQ

HGSDGFIKPDLAAPGTEIVSAAVGTGNKGVSFTGTSMATPHVAGVAALVM

QAHQDYNPQMIKAALMNGASTPIKNEQGAQYAVDRVGTGMVNARAAVDAK

VIAYDAKTPERVSTAFGVLEYTPDSGIQTVQREIVLDNTDSQAHTYTLSY
```

EASTTIPGVEYSYPQQVSVGAGERKNVTVTVRIDPSKLEKTMDPAMSADQ

VAQDWTTGKTLAAGKRQYIASASGRLIFSENGREAIRQSIHVAPKPVSKM

RVDASRIDYKGISDKESTVTLRGTTLNQGGYRSLLGAFELGAVSDRIPSG

QLKLPSNQSVDLQYVGAASDAPALKAAGKNPNDGSLFFGISTWGTWDSMH

WGRQVQVQIDTNNDSTADYVLEVTREKGLDYPLVKVWSISGNASTVVARY

PLNSAWGDTDTNIMDTNTMILGVPLKDLGLTAEKAQSIKYTVQTDTWHNE

GNSYVDTTSTIEYSPFNPGVWFTGEESGVPGLFVDRDGGQLTVHRKNNNK

ERQALFLHMHNATGDLSGRKTANGVAAGDRAQVVKVARTIHDARFTDVPA

DNQFYREITWIAARQIDRGYQDGTFRPLNNMDRATMAAYFYRMSGSPQYT

APSTPSFSDVPLNHPYYKEIEWMKAQGITTGWPDGTYRPEGSVNRDAMAA

FFYRYAGSPEYTAPAQARFTDVPTDKQFYREISWLAEQGVTTGWPDGSFR

PVEPVHRDAMAAFVYRYSTGVLKESPEI

C6R5W1|C6R5W1_9MICC Uncharacterized protein OS =
Rothia mucilaginosa ATCC 25296 GN = ROTMU0001_0243
PE = 3 SV = 1 Also known as WP_044143865.1
peptidase S8
(SEQ. ID. NO: 2)
MQHTASPNPRGRSHRRRIGSGLLTLSMALSPLAALGTTAHAAEDPDAVKQ

VLSESMKNASGTVTAFVRFKGKGAFEQTQPAGVRAGVQAPVNTSSQVQAT

ASQVQSQAQQVSSQSGAQVLYTTHNAVRGVAVRGDAESIKALANRPDVEK

ISPILPKYRQNAGAAIDAGSLATWTGTTNPAGAGGYTGKGVKIAVIDSGI

DYTHTDFGGSGKLEDYEKASKLTELPSADSGLINRTKVAGGYDLVGDAYD

GSNTATPDGNPLDCTTGGHGTHVAGTAAGYGVNADGSTFTGDYSKLTAEQ

LKTMKIGPGVAPDAEIYAFRVFGCSGSTNVVIEALDRALDPNGDGDFSDR

VNVVNMSLGGEFSPQDDPEAYAVDALTRAGVLSVISAGNANDYSLRGDTY

SNSGHPATAASAITVANAYGSTRAVDAAELTDPATGTTRKVRGDYSVSYP

WAQAGTKEFTGELTAISENNRYACNALSADEAAAVKGKWVLIDWAKDDGE

LACGSKVRFDNLEAAGAKGVLLAGNDEEPGLGIAGNDTLPGFRLAASAAK

DLRAQITAAEAAGKPLTVRLGNELKSSLRVDTDKLDQLNPMSARGFHGSY

GYTKPDIAAPGSYITSAAVATGNNSVTFSGTSMAAPYVTGSAALVMQSHP

TYTPAQVKSALMNTATHDVRTESGATYAVDRVGAGRVDTLAAVQSKSLVY

NADKSGTVSLSFGVLEYAPDAGVQTLTREVTVENTDSVAHTYALSYAEST

NIPGVEYSFPSAVTLAPGETKKFEVTVRIDPSKLEKTRDAAMDTTQNATD

YYTGNETVPEQYRQYIASASGRLVLTEDGTKALRLPVHVAPKPVSTMHAA

EDTVTFTQKPSSDEAQKADTGWTKSQISLRGTEVNQGGYRSLLGAFEYGA

SVDRVAPTSLSLNSNVKANLQYVGAFSDAPALKAAGGNADDGTLRFGIST

WANWDVVSYENTFTVEIDTDGNNRADYKLVTDRAKGLDYPLVRLYGYKNG

NLVELGYYPLNGAWGDVDTNMMDTNTLIMSAPLKDLGLTSANNPDIQYRV

SATTQYEWGNVSETGWIKYRPFSPKLWFSGDSSAVAGLHPDASTTTLTAH

RSADAIPALGESGTPAKALLLHLHNGTGDLSGTNGAKGNRAEVLNIKEQQ

TEYITPSRFTDVKNTDQFYTEISWLAQRGITTGYPDGTYRPLESVERGAM

AAFFYRMQGSPQFTAPSTPSFKDVPTTHPFYKEIEWMKAQGITTGYSDGT

FRPSAPVNRDAMAAFFYRAAGSPHVDLPATSHFSDVSTDNQFYREITWLA

SKGISTGWPDGTYRPVTPIARDAMAAFIYRYTEKVANQAGR

C6R5V8|C6R5V8_9MICC Uncharacterized protein OS =
Rothia mucilaginosa ATCC 25296 GN = ROTMU0001_0240
PE = 3 SV = 1 Also known as WP_005509166.1
peptidase S8
(SEQ. ID. NO: 3)
MATFPEATPARAARHIQPGRLKQLARSCGALTLGLILGLIALPFGTAAYA

APGVVRGADRDAPHQNTGIGENNNEVLSPSLDGATGERAVFVRFKGQGAY

AQTQPDAVRSRAQAPVNAQAQVQAIRASVQQQGASAAKESGAQVLYTTHN

TMRGVALYGNVEQTRALANRDDVERISIIEDMAPQNSGTLIDTDTLSVWA

KSPANPASTGYTGKGVKIVVLDTGIDYTHADLGGPGTQEAFDKAKASDTI

PEGTYDPKKFLGGYDLVGDDYNSGKKETSTPHPDNNPLDCGGHGSHVAGT

AAGYGVNADGSTFHGDYSKLTEEQLKDMKIGPGSAPDAQLIGLRIFGCKG

ITAFVPKGLDRVLTPNDDGDFSDRADIANLSLGNEFGVEDETVNYAVGSL

YREGILSVVAAGNANNYNAVGDTYSNSGGPGISAYGLIVANSIGSTQLVD

RVKILAPANEADTYGDYSVSFDYSKATEDQLRGIVVRAASRNRYACEAFT

EEEAAALKGKWALIDWADADGTAPCGSKVRFDNLQAAGATGVVLTSNTEV

GDTAIGGNSSIPGVRLAKSQVERLSVQIDSGELTLQLGENLRDSIRVPNG

KLDQANTSTARGLHGSHGITKPDVAAPGINISSIEVGSGTGSSVKTGTSM

STPFVAGVAALIMQAHPEYGPRMLKTVIMNTADHHMQDAWGNPYAVDRVG

TGRINTRAAVADRVMLFNATRPEQVSDIFGVLEYTPNAGVQTLQHRVSVE

NTDSVAHTYALNYEGSTSIPGVEFSYPQSVSVGAGQKATFTVTVRIDPSK

LEKTRDPSMYPNQDSVNYSTGTVTISGARQYIASASGRLILTDADSSAAV

KTLRMPLHVAPKPVSAMRVAGSDIAFDAEGSGATEQTLTLQGTAVDQGGY

RSLLGAFELGASSPRIPTAKLGVGSDSRMDLQYVGAASNVAALKAAGADT

SEARLSEGISTWGNWQEVTPRGTYYVFVDTNKDGISDYRLQTVREKGLDY

PLVKVSKRSNGKWQATENALYPLNGTWGDTDTNIMDSNTLVMTVPLNVLG

LDPDAESTEISYSVTTSSAFSATTVVDTTDSVVFNYAAPKLWFSGDSAGV

PNLFVDAPETQLVAHRNGDAKNVSALFLHMHNATGDLSGVNGAAGERAQV

LRVSSNSEATAASAHFTDVPADYPFVNDINWLAQRRITTGYPDGTFRPNG

SVERGAMAAFFYRMAGSPQFTAPSTPSFKDVPRDHPFYKEIEWMRARGIT

TGWSDGTFRPNAAVNRDAMAAFFYRFAGSPAYSAPAASPFSDVAAGSQFY

REISWLAEQRITTGWADGSFRPVQPIERGAMAAFLHRYNVRVLNNR

One protein was identified from *Rothia dentocariosa* KGJ00122.1 from the excised bands 1-4 in FIG. 12. The protein had gluten-degrading properties in the casein degradation assay shown in FIG. 12. The amino acid sequence of *R. dentocariosa* KGJ00122.1 is shown below. Peptides derived from this sequence were identified in the bands 1-4.

>KGJ00122.1 peptidase S8, *Rothia dentocariosa*
(SEQ. ID. NO: 33)
MPKNTPIRGLSRACLSATLGVTMAITAGLPATAAPAGDPDTPVAQDIARN

SREHAVLSDSMKKAEGNIPVFVQFKGKGAYEQTQSPAVLANKQAPINKQA

EVQAIKTQVQSQAQAAAQSTGAKTLYTTHNIMRGVALQGDAAQIRALANN

PEVERITPIVPKKKQNAGSVVDTGAAENWARENSGYIGKDVKIAVVDSGI
DYTHSDEGGPGIVEAFNKATKLTEMPAADSGLYDAKKYIGGYDLVGDSYD
GINQTTPDNNPIDCSAGGHGTHVAGTAAGYGVNQDGTTFRGDYSKLTAEQ
LNQMKIGPGAAPEAQLYSFRVFGCTGTTAVVVQALDRTLDPNGDGDFSDR
ANIVNLSIGGEFSPPDDADAYAVESLNRQGVLAVVSAGNATDYYGRGDTY
SDSGQPANAVSALTVANSIGSSYAVDSMEIQAPANVAGKVPGDYTVSYTY
TGAKPEALTGTVVTPSESNKFGCEAFSAEDAAKIKDKWVFIEWANADGSL
PCGSKVRFDNVEKAGGKGVVLSSEEEKPALPIGGNESIPGFRVAKSASAK
VREAAATGELKVRLGADLKESLRVPSNKKDQLTASSARGYHGTYGYTKPD
VAAPGNNISSARVGTGTGGISYTGTSMSAPFAAGVAAQVLQANQSYGPTQ
LKAAIMNSANHDVRTADGNVYAVDRVGSGRIDAKAAAETKVLLYNADRPA
QVSQTFGVLEYAVNEGKQTLTREMTVENFDSHTHTYNISYAGSTDMPGVE
FSLPSNITVNPGEKKNFTVTITIDPAAMEKTMDPAMEKTHNSVDPYGDGT
ELVPEQYRQFIASESGRILLTEGAATLRAPIHAAPKPASAMKVEGSSVEI
PAGEHQANLKLTGTELNQRGYKSLLGAFEHGASIERTSPVKLDVSSNAKA
NMQHVGAASTAPALKASGGNPNDGLLAFGISTWANWDVVSTENTFTVNID
IDGNNRADYMLVTDRAKGIDEPIVRLYGYKNGNLEQTAYYPLNNAWGDTD
TNMMDSNALVMAVPLKDLGLSAEKTKDIKYSVSATTQYAWTNVSETGWIN
YRPFDPKLWFSGTAATVPGFEADAPSSELVAHRAEGATDVKALFLHMHNI
TGDLSGLNGAAGNRAQVLEVTEQQQLDPAPSRFTDVPAENQFYAEINWLA
QRRITTGYPDGTFRPGENVERGAMAAYFYRLAGTPQFTAPDNPTFSDVPK
SHPFYKEIEWMAARGITTGYGDGTFRPSDSVNRDAMAAFFYRYANSPQFA
APAASPFKDVPANSQFYKEIAWLAEQGITKGWDDGTYRPGEPIHRDAMAA
FLYRYSDKVLK

The amino acid sequence of a protein in *Rothia aeria* BAV86562.1 that belong to the peptidase S8 family is shown below. The section with amino acid residues in bold is the cd07474 domain that is typically representative of the peptidase S8 family domain. Underlined amino acids are the D, S and H residues comprising the catalytic triad.

```
>BAV86562.1 glycerol-3-phosphate ABC transporter,
Rothia aeria
                                     (SEQ. ID. NO: 34)
MAITAGLPATAAPAGDPDTPVAQDIARNSREHAVLSDSMKKAEGNIPVFV
QFKGKGAYEQTQSPAVLANKQAPINKQAEVQAIKTQVQSQAQAAAQSTGA
KTLYTTHNIMRGVALQGDAAQIRALANNPEVERITPIVPKKKQNAGSVVD
TGAAENWARENSGYTGKDVKIAVVDSGIDYTHADEGGPGTVEAFNKATKL
TEMPAADSGLYDAKKYIGGYDLVGDSYDGTNQTAPDNNPIDCSAGGHGTH
VAGTAAGYGVNQDGTTERGDYSKLTAEQLNQMKIGPGAAPEAQLYSFRVE
GCTGTTGVVVQALDRTLDPNGDGDFSDRANIVNLSIGGEFSPPDDADAYA
VESLNRQGVLAVVSAGNATDYYGRGDTYSDSGQPANAVSALTVANSIGSS
YAVDSMEIQAPANVAGKVPGDYTVSYTYTGAKPEALTGTVVTPSESNKFG
CEAFSAEDAAKIKDKWVFLEWANADGSLPCGSKVREDNVEKAGGKGVVLS
SEEEKPALPIGGNESIPGFRVAKSASAKVREAAANGELKVRLGTDLKESL
RVPSNKKDQLTASSARGYHGTYGYTKPDVAAPGNNISSARVGTGTDGISY
TGTSMSAPFAAGVAAQVLQANQSYGPTQLKAAIMNSANHDVRTADGNVYA
VDRVGSGRIDAKAAAETKVLLYNADRPAQVSQTEGVLEYAVNEGKQTLIR
EMTVENFDSHIHTYNISYAGSTDMPGVEFSLPSNITVNPGEKKNFTVTIT
IDPAAMEKTMDPAMEKTHNSVDPYGDGTELVPEQYRQFIASESGRILLTE
GAATLRAPIHAAPKPASAMKVEGSSVEIPAGEHQANLKLTGTELNQRGYK
SLLGAFEHGASIERTSPVKLDVSSNAKANMQHVGAASTAPALKASGGNPN
DGLLAFGISTWANWDVVSTENTFTVNIDIDGNNRADYMLVTDRAKGIDEP
IVRLYGYKNGNLEQTAYYPLNNAWGDIDINMMDSNALVMAVPLKDLGLSA
EKTKDIKYSVSATTQYAWTNVSETGWINYRPFDPKLWFSGTAATVPGFFA
DAPSSELVAHRAEGATDVKALFLHMHNITGDLSGLNGAAGNRAQVLEVIE
QQQLDPAPSRFTDVPAENQFYAEINWLAQRRITTGYPDGTFRPGENVERG
AMAAYFYRLAGTPQFTAPDNPTFSDVPKSHPFYKEIEWMAARGITTGYGD
GTFRPSASVNRDAMAAFFYRYANSPQFAAPAASPFKDVPANSQFYKEIAW
LAEQGITKGWDDGTYRPGEPIHRDAMAAFLYRYSDKVLK
```

*Bacillus subtilis* Bacteria Spp. Subtilisins

The amino acid sequences of *Bacillus licheniformis* subtilisin A (subtilisin Carlsberg) and *B. subtilis* subtilisin NAT (nattokinase) are shown below.

```
P00780.1; Subtilisin Carlsberg
                                     (SEQ. ID. NO: 35)
MMRKKSFWLGMLTAFMLVFTMAFSDSASAAQPAKNVEKDYIVGFKSGVKT
ASVKKDIIKESGGKVDKQFRIINAAKAKLDKEALKEVKNDPDVAYVEEDH
VAHALAQTVPYGIPLIKADKVQAQGFKGANVKVAVLDTGIQASHPDLNVV
GGASFVAGEAYNTDGNGHGTHVAGTVAALDNTTGVLGVAPSVSLYAVKVL
NSSGSGTYSGIVSGIEWATTNGMDVINMSLGGPSGSTAMKQAVDNAYARG
VVVVAAAGNSGSSGNTNTIGYPAKYDSVIAVGAVDSNSNRASFSSVGAEL
EVMAPGAGVYSTYPTSTYATLNGTSMASPHVAGAAAILSKHPNLSASQV
RNRLSSTATYLGSSFYYGKGLINVEAAAQ P35835.1; Subtilisin NAT or Nattokinase
                                     (SEQ. ID. NO: 36)
MRSKKLWISLLFALTLIFTMAFSNMSAQAAGKSSTEKKYIVGFKQTMSAM
SSAKKKDVISEKGGKVQKQFKYVNAAAATLDEKAVKELKKDPSVAYVEED
HIAHEYAQSVPYGISQIKAPALHSQGYIGSNVKVAVIDSGIDSSHPDLNV
RGGASFVPSETNPYQDGSSHGTHVAGTIAALNNSIGVLGVAPSASLYAVK
VLDSTGSGQYSWIINGIEWAISNNMDVINMSLGGPTGSTALKTVVDKAVS
SGIVVAAAAGNEGSSGSTSTVGYPAKYPSTIAVGAVNSSNQRASFSSVGS
ELDVMAPGVSIQSTLPGGTYGAYNGTSMATPHVAGAAALILSKHPTWTNA
QVRDRLESTATYLGNSFYYGKGLINVQAAAQ
```

Additional Gluten-Degrading Enzymes that are not Subtilisin or Subtilisin-Like

The additional gluten-degrading enzymes or glutamine endoproteases useful for the methods, formulations, and compositions of this disclosure include those that have been previously disclosed in the PCT Patent Application No:

PCT/US11/43118, PCT Patent publication No: WO2012006384, the US Patent Application No. 20130171109, U.S. Pat. Nos. 7,628,985, and 8,685,392, the contents of each of which are incorporated by reference in their entity.

In some embodiments, the additional gluten-degrading enzymes or glutamine endoproteases useful for the methods, formulations, and compositions of this disclosure are derived from *Rothia* species bacteria and they retain gluten-degrading activity throughout a wide range of pH (e.g., pH 3.0-10), unlike the *Rothia* subtilisin or subtilisin-like enzymes that have gluten-degrading activity at a pH range of about 6.0-10.0 and have low or negligible gluten-degrading activity at pH values below 5.0 and pH higher than 10.0. In some embodiments, these additional gluten-degrading enzymes are glutamine endopeptidases.

Accordingly, in some embodiments, the glutamine endopeptidase enzymes of a *Rothia* species described herein is capable of cleaving of any of the following peptides, including known T cell epitopes in gluten, under optimal conditions: QLQPFPQPQLPY (SEQ ID NO: 8) or PFPQPQLPY (SEQ ID NO: 9), PQPQLPYPQPQLPY (SEQ ID NO: 10) or PQPQLPYPQ (SEQ ID NO: 11), QPQQSFPQQQ (SEQ ID NO: 12) or PQQSFPQQQ (SEQ ID NO: 13), QLQPFPQPELPY (SEQ ID NO: 14), PQPELPYPQPELPY (SEQ ID NO: 15), QPQQSFPEQQ (SEQ ID NO: 16); IQPQQPAQL (SEQ ID NO: 17); QQPQQPYPQ (SEQ ID NO: 18); SQPQQQFPQ (SEQ ID NO: 19); QQPFPQQPQ (SEQ ID NO: 20); or PFSQQQQPV (SEQ ID NO: 8), including 33-mer from alpha-gliadin, LQLQPF(PQPQLPY) 3PQPQPF (SEQ ID NO: 5), and the 26-mer from gamma-gliadin, FLQPQQPFPQQPQQPYPQQPQQPFPQ (SEQ ID NO: 6). In some embodiments, the glutamine endopeptidase of a *Rothia* species described herein have a kcat/Km of at least about 2.5 s$^{-1}$ M$^{-1}$, usually at least about 250 s$^{-1}$ M$^{-1}$ and preferably at least about 25000 s$^{-1}$ for cleaving of any of the peptides described herein. A glutamine endopeptidase of a *Rothia* species described herein have a specificity kcat/Km>2 mM$^{-1}$ s$^{-1}$ for the quenched fluorogenic substrate Abz-QPQQP-Tyr(NO2)-D (SEQ ID NO: 37). Methods of assaying such enzymatic activities are known to those skilled in the art, e. g. by HPLC or fluorescence spectroscopy and as described, for example, in U.S. Pat. No. 7,534,426. For fluorescence spectroscopy-based assays, suitable fluorophores can be attached to the amino- and carboxy-termini of the peptides.

in some embodiments, the additional gluten-degrading enzymes described herein are isolated enzymes, extracts, or enriched extracts derived from *Rothia* species bacteria (e.g., *Rothia* spp. of 188, also known as *Rothia* sp. HOT-188 and *Rothia aeria*). Such gluten-degrading enzymes can be, in one embodiment, a glutamine endopeptidase enzyme (e.g., a metal-ion dependent serine protease). In one embodiment, the glutamine endopeptidase enzyme present in the extract, derived or isolated from a *Rothia* species bacterium is inhibited by 1 mM 1-10 Phenanthroline. Addition of the serine protease inhibitor, phenylmethanesulphonylfluoride or phenylmethylsulphonyl fluoride (PMSF) can also inhibit YPQ, QQP, PPF and/or PFP cleavage activity, indicating that the enzyme is a serine protease. In one embodiment, the glutamine endopeptidase enzyme present in the extract, derived or isolated from a *Rothia* species bacterium is inhibited by 0.1-1 mM PMSF. In one embodiment, the glutamine endopeptidase enzyme present in the extract, derived or isolated from a *Rothia* species bacterium is inhibited by 0.1-1 mM 4-(2-Aminoethyl) benzenesulfonyl fluoride hydrochloride (AEBSF).

In one embodiment, the glutamine endopeptidase enzyme is isolated from a *Rothia* species bacterium by conventional protein purification methods known to those skilled in the art, e. g. as described in the Current Protocols in Molecular Biology and the Current Protocols in Protein Sciences. The protein fraction of an extract from a *Rothia* species bacterium can be concentrated by ammonium sulphate precipitation, and then purified by ion exchange chromatography on DEAE SEPHAROSE® CL-6B and gel filtration on SEPHADEX® G-100. Sample fractions are taken at each step and assayed for -XPQ-, -QQP-, -PPF- and/or -PFP- cleavage activity in order to follow the location of the enzyme. For example, the enzyme can be at least 20% pure, at least 35% pure, at least 45% pure, at least 55% pure, at least 65% pure, at least 75% pure, at least 85% pure, at least 95% pure, at least 95% pure, at least 99% pure, wherein all the percentages between 20 and 99 are explicitly included.

The enzyme or enzymes can be further purified, for example, from the 70 kDa, or 75-80 kDa, or ~125 kDa fractions using standard purification schemes known in the art, e. g. size exclusion chromatography to isolate the 70 kDa fraction from a clarified crude extract of a *Rothia* species bacteria cell lysate. The bacteria can be lysed by standard methods known in the art, e. g. with lysozymes and treatment in a par bomb. The lysate can then be clarified by ultracentrifugation at 100,000×G force for 1 hour at 4° C. The clarified lysate can then be concentrated and then fractioned with commercially available gel filtration matrix such as SEPHACRYL® (S-100/200/300/400/500) from GE Healthcare Life Sciences. Fractions with glutamine endopeptidase activity can be determined by methods known in the art and those described herein. One skilled in the art will be able to make minor modification for the enzyme being studied.

In other embodiments, the enzymes can be further purified according to the methods described in the Example Section.

In one embodiment, the glutamine endopeptidase enzyme attenuates gluten toxicity by cleaving the peptide bond after glutamine at -XPQ- and after tyrosine in XPY motifs in gluten-containing foodstuff, wherein X=any amino acids, P=proline, Q=glutamine, and Y is tyrosine. In one embodiment, the cleavage is at peptide bonds of non-terminal amino acids (i.e. within a protein or peptide molecule) immediately after the proline residue for -QQP- or -PFP- sequence, and immediately after the phenylalanine residue for -PPF- sequence.

Acidic Gluten-Degrading Enzymes from *Rothia* Species Bacteria

The enzymes with gluten-degrading activity at acidic pH described in the US Patent Application No. 20130171109 have a significant advantage over other microbial enzymes that degrade gluten due to their acidic character and ability to retain protease activity at varying pH (e.g., pH 3 to 10) including acidic pHs, such as those found in the stomach. The enzymes described herein have an isoelectric focusing point pH fractions of pH 2.5, 3 and 4. In the most acidic fraction (tested as described herein in the Examples section) a high molecular weight protease of approximately ~125 kD to ~140 kD can be isolated for use with the methods as described herein.

Another advantage of the enzymes with activity at acidic pH described in the US Patent Application No. 20130171109 is that the *R. aeria* enzyme retains gluten-degrading activity throughout a wide range of pH (e.g., 3-10). As used herein, the term "retains gluten-degrading activity" or "retains activity" means that an enzyme as described herein retains at least 20% of the gluten-degrading activity (as measured by e.g., an in vitro gliadin or gliadin peptide cleavage assay as described in e.g., the Examples section) measured at a range of test pHs (e.g., in pHs of 2-12) compared to the activity measured at the environmental pH for the enzyme (e.g., pH 7-8 or the native pH environment in which the enzyme is found); preferably the enzyme retains at least 30%, at least 40%, at least 50%, at least 60%, at least 70%, at least 80%, at least 90%, at least 95%, at least 99%, or even 100% of the activity compared to the activity measured when the assay is conducted at the enzyme's environmental pH (e.g., pH 7-8). It is contemplated herein that the isolated subtilisin enzyme together with the addition gluten-degrading enzyme described in this disclosure be taken prior to ingestion (e.g., 20 min to 1 hr before), concomitant with ingestion (e.g., at the same time), or shortly after ingestion (e.g., 20 min to 1 hr after) of a gluten-containing foodstuff. The enzymes described herein can transit the gastrointestinal tract with the gluten-containing foodstuff and can de-toxify gluten or fragments thereof that are formed during digestion. Since the enzymes are active in vitro at pHs observed in essentially every region of the gastrointestinal tract (e.g., oral cavity, stomach, small intestine etc), the enzymes with activity at acidic pH described in the US Patent Application No. 20130171109 will have a higher predicted efficiency for degrading gluten than a comparable enzyme that is inactivated by low pH (e.g., stomach pH). As used herein, the term "higher efficiency for degrading gluten" means that at least 20% more gluten will be degraded during passage through the gastrointestinal tract by the enzymes described herein (as measured by appearance of gluten degradation products or by a more favorable response of a subject to a gluten challenge) compared to an enzyme having similar activity but that does not operate at a wide range of pH (e.g., only works within a narrow pH range of 7-8); preferably at least 30% more, at least 40% more, at least 50% more, at least 60% more, at least 70% more, at least 80% more, at least 90% more, at least 95% more, at least 99% more, at least 1-fold more, at least 2-fold more, at least 5-fold more, at least 10-fold more, at least 20-fold more, at least 100-fold more, at least 200-fold more, at least 500-fold more, at least 1000-fold more gluten is degraded during passage through the gastrointestinal tract by the enzymes described herein that retain activity at a wide range of pH.

The combination of isolated subtilisin enzyme together with the addition gluten-degrading enzyme described herein are advantageous over previous gluten-degrading enzymes described.

In one embodiment, the addition gluten-degrading enzyme with activity at acidic pH described in the US Patent Application No. 20130171109 retains protease activity at pH 2.5. In one embodiment, the enzyme described herein retains protease activity at pH 3.0. In another embodiment, the addition gluten-degrading enzyme described herein retains protease activity up to pH 7.0. In one embodiment, the addition gluten-degrading enzyme described herein retains protease activity between pH 2.5 to 7.0. In some embodiments, the addition gluten-degrading enzyme described herein retains protease activity between pH 2.5 to 3.0, between pH 2.5 to 4.0, between pH 3.0 to 4.0, between pH 3.0 to 6.0, between pH 2.5 to 5.0, between pH 2.5 to 6.0, between pH 5.0 to 7.0, between pH 5.0 to 6.0, and between pH 6.0 to 7.0.

In one embodiment, the addition gluten-degrading enzyme with activity at acidic pH described in the US Patent Application No. 20130171109 exhibits protease activity at pH 3.0 after 3-4 hours of digestion, e.g., in an in vitro gliadin degradation assay using a synthetic substrate Z-YPQ-pNA described herein. In one embodiment, the addition gluten-degrading enzyme described herein exhibited at least 5% protease activity at pH 3.0 after 3-4 hours of digestion in comparison the activity observed when assayed at pH 8.0 for 3-4 hours.

In one embodiment, the addition gluten-degrading enzyme with activity at acidic pH described in the US Patent Application No. 20130171109 retains protease activity at pH 2.5 and has an approximate molecular size of 140 kDa as determined by a gliadin zymogram or characterized as in FIG. 6. In one embodiment, the addition gluten-degrading enzyme with activity at acidic pH described in the US Patent Application No. 20130171109 retains protease activity at pH 2.5 and has an approximate molecular size of 125 kDa as determined by a gliadin zymogram. In another embodiment, the addition gluten-degrading enzyme described herein retains protease activity at pH 2.5 and has an approximate molecular size range of 120-150 kDa as determined by gliadin zymography. In another embodiment, the addition gluten-degrading enzyme described herein retains protease activity at pH 2.5 and has an approximate molecular size range of 135-145 kDa as determined by gliadin zymography. In another embodiment, the addition gluten-degrading enzyme described herein retains protease activity at pH 2.5 and has an approximate molecular size range of 125-145 kDa as determined by gliadin zymography.

In one embodiment, the gluten-degrading enzyme with activity at acidic pH described in the US Patent Application No. 20130171109 retains protease activity in the range between pH 3.0-4.0 and has an approximate molecular size of 140 kDa as determined by a gliadin zymogram or characterized as in FIG. 6. In another embodiment, the addition gluten-degrading enzyme with activity at acidic pH described in the US Patent Application No. 20130171109 retains protease activity in the range between pH 3.0-4.0 and has an approximate molecular size of 125 kDa as determined by a gliadin zymogram. In another embodiment, the addition gluten-degrading enzyme described herein retains protease activity in the range between pH 3.0-4.0 and has an approximate molecular size range of 120-150 kDa as determined by gliadin zymography. In another embodiment, the addition gluten-degrading enzyme described herein retains protease activity in the range between pH 3.0-4.0 and has an approximate molecular size range of 135-145 kDa as determined by gliadin zymography. In another embodiment, the addition gluten-degrading enzyme described herein retains protease activity in the range between pH 3.0-4.0 and has an approximate molecular size range of 125-145 kDa as determined by gliadin zymography. In another embodiment, the addition gluten-degrading enzyme described herein retains protease activity in the range between pH 3.0-4.0 and has an approximate molecular size range of 50-90 kDa as determined by gliadin zymography. In another embodiment, the addition gluten-degrading enzyme described herein retains protease activity in the range between pH 3.0-4.0 and has an approximate molecular size range of 65-75 kDa as determined by gliadin zymography. In another embodiment, the addition gluten-degrading enzyme described herein retains protease activity in the range between pH 3.0-4.0 and has an approximate molecular size range of 65-80 kDa as determined by gliadin zymography. In another embodiment, the addition gluten-degrading enzyme described herein retains protease activity in the range between pH 3.0-4.0 and has an approximate molecular size range of 75-80 kDa as determined by gliadin zymography.

In one embodiment, the addition gluten-degrading enzyme with activity at acidic pH described in the US Patent Application No. 20130171109 retains protease activity in the range between pH 5.0-7.0 and has an approximate molecular size of 140 kDa as determined by a gliadin zymogram or characterized as in FIG. 6. In one embodiment, the addition gluten-degrading enzyme with activity at acidic pH described in the US Patent Application No. 20130171109 retains protease activity in the range between pH 5.0-7.0 and has an approximate molecular size of 125 kDa as determined by a gliadin zymogram. In another embodiment, the addition gluten-degrading enzyme described herein retains protease activity in the range between pH 5.0-7.0 and has an approximate molecular size range of 120-150 kDa as determined by gliadin zymography. In another embodiment, the addition gluten-degrading enzyme described herein retains protease activity in the range between pH 5.0-7.0 and has an approximate molecular size range of 135-145 kDa as determined by gliadin zymography. In another embodiment, the addition gluten-degrading enzyme described herein retains protease activity in the range between pH 5.0-7.0 and has an approximate molecular size range of 125-145 kDa as determined by gliadin zymography. In another embodiment, the addition gluten-degrading enzyme described herein retains protease activity in the range between pH 5.0-7.0 and has an approximate molecular size range of 50-90 kDa as determined by gliadin zymography. In another embodiment, the addition gluten-degrading enzyme described herein retains protease activity in the range between pH 5.0-7.0 and has an approximate molecular size range of 65-75 kDa as determined by gliadin zymography. In another embodiment, the addition gluten-degrading enzyme described herein retains protease activity in the range between pH 5.0-7.0 and has an approximate molecular size range of 65-80 kDa as determined by gliadin zymography. In another embodiment, the addition gluten-degrading enzyme described herein retains protease activity in the range between pH 5.0-7.0 and has an approximate molecular size range of 75-80 kDa as determined by gliadin zymography.

In one embodiment, the addition gluten-degrading enzyme with activity at acidic pH described in the US Patent Application No. 20130171109 retains protease activity in the range between pH 2.5-5.0 and has an approximate molecular size of 140 kDa as determined by a gliadin zymogram or characterized as in FIG. 6. In one embodiment, the addition gluten-degrading enzyme with activity at acidic pH described in the US Patent Application No. 20130171109 retains protease activity in the range between pH 2.5-5.0 and has an approximate molecular size of 125 kDa as determined by a gliadin zymogram. In another embodiment, the addition gluten-degrading enzyme described herein retains protease activity in the range between pH 2.5-5.0 and has an approximate molecular size range of 120-150 kDa as determined by gliadin zymography. In another embodiment, the addition gluten-degrading enzyme described herein retains protease activity in the range between pH 2.5-5.0 and has an approximate molecular size range of 135-145 kDa as determined by gliadin zymography. In another embodiment, the addition gluten-degrading enzyme described herein retains protease activity in the range between pH 2.5-5.0 and has an approximate molecular size range of 125-145 kDa as determined by gliadin zymography. In another embodiment, the addition gluten-degrading enzyme described herein retains protease activity in the range between pH 2.5-5.0 and has an approximate molecular size range of 50-90 kDa as determined by gliadin zymography. In another embodiment, the addition gluten-degrading enzyme described herein retains protease activity in the range between pH 2.5-5.0 and has an approximate molecular size range of 65-75 kDa as determined by gliadin zymography. In another embodiment, the addition gluten-degrading enzyme described herein retains protease activity in the range between pH 2.5-5.0 and has an approximate molecular size range of 65-80 kDa as determined by gliadin zymography. In another embodiment, the addition gluten-degrading enzyme described herein retains protease activity in the range between pH 2.5-5.0 and has an approximate molecular size range of 75-80 kDa as determined by gliadin zymography.

In one embodiment, the addition gluten-degrading enzyme with activity at acidic pH described in the US Patent Application No. 20130171109 retains protease activity in the range between pH 2.5-7.0 and has an approximate molecular size of 140 kDa as determined by a gliadin zymogram. In one embodiment, the addition gluten-degrading enzyme with activity at acidic pH described in the US Patent Application No. 20130171109 retains protease activity in the range between pH 2.5-7.0 and has an approximate molecular size of 125 kDa as determined by a gliadin zymogram. In another embodiment, the addition gluten-degrading enzyme described herein retains protease activity in the range between pH 2.5-7.0 and has an approximate molecular size range of 120-150 kDa as determined by gliadin zymography. In another embodiment, the addition gluten-degrading enzyme described herein retains protease activity in the range between pH 2.5-7.0 and has an approximate molecular size range of 135-145 kDa as determined by gliadin zymography. In another embodiment, the addition gluten-degrading enzyme described herein retains protease activity in the range between pH 2.5-7.0 and has an approximate molecular size range of 125-145 kDa as determined by gliadin zymography. In another embodiment, the addition gluten-degrading enzyme described herein retains protease activity in the range between pH 2.5-7.0 and has an approximate molecular size range of 50-90 kDa as determined by gliadin zymography. In another embodiment, the addition gluten-degrading enzyme described herein retains protease activity in the range between pH 2.5-7.0 and has an approximate molecular size range of 65-75 kDa as determined by gliadin zymography. In another embodiment, the addition gluten-degrading enzyme described herein retains protease activity in the range between pH 2.5-7.0 and has an approximate molecular size range of 65-80 kDa as determined by gliadin zymography. In another embodiment, the addition gluten-degrading enzyme described herein retains protease activity in the range between pH 2.5-7.0 and has an approximate molecular size range of 75-80 kDa as determined by gliadin zymography.

Formulations and Compositions

A formulation as described herein comprises an isolated subtilisin enzyme derived from *Rothia* species bacteria. The formulation comprises an effective amount or effective does of the enzyme. In one embodiment, the effective dose of the isolated subtilisin enzyme from the *Rothia* species bacterium is administered orally. In one embodiment, pharmaceutical formulation and compositions are provided herein.

In one embodiment, the isolated subtilisin enzyme derived from *Rothia* species bacteria is admixed to the gluten-containing foodstuff. For example, the subtilisin enzyme derived from *Rothia* species bacteria is mixed with the gluten-containing foodstuff prior to ingesting.

In one embodiment, the isolated subtilisin enzyme derived from *Rothia* species bacteria is formulated with a pharmaceutically acceptable excipient or carrier. In one embodiment, the pharmaceutical formulation and compositions comprise an isolated subtilisin enzyme derived from *Rothia* species bacteria and a pharmaceutically acceptable excipient or carrier. The pharmaceutical formulation and compositions further comprise at least one addition gluten-degrading enzyme or a glutamine endoprotease. In another embodiment, the pharmaceutical formulation and compositions further comprise a PEP.

In one embodiment, the isolated subtilisin enzyme derived from *Rothia* species bacteria is contained in a formulation that comprises an enteric coating.

In one embodiment, the isolated subtilisin enzyme derived from *Rothia* species bacteria is a lyophilized preparation. Lyophilization or freeze-drying is a means of drying achieved by freezing a wet substance and causing the ice to sublime directly to vapor by exposing it to a low partial pressure of water vapor. In practice, the substance may not be completely frozen, especially if non-aqueous solutions are present, and most lyophilization processes are completed by a period of desorption drying. The purpose of freeze-drying is to increase the shelf life, or preserve a specimen, be it food, microbial organisms, or, in some circumstances to decrease the size of the product. For various purposes, such as stable storage, the isolated enzyme can be lyophilized. Lyophilization is preferably performed on an initially concentrated preparation, e.g. of at least about 1 mg/ml for isolated enzyme preparation and 1000 bacteria/ml. Additives can be added to improve enzyme stability in the lyophilization process if so desired. Such additives are known in the art, for example, PEG, albumin, disaccharides such as maltitol, mannitol, corn syrup solids, sorbitol and branched polymers of sucrose. These are described in U.S. Pat. No. 6,294,365, the contents are incorporated here by reference. In some embodiments, lyophilization of an isolated enzyme can be performed without loss of specific activity (e.g., gluten-degrading activity). Lyophilized extracts are useful in the production of enteric-coated capsules, enteric-coated tablets, capsules, granules or tablets.

In one embodiment of the methods described herein further comprises administering an effective dose of subtilisin enzyme ranging from 0.01 mg to 500 mg/kg body weight. In some embodiments, the formulations or compositions administered to the subject is a combination of subtilisin and at least one addition gluten-degrading enzyme or a glutamine endopeptidase described in this disclosure. This combination can further comprise a PEP. The prolyl endopeptidase can be provided in a separate formulation or can be formulated with the active species (e.g., extract, isolated enzyme etc) described herein. Prolyl endopeptidase (PREP or PEP) or prolyl oligopeptidase (EC 3.4.21.26), (sometimes also known as post-proline cleaving enzyme) is a large cytosolic enzyme that belongs to a distinct class of serine peptidases. The enzyme cleaves peptide bonds at the C-terminal side of proline residues. Its activity is confined to action on oligopeptides of less than 10 kDa and it has an absolute requirement for the trans-configuration of the peptide bond preceding proline. Some types of prolyl endopeptidase from A. *Niger* have been used in studies to decrease the propensity of gluten-containing wheat products to aggravate celiac disease (Stepniak D, et al., 2006, Am J Physiol Gastrointest Liver Physiol 291 (4): G621-9), e. g. PEP derived or isolated from *Aspergillus tiger, Flavobacterium meningosepticum, Sphingomonas capsulate, Penicillium citrinum, Lactobacillus helveticus* and *Myxococcus Xanthus* in US Patent Application 20060002917 and 20080193436, and in U.S. Pat. Nos. 7,563,864, 7,303,871, and 7,320,788, the contents are incorporated here by reference.

In some embodiments of the pharmaceutical formulations described herein, the glutamine endopeptidase enzyme useful in the compositions or formulations is about 70-80 kDa, is active in a saliva sample, serine protease, and detoxifies gluten by cleaving the peptide bond after glutamine at -XPQ-motifs in gluten-containing foodstuff, wherein X=any amino acids, P=proline, and Q=glutamine. In one embodiment, glutamine endopeptidase enzyme is active in a buffer that mimics the ion composition of saliva, e. g. saliva ion buffer described herein.

In one embodiment of the pharmaceutical formulations described herein, the *Rothia* species bacteria is *Rothia* species of 188 (also known as *Rothia* sp. HOT-188, *Rothia aeria* strain F0474 (HMP ID 1324), *Rothia aeria* HM-818, and *Rothia aeria* strain WSA-8) and *Rothia aeria*.

In some embodiments of the pharmaceutical formulations described herein, the effective dose of the subtilisin enzyme derived from *Rothia* species bacteria ranges from 0.01 mg to 500 mg/kg body weight when the formulation comprises the isolated subtilisin enzyme.

In some embodiments of the pharmaceutical formulations described herein, the formulation is suitable for oral administration, e. g. a tablet or a capsule.

In some embodiments of the pharmaceutical formulations described herein, the formulation comprises an enteric coating.

In one embodiment, the isolated subtilisin enzyme derived from *Rothia* species bacteria described herein are formulated into pharmaceutical compositions by combination with appropriate, pharmaceutically acceptable carriers or diluents, and are formulated into preparations in solid, semi-solid, or liquid forms, such as tablets, capsules, powders, granules, solutions, gels, and microspheres. As such, administration of the extract, *Rothia* species bacteria, or the enzyme described herein can be achieved by oral administration.

In pharmaceutical dosage forms, the subtilisin enzyme derived from *Rothia* species bacteria described herein can be administered alone or in appropriate association, as well as in combination, with other pharmaceutically active compounds. For example, the methods and compositions provided herein can be combined with pharmaceutically active compounds used in the treatment and alleviation of symptoms of Celiac Sprue including, but not limited to, the following: an inhibitor of tissue transglutaminase (see U.S. Pat. No. 7,579,313), an anti-inflammatory agent, an anti-ulcer agent, a mast cell-stabilizing agent, and/or and anti-allergy agent. Examples of such agents include HMG-CoA reductase inhibitors with anti-inflammatory properties such as compactin, lovastatin, simvastatin, pravastatin and atorvastatin; anti-allergic histamine H1 receptor antagonists such as acrivastine, cetirizine, desloratadine, ebastine, fexofenadine, levocetirizine, loratadine and mizolastine; leukotriene receptor antagonists such as montelukast and zafirlukast; COX2 inhibitors such as celecoxib and rofecoxib; p38 MAP kinase inhibitors such as BIRB-796; and mast cell stabilizing agents such as sodium chromoglycate (chromolyn), pemirolast, proxicromil, repirinast, doxantrazole, amlexanox nedocromil and probicromil.

In one embodiment, the formulation or administration protocol combines an extract, *Rothia* species bacteria, subtilisin enzyme derived from *Rothia* species bacteria, and/or glutamine endopeptidase enzyme described herein with an inhibitor of transglutaminase 2 (TG2) (see U.S. Pat. No. 7,579,313). Such formulations can provide additional protection from gluten mediated enteropathy, as TG2 has been shown to have a significant pro-inflammatory effect on gluten peptides in the celiac gut. In particular, TG2 inhibitors containing halo-dihydroisoxazole, diazomethylketone or dioxoindole moieties are useful for this purpose.

In one embodiment, the formulation or administration protocol combines an extract, *Rothia* species bacteria, subtilisin enzyme derived from *Rothia* species bacteria, and/or glutamine endopeptidase enzyme described herein with an anti-inflammatory agent, e.g. a statin; p38 MAP kinase inhibitor; anti-TNFalpha agent; etc.

In one embodiment, the formulation comprises the subtilisin enzyme derived from *Rothia* species bacteria, and/or an additional gluten-degrading enzyme, and/or the glutamine endopeptidase enzyme, and/or a PEP described herein or a PEGylated form thereof. PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. PEGylation can also provide water solubility to hydrophobic drugs and proteins.

Methods of PEGylating proteins are known to one of ordinary skill in the art, e. g. U.S. Pat. No. 7,585,837 and also described herein. The first step of the PEGylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates and carbonates. In the second generation PEGylation chemistry more efficient functional groups such as aldehyde, esters, amides etc made available for conjugation. Preferred end groups for heterobifunctional PEGs are maleimide, vinyl sulfones, pyridyl disulfide, amine, carboxylic acids and NHS esters.

Pharmaceutical formulations can be formulated for administration by any known route. By way of example, the composition can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection, infusion and other injection or infusion techniques, without limitation. It is preferred herein that the formulations described herein are administered orally (or mixed with gluten-containing foodstuff) to a subject afflicted with celiac disease or a related disorder.

For oral preparations, the subtilisin enzyme derived from *Rothia* species bacteria described herein can be used alone or in combination with appropriate additives to make tablets, powders, granules or capsules, for example, with conventional additives, such as lactose, mannitol, corn starch or potato starch; with binders, such as microcrystalline cellulose, cellulose derivatives, acacia, corn starch or gelatins; with disintegrants, such as corn starch, potato starch or croscarmellose sodium; with lubricants, such as talc or magnesium stearate; and if desired, with diluents, buffering agents, moistening agents, preservatives, colorants, and flavoring agents.

For enteral administration, a composition can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet can be made by compression or molding, optionally with one or more accessory ingredients. Compressed tablets can be prepared by compressing in a suitable machine the active compound in a free-flowing form, e.g., a powder or granules, optionally mixed with accessory ingredients, e.g., binders, lubricants, inert diluents, surface active or dispersing agents. Molded tablets can be made by molding in a suitable machine, a mixture of the powdered active compound with any suitable carrier.

A syrup or suspension can be made by adding the extract, *Rothia* species bacteria, or isolated enzyme described herein to a concentrated, aqueous solution of a sugar, e.g., sucrose, to which can also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for oral administration can be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycocholate, and sodium fusidate; chelating agents including citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethylammonio-1-propanesulfonate), Big-CHAPS (N, N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate.

While not required, in one embodiment, the formulations comprising the subtilisin enzyme derived from *Rothia* species bacteria described herein and the oral formulations comprise enteric coatings, so that the subtilisin enzyme derived from *Rothia* species bacteria described herein is delivered to the intestinal tract. Enteric formulations are often used to protect an active ingredient from the strongly acid contents of the stomach. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

A subtilisin enzyme derived from *Rothia* species bacteria described herein, can be prepared as a tablet formulation comprising the extract, the *Rothia* species bacteria, or the enzyme described herein with an enteric polymer casing. An example of such a preparation can be found in WO2005/021002. The active material in the core can be present in a micronized or solubilized form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropyl-cellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, coloring agents, flavors etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The extract, the *Rothia* species bacteria, or the enzyme described herein preferably comprises between 10 and 50% of the weight of the core, more preferably between 15 and 35% of the weight of the core (calculated as free base equivalent). The core can contain any therapeutically suitable dosage level of the active ingredient, but preferably contains up to 150 mg as free base of the active ingredient. The core can contain 20, 30, 40, 50, 60, 80 or 100 mg as free base of the active ingredient. The active ingredient can be present as the free base, or as any pharmaceutically acceptable salt. If the active ingredient is present as a salt, the weight is adjusted such that the tablet contains the desired amount of active ingredient, calculated as free base of the salt. Preferably, the active ingredient is present as a hydrochloride salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional cross-linking agents such as epichlorohydrin, dichlorohydrin or 1, 2-, 3, 4-diepoxybutane. The casing can also include starch and/or dextrin.

Exemplary enteric coating materials are the commercially available EUDRAGIT® enteric polymers such as EUDRAGIT® L, EUDRAGIT® S and EUDRAGIT® NE used alone or with a plasticiser. Such coatings are normally applied using a liquid medium, and the nature of the plasticiser depends upon whether the medium is aqueous or non-aqueous. Plasticizers for use with aqueous medium include propylene glycol, triethyl citrate, acetyl triethyl citrate or CITROFLEX® or CITROFLEX® A2. Non-aqueous plasticizers include these, and also diethyl and dibutyl phthalate and dibutyl sebacate. A preferred plasticiser is triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticiser and up to around 50 wt % of anti-tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876.

In an example, lactose monohydrate, microcrystalline cellulose, the active ingredient—e. g. the extract form *Rothia* species, the hydroxypropyl methyl cellulose and half of the croscarmellose sodium are screened into a 10 Litre Fielder high-shear blender (any suitable high shear blender could be used) and blended for 5 minutes at 300 rpm with the chopper off. The mixture is then granulated by the addition of about 750 ml water whilst continuing to blend. The granules are dried in a Glatt 3/5 fluid bed drier, screened by Comil into a Pharmatec 5 Litre bin blender and then blended with any lactose anhydrous given in the formula plus the remainder of the croscarmellose sodium over 5 minutes at 20 rpm. Magnesium stearate is screened into the blender and the mixing process continued for a further 1 minute at 10 rpm. The lubricated mix is compressed using a Riva Piccolla rotary tablet press fitted with 9.5 mm round normal convex punches (any suitable tablet press could be used). The sealcoat, and subsequently the enteric coat, are applied by spraying of an aqueous suspension of the coat ingredients in a Manesty 10 coater using parameters for the coating process as recommended by the manufacturers of the coating polymers (again, any suitable coater could be used).

Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) J Control Release 71(3):307-18. Other enteric-coated preparations of this sort can be prepared by one skilled in the art, using these materials or their equivalents.

The compositions can be formulated as a sustained release composition. For example, sustained-release means or delivery devices are known in the art and include, but are not limited to, sustained-release matrices such as biodegradable matrices or semi-permeable polymer matrices in the form of shaped articles, e.g., films, or microcapsules that comprise the extract, *Rothia* species bacteria, or enzyme described herein A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of polylactide, polyglycolide, or polylactide co-glycolide (co-polymers of lactic acid and glycolic acid).

Sustained-release matrices include polylactides (U.S. Pat. No. 3,773,919, EP 58,481), copolymers of L-glutamic acid and gamma-ethyl-L-glutamate (U. Sidman el al., Biopolymers 22:547-556 (1983)), poly (2-hydroxyethyl methacrylate) (R. Langer et al., J. Biomed Mater. Res. 15:167-277 (1981), and R. Langer, Chem. Tech. 12:98-105 (1982)), ethylene vinyl acetate (R. Langer et al., Id.) or poly-D-(-)-3-hydroxybutyric acid (EP 133,988). Sustained-release compositions also include liposomally entrapped extract, *Rothia* species bacteria, or enzyme described herein. Such liposomes can be prepared by methods known per se: DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy. Other biodegradable polymers and their use are described, for example, in detail in Brem et al. (1991, J. Neurosurg. 74:441-446). For examples of sustained release compositions, see U.S. Pat. No. 3,773,919, EP 58,481A, U.S. Pat. No. 3,887,699, EP 158,277A, Canadian Patent No. 1176565, U. Sidman et al., Biopolymers 22:547 (1983) and R. Langer et al., Chem. Tech. 12:98 (1982).

Methods for preparing liposomes and microspheres for administration to a patient are known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres or composite of microspheres, implanted for slow release over a period of time ranging from days to months. See, for example, U.S. Pat. Nos. 4,906,474, 4,925,673 and 3,625,214, the contents of each of which are hereby incorporated by reference in their entirety, and Jein, TIPS 19:155-157 (1998).

Preferred micro particles are those prepared from biodegradable polymers, such as polyglycolide, polylactide and copolymers thereof. Those of skill in the art can readily determine an appropriate carrier system depending on various factors, including the desired rate of drug release and the desired dosage.

The pharmaceutically acceptable excipients, such as vehicles, adjuvants, carriers or diluents that are inherently nontoxic and nontherapeutic, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2 dimethylaminoethanol, 2 diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol.

In one embodiment, other ingredients may be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA, and sugar alcohols such as mannitol or sorbitol.

In one embodiment, the pharmaceutical formulation to be used for therapeutic administration must be sterile. Sterility is readily accomplished by filtration through sterile filtration membranes (e.g., 0.2 micron membranes).

Dosage and Administration

Depending on the subject, severity of disease and condition being treated and on the administration route, the subtilisin enzyme derived from *Rothia* species bacteria described herein can be administered in dosages of 0.01 mg to 500 mg/kg body weight per day, e.g. about 20, 100, 250, 500 or more mg/day or about 0.5, 1, 1.5, or more g/day for an average person for the enzyme. A typical dose of the enzyme described herein in subjects will be at least about 1 mg/adult subject, at least about 10 mg/adult subject; or at least about 50, 150, 250, 500 or more mg/adult subject. In some embodiments, the dosage is no more than about 5 g, no more than about 1 g, or no more than about 500 mg/adult subject. Efficient proteolysis of gluten in vivo for an adult can, depending on diet and other factors, require at least about 500 units of a therapeutically efficacious the subtilisin enzyme derived from *Rothia* species bacteria or glutamine endopeptidase from *Rothia* species bacteria described herein. In some embodiments, low dose of subtilisin enzyme glutamine endopeptidase, such as 1000 units, can be used. In other embodiments, such as for the rapid detoxification of 5-10 g ingested gluten, as much as 20,000-50,000 units can be provided in unit dose form. One unit is defined as the amount of enzyme required to hydrolyze $\mu$mol of Z-KPQ-pNA or Z-YPQ-pNA per min under specified conditions. For example, most PEPs have specific activities in the range of 5-50 units/mg protein. For barley EP-B2 (whose specific activity is in the 1000 Units/mg range, as measured with Cbz-Phe-Arg-pNA), low dose glutenase may consist of 10,000-100,000 Units, whereas high-dose PEPs contains as much as 1,000,000 Units. It will be understood by those of skill in the art that the dose can be raised, but that additional benefits may not be obtained by exceeding the useful dosage. Dosages will be appropriately adjusted for pediatric formulation. In children the effective dose may be lower, for example at least about 0.1, 0.5, 1, 10, 20, 100, 150, 250 or more mg.

In one embodiment, the compositions or formulations are admixed with gluten-containing foodstuff in vitro for the purpose of detoxifying the gluten-containing foodstuff, i.e., reducing the production of toxic gluten oligopeptides when ingested and further digested by a subject. The effective dosage for in vitro detoxification will depend on many factors, e.g., the degree of detoxification desired (partial or complete), the state of the gluten-containing foodstuff, the time and pH of digestion and the ratio of composition or formulation to the amount of gluten-containing foodstuff to be digested. A typical dose for the enzyme can be 10 units per 1 g for a 24 hour complete digestion. One skilled in the art will be able to vary the units in proportion to the amount of gluten-containing foodstuff and the time allowed for digestion to attained the desired level of digestion.

The skilled artisan will appreciate that certain factors may influence the dosage and timing required to effectively treat a subject, including but not limited to the severity of the disease or disorder, previous treatments, the general health and/or age of the subject, and other diseases present. The dose levels can also depend on whether the extract, *Rothia* species bacteria, or enzyme is used, the severity of the symptoms and the susceptibility of the subject to side effects. The isolated enzyme can be more potent than the extract or the bacteria. Moreover, treatment of a subject with a therapeutically effective dose can include a single treatment or a series of treatments. Estimates of effective dosages and in vivo half-lives for the extract, *Rothia* species bacteria, or enzyme encompassed by the invention can be made using conventional methodologies or on the basis of in vivo testing using an appropriate animal model, as known in the art, or as described herein. Preferred dosages for a given enzyme are readily determinable by those of skill in the art by a variety of means.

The therapeutic effect can be measured in terms of clinical outcome or can be determined by immunological or biochemical tests. For example, in the treatment of Celiac sprue, suppression of the deleterious T-cell activity can be measured by enumeration of reactive Th 1 cells, by quantitating the release of cytokines at the sites of lesions, or using other assays for the presence of autoimmune T cells known in the art. Alternatively, one can look for a reduction in symptoms of celiac disease as described herein or, e.g. as set forth in Pyle et al, Clin. Gastroenterol. Hepatol. 3:679-686, 2005.

Various methods for administration may be employed, it being appreciated that the formulations of the extract, *Rothia* species bacteria, or enzyme described herein provided by the present invention provide improved formulations for oral administration. For example, in the treatment of Celiac Sprue with a subtilisin enzyme derived from *Rothia* species bacteria described herein, the present invention provides unit dose forms of the extract, *Rothia* species bacteria, or enzyme described herein suitable for administration with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semi-weekly, or otherwise as needed to maintain an effective dosage level.

Lyophilized formulations of subtilisin enzyme derived from *Rothia* species bacteria and excipients is useful in the production of enteric-coated capsules or tablets, e.g. a single capsule or tablet can contain at least about 1 mg usually at least about 10 mg of isolated subtilisin enzyme derived from *Rothia* species bacteria and may contain at least 100 mg subtilisin enzyme derived from *Rothia* species bacteria, at least about 200 mg, at least about 300 mg, at least about 400 mg, at least about 500 mg, up to about 1000 mg protein, including all the numbers between 1-1000 mg. Where there are additional enzymes in the formulation or compositions, e.g., isolated additional gluten-degrading enzyme or isolated glutamine endopeptidase enzyme or isolated PEP, each of these enzymes ranges from at least about 1 mg usually at least about 10 mg in the composition or formulation. It is contemplated that these additional enzymes can range from at least about 200 mg, at least about 300 mg, at least about 400 mg, at least about 500 mg, up to about 1000 mg protein, including all the numbers between 1-1000 mg. As described in detail here, enteric coatings can be applied, where a substantial fraction of the activity is retained, and is stable for at least about 1 month at 4° C. The method of lyophilizing bacteria is known to one skilled in the art, e. g. U.S. Pat. Nos. 4,205,132, 4,444,760, RE40023, 5192743, 5529915, 6750330, and 7572893, all of which are incorporated by reference in their entirety.

In one embodiment, the effective dose of the subtilisin enzyme derived from *Rothia* species bacteria ranges from 0.01 mg to 500 mg/kg body weight. In another embodiment, wherein the glutamine endopeptidase enzyme derived or isolated from a *Rothia* species bacterium is used, the effective dose of the enzyme is from 0.01 mg to 500 mg/kg body weight.

In one embodiment, the method is practiced when the subject is consuming any gluten-containing foodstuff. In another embodiment, the method is practiced prior to the consumption of gluten-containing foodstuff, wherein the subject is preparing to ingest gluten-containing food or the subject suspects that there might be gluten or wheat-derived ingredients in the food that the subject is about to consume. In another embodiment, the method is practiced whenever food is consumed or e.g., three times a day with the three major meals of a day: breakfast, lunch and dinner.

Accordingly, in some embodiments, the formulation or compositions comprising the isolated subtilisin enzyme derived from *Rothia* species bacteria is administered just before, during, or just after consumption of gluten-containing foodstuff.

In one embodiment, the formulation or compositions comprising the isolated subtilisin enzyme derived from *Rothia* species bacteria is administered prior to consumption of gluten-containing foodstuff. In one embodiment, the formulation or compositions comprising the isolated subtilisin enzyme derived from *Rothia* species bacteria is administered in a gluten-containing foodstuff.

In one embodiment, the pharmaceutical formulation as described herein is administered in an amount sufficient to attenuate gluten toxicity, as that term is used herein.

Formulations are typically provided in a unit dosage form, where the term "unit dosage form," refers to physically discrete units suitable as unitary dosages for the subjects, each unit containing a predetermined quantity of the formulation or compositions comprising the isolated subtilisin enzyme derived from *Rothia* species bacteria described herein in an amount sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

Attenuates Gluten Toxicity

In the context of an enzyme or enzyme preparation, "attenuates gluten toxicity" refers to the action of an endopeptidase enzyme to reduce the amount, level or density of toxic gluten oligopeptides produced from gluten-containing foodstuff in the gut. Some toxic gluten oligopeptides are produced during digestion of gluten-containing foodstuff by endogenous trypsin, chymotrypsin, elastase and carboxypeptidase in the gastrointestinal tract. Attenuation of gluten toxicity is achieved by digesting toxic gluten oligopeptides to smaller peptide fragments that lack T cell epitopes in glutens recognized by the subject's immune system. The activity of a glutamine endopeptidase from *Rothia* species described herein, before and/or after the digestion of gluten oligopeptides produced by endogenous trypsin, chymotrypsin, elastase and carboxypeptidase would result in less than 10% of the post-digestion products being longer than PQPQLPYPQ (SEQ ID NO: 11) which has nine amino acid residues. This can be assessed by the longer retention times on a C18 reverse phase HPLC column monitored at A215 and such methods are well known to one skilled in the art.

In one embodiment, the attenuation of gluten toxicity occurs in vitro prior to the ingestion of the gluten-containing foodstuff. For example, the compositions or the formulation described herein is admixed to the gluten-containing foodstuff during the manufacture of the foodstuff.

The assessment of attenuation of gluten toxicity can be determined using a cell-based or in vitro assay by measuring the ability of the isolated subtilisin enzyme derived from *Rothia* species bacteria or isolated glutamine endopeptidase from *Rothia* species described herein to increase the concentration of free NH2-termini in a reaction mixture containing e.g., 1 mg/ml of undigested or trypsin/chymotrypsin/elastase/carboxypeptidase pre-digested gluten substrate, and 10 µg/ml of the extract or isolated glutamine endopeptidase from a *Rothia* species, which can be incubated at 37° C. for 1 hour. Thus, attenuation of gluten toxicity in this context refers to an increase the concentration of free amino termini under such conditions by at least 25%, at least 30%, at least 40%, at least 50%, at least 60%, at least 70%, at least 80%, at least 90%, at least 95%, at least 99% or even 100% (no gluten toxicity). Additionally, a reduction in the residual molar concentration of oligopeptides greater than about e.g.,1000 Da can be measured using e.g., 1 mg/ml trypsin/chymotrypsin/elastase/carboxypeptidase pre-digested gluten substrate after a 1 hour incubation with 10 µg/ml of the extract or enzyme, which detects an increase in degradation of gluten toxic intermediates. This reduction in molar concentration is at least 50%, at least 1-fold, at least 2-fold, at least 5-fold, at least 10-fold, at least 100-fold, at least 1000-fold or more. The concentration of such oligopeptides can be estimated by methods known in the art, for example size exclusion chromatography and the like.

Alternatively, an in vitro based assay measuring the degradation of highly immunogenic peptides can be used; such highly immunogenic peptides can include those derived from α-gliadin (LQLQPFPQPQLPYPQPQLPYPQPQLPYPQPQPF; a 33-mer; SEQ ID NO: 5) or γ-gliadin (FLQPQQPFPQQPQQPYPQQPQQPFPQ; 26-mer; SEQ ID NO: 6). For example, gliadin peptides (10 mg/mL) are contacted with an enzyme sample (e.g., extract, isolated enzyme, whole saliva) to be tested and incubated at various time points (e.g., 10 min, 30 min, 1 h, 2 h, 6 h, 12 h, 24 h, etc). The assay is stopped by heat inactivation (e.g., boiling) and the peptide sample is subjected to RP-HPLC to determine the presence, absence or degree of degradation.

In one embodiment, "attenuates gluten toxicity" also refers to reducing the ability of a gluten oligopeptide to bind to HLA-DQ (e.g., a decreased number of epitopes for recognition by a subject's immune system). The ability of a substrate to bind to HLA-DQ is indicative of its toxicity; fragments smaller than about 8 amino acids are generally not stably bound to Class II MHC. The detoxification of whole gluten can be monitored by polyclonal T cell lines derived from intestinal biopsies of celiac or gluten allergic patients, by LC-MS-MS and by ELISA assays using monoclonal antibodies capable of recognizing sequences specific to gliadin. For example, an extract of a *Rothia* species or an isolated glutamine endopeptidase from *Rothia* species described herein can reduce the potency by which a trypsin/chymotrypsin/elastase/carboxypeptidase pre-digested gluten substrate can antagonize binding of PQPELPYPQPQLP (SEQ ID NO: 38) to HLA-DQ2. Treatment with an isolated enzyme or extract of *Rothia* species bacteria or *Rothia* bacteria described herein permits digestion of toxic oligopeptides, thereby preventing the toxic oligopeptides from competing with a test peptide for MHC binding. Such a competition assay can be performed by incubating 1 mg/ml trypsin/chymotrypsin/elastase/carboxypeptidase pre-digested gluten substrate with 10 μg/ml of the extract or enzyme, and the ability of the resulting solution to displace radioactive PQPELPYPQPQPLP (SEQ ID NO: 39) pre-bound to HLA-DQ2 molecules can then be quantified, with a reduction of displacement, relative to a non-treated control, indicative of utility in the methods of the present invention.

In one embodiment, "attenuates gluten toxicity" also refers to reducing the anti-tTG antibody and/or anti-gliadin antibodies response to a "gluten challenge diet" in a Celiac sprue or gluten allergic/gluten intolerance patient by at least 50%, at least 1-fold, at least 2-fold, at least 5-fold, at least 10-fold, at least 100-fold or more. A "gluten challenge diet" is defined as the intake of 100 g bread per day for 3 days by an adult Celiac sprue or gluten allergic patient previously on a gluten-free diet. The anti-tTG antibody (ATA) and anti-gliadin antibodies (AGA) response can be measured in peripheral blood using standard clinical diagnostic procedures, as known in the art.

The present invention can be defined in any of the following numbered paragraphs:

[1] A foodstuff comprising a formulation comprising a subtilisin enzyme derived from a *Rothia* sp. bacteria.
[2] The foodstuff of paragraph 1, wherein the *Rothia* sp. bacteria is selected from the group consisting of *Rothia mucilaginosa* of 681 (strain WSA-2B), *Rothia mucilaginosa* ATCC 25296, *Rothia* species of 188 (strain WSA-8), *Rothia aeria* BAV86562.1 and *Rothia dentocariosa* KGJ00122.1.
[3] The foodstuff of paragraph 1, wherein the *Rothia* sp. bacteria is selected from the group consisting of *Rothia mucilaginosa*, *Rothia aeria* and *Rothia dentocariosa*.
[4] The foodstuff of paragraph 1 or 2 or 3, wherein the subtilisin has the sequence of the hypothetical ROTMU0001_0241 (C6R5V9_9MICC), ROTMU0001_0243 (C6R5W1_9MICC) or ROTMU0001_240 (C6R5V8_9MICC) proteins.
[5] The foodstuff of any one of paragraphs 1-4, wherein the subtilisin is at least 90% identical to the sequences of the hypothetical ROTMU0001_0241 (C6R5V9_9MICC), ROTMU0001_0243 (C6R5W1_9MICC) or ROTMU0001_240 (C6R5V8_9MICC) proteins described herein.
[6] The foodstuff of any one of paragraphs 1-5, wherein the subtilisin comprises the catalytic triad with Asp (D), His (H) and Ser (S) in the D-H-S order that is characteristic of the S8A family of serine protease family.
[7] The foodstuff of any one of paragraphs 1-6, wherein the subtilisin cleaves proline-containing proteins, cleaving the second peptide bond after proline in the XPX$_1$ motif, where X is any amino acid, P is proline and X1 is a hydrophobic amino acid, i.e., cleaving at the peptide bond after X1, e.g. the XPQ motif, where Q is glutamine.
[8] The foodstuff of any one of paragraphs 1-7, wherein the subtilisin cleaves succinyl-Ala-Ala-Pro-Phe-paranitroanilide (SEQ ID NO: 4), a substrate for subtilisin, cleaving at the second peptide bond after proline in the P2 position.
[9] The foodstuff of any one of paragraphs 1-8, wherein the subtilisin degrades the highly immunogenic gliadin-derived 33-mer peptide.
[10] The foodstuff of any one of paragraphs 1-9, wherein the subtilisin does not cleave the 2nd peptide bond after Proline in the P2 position in a tripeptide having the -PFP-motif, wherein F=Phenylalanine=Phe; P=proline=Pro.
[11] The foodstuff of any one of paragraphs 1-10, wherein the subtilisin does not cleave the 2nd peptide bond after Proline in the P2 position in a tripeptide having the -PPF-motif, wherein F=Phenylalanine; P=proline.
[12] The foodstuff of any one of paragraphs 1-11, wherein the subtilisin is more effective glutenase compared with *Bacillus* sp. subtilisin A with respect to certain immunogenic epitopes.
[13] The foodstuff of any one of paragraphs 1-12, wherein the subtilisin has an apparent molecular weight of about 75-80 kDa as determined by gliadin zymograms or by sodium dodecyl sulfate polyacrylamide gel electrophoresis or as described in FIGS. 2A-2E; or have a predicted molecular weight of ~125 kDa as described in the example section.
[14] The foodstuff of any one of paragraphs 1-13, wherein the subtilisin enzyme has a functional pH range of 6.0-10.0.
[15] The foodstuff of any one of paragraphs 1-14, wherein the subtilisin enzyme has low or negligible enzyme activity at pH values below 5.0 or pH values higher than 11.0.
[16] The foodstuff of any one of paragraphs 1-15, wherein the subtilisin is 100% inhibited by 1 mM of PMSF.
[17] The foodstuff of any one of paragraphs 1-16, wherein the subtilisin is not inhibited by E64 or EDTA.
[18] The foodstuff of any one of paragraphs 1-17, wherein the subtilisin is not stable in acid conditions.
[19] The foodstuff of any one of paragraphs 1-18, wherein the subtilisin is lyophilized.
[20] The foodstuff of any one of paragraphs 1-19, wherein the subtilisin is a recombinant protein.
[21] The foodstuff of any one of paragraphs 1-20, wherein the subtilisin has an amino acid sequence that show at least 60% similarity to SEQ ID NO: 1, 2 or 3 or 33 or 34.
[22] The foodstuff of any one of paragraphs 1-21, wherein the subtilisin comprises SEQ ID NO: 1, 2 or 3 or 33 or 34.
[23] The foodstuff of any one of paragraphs 1-22, wherein the subtilisin consists essentially of SEQ ID NO: 1, 2 or 3 or 33 or 34.
[24] The foodstuff of any one of paragraphs 1-23, wherein the subtilisin is SEQ ID NO: 1, 2 or 3 or 33 or 34.
[25] The foodstuff of any one of paragraphs 1-24, the formulation further comprising a prolyl endopeptidase.
[26] The foodstuff of any one of paragraphs 1-25, the formulation further comprising at least one additional gluten-degrading enzyme isolated from a *Rothia* species bacteria, wherein the at least one additional gluten-degrading enzyme retains protease activity at an acidic pH of 3.0 as measured in an in vitro gliadin degradation assay for 3 hours using a synthetic substrate Z-YPQ-pNA, and wherein the at least one enzyme comprises an isoelectric point in a pH range of 2.0-7.0, inclusive.

[27] The foodstuff of any one of paragraphs 1-26, the formulation further comprising at least one isolated additional glutamine endopeptidase enzyme that cleaves a peptide bond after a QPF and a PFP motif in glutens.

[28] A method for degrading gluten or an amylase-trypsin inhibitor in a gluten-containing foodstuff the method comprises contacting the gluten-containing foodstuff with an effective dose of a formulation comprising a subtilisin enzyme derived from a *Rothia* sp. bacteria.

[29] The method of paragraph 28, wherein the contacting is performed in vitro prior to consumption of the gluten-containing food stuff.

[30] The method of paragraph 28, wherein the contacting is performed in vivo concurrent with or after consumption of the gluten-containing food stuff

[31] The method of paragraph 28, 29, or 30, wherein the *Rothia* sp. bacteria is selected from the group consisting of *Rothia mucilaginosa* ot 681 (strain WSA-2B), *Rothia mucilaginosa* ATCC 25296, *Rothia* species ot 188 (strain WSA-8), *Rothia aeria* BAV86562.1 and *Rothia dentocariosa* KGJ00122.1.

[32] The method of any one of paragraphs 28-31, wherein the *Rothia* sp. bacteria is selected from the group consisting of *Rothia mucilaginosa*, *Rothia aeria* and *Rothia dentocariosa*.

[33] The method of any one of paragraphs 28-32, wherein the subtilisin has the sequence of the hypothetical ROTMU0001_0241 (C6R5V9_9MICC), ROTMU0001_0243 (C6R5W1_9MICC) or ROTMU0001_240 (C6R5V8_9MICC) proteins.

[34] The method of any one of paragraphs 28-33, wherein the subtilisin is at least 90% identical to the sequences of the hypothetical ROTMU0001_0241 (C6R5V9_9MICC), ROTMU0001_0243 (C6R5W1_9MICC) or ROTMU0001_240 (C6R5V8_9MICC) proteins, (SEQ ID NOS: 1-3) or SEQ ID NOS: 33-34.

[35] The method of any one of paragraphs 28-34, wherein the subtilisin comprises the catalytic triad with Asp (D), His (H) and Ser (S) in the D-H-S order that is characteristic of the S8A family of serine protease family.

[36] The method of any one of paragraphs 28-35, wherein the subtilisin cleaves proline-containing proteins, cleaving the second peptide bond after proline in the XPX1 motif, where X is any amino acid, P is proline and X1 is a hydrophobic amino acid, i.e., cleaving at the peptide bond after X1, e.g. the XPQ motif, where Q is glutamine.

[37] The method of any one of paragraphs 28-36, wherein the subtilisin cleaves succinyl-Ala-Ala-Pro-Phe-paranitroanilide (SEQ ID NO: 4), a substrate for subtilisin, cleaving at the second peptide bond after proline in the P2 position.

[38] The method of any one of paragraphs 28-37, wherein the subtilisin degrades the highly immunogenic gliadin-derived 33-mer peptide.

[39] The method of any one of paragraphs 28-38, wherein the subtilisin does not cleave the 2nd peptide bond after Proline in the P2 position in a tripeptide having the -PFP-motif, wherein F=Phenylalanine=Phe; P=proline=Pro.

[40] The method of any one of paragraphs 28-39, wherein the subtilisin does not cleave the 2nd peptide bond after Proline in the P2 position in a tripeptide having the -PPF-motif, wherein F=Phenylalanine; P=proline.

[41] The method of any one of paragraphs 28-40, wherein the subtilisin is more effective glutenase compared with *Bacillus* sp. subtilisin A with respect to certain immunogenic epitopes, e.g. the 33mer peptide.

[42] The method of any one of paragraphs 28-41, wherein the subtilisin has an apparent molecular weight of about 75-80 kDa as determined by gliadin zymograms or by sodium dodecyl sulfate polyacrylamide gel electrophoresis, or a predicted molecular weight of ~125 kDa as described in the Examples Section.

[43] The method of any one of paragraphs 28-42, wherein the subtilisin enzyme has a functional pH range of 6.0-10.0.

[44] The method of any one of paragraphs 28-43, wherein the subtilisin enzyme has low or negligible enzyme activity at pH values below 5.0 or pH values higher than 11.0.

[45] The method of any one of paragraphs 28-44, wherein the subtilisin is 100% inhibited by 1 mM of PMSF. (or just inhibited PMSF)

[46] The method of any one of paragraphs 28-45, wherein the subtilisin is not inhibited by E64 or EDTA.

[47] The method of any one of paragraphs 28-46, wherein the subtilisin is not stable in acid conditions.

[48] The method of any one of paragraphs 28-47, wherein the subtilisin is lyophilized.

[49] The method of any one of paragraphs 28-48, wherein the subtilisin is a recombinant protein.

[50] The method of any one of paragraphs 28-49, wherein the subtilisin has an amino acid sequence that show at least 60% similarity to SEQ ID NO: 1, 2 or 3 or 33 or 34.

[51] The method of any one of paragraphs 28-50, wherein the subtilisin comprises SEQ ID NO: 1, 2 or 3 or 33 or 34.

[52] The method of any one of paragraphs 28-51, wherein the subtilisin consists essentially of SEQ ID NO: 1, 2 or 3 or 33 or 34.

[53] The method of any one of paragraphs 28-52, wherein the subtilisin is SEQ ID NO: 1, 2 or 3 or 33 or 34.

[54] The method of any one of paragraphs 28-53, the formulation further comprising a prolyl endopeptidase.

[55] The method of any one of paragraphs 28-54, the formulation further comprising at least one additional gluten-degrading enzyme isolated from a *Rothia* species bacteria, wherein the at least one additional gluten-degrading enzyme retains protease activity at an acidic pH of 3.0 as measured in an in vitro gliadin degradation assay for 3 hours using a synthetic substrate Z-YPQ-pNA, and wherein the at least one enzyme comprises an isoelectric point in a pH range of 2.0-7.0, inclusive.

[56] The method of any one of paragraphs 28-55, the formulation further comprising at least one isolated additional glutamine endopeptidase enzyme that cleaves a peptide bond after a QPF and a PFP motif in glutens.

[57] A composition comprising (a) an isolated subtilisin enzyme derived from a *Rothia* sp. bacteria, and (b) a prolyl endopeptidase (PEP).

[58] The composition of paragraph 57, wherein the *Rothia* sp. bacteria is selected from the group consisting of *Rothia mucilaginosa* ot 681 (strain WSA-2B), *Rothia*

*mucilaginosa* ATCC 25296, *Rothia* species ot 188 (strain WSA-8), *Rothia aeria* BAV86562.1 and *Rothia dentocariosa* KGJ00122.1.

[59] The composition of 57 or 58, wherein the *Rothia* sp. bacteria is selected from the group consisting of *Rothia mucilaginosa*, *Rothia aeria* and *Rothia dentocariosa*.

[60] The composition of any one of paragraphs 28-32, wherein the subtilisin has the sequence of the hypothetical ROTMU0001_0241 (C6R5V9_9MICC), ROTMU0001_0243 (C6R5W1_9MICC) or ROTMU0001_240 (C6R5V8_9MICC) proteins.

[61] The composition of any one of paragraphs 57-60, wherein the subtilisin is at least 90% identical to the sequences of the hypothetical ROTMU0001_0241 (C6R5V9_9MICC), ROTMU0001_0243 (C6R5W1_9MICC) or ROTMU0001_240 (C6R5V8_9MICC) proteins, (SEQ ID NOS: 1-3) or SEQ ID NOS: 33-34.

[62] The composition of any one of paragraphs 57-61, wherein the subtilisin comprises the catalytic triad with Asp (D), His (H) and Ser (S) in the D-H-S order that is characteristic of the S8A family of serine protease family.

[63] The composition of any one of paragraphs 57-62, wherein the subtilisin cleaves proline-containing proteins, cleaving the second peptide bond after proline in the $XPX_1$ motif, where X is any amino acid, P is proline and X1 is a hydrophobic amino acid, i.e., cleaving at the peptide bond after $X_1$, e.g. the XPQ motif, where Q is glutamine.

[64] The composition of any one of paragraphs 57-63, wherein the subtilisin cleaves succinyl-Ala-Ala-Pro-Phe-paranitroanilide (SEQ ID NO: 4), a substrate for subtilisin, cleaving at the second peptide bond after proline in the P2 position.

[65] The composition of any one of paragraphs 57-64, wherein the subtilisin degrades the highly immunogenic gliadin-derived 33-mer peptide.

[66] The composition of any one of paragraphs 57-65, wherein the subtilisin does not cleave the 2nd peptide bond after Proline in the P2 position in a tripeptide having the -PFP-motif, wherein F=Phenylalanine=Phe; P=proline=Pro.

[67] The composition of any one of paragraphs 57-66, wherein the subtilisin does not cleave the 2nd peptide bond after Proline in the P2 position in a tripeptide having the -PPF-motif, wherein F=Phenylalanine; P=proline.

[68] The composition of any one of paragraphs 57-67, wherein the subtilisin is more effective glutenase compared with *Bacillus* sp. subtilisin A with respect to certain immunogenic epitopes, e.g. the 33mer peptide.

[69] The composition of any one of paragraphs 57-68, wherein the subtilisin has an apparent molecular weight of about 75-80 kDa as determined by gliadin zymograms or by sodium dodecyl sulfate polyacrylamide gel electrophoresis, or a predicted molecular weight of ~125 kDa as described in the Examples Section.

[70] The composition of any one of paragraphs 57-69, wherein the subtilisin undergo autocatalytic activation to produce a shorter mature enzyme.

[71] The composition of any one of paragraphs 57-70, wherein the subtilisin enzyme has a functional pH range of 6.0-10.0.

[72] The composition of any one of paragraphs 57-71, wherein the subtilisin enzyme has low or negligible enzyme activity at pH values below 5.0 or pH values higher than 11.0.

[73] The composition of any one of paragraphs 57-72, wherein the subtilisin is 100% inhibited by 1 mM of PMSF (or just inhibited PMSF).

[74] The composition of any one of paragraphs 57-73, wherein the subtilisin is not inhibited by E64 or EDTA.

[75] The composition of any one of paragraphs 57-74, wherein the subtilisin is not stable in acid conditions.

[76] The composition of any one of paragraphs 57-75, wherein the subtilisin is lyophilized.

[77] The composition of any one of paragraphs 57-76, wherein the subtilisin is a recombinant protein.

[78] The composition of any one of paragraphs 57-77, wherein the subtilisin has an amino acid sequence that show at least 60% similarity to SEQ ID NO: 1, 2 or 3 or 33 or 34.

[79] The composition of any one of paragraphs 57-78, wherein the subtilisin comprises SEQ ID NO: 1, 2 or 3 or 33 or 34.

[80] The composition of any one of paragraphs 57-79, wherein the subtilisin consists essentially of SEQ ID NO: 1, 2 or 3 or 33 or 34.

[81] The composition of any one of paragraphs 57-80, wherein the subtilisin is SEQ ID NO: 1, 2 or 3 or 33 or 34.

[82] The composition of any one of paragraphs 57-81, the formulation further comprising at least one additional gluten-degrading enzyme isolated from a *Rothia* species bacteria, wherein the at least one additional gluten-degrading enzyme retains protease activity at an acidic pH of 3.0 as measured in an in vitro gliadin degradation assay for 3 hours using a synthetic substrate Z-YPQ-pNA, and wherein the at least one enzyme comprises an isoelectric point in a pH range of 2.0-7.0, inclusive.

[83] The composition of any one of paragraphs 57-82, the formulation further comprising at least one isolated additional glutamine endopeptidase enzyme that cleaves a peptide bond after a -QPF- and a -PFP-motif in glutens.

[84] The composition of any one of paragraphs 57-83, wherein the PEP is derived from the microorganism selected from the group consisting of *Aspergillus niger, Flavobacterium meningosepticum, Sphingomonas capsulata, Penicillium citrinum, Hordeum vulgare*, and *Myxococcus xanthus*.

[85] The composition of any one of paragraphs 57-84, the composition further comprising a glutamine specific protease which is selected from the group consisting of *Hordeum vulgare* endoprotease, *Aspergillus oryzae* X-Pro dipeptidase, and *Aspergillus saitoi* carboxypeptidase. (as described in U.S. Pat. No. 7,628,985, incorporated by reference in its entirety).

[86] The composition of any one of paragraphs 57-85, the composition further comprising a pharmaceutically acceptable carrier.

[87] A method for treating celiac disease or a related disorder such as gluten allergy, gluten intolerance, non-celiac/non-allergy wheat sensitivity due to in amylase-trypsin inhibitors, and dermatitis herpetiformis, the method comprising administering to a subject an effective dose of a composition comprising a subtilisin enzyme derived from a *Rothia* sp. bacteria, or administering an effective dose of a composition of any one of paragraphs 57-86.

[88] The treatment method of paragraph 87, wherein the administering is performed in vitro prior to consumption of the gluten-containing food stuff.

[89] The treatment method of paragraph 87, wherein the administering is performed in vivo concurrent with or after consumption of the gluten-containing food stuff.

[90] The treatment method of paragraph 87, wherein the administering is performed in vitro prior to and also concurrent with or after consumption of the gluten-containing food stuff.

[91] The treatment method of any one of paragraphs 87-90, wherein the *Rothia* sp. bacteria is selected from the group consisting of *Rothia mucilaginosa* ot 681 (strain WSA-2B), *Rothia mucilaginosa* ATCC 25296, *Rothia* species ot 188 (strain WSA-8), *Rothia aeria* BAV86562.1 and *Rothia dentocariosa* KGJ00122.1.

[92] The treatment method of any one of paragraphs 87-91, wherein the *Rothia* sp. bacteria is selected from the group consisting of *Rothia mucilaginosa*, *Rothia aeria* and *Rothia dentocariosa*.

[93] The method of any one of paragraphs 28-32, wherein the subtilisin has the sequence of the hypothetical ROTMU0001_0241 (C6R5V9_9MICC), ROTMU0001_0243 (C6R5W1_9MICC) or ROTMU0001_240 (C6R5V8_9MICC) proteins.

[94] The treatment method of any one of paragraphs 87-93, wherein the subtilisin is at least 90% identical to the sequences of the hypothetical ROTMU0001_0241 (C6R5V9_9MICC), ROTMU0001_0243 (C6R5W1_9MICC) or ROTMU0001_240 (C6R5V8_9MICC) proteins, (SEQ ID NOS: 1-3) or SEQ ID NOS: 33-34.

[95] The treatment method of any one of paragraphs 87-94, wherein the subtilisin comprises the catalytic triad with Asp (D), His (H) and Ser (S) in the D-H-S order that is characteristic of the S8A family of serine protease family.

[96] The treatment method of any one of paragraphs 87-95, wherein the subtilisin cleaves proline-containing proteins, cleaving the second peptide bond after proline in the $XPX_1$ motif, where X is any amino acid, P is proline and $X_1$ is a hydrophobic amino acid, i.e., cleaving at the peptide bond after $X_1$, e.g. the XPQ motif, where Q is glutamine.

[97] The treatment method of any one of paragraphs 87-96, wherein the subtilisin cleaves succinyl-Ala-Ala-Pro-Phe-paranitroanilide (SEQ ID NO: 4), a substrate for subtilisin, cleaving at the second peptide bond after proline in the P2 position.

[98] The treatment method of any one of paragraphs 87-97, wherein the subtilisin degrades the highly immunogenic gliadin-derived 33-mer peptide.

[99] The treatment method of any one of paragraphs 87-98, wherein the subtilisin does not cleave the second peptide bond after Proline in the P2 position in a tripeptide having the -PFP-motif, wherein F=Phenylalanine=Phe; P=proline=Pro.

[100] The treatment method of any one of paragraphs 87-99, wherein the subtilisin does not cleave the second peptide bond after Proline in the P2 position in a tripeptide having the -PPF-motif, wherein F=Phenylalanine; P=proline.

[101] The treatment method of any one of paragraphs 87-100, wherein the subtilisin is more effective glutenase compared with *Bacillus* sp. subtilisin A with respect to certain immunogenic epitopes, e.g. the 33mer peptide.

[102] The treatment method of any one of paragraphs 87-101, wherein the subtilisin has an apparent molecular weight of about 75-80 kDa as determined by gliadin zymograms or by sodium dodecyl sulfate polyacrylamide gel electrophoresis, or a predicted molecular weight of ~125 kDa as described in the Example Section.

[103] The treatment method of any one of paragraphs 87-102, wherein the subtilisin undergoes autocatalytic activation to produce a shorter mature enzyme.

[104] The treatment method of any one of paragraphs 87-103, wherein the subtilisin enzyme has a functional pH range of 6.0-10.0.

[105] The treatment method of any one of paragraphs 87-104, wherein the subtilisin enzyme has low or negligible enzyme activity at pH values below 5.0 or pH values higher than 11.0.

[106] The method of any one of paragraphs 87-105, wherein the subtilisin is 100% inhibited by 1 mM of PMSF. (or just inhibited PMSF)

[107] The treatment method of any one of paragraphs 87-106, wherein the subtilisin is not inhibited by E64 or EDTA.

[108] The treatment method of any one of paragraphs 87-107, wherein the subtilisin is not stable in acid conditions.

[109] The treatment method of any one of paragraphs 87-108, wherein the subtilisin is lyophilized.

[110] The treatment method of any one of paragraphs 87-109, wherein the subtilisin is a recombinant protein.

[111] The treatment method of any one of paragraphs 87-110, wherein the subtilisin has an amino acid sequence that show at least 60% similarity to SEQ ID NO: 1, 2 or 3 or 33 or 34.

[112] The treatment method of any one of paragraphs 87-111, wherein the subtilisin comprises SEQ ID NO: 1, 2 or 3 or 33 or 34.

[113] The treatment method of any one of paragraphs 87-112, wherein the subtilisin consists essentially of SEQ ID NO: 1, 2 or 3 or 33 or 34.

[114] The treatment method of any one of paragraphs 87-113, wherein the subtilisin is SEQ ID NO: 1, 2 or 3 or 33 or 34.

[115] The treatment method of any one of paragraphs 87-114, the formulation further comprising a prolyl endopeptidase.

[116] The treatment method of any one of paragraphs 87-115, the formulation further comprising an effective amount of at least one additional gluten-degrading enzyme isolated from a *Rothia* species bacteria, wherein the at least one additional gluten-degrading enzyme retains protease activity at an acidic pH of 3.0 as measured in an in vitro gliadin degradation assay for 3 hours using a synthetic substrate Z-YPQ-pNA, and wherein the at least one enzyme comprises an isoelectric point in a pH range of 2.0-7.0, inclusive.

[117] The treatment method of any one of paragraphs 87-116, the formulation further comprising an isolated second additional glutamine endopeptidase enzyme that cleaves a peptide bond after a -QPF- and a -PFP- motif in glutens.

[118] The treatment method of any one of paragraphs 87-117, wherein the related disorder is selected from the group consisting of refractory celiac disease, gluten allergy, gluten intolerance, non-celiac/non-allergy wheat sensitivity due to amylase-trypsin inhibitors, and dermatitis herpetiformis.

[119] Use of a subtilisin enzyme derived from a *Rothia* sp. bacteria to attenuate gluten toxicity in gluten-containing food stuff or for the treatment of celiac disease or a related disorder.

[120] Use of a subtilisin enzyme derived from a *Rothia* sp. bacteria for the manufacture of medicament to treat of celiac disease or a related disorder.

[121] Use of a formulation comprising a subtilisin enzyme derived from a *Rothia* sp. bacteria, or a composition of any one of paragraphs 57-86 to attenuate gluten toxicity in gluten-containing food stuff or for the treatment of celiac disease or a related disorder.

[122] Use of a formulation comprising a subtilisin enzyme derived from a *Rothia* sp. bacteria, or a composition of any one of paragraphs 57-86 for the manufacture of medicament for the treatment of celiac disease or a related disorder.

[123] Use of any one of paragraphs 119-122, wherein the related disorder is selected from the group consisting of refractory celiac disease, gluten allergy, gluten intolerance, non-celiac/non-allergy wheat sensitivity due to in amylase-trypsin inhibitors, and dermatitis herpetiformis.

[124] Use of a formulation comprising a subtilisin enzyme derived from a *Rothia* sp. bacteria, or a composition of any one of paragraphs 57-86 to degrade amylase-trypsin inhibitors (ATIs) in gluten-containing food stuff or for the treatment of non-celiac/non-allergy wheat sensitivity due to ATIs.

[125] Use of a formulation comprising a subtilisin enzyme derived from a *Rothia* sp. bacteria, or a composition of any one of paragraphs 57-86 for the manufacture of medicament for the treatment of non-celiac/non-allergy wheat sensitivity due to ATIs.

[126] Use of a subtilisin enzyme derived from a *Rothia* sp. bacteria for the manufacture of medicament to treat non-celiac/non-allergy wheat sensitivity due to ATIs.

[127] Use of a subtilisin enzyme derived from a *Rothia* sp. bacteria to degrade amylase-trypsin inhibitors (ATIs) in gluten-containing food stuff or for the treatment of non-celiac/non-allergy wheat sensitivity due to ATIs.

This invention is further illustrated by the following example which should not be construed as limiting.

Those skilled in the art will recognize, or be able to ascertain using not more than routine experimentation, many equivalents to the specific embodiments of the invention described herein. Such equivalents are intended to be encompassed by the following claims.

EXAMPLES

Example 1—Gluten-Degrading Subtilisins from *Rothia mucilaginosa* and *Bacillus* sp Gluten are proline and glutamine-rich proteins present in wheat, barley and rye, which contain the immunogenic sequences that drive celiac disease (CD). *Rothia mucilaginosa*, a harmless oral colonizer, contain enzymes that can cleave these gluten epitopes. The inventors have identified these enzymes and evaluate their potential as enzyme therapeutics.

The membrane-associated *R. mucilaginosa* proteins were extracted and separated by DEAE chromatography. Enzyme activities were monitored with paranitroanilide derivatized- and FRET peptide substrates, and by gliadin zymography. Epitope elimination was determined by ELISA. Gliadin-degrading enzymes were identified by LC-ESI-MS/MS.

Proteolytic degradation of protease-resistant domains in gluten require enzymatic cleavage specificities that are not readily available in the repertoire of mammalian digestive enzymes. Recent studies have revealed that the oral cavity contains microorganisms producing endoprotease(s) with cleavage specificity after a glutamine residue (Helmerhorst E J, et al. J Biol Chem 2008; 283: 19957-66). The activity was found by analyzing the sequences of salivary peptides that are naturally present in human whole saliva. The salivary peptidome contains multiple peptides derived from human salivary basic proline-rich proteins that were cleaved after the Xaa-Pro-Gln (-XPQ-) tripeptide sequence (Helmerhorst E J, et al., J Biol Chem 2008; 283:19957-66; Vitorino R, et al. Prot Clin Appl 2009; 3: 528-540; Messana I, et al. Mol Cell Proteomics 2008; 7:911-26). The structural similarity between gliadins and basic proline-rich proteins was studied to investigate if gliadins are substrates for oral microbial proteases and can be degraded into non-immunogenic peptides.

The inventors have found natural gluten degrading microorganisms are associated with the oral cavity, i.e. the very proximal GI tract, and this discovery open new avenues to neutralize the deleterious effects of gluten in patients with celiac disease.

Methods

Bacterial culturing—*R. mucilaginosa* ATCC 25296 was routinely grown on a *Brucella*-agar plates (Hardy Diagnostics, Santa Maria, Calif.) at 37° C. for 24 h under aerobic conditions. Individual bacterial colonies were transferred to 100 ml of Todd-Hewitt broth (Beckton Dickinson, Sparks, Md.) supplemented with 0.5% Tween-80 (THT), and subcultured into 4 L of THT. All incubations were carried out in Erlenmeyer flasks, while shaking at 200 rpm for 48 h at 37° C.

Preparation of a *R. mucilaginosa* cell extract—Cells were harvested from the 4 L THT culture by centrifugation at 16,000×g at 4° C. for 30 min, washed two times with 20 mM TrisHCl buffer, pH 7.5, and then re-suspended in 150 ml of 20 mM TrisHCl buffer containing 596 kU/ml lysozyme (Sigma, St. Louis, Mo., USA). After incubation at 37° C. for 1 h, 25 mg/ml n-Octyl-β-D-glucopyranoside was added (Thermo Fisher, Waltham Mass.) as well as 0.3 mg/ml of L-cysteine. The cell suspension was frozen at −20° C., defrosted, and then sonicated on ice using a sonifier with a macro tip (Branson sonifier 450, VWR Scientific, Bridgeport, N.J.). The chemical pretreatment of the cells combined with the sonication reduced the $OD_{620}$ of the suspension by 60%. The suspension was centrifuged for at 31,209×g for 30 min at 4° C. The supernatant was harvested and centrifuged at 151,243×g, for 1 h at 4° C. The pellet, containing most of the activity, was resuspended in 4 ml of 20 mM TrisHCl, pH 7.5. The protein concentration was determined using the bicinchoninic acid assay (Pierce Biotechnology, Rockford, Ill., USA). Samples were stored at −80° C.

DEAE anion exchange chromatography—Four ml of the resuspended pellet sample was thawed, and solubilized by the addition of 40 mg/ml n-Octyl-β-D-glucopyranoside. A 6 ml volume of 50 mM Tris-HCl containing 0.3 M NaCl, pH 7.0, (DEAE buffer A) was added. The 10 ml sample was then loaded onto an anion-exchange DEAE sepharose fast flow column with a column size of 2.6 cm diameter×27 cm length with a column volume (CV) of 143 ml. The resin used was a cross-linked agarose with the diethylaminoethyl exchange group ($-O-CH_2CH_2N+H(CH_2CH^3)_2$; GE Healthcare, Bjorkgatan, Sweden). The column was coupled to a FPLC system (AKTApurifier 10, GE Healthcare, Bjorkgatan, Sweden) and the flow rate applied was 1 ml/min. The buffers employed for protein elution were buffer A, containing 50 mM Tris-HCl, 0.3 M NaCl, pH 7.0, and buffer B, containing 50 mM Tris-HCl, 1 M NaCl, pH 7.0. Proteins were separated using a two-step gradient of 0% buffer B for 2.0 column volumes (286 ml) (isocratic conditions), followed by 100% elution buffer B for 1.5 column volume (215 ml). The absorbance was monitored at 219 nm and the eluate was collected in 10 ml fractions.

Analytical SDS-PAGE—The protein content of individual DEAE fractions (100 µl) and pooled DEAE fractions (400 µl) was determined using pre-casted discontinuous 4-12% SDS PAGE gels (NuPAGE, Thermofisher, Cambridge, Mass.) under reducing conditions. After electrophoresis gels were silver-stained as described (24).

Gliadin zymography—Pooled DEAE fractions F1-F7 were desalted using 30 kDa cut-off membranes and aliquots of 200 µl were analyzed for gluten-degrading enzyme activities on a 6% gliadin zymogram gel. The zymogram gel composition and renaturing and developing conditions were reported previously (22, 25).

PAGE and Casein zymography—The F2 fraction, containing the highest enzyme activity (hereafter called *R. mucilaginosa* enzyme preparation or Rmep) was applied in amounts ranging from 2-32 µg on a 6% PAGE gel under non-reducing conditions. The composition of the gel was the same as the 6% gliadin zymogram gel, but without the incorporated gliadin. After electrophoresis the gel was divided in half. One half of the gel was silver-stained, the other half was developed as a zymogram gel using externally added casein as the enzyme substrate, as described (24).

LC-ESI-MS/MS—Proteins of interest were excised from the silver-stained gel half, and in-gel digested with sequencing-grade trypsin (Promega, Madison, Wis.), as described (24). The peptides were eluted from the gel, separated by in line C18 chromatography and sequenced using an LTQ Orbitrap mass spectrometer (ThermoFinnigan, San Jose, Calif.). The obtained b- and y-ion spectra were searched against a database of *R. mucilaginosa* ATCC 25296, containing 1737 *Rothia* protein entries, and 132 non-*Rothia* decoy proteins.

Hydrolysis of paranitroanilide-derivatized substrates—Paranitroanilide (pNA)-derivatized tripeptide substrates were chemically synthesized at >90% purity (21st Century Biochemicals, Marlborough, Mass.). The substrates obtained were Z-YPQ-pNA, Z-QQP-pNA, Z-LPY-pNA, Z-PFP-pNA, Z-PPF-pNA, where Z=benzyloxycarbonyl, Y=tyrosine, P=proline, Q=glutamine, L=leucine, and F=phenylalanine Suc-AAPF-pNA (SEQ ID NO: 4) was obtained from Sigma, where Suc=N-succinyl and A=alanine. The peptides were dissolved in 75-100% DMSO at 10 mM, and were used at a final concentration of 200 µM in 50 mM TrisHCl pH 8.0. Purified *Rothia* enzyme or subtilisin A from *Bacillus licheniformis* (Sigma) were tested at final concentrations of 1 µg/ml. Some experiments were conducted in the presence of inhibitors 4-(2-Aminoethyl) benzenesulfonyl fluoride (AEBSF), Aprotinin, E-64, EDTA, phenylmethanesulfonyl fluoride (PMSF) and Eglin C, which were tested at final concentrations of 10 mM, 0.08 mM, 0.1 mM, 1.5 mM, 1 mM, and 0.06-1.2 µM, respectively. Enzymes were preincubated with the inhibitors for 20 min before adding Suc-AAPF-pNA (SEQ ID NO: 4). Substrate hydrolysis was monitored for 10 h at 405 nm using a Genios microtiter plate reader (Tecan, Männedorf, Switzerland) in the kinetic mode at 37° C.

FRET substrate hydrolysis—Three fluorescence resonance energy transfer (FRET) substrates comprising the hexapeptides QPQLPY (SEQ ID NO: 22), PQPQPQ (SEQ ID NO: 23) and QGSFQP (SEQ ID NO: 24) were synthesized with at the N-terminus the HILYTE FLUOR™ 488 label, and at the C-terminus with K(QXL520) (Anaspec, Fremont, Calif.). Rmep (1 µg/ml) and subtilisin A (0.5 µg/ml) were incubated with the substrates (100 µM) in 50 mM TrisHCl pH 8.0. Samples were incubated at 37° C. and fluorescence increase, indicating hydrolysis, was measured every 5 min for 30 min, and every 10 min for the next 30 min, at λex 485 nm and λem 520 nm, using a Genios microtiter plate reader in the kinetic mode.

Degradation of mixed gliadins and the 33-mer peptide—Mixed gliadins were obtained from Sigma. A synthetic highly immunogenic α-gliadin derived 33-mer peptide (26) was synthesized at a purity of >90% (21st Century Biochemicals). Mixed gliadins or the 33-mer peptide (each at final concentration 250 µg/ml) were incubated with Rmep or subtilisin A (each at 57 µg/ml) in 50 mM TrisHCl, pH 8.0. After t=0, 15 min, 30 min, and 2 h, 100 µl sample aliquots were removed and boiled. Gliadin degradation was assessed by 4-12% SDS-PAGE followed by Coomassie staining, and 33-mer degradation was determined by RP-HPLC.

Reversed-phase high performance liquid chromatography (RP-HPLC)—Separation of the 33-mer peptide and its fragments was achieved by RP-HPLC, using buffer A (0.1% trifluoroacetic acid) and buffer B (0.1% trifluoroacetic acid in 80% acetonitrile) at a gradient of 0-55% buffer B over 75 min time interval. The equipment used was an HPLC Model 715 (Gilson, Middleton, Wis.) and a C-18 column (TSK-GEL 5 mm, ODS-120T, TOSOHaas, Montgomeryville, Pa.) (22, 25).

R5 and G12 ELISA assays—Gluten epitope elimination in the gliadin-Rmep and gliadin-subtilisin A digests was assessed using two sandwich ELISA assays employing the R5 monoclonal antibody (RIDASCREEN Gliadin, R-Biopharm, Darmstadt, Germany) or the G12 monoclonal antibody (AgraQuant® ELISA Gluten G12, Romer labs, Union, Mo.). To prevent high background values, the R5 plate wells were blocked with 1% skim milk in PBS prior to incubation with the samples. The assays were performed according to the manufacturers' instructions and as described (21, 24).

Results

Figure 1B:
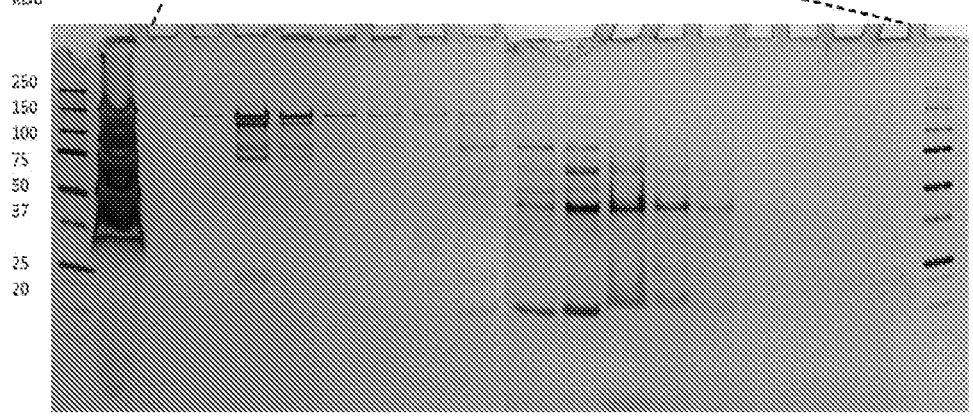
Figure 1C:
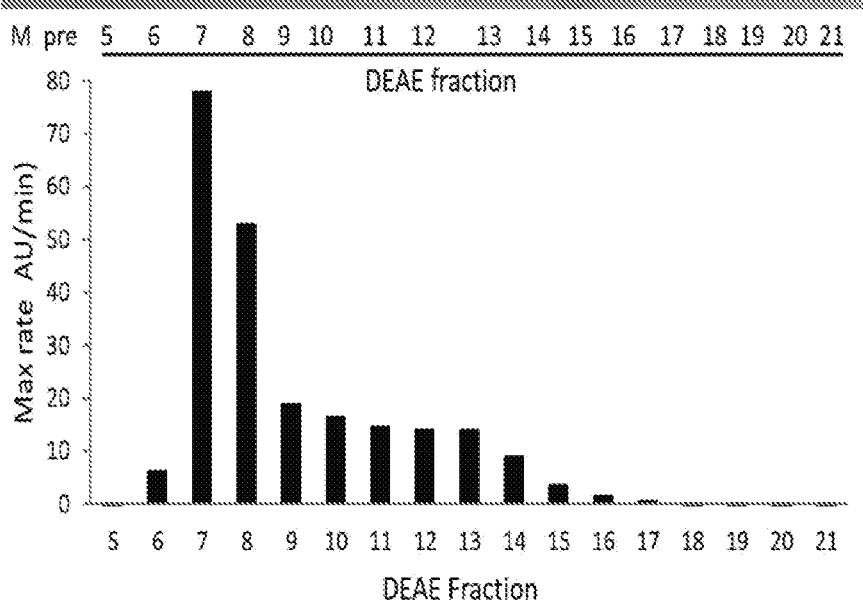

Purification of the enzyme from *Rothia mucilaginosa*—The inventors observed that the gluten-degrading enzyme activity of *R. mucilaginosa* was primarily cell associated. Therefore, to isolate the enzyme(s), cells were treated with lysozyme, an N-acetylmuramidase to break down the peptidoglycan layer, and then sonicated and centrifuged. The supernatant, which was turbid and contained microscopic vesicles, was ultracentrifuged. Enzyme activities, monitored with the substrate Z-YPQ-pNA, were primarily localized in the (vesicular) pellet. It was dissolved to clarity with the mild detergent n-Octyl-β-D-glucopyranoside and then subjected to DEAE chromatography applying an isocratic gradient. FIG. 1A shows the DEAE chromatogram, FIG. 1B the protein content in fraction aliquots analyzed by SDS-PAGE, and FIG. 1C the enzyme activity, determined with Z-YPQ-pNA. Most activity was contained in fractions 7 and 8 with some activity trailing in fractions 9-14. Fractions 7 and 8 contained proteins migrating between 75 and 150 kDa. Based on protein patterns and enzyme activities the fractions were pooled into seven fractions as follows: F1: fractions 1-5, F2: fractions 6-8, F3, fractions 9-12, F4, fractions 13-20, F5, fractions 21-52, F6, fractions 53-56 and F7: fractions 57-65.

The protein composition in F1-F7 is shown in FIG. 2A. F2, containing the enzyme activity and hereafter called *R.*

*mucilaginosa* enzyme preparation (Rmep), displayed a major band between 100-150 kDa, and a double band between 75 and 100 kDa. Gliadin zymography of F1-F7 showed evidence for a double enzyme band in F2 of ~75-80 kDa (FIG. 2B). As expected, the highest specific activity was associated with F2 (not shown). Rmep was subsequently analyzed at 4 different concentrations on a 6% SDS gel under non-reducing conditions. After electrophoresis half of the gel was silver stained (FIG. 2C) and the other half was developed as a zymogram with externally added casein as the substrate (FIG. 2D). This permitted a true comparison in electrophoretic mobilities of proteins in both gel halves. Enzyme activities were again associated with the ~75-80 kDa double band, and not with the also prominent ~125 kDa band. Several bands were excised from the SDS- and the zymogram gel for protein identification by LC-ESI-MS/MS. The inactive 125 kDa band was labeled as band a, the active ~80 kDa band as b/d and the active ~75 kDa band as c/e. The major proteins identified in bands a-e were ROTMU0001_0241 (WP_044143864.1; C6R5V9_9MICC), ROTMU0001_0243 (WP_044143865.1; C6R5W1_9MICC) and ROTMU0001_0240 (WP_005509166.1; C6R5V8_9MICC) (FIG. 2E). Their relative abundances in the respective bands, determined at the MS1 level, are indicated. It shows that the ~125 kDa band contains a mixture of primarily C6R5V9_9MICC and C6R5W1_9MICC, in a 32%/67% ratio. The ~80 kDa protein is a fragment of C6R5V9_9MICC, and the ~75 kDa band is derived from C6R5W1_9MICC. As a control, three other bands were excised from the gel shown in FIG. 1B (fraction 13, lowest band, and fraction 14 two middle bands), yielding identifications other than subtilisin enzymes (data not shown).

Figure 10:
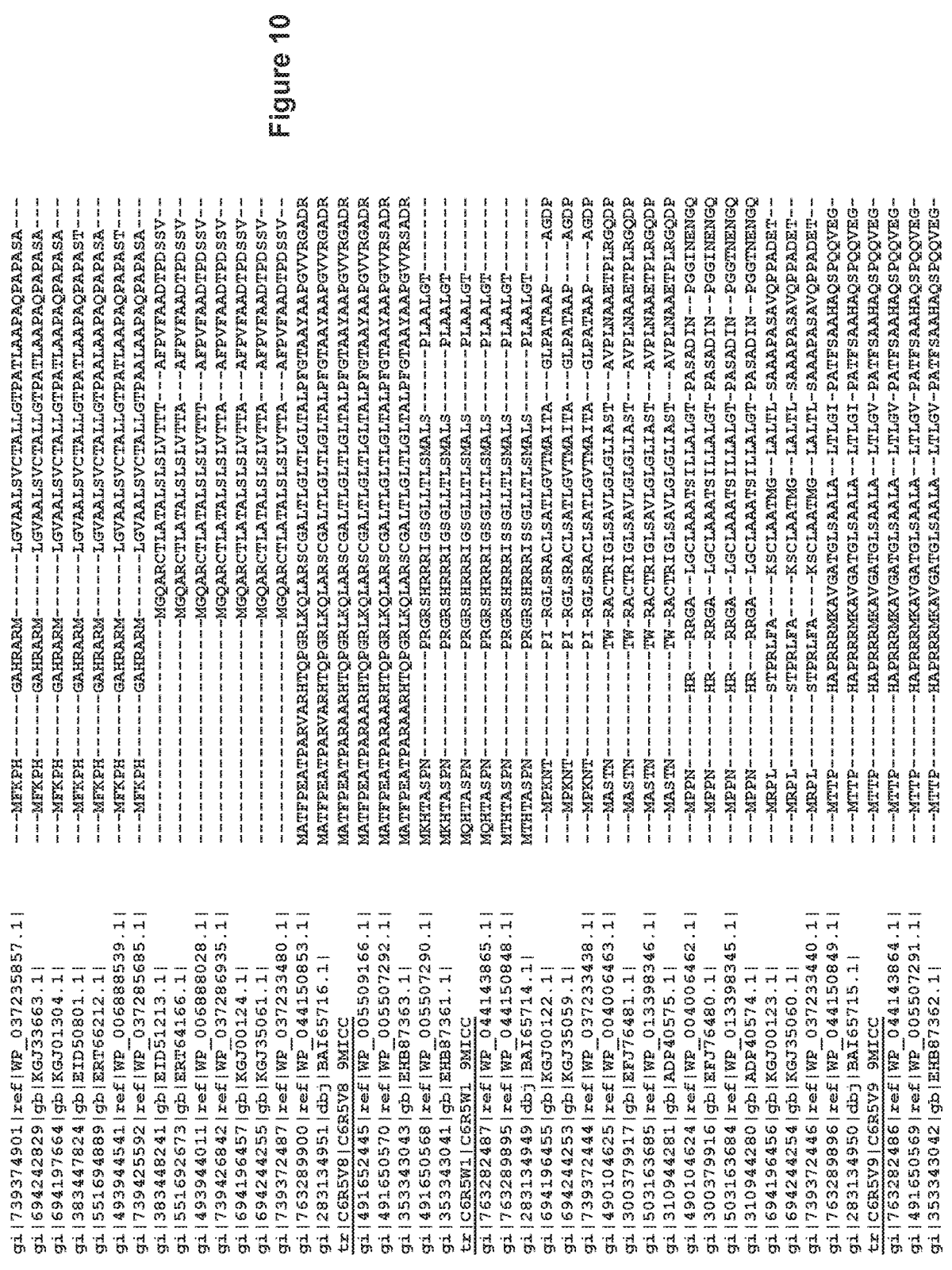
Figure 10:
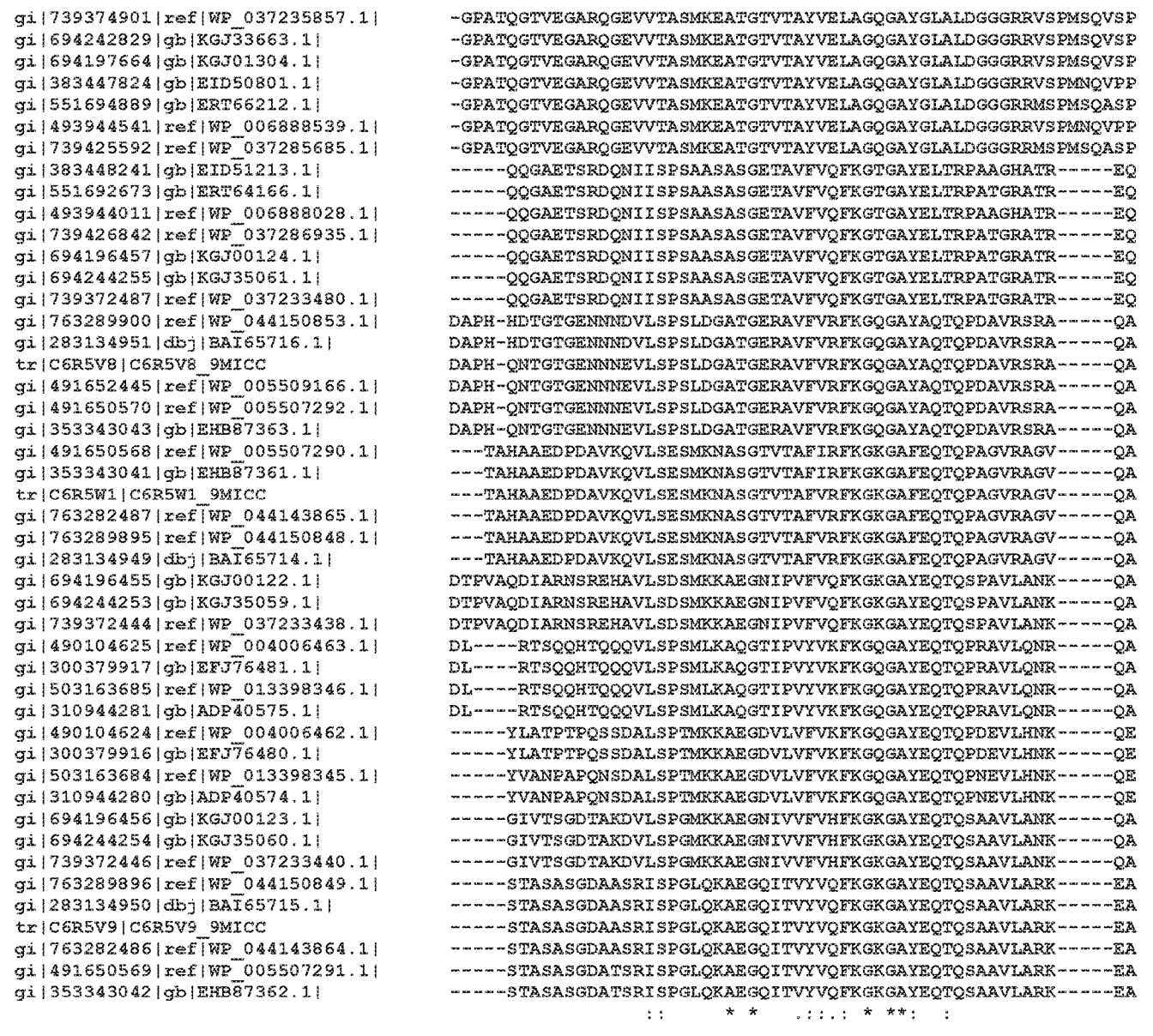
Figure 10:
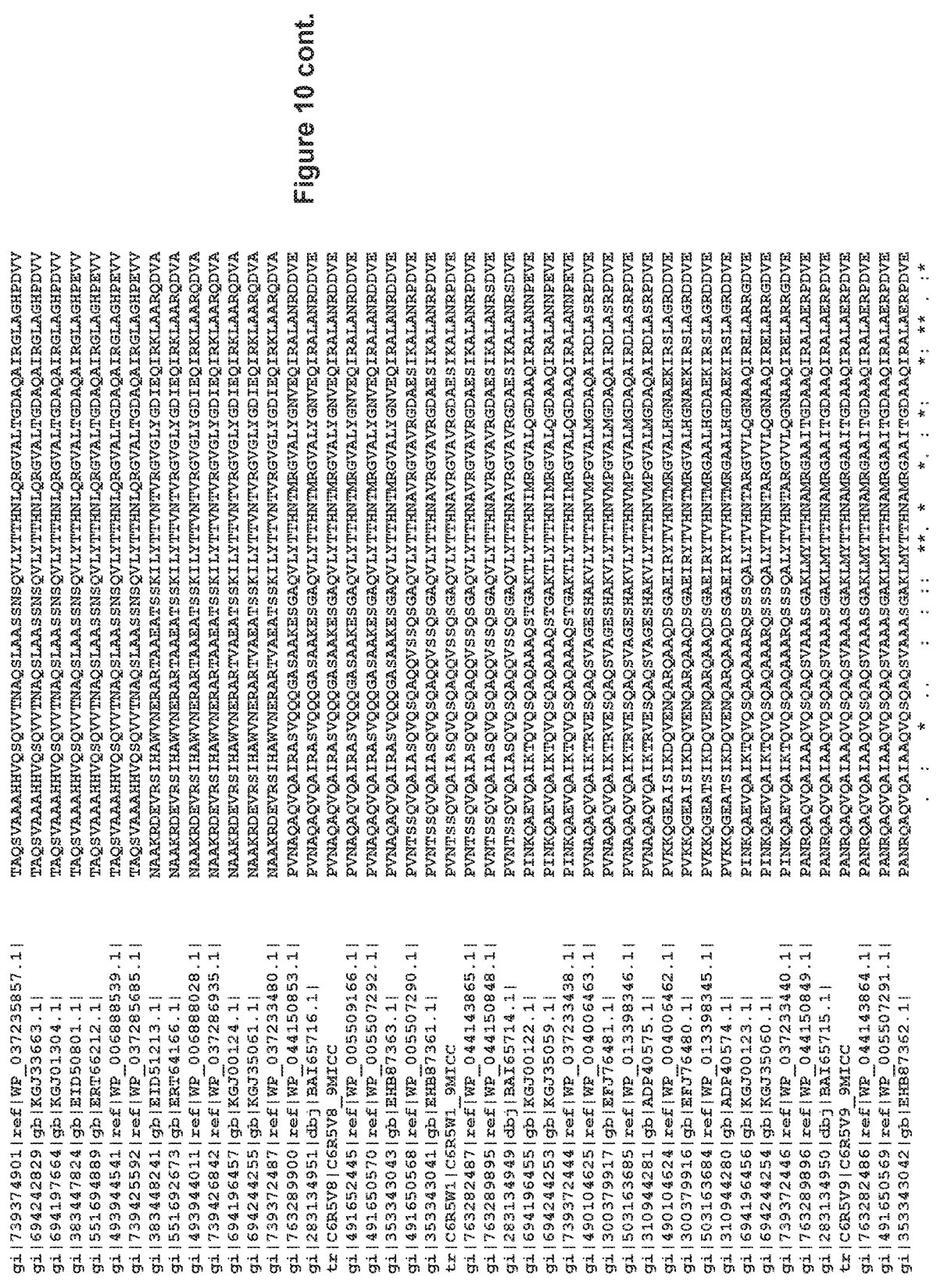
Figure 10:
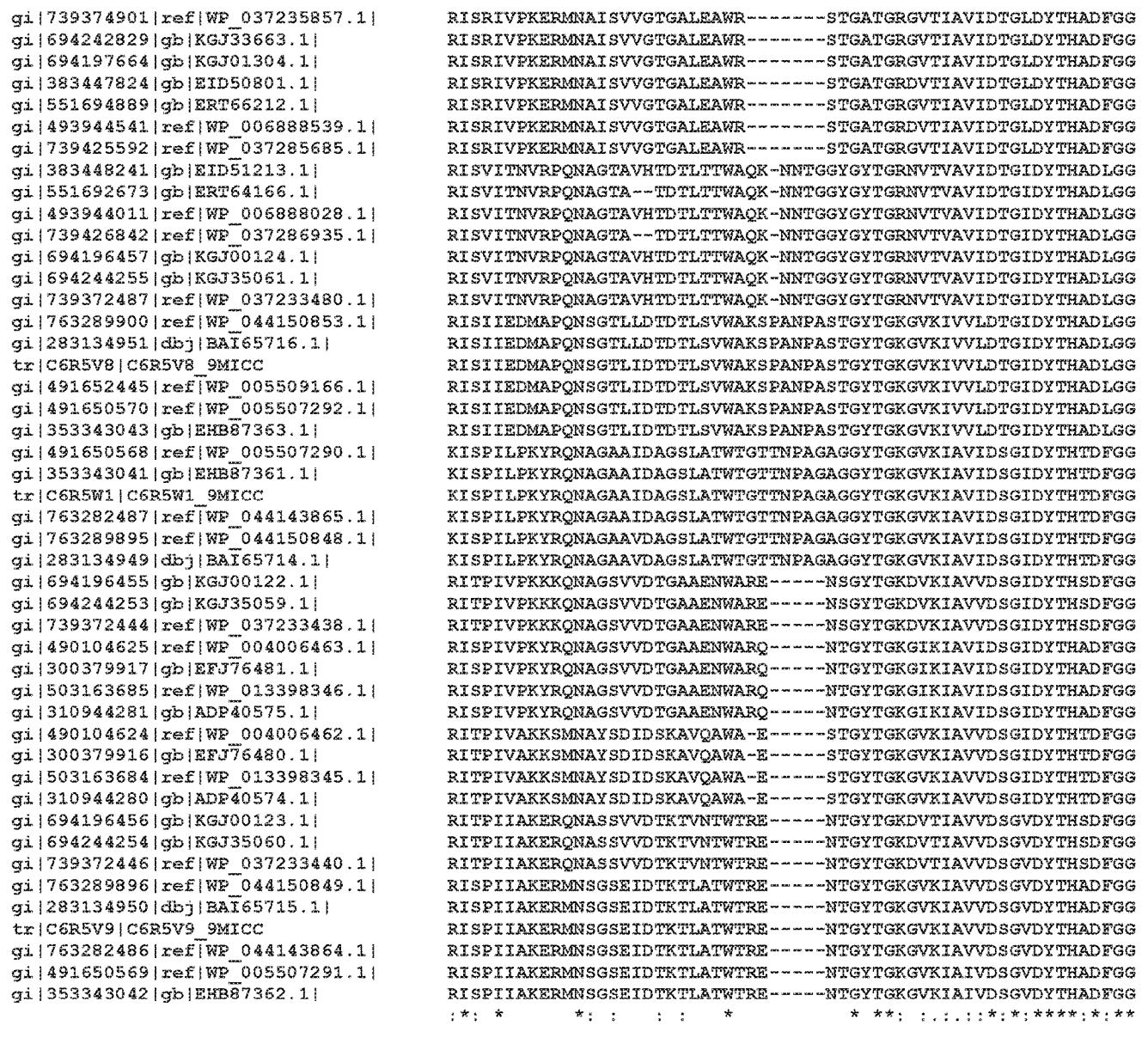
Figure 10:
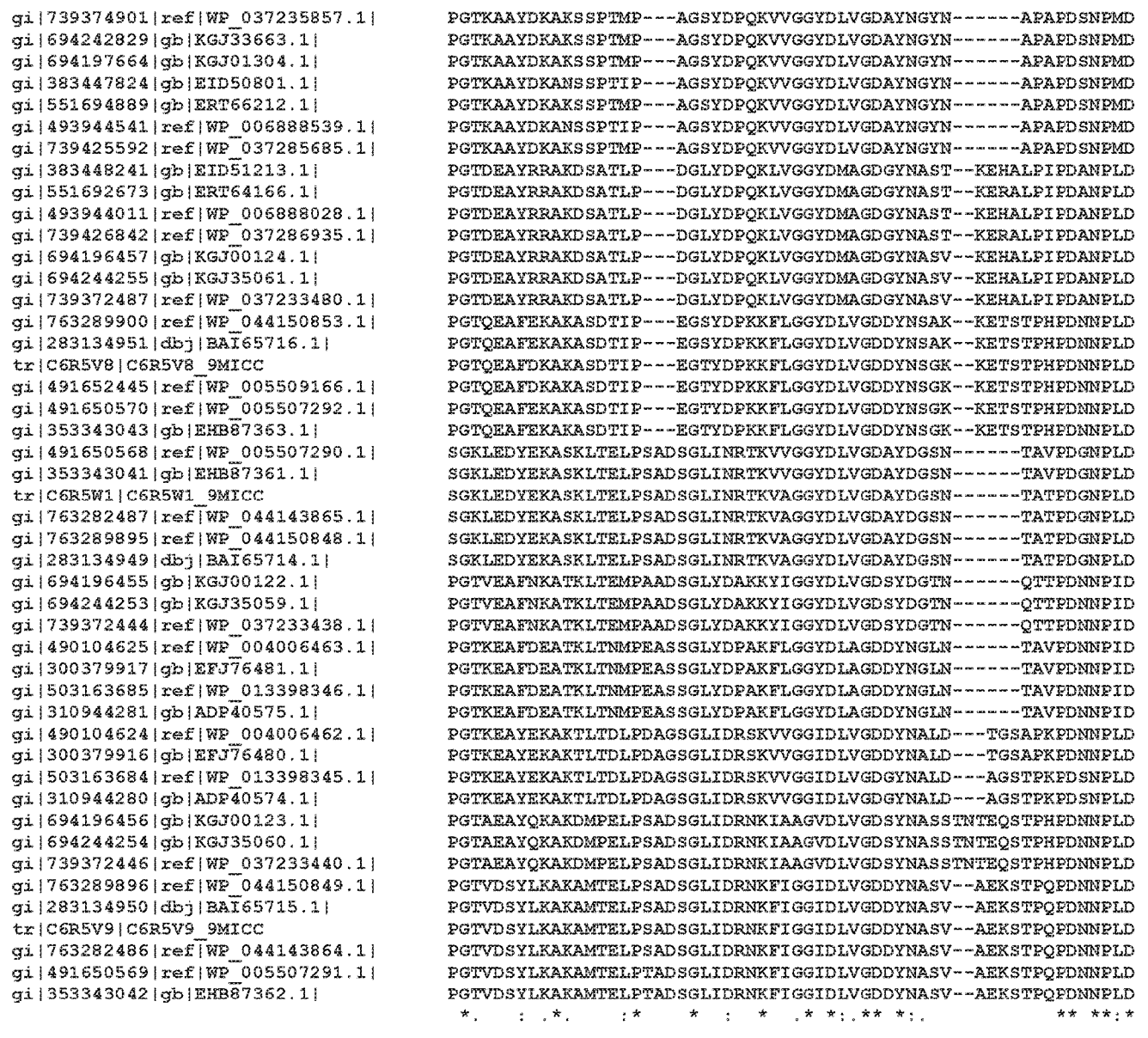
Figure 10:
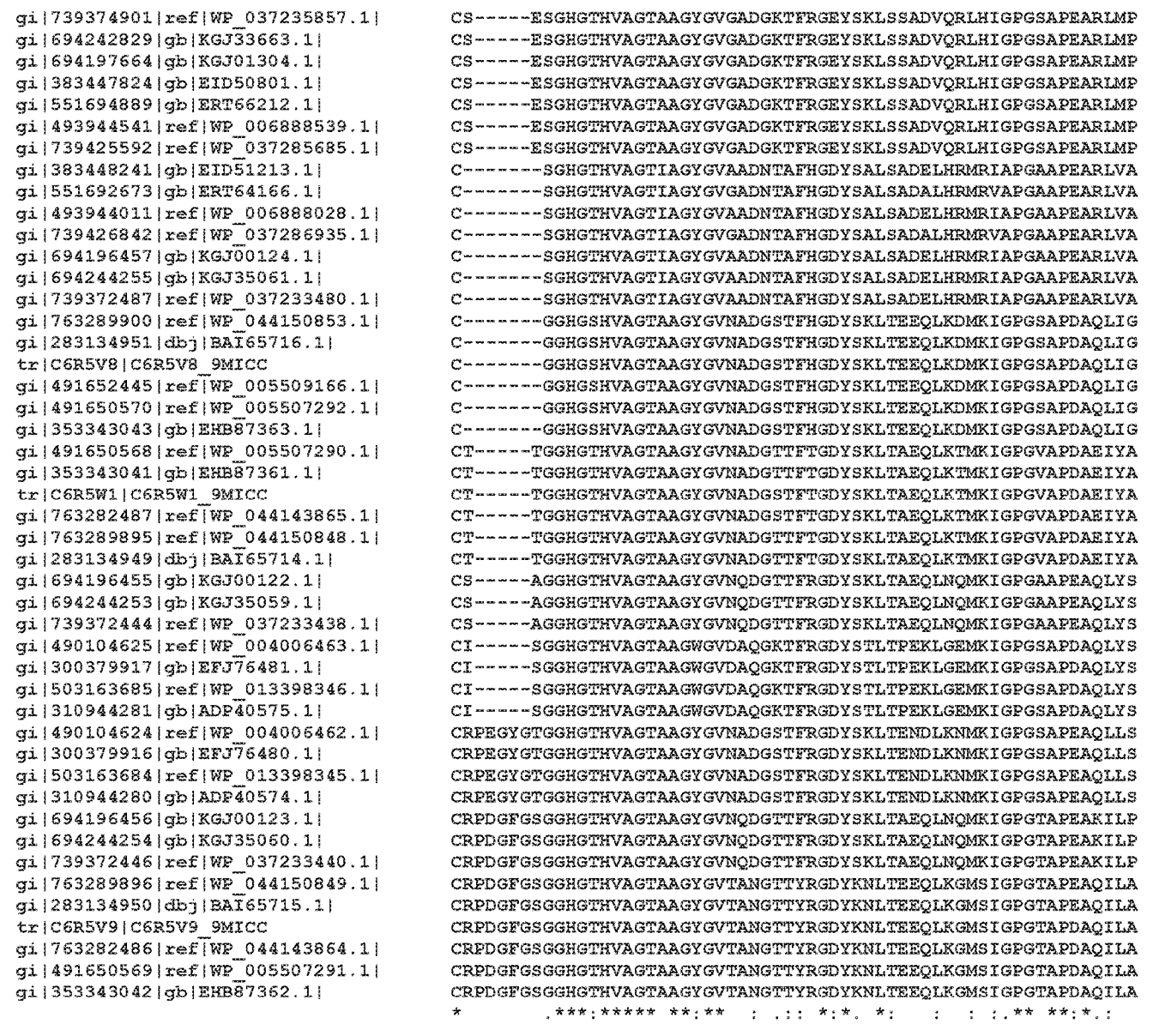
Figure 10:
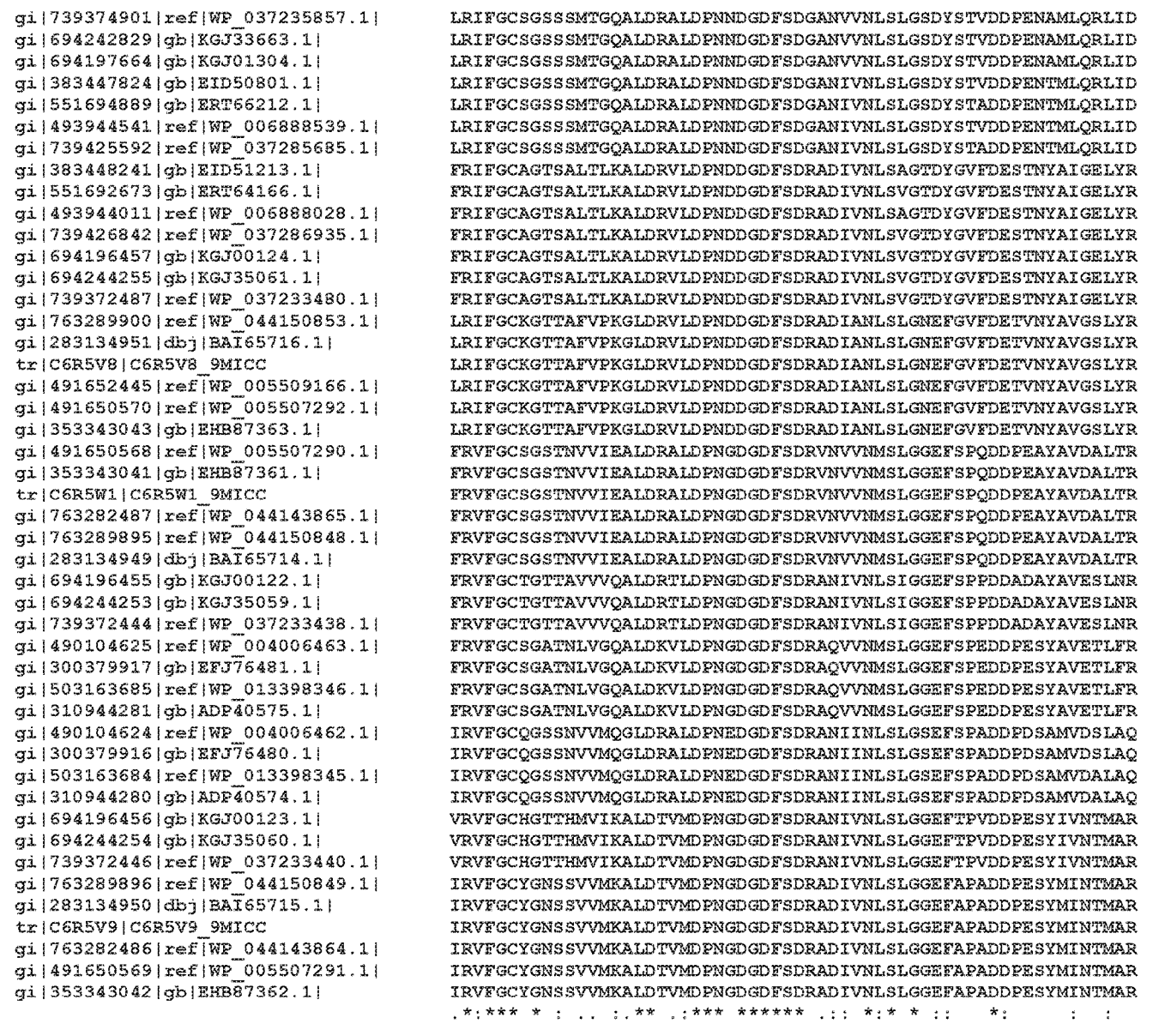
Figure 10:
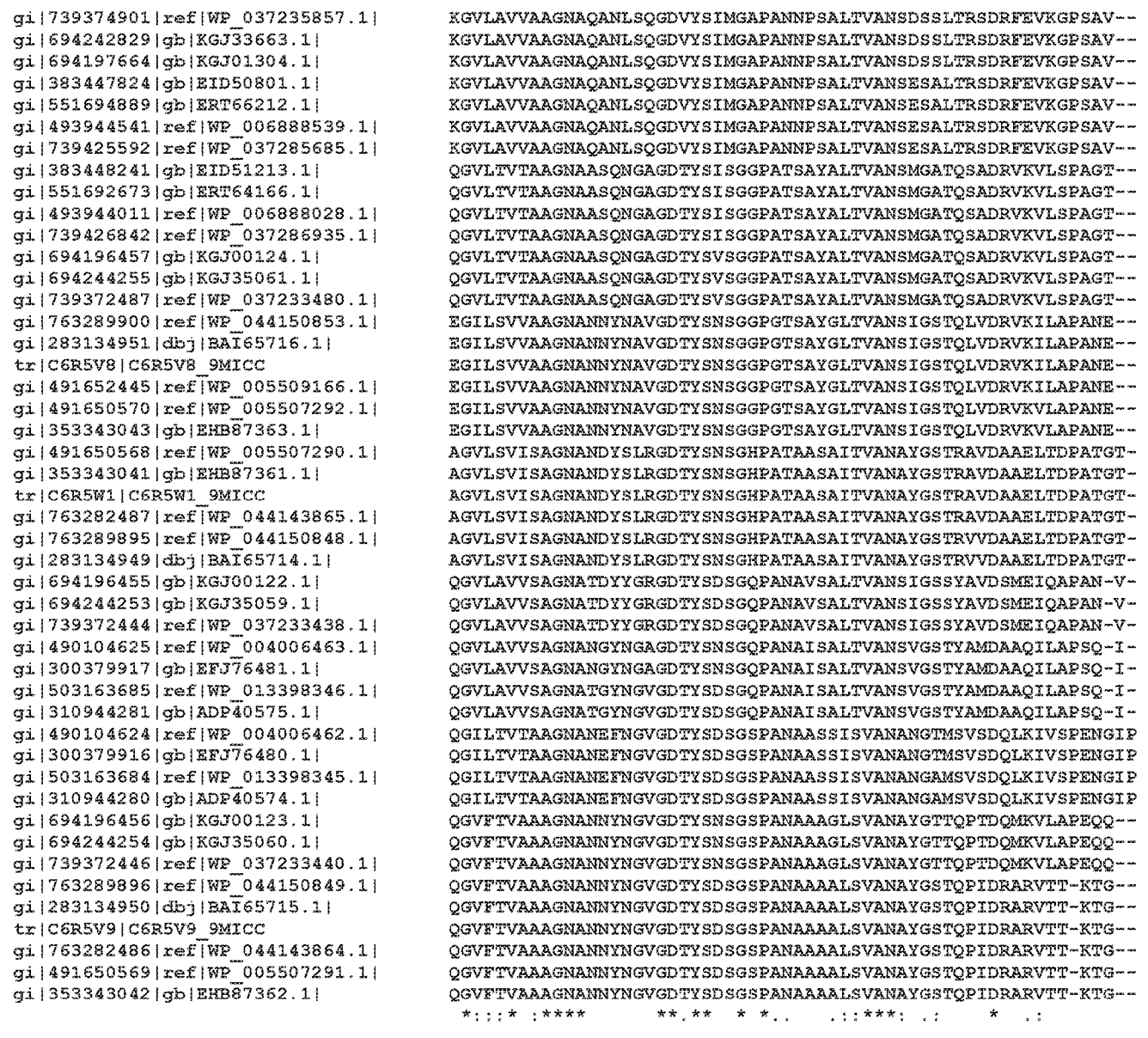
Figure 10:
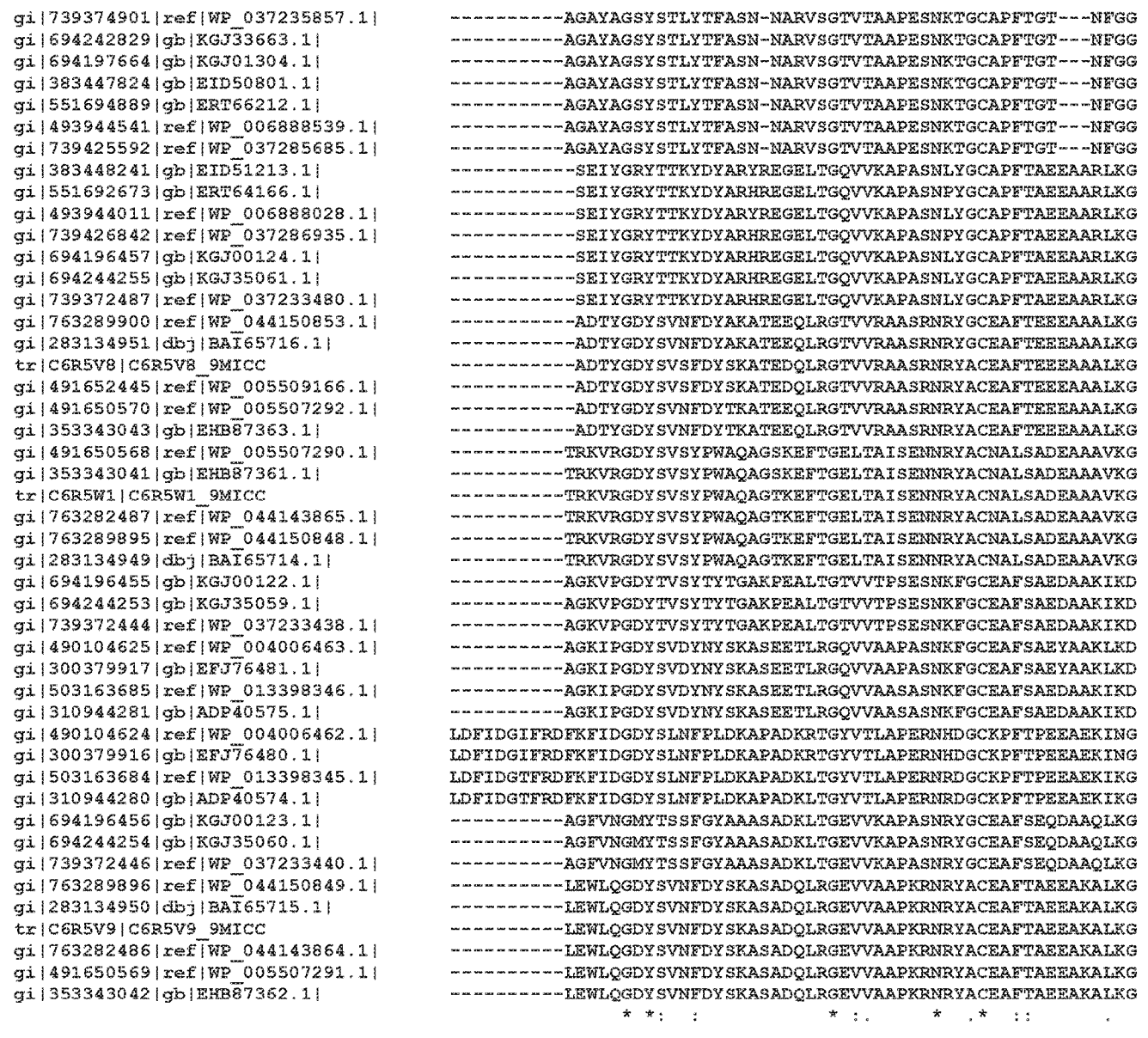
Figure 10:
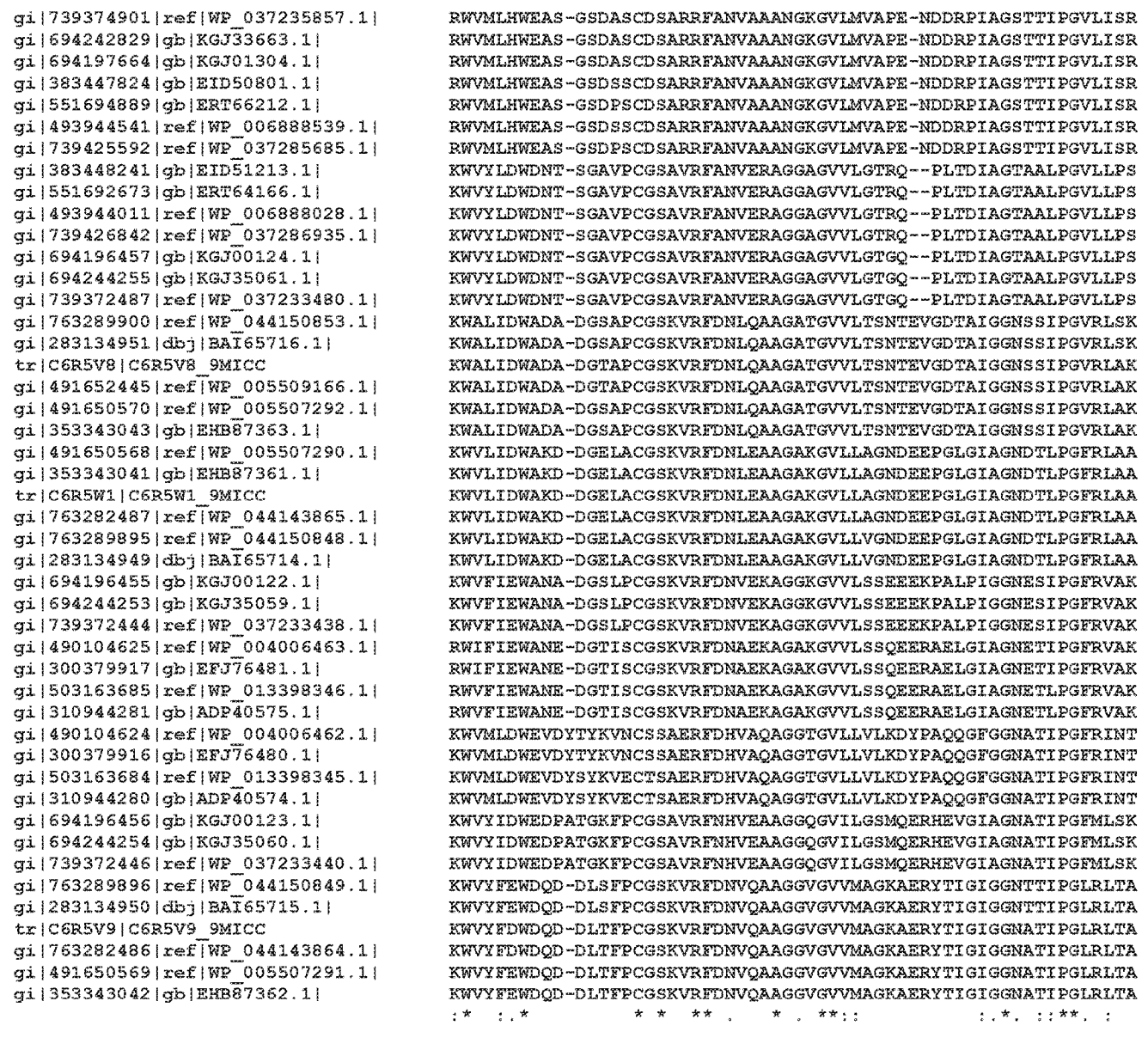
Figure 10:
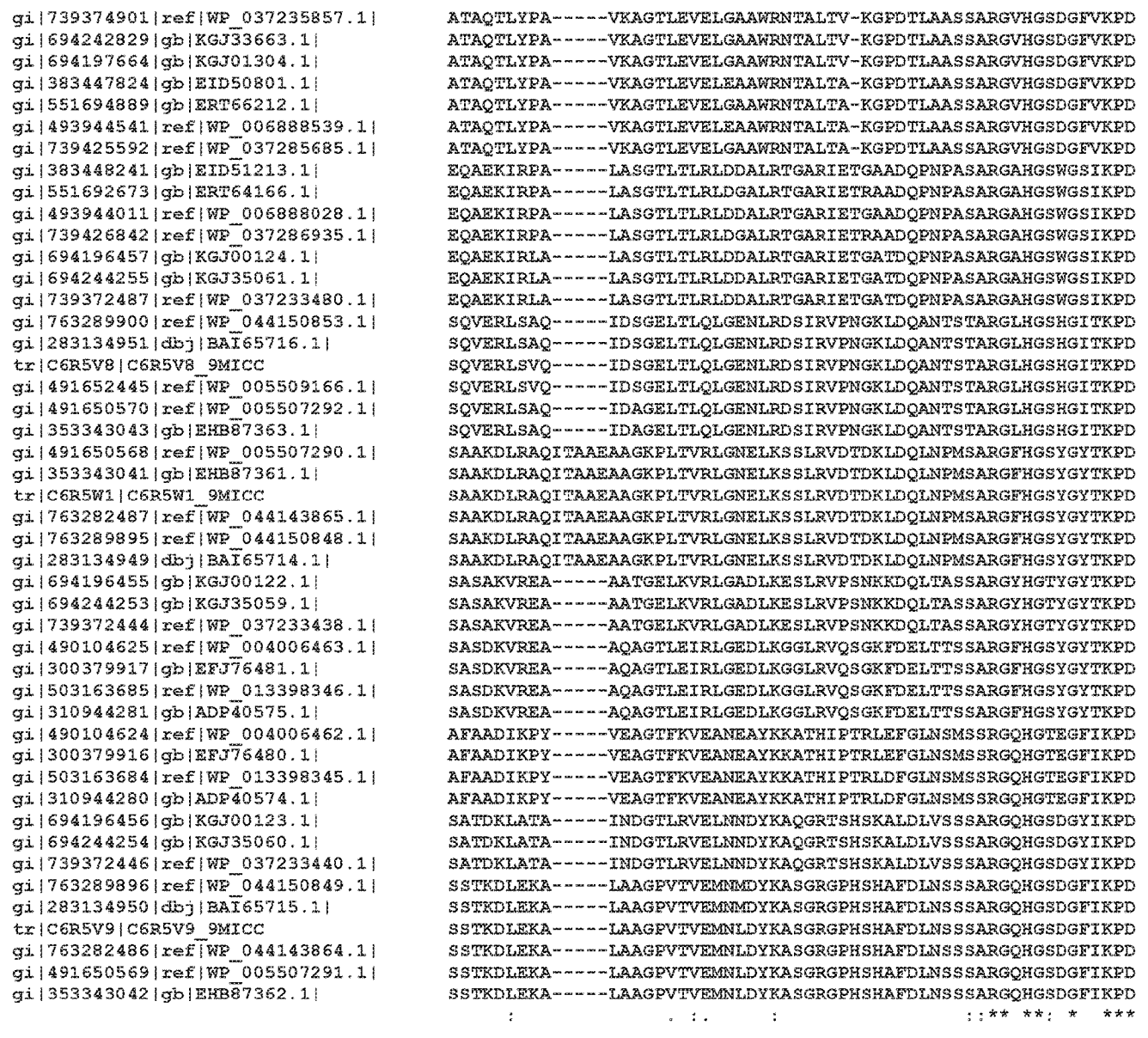
Figure 10:
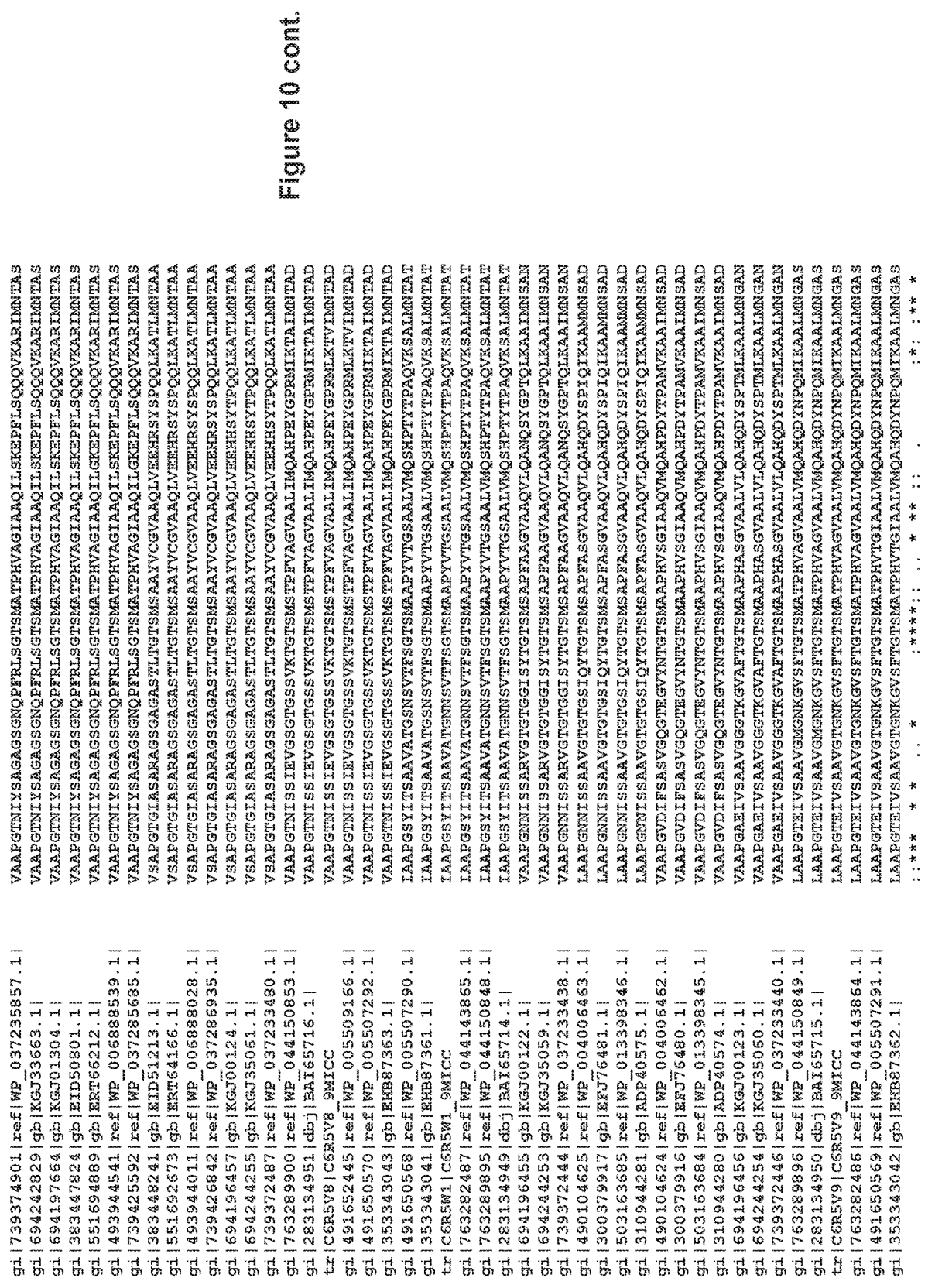
Figure 10:
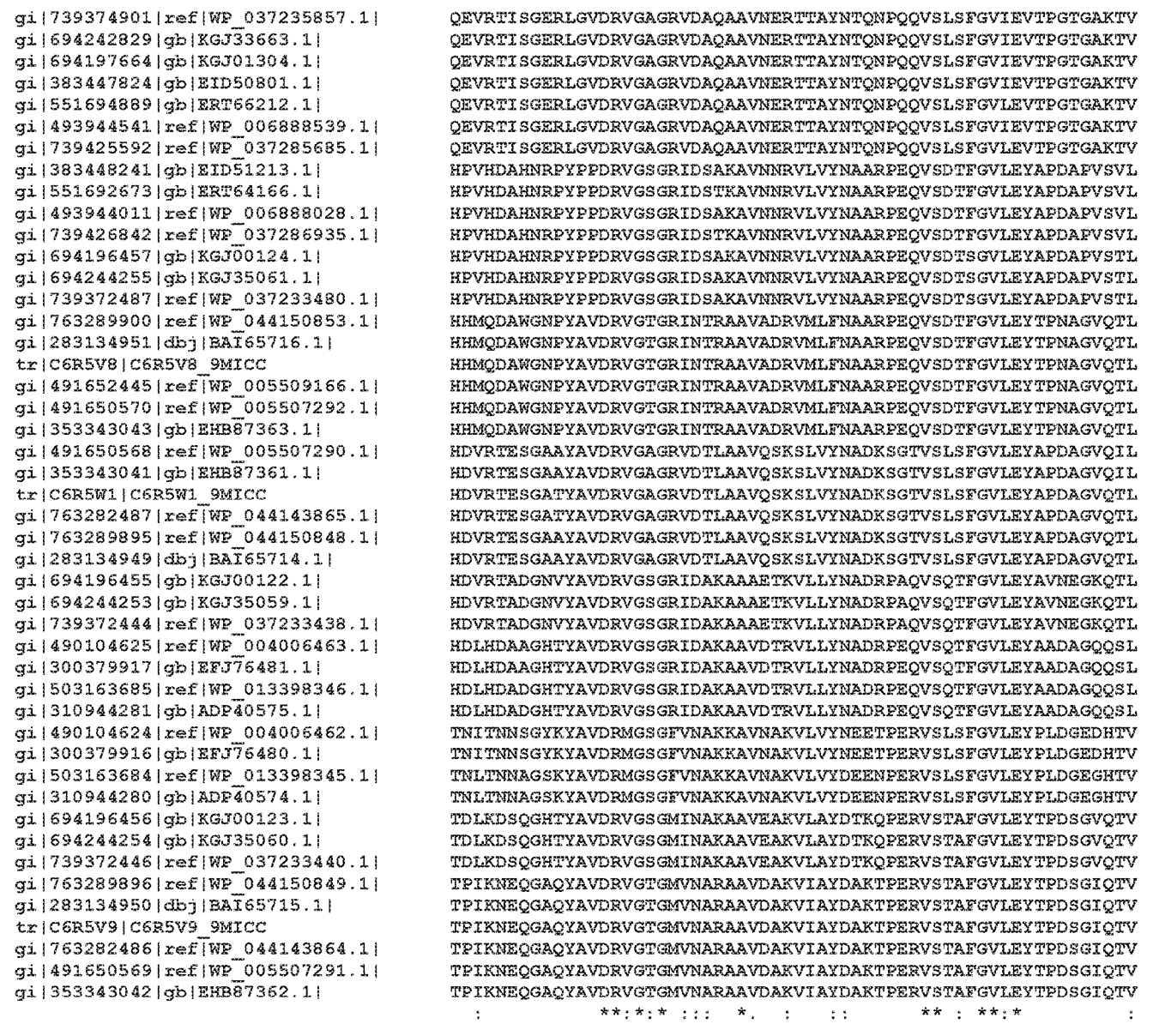
Figure 10:
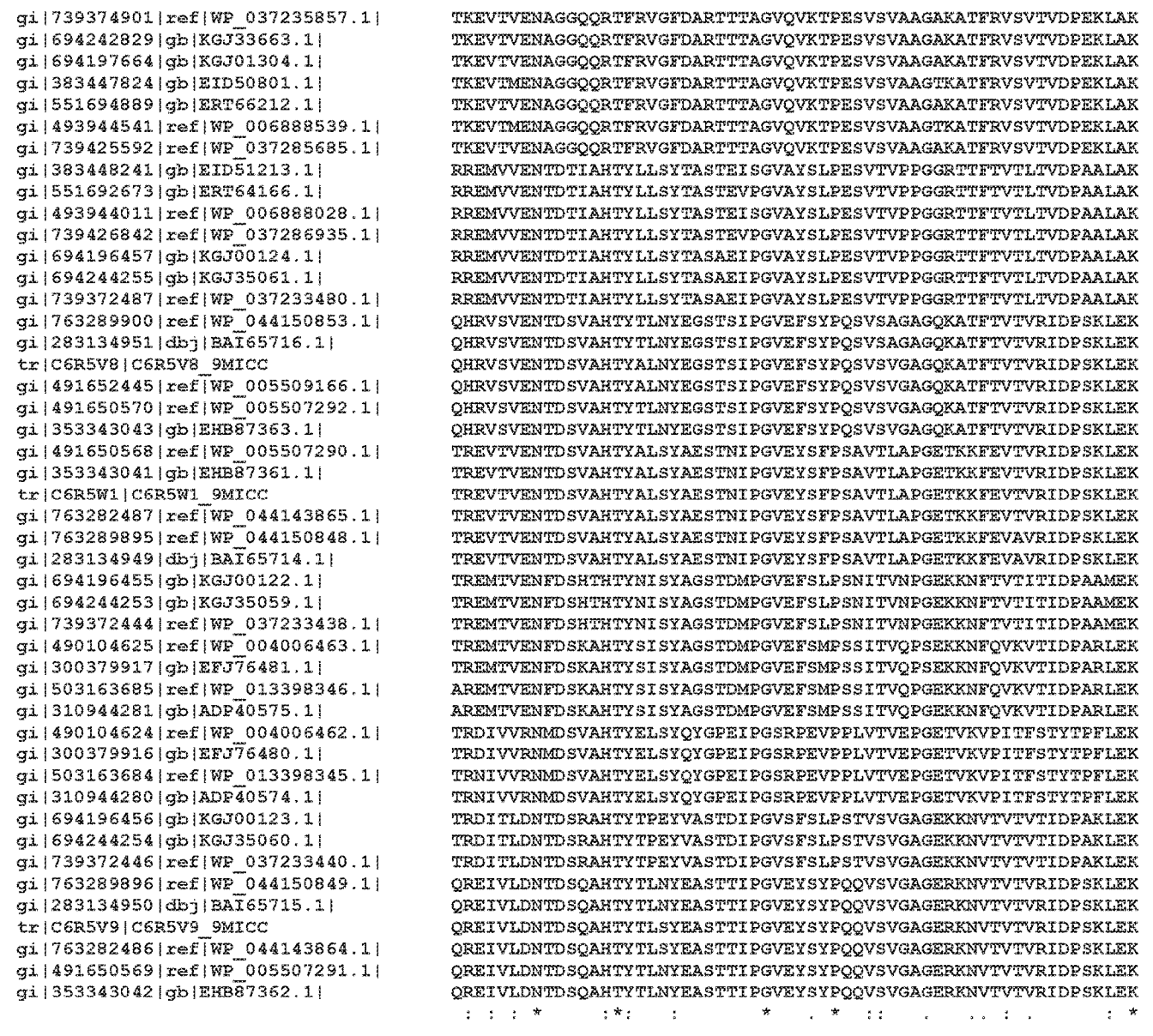
Figure 10:
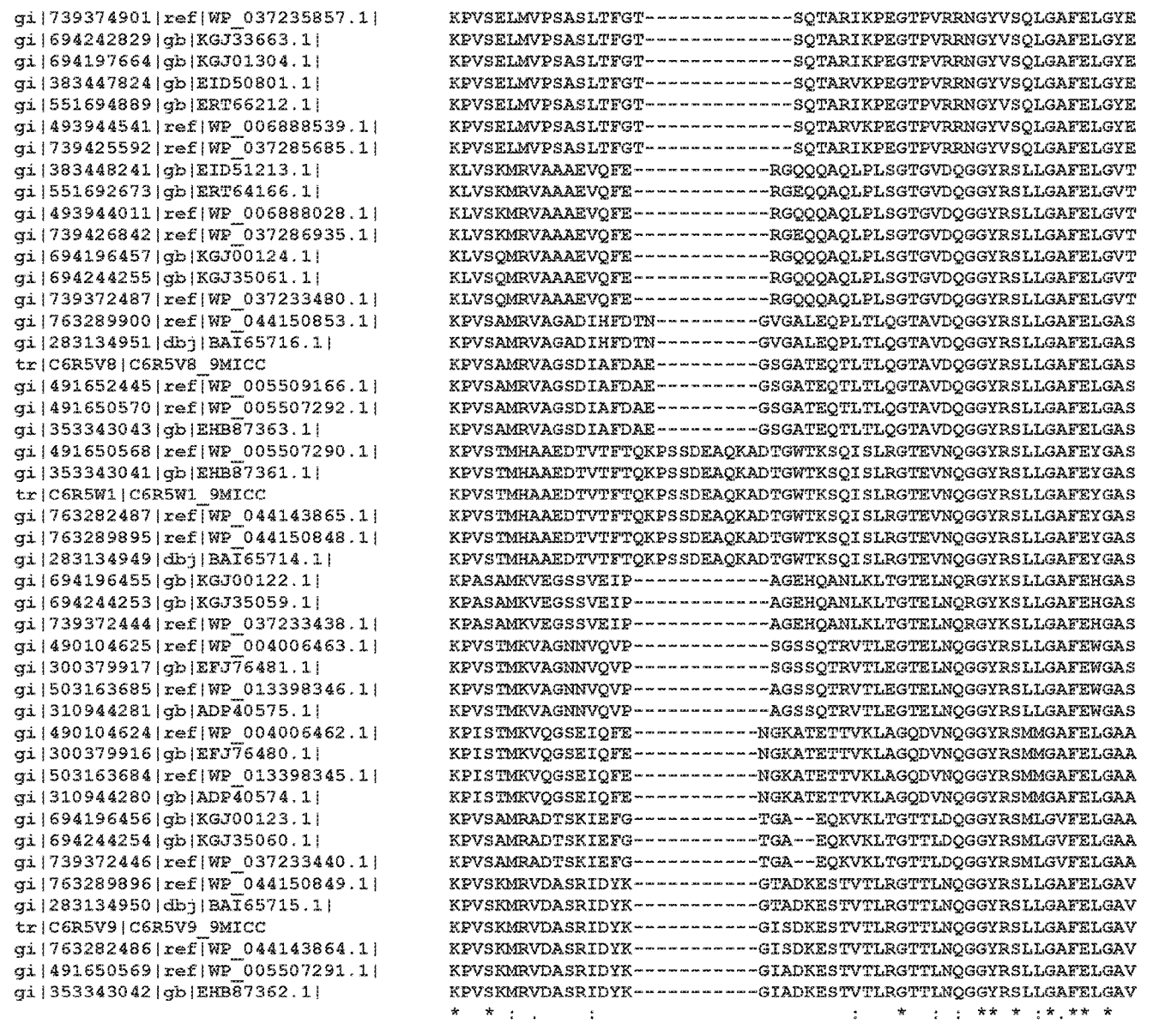
Figure 10:
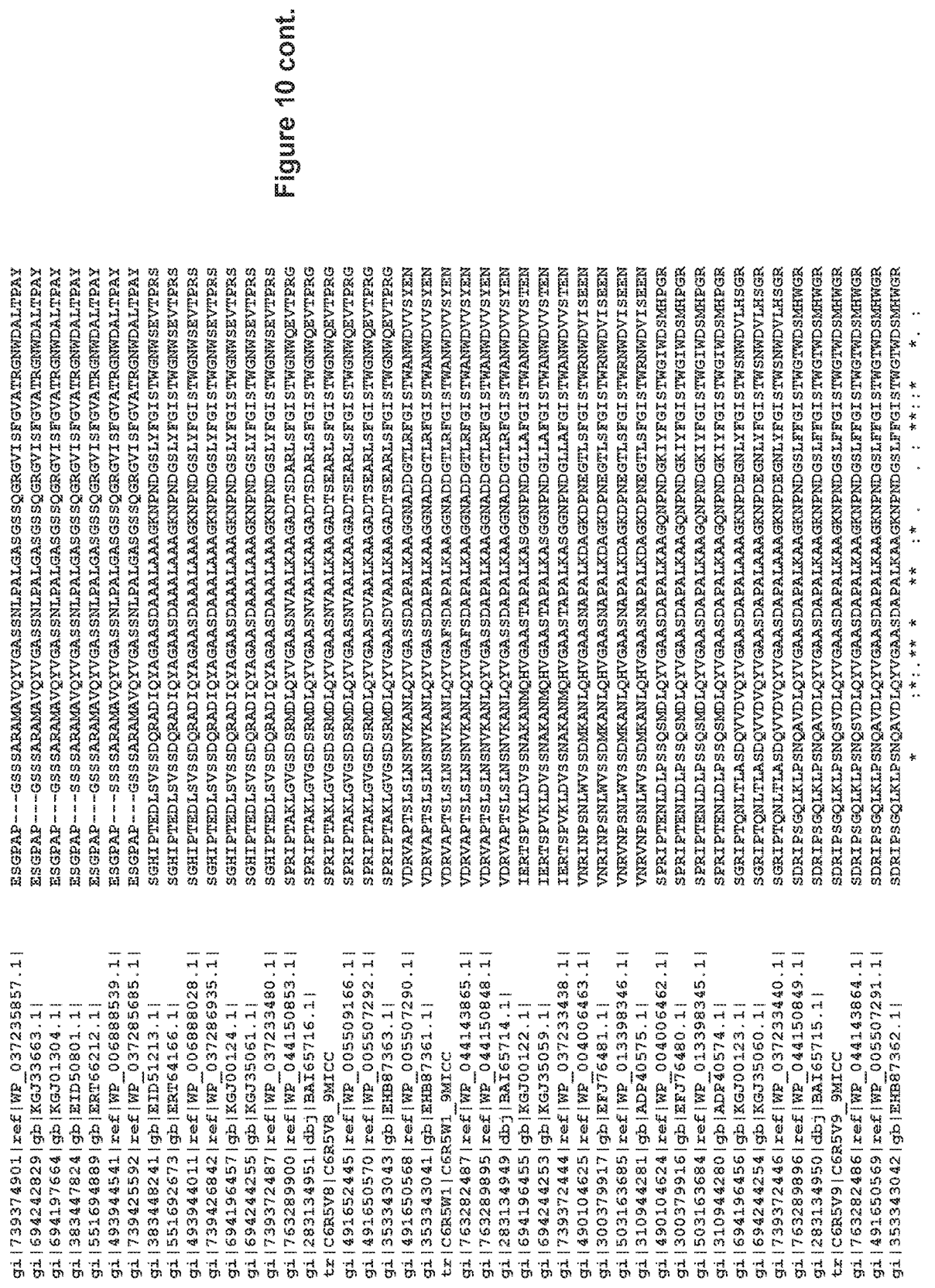
Figure 10:
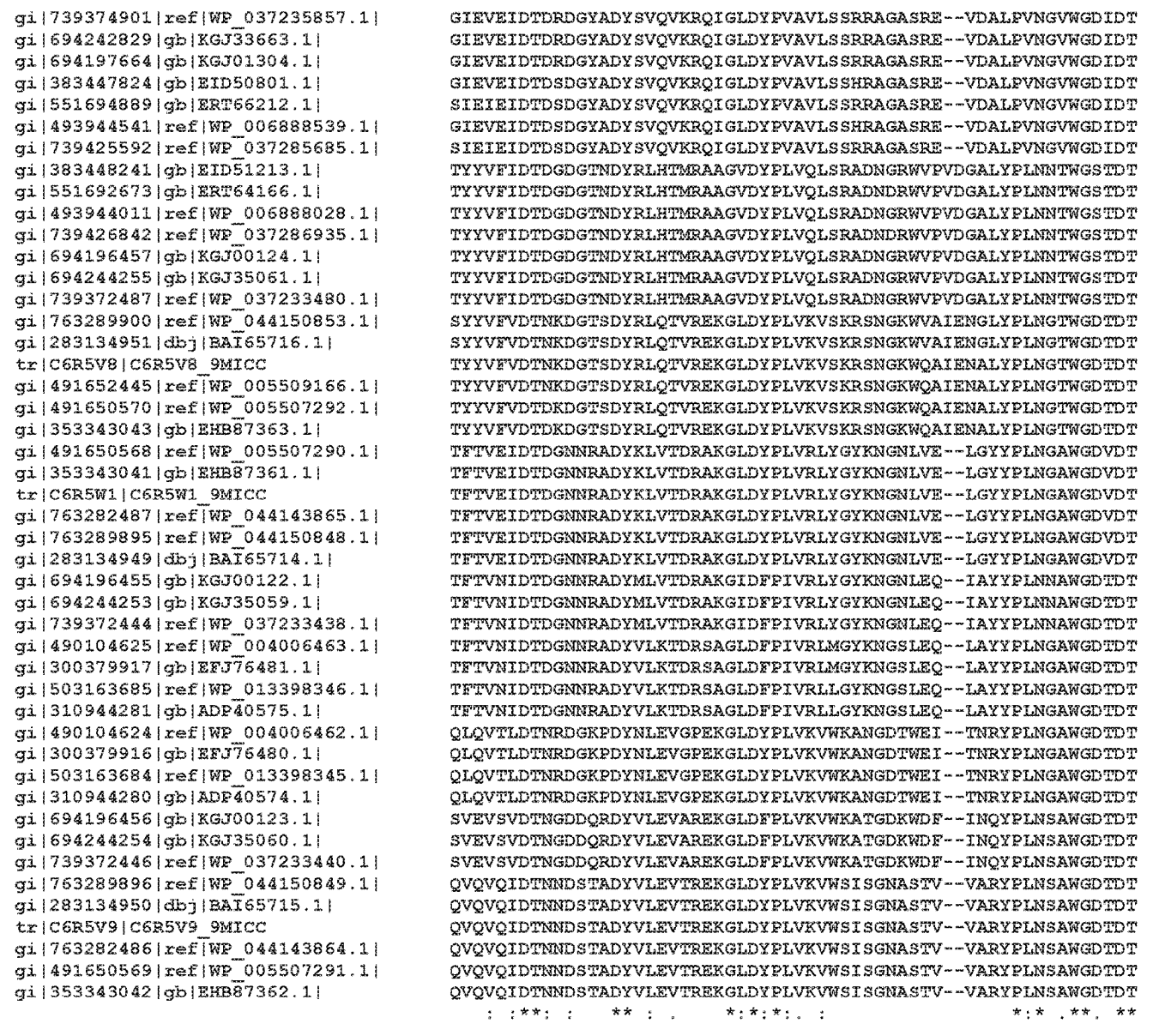
Figure 10:
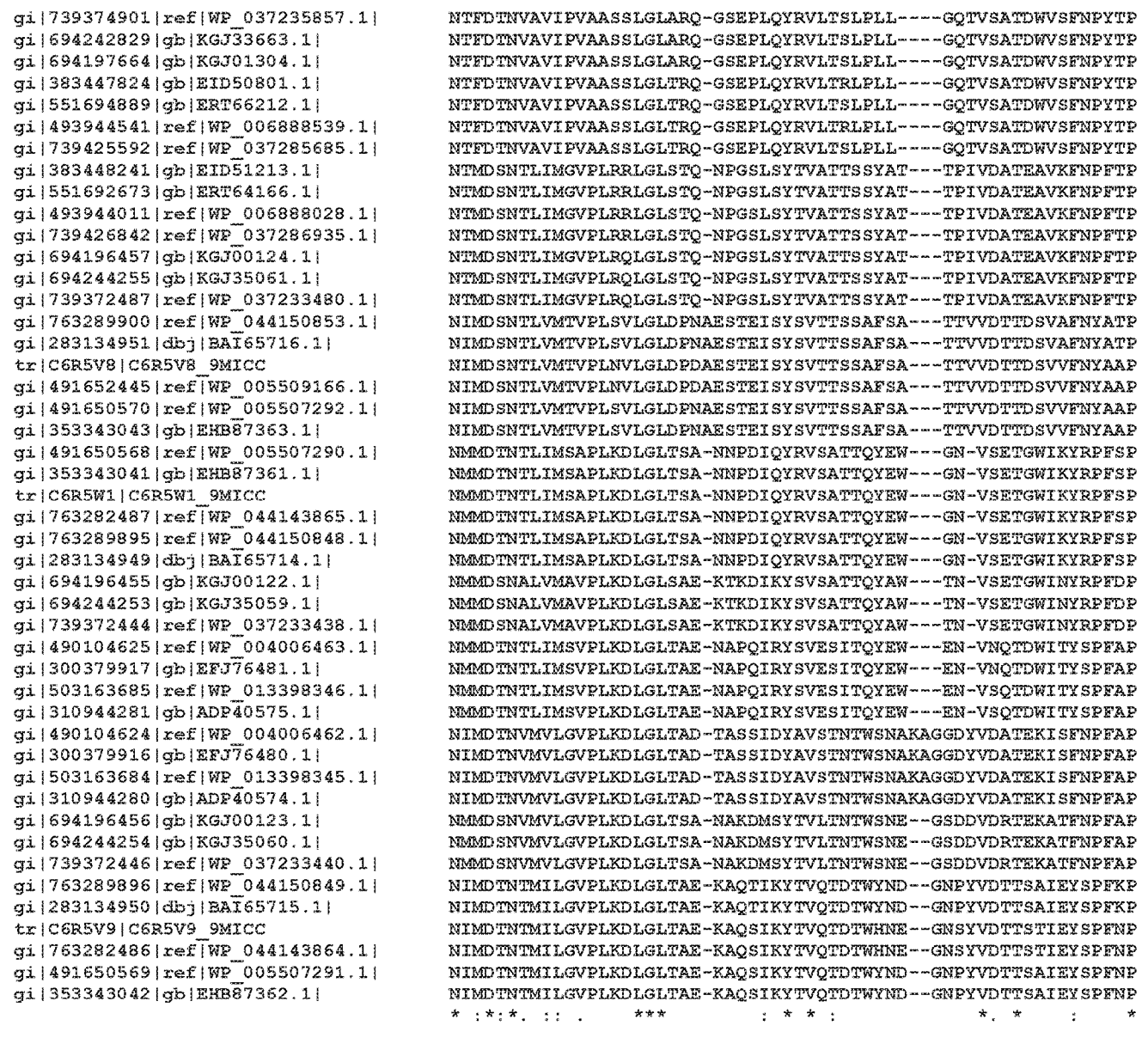
Figure 10:
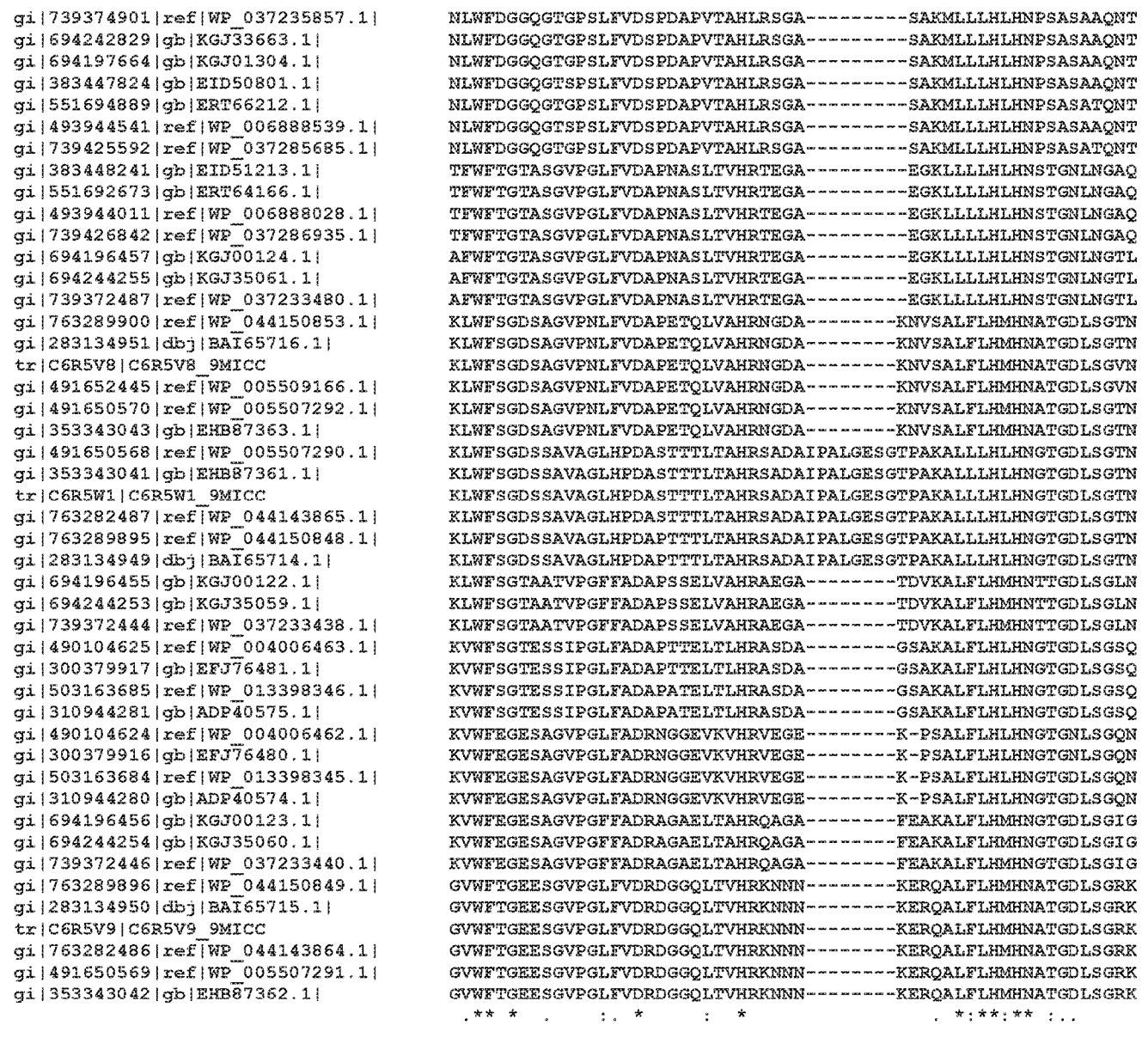
Figure 10:
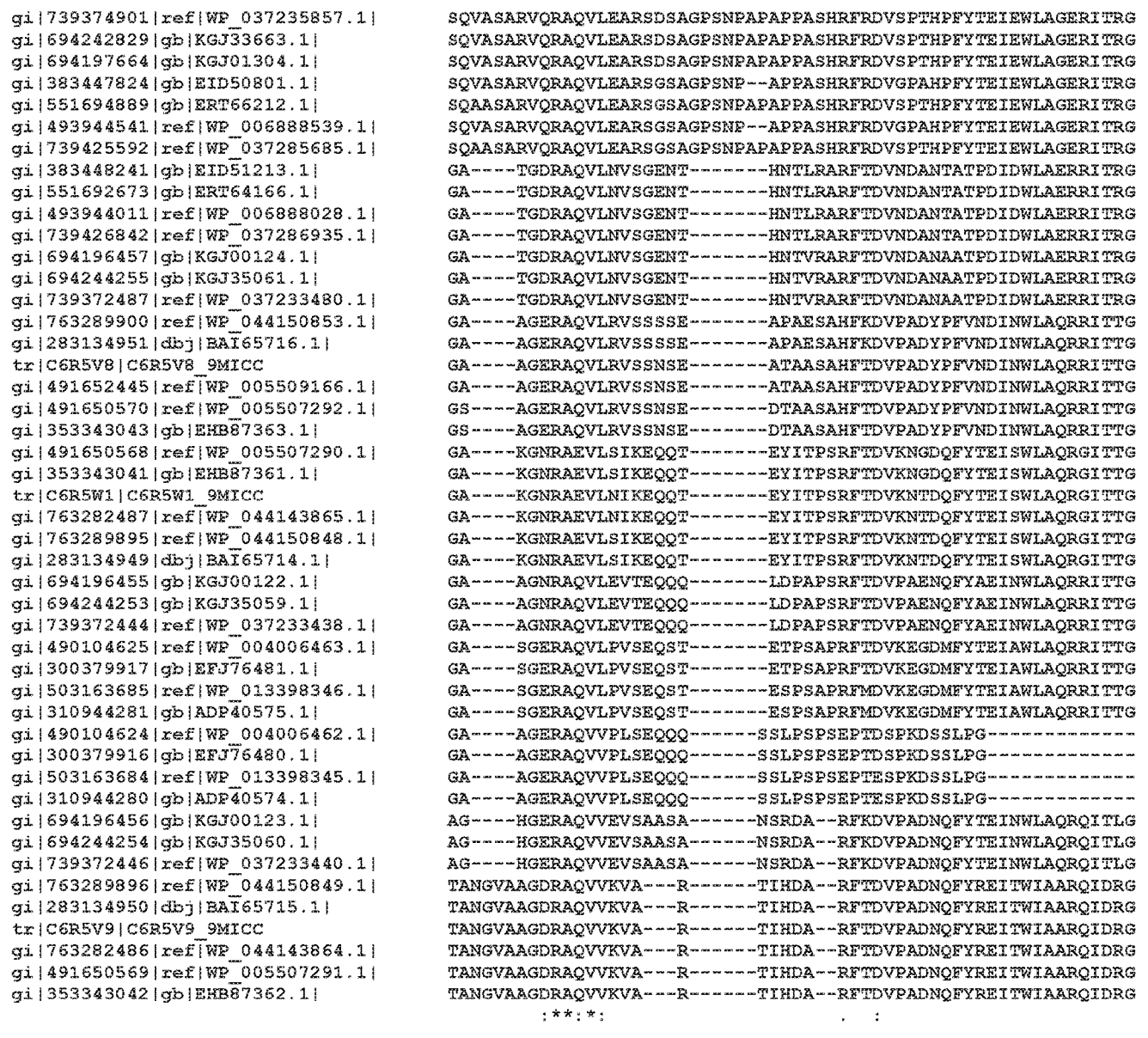
Figure 10:
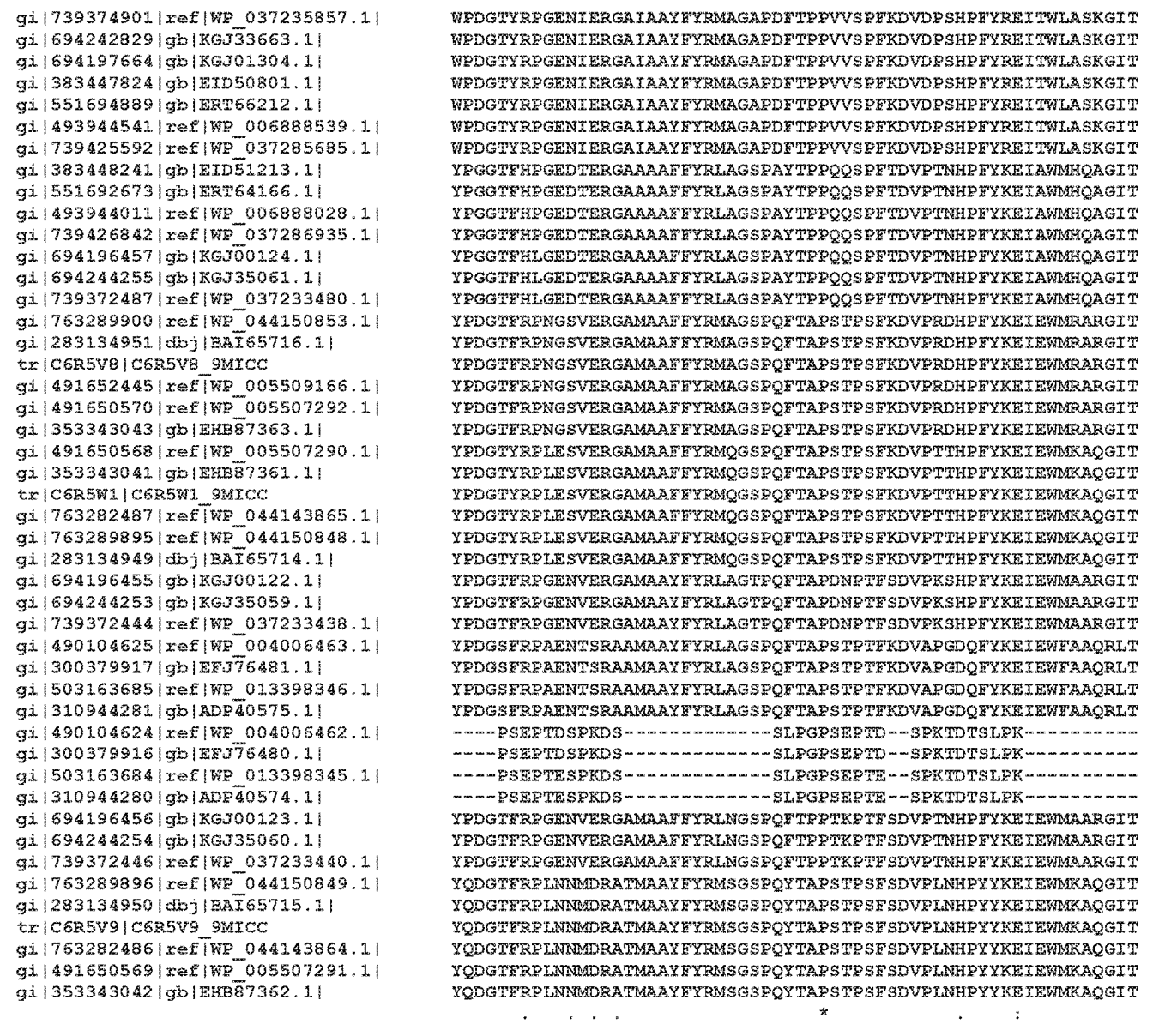
Figure 10:
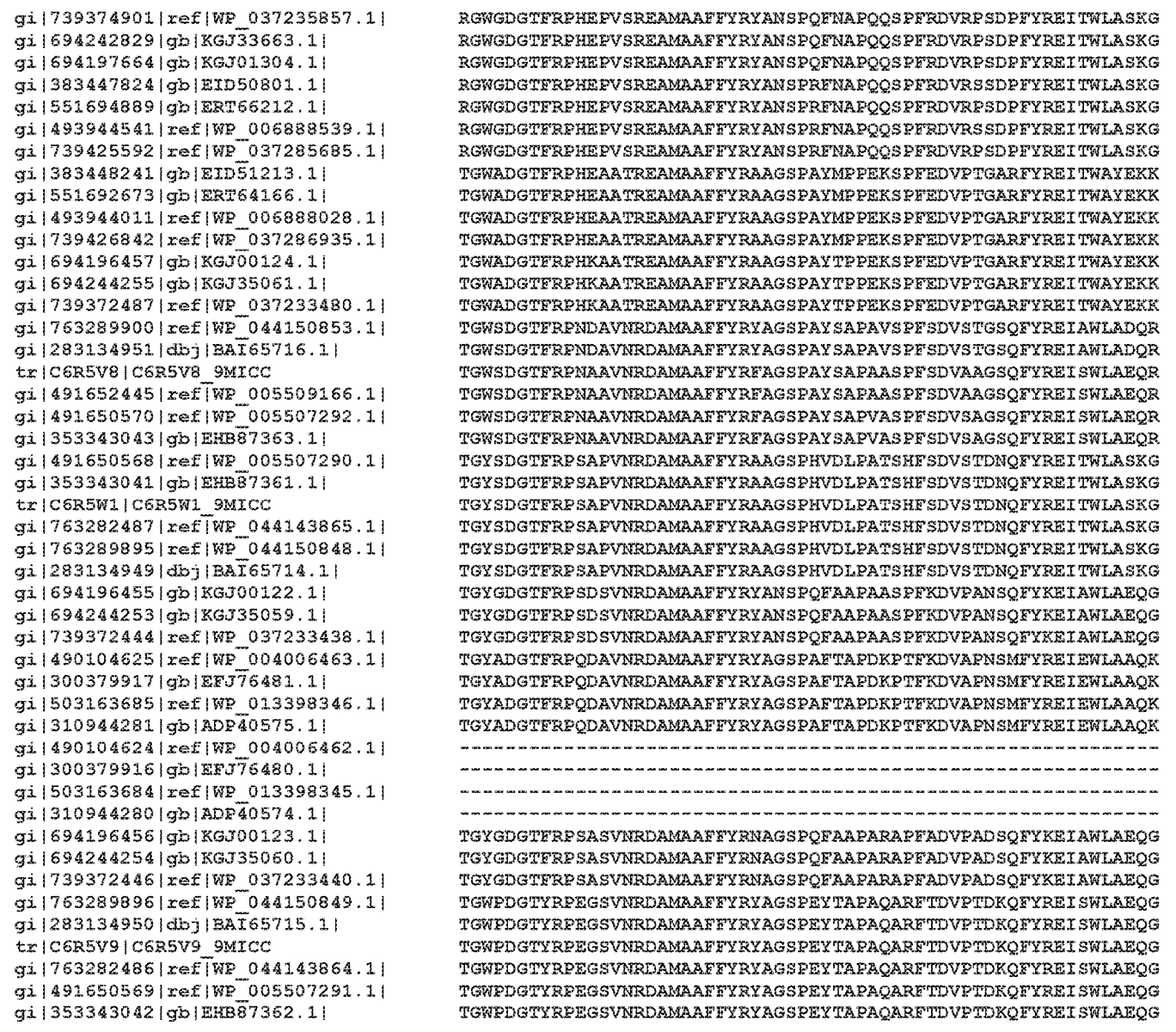
Figure 10:
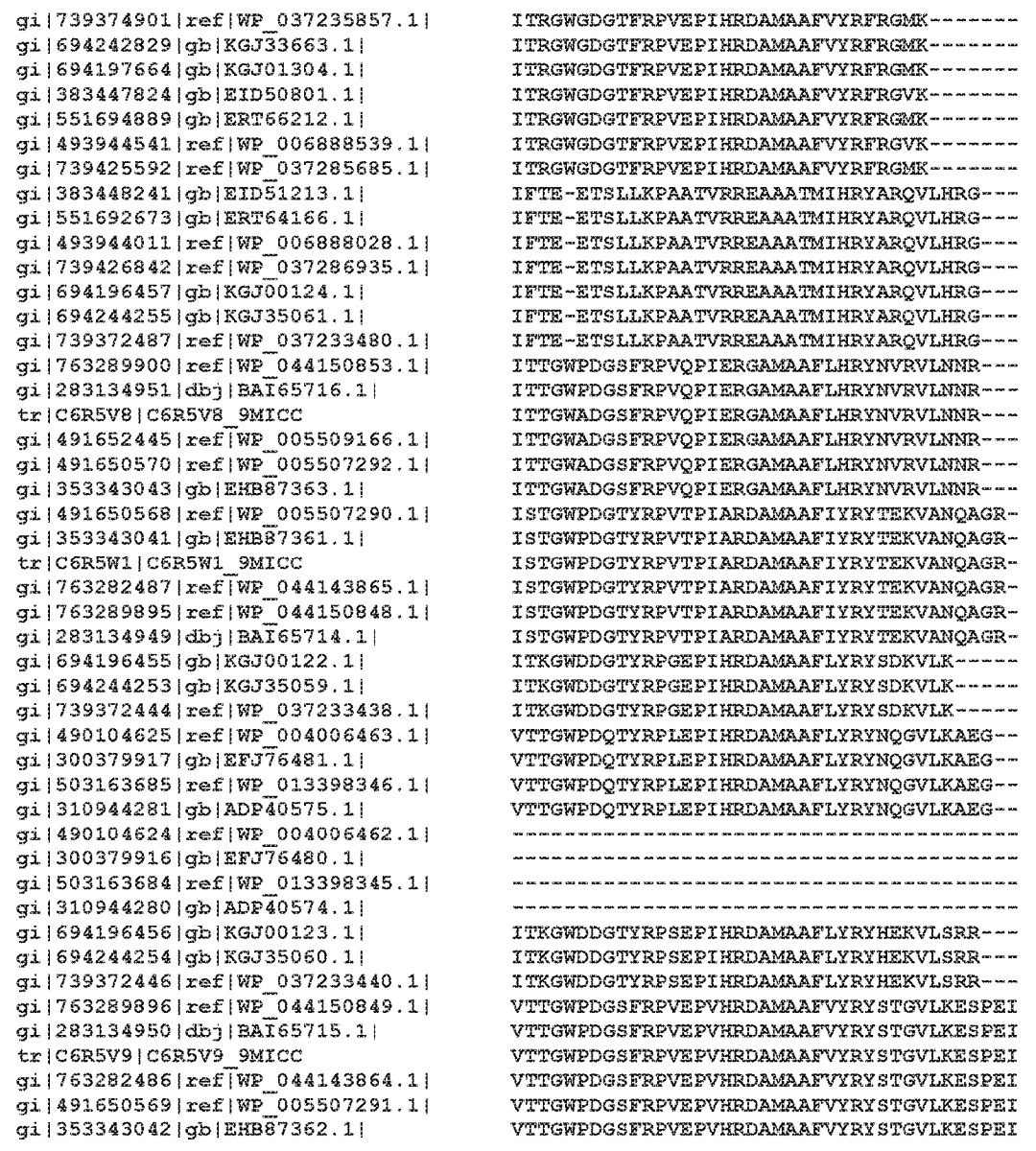

The amino acid sequences of the identified subtilisins ROTMU0001_0241, ROTMU0001_0243 and ROTMU0001_0240 are described in the Section on subtilisins and subtilisin-like enzymes. They are classified as WP_044143864.1 peptidase S8, WP_044143865.1 peptidase S8, and WP_005509166.1 peptidase S8 respectively. A blast search revealed that all are members of the S8 peptidase family, which share a conserved catalytic triad comprising Asp (D), His (H) and Ser (S) in the catalytic domain of the enzyme. The signal peptide cleavage sites as well as the catalytic triads are indicated. The protein sequences of all subtilisin genes in the three known members of the *Rothia* genus, *Rothia aeria*, *Rothia mucilaginosa* and *Rothia dentocariosa* were aligned using Clustal Omega (FIG. 10). The three variants identified by LC-ESI-MS/MS are highlighted. A phylogenetic tree was drawn using Clustal Omega, showing evidence for 8-9 different *Rothia* subtilisin sequence types based on sequence conservation around the catalytic residues D, H and S (FIG. 11). It shows that the three identified subtilisis belong to different sub groups.

Enzymatic characteristics of Rmep—Rmep was further tested for enzyme activities and specificities relevant for CD. The enzyme was active over a pH range of 6.0-10.0, with low or negligible activities at pH values lower than 5.0 or higher than 11.0 (FIG. 3A). Activity was inhibited effectively by PMSF and AEBSF (serine protease inhibitors), with partial inhibition by aprotinin, but not by E64 (cysteine protease inhibitor) or EDTA (metalloprotease inhibitor) (FIG. 3B). These findings are consistent with the characteristics of subtilisins, which are of the serine proteases type. Rmep was only partly inhibited by high concentrations of Eglin C, an effective inhibitor of *B. licheniformis* subtilisin A (FIG. 3C, FIG. 3D).

Figure 4A:
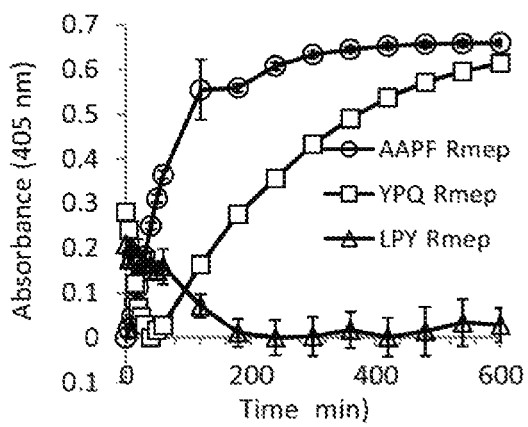
FIGS. 4A-4E demonstrate the cleavage specificities of *R. mucilaginosa* enzyme preparation (Rmep) and *B. subtilis* subtilisin A.
Figure 4B:
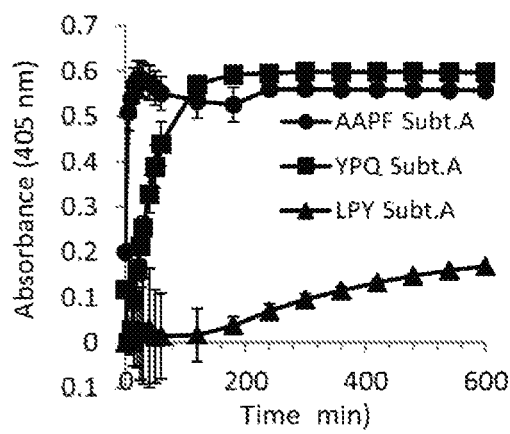
Figure 4C:
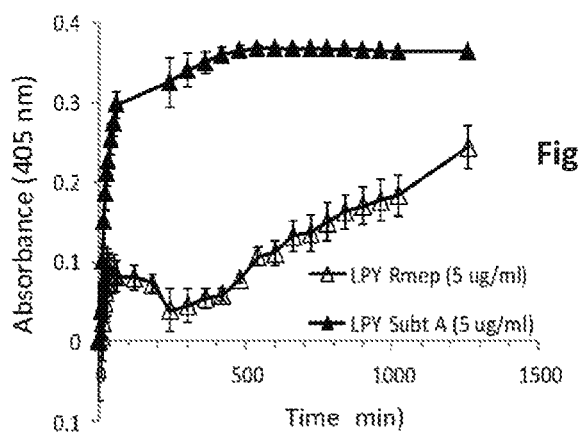

In order to compare the gliadin-relevant substrate specificities of Rmep and subtilisin A in more detail, hydrolysis of Z-YPQ-pNA, Z-QQP-pNA, Z-LPY-pNA, Z-PFP-pNA, Z-PPF-pNA and Suc-AAPF-pNA (SEQ ID NO: 4) was monitored. The tripeptides are all contained with high frequency in the immunogenic gliadin domains, and Suc-AAPF-pNA (SEQ ID NO: 4) is a typical substrate for subtilisins. Z-QQP-pNA and Z-PFP-pNA were not hydrolyzed (data not shown), while substrates with a P residue in the P2 position were cleaved, albeit at quite different rates; Suc-AAPF-pNA (SEQ ID NO: 4) was cleaved most rapidly (FIG. 4A, FIG. 4B), followed by Z-YPQ-pNA. The rapid hydrolysis of Suc-AAPF-pNA (SEQ ID NO: 4) by Rmep further points to subtilisin-like enzyme activity in this preparation. LPY hydrolysis could be demonstrated at five-fold increased enzyme concentrations and longer incubation times (FIG. 4C). PPF was hydrolyzed by subtilisin A at fifty-fold increased enzyme concentrations, but not by Rmep (data not shown).

Figure 4D:
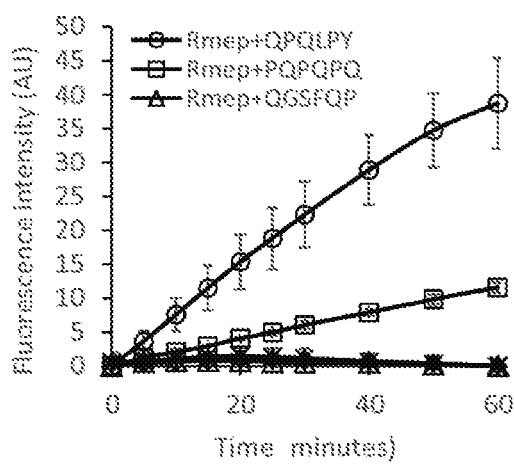
Figure 4E:
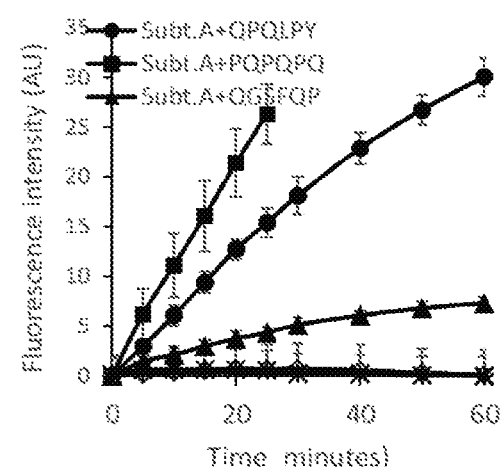
Figure 9:
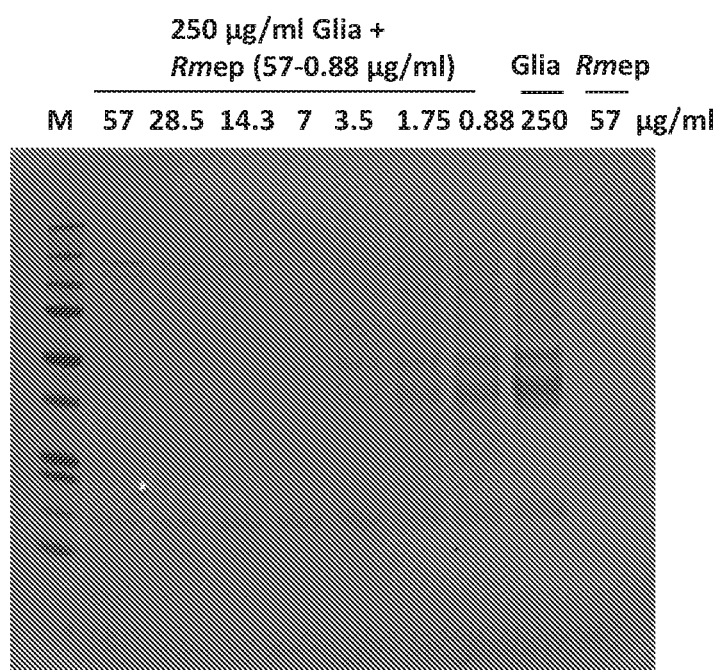
FIG. 9 is a representative SDS-PAGE gel showing the gliadin degradation by a dilution series of Rmep from *R. mucilaginosa*. Mixed gliadins (250 µg/ml) in 50 mM Tris, pH 8.0 were incubated with Rmep ranging from 57 to 0.88 µg/ml for 30 min. Aliquots of 100 µl are loaded on the gel. Right lanes, gliadin and Rmep controls.

Activities were also determined towards three gliadin-derived FRET substrates (FIG. 4D, 4E). The substrates were QPQLPY (SEQ ID NO: 22), contained in three immunogenic gliadin epitopes; PQPQPQ (SEQ ID NO: 23), a theoretical substrate for *Rothia* enzymes, and QGSFQP (SEQ ID NO: 24), contained in two gliadin epitopes. The first two peptides, containing XPX motifs, were rapidly hydrolyzed by Rmep (FIG. 4D). In contrast, QGSFQP, not containing XPX, was not cleaved. Subtilin A showed the highest activity towards the PQPQPQ substrate (FIG. 4E).

Elimination of immunogenic epitopes by Rmep—Hydrolysis of the FRET substrates would suggest CD-relevant epitope degradation. To further investigate this, the time courses of degradation of mixed gliadins and the highly immunogenic 33-mer α-gliadin peptide were determined. Furthermore, epitope elimination was monitored by two ELISA assays employing the R5 antibody recognizing QQPFP (SEQ ID NO: 40) and related pentapeptides (27, 28) and the G12 antibody recognizing QPQLPY (SEQ ID NO: 22) contained in the 33-mer peptide (29, 30). Data obtained with Rmep are shown in FIG. 5, and with subtilisin A in FIG. 6.

Rmep rapidly degraded mixed gliadins within 15 min incubation and completed 33-mer peptide degradation within 30 min of incubation (FIGS. 5A and 5B, respectively). R5 epitope abolishment in the Rmep digest of gliadins could already be observed in the t=0 sample (46% reduction in antibody binding compared to the control, corrected for enzyme only values). After 15 min virtually all R5 epitopes were eliminated (FIG. 5C). After 30 min the G12 antibody binding had decreased by 65% and showed a time-dependent decline to 85% reduction after 2 h of incubation (FIG. 5D). Subtilisin A degraded gliadins even faster, with near complete degradation in the t=0 sample (FIG. 6A). However, the 33-mer peptide was not as efficiently cleaved, and after 2 h of incubation residual 33-mer still remained (74% degradation; FIG. 6B). The R5 epitopes in the gliadin-subtilisin A digest were rapidly eliminated, by 90% at t=0, and by 100% within 15 min of incubation (FIG. 6C). In contrast, the G12 epitopes were quite resistant to subtilisin A, and were degraded by 22% at t=0 and 45% at 2 h (FIG. 6D). This agrees with the modest activity towards the 33-mer.

The gluten-degrading enzymes of *Rothia* were identified as members of the subtilisin protease family, and the gluten-degrading activities of this class of enzymes were shown to extend beyond the *Rothia* genus. The cleavage specificity of subtilisins is XPX↓ with X in the P1 position preferably being a hydrophobic amino acid. In accordance, substrates with Q in the P1 position were found to be highly susceptible to cleavage by Rmep and subtilisin A. XPQ is present in the majority of the antigenic gluten epitopes relevant in CD (31). A subset of such Q residues in gliadins are deamidated by the enzyme tissue transglutaminase 2 (TG2) in the patients' lamina propria, a key step in the pathogenesis of CD (32). This deamidation of increases the peptides' affinity for HLA-DQ2 and HLA-DQ8 expressed on antigen-presenting cells and triggers the destructive mucosal T cell response. Glutamine residues in the XPQXP context are particularly prone to such deamidation (33, 34). Selective cleavage after Q in this context will prevent this T cell activation. Based on the here reported cleavage preferences of *Rothia* and *Bacillus* subtilisins, they can both be considered efficient enzymes for degradation of these major gluten epitopes before they reach the lamina propria. This is further supported by the elimination of major gluten epitopes in the two independent ELISA assays.

The three major *Rothia* species are *R. aeria*, *R. mucilaginosa* and *R. dentocariosa*. Analysis of the gluten degrading *Rothia* enzymes showed that they belong to the D-H-S class of subtilisins (35, 36) and not to the family of kexins (an S8 protease sub-family). All contain a signal peptide for secretion, which is presumably cleaved off as most contain the consensus sequence AxA|A which is recognized by a signal peptidase. Using NCBI BlastP (or InterPro) analysis it was found that none of the sequences contain a C-terminal LPxTG-type peptidoglycan anchor ("LPxTG" disclosed as SEQ ID NO: 41), a motif that is typically preceded by a transmembrane sequence of hydrophobic residues, followed by several positively charged residues (R,_K) at the very end of the protein sequence. However, most *Rothia* subtilisins did contain two to three C-terminal SLH (surface layer homology) domains, called Pfam00395(37). Such bacterial SLH domain proteins are non-covalently anchored to the cell surface via a conserved mechanism involving cell wall polysaccharide pyruvylation. The theoretical cell-envelope association agrees with our finding that *Rothia* subtilisins could be isolated from cell-derived vesicles that could be harvested by ultracentrifugation.

The mass spectrometric identification of subtilisins prompted the exploration of other subtilisins from other microbes, specifically *Bacillus* species, for activity, and they were here identified also to degrade gluten. Like Rmep, subtilisin A indeed degraded gluten with similar efficacy. Like *Rothia*, the *Bacillus* genomes encodes for several extracellular subtilisins. In general, bacteria that express multiple extracellular proteases reside in a protein-rich environment, and use proteases to degrade proteins into peptides that can subsequently be utilized for growth. This is the case for the natural habitat of *Rothia* species, the oral cavity, where XPQ-containing substrates are prevalent. The XPQ-rich proteins are not only represented by the ingested gluten proteins, but also by salivary proline-rich proteins that are produced constitutively by the salivary glands (38-41). In this context it is of interest to note that both *B. subtilis* and *Rothia* colonize the oral cavity (42) and that the salivary basic proline-rich proteins undergo extensive proteolytic fragmentation, with primary cleavage after XPQ↓ (43-45). Based on our data, these cleavages are carried out most likely by the identified oral bacterial subtilisins.

Some interesting observations were made when the substrate specificities of subtilisin A and Rmep were compared. First, both enzymes cleaved AAPF (SEQ ID NO: 4) rapidly, but not PPF. This indicates that a Pro in the P3 position interferes with substrate recognition by both enzymes. In most gluten immunogenic domains containing the XPF sequence, X is represented by a Q, and not a P. Accordingly, the FRET results indicate that QPF is efficiently cleaved. Also abundant in gliadin immunogenic domains is LPY, which is cleaved, albeit at lower efficiency. The relative inefficiency of subtilisin A towards the 33-mer peptide, rich in XPQ and LPY, is not easily explained, other than e.g. by allosteric inhibitory effects of certain degradation fragments on the enzyme itself. However, Rmep cleaved this epitope very efficiently.

There were two observations in the subtilisin identification made in Rmep. First, Rmep was significantly less sensitive to the inhibitory effect of Eglin C than subtilisin A. This difference in sensitivity between both enzymes can best be explained by the significant structural differences between Rmep and subtilisin A in domains flanking their active sites. Secondly, the molecular weight of the subtilisins identified in the ~75-80 kDa gel bands did not match their predicted molecular weight (~125 kDa). Given that the catalytic triad is located at the N-terminal portion of the protein, we postulate that the parent inactive precursor proteins C6R5V9_9MICC and C6R5W1_9MICC are processed at the N-termini to remove the inhibitory propeptide, and at the C-terminus between the Ig-like segment and SLH domains, generating the ~75 and ~80 kDa mature enzymes, as outlined in FIG. 7. It is well known that subtilisins from *Bacillus* species undergo autocatalytic activation to produce a shorter mature enzyme (46). Further structural analysis should reveal the exact primary, secondary and tertiary structures of active *Rothia* subtilisins.

*B. subtilis* is food safe and has been consumed for decades, e.g. in a product called natto, a Japanese fermented soy bean dish. In natto the active enzyme is nattokinase, a 27.7 kDa subtilisin enzyme (subtilisin NAT or NattoK) (47). It is available in pure form as a dietary supplement. Like Rmep (FIG. 8A) NattoK degraded gliadins effectively (FIG. 8A, FIG. 8B), hydrolyzed Z-AAPF-pNA (SEQ ID NO: 4) (FIG. 8C), and degraded the 33-mer peptide (FIG. 8D), although a large fragment eluting just prior to the 33-mer in the RP-HPLC chromatogram remained. It abolished the R5 epitopes (FIG. 8E), but not the G12 epitopes (FIG. 8F). Despite a long history of consumption of *B. subtilis* and its products, there are very few reports of adverse events. The natto dish is believed to promote a healthy gut flora and to facilitate the uptake of vitamin K2. Apart from uses as dietary food and feed additives/supplements, subtilisins are being used in detergents and household cleaning products. Overall, the food-grade status of *B. subtilis* and its already widely consumed products including nattokinase suggest readily available options for CD patients to achieve improved immunogenic gluten removal in vivo. Importantly, the *R. mucilaginosa* subtilisins have superior epitope-detoxifying capacities compared to *Bacillus* subtilisins, and thus can be considered highly promising future food additives for this purpose. A potential shortcoming of subtilisins is their relatively low activity at acidic pH, which would reduce efficacy during gastric transit. This can be addressed by focusing future efforts on the *R. aeria* subtilisins, which are active at more acidic pH values as low as 3.0 (22). Furthermore, with molecular approaches further improvement of activity of subtilisins at low pH can be anticipated.

Example 2—Gluten-Degrading Subtilisin from *Rothia aeria*

With the genomic sequence information of *R. aeria* becoming available, the inventors were able to identify additional gluten-degrading, subtilisin and subtilisin-like enzymes from *R. aeria* based on the results obtained from *Rothia mucilaginosa* and *Bacillus* species in Example 1. The enzyme was found to be a member of the subtilisin family and is encoded by BAV86562.1. The *R. aeria* enzyme is substantially different from the previously isolated *R. mucilaginosa* enzymes (WP_044143864.1 and WP_044143865.1). However, much larger differences were observed when the *Rothia*-encoded subtilisins were aligned with two *Bacillus*-encoded subtilisins (P00780.1 and P35835.1) (FIG. 14). Analysis of the catalytic region of these enzymes show conserved amino acid sequences (named regions 1-3) and regions that were present only in the *Rothia* subtilisins (regions 4-7). A blast search with sequence of region 6, HGTHVAGTAAGYGV, (SEQ ID NO: 42) identified *Rothia*-like subtilisins in a number of other microbial species. Given that *Rothia*, but not Bacilllus subtilisins can cleave the immunogenic gliadin-derived G12 epitope (QPQLPY, (SEQ ID NO: 22)), it is speculated that one or more of the regions 4-7 is necessary to confer specificity towards the G12 epitope.

Methods

Cultivation of *Rothia aeria*—*Rothia aeria* strain WSA-8[1] has been deposited as strain HM-818 to the BEI resources (beiresources.org) and has been sequenced. It is equivalent to *R. aeria* Oral Taxon 188, strain F0474 (HMP ID 1324). To identify the gluten-degrading enzyme(s) produced by *R. aeria*, the bacteria were cultured on *Brucella* agar plates (Hardy Diagnostics, Santa Maria, Calif.) at 37° C. for 48 h under aerobic conditions. The cells were harvested from plate with a cotton swab and suspended in sterile PBS to an $OD_{620}$ 5.0. Four aliquots of 1.5 ml of the suspension were centrifuged and the supernatants were removed.

SDS-PAGE and casein zymography—The four cell pellets were resuspended each in 200 µl zymogram sample buffer[2]. To separate the proteins, the samples were applied to a non-reducing (no DTT or β-mercaptoethanol-containing) 6% SDS-PAGE gel of 16 cm×20 cm×0.15 cm, using a protean II xi cell system (Bio-Rad, Hercules, Calif.). The composition of this gel was the same as that of previously published 6% gliadin zymogram gels but without incorporation of gliadin[2]. After electrophoresis at a constant voltage of 120V at 4° C., the gel was divided in two halves ("A-gel" and "B-gel"). One-half ("A-gel") was stained with 0.1% Coomassie Brilliant Blue in 40% (v/v) methanol/10% (v/v) acetic acid. The other half ("B-gel") was developed as a zymogram gel[3]. (See FIGS. 12A and 12B). For this, the B-gel was washed twice for 30 min in buffer containing 2.5% Triton X-100 (renaturing buffer; Life Technologies, Carlsbad, Calif.), followed by washing twice for 1 h in buffer containing 20 mM Tris-HCl, pH 7.5 (developing buffer; Life Technologies, Carlsbad, Calif.). The B-gel was then incubated in developing buffer supplemented with 1% casein (Sigma, St. Louis, Mo.) at 37° C. for 1.5 h. After washing with water for 2 min, the B-gel was stained with 0.1% (w/v) Coomassie Brilliant Blue in 40% (v/v) methanol/10% (v/v) acetic acid for 24 h. Both the A-gel and B-gel were destained in 40% (v/v) methanol/10% (v/v) acetic acid until optimal contrast was achieved.

LC-ESI-MS/MS—The A-gel and B-gel halves were aligned, and the protein displaying enzyme activity in the B-gel was excised from the duplicate lanes, and the matching band in the A-gel was also excised in duplo. The proteins were digested in-gel with sequencing-grade trypsin, and the peptides were eluted and separated by in line C18 chromatography. The amino acid sequences of the peptide ions were obtained with an LTQ Orbitrap mass spectrometer (ThermoFinnigan, San Jose, Calif.). The b- and y-ion spectra were searched against a database of *R. aeria* F0474, supplemented with decoy proteins as well as the 46 *Rothia* subtilisin genes shown in FIG. 10. The filter settings selected were X-corr values >2.2 and 3.5 for Z=2, and 3, respectively. The deltaCn and peptide probability settings were >0.1 and <0.01, resp., as previously applied[3].

Database searches—The amino acid sequences of subtilisins WP_044143865.1 (*R. mucilaginosa*), WP_044143864.1 (*R. mucilaginosa*), BAV86562.1 (*R. aeria*), P00780.1 (subtilisin A; *B. licheniformis*) and P35835.1 (nattokinase; *B. subtilis* NAT) were aligned using the aligner tool at the website justbio. Region 6 (HGTHVAGTAAGYGV, (SEQ ID NO: 42)) was blast-searched using the "blastp" suite at the website of the National Center for Biotechnology Information (NCBI) at world wide web site. The default settings were used, except for an increased threshold value of 1,000. Searches were conducted against the non-redundant protein sequences database with "subtilisin" in the entrez query.

Results

The sequences of *Bacillus licheniformis* subtilisin A (P00780.1) and *B. subtilis* NAT nattokinase (P35835.1) are shown in FIG. 13.

The strategy for identifying the gluten-degrading enzyme from *R. aeria* was to use a large SDS gel (16×20 cm) instead of a mini SDS gel (8×8 cm) to achieve better protein separation. A low percentage gel (6%) facilitated separation of proteins with molecular weights >50 kDa.

Figure 12A:
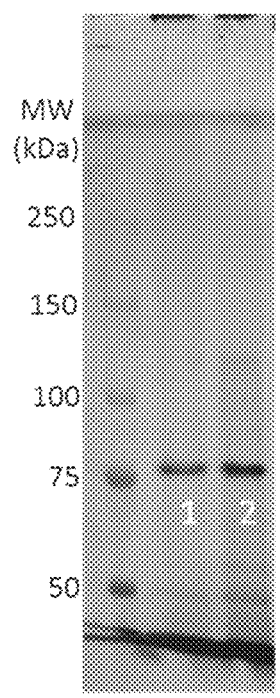
FIGS. 12A-12B show the identification of the gluten-degrading enzyme, subtilisin proteins from *Rothia aeria*.
Figure 12B:
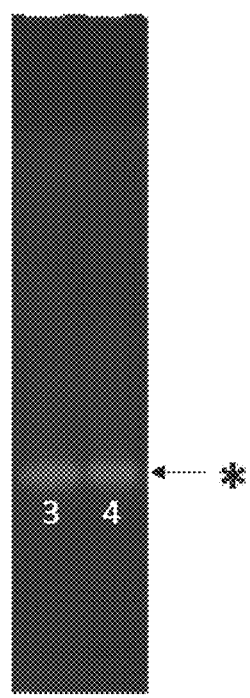

The gel results are shown in FIGS. 12A and 12B. The zymogram gel part (FIG. 12B) gave evidence for a single enzyme band with an apparent molecular weight of around ~78 kDa, and the matching gel in FIG. 12A showed a major band migrating at the same position. Four bands in total were excised and subjected to mass spectrometric analysis. The most prominent protein, identified with high confidence in all four gel bands, was peptidase S8, KGJ00122.1. The sequence is also shown in FIG. 10, line 27. It is a subtilisin from *R. dentocariosa*, represented by 33, 41, 32 and 30 unique peptides respectively. Since the loaded bacteria was *R. aeria* and not *R. dentocariosa*, this indicated that the subtilisin protein from *R. aeria* protein was highly homologous to KGJ00122.1. A blast search of KGJ00122.1 revealed that it is 99% homologous to a *R. aeria* protein annotated as glycerol-3P-ABC transporter on NCBI (BAV86562.1). Sequence analysis of BAV86562.1 revealed that it is an enzyme, and that it belongs to the subtilisin family of proteases. The amino acid sequence is shown in this disclosure, and in the amino acid section in bold is the cd07474 domain, representing the Peptidase S8 family domain. The D, S and H amino acids of the catalytic triad are underlined. Alignment of KGJ00122.1 (from *R. dentocariosa*) and BAV86562.1 (from *R. aeria*) showed very few differences, as expected (FIG. 13). The natural expression level of BAV86562.1 in *R. aeria* is high (FIG. 12A). Furthermore, the enzyme retains activity at pH values as low as 3.0[1], indicating that it may be active under gastric pH conditions.

To probe for structural similarities among the subtilisins identified in *Rothia* and *Bacillus* species, the amino acid sequences of WP_044143865.1 (*R. mucilaginosa*), WP_044143864.1 (*R. mucilaginosa*), BAV86562.1 (*R. aeria*), P00780.1 (subtilisin A; *B. licheniformis*) and P35835.1 (nattokinase; *B. subtilis* NAT) were aligned (FIG. 14). Major differences in the enzyme lengths and overall sequences were observed, consistent with earlier subtilisin comparisons[4,5]. Domains comprising the catalytic triad residues D, H and S (underlined) however were conserved. Both *Bacillus* and *Rothia* subtilisins hydrolyze the immunogenic R5 gluten epitope[3, 6, 7]. Since *Rothia* subtilisins but not the *Bacillus* subtilisins efficiently cleave the immunogenic G12 gluten epitope[3,8], the inventors looked for subtle differences in the substrate binding regions that could explain such difference in substrate specificity. Several differences were observed just before or after the conserved regions 1-3 that distinguished *Rothia* subtilisins from the *Bacillus* subtilisins. These were designated regions 4-7. It is proposed that regions 1-3 are necessary for R5 epitope elimination, and that one or more of the regions 4-7 are necessary to confer specificity towards the G12 epitope. Subsequent searches with region 6 (HGTHVAGTAAGYGV, (SEQ ID NO: 42)) in the non-redundant (all-encompassing) limited to subtilisins identified *Rothia*-like peptidase S8 enzymes in *Cellulomonas, Curtobacterium, Sanguibacter, Arthrobacter, Kitasatospora, Prauserella, Streptomyces, Pseudoglutamicibacter, Actinosynema*, and *Modestobacter* genera, but not in *Bacillus*. It is predicted that these species produce enzymes that can cleave gluten, including the G12 epitope.

Example 3—Degradation of Cereal Amylase-Trypsin Inhibitors (ATIs) by Gluten-Degrading Subtilisin from *Rothia* sp Non-celiac/non-allergy wheat sensitivity (NCWS) has an estimated prevalence of 5-10% in wheat (cereal) consuming populations[1-3]. NCWS is characterized by intestinal and extra-intestinal symptoms related to the consumption of gluten-containing foods that are also enriched in amylase-trypsin inhibitors (ATIs)[2]. The diagnosis is made after CD and wheat allergy have been excluded and if the patients display typical symptoms and complaints within hours to days after consumption of ATI-containing cereals, mainly wheat, and remission of these symptoms within a few hours to days after stopping their consumption1. The wheat components responsible for the initiation of an innate immune responses to wheat and related cereals in NCWS have been identified as ATIs4. Wheat ATIs are a family of disulfide-linked and protease resistant proteins that occur as monomers, dimers and tetramers with molecular weights ranging from 12-60 kDa. ATIs bind to and activate the TLR4-MD2-CD14 complex on mainly myeloid cells (dendritic cells, macrophages, monocytes), ultimately resulting in the release of proinflammatory innate cytokines[3, 4].

*Rothia* and *Bacillus*-derived subtilisins can cleave gluten proteins, with an apparent specificity after XPQ↓[5]. XPX sequences and other sequences cleavable by subtilisins are also present in ATIs. Like gluten, ATIs are highly resistant to degradation by mammalian digestive enzymes[3]. A dietary enzyme that could eliminate immunotoxicity of both gluten and ATIs would clearly be beneficial for the treatment of the spectrum of wheat (cereal)-associated gastrointestinal disorders comprising CD and NCWS. Therefore, we investigated if the *Bacillus* and *Rothia*-derived subtilisins can degrade ATIs.

Methods

ATIs were isolated from wheat cultivars as described[3]. They were incubated at a final concentration of 500 µg/ml with 10, 25 or 50 µg/ml Rmep (from *R. mucilaginosa*), or nattokinase (from *B. subtilis*). The controls incubations were carried out with heat-inactivated Rmep and nattokinase. Experiments were conducted in 50 mM Tris-HCl, pH 8.0. After 0, 15 min, 30 min, 1 h, and 4 h incubation, 20 µl aliquots were removed, mixed with SDS-sample buffer, heated at 85° C. for 5 min and analyzed by 4-12% SDS PAGE. Proteins were visualized with Coomassie Blue staining.

Results

Figures 15A, 15B:
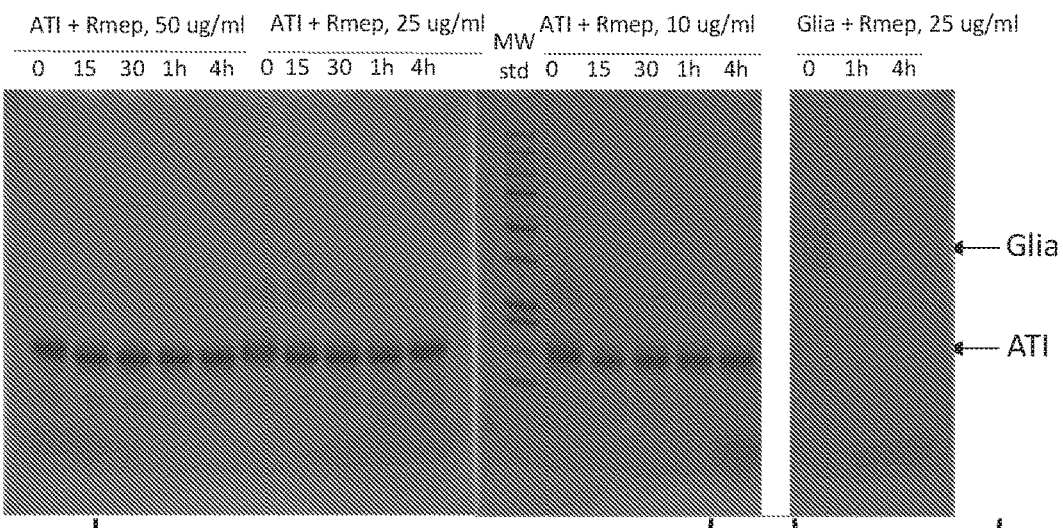
FIGS. 15A-15F show effective ATI degradation by subtilisins from *B. subtilis* (nattokinase). This demonstrates that nattokinase (and other subtilisin-related enzymes) can also be used to inactivated ATIs in gluten and thus be of benefit for patients with non-celiac wheat sensitivity. ATI (500 µg/ml) incubated with Rmep from *R. mucilaginosa* (FIG. 15A) or nattokinase from *B. subtilis* (FIG. 15C) at 50, 25, or 10 µg/ml.
Figures 15C, 15D:
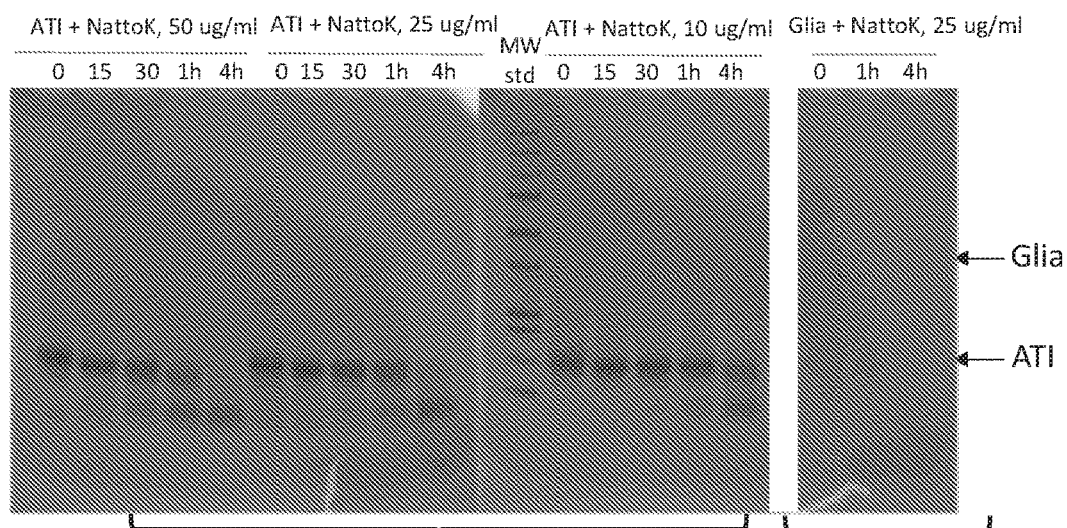
Figures 15E, 15F:
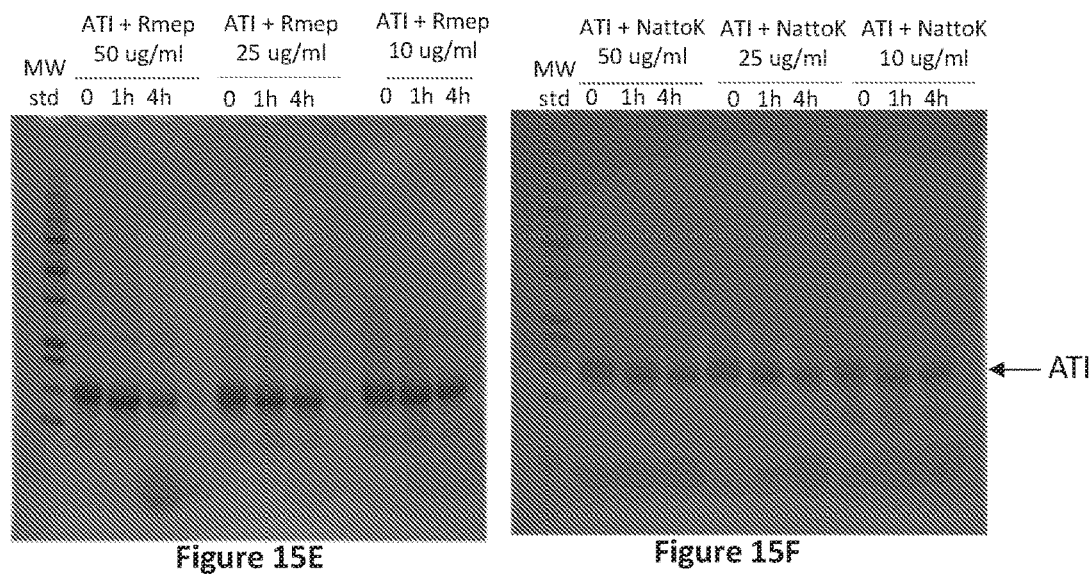

The wheat ATI proteins, migrating at ~15 kDa, were resistant to degradation by Rmep (FIG. 15A). Protease activity in the Rmep preparation was confirmed with gliadin as the substrate (FIG. 15B). While the gliadins were degraded, the ATI contaminant in the gliadin preparation was not, consistent with the observations made with the purified ATIs (indicated with an arrow). On the other hand, ATIs were susceptible to proteolysis by nattokinase. Approximately 50% of the ATIs (500 µg/ml) were degraded after 1 h incubation with 50 µg/ml nattokinase, or after 4 h incubation with 10 µg/ml nattokinase (FIG. 15C). As expected, nattokinase also rapidly degraded gliadins (FIG. 15D). ATIs were stable when incubated with heat-inactivated Rmep or nattokinase (FIGS. 15E and 15F). The results show that nattokinase is unique in being able to cleave ATIs and potentially to abolish their pro-inflammatory properties implicated in NCWS.

Example 4—Preparation of Non-Viable Bacteria Composition Having Gluten Degrading Activity Methods Bacterial strains—Two gluten-degrading *P. aeruginosa* strains (FA-10 and FA-13) were isolated from human feces, which is described herein. The isolation and characterization of gluten-degrading *Rothia mucilaginosa* and *R. aeria* (WSA-8) from human saliva samples has been described herein. The *R. mucilaginosa* strain used in the present study was obtained from the American Type Culture Collection (ATCC strain 25296).

Bacteria cell inactivation—The two *P. aeruginosa* isolates, *R. mucilaginosa* and *R. aeria* strains were cultured aerobically on *Brucella* agar plates (Hardy Diagnostics, Santa Monica, Calif.) at 37° C. After 48 h incubation, cells were harvested with a sterile cotton swab and diluted to an $OD_{620}$ of 1.2 in either 1 ml of 70% ethanol (EtOH) or in 1 ml of saliva ion buffer (SIB, control) containing 50 mM KCl, 1.5 mM potassium phosphate, 1 mM $CaCl_2$ and 0.1 mM $MgCl_2$, pH 7.0. Suspensions were incubated for 30 min at 37° C. after which 5 µl aliquots were plated in triplicate on *Brucella* agar to assess cell viability. The residual 995 µl aliquots were lyophilized to dryness using a SpeedVac (Thermo Fisher). The lyophilized bacteria that had been incubated in 70% ethanol were reconstituted in 1 ml sterile SIB, and the bacteria that had been incubated in SIB (control) were reconstituted in deionized sterile water, yielding the same final ion composition in both samples. Enzyme activities in the reconstituted suspensions were assessed by gliadin zymography and by determining the hydrolysis of tripeptide substrates.

Gliadin zymography-Gliadin zymogram gels (6%) were prepared with mixed gliadin from wheat (Sigma, St. Louis, Mo.) as the gel incorporated substrate, as previously described[6]. The reconstituted EtOH-treated and control cells, each suspended in SIB $OD_{620}$ 1.2, were harvested by centrifugation. The aliquots centrifuged were 625 µl for each of the *Rothia* strains, and 208 µl for the *P. aeruginosa* strains. The pelleted cells were resuspended in 40 µl non-denaturing zymogram sample buffer and loaded onto the zymogram gel. Electrophoresis was carried out at 100 V at 4° C., and gels were renatured and developed in zymogram renaturing and developing buffers (InVitrogen, Carlsbad, Calif., USA) according to the manufacturer's instructions. After 48 h of development at 37° C., gels were stained with 0.1% Coomassie Brilliant blue in a mixture of 40% methanol/10% acetic acid, and destained until the contrast between clear bands and background was optimal.

Synthetic tripeptide substrates hydrolysis-Aliquots of 200 μl reconstituted ethanol-treated and untreated *P. aeruginosa* cells in SIB (OD 1.2) were mixed with benzyloxycarbonyl-Leu-Pro-Tyr-paranitroanilide (Z-LPY-pNA) and aliquots 200 μl aliquots of the *Rothia* strains were mixed with Z-Tyr-Pro-Gln-pNA (Z-YPQ-pNA) (21st Century Biochemicals, Marlborough, Mass.). The final concentration of the tripeptide substrates was 200 μM. All experiments were performed in triplicate. Substrate hydrolysis was monitored spectrophotometrically at 405 nm, using a Genios microtiter plate reader (Tecan Group Ltd., Männedorf, Switzerland) and Deltasoft software, with the equipment temperature set at 37° C. Readings were performed in the kinetic mode at the indicated time intervals.

Results

Effect of cell killing on enzymatic activity—The bactericidal treatment of choice was 70% ethanol since it can be removed by lyophilization after treatment. Aliquots plated in triplicate of the treated cells showed complete loss of cell viability as expected whereas the untreated cells were viable (FIG. 16A). Enzyme activities in the treated and untreated cell suspensions were evaluated qualitatively by zymography (FIG. 16B), and quantitatively with the tripeptide substrate Z-LPY-pNA or Z-YPQ-pNA (FIG. 16C). The maximum rates of Z-LPY-pNA and Z-YPQ-pNA hydrolysis are depicted in FIG. 16D. Results show that gliadin-degrading enzyme activities were unaffected by ethanol treatment, as evidenced from clear bands in the gliadin zymogram gels (FIG. 16B). From the rates of tripeptide hydrolysis depicted in FIGS. 16C and 61D it could be calculated that <10% enzyme activity was lost after 70% ethanol treatment. The results show that the added ethanol could be fully eliminated by lyophilization after treatment, yielding an active enzyme preparation that was unadulterated with respect to the starting material, apart from being devoid of life cells.

REFERENCES FOR EXAMPLE 1

1. Abadie V, et al. Integration of genetic and immunological insights into a model of celiac disease pathogenesis. Annu Rev Immunol 2011; 29:493-525.
2. Schuppan D, et al. Celiac disease: from pathogenesis to novel therapies. Gastroenterology 2009; 137:1912-33.
3. Abadie V, et al. Intraepithelial lymphocytes in celiac disease immunopathology. Semin Immunopathol 2012; 34:551-66.
4. Shah S, et al. Patient perception of treatment burden is high in celiac disease compared with other common conditions. Am J Gastroenterol 2014; 109:1304-11.
5. Norsa L, et al. Gluten-free diet or alternative therapy: a survey on what parents of celiac children want. Int J Food Sci Nutr 2015; 66:590-4.
6. Rubio-Tapia et al. ACG clinical guidelines: diagnosis and management of celiac disease. Am J Gastroenterol 2013; 108:656-76; quiz 677.
7. Sollid L M, and Khosla C. Novel therapies for coeliac disease. J Intern Med 2011; 269:604-13.
8. Kaukinen K, and Lindfors K. Novel treatments for celiac disease: glutenases and beyond. Dig Dis 2015; 33:277-81.
9. Landeaho M L, et al. The Glutenase ALV003 Attenuates Gluten-Induced Mucosal Injury in Patients with Celiac Disease. Gastroenterology 2014.
10. Bethune Mont., and Khosla C. Oral enzyme therapy for celiac sprue. Methods Enzymol 2012; 502:241-71.
11. Siegel M, et al. Rational design of combination enzyme therapy for celiac sprue. Chem Biol 2006; 13:649-58.
12. Stepniak D, et al. Highly efficient gluten degradation with a newly identified prolyl endoprotease: implications for celiac disease. Am J Physiol Gastrointest Liver Physiol 2006; 291:G621-9.
13. Tack G J, et al. Consumption of gluten with gluten-degrading enzyme by celiac patients: a pilot-study. World J Gastroenterol 2013; 19:5837-47.
14. Siegel M, et al. Safety, tolerability, and activity of ALV003: results from two phase 1 single, escalating-dose clinical trials. Dig Dis Sci 2012; 57:440-50.
15. Freitag T L, et al. Testing safety of germinated rye sourdough in a celiac disease model based on the adoptive transfer of prolamin-primed memory T cells into lymphopenic mice. Am J Physiol Gastrointest Liver Physiol 2014; 306:G526-34.
16. Lindfors K, et al. Live probiotic *Bifidobacterium lactis* bacteria inhibit the toxic effects induced by wheat gliadin in epithelial cell culture. Clin Exp Immunol 2008; 152: 552-8.
17. Rollan G, et al. Proteolytic activity and reduction of gliadin-like fractions by sourdough lactobacilli. J Appl Microbiol 2005; 99:1495-502.
18. Caminero A, et al. Diversity of the cultivable human gut microbiome involved in gluten metabolism: isolation of microorganisms with potential interest for coeliac disease. FEMS Microbiol Ecol 2014; 88:309-19.
19. De Angelis M, et al. VSL #3 probiotic preparation has the capacity to hydrolyze gliadin polypeptides responsible for Celiac Sprue. Biochim Biophys Acta 2006; 1762:80-93.
20. Helmerhorst E J, et al. Discovery of a novel and rich source of gluten-degrading microbial enzymes in the oral cavity. PLoS One 2010; 5:e13264.
21. Tian N, Wei G, et al. Effect of *Rothia mucilaginosa* enzymes on gliadin (gluten) structure, deamidation, and immunogenic epitopes relevant to celiac disease. Am J Physiol Gastrointest Liver Physiol 2014; 307:G769-76.
22. Zamakhchari M, et al. Identification of *Rothia* bacteria as gluten-degrading natural colonizers of the upper gastro-intestinal tract. PLoS One 2011; 6:e24455.
23. Fernandez-Feo M, et al. The cultivable human oral gluten-degrading microbiome and its potential implications in coeliac disease and gluten sensitivity. Clin Microbiol Infect 2013; 19:E386-94.
24. Wei G, et al. Identification of Pseudolysin (lasB) as an Aciduric Gluten-Degrading Enzyme with High Therapeutic Potential for Celiac Disease. Am J Gastroenterol 2015; 110:899-908.
25. Helmerhorst E J, and Wei G. Experimental strategy to discover microbes with gluten-degrading enzyme activities. Proc. SPIE 2014; 9112:91120D1-11.
26. Shan L, et al. Structural basis for gluten intolerance in celiac sprue. Science 2002; 297:2275-9.
27. Osman A A, Uhlig H H, Valdes I, et al. A monoclonal antibody that recognizes a potential coeliac-toxic repetitive pentapeptide epitope in gliadins. Eur J Gastroenterol Hepatol 2001; 13:1189-93.
28. Valdes I, et al. Innovative approach to low-level gluten determination in foods using a novel sandwich enzyme-linked immunosorbent assay protocol. Eur J Gastroenterol Hepatol 2003; 15:465-74.

29. Moron B, et al. Toward the assessment of food toxicity for celiac patients: characterization of monoclonal antibodies to a main immunogenic gluten peptide. PLoS One 2008; 3:e2294.
30. Moron B, et al. Sensitive detection of cereal fractions that are toxic to celiac disease patients by using monoclonal antibodies to a main immunogenic wheat peptide. Am J Clin Nutr 2008; 87:405-14.
31. Sollid L M, et al. Nomenclature and listing of celiac disease relevant gluten T-cell epitopes restricted by HLA-DQ molecules. Immunogenetics 2012; 64:455-60.
32. van de Wal Y, et al. Selective deamidation by tissue transglutaminase strongly enhances gliadin-specific T cell reactivity. J Immunol 1998; 161:1585-8.
33. Sollid LM. Coeliac disease: dissecting a complex inflammatory disorder. Nat Rev Immunol 2002; 2:647-55.
34. Vader L W, et al. Specificity of tissue transglutaminase explains cereal toxicity in celiac disease. J Exp Med 2002; 195:643-9.
35. Siezen R J, and Leunissen J A. Subtilases: the superfamily of subtilisin-like serine proteases. Protein Sci 1997; 6:501-23.
36. Siezen R J, et al. Evolution of prokaryotic subtilases: genome-wide analysis reveals novel subfamilies with different catalytic residues. Proteins 2007; 67:681-94.
37. Mesnage S, et al. Bacterial SLH domain proteins are non-covalently anchored to the cell surface via a conserved mechanism involving wall polysaccharide pyruvylation. EMBO J 2000; 19:4473-84.
38. Azen E A, et al. PRB1, PRB2, and PRB4 coded polymorphisms among human salivary concanavalin-A binding, II-1, and Po proline-rich proteins. Am J Hum Genet 1996; 58:143-53.
39. Helmerhorst E J, and Oppenheim F G. Saliva: a dynamic proteome. J Dent Res 2007; 86:680-93.
40. Inzitari R, et al. Detection in human saliva of different statherin and P-B fragments and derivatives. Proteomics 2006; 6:6370-9.
41. Tian N, et al. Salivary proline-rich proteins and gluten: Do structural similarities suggest a role in celiac disease? Proteomics Clin Appl 2015; 9:953-64.
42. Dewhirst F E, et al. The human oral microbiome. J Bacteriol 2010; 192:5002-17.
43. Helmerhorst E J, et al. Identification of Lys-Pro-Gln as a novel cleavage site specificity of saliva-associated proteases. J Biol Chem 2008; 283:19957-66.
44. Messana I, et al. Trafficking and postsecretory events responsible for the formation of secreted human salivary peptides: a proteomics approach. Mol Cell Proteomics 2008; 7:911-26.
45. Vitorino R, et al. Towards defining the whole salivary peptidome. Proteomics Clin Appl 2009; 3:528-540.
46. Gallagher T, et al. The prosegment-subtilisin BPN' complex: crystal structure of a specific 'foldase'. Structure 1995; 3:907-14.
47. Dabbagh F, Negandaripour M, Berenjian A, et al. Nattokinase: production and application. Appl Microbiol Biotechnol 2014; 98:9199-206.

REFERENCES FOR EXAMPLE 2

1. Zamakhchari M, et al. Identification of *Rothia* bacteria as gluten-degrading natural colonizers of the upper gastrointestinal tract. PLoS One 2011; 6:e24455.
2. Helmerhorst E J, and Wei G. Experimental Strategy to Discover Microbes with Gluten-degrading Enzyme Activities. Proc SPIE Int Soc Opt Eng 2014; 9112.
3. Wei G, et al. Identification of food-grade subtilisins as gluten-degrading enzymes to treat celiac disease. Am J Physiol Gastrointest Liver Physiol 2016; 311:G571-G580.
4. Siezen R J, and Leunissen J A. Subtilases: the superfamily of subtilisin-like serine proteases. Protein Sci 1997; 6:501-23.
5. Siezen R J, et al. Evolution of prokaryotic subtilases: genome-wide analysis reveals novel subfamilies with different catalytic residues. Proteins 2007; 67:681-94.
6. Osman A A, et al. A monoclonal antibody that recognizes a potential coeliac-toxic repetitive pentapeptide epitope in gliadins. Eur J Gastroenterol Hepatol 2001; 13:1189-93.
7. Valdes I, et al. Innovative approach to low-level gluten determination in foods using a novel sandwich enzyme-linked immunosorbent assay protocol. Eur J Gastroenterol Hepatol 2003; 15:465-74.
8. Moron B, et al. Toward the assessment of food toxicity for celiac patients: characterization of monoclonal antibodies to a main immunogenic gluten peptide. PLoS One 2008; 3:e2294.
9. Schuppan D, et al. Non-celiac wheat sensitivity: differential diagnosis, triggers and implications. Best Pract Res Clin Gastroenterol 2015; 29:469-76.
10. Schuppan D, and Zevallos V. Wheat amylase trypsin inhibitors as nutritional activators of innate immunity. Dig Dis 2015; 33:260-3.
11. Zevallos V F, et al. Nutritional Wheat Amylase-Trypsin Inhibitors Promote Intestinal Inflammation via Activation of Myeloid Cells. Gastroenterology 2016.
12. Junker Y, et al. Wheat amylase trypsin inhibitors drive intestinal inflammation via activation of toll-like receptor 4. J Exp Med 2012; 209:2395-408.

REFERENCES FOR EXAMPLE 3

1. Schuppan D, et al. Non-celiac wheat sensitivity: differential diagnosis, triggers and implications. Best Pract Res Clin Gastroenterol 2015; 29:469-76.
2. Schuppan D, and Zevallos V. Wheat amylase trypsin inhibitors as nutritional activators of innate immunity. Dig Dis 2015; 33:260-3.
3. Zevallos V F, et al. Nutritional Wheat Amylase-Trypsin Inhibitors Promote Intestinal Inflammation via Activation of Myeloid Cells. Gastroenterology 2016.
4. Junker Y, et al. Wheat amylase trypsin inhibitors drive intestinal inflammation via activation of toll-like receptor 4. J Exp Med 2012; 209:2395-408.
5. Wei G, et al. Identification of food-grade subtilisins as gluten-degrading enzymes to treat celiac disease. Am J Physiol Gastrointest Liver Physiol 2016; 311:G571-G580.

The invention claimed is:

1. A foodstuff comprising a formulation comprising an ethanol treated and lyophilized population of *Rothia* sp. bacteria and a subtilisin enzyme derived from the population of *Rothia* sp. bacteria,
   wherein the *Rothia* sp bacteria are not viable, and
   wherein the subtilisin enzyme comprises gluten- or gliadin-degrading activity.

2. The foodstuff of claim 1, wherein the *Rothia* sp. bacteria is selected from the group consisting of *Rothia mucilaginosa* ot 681 (strain WSA-2B), *Rothia mucilaginosa* ATCC 25296, *Rothia* species ot 188 (strain WSA-8), *Rothia aeria* BAV86562.1 and *Rothia dentocariosa* KGJ00122.1.

3. The foodstuff of claim 1,
   wherein the subtilisin cleaves proline-containing proteins, cleaving the second peptide bond after proline in the $XPX_1$ motif, where X is any amino acid, P is proline and $X_1$ is a hydrophobic amino acid, or
   wherein the subtilisin cleaves succinyl-Ala-Ala-Pro-Phe-paranitroanilide (SEQ ID NO: 4), a substrate for subtilisin, cleaving at the $2^{nd}$ peptide bond after proline in the P2 position; or
   wherein the subtilisin degrades the highly immunogenic gliadin-derived 33-mer peptide; or
   wherein the subtilisin does not cleave the $2^{nd}$ peptide bond after Proline in the P2 position in a tripeptide having the -PFP-motif, wherein F=Phenylalanine=Phe; P=proline=Pro; or
   wherein the subtilisin does not cleave the $2^{nd}$ peptide bond after Proline in the P2 position in a tripeptide having the -PPF-motif, wherein F=Phenylalanine; P=proline.

4. The foodstuff of claim 1, wherein the subtilisin comprises SEQ. ID. NO: 1, 2 or 3.

5. The foodstuff of claim 1, the formulation further comprising a prolyl endopeptidase; and/or
   further comprising at least one additional gluten-degrading enzyme isolated from a *Rothia* species bacteria, wherein the at least one additional gluten-degrading enzyme retains protease activity at an acidic pH of 3.0 as measured in an in vitro gliadin degradation assay for 3 hours using a synthetic substrate Z-YPQ-pNA, and wherein the at least one enzyme comprises an isoelectric point in a pH range of 2.0-7.0, inclusive; and/or
   further comprising at least one isolated additional glutamine endopeptidase enzyme that cleaves a peptide bond after a QPF and a PFP motif in glutens.

6. A method for degrading gluten in a gluten-containing foodstuff, the method comprises contacting the gluten-containing foodstuff with an effective dose of a formulation comprising an ethanol treated and lyophilized population of *Rothia* sp. bacteria and a subtilisin enzyme derived from the population of *Rothia* sp. bacteria,
   wherein the *Rothia* sp bacteria are not viable, and
   wherein the subtilisin enzyme degrades the gluten in the gluten-containing foodstuff.

7. The method of claim 6, wherein the contacting is performed in vitro prior to consumption of the gluten-containing food stuff, or performed in vivo concurrent with or after consumption of the gluten-containing food stuff.

8. The method of claim 6, wherein the *Rothia* sp. bacteria is selected from the group consisting of *Rothia mucilaginosa* ot 681 (strain WSA-2B), *Rothia mucilaginosa* ATCC 25296, *Rothia* species ot 188 (strain WSA-8), *Rothia aeria* BAV86562.1 and *Rothia dentocariosa* KGJ00122.1.

9. The method of 6,
   wherein the subtilisin cleaves proline-containing proteins, cleaving the second peptide bond after proline in the $XPX_1$ motif, where X is any amino acid, P is proline and $X_1$ is a hydrophobic amino acid, or
   wherein the subtilisin cleaves succinyl-Ala-Ala-Pro-Phe-paranitroanilide (SEQ ID NO: 4), a substrate for subtilisin, cleaving at the $2^{nd}$ peptide bond after proline in the P2 position; or
   wherein the subtilisin degrades the highly immunogenic gliadin-derived 33-mer peptide; or
   wherein the subtilisin does not cleave the $2^{nd}$ peptide bond after Proline in the P2 position in a tripeptide having the -PFP-motif, wherein F=Phenylalanine=Phe; P=proline=Pro; or
   wherein the subtilisin does not cleave the $2^{nd}$ peptide bond after Proline in the P2 position in a tripeptide having the -PPF-motif, wherein F=Phenylalanine; P=proline.

10. The method of 6, wherein the subtilisin comprises SEQ. ID. NO: 1, 2 or 3.

11. The method of claim 6, the formulation further comprising a prolyl endopeptidase; and/or further comprising at least one additional gluten-degrading enzyme isolated from a *Rothia* species bacteria, wherein the at least one additional gluten-degrading enzyme retains protease activity at an acidic pH of 3.0 as measured in an in vitro gliadin degradation assay for 3 hours using a synthetic substrate Z-YPQ-pNA, and wherein the at least one enzyme comprises an isoelectric point in a pH range of 2.0-7.0, inclusive; and/or further comprising at least one isolated additional glutamine endopeptidase enzyme that cleaves a peptide bond after a QPF and a PFP motif in glutens.

12. A composition comprising (a) an ethanol treated and lyophilized population of *Rothia* sp. bacteria and a subtilisin enzyme derived from the population of *Rothia* sp. bacteria, and (b) a prolyl endopeptidase (PEP), wherein the *Rothia* sp bacteria are not viable, and wherein the subtilisin enzyme comprises gluten- or gliadin-degrading activity.

13. The composition of claim 12, wherein the *Rothia* sp. bacteria is selected from the group consisting of *Rothia mucilaginosa* ot 681 (strain WSA-2B), *Rothia mucilaginosa* ATCC 25296, *Rothia* species ot 188 (strain WSA-8), *Rothia aeria* BAV86562.1 and *Rothia dentocariosa* KGJ00122.1.

14. The composition of claim 12, wherein the subtilisin cleaves proline-containing proteins, cleaving the second peptide bond after proline in the XPX$_1$ motif, where X is any amino acid, P is proline and X$_1$ is a hydrophobic amino acid or wherein the subtilisin cleaves succinyl-Ala-Ala-Pro-Phe-paranitroanilide (SEQ ID NO: 4), a substrate for subtilisin, cleaving at the 2$^{nd}$ peptide bond after proline in the P2 position; or wherein the subtilisin degrades the highly immunogenic gliadin-derived 33-mer peptide; or wherein the subtilisin does not cleave the 2$^{nd}$ peptide bond after Proline in the P2 position in a tripeptide having the -PFP-motif, wherein F=Phenylalanine=Phe; P=proline=Pro; or wherein the subtilisin does not cleave the 2$^{nd}$ peptide bond after Proline in the P2 position in a tripeptide having the -PPF-motif, wherein F=Phenylalanine; P=proline.

15. The composition of claim 12, wherein the subtilisin undergoes autocatalytic activation to produce a shorter mature enzyme.

16. The composition of claim 12, wherein the subtilisin comprises SEQ. ID. NO: 1, 2 or 3 or 33 or 34.

17. The composition of claim 12, the formulation further comprising at least one additional gluten-degrading enzyme isolated from a *Rothia* species bacteria, wherein the at least one additional gluten-degrading enzyme retains protease activity at an acidic pH of 3.0 as measured in an in vitro gliadin degradation assay for 3 hours using a synthetic substrate Z-YPQ-pNA, and wherein the at least one enzyme comprises an isoelectric point in a pH range of 2.0-7.0, inclusive; and/or further comprising at least one isolated additional glutamine endopeptidase enzyme that cleaves a peptide bond after a -QPF- and a -PFP-motif in glutens.

18. The composition of claim 12, wherein the PEP is derived from the microorganism selected from the group consisting of: *Aspergillus niger, Flavobacterium meningosepticum, Sphingomonas capsulata, Penicillium citrinum, Hordeum vulgare*, and *Myxococcus xanthus*.

19. The composition of claim 12, the composition further comprising a glutamine specific protease selected from the group consisting of: *Hordeum vulgare* endoprotease, *Aspergillus oryzae* X-Pro dipeptidase, and *Aspergillus saitoi* carboxypeptidase; and/or further comprising a pharmaceutically acceptable carrier.

20. The foodstuff of claim 1, wherein the formulation comprises an enteric-coated formulation or a granular formulation.

21. The foodstuff of claim 1, wherein the foodstuff comprises gluten or gliadins.

22. The composition of claim 12, wherein the composition is formulated as an enteric-coated formulation or a granular formulation.

* * * * *